US008383096B2

(12) United States Patent
Ambinder et al.

(10) Patent No.: US 8,383,096 B2
(45) Date of Patent: Feb. 26, 2013

(54) CANCER IMMUNOTHERAPY WITH A VIRAL ANTIGEN-DEFINED, IMMUNOMODULATOR-SECRETING CELL VACCINE

(75) Inventors: Richard F. Ambinder, Lutherville, MD (US); Yiping Yang, Chapel Hill, NC (US); Ivan M. Borrello, Baltimore, MD (US); Hyam I. Levitsky, Owing Hills, MD (US)

(73) Assignee: Johns Hopkins University School of Medicine, Baltimore, MD (US)

( * ) Notice: Subject to any disclaimer, the term of this patent is extended or adjusted under 35 U.S.C. 154(b) by 273 days.

(21) Appl. No.: 12/756,364

(22) Filed: Apr. 8, 2010

(65) Prior Publication Data

US 2010/0272760 A1 Oct. 28, 2010

Related U.S. Application Data

(62) Division of application No. 10/528,311, filed as application No. PCT/US03/29684 on Sep. 19, 2003, now Pat. No. 7,740,871.

(60) Provisional application No. 60/411,990, filed on Sep. 19, 2002.

(51) Int. Cl.
*A61K 35/12* (2006.01)
*C12P 21/00* (2006.01)

(52) U.S. Cl. .......................... 424/93.3; 435/325; 514/44

(58) Field of Classification Search ........................ None
See application file for complete search history.

(56) References Cited

U.S. PATENT DOCUMENTS 6,464,973 B1 10/2002 Levitsky et al.

FOREIGN PATENT DOCUMENTS

WO 99/38954 8/1999

OTHER PUBLICATIONS

Draneff et al. 2002, vol. 188, pp. 147-154.*
Nedospasov et al. Molecular Biology 2007, vol. 41, No. 2, pp. 316-328, especially, p. 324.*
Asada et al., “Significant Antitumor Effects Obtained by Autologous Tumor Cell Vaccine Engineered to Secrete Interleukin (IL)-12 and IL-18 by Means of the EBV/Lipoplex,” *Molecular Therapy*, 5(5): 387-405 (1995).
Borrello et al., *Human Gen. Therapy*, 10: 1983-1991 (1999).
Draneff et al., *Immunological Reviews*, 188: 147-154 (2002).
Khanna et al., “Immune Regulation in Epstein-Barr Virus-Associated Diseases,” *Microbiological Reviews*, 59(3): 387-405 (1995).
Lee et al., *J. Immunol.*, 158: 3325-3334 (1997).
Nawrocki et al., *Cancer Treatment Reviews*, 25(1): 29-46 (1999).
Nedospasov et al., *Molecular Biology*, 41(2): 316-328 (2007).
Morishima et al., *J. Exp. Immunol*, 115: 385-392 (1999).

* cited by examiner

*Primary Examiner* — Bao Li
(74) *Attorney, Agent, or Firm* — Barnes & Thornburg LLP

(57) ABSTRACT

A human cell line, which lacks major histocompatibility class I (MHC-I) antigens and major histocompatibility class II (MHC-II) antigens and which has been modified to comprise and express (i) a nucleotide sequence encoding an immunomodulator and (ii) a nucleotide sequence encoding a viral antigen, and a method of inducing or stimulating an immune response in a human to a viral-associated disease or cancer comprising administering to the human (i) the aforementioned human cell line in an amount sufficient to induce or stimulate an immune response to the viral associated disease or cancer, (ii) a human cell line, which lacks MHC-I and MHC-11 antigens and which has been modified to comprise and express a nucleotide sequence encoding an immunomodulator, and a human cell line, which lacks MHC-I and MHC-II antigens and which has been modified to comprise and express a nucleotide sequence encoding an antigen of EBV, simultaneously or sequentially in either order, by the same or different routes, in amounts sufficient to induce or stimulate an immune response to the viral-associated disease or cancer, or (iii) an immunomodulator and a human cell line, which lacks MHC-I and MHC-II antigens and which has been modified to comprise and express a nucleotide sequence encoding an antigen of EBV, simultaneously or sequentially in either order, by the same or different routes, in amounts sufficient to induce or stimulate an immune response to the viral associated disease or cancer.

11 Claims, 186 Drawing Sheets

Homo sapiens interferon, alpha 1 (IFNA1), mRNA.
ACCESSION NM_024013
VERSION NM_024013.1 GI:13128949
1 agaacctaga gcccaaggtt cagagtcacc catctcagca agcccagaag tatctgcaat
61 atctacgatg gcctcgccct ttgctttact gatggtcctg gtggtgctca gctgcaagtc
121 aagctgctct ctgggctgtg atctccctga gacccacagc ctggataaca ggaggacctt
181 gatgctcctg gcacaaatga gcagaatctc tccttcctcc tgtctgatgg acagacatga
241 ctttggattt ccccaggagg agtttgatgg caaccagttc cagaaggctc cagccatctc
301 tgtcctccat gagctgatcc agcagatctt caacctcttt accacaaaag attcatctgc
361 tgcttgggat gaggacctcc tagacaaatt ctgcaccgaa ctctaccagc agctgaatga
421 cttggaagcc tgtgtgatgc aggaggagag ggtgggagaa actcccctga tgaatgcgga
481 ctccatcttg gctgtgaaga aatacttccg aagaatcact ctctatctga cagagaagaa
541 atacagccct tgtgcctggg aggttgtcag agcagaaatc atgagatccc tctctttatc
601 aacaaacttg caagaaagat taaggaggaa ggaataacat ctggtccaac atgaaaacaa
661 ttcttattga ctcatacacc aggtcacgct ttcatgaatt ctgtcatttc aaagactctc
721 acccctgcta taactatgac catgctgata aactgattta tctatttaaa tatttattta
781 actattcata agatttaaat tatttttgtt catataacgt catgtgcacc tttacactgt
841 ggttagtgta ataaaacatg ttccttatat ttactc Homo sapiens interferon, alpha 2 (IFNA2), mRNA.
ACCESSION NM_000605
VERSION NM_000605.2 GI:11067750
1 gagaacctgg agcctaaggt ttaggctcac ccatttcaac cagtctagca gcatctgcaa
61 catctacaat ggccttgacc tttgctttac tggtggccct cctggtgctc agctgcaagt
121 caagctgctc tgtgggctgt gatctgcctc aaacccacag cctgggtagc aggaggacct
181 tgatgctcct ggcacagatg aggagaatct ctcttttctc ctgcttgaag gacagacatg
241 actttggatt tccccaggag gagtttggca accagttcca aaaggctgaa accatccctg
301 tcctccatga gatgatccag cagatcttca atctcttcag cacaaaggac tcatctgctg
361 cttgggatga gaccctccta gacaaattct acactgaact ctaccagcag ctgaatgacc
421 tggaagcctg tgtgatacag ggggtggggg tgacagagac tcccctgatg aaggaggact
481 ccattctggc tgtgaggaaa tacttccaaa gaatcactct ctatctgaaa gagaagaaat
541 acagcccttg tgcctgggag gttgtcagag cagaaatcat gagatctttt tctttgtcaa
601 caaacttgca agaaagttta agaagtaagg aatgaaaact ggttcaacat ggaaatgatt
661 ttcattgatt cgtatgccag ctcacctttt tatgatctgc catttcaaag actcatgttt
721 ctgctatgac catgacacga tttaaatctt ttcaaatgtt tttaggagta ttaatcaaca
781 ttgtattcag ctcttaaggc actagtccct tacagaggac catgctgact gatccattat
841 ctatttaaat atttttaaaa tattatttat ttaactattt ataaaacaac ttatttttgt
901 tcatattatg tcatgtgcac ctttgcacag tggttaatgt aataaaatgt gttctttgta

Fig. 3

961 tttggtaaat ttattttgtg ttgttcattg aacttttgct atggaacttt tgtacttgtt
1021 tattctttaa aatgaaattc caagcctaat tgtgcaacct gattacagaa taactggtac
1081 acttcatttg tccatcaata ttatattcaa gatataagta aaaataaact ttctgtaaac
1141 ca

Fig. 3 (cont.)

Homo sapiens interferon, gamma (IFNG), mRNA.
ACCESSION NM_000619
VERSION NM_000619.1 GI:10835170

1 tgaagatcag ctattagaag agaaagatca gttaagtcct ttggacctga tcagcttgat
61 acaagaacta ctgatttcaa cttctttggc ttaattctct cggaaacgat gaaatataca
121 agttatatct tggcttttca gctctgcatc gttttgggtt ctcttggctg ttactgccag
181 gacccatatg taaaagaagc agaaaacctt aagaaatatt ttaatgcagg tcattcagat
241 gtagcggata atggaactct tttcttaggc attttgaaga attggaaaga ggagagtgac
301 agaaaaataa tgcagagcca aattgtctcc ttttacttca aactttttaa aaactttaaa
361 gatgaccaga gcatccaaaa gagtgtggag accatcaagg aagacatgaa tgtcaagttt
421 ttcaatagca acaaaaagaa acgagatgac ttcgaaaagc tgactaatta ttcggtaact
481 gacttgaatg tccaacgcaa agcaatacat gaactcatcc aagtgatggc tgaactgtcg
541 ccagcagcta aaacagggaa gcgaaaaagg agtcagatgc tgtttcaagg tcgaagagca
601 tcccagtaat ggttgtcctg cctgcaatat ttgaatttta aatctaaatc tatttattaa
661 tatttaacat tatttatatg gggaatatat ttttagactc atcaatcaaa taagtattta
721 taatagcaac ttttgtgtaa tgaaaatgaa tatctattaa tatatgtatt atttataatt
781 cctatatcct gtgactgtct cacttaatcc tttgttttct gactaattag gcaaggctat
841 gtgattacaa ggctttatct caggggccaa ctaggcagcc aacctaagca agatcccatg
901 ggttgtgtgt ttatttcact tgatgataca atgaacactt ataagtgaag tgatactatc
961 cagttactgc cggtttgaaa atatgcctgc aatctgagcc agtgctttaa tggcatgtca
1021 gacagaactt gaatgtgtca ggtgaccctg atgaaaacat agcatctcag gagatttcat
1081 gcctggtgct tccaaatatt gttgacaact gtgactgtac ccaaatggaa agtaactcat
1141 ttgttaaaat tatcaatatc taatatatat gaataaagtg taagttcaca act

Fig. 3 (cont.)

Human papilloma virus type 59, complete viral genome.

ACCESSION X77858

VERSION X77858.1 GI:557236

Rho,J., Roy-Burman,A., Kim,H., de Villiers,E.M., Matsukura,T. and Choe,J.

TITLE Nucleotide sequence and phylogenetic classification of human papillomavirus type 59

JOURNAL Virology 203 (1), 158-161 (1994)

1 gttaagaccg aaaacggtgc atataaaggt agttgaaaag aaaagggcaa cggcatggca
61 cgctttgagg atcctacaca acgaccatac aaactgcctg atttgagcac aacattgaat
121 attcctctgc atgatattcg catcaattgt gtgttttgca aaggggaact gcaagaaaga
181 gaggtatttg aatttgcttt taatgactta tttatagtgt atagagactg tacaccgtat
241 gcagcgtgtc tgaaatgcat ttcattttat gcaagagtaa gagaattaag atattataga
301 gattccgtgt atggagaaac attagaggct gaaaccaaga caccgttaca tgagctgctg
361 atacgctgtt atagatgcct aaaacctcta tgtccaacag ataaattaaa gcatataact
421 gaaaaaagaa gattccataa tatagctgga atatatacag gacagtgtcg tgggtgtcgg
481 acccgagcaa gacacctaag acagcaacga caagcgcgta gtgaaacact ggtgtaaaac
541 aatgcatgga ccaaaagcaa cactttgtga cattgtttta gatttggaac cacaaaatta
601 tgaggaagtt gaccttgtgt gctacgagca attacctgac tccgactccg agaatgaaaa
661 agatgaacca gatggagtta atcatccttt gctactagct agacgagctg aaccacagcg
721 tcacaacatt gtgtgtgtgt gttgtaagtg taataatcaa cttcagctag tagtagaaac
781 ctcgcaagac ggattgcgag ccttacagca gctgtttatg gacacactat cctttgtgtg
841 tcctttgtgt gcagcaaacc agtaacctgc aatggccgat tcggaaggta cagatgggga
901 agggacgggg tgcaatggat ggttttttgt gcaggcaata gtagataaaa aaacaggtga
961 caaaatttca gatgacgagg atgaaaatgc aacagataca ggttcagact tggtagattt
1021 tattgatgat accacaacaa tttgtgtaca ggcagagcgc gagacagcac aggccttgtt
1081 taatgtgcag gaagcccaaa gggatgcacg ggaaatgcat gttttaaaac gaaagtttgg
1141 gtgcagtata gaaaacagta gtgagaaagc ggcggcagga aaaaaagcta agtcaccatt
1201 acaagaaata tcagtaaatg ttaaccaccc aaaagtaaaa agaaggttaa taacagtgcc
1261 agacagcggc tatggctatt ctgaagtgga aatgctcgag actcaggtaa ccgtggagaa
1321 tactggaaat ggggatagca atggcagtgt ttgtagcgac agtcaaatag actgtagcga
1381 cagcagtaac atggatgttg aaaacatagt tccaacatcc cccactaatc aattgttaca
1441 gttattacat agcaaaaata agaaagcagc tatgtatgca aaatttaaag aattgtatgg
1501 gttatcattt caagatttgg ttaggacatt taaaagtgac agaactacct gtagcgattg
1561 ggtaaccgcc atttttggtg ttaatccaac tgtagcagaa ggatttaaaa cattaataca
1621 accctatgtg ctatatgcac atatacaatg cttagattgt gcatggggag tagtaatatt
1681 agcattatta agatataaat gtggaaaaaa tagaataaca gttgcaaaag gacttagcac
1741 attactacat gtaccagata cgtgcatgtt aattgaacca cccaaattgc gtagtggtgt
1801 tgcagcacta tattggtaca gaacaggaat gtccaatatt agtgaagtta taggggaaac
1861 gcccgaatgg atacaaagac taacaattat acaacatgga gttgatgata gcgtgtttga
1921 cctgtcagaa atgatacaat gggcgtttga taatgaccta acagatgaaa gtgatattgc

Fig. 3 (cont.)

1981 atatgaatat gcattaatag cagatagtaa tagtaacgcc gctgcatttt taaaaagcaa
2041 ctgccaggca aaatacctaa aagattgtgc agttatgtgt aggcattata aaagagcaca
2101 aaaaagacaa atgagtatgt cacagtggat aaaatggaga tgtgataaaa tagaagaggg
2161 gggagattgg aaacccatag tacaattttt aagatatcaa ggagtagaat ttataacgtt
2221 tttatgtgca ttaaaagatt ttttaaaagg taccccaaaa agaaattgca ttgtgctgtg
2281 tgggccagca aatacaggca agtcatactt tggaatgagc ctgctacatt ttttacaagg
2341 aactgtaatt tcacatgtaa attcaaatag tcacttttgg ctagaacctt taacagatcg
2401 taaattagct atgctagacg atgcaacaga tagttgttgg acatattttg atacatatat
2461 gcgaaatgct ttggatggca atcctataag tgtagataga aagcataggc acctagtaca
2521 aattaaatgt ccaccaatgc ttattacatc aaatacaaat ccagttacag ataacaggtg
2581 gccatattta aatagcagat taatggtatt taaatttcca aacaaattgc catttgacaa
2641 aaatagaaat ccagtatata caattaatga cagaaactgg aaatgttttt ttgaaaggac
2701 gtggtgcaga ttagatttga acgaggaaga ggaagatgca gacagtgatg gacacccttt
2761 cgcagcgttt aagtgtgtta caggatcaaa tattagaaca ttatgaaaac gatagtaaag
2821 acattaatga acacataaac tattggaaac tggtgcgtat ggaaaatgta attttatttg
2881 cagcaagaga gaacaatata catacattaa accaccaggt ggtgccaacg tttttggtgt
2941 ctaaaaacaa ggcatgtgaa gctattgaac tgcagtcaaa ccgtacttcc actgtaatgc
3001 cctgtttttt aaaacatttt ttaggtgctg tttgccatag ttcttggcat gtttcttgca
3061 ttgtccattg ctcattttta aactcagttt gtgccaaact ctctaacgcc atctgcagca
3121 aggaaaacac aatgcattac acaagctgga catttatata ttatgtaaat gatgtaggac
3181 agtggtgtaa aaccacagga aatgtggact tttggggact atattataaa gtggaagagg
3241 aacaggtgta ctatgtaaaa tttatacatg atgccaaaaa atatgggact acagacaagt
3301 gggaagtgca ttataatggc aaggttattg attgttatga ctctatgtgc agtaccagtg
3361 acgagcaagt atccactgct ggatcttctg agcaactatc ataccccctcc gcaacgcccc
3421 ccgaagccac gtacttgggc ccccaaacgt ggaaccgtca gacgaagact ggaaagcgac
3481 caagacagtg tggatacaca cagcaccctc agtctaccag cgtgtcagtg gactactgtg
3541 acaacccagt cgtccgtttg catccaggca acaacccgcg acggcacatc ccttgcagta
3601 acactacgcc tataatacac ttaaaaggtg acaaaaatgg ccttaagtgt ttaaggtata
3661 gattaagaaa agtacactgg ttatttgaaa atatttcctc tacctggcat tggacaggaa
3721 acagaggatc agccaaaaca ggcattttaa cattaacata tacaagcgaa acacaacgca
3781 atgaattttt agatactgta aaaattccta atagtgtaca aatacatgtt gggtatatga
3841 gtgtgtaatg gttgttatgc aaatgtaaca caagccaata ctgctgctat attgtatagc
3901 tgaggaaatg ataacccttg tatttgtgtg ttgtgtttgt gtttgcttgt gtgtgtgttg
3961 caatgtcccg cttctgcaat ctgtctatat gtgtgcatat acatggttac tagtatttgt
4021 gtatattgtg gttatcacct cctcatatga gtgtttttta ctatatatat tgttttttat
4081 aattccactg ttactactat atgcccatgc aatactgtcc atacaataat tgctgtatat
4141 tgtaaattac attgcactgt attgtacagt atattttaaa cacattatta tttttgttag
4201 gtgttggttt tgttacattt ataataaaac atggtttccc atcgtgctgc tcgtcgtaaa
4261 cgtgcctcag caacagactt atataaaact tgcaagcagg caggtacatg cccttctgat

Fig. 3 (cont.)

4321 gttattaata aagttgaagg tacaacttta gctgataaaa tattgcagtg gaccagccta
4381 ggaatatttt taggtggact aggtattggt actggatctg gtaccggtgg cagaacaggg
4441 tacatacctt taggggggcg tacaaacact atagtagatg tatcgcctgc taaaccacca
4501 gtagttattg aacctgttgg acctacagat ccatctatag ttacattagt tgaggattct
4561 agtgttataa catctggagc cctgccccca acatttacag gtacttcagg atttgaaata
4621 tctacctcta gtacaacaac accagctgtt ttggatataa ccccaacctc ttctgttcaa
4681 attagtagct ctagttttat aaatcctgca tttacagacc cttctgtcat tgaggttccc
4741 caaacaggtg aaatttctgg taatatatta attagtaccc ctacctctgg tgcacatggc
4801 tatgaagaaa ttccaatgca aacgtttgct acggaaggta ctggtttgga acccattagc
4861 agtacccccca atccaacagt acgtcgtgtg gctggaccta gattgtacag tagggctaat
4921 caacaagttc gggtgtctaa cgctgacttt ttaacacgtc catccacatt tgttacatat
4981 gataaccctg cttatgatcc aattgatact acattaactt ttgacccctc atcagaggtt
5041 ccagacccgg actttatgga tatagttcgt ttgcataggc ctgcattaac atccagacgc
5101 agcactgtaa ggtttagtag gctaggacaa cgggcaacca tgtttacccg tagtggtaaa
5161 caaattgggg cccgtgtaca tttttatcat gatataagcc ctataccaca tgctgaagat
5221 attgaattgc aacctcttgt ttcttcccag gctgctactg atgatatata tgatatatat
5281 gcagatatta cagatgaagc acctactagt actgccaaca ctgcatttac aattcctaaa
5341 tcttcttttc aaagtttgtc attaacacgg tcggcatcta gcaccttttc aaatgtaact
5401 gttcctttgg ctactgcctg ggatgttcct gtaaatacag gacccgatat agttttacct
5461 aatactaata ttgttgaacc cacttattct actacaccct ttaccaccat acagtctatt
5521 aatatagaag gcacaaatta ttttttatgg cctatatatt attttttacc tcgtaaacgt
5581 aaacgtgttc cctatttttt tacagatggc tctatggcgt tctagtgaca acaaggtgta
5641 tctacctcca ccttcggtag ctaaggttgt cagcactgat gagtatgtca cccgtaccag
5701 tattttctac cacgcaggca gttccagact tcttacagtt ggacatccat attttaaagt
5761 acctaaaggt ggtaatggta gacaggatgt tcctaaggtg tctgcatatc aatacagagt
5821 atttagggtt aagttacctg atcccaataa atttggcctt ccagataaca cagtatatga
5881 tcctaactct caacgcttgg tctgggcctg tgtaggtgtt gaaatcggtc ggggccaacc
5941 tttaggggta ggactcagtg gtcatccatt atataataaa ttggatgaca ctgaaaactc
6001 tcatgtagca tctgctgttg ataccaaaga tacacgtgat aatgtatctg tggattataa
6061 acaaactcag ctgtgtatta ttggctgtgt acctgccatt ggagaacact ggacaaaggg
6121 cactgcttgt aagcctacta ctgtggttca gggcgattgt cctccactag aattaataaa
6181 tacaccaatt gaagatggtg atatggtaga cacaggatat ggggctatgg actttaaatt
6241 gttgcaggat aacaaaagtg aagtaccatt ggatatttgt cagtctattt gtaaatatcc
6301 tgattattta caaatgtcag cagatgctta tggagacagt atgttttttt gtttaaggcg
6361 agaacaggtt tttgccagac atttttggaa tagatctggt actatgggtg atcaacttcc
6421 tgaatcacta tatattaaag gtactgacat acgtgccaac ccaggcagtt atttatattc
6481 cccttcccca agtgggtctg tggttacttc tgattcacaa ttatttaata aaccatattg
6541 gctgcacaag gctcagggtt taaacaatgg tatatgttgg cacaatcaat tgtttttaac
6601 agttgtagat actactcgca gcaccaatct ttctgtgtgt gcttctacta cttcttctat

Fig. 3 (cont.)

6661 tcctaatgta tacacaccta ccagttttaa agaatatgcc agacatgtgg aggaatttga
6721 tttgcagttt atatttcaac tgtgtaaaat aacattaact acagaggtaa tgtcatacat
6781 tcataatatg aataccacta ttttggagga ttggaatttt ggtgttacac cacctcctac
6841 tgctagttta gttgacacat accgttttgt tcaatctgct gctgtaactt gtcaaaagga
6901 caccgcaccg ccagttaaac aggaccctta tgacaaacta aagttttggc ctgtagatct
6961 taaggaaagg ttttctgcag atcttgatca gtttcctttg ggacgtaaat ttttattgca
7021 attaggagct agacctaagc ccactatagg cccacgcaaa cgtgcagcgc ctgcccctac
7081 ctctacccca tcaccaaaac gtgttaagcg tcgcaagtct tccagaaaat agtgttgttt
7141 gttatgtgtt tgtatgtgtg catgttgtat gttttgtatt gtttgcctgt ttgtatgttg
7201 tgtatatgta catgtttgtt tgtctgctgt atgtgtgtat ttgtttttgt acataataaa
7261 gtatgcatga cagtttcatg tgtggttgca cccaatgagt aaggtactgt ccctttattg
7321 tttctttgtc cttattacac attattacac attgccctac ttacataggt gtgtttgttc
7381 cttcattttg tcctgaatgt ccagttttgc atttgcacat tatatggcgt ccattttatc
7441 ctttaaatcc tccattttgc tgtgcaaccg ttttcggtta ccttggttta accttacctt
7501 tttgaacaat taatctgttt aaacatcagc aaaacagtta atccccatct tgtttcctcc
7561 tacacgccta gactactaac acaacttaca aacgccaaat agttagtcat catcctgtcc
7621 aggtgcactc taacaatact tgcataactt tggtggcgcc cttgttaata aaacagcttt
7681 taggcacata ttttcactgt ttttactact ttaattgcat aattggcttg caaaactact
7741 gtgcaatcca agaatgtgtc tataatttat tgtaaaaaac atgactaagg tttttgtcat
7801 tgttaagcaa ccgaaaaagg tcgggcaagt acatgcacac tttctactta ttacttttta
7861 caatcatagt aataaaaaag ggtgtaaccg aaaacg

Fig. 3 (cont.)

Human papilloma virus type 59, complete viral genome.
ACCESSION X77858
VERSION X77858.1 GI:557236

3908..4129 gene="ORF putative E5"
atg ataacccttg tatttgtgtg ttgtgtttgt gtttgcttgt gtgtgtgttg
3961 caatgtcccg cttctgcaat ctgtctatat gtgtgcatat acatggttac tagtatttgt
4021 gtatattgtg gttatcacct cctcatatga gtgtttttta ctatatatat tgtttttttat
4081 aattccactg ttactactat atgcccatgc aatactgtcc atacaataa 55..537 gene="ORF putative E6"
atggca
61 cgctttgagg atcctacaca acgaccatac aaactgcctg atttgagcac aacattgaat
121 attcctctgc atgatattcg catcaattgt gtgttttgca aaggggaact gcaagaaaga
181 gaggtatttg aatttgcttt taatgactta tttatagtgt atagagactg tacaccgtat
241 gcagcgtgtc tgaaatgcat ttcattttat gcaagagtaa gagaattaag atattataga
301 gattccgtgt atggagaaac attagaggct gaaaccaaga caccgttaca tgagctgctg
361 atacgctgtt atagatgcct aaaacctcta tgtccaacag ataaattaaa gcatataact
421 gaaaaaagaa gattccataa tatagctgga atatatacag gacagtgtcg tgggtgtcgg
481 acccgagcaa gacacctaag acagcaacga caagcgcgta gtgaaacact ggtgtaa 542..865 gene="ORF putative E7"
atgcatgga ccaaaagcaa cactttgtga cattgtttta gatttggaac cacaaaatta
601 tgaggaagtt gaccttgtgt gctacgagca attacctgac tccgactccg agaatgaaaa
661 agatgaacca gatggagtta atcatccttt gctactagct agacgagctg aaccacagcg
721 tcacaacatt gtgtgtgtgt gttgtaagtg taataatcaa cttcagctag tagtagaaac
781 ctcgcaagac ggattgcgag ccttacagca gctgtttatg gacacactat cctttgtgtg
841 tcctttgtgt gcagcaaacc agtaa

Fig. 3 (cont.)

Human papilloma virus type 13 DNA.

ACCESSION X62843 S43933

VERSION X62843.1 GI:60295

Van Ranst,M., Fuse,A., Fiten,P., Beuken,E., Pfister,H., Burk,R.D. and Opdenakker,G.

TITLE Human papillomavirus type 13 and pygmy chimpanzee papillomavirus type 1: comparison of the genome organizations JOURNAL Virology 190 (2), 587-596 (1992)

1 gtttctaaca atcttaagtt taaaaaatag gtgggaccga aaacggtttt aaccgaaaac
61 ggtgatatat aaaccagccc aaaaattgag caagcggggc ataatggaaa gtgcaaatgc
121 ctccacgcct gcaaaaacta tagaccagtt gtgcaaggag tgcaaccttt ctatgcacag
181 cttgcaaatt ctatgcgtgt tctgcaggaa aaccctgtcc acggcagagg tttatgcatt
241 tcagtataag agtttatata tagtgtggcg aggacagttt ccatttgcgg cttgtgcatg
301 ctgcttagaa atacaaggaa agattaacca gtttaggcat tttgacttcg cgggatttgc
361 tgtaacagtt gaagaagaca caaagcagtc aattttggat gtgctaattc gctgctattt
421 atgccacaaa ccattgtgtg aagtggagaa actaagacat attttgcaga aggcacgatt
481 tattaaatta aacagcagtt ggaaaggccg ctgttttcat tgctggtcat catgcatgga
541 aaatatccta ccttaaaaga cattgtttta gagctgactc ctgaccctgt aggtctacat
601 tgcaatgagc aattagacag ctcagaagac gaggtggacg aacaagccac gcaagccacg
661 caagccacgc aacatagcac actattacaa tgctaccaaa tactaacgtc ctgtagtaaa
721 tgttgtagca acgtccggct ggtggtggag tgtacaggac ctgacattca cgacctacac
781 gacctactgc tgggcacgct gaatatagtg tgccctttgt gtgcaccaaa aagctaacca
841 cgatggcaga ggatacaggt actaataatg aggggacggg atgctcagga tggtttttag
901 tagaggctgt agtagaacga acaactgggc aacaaatatc agatgatgag gatgaaacag
961 tggaagatag tgggttggat atggtggatt tcatagatga cagacctatt acacacaatt
1021 ccgtggaagc acaggcattg ttaaacgagc aggaggcgga tgctcattat gcggctgtgc
1081 aggacctaaa acgaaagtat ttaggcagtc catatgttag tcccctagga catgttgaac
1141 agtcagtgga ctgtgatata agtcctcgat tggacgctat aaaattaagt agaaattcta
1201 aaaaagtaaa gcgacggctg tttcaatcaa gggaaataac ggacagtgga tatggctatt
1261 ctgaagtgga agctgaaacg caggtagaga gaaatggcga accggaaaat gattgtgggg
1321 gtggtggaca cggaagggac aaagaggggg agggacaggt gcacacggaa gtgcacacag
1381 gcagccagat agaagagcac acagggacca cgcgggtgtt agaactcctt aaatgtaagg
1441 atgtaagggc tacattgtat ggtaagttta aagactgtta tgggttatca tttacagatt
1501 taattagacc atttaaaagt gataaaacaa catgtgggga ctgggtggtt gcagcatttg
1561 gtatacatca tagtgtatca gaggcatttg aaaagttaat gcagccatta acaacatata
1621 tgcatataca atggcttaca aatgcatggg ggatggtatt gttagtatta ataagattta
1681 aagtaaataa aagtagatgc acagtggcgc gaacactggc aacctttctt aatattcctg
1741 aggaccacat gttaattgaa cctcccaaaa tacaaagcag tgtggcagca ttatactggt
1801 ttagaacagg tatttctaat gctagtatag taactggtga aacaccagaa tggataaaaa
1861 ggcaaacaat tgtagagcat ggacttgcag ataatcaatt taaattaact gaaatggtgc

Fig. 3 (cont.)

1921 agtgggcata tgataatgat ttttgtgatg aaagcgaaat agcatttgaa tatgcacaac
1981 gaggagattt tgattcaaat gccagggcat ttttaaatag taattgtcag gcaaaatatg
2041 taaaagattg tgcaacaatg tgcaagcatt ataaaaatgc agaaatgaaa aaaatgtcta
2101 tgaaacaatg gataacatat agaagtaaaa aaatagagga agcaggaaat tggaaaccaa
2161 tagtacaatt tttaaggcat caaaatatag aatttattcc atttttaagt aaattaaaat
2221 tgtggcttca tggcacgcca aagaaaaact gtattgcaat agtggggcca ccagatacag
2281 gcaaatcatg tttttgcatg agcttaatta agtttttagg gggcacagta attagttatg
2341 taaattcaag tagccatttt tggctgcagc cattatgtaa tgcaaaggta gctttgctag
2401 atgatgcaac gcagtcatgc tgggtatata tggacacata catgagaaat ttattagatg
2461 gcaatccaat gagcattgat agaaaacata agtctttagc attaataaaa tgtccgccat
2521 tattagtaac atctaatgta gacattacca aagatgacaa atataaatat ttgtatagta
2581 gagtaacaac acttacattt ccaaatccat tcccttttga cagaaatggg aatgcagtat
2641 atgagttgtc tgatgcaaac tggaaatgtt tttttacaag attgtcagca agcctagata
2701 tacaggactc tgaggacgag gacgatggag acaatagcca agcatttaga tgcgtgccag
2761 gaacagttgt tagaactgta tgaagaaaat agtaatgaac ttaaaaaaca tatacaacat
2821 tggaaatgct taaggtacga aagtgtactc ttacacaaag cacgccaaat gggcctaagc
2881 cacattggat tacaagtggt gccaccattg acagtatcac aagctaaggg acatgaggca
2941 attgaaatgc aaatgacttt agagacatta ctagagtctg agtttggtat ggaaccatgg
3001 actttacaag atacaagtcg tgaaatgtgg ctaacacccc caaaacgctg ttttaagaaa
3061 cagggacaaa ctgtggaagt aaaatatgac tgtaatacag acaatagaat ggattatgtg
3121 tcgtggacat acatatatgt gtttgacaca gataaatgga caaaggtgaa aggaatggta
3181 gattataaag ggttgtacta catacatgga aatttgaaaa catattattt agagtttgaa
3241 aaggaggcta aaaaatatgg ggaaacgtta caatgggaag tatgtattgg cagcacagtc
3301 atatgttctc ctgcatctgt atctagtact gtacaagaag tatccattgc tgggcctgct
3361 tcatactcca ccaccacctc cacacaggcc tccaccgcag tgtcctgcag cgcctcggaa
3421 gaatgtgtgc aagcgccgcc ttgtaaacga caacgaggac cttcacgtcc cattggaaac
3481 ccccagaaca cacaaagcat tgtgtgtgtc acagactacg acaccctgga cagtgcaaac
3541 aacaacatca acgttaacca ttacaacaat aacaaaggac gggacaacag ttactgtgca
3601 gctacaccta tagttcaatt acaaggtgac tctaattgtc taaagtgttt tcgatataga
3661 ttacatgaaa aatataaaga tttatttttg ttagcatcat ctacatggca ttggaccgcc
3721 cctaataatt cacaaaaaca tgcactggta accttaacct atgtaaatga acaacaaaga
3781 caagactttt taaaaactgt aaaaatacct ccaaccataa cacataaact aggttttatg
3841 tcattgcaat tgttataaca gcatatattg tatgtaaata tttgttgtgt gtgtgtatat
3901 attgtaaatg gaatttatac ctgtggatgt tagtacacag gcaaccagca agtcattact
3961 gccacttgta attgcactta cagtgtgtgt agttagcatt ataacaatat tgtgcatatc
4021 agagttcttg gtgtacacaa acgttttagt actaacatta attttatatg tacttttgtg
4081 gcttttacta acaactccct tgcaattcta tttactaacc ctgtctcttt gctttcttcc
4141 tgcgttgtgt gtacaccaat atattttaca aacacaagaa taactataca caatgttaac
4201 ctgtactttt gatgatggtg acacatggtt gctattatgg ttaattttat catttattgt

Fig. 3 (cont.)

4261 agccattcta gggttactgt tgctgtatat aagaactgga catatgcatt gccagtgctg
4321 gagtaaataa gtggttttat attttgtgtg tattcattta attatggcac atagtagggc
4381 tcgcagacgc aaacgcgctt cagctacaca actatatcaa acttgtaagg cttctggaac
4441 atgtcctcct gatgttatac caaaggttga acaaaacact cttgcagata aaatattaaa
4501 gtggggcagt ttaggagtat tttttggggg gcttggcatt ggcacaggct ctggtactgg
4561 cggtaggact ggctatgtac cagtaggatc caccccacgc cctgccatat caactgggcc
4621 tactgcacgt cctcctattg ttgttgatac tgttgggcct acagaccctt ctattgtatc
4681 tttggtagag gaatcagcta ttattaattc tggagtacct gaccctttgc ctcccgttca
4741 tgggggtttt gaaatcacca catctcaatc agccactcca gcaatattgg atgtgtctgt
4801 tacaacacaa aacactacgt ccacaagtat atttagaaat cctgtttttt cagaaccttc
4861 tattacacaa tctcaacctt ctattgaaag tggtgcacac gtgtttatat cgccatctac
4921 tatttcccct cattctacag aagacattcc tttagataca tttattgtat cttcctcaga
4981 tagtaatcct gcatcaagca cccctgttcc agcaactgtt gcacgtccac gtctaggcct
5041 ttacagtagg gccttacatc aagtacaggt tactgatcct gcctttttat cgtcgcccca
5101 acgccttata acctttgata accctacata tgaaggtgaa gatataagtt tgcagtttgc
5161 acacaatacc attcatgaac cccctgatga ggcatttatg gatattataa gactacatag
5221 gccagccata acatcacggc gtggtcttgt taggtttagt agaattggtc agagggggtc
5281 tatgtatact cgaagcggca agcatatagg tggaagggtc catttcttta aggatatttc
5341 tcctatatct gcagctgcag aagaaataga attacacccc cttgtggctg ctgcacagga
5401 tcacagtggt ttgtttgata tttatgcaga acctgaccct gaccctgtgg ctgtaaacac
5461 ctctgggtca ttgtcttctg cctccacacc atttgcacaa tcttctttgt cttccgcccc
5521 atggggtaat actactgttc ctctttcact accaggtgat atatttatac agcctggtcc
5581 tgacataaca ttcccaactg cacctacagt aacgccttat aatcctgtta cgcctgcttt
5641 acctacaggt cctgttttta ttactgcttc tggattttat ttatatccta catggtattt
5701 tacacgcaaa cgccgtaaac gtgtttcctt gttttttaca gatgtggcgg cctagtgaca
5761 acaaactata tgtgcctcct cccgcccctg tatcaaaagt aattactacg gatgcctatg
5821 ttacacgtac caacatattt tatcatgcta gcagttctag actacttgca gtgggaaatc
5881 cttattttcc tattaagaaa caaaacaaaa ctgttgtccc taaggtatct ggttatcagt
5941 ttagggtatt taaagttgta ttacctgacc ctaataaatt tgccctgcct gacacatcta
6001 tatttgactc aactagtcaa cgcttagtgt gggcctgtac aggtttagag gttggtaggg
6061 gtcaaccctt aggtgttggt attagtggtc atccattatt aaataaatat gatgatgtgg
6121 aaaattctgc aagttatgct gccaatcctg gtcaggataa tagggttaat gtggccatgg
6181 actataaaca aacacagtta tgtttagtgg gctgtgcacc tcctttaggt gaacattggg
6241 gacagggcaa gcaatgtact ggtgtaaatg tacaacctgg agattgccct cctttagaat
6301 taattagtag tgtaattcag gatggtgaca tggtggatac aggatttgga gccatgaatt
6361 ttgcggaatt gcaatctaat aaatctgatg tgccactaga catatgcacg tccacatgca
6421 aatatcctga ctatttacaa atggctgcgg atccttatgg agacagatta ttttttatc
6481 tgcgaaagga acaaatgttt gcaaggcatt tctttaacag ggcaggctct gttggtgaac
6541 aaatcccagc agaattatat gttaagggta gtaatacact ttctaatagt atttactata

Fig. 3 (cont.)

6601 atactcccag tggctctctt gtgtcttctg aggcccagtt gtttaataaa ccttattggt
6661 tacaaaaggc ccagggacac aataatggta tatgttgggg caatcacttg tttgttactg
6721 tagttgatac tacacgcagt actaacatga ctgtgtgtgc agccactaca tcatctcttt
6781 cagacacata taaggccaca gaatataaac agtacatgcg acatgtagaa gaatttgatt
6841 tacaatttat ttttcaattg tgcactatta aattaactgc agaggttatg tcatatattc
6901 atactatgaa tcctacaatt ctagaagact ggaactttgg gctatctccc cctcctaatg
6961 gaacattaga agacacatat agatatgtac aatctcaggc cataacgtgt caaaagccta
7021 cacctgataa agaaaaacag gatccgtatg cgggtcttag tttttgggag gttaatctta
7081 aggaaaagtt ttctagtgaa ctagatcagt atccccttgg cagaaagttt ttattacaaa
7141 caggcgttca gtctaggtcc cctattcgtg taggtaggaa acgtgctgca tctacatcta
7201 ctgccacacc tactacacgt aaaaaagcta aaaggaaata atagtttgtt tatgattgtg
7261 tatgtatgtc acgtttgttt gtactgtatg tatgttgtgt actgtatgtg taatgttgta
7321 tgtatgtgca tgttacttat taaagaatgt gtgtgtgtgt ttgtatgcaa taaatctaat
7381 ctgtggtgtc ctgttccacc ctatgagtaa gtggtatgtt gtgtctcgtg tggtgttttg
7441 tatactatac tataacatta gtgcaaccat tttgtaactt ttcttacatt ttacgtctcc
7501 atattaagtg caaccgattt cggttgctat tgtttctgcg accgatttgt tgcagcacgc
7561 tgtttatata atcttaccta ccgcctgcca aaattatcca ccgcttgcca aaatcaccca
7621 cacacctggc gttgctaggg cgcggttata tatatttact aaatcttact aatctttcta
7681 tcactcattt tacctttata acaatacttt tgcttttcaa gtacattttt gtacttacta
7741 gccaatgcct gaaaggtttt ttggctacca gcactacatt tttgtacagt taatgttaca
7801 tgtataaaat gagtaaccta aggtcacaca cctgcaaacc ggtatcggtt aaaacacacc
7861 ctctatagtt ccttataatt

Fig. 3 (cont.)

Human papilloma virus type 13 DNA.
ACCESSION X62843 S43933
VERSION X62843.1 GI:60295

3908..4183 gene="E5"
atg gaatttatac ctgtggatgt tagtacacag gcaaccagca agtcattact
3961 gccacttgta attgcactta cagtgtgtgt agttagcatt ataacaatat tgtgcatatc
4021 agagttcttg gtgtacacaa acgttttagt actaacatta attttatatg tacttttgtg
4081 gcttttacta acaactccct tgcaattcta tttactaacc ctgtctcttt gctttcttcc
4141 tgcgttgtgt gtacaccaat atattttaca aacacaagaa taa 104..556 gene="E6"
atggaaa gtgcaaatgc
121 ctccacgcct gcaaaaacta tagaccagtt gtgcaaggag tgcaaccttt ctatgcacag
181 cttgcaaatt ctatgcgtgt tctgcaggaa aaccctgtcc acggcagagg tttatgcatt
241 tcagtataag agtttatata tagtgtggcg aggacagttt ccatttgcgg cttgtgcatg
301 ctgcttagaa atacaaggaa agattaacca gtttaggcat tttgacttcg cgggatttgc
361 tgtaacagtt gaagaagaca caaagcagtc aattttggat gtgctaattc gctgctattt
421 atgccacaaa ccattgtgtg aagtggagaa actaagacat atttgcaga aggcacgatt
481 tattaaatta aacagcagtt ggaaaggccg ctgttttcat tgctggtcat catgcatgga
541 aaatatccta ccttaa 532..837 gene="E7"
atgcatgga
541 aaatatccta ccttaaaaga cattgtttta gagctgactc ctgaccctgt aggtctacat
601 tgcaatgagc aattagacag ctcagaagac gaggtggacg aacaagccac gcaagccacg
661 caagccacgc aacatagcac actattacaa tgctaccaaa tactaacgtc ctgtagtaaa
721 tgttgtagca acgtccggct ggtggtggag tgtacaggac ctgacattca cgacctacac
781 gacctactgc tgggcacgct gaatatagtg tgccctttgt gtgcaccaaa aagctaa

Fig. 3 (cont.)

Homo sapiens erythropoietin (EPO), mRNA.
ACCESSION NM_000799
VERSION NM_000799.1 GI:4503588
1 cccggagccg gaccggggcc accgcgcccg ctctgctccg acaccgcgcc ccctggacag
61 ccgccctctc ctccaggccc gtggggctgg ccctgcaccg ccgagcttcc cgggatgagg
121 gcccccggtg tggtcacccg gcgcgcccca ggtcgctgag ggaccccggc caggcgcgga
181 gatgggggtg cacgaatgtc ctgcctggct gtggcttctc ctgtccctgc tgtcgctccc
241 tctgggcctc ccagtcctgg gcgccccacc acgcctcatc tgtgacagcc gagtcctgga
301 gaggtacctc ttggaggcca aggaggccga gaatatcacg acgggctgtg ctgaacactg
361 cagcttgaat gagaatatca ctgtcccaga caccaaagtt aatttctatg cctggaagag
421 gatggaggtc gggcagcagg ccgtagaagt ctggcagggc ctggccctgc tgtcggaagc
481 tgtcctgcgg ggccaggccc tgttggtcaa ctcttcccag ccgtgggagc ccctgcagct
541 gcatgtggat aaagccgtca gtggccttcg cagcctcacc actctgcttc gggctctgcg
601 agcccagaag gaagccatct cccctccaga tgcggcctca gctgctccac tccgaacaat
661 cactgctgac actttccgca aactcttccg agtctactcc aatttcctcc ggggaaagct
721 gaagctgtac acaggggagg cctgcaggac aggggacaga tgaccaggtg tgtccacctg
781 ggcatatcca ccacctccct caccaacatt gcttgtgcca caccctcccc cgccactcct
841 gaaccccgtc gaggggctct cagctcagcg ccagcctgtc ccatggacac tccagtgcca
901 gcaatgacat ctcaggggcc agaggaactg tccagagagc aactctgaga tctaaggatg
961 tcacagggcc aacttgaggg cccagagcag gaagcattca gagagcagct ttaaactcag
1021 ggacagagcc atgctgggaa gacgcctgag ctcactcggc accctgcaaa atttgatgcc
1081 aggacacgct ttggaggcga tttacctgtt ttcgcaccta ccatcaggga caggatgacc
1141 tggagaactt aggtggcaag ctgtgacttc tccaggtctc acgggcatgg gcactccctt
1201 ggtggcaaga gcccccttga caccggggtg gtgggaacca tgaagacagg atgggggctg
1261 gcctctggct ctcatggggt ccaagttttg tgtattcttc aacctcattg acaagaactg
1321 aaaccaccaa aaaaaaaaaa aa Mus musculus FMS-like tyrosine kinase 3 ligand (Flt3l), mRNA.
ACCESSION NM_013520
VERSION NM_013520.2 GI:31982427
1 gaattcgcgg ccgcgtcgac attctgggga cgtcggtcgg ggttcttaga agaggagatg
61 acttttcaca gtcactgagg ctcgtgcagg aagcctgggg gagcaggagg cggaaaccga
121 cccacatcaa gggcggcagg gccgggcggc ggggtacagg ggttgggggg gaaggggctg
181 cagggtatga gcccgagacc tgccctcctg tcacttccaa gaacctgtca caggcatgag
241 gggtccccgg cagagatgac agtgctggcg ccagcctgga gcccaaattc ctccctgttg
301 ctgctgttgc tgctgctgag tccttgcctg cgggggacac ctgactgtta cttcagccac
361 agtcccatct cctccaactt caaagtgaag tttagagagt tgactgacca cctgcttaaa
421 gattacccag tcactgtggc cgtcaatctt caggacgaga agcactgcaa ggccttgtgg
481 agcctcttcc tagcccagcg ctggatagag caactgaaga ctgtggcagg gtctaagatg

Fig. 3 (cont.)

541 caaacgcttc tggaggacgt caacaccgag atacattttg tcacctcatg taccttccag
601 cccctaccag aatgtctgcg attcgtccag accaacatct cccacctcct gaaggacacc
661 tgcacacagc tgcttggtct gaagccctgt atcgggaagg cctgccagaa tttctctcgg
721 tgcctggagg tgcagtgcca gccggactcc tccaccctgc tgcccccaag gagtcccata
781 gccctagaag ccacggagct cccagagcct cggcccaggc agctgttgct cctgctgctg
841 ctgctgctgc ctctcacact ggtgctgctg gcagccgcct ggggccttcg ctggcaaagg
901 gcaagaagga ggggggagct ccaccctggg gtgcccctcc cctcccatcc ctaggatgcg
961 agccttgtgc atcgttgact cagccagggt cttatctcga tgaggtctca atatgttgcc
1021 caaactgact ttgaaaacct cgatgcacct tcctgcccca caaacttcca aacagctggg
1081 cttacgggca tgctatatac aacaaggctt tcttttcttc tttcttggtg ctagagttgg
1141 gaaccaaaac aa Homo sapiens macrophage colony-stimulating factor (M-CSF1) cDNA to mRNA, complete cds.

ACCESSION M27087

VERSION M27087.1 GI:508985

1 agccgctctc cgcatcccag gacagcggtg cggccctcgg ccggggcgcc cactccgcag
61 cacccagcga gcgagcgagc gagcgagggc ggccgacgcg cccggccggg acccagctgc
121 ccgtatgacc gcgccgggcg ccgccgggcg ctgccctccc acgacatggc tgggctccct
181 gctgttgttg gtctgtctcc tggcgagcag gagtatcacc gaggaggtgt cggagtactg
241 tagccacatg attgggagtg gacacctgca gtctctgcag cggctgattg acagtcagat
301 ggagacctcg tgccaaatta catttgagtt tgtagaccag gaacagttga aagatccagt
361 gtgctacctt aagaaggcat ttctcctggt acaagacata atggaggaca ccatgcgctt
421 cagagataac acccccaatg ccatcgccat tgtgcagctg caggaactct ctttgaggct
481 gaagagctgc ttcaccaagg attatgaaga gcatgacaag gcctgcgtcc gaactttcta
541 tgagacacct ctccagttgc tggagaaggt caagaatgtc tttaatgaaa caaagaatct
601 ccttgacaag gactggaata ttttcagcaa gaactgcaac aacagctttg ctgaatgctc
661 cagccaagat gtggtgacca agcctgattg caactgcctg taccccaaag ccatccctag
721 cagtgacccg gcctctgtct cccctcatca gcccctcgcc ccctccatgg cccctgtggc
781 tggcttgacc tgggaggact ctgagggaac tgagggcagc tccctcttgc ctggtgagca
841 gcccctgcac acagtggatc caggcagtgc caagcagcgg ccacccagga gcacctgcca
901 gagctttgag ccgccagaga ccccagttgt caaggacagc accatcggtg gctcaccaca
961 gcctcgcccc tctgtcgggg ccttcaaccc cgggatggag gatattcttg actctgcaat
1021 gggcactaat tgggtcccag aagaagcctc tggagaggcc agtgagattc ccgtacccca
1081 agggacagag ctttccccct ccaggccagg agggggcagc atgcagacag agcccgccag
1141 acccagcaac ttcctctcag catcttctcc actccctgca tcagcaaagg gccaacagcc
1201 ggcagatgta actggtaccg ccttgcccag ggtgggcccc gtgaggccca ctggccagga
1261 ctggaatcac accccccaga agacagacca tccatctgcc ctgctcagag accccccgga
1321 gccaggctct cccaggatct catcaccgcg cccccagggc ctcagcaacc cctccaccct

Fig. 3 (cont.)

1381 ctctgctcag ccacagcttt ccagaagcca ctcctcgggc agcgtgctgc cccttgggga
1441 gctggagggc aggaggagca ccagggatcg gaggagcccc gcagagccag aaggaggacc
1501 agcaagtgaa ggggcagcca ggcccctgcc ccgttttaac tccgttcctt tgactgacac
1561 acatgagagg cagtccgagg gatcctccag cccgcagctc caggagtctg tcttccacct
1621 gctggtgccc agtgtcatcc tggtcttgct ggccgtcgga ggcctcttgt tctacaggtg
1681 gaggcggcgg agccatcaag agcctcagag agcggattct cccttggagc aaccagaggg
1741 cagccccctc actcaggatg acagacaggt ggaactgcca gtgtagaggg aattctaaga
1801 cccctcacca tcctggacac tctcgtttgt caatgtccct ctgaaaatgt gacgcccagc
1861 cccggacaca gtactccaga tgttgtctga ccagctcaga gagagtacag tgggactgtt
1921 accttccttg atatggacag tattcttcta tttgtgcaga ttaagattgc attagttttt
1981 ttcttaacaa ctgcatcata ctgttgtcat atgttgagcc tgtggtctat aaaacccccta
2041 gttccatttc ccataaactt ctgtcaagcc agaccatctc taccctgtac ttggacaact
2101 taactttttt aaccaaagtg cagtttatgt tcacctttgt taaagccacc ttgtggtttc
2161 tgcccatcac ctgaacctac tgaagttgtg tgaaatccta attctgtcat ctccgtagcc
2221 ctcccagttg tgcctcctgc acattgatga gtgcctgctg ttgtctttgc ccatgttgtt
2281 gatgtagctg tgaccctatt gttcctcacc cctgcccccc gccaacccca gctggcccac
2341 ctcttccccc tcccacccaa gcccacagcc agcccatcag gaagccttcc tggcttctcc
2401 acaaccttct gactgtcttt tcagtcatgc cccctgctct tttgtatttg gctaatagta
2461 tatcaatttg cactt cDNA encoding Granulocyte-Colony stimulating factor.

ACCESSION E08531

VERSION E08531.1 GI:2176646

1 cggagcctgc agcccagccc cacccagacc catggctgga cctgccaccc agagccccat
61 gaagctgatg gccctgcagc tgctgctgtg gcacagtgca ctctggacag tgcaggaagc
121 caccccccctg ggccctgcca gctccctgcc ccagagcttc ctgctcaagt gcttagagca
181 agtgaggaag atccagggcg atggcgcagc gctccaggag aagctggtga gtgagtgtgc
241 cacctacaag ctgtgccacc ccgaggagct ggtgctgctc ggacactctc tgggcatccc
301 ctgggctccc ctgagcagct gccccagcca ggccctgcag ctggcaggct gcttgagcca
361 actccatagc ggccttttcc tctaccaggg gctcctgcag gccctggaag ggatctcccc
421 cgagttgggt cccaccttgg acacactgca gctggacgtc gccgactttg ccaccaccat
481 ctggcagcag atggaagaac tgggaatggc ccctgccctg cagcccaccc agggtgccat
541 gccggccttc gcctctgctt tccagcgccg ggcaggaggg gtcctggttg cctcccatct
601 gcagagcttc ctggaggtgt cgtaccgcgt tctacgccac cttgcccagc cctgagccaa
661 gccctcccca tcccatgtat ttatctctat ttaatattta tgtctattta agcctcatat
721 ttaaagacag ggaagagcag aacggagccc caggcctctg tgtccttccc tgcatttctg
781 agtttcattc tcctgcctgt agcagtgaga aaaagctcct gtcctcccat cccctggact
841 gggaggtaga taggtaaata ccaagtattt attactatga ctgctcccca gccctggctc
901 tgcaatgggc actgggatga gccgctgtga gcccctggtc ctgagggtcc ccacctggga

Fig. 3 (cont.)

961 cccttgagag tatcaggtct cccacgtggg agacaagaaa tccctgttta atatttaaac
1021 agcagtgttc cccatctggg tccttgcacc cctcactctg gcctcagccg actgcacagc
1081 ggcccctgca tccccttggc tgtgaggccc ctggacaagc agaggtggcc agagctggga
1141 ggcatggccc tggggtccca cgaatttgct ggggaatctc gtttttcttc ttaagacttt
1201 tgggacatgg tttgactccc gaacatcacc gacgcgtctc ctgtttttct gggtggcctc
1261 gggacacctg ccctgccccc acgagggtca ggactgtgac tctttttagg gccaggcagg
1321 tgcctggaca tttgccttgc tggacgggga ctggggatgt gggagggagc agacaggagg
1381 aatcatgtca ggcctgtgtg tgaaaggaag ctccactgtc accctccacc tcttcacccc
1441 ccactcacca gtgtcccctc cactgtcaca ttgtaactga acttcaggat aataaagtgt
1501 ttgcctccaa aaaaaaaaaa aaaaaaaaaa a Granulocyte-Colony stimulating factor gene.
ACCESSION E08530
VERSION E08530.1 GI:2176645
1 ctgccgcttc caggcgtcta tcagcggctc agcctttgtt cagctgttct gttcaaacac
61 tctggggcca ttcaggcctg ggtggggcag cgggaggaag ggagtttgag gggggcaagg
121 cgacgtcaaa ggaggatcag agattccaca atttcacaaa actttcgcaa acagcttttt
181 gttccaaccc ccctgcattg tcttggacac caaatttgca taaatcctgg gaagttatta
241 ctaagcctta gtcgtggccc caggtaattt cctcccaggc ctccatgggg ttatgtataa
301 agggccccct agagctgggc cccaaaacag cccggagcct gcagcccagc cccacccaga
361 cccatggctg gacctgccac ccagagcccc atgaagctga tgggtgagtg tcttggccca
421 ggatgggaga gccgcctgcc ctggcatggg agggaggctg gtgtgacaga ggggctgggg
481 atccccgttc tgggaatggg gattaaaggc acccagtgtc cccgagaggg cctcaggtgg
541 tagggaacag catgtctcct gagcccgctc tgtccccagc cctgcagctg ctgctgtggc
601 acagtgcact ctggacagtg caggaagcca cccccctggg ccctgccagc tccctgcccc
661 agagcttcct gctcaagtgc ttagagcaag tgaggaagat ccagggcgat ggcgcagcgc
721 tccaggagaa gctggtgagt gaggtgggtg agagggctgt ggagggaagc ccggtgggga
781 gagctaaggg ggatggaact gcagggccaa catcctctgg aagggacatg ggagaatatt
841 aggagcagtg gagctgggga aggctgggaa gggacttggg gaggaggacc ttggtgggga
901 cagtgctcgg gagggctggc tgggatggga gtggaggcat cacattcagg agaaagggca
961 agggcccctg tgagatcaga gagtgggggt gcagggcaga gaggaactga acagcctggc
1021 aggacatgga gggaggggaa agaccagaga gtcggggagg acccgggaag gagcggcgac
1081 ccggccacgg cgagtctcac tcagcatcct tccatcccca gtgtgccacc tacaagctgt
1141 gccaccccga ggagctggtg ctgctcggac actctctggg catcccctgg gctcccctga
1201 gcagctgccc cagccaggcc ctgcagctgg tgagtgtcag gaaaggataa ggctaatgag
1261 gagggggaag gagaggagga acacccatgg gctcccccat gtctccaggt tccaagctgg
1321 gggcctgacg tatctcaggc agcaccccct aactcttccg ctctgtctca caggcaggct
1381 gcttgagcca actccatagc ggcctttcc tctaccaggg gctcctgcag gccctggaag
1441 ggatctcccc cgagttgggt cccaccttgg acacactgca gctggacgtc gccgactttg

Fig. 3 (cont.)

1501 ccaccaccat ctggcagcag gtgagccttg ttgggcaggg tggccaaggt cgtgctggca
1561 ttctgggcac cacagccggg cctgtgtatg ggccctgtcc atgctgtcag cccccagcat
1621 ttcctcattt gtaataacgc ccactcagaa gggcccaacc actgatcaca gctttccccc
1681 acagatggaa gaactgggaa tggcccctgc cctgcagccc acccagggtg ccatgccggc
1741 cttcgcctct gctttccagc gccgggcagg aggggtcctg gttgcctccc atctgcagag
1801 cttcctggag gtgtcgtacc gcgttctacg ccaccttgcc cagccctgag ccaagccctc
1861 cccatcccat gtatttatct ctatttaata tttatgtcta tttaagcctc atatttaaag
1921 acagggaaga gcagaacgga gccccaggcc tctgtgtcct tccctgcatt tctgagtttc
1981 attctcctgc ctgtagcagt gagaaaaagc tcctgtcctc ccatcccctg gactgggagg
2041 tagataggta aataccaagt atttattact atgactgctc cccagccctg gctctgcaat
2101 gggcactggg atgagccgct gtgagcccct ggtcctgagg gtccccacct gggacccttg
2161 agagtatcag gtctcccacg tgggagacaa gaaatccctg tttaatattt aaacagcagt
2221 gttccccatc tgggtccttg cacccctcac tctggcctca gccgactgca cagcggcccc
2281 tgcatcccct tggctgtgag gcccctggac aagcagaggt ggccagagct gggaggcatg
2341 gccctggggt cccacgaatt tgctggggaa tctcgttttt cttcttaaga cttttgggac
2401 atggtttgac tcccgaacat caccgacgtg tctcctgttt ttctgggtgg cctcgggaca
2461 cctgccctgc ccccacgagg gtcaggactg tgactctttt tagggccagg caggtgcctg
2521 gacattgcc ttgctggatg gggactgggg atgtgggagg gagcagacag gaggaatcat
2581 gtcaggcctg tgtgtgaaag gaagctccac tgtcaccctc cacctcttca ccccccactc
2641 accagtgtcc cctccactgt cacattgtaa ctgaacttca ggataataaa gtgtttgcct
2701 ccagtcacgt ccttcctcct tcttgagtcc agctggtgcc tggccagggg ctggggaggt
2761 ggctgaaggg tgggagaggc cagagggagg tcggggagga ggtctgggga ggaggtccag
2821 ggaggaggag gaaagttctc aagttcgtct gacattcatt ccgttagcac atatttatct
2881 gagcacctac tctgtgcaga cgctgggcta agtgctgggg acacagcagg gaacaaggca
2941 gacatggaat ctgcactcga Homo sapiens MCP1 (MCP1) gene, promoter region and partial cds.

ACCESSION AY357296

VERSION AY357296.1 GI:34559719

1 ccgagatgtt cccagcacag ccccatgtga gagctccctg gctccgggcc cagtatctgg
61 aatgcaggct ccagccaaat gcattctctt ctacgggatc tgggaacttc caaagctgcc
121 tcctcagagt gggaatttcc actcacttct ctcacgccag cactgacctc ccagcggggg
181 agggcatctt ttcttgacag agcagaagtg ggaggcagac agctgtcact ttccagaaga
241 ctttcttttc tgattcatac ccttcacctt ccctgtgttt actgtctgat atatgcaaag
301 gccaagtcac tttccagaga tgacaactcc ttcctgaagt agagacatgc ttccaacact
361 cagaagccta tgtgaacact cagccagcaa agctgggaag tttttctctg tgaccatggg
421 ctaattggtc tccttctctg gattgtggct ttatcagata aaaacaagtg gtcatgccac
481 aggatgtcta taagcccatt gattctggga ttctatgagt gatgctgata tgactaagcc
541 aggagagact tatttaaaga tctcagcatc tttcagcttg ttaacctaga gaaaacccga

Fig. 3 (cont.)

601 agcatgactg gattataaag ggaaattgaa tgcggtccac caagttcatg gtaaaggatg
661 cactaacaga ttagagagag gtttcccctg atatgaggaa aacttcttgg aagatgaggt
721 gagatggcct aggaagaaat tcctacacaa aattgcacag tctctagtcc tggaaacatt
781 ttattcattg gataagaatg gattgaggca tgagcagagg actgagacaa acacagagaa
841 gtttcaacac tggttgggga gaaaaggagt aactagtgag attcaggcag aacaagaata
901 aggctcctca agaggcacaa gcaaagcagg gctcgagttg atttgttctc tcttcatcct
961 gctttttgta attccaccag agtctgaaat gaccactcca tagagtctct gctctgggat
1021 tctccaggaa accaatatcc atcatgagac atcaagtcta gtcccaggaa gaagagattc
1081 tggaatggaa acatcctggg tgggagtctc agcacatcta ctattctgtc tgagttactg
1141 gacaaataac ttcagtttta acctaacgaa agctgggttg gttggaggac tgggcaggca
1201 gcgctggaaa gtatgtcagc accatacctg actccctgaa tgcactcaac aatgccatta
1261 ctgaccactt actagaaata aaacagtcat ttgttgaata caacccgttt ctttttacaa
1321 gtgtagtgaa aagtgttttc tttcaagaaa ccccatgcat ttatagacat tgcctcagtg
1381 accctttatg aaagaagtca ctagtctttg tatgcccatt gggcaagggc accgcaaggc
1441 tcagaaggag gaggcagtgg gctaggagaa tggagagatc agaattttaa actcagccca
1501 gccattaaca tgcctcaagt actcctatca tatttgtaag agacaacagt tcactgaaat
1561 gaattctaag gtctttgggt ttttatcagt gtgcttctgt agtttctgag gaaatctaag
1621 gcacaactga ggaatgaagt caggctttcc aattccccgaa atactcctcc actgcttact
1681 catgtccctt ggaaattaag aaggaagcca ggagaatagc tgccataacc agggatgaac
1741 ttcttgtcca ctgctgcctg ctatgctagc aacagcctcc taactcataa tgacttagcc
1801 atgaggaatg tttctagatt ctcctttagc tgtctgccca tttggaagat gctgaggaca
1861 gagagaggac ccaagcaggc aactagttgg aggacttgta cacgtttcct tccagcagta
1921 tgtcagagag gtgagcagcc cactggggac agggctgcct gggttctgtg ctcgagggga
1981 ccttgagcag gctatttaac ccttctgtgc ctcagttgcc tgatctataa catgaaaatt
2041 agcaatccct actagataaa gttggggaat ttacagagtt aatatttgta aaggtctgag
2101 aatattcctg gcagagtaag cactctgtga gtatgacact ggcatttctt ctgcagcact
2161 acatgctgtc tatgcctttg tccaagtctg aaaccctaga actcttagaa ttcagttcaa
2221 tgtttacaca atcctacagt tctgctaggc ttctatgatg ctactattct gcatttgaat
2281 gagcaaatgg atttaatgca ttgtcaggga gccggccaaa gcttgagagc tccttcctgg
2341 ctgggaggcc ccttggaatg tggcctgaag gtaagctggc agcgagcctg acatgctttc
2401 atctagtttc ctcgcttcct tccttttctg cagttttcgc ttcacagaaa gcagaatcct
2461 taaaaataac cctcttagtt cacatctgtg gtcagtctgg gcttaatggc accccatcct
2521 ccccatttgc tcatttggtc tcagcagtga atggaaaaag tgtctcgtcc tgaccccctg
2581 cttccctttc ctacttcctg gaaatccaca ggatgctgca tttgctcagc agatttaaca
2641 gcccacttat cactcatgga agatccctcc tcctgcttga ctccgccctc tctccctctg
2701 cccgctttca ataagaggca gagacagcag ccagaggaac cgagaggctg agactaaccc
2761 agaaacatcc aattctcaaa ctgaagctcg cactctcgcc tccagcatga aagtctctgc
2821 cgcccttctg tgcctgctgc tcatagcagc caccttcatt ccccaagggc tcgctcagcc
2881 aggtaaggcc ccctcttctt ctccttgaac cacattgtct tctctctgag ttatcatgga

Fig. 3 (cont.)

2941 ccatccaagc agacgtggta cccacagtct tgctttaacg ctacttttcc aagataaggt
3001 gactcagaaa aggacaaggg gtgagcccaa ccacacagct gctgctcggc agagcctgaa
3061 ctagaattcc agctgtgaac cccaaatcca gctccttcca ggattccagc tctgggaaca
3121 cactcagcgc agttactccc ccagctgctt ccagcagagt ttggggatca gggtaatcaa
3181 agagagggtg ggtgtgtagg ctgtttccag acacgctgga g Homo sapiens macrophage migration inhibitory factor
(glycosylation-inhibiting factor) (MIF), mRNA.
1 accacagtgg tgtccgagaa gtcaggcacg tagctcagcg gcggccgcgg cgcgtgcgtc
61 tgtgcctctg cgcgggtctc ctggtccttc tgccatcatg ccgatgttca tcgtaaacac
121 caacgtgccc cgcgcctccg tgccggacgg gttcctctcc gagctcaccc agcagctggc
181 gcaggccacc ggcaagcccc cccagtacat cgcggtgcac gtggtcccgg accagctcat
241 ggccttcggc ggctccagcg agccgtgcgc gctctgcagc ctgcacagca tcggcaagat
301 cggcggcgcg cagaaccgct cctacagcaa gctgctgtgc ggcctgctgg ccgagcgcct
361 gcgcatcagc ccggacaggg tctacatcaa ctattacgac atgaacgcgg ccaatgtggg
421 ctggaacaac tccaccttcg cctaagagcc gcagggaccc acgctgtctg cgctggctcc
481 acccgggaac ccgccgcacg ctgtgttcta ggcccgccca ccccaacctt ctggtgggga
541 gaaataaacg gtttagagac t Homo sapiens macrophage inflammatory protein-1-alpha/RANTES
receptor mRNA, complete cds.
ACCESSION L10918
VERSION L10918.1 GI:292416
1 ggcacgagcc cagaaacaaa gacttcacgg acaaagtccc ttggaaccag agagaagccg
61 ggatggaaac tccaaacacc acagaggact atgacacgac cacagagttt gactatgggg
121 atgcaactcc gtgccagaag gtgaacgaga gggcctttgg ggcccaactg ctgccccctc
181 tgtactcctt ggtatttgtc attggcctgg ttggaaacat cctggtggtc ctggtccttg
241 tgcaatacaa gaggctaaaa aacatgacca gcatctacct cctgaacctg gccatttctg
301 acctgctctt cctgttcacg cttcccttct ggatcgacta caagttgaag gatgactggg
361 tttttggtga tgccatgtgt aagatcctct ctgggtttta ttacacaggc ttgtacagcg
421 agatcttttt catcatcctg ctgacgattg acaggtacct ggccatcgtc cacgccgtgt
481 ttgccttgcg ggcacggacc gtcacttttg gtgtcatcac cagcatcatc atttgggccc
541 tggccatctt ggcttccatg ccaggcttat acttttccaa gacccaatgg gaattcactc
601 accacacctg cagccttcac tttcctcacg aaagcctacg agagtggaag ctgtttcagg
661 ctctgaaact gaacctcttt gggctggtat tgcctttgtt ggtcatgatc atctgctaca
721 cagggattat aaagattctg ctaagacgac caaatgagaa gaaatccaaa gctgtccgtt
781 tgatttttgt catcatgatc atctttttc tctttggac cccctacaat ttgactatac
841 ttatttctgt tttccaagac ttcctgttca cccatgagtg tgagcagagc agacatttgg
901 acctggctgt gcaagtgacg gaggtgatcg cctacacgca ctgctgtgtc aacccagtga
961 tctacgcctt cgttggtgag aggttccgga agtacctgcg gcagttgttc cacaggcgtg

Fig. 3 (cont.)

1021 tggctgtgca cctggttaaa tggctcccct tcctctccgt ggacaggctg gagagggtca
1081 gctccacatc tccctccaca ggggagcatg aactctctgc tgggttctga ctcagaccat
1141 aggaggccaa cccaaaataa gcaggcgtga cctgccaggc acactgagcc agcagcctgg
1201 ctctcccagc caggttctga ctcttggcac agcatggagt cacagccact tgggatagag
1261 agggaatgta atggtggcct ggggcttctg aggcttctgg ggcttcagtc ttttccatga
1321 acttctcccc tggtagaaag aagatgaatg agcaaaacca aatattccag agactgggac
1381 taagtgtacc agagaagggc ttggactcaa gcaagatttc agatttgtga ccattagcat
1441 ttgtcaacaa agtcacccac ttcccactat tgcttgcaca aaccaattaa acccagtagt
1501 ggtgactgtg ggctccattc aaagtgagct cctaagccat gggagacact gatgtatgag
1561 gaatttctgt tcttccatca cctccccccc cccgccaccc tcccactgcc aagaacttgg
1621 aaatagtgat ttccacagtg actccactct gagtcccaga gccaatcagt agccagcatc
1681 tgcctcccct tcactcccac cgcaggattt gggctcttgg aatcctgggg aacatagaac
1741 tcatgacgga agagttgaga cctaacgaga aatagaaatg ggggaactac tgctggcagt
1801 ggaactaaga aagcccttag gaagaatttt tatatccact aaaatcaaac aattcaggga
1861 gtgggctaag cacgggccat atgaataaca tggtgtgctt cttaaaatag ccataaaggg
1921 gagggactca tcatttccat ttacccttct tttctgacta tttttcagaa tctctcttct
1981 tttcaagttg ggtgatatgt tggtagattc taatggcttt attgcagcga ttaataacag
2041 gcaaaaggaa gcagggttgg tttcccttct ttttgttctt catctaagcc ttctggtttt
2101 atgggtcaga gttccgactg ccatcttgga cttgtcagca aaaaaaaaaa aaaaaa Mouse macrophage inflammatory protein 1-beta (MIP-1) mRNA, complete cds.
ACCESSION M35590
VERSION M35590.1 GI:199696
1 gcttctgaag cttctgggcc ctgcagtccc agctctgtgc aaacctaacc ccgagcaaca
61 ccatgaagct ctgcgtgtct gccctctctc tcctcttgct cgtggctgcc ttctgtgctc
121 cagggttctc agcaccaatg ggctctgacc ctcccacttc ctgctgtttc tcttacacct
181 cccggcagct tcacagaagc tttgtgatgg attactatga gaccagcagt ctttgctcca
241 agccagctgt ggtattcctg accaaaagag gcagacagat ctgtgctaac cccagtgagc
301 cctgggtcac tgagtacatg agtgacttgg agttgaactg agcagctcca gcggcagggc
361 aggaggagcc acttcaggag aggcctcctc agccctgatg cttctcactg agaagcgtcc
421 ttgctcctca cgttcagatt tcctgcccct cttcttaatt taaatctctg tgtagacttt
481 gttttgtttt tttgggggag tattatttct attatttatg ttttagttat aggacgcgtg
541 tctcccatgg agatggtcca ccattgctgt ttctctgcta ttgtggatat gactgtgaaa
601 ttgatttcat gcattttcat aataaatctt tctttaag Human macrophage inflammatory protein 3 alpha (MIP-3a) mRNA, complete cds.
ACCESSION U77035
VERSION U77035.1 GI:1790924

Fig. 3 (cont.)

1 atgtgctgta ccaagagttt gctcctggct gctttgatgt cagtgctgct actccacctc
61 tgcggcgaat cagaagcagc aagcaacttt gactgctgtc ttggatacac agaccgtatt
121 cttcatccta aatttattgt gggcttcaca cggcagctgg ccaatgaagg ctgtgacatc
181 aatgctatca tctttcacac aaagaaaaag ttgtctgtgt gcgcaaatcc aaaacagact
241 tgggtgaaat atattgtgcg tctcctcagt aaaaaagtca agaacatgta aaaactgtgg
301 cttttctgga atggaattgg acatagccca agaacagaaa gaaccttgct ggggttggag
361 gtttcacttg cacatcatgg agggtttagt gcttatctaa tttgtgcctc actggacttg
421 tccaattaat gaagttgatt catattgcat catagtttgc tttgtttaag catcacatta
481 aagttaaact gtattttatg ttatttatag ctgtaggttt tctgtgttta gctatttaat
541 actaattttc cataagctat tttggtttag tgcaaagtat aaaattatat ttgggggga
601 ataagattat atggactttt ttgcaagcaa caagctattt tttaaaamma actatttaac
661 attcttttgt ttatattgtt ttgtctccta aattgttgta attgcattat aaaataagaa
721 aaatattaat aagacaaata ttgaaaataa agaaacaaaa agtt Human macrophage inflammatory protein 3 beta (MIP-3beta) mRNA, complete cds.

ACCESSION U77180

1 atggccctgc tactggccct cagcctgctg gttctctgga cttccccagc cccaactctg
61 agtggcacca atgatgctga agactgctgc ctgtctgtga cccagaaacc catccctggg
121 tacatcgtga ggaacttcca ctaccttctc atcaaggatg gctgcagggt gcctgctgta
181 gtgttcacca cactgagggg ccgccagctc tgtgcacccc cagaccagcc ctgggtagaa
241 cgcatcatcc agagactgca gaggacctca gccaagatga agcgccgcag cagttaacct
301 atgaccgtgc agagggagcc cggagtccga gtcaagcatt gtgaattatt acctaacctg
361 gggaaccgag gaccagaagg aaggaccagg cttccagctc ctctgcacca gacctgacca
421 gccaggacag ggcctggggt gtgtgtgagt gtgagtgtga gcgagagggt gagtgtggtc
481 tagagtaaag ctgctccacc cccagattgc aatgctacca ataaagccgc ctggtgttta
541 caact H.sapiens gene for chemokine HCC-1.

ACCESSION Z49269

VERSION Z49269.1 GI:1004266

1 gagctccgtt gggagtccca tgtttcttta tggcataatg ggtgagaaca cagacttgga
61 agccaaacca cctgaatttg aaccccagtt ccatttacca actgtcaaaa gcttaggctt
121 tgattctaag cctgtttcct caactgctgt tctaaagatt aaataggcta atattcataa
181 ggcaactggg acagtggctt gtgtgtatag caaccattat ataagtgaat tatctactga
241 gcaccacagc acttcttcac tccatggtgt ggtgaccaga atggagatga gacagagaac
301 tgcaggttct gcttcgagtt taagttagga tttcccttga ccaatgagac ctgacttgga

Fig. 3 (cont.)

361 ggagtcctgg cctcattcca ttaccccaaa caccctctag tctctagatg aacagatcct
421 gaatgtccag gccccacgtg gcctgttcta aggcctgaga tggaattgga tacaggacac
481 atccagcctt gagatctttt gctaagtgtg acacagtgcc cccagccctg tgctcatgtt
541 catgcctagg gaaaggcttc tatcaaaaga gttgaacttc ttcccactgg ggatggaaga
601 ccatttcctc ccttaaacct tggctctccc tgcttccttc aggccaccaa caacacatgt
661 gcaggatatg aaattgctga ggcatcactg ctttcctact tcccttccaa gtctcagctc
721 ccttatttta aaaaatattt ggcctcaatg atcatttctc aacaattcct caccgcagga
781 gcctctgaag ctcccaccag gccagctctc ctcccacaac agcttcccac agcatgaaga
841 tctccgtggc tgccattccc ttcttcctcc tcatcaccat cgccctaggg accaagactg
901 aatcctcctc acgtgagtgc aatgccttgt cttccttcca acctagagcc tgcagggaaa
961 taagcaggag tgaggttggg gctcagggga agaccaggag cagggactca gaaaggaggg
1021 ctggtatctt cttgaaattg tgtgtatagc aacattatat aaatgaatta tctactgagc
1081 accacagcac ttcaccccat ggtgtggtga gcaggatgga gatgagactt aggactgtag
1141 gttctgctta agagtttaag ttgggatctt ccagccttga ccaatgagac ttgacttggg
1201 agactccagg cttcattcca ctaccccaaa tgccctctag tctccaaata aacagatcct
1261 gaatctccag gcctcacatg gccttgatct cttatcattg ccccccagga ccagtccccc
1321 cttgccctca aggacatgga gtgagaccag cctgcctctc tactccctca atttctctct
1381 ctttgccgct aagcaaaaga gtggcccacc ccatttgggg tatatttcct cagggagatt
1441 aggagcagtg tcttgagccc ctcaagggca tttttctatt ggcctcctga ggtttgggcc
1501 cagcctgctt ccagcgtcac ctgtgcccag tgagtgcagc attgcttggg tatgggctgg
1561 ggggaaacac gacagtgtgg ggtccatcct aggccccctt ttctcagctg atttcttaga
1621 ataagctgcc tttagagata accaaaacta tttatcactc ttccatttta cctactctcc
1681 ttttcagaaa ctggggggaa accgaaggtt gttaaaatac agctaaagtt ggtgggtatg
1741 tgcacagttt gacttgccct ctccgatgtc atttgtcagc tcagaggaac aaggtgggag
1801 agtataggag ctctgactgg gtctcaggaa acaggggccc cttatgccgt tctttggatc
1861 gtgaggatgc tgcctggaat ggagctggaa aacaggatga gacccttcca cccagacatc
1921 tggccaccct cagtgacctc tgaggccatt gtgatgcaca tccatgattc tatgaagcag
1981 ggtcacataa catgcacaca cctgatttct ccactccata accacaacat gtgcctgttt
2041 gtacagggct cttggcctac aatgtccttc ctgctacctc tataattcaa gcttggggtg
2101 gctgctgtca ccttgcttct cctataaaag ccatgaaact tctcaatcag aaaatagatg
2161 aaaaaatcac ccaatccagt gatttttaaa actttttaga ccacaaaacc ttttcttcaa
2221 gcaatatctt ccacagaggc ccaatatgta aaacagaaaa aatgggttga gtagggtaca
2281 agacaccact ctcaaatgca gcaaggcctc cacaatagtc cctgaggccc ccagagctca
2341 gtgtaaaaac cactgatgca gtccaagggc ctcatttaca gaggagggaa caggggggaaa
2401 gtaaaatggc cacagtacac aggaagcaca ggcaaggtta ggttaggatt tgggtgccct
2461 gactctgtgg cctttgtcct tggggcttgc tgtgggcatc ctgctctctc tgcaggttgt
2521 cggttcaatg gggacatggg cagggtggag cactaggagg ggctgggttt gcattcccaa
2581 atggcatgtc tccaaatccc tattgggatt tcttccaaat attcctccta tttggagcac
2641 ctttcccgaa taaggcatga aggctgcatg atattggcca agtccctagc cttctctgcc

Fig. 3 (cont.)

2701 agtcggcccc cagagatggt gtaagaagat ctgagtgtgc tgctcttcaa tcctggagtt
2761 gaaagtcatc caccagtctt tccaagaggg gttgaagaaa aggaggaagg gtgattgatg
2821 atgagggagg agaaaaagaa gagcccagga gtaccatgga gaaggagaag agaagatgag
2881 gaaagcctac tctcccctcc aagttctgag gggctgtctc ctccttcctt ccctcctcca
2941 tgccctcagc ttgcaggagc agccaatggt atggccttta acaaggggcc cctcctcagc
3001 atctgatgct ctctcctcag ggggacctta ccacccctca gagtgctgct tcacctacac
3061 tacctacaag atcccgcgtc agcggattat ggattactat gagaccaaca gccagtgctc
3121 caagcccgga attgtgtagg tggtacacac acatcacact ggggggagag ggagccagca
3181 gggcctcctg gagggaagca gggagtggtg gtggaatggg gacccccagc gtacctccca
3241 ggtgtgacta catggggaga ggcagctgag ggcaatctg agcgctttct ggctggagcc
3301 tgcaggagcc atggggaaac tgaccccatg gatggggaga tgacagagaa gggagaagaa
3361 ggcaagaggg cacttcctca gggggacaca gagactagat gggtctaggg gtcctaggaa
3421 ccgaagagta tgtctcagag aggagactgg ctctaagctg cctctgtgga agaaaggaaa
3481 agcagtatag gtcaggtggg gaatttagga gggagggaag atgggctgtc tcttccggcc
3541 actgggcccc tcggtttgtg atccttctcc ctcttgctcc acagcttcat caccaaaagg
3601 ggccattccg tctgtaccaa ccccagtgac aagtgggtcc aggactatat caaggacatg
3661 aaggagaact gagtgaccca gaaggggtgg cgaaggcaca gctcagagac ataaagagaa
3721 gatgccaagg ccccctcctc cacccaccgc taactctcag ccccagtcac cctcttggag
3781 cttccctgct ttgaattaaa gaccactcat gctcttccct ggcctcattc ctttctacgg
3841 gatttactca ttggccatgc actgaggaca ccagggtgtg gcaccctcgg catcaagcct
3901 cgctctgcag aagttttggt ggagcctggt acaaaaaata ggtcaggcct gcaatgcagg
3961 tagtgagaag cagaaagtga gaaagaaaag cagtgtaaag accgtctcct cctcagcagc
4021 aacagtagca gaccccg H.sapiens mRNA for chemokine HCC-1.
ACCESSION Z49270
VERSION Z49270.1 GI:1004268
1 agcctctgaa gctcccacca ggccagctct cctcccacaa cagcttccca cagcatgaag
61 atctccgtgg ctgccattcc cttcttcctc ctcatcacca tcgccctagg gaccaagact
121 gaatcctcct cacggggacc ttaccacccc tcagagtgct gcttcaccta cactacctac
181 aagatcccgc gtcagcggat tatggattac tatgagacca acagccagtg ctccaagccc
241 ggaattgtct tcatcaccaa aaggggccat tccgtctgta ccaaccccag tgacaagtgg
301 gtccaggact atatcaagga catgaaggag aactgagtga cccagaaggg gtggcgaagg
361 cacagctcag agacataaag agaagatgcc aaggcccccct cctccaccca cccctaactc
421 tcagccccag tcaccctctt ggagcttccc tgctttgaat taaagaccac tcatgctctt
481 c Human myeloid progenitor inhibitory factor-1 MPIF-2 mRNA, complete

Fig. 3 (cont.)

cds.
ACCESSION U85768
VERSION U85768.1 GI:1916251
1 atggcaggcc tgatgaccat agtaaccagc cttctgttcc ttggtgtctg tgcccaccac
61 atcatcccta cgggctctgt ggtcataccc tctccctgct gcatgttctt tgtttccaag
121 agaattcctg agaaccgagt ggtcagctac cagctgtcca gcaggagcac atgcctcaag
181 ggaggagtga tcttcaccac caagaagggc cagcagttct gtggcgaccc caagcaggag
241 tgggtccaga ggtacatgaa gaacctggac gccaagcaga agaaggcttc ccctagggcc
301 agggcagtgg ctgtcaaggg ccctgtccag agatatcctg gcaaccaaac cacctgctaa Mus musculus mRNA for thymus and activation regulated chemokine
(TARC gene).
ACCESSION AJ242587
VERSION AJ242587.1 GI:5102777
1 gaagaccttc acctcagctt ttggtaccat gaggtcactt cagatgctgc tcctggctgc
61 tctgcttctg gggacttttc tgcagcatgc cagagctgct cgagccacca atgtaggccg
121 agagtgctgc ctggattact tcaaaggggc cattcctatc aggaagttgg tgagctggta
181 taagacctca gtggagtgtt ccagggatgc catcgtgttt ctgactgtcc agggcaagct
241 catctgtgca gaccccaaag acaaacatgt gaagaaggcc atcagattgg tgaaaaaccc
301 aaggccgtga ccttcccgct gaggcatttg gagacgccag ggctgctgtc catggtttca
361 acataaagcg gcctgtgacc agcagagccc aagagcagcc acagagcaga agtccctgtt
421 cccttttta tggactctta tgcactacag gcgaacacaa aaaaaagcaa cggaataaag
481 ccttcctccc tc Human line-1 reverse transcriptase gene, partial cds, and
granulocyte chemotactic protein-2 (GCP-2) gene, complete cds.
ACCESSION U83303
VERSION U83303.1 GI:1916228
1 aagaaagtca ttggtagctt gatggggatg gtattgaatc tataagttac cttgggcagt
61 atggccatat tcacgatatt gatttttcct acccatgagc atggaatatt cttccatttg
121 tttgtatcct cttttatttc attgagcagt ggtttgtagt tctccttgaa gaggtccttc
181 atgtcccttg taagttggat tcctaggtat tttattctct ttgaagcaat tgtgaatggg
241 agttcactca tgatttggct ctctgtttgt ttgttattgg tgtataagaa tgcttgtgat
301 ttttgtgcat tgattttgta tcctgagact ttgctgaagt tgcttatcag cttaaggaga
361 ttttgggctg agaccatggg gttttctaga tatacaatta tgtaatttgc aaatagggac
421 aatttgactt cctcttttcc taattgaata ccctttattt ccttctcctg cctaattgtc
481 ctggccattg gagaggagga gcatctccca gacagctgcg tgcctcagag aagccagcct

Fig. 3 (cont.)

541 cgctaacccc tcaagcccag gggatgagac cctcctgaat cgctgctcta ttttggctgg
601 agccacagct ccctccaccg cggggcgggg ctaaaatgtc ctccccctta agggagcagg
661 cagctcctcc cagccaccca ccccaccaat tcccatcctc ccgccccct ccaccaaccc
721 cttctttcca cactgccccc tgagttcagg gaatttcccc agcatcccaa agcttgagtt
781 tcctgccagt cgggagggat gaatgcagat aaagggagtg cagaaggcac gaggaaacca
841 aagtgctctg tatcctccag tctccgcgcc tccacccagc tcaggaaccc gcgaaccctc
901 tcttgaccac tatgagcctc ccgtccagcc gcgcggcccg tgtcccgggt ccttcgggct
961 ccttgtgcgc gctgctcgcg ctgctgctcc tgctgacgcc gccggggccc ctcgccagcg
1021 gtgagagctc ctggcactgg ggtgcatccc agcctctgcg gggccgctgc gttccaggga
1081 actctcccag caacctgccc tataaaaatg tctttcttcc ccagctggtc ctgtctctgc
1141 tgtgctgaca gagctgcgtt gcacttgttt acgcgttacg ctgagagtaa accccaaaac
1201 gattggtaaa ctgcaggtgt tccccgcagg cccgcagtgc tccaaggtgg aagtggtgta
1261 agttctcctg tgttgctgtg tccactgtga cttaggcaag tcctccagcc tgggtcgtca
1321 acctttgtgg ctcatgggtg catcctcttt ttctttactt cagagcctcc ctgaagaacg
1381 ggaagcaagt ttgtctggac ccggaagccc cttttctaaa gaaagtcatc cagaaaattt
1441 tggacaggta tttgtccctt tgatctttgt ggtgttttaa tatcttctat ggaaagcata
1501 tacttcacaa tgtccttatt ctctctgtag gatttagact atgcttagaa ttataaggtt
1561 gttaagaaga ataaggaaac tttttttctg gaatgttctg ggtaaacctt tatcaccaat
1621 cttacatgcc tgaacaatta cacagagctc attactgaca tctatttttt gtctgctctt
1681 tgcttttatt gattttttc ccccaccaaa cgcttttgaa aaccaaatgt agcatacaag
1741 agtgtgggaa ttggttatac taatataact cttttctcaa cagtggaaac aagaaaaact
1801 gagtaacaaa aaagaccatg catcataaaa ttgcccagtc ttcagcggag cagttttctg
1861 gagatccctg gacccagtaa gaataagaag gaagggttgg tttttttcca ttttctacat
1921 ggattcccta ctttgaagag tgtgggggaa agcctacgct tctccctgaa gtttacagct
1981 cagctaatga agtactaata tagtatttcc actatttact gttattttac ctgataagtt
2041 attgaaccct ttggcaattg accatattgt gagcaaagaa tcactggtta ttagtctttc
2101 aatgaatatt gaattgaaga taactattgt atttctatca tacattcctt aaagtcttac
2161 cgaaaaggct gtggatttcg tatggaaata atgttttatt agtgtgctgt tgagggaggt
2221 atcctgttgt tcttactcac tcttctcata aaataggaaa tattttagtt ctgtttcttg
2281 gggaatatgt tactctttac cctaggatgc tatttaagtt gtactgtatt agaacactgg
2341 gtgtgtcata ccgttatctg tgcagaatat atttccttat tcagaatttc taaaaattta
2401 agttctgtaa gggctaatat attctcttcc tatggtttta gacgtttgat gtcttcttag
2461 tatggcataa tgtcatgatt tactcattaa actttgattt tgtatgctat tttttcacta
2521 taggatgact ataattctgg tcactaaata tacactttag atagatgaag aagcccaaaa
2581 acagataaat tcctgattgc taatttacat agaaatgtat tctcttggtt ttttaaataa
2641 aagcaaaatt aacaatgatc tgtgctctga aagttttgaa aatatatttg aacaatttga
2701 atataaattc atcatttagt cctcaaaata tatacagcat tgctaagatt ttcagatatc
2761 tattgtggat cttttaaagg ttttgaccat tttgttatga ggaattatac atgtatcaca
2821 ttcactatat taaaattgca cttttatttt ttcctgtgtg tcatgttggt ttttggtact

Fig. 3 (cont.)

2881 tgtattgtca tttggagaaa caataaaaga tttctaaacc actgatgttg tttctccttc
2941 ttatacagtt actatttatc tttaattcta cattattcaa aatattacct ctgctcttct
3001 ctggctggca gagaggccct cattacccaa taccattgca ttggttcaac ttttctccat
3061 gttcagcccc cttccagtta ctccttcaca gcaccaatag cctctggggt ctttagaaaa
3121 cacaaatagg ataagatttt cctatctaaa ttcttaaatg gctccctgtt tcctagacat
3181 gaaataaaag ttgctaaaca tgatgaatga ggttctgtct catctcactc ctgatcatcg
3241 gtacttcaac ttccctgtg cctcacattc actatagtca ggcgttcagt tccctaacta
3301 ggcatgttct ttccccaggc tcatgacttt gtatttgcta gggtctctac ctggaaagca
3361 tttacgtttt cctgcgtata agaggaggct tattcatcct tcagaactca gttcaagcaa
3421 tatctccttc gtgaattttc cttggcacac tcagcaaagc H.sapiens mRNA for granulocyte chemotactic protein.
ACCESSION Y08770
VERSION Y08770.1 GI:1769436
1 ggtcctgtct ctgctgtgct cacggagctg cgttgcactt gtttacgcgt tacgctgaga
61 gtaaacccca aaacgattgg taaactgcag gtgttccccg caggcccgca gtgctccaag
121 gtggaagtgg tagcctccct gaagaacggg aagcaagttt gtctggaccc ggaagcccct
181 tttctaaaga aagtcatcca gaaaattttg gacagtggaa acaagaaaaa ctgagtaaca
241 gtcgacgcgg ccgc Human gro alpha gene 5' end.
ACCESSION M65005
VERSION M65005.1 GI:183624
1 tcccacctct caggtggtat cttcagcgca ggctgccact cagccccccct ccagggatct
61 ggggcagaag gcgaatatcc cagagtctca gagtccacag gagttactct gaagggcgag
121 ccgcgggctg catcagtgga cccccacacc ccacccgcac cccaagcgct ccaccctggg
181 ggcggggccg tcgccttcct tccggactcg ggatcgatct ggaactccgg gaatttccct
241 ggcccggggg ctccgccctt tccagcccca accatgcata aaaggggttc gcggatctcg
301 gagagccaca gagcccgggc cgcaggcacc tcctcgccag ctcttccgct cctctcacag
361 ccgccagacc cgcctgctga gccccatggc ccg Human gro beta gene 5' end.
ACCESSION M65006
VERSION M65006.1 GI:183630
1 cgcctcctcg caggcggtta tctcggtatc tctgagagcg gcgggctctc gctcccgctc
61 cagggattcg gggcagaaag agaacatccc acagttggcg ggagttacgc aagacagtca
121 gacccggacg tcactcgtga gtgccccgac ccccctccac cccagaggcg gggccatcgc

Fig. 3 (cont.)

181 cttccttccg aactcgggat cgatctggag ctccgggaat ttccctggcc cgggactccg
241 gctttccagc cccaaccatg cataaaaggg gttcgccgtt ctcggagagc cacagagccc
301 gggccacagg cagctccttg ccagctctcc tcctcgcaca gccgctcgaa ccgcctgctg
361 agccccatgg cccg Human cytokine (GRO-gamma) mRNA, complete cds.
ACCESSION M36821
VERSION M36821.1 GI:183632
1 cacagccggg tcgcaggcac ctccccngcc agctctcccg cattctgcac agcttcccga
61 cgcgtctgct gagccccatg gcccacgcca cgctctccgc cgccccccagc aatccccggc
121 tcctgcgggt ggcgctgctg ctcctgctcc tggtgggcag ccggcgcgca gcaggagcgt
181 ccgtggtcac tgaactgcgc tgccagtgct tgcagacact gcagggaatt cacctcaaga
241 acatccaaag tgtgaatgta aggtcccccg gaccccactg cgcccaaacc gaagtcatag
301 ccacactcaa gaatgggaag aaagcttgtc tcaaccccgc atcccccatg gttcagaaaa
361 tcatcgaaaa gatactgaac aaggggagca ccaactgaca ggagagaagt aagaagctta
421 tcagcgtatc attgacactt cctgcagggt ggtccctgcc cttaccagag ctgaaaatga
481 aaaagagaac agcagctttc tagggacagc tggaaaggga cttaatgtgt ttgactattt
541 cttacgaggg ttctacttat ttatgtattt atttttgaaa gcttgtattt taatatttta
601 catgctgtta tttaaagatg tgagtgtgtt tcatcaaaca tagctcagtc ctgattattt
661 aattggaata tgatgggttt taaatgtgtc attaaactaa tatttagtgg gagaccataa
721 tgtgtcagcc accttgataa atgacagggt ggggaactgg agggtngggg gattgaaatg
781 caagcaatta gtggatcact gttagggtaa gggaatgtat gtacacatct attttttata
841 cttttttttt taaaaaagaa tgtcagttgt tatttattca aattatctca cattatgtgt
901 tcaacatttt tatgctgaag tttcccttag acattttatg tcttgcttgt agggcataat
961 gccttgttta atgtccattc tgcagcgttt ctctttccct tggaaaagag aatttatcat
1021 tactgttaca tttgtacaaa tgacatgata ataaaagttt tatg
//
Homo sapiens neutrophil-activating peptide 78 (ENA-78) gene,
complete cds.
ACCESSION L37036 Z46254
VERSION L37036.1 GI:607030
1 gaattctcag taagcggact taccaaagta ggtgatctgt aggggagtta acaaaattca
61 gtggtccttt caggccactg acttcaagtg gcaagagaca agggtctctt gttatcatgt
121 tatcttggct tccaaagctg gttgaagtcc agagattcat aaagtcattc aagaaaccta
181 gaatgacctg cctgcaagaa gacaggaagg actttcagtt tatagcaatt caaacatgaa
241 taacatttcc tgattaatag taataataat tagaaaggat tgactttcag aaatttttct
301 caaatcaagg ctcctgttac tttggttcca ccttttctct ctagaaggag aggaggagca
361 tctcccagat gctgcgtgct ccagaaaagc cggcatccct agccccgctct ggcacaggcc

Fig. 3 (cont.)

421 atgaggcgct gctgaatcct gctgaatagc tactcccttc tagctggagc cacagctccc
481 tccaccgcgg aacagggtta caacgtccct ctcggtagag gtgcacgcag ctcctcctgg
541 ccaccctccc caccagttcc cattgtctgg ccccccctccc ccaacctctt ctttccacac
601 tgccccatga gttcagggaa tttccccagc atcccaaagc ttgagtttcc tgtcagtggg
661 gagagatgag tgtagataaa aggagtgcag aaggaacgag gaagccacag tgctccggat
721 cctccaatct tcgctcctcc aatctccgct cctccaccca gttcaggaac ccgcgaccgc
781 tcgcagcgct ctcttgacca ctatgagcct cctgtccagc cgcgcggccc gtgtccccgg
841 tccttcgagc tccttgtgcg cgctgttggt gctgctgctg ctgctgacgc agccagggcc
901 catcgccagc ggtgagagcg catggcgcgc gggacgcact cgcactcggg cacagaggtg
961 catcccagcc tctgcggggt cgctgcgttc cagggaactc tcccagcaac ctgccctata
1021 aagggtgtct ctctttcttc cccagctggt cctgccgctg ctgtgttgag agagctgcgt
1081 tgcgtttgtt tacagaccac gcaaggagtt catcccaaaa tgatcagtaa tctgcaagtg
1141 ttcgccatag gcccacagtg ctccaaggtg gaagtggtgt aagttctgtg ctgctgtgtc
1201 cgctgtgacc ttggcaagag agaaatcccg cagcctgggt cttcaacctt ggtatctcat
1261 gagtgtatct tctttttctt tccttcagag cctccctgaa gaacgggaag gaaatttgtc
1321 ttgatccaga agcccctttt ctaaagaaag tcatccagaa aatttggac gggtacttgt
1381 cactttgatc tttgtggttt ctaaatctga tctagggaga ccatagactt cacaaggtct
1441 ttattctctg tacgatttaa gtaacacttt tcatgtttag aattaaaagg ttgttgaatt
1501 gggaaagttt ttctggattg tcctgggaaa atataccaat cttacatgta attacttgag
1561 caattacaca cagcttgtca ctaagttatg ttttttgttt acccattgct tttattgatt
1621 tttgtattct cctttttac caaacatcat aaacgctgag ttttgacaag ggtggagtag
1681 aaaggagtgt gaaaaatggt taaactaata taacattttt ctcaacagtg gaaacaagga
1741 aaactgatta agagaaatga gcacgcatgg aaaagtttcc cagtcttcag cagagaagtt
1801 ttctggaggt ctctgaaccc agggaagaca agaaggaaag attttgttgt tgtttgttta
1861 tttgtttttc cagtagttag ctttcttcct ggattcctca ctttgaagag tgtgaggaaa
1921 acctatgttt gccgcttaag ctttcagctc agctaatgaa gtgtttagca tagtacctct
1981 gctatttgct gttattttat ctgctatgct attgaagttt tggcaattga ctatagtgtg
2041 agccaggaat cactggctgt taatctttca aagtgtcttg aattgtaggt gactattata
2101 tttccaagaa atattcctta agatattaac tgagaaggct gtggatttaa tgtggaaatg
2161 atgtttcata agaattc Rattus norvegicus monokine induced by gamma interferon (Mig) mRNA, complete cds.
ACCESSION AF537208
VERSION AF537208.1 GI:33331077
1 tttcctaaat aaatatgacc accaagaaca tgttctctga agacattctc agccttgact
61 ccagcacggt gacttaatag agctcggctc tgccatgaag tccgttgctc tattcctcat
121 gggcatcatc ttcctggatc actgtggagt tcgaggaacc ctagtgataa ggaatcagcg
181 atgctcctgc atcagcacca gccaaggcac attccactac aaatccctca aagacctcaa

Fig. 3 (cont.)

241 acagtttgcc ccaagcccta actgcaacaa aactgaaatc atcgctacac tgaagaacgg
301 agatcaaacc tgcctagacc cagattcagc aagggtgaag aagctgatga aagaatggga
361 gaaaaagatc agccaaaaga aaaagcaaaa gagggggaaa aaccatcaaa ggagcaagaa
421 aacccgaaaa gctaaaacac cccaccatcc ggagtcaaag aagactgcat aagagaccac
481 tttaccaaca agcgctctgc atctaaacgg cttttagatc atactaaaac gccttccctt
541 taatacacaa ctcg Rattus norvegicus interferon-inducible T-cell a chemoattractant
I-TAC mRNA, complete cds.
ACCESSION AY340181
VERSION AY340181.1 GI:33304495
1 atcaccagag ccacagcaga gagctgcagc tgccgctgag atgaacagga cgggcatggc
61 cgtagccctg gctatgatca tctgggccac aacggttcca ggcttcgtta tgttcaaagg
121 ggggcgctgt ctttgcatcg accgcggagt gaaagtggtc aaaatggcag caatcaagga
181 agtttctgta atttacccga gtaacggctg tgacaaagtt gaagtgattg ttaccctgaa
241 ggctcataaa ggacaaaggt gcctggaccc cacatccaag caagctcgcc tcataatgca
301 gacaatacaa aaaaagaatt ttttaaggcg ccagaacatg tgatgggccc tcaaattcga
361 gctctgtgcc aagaagctga ccctctcctg tcttggaata tgcatccgtt ttgccagatt
421 gcagaactcg ctaggaggtc ggatacctct aaactattct gcttggctat gaaaatattt
481 atctcgaaga gtcatgtgtc tctgtgtgtg caca
//
Homo sapiens chemokine (C-X-C motif) ligand 12 (stromal
cell-derived factor 1) (CXCL12), mRNA.
ACCESSION NM_000609
VERSION NM_000609.2 GI:29837664
1 tctccgtcag ccgcattgcc cgctcggcgt ccggcccccg acccgtgctc gtccgcccgc
61 ccgcccgccc gcccgcgcca tgaacgccaa ggtcgtggtc gtgctggtcc tcgtgctgac
121 cgcgctctgc ctcagcgacg ggaagcccgt cagcctgagc tacagatgcc catgccgatt
181 cttcgaaagc catgttgcca gagccaacgt caagcatctc aaaattctca acactccaaa
241 ctgtgccctt cagattgtag cccggctgaa gaacaacaac agacaagtgt gcattgaccc
301 gaagctaaag tggattcagg agtacctgga gaaagcttta aacaagaggt tcaagatgtg
361 agagggtcag acgcctgagg aacccttaca gtaggagccc agctctgaaa ccagtgttag
421 ggaagggcct gccacagcct cccctgccag ggcagggccc caggcattgc caagggcttt
481 gttttgcaca ctttgccata ttttcaccat ttgattatgt agcaaaatac atgacattta
541 tttttcattt agtttgatta ttcagtgtca ctggcgacac gtagcagctt agactaaggc
601 cattattgta cttgccttat tagagtgtct ttccacggag ccactcctct gactcagggc
661 tcctgggttt tgtattctct gagctgtgca ggtggggaga ctgggctgag ggagcctggc
721 cccatggtca gccctagggt ggagagccac caagagggac gcctgggggt gccaggacca
781 gtcaacctgg gcaaagccta gtgaaggctt ctctctgtgg gatgggatgg tggagggcca

Fig. 3 (cont.)

841 catgggaggc tcaccccctt ctccatccac atgggagccg ggtctgcctc ttctgggagg
901 gcagcagggc taccctgagc tgaggcagca gtgtgaggcc agggcagagt gagacccagc
961 cctcatcccg agcacctcca catcctccac gttctgctca tcattctctg tctcatccat
1021 catcatgtgt gtccacgact gtctccatgg ccccgcaaaa ggactctcag gaccaaagct
1081 ttcatgtaaa ctgtgcacca agcaggaaat gaaaatgtct tgtgttacct gaaaacactg
1141 tgcacatctg tgtcttgtgt ggaatattgt ccattgtcca atcctatgtt tttgttcaaa
1201 gccagcgtcc tcctctgtga ccaatgtctt gatgcatgca ctgttccccc tgtgcagccg
1261 ctgagcgagg agatgctcct tgggcccttt gagtgcagtc ctgatcagag ccgtggtcct
1321 ttggggtgaa ctaccttggt tcccccactg atcacaaaaa catggtgggt ccatgggcag
1381 agcccaaggg aattcggtgt gcaccagggt tgaccccaga ggattgctgc cccatcagtg
1441 ctccctcaca tgtcagtacc ttcaaactag ggccaagccc agcactgctt gaggaaaaca
1501 agcattcaca acttgttttt ggtttttaaa acccagtcca caaaataacc aatcctggac
1561 atgaagattc tttcccaatt cacatctaac ctcatcttct tcaccatttg gcaatgccat
1621 catctcctgc cttcctcctg ggccctctct gctctgcgtg tcacctgtgc ttcgggccct
1681 tcccacagga catttctcta agagaacaat gtgctatgtg aagagtaagt caacctgcct
1741 gacatttgga gtgttcccct cccactgagg gcagtcgata gagctgtatt aagccactta
1801 aaatgttcac ttttgacaaa ggcaagcact tgtgggtttt tgttttgttt ttcattcagt
1861 cttacgaata cttttgccct ttgattaaag actccagtta aaaaaaattt taatgaagaa
1921 agtggaaaac aaggaagtca aagcaaggaa actatgtaac atgtaggaag taggaagtaa
1981 attatagtga tgtaatcttg aattgtaact gttcgtgaat ttaataatct gtagggtaat
2041 tagtaacatg tgttaagtat tttcataagt atttcaaatt ggagcttcat ggcagaaggc
2101 aaacccatca acaaaaattg tcccttaaac aaaaattaaa atcctcaatc cagctatgtt
2161 atattgaaaa aatagagcct gagggatctt tactagttat aaagatacag aactctttca
2221 aaaccttttg aaattaacct ctcactatac cagtataatt gagttttcag tggggcagtc
2281 attatccagg taatccaaga tattttaaaa tctgtcacgt agaacttgga tgtacctgcc
2341 cccaatccat gaaccaagac cattgaattc ttggttgagg aaacaaacat gaccctaaat
2401 cttgactaca gtcaggaaag gaatcatttc tatttctcct ccatgggaga aaatagataa
2461 gagtagaaac tgcagggaaa attatttgca taacaattcc tctactaaca atcagctcct
2521 tcctggagac tgcccagcta aagcaatatg catttaaata cagtcttcca tttgcaaggg
2581 aaaagtctct tgtaatccga atctcttttt gctttcgaac tgctagtcaa gtgcgtccac
2641 gagctgttta ctagggatcc ctcatctgtc cctccgggac ctggtgctgc ctctacctga
2701 cactcccttg ggctccctgt aacctcttca gaggccctcg ctgccagctc tgtatcagga
2761 cccagaggaa ggggccagag gctcgttgac tggctgtgtg ttgggattga gtctgtgcca
2821 cgtgtatgtg ctgtggtgtg tccccctctg tccaggcact gagataccag cgaggaggct
2881 ccagagggca ctctgcttgt tattagagat tacctcctga gaaaaaagct tccgcttgga
2941 gcagaggggc tgaatagcag aaggttgcac ctcccccaac cttagatgtt ctaagtcttt
3001 ccattggatc tcattggacc cttccatggt gtgatcgtct gactggtgtt atcaccgtgg
3061 gctccctgac tgggagttga tcgcctttcc caggtgctac accctttcc agctggatga
3121 gaatttgagt gctctgatcc ctctacagag cttccctgac tcattctgaa ggagccccat

Fig. 3 (cont.)

3181 tcctgggaaa tattccctag aaacttccaa atcccctaag cagaccactg ataaaaccat
3241 gtagaaaatt tgttattttg caacctcgct ggactctcag tctctgagca gtgaatgatt
3301 cagtgttaaa tgtgatgaat actgtatttt gtattgtttc aagtgcatct cccagataat
3361 gtgaaaatgg tccaggagaa ggccaattcc tatacgcagc gtgctttaaa aaataaataa
3421 gaaacaactc tttgagaaac aacaatttct actttgaagt cataccaatg aaaaaatgta
3481 tatgcactta taattttcct aataaagttc tgtactcaaa tgta

Fig. 3 (cont.)

Human tumor necrosis factor-beta (TNFB) gene, complete cds.

ACCESSION M55913

VERSION M55913.1 GI:339742

1 ccgacctaga acccgcccgc tgcctgccac gctgccactg ccgcttcctc tataaaggga
61 cctgagcgtc cgggcccagg ggctccgcac agcaggtgag gctctcctgc cccatctcct
121 tgggctgccc gtgcttcgtg ctttggacta ccgccccgca gtgtcctgcc ctctgcctgg
181 gcctcggtcc ctcctgcacc tgctgcctgg atccccggcc tgcctgggcc tgggccttgg
241 tgggtttggt tttggtttcc ttctctgtct ctgactctcc atctgtcagt ctcattgtct
301 ctgtcacaca ttctctgttt ctgccatgat tcctctctgt tcccttcctg tctctctctg
361 tctccctctg ctcaccttgg ggtttctctg actgcatctt gtccccttct ctgtcgatct
421 ctctctcggg ggtcgggggg tgctgtctcc cagggcggga ggtctgtctt ccgccgcgtg
481 ccccgccccg ctcactgtct ctctctctct ctctctttct ctgcaggttc tccccatgac
541 accacctgaa cgtctcttcc tcccaagggt gtgtggcacc accctacacc tcctccttct
601 ggggctgctg ctggttctgc tgcctggggc ccaggtgagg cagcaggaga atgggggctg
661 ctggggtggc tcagccaaac cttgagccct agagcccccc tcaactctgt tctcccctag
721 gggctccctg gtgttggcct cacaccttca gctgcccaga ctgcccgtca gcaccccaag
781 atgcatcttg cccacagcac cctcaaacct gctgctcacc tcattggtaa acatccacct
841 gacctcccag acatgtcccc accagctctc ctcctacccc tgcctcagga acccaagcat
901 ccacccctct cccccaactt ccccccacgct aaaaaaaaca gagggagccc actcctatgc
961 ctccccctgc catcccccag gaactcagtt gttcagtgcc cacttcctca gggattgaga
1021 cctctgatcc agacccctga tctcccaccc ccatccccta tggctcttcc taggagaccc
1081 cagcaagcag aactcactgc tctggagagc aaacacggac cgtgccttcc tccaggatgg
1141 tttctccttg agcaacaatt ctctcctggt ccccaccagt ggcatctact tcgtctactc
1201 ccaggtggtc ttctctggga aagcctactc tcccaaggcc ccctcctccc cactctacct
1261 ggcccatgag gtccagctct tctcctccca gtacccccttc catgtgcctc tcctcagctc
1321 ccagaagatg gtgtatccag ggctgcagga accctggctg cactcgatgt accacggggc
1381 tgcgttccag ctcacccagg gagaccagct atccacccac acagatggca tcccccacct
1441 agtcctcagc cctagtactg tcttctttgg agccttcgct ctgtagaact tggaaaaatc
1501 cagaaagaaa aaataattga tttcaagacc ttctccccat tctgcctcca ttctgaccat
1561 ttcaggggtc gtcaccacct ctcctttggc cattccaaca gctcaagtct tccctgatca
1621 agtcaccgga gctttcaaag aaggaattct aggcatccca ggggaccaca cctccctgaa
1681 ccatccctga tgtctgtctg gctgaggatt tcaagcctgc ctaggaattc ccagcccaaa
1741 gctgttggtc ttgtccacca gctaggtggg gcctagatcc acacacagag gaagagcagg
1801 cacatggagg agcttggggg atgactagag gcagggaggg gactatttat gaaggcaaaa
1861 aaattaaatt atttatttat ggaggatgga gagaggggaa taatagaaga acatccaagg
1921 agaaacagag acaggcccaa gagatgaaga gtgagagggc atgcgcacaa ggctgaccaa
1981 gagagaaaga agtaggcatg agggatcaca gggccccaga aggcagggaa aggctctgaa
2041 agccagctgc cgaccagagc cccacacgga ggcatctgca ccctcgatga agcccaataa
2101 acctcttttc tctgaaatgc tgtctgcttg tgtgtgtgtg

Fig. 3 (cont.)

Homo sapiens interleukin 1, beta (IL1B), mRNA.

ACCESSION NM_000576

VERSION NM_000576.2 GI:27894305

1 accaaacctc ttcgaggcac aaggcacaac aggctgctct gggattctct tcagccaatc
61 ttcattgctc aagtgtctga agcagccatg gcagaagtac ctgagctcgc cagtgaaatg
121 atggcttatt acagtggcaa tgaggatgac ttgttctttg aagctgatgg ccctaaacag
181 atgaagtgct ccttccagga cctggacctc tgccctctgg atggcggcat ccagctacga
241 atctccgacc accactacag caagggcttc aggcaggccg cgtcagttgt tgtggccatg
301 gacaagctga ggaagatgct ggttccctgc ccacagacct tccaggagaa tgacctgagc
361 accttctttc ccttcatctt tgaagaagaa cctatcttct tcgacacatg ggataacgag
421 gcttatgtgc acgatgcacc tgtacgatca ctgaactgca cgctccggga ctcacagcaa
481 aaaagcttgg tgatgtctgg tccatatgaa ctgaaagctc tccacctcca gggacaggat
541 atggagcaac aagtggtgtt ctccatgtcc tttgtacaag gagaagaaag taatgacaaa
601 atacctgtgg ccttgggcct caaggaaaag aatctgtacc tgtcctgcgt gttgaaagat
661 gataagccca ctctacagct ggagagtgta gatcccaaaa attacccaaa gaagaagatg
721 gaaaagcgat ttgtcttcaa caagatagaa atcaataaca agctggaatt tgagtctgcc
781 *cagttcccca actggtacat cagcacctct caagcagaaa acatgcccgt cttcctggga*
841 gggaccaaag gcggccagga tataactgac ttcaccatgc aatttgtgtc ttcctaaaga
901 gagctgtacc cagagagtcc tgtgctgaat gtggactcaa tccctagggc tggcagaaag
961 ggaacagaaa ggtttttgag tacggctata gcctggactt tcctgttgtc tacaccaatg
1021 cccaactgcc tgccttaggg tagtgctaag aggatctcct gtccatcagc caggacagtc
1081 agctctctcc tttcagggcc aatccccagc ccttttgttg agccaggcct ctctcacctc
1141 tcctactcac ttaaagcccg cctgacagaa accacggcca catttggttc taagaaaccc
1201 tctgtcattc gctcccacat tctgatgagc aaccgcttcc ctatttattt atttatttgt
1261 ttgtttgttt tattcattgg tctaatttat tcaaaggggg caagaagtag cagtgtctgt
1321 aaaagagcct agtttttaat agctatggaa tcaattcaat ttggactggt gtgctctctt
1381 taaatcaagt cctttaatta agactgaaaa tatataagct cagattattt aaatgggaat
1441 atttataaat gagcaaatat catactgttc aatggttctg aaataaactt cactgaag Homo sapiens interleukin 1, alpha (IL1A), mRNA.

ACCESSION NM_000575

VERSION NM_000575.3 GI:27894329

1 accaggcaac accattgaag gctcatatgt aaaaatccat gccttccttt ctcccaatct
*61 ccattcccaa acttagccac tggcttctgg ctgaggcctt acgcatacct cccggggctt*
121 gcacacacct tcttctacag aagacacacc ttgggcatat cctacagaag accaggcttc
181 tctctggtcc ttggtagagg gctactttac tgtaacaggg ccagggtgga gagttctctc
241 ctgaagctcc atcccctcta taggaaatgt gttgacaata ttcagaagag taagaggatc
301 aagacttctt tgtgctcaaa taccactgtt ctcttctcta ccctgcccta accaggagct

Fig. 3 (cont.)

361 tgtcacccca aactctgagg tgatttatgc cttaatcaag caaacttccc tcttcagaaa
421 agatggctca ttttccctca aaagttgcca ggagctgcca agtattctgc caattcaccc
481 tggagcacaa tcaacaaatt cagccagaac acaactacag ctactattag aactattatt
541 attaataaat tcctctccaa atctagcccc ttgacttcgg atttcacgat ttctcccttc
601 ctcctagaaa cttgataagt ttcccgcgct tcccttttttc taagactaca tgtttgtcat
661 cttataaagc aaaggggtga ataaatgaac caaatcaata acttctggaa tatctgcaaa
721 caacaataat atcagctatg ccatctttca ctattttagc cagtatcgag ttgaatgaac
781 atagaaaaat acaaaactga attcttccct gtaaattccc cgttttgacg acgcacttgt
841 agccacgtag ccacgcctac ttaagacaat tacaaaaggc gaagaagact gactcaggct
901 taagctgcca gccagagagg gagtcatttc attggcgttt gagtcagcaa agaagtcaag
961 atggccaaag ttccagacat gtttgaagac ctgaagaact gttacagtga aaatgaagaa
1021 gacagttcct ccattgatca tctgtctctg aatcagaaat ccttctatca tgtaagctat
1081 ggcccactcc atgaaggctg catggatcaa tctgtgtctc tgagtatctc tgaaacctct
1141 aaaacatcca agcttacctt caaggagagc atggtggtag tagcaaccaa cgggaaggtt
1201 ctgaagaaga gacggttgag tttaagccaa tccatcactg atgatgacct ggaggccatc
1261 gccaatgact cagaggaaga aatcatcaag cctaggtcag cacctttttag cttcctgagc
1321 aatgtgaaat acaactttat gaggatcatc aaatacgaat tcatcctgaa tgacgccctc
1381 aatcaaagta taattcgagc caatgatcag tacctcacgg ctgctgcatt acataatctg
1441 gatgaagcag tgaaatttga catgggtgct tataagtcat caaaggatga tgctaaaatt
1501 accgtgattc taagaatctc aaaaactcaa ttgtatgtga ctgcccaaga tgaagaccaa
1561 ccagtgctgc tgaaggagat gcctgagata cccaaaacca tcacaggtag tgagaccaac
1621 ctcctcttct tctgggaaac tcacggcact aagaactatt tcacatcagt tgcccatcca
1681 aacttgttta ttgccacaaa gcaagactac tgggtgtgct tggcaggggg gccaccctct
1741 atcactgact ttcagatact ggaaaaccag gcgtaggtct ggagtctcac ttgtctcact
1801 tgtgcagtgt tgacagttca tatgtaccat gtacatgaag aagctaaatc ctttactgtt
1861 agtcatttgc tgagcatgta ctgagccttg taattctaaa tgaatgttta cactctttgt
1921 aagagtggaa ccaacactaa catataatgt tgttatttaa agaacaccct atattttgca
1981 tagtaccaat cattttaatt attattcttc ataacaattt taggaggacc agagctactg
2041 actatggcta ccaaaaagac tctacccata ttacagatgg gcaaattaag gcataagaaa
2101 actaagaaat atgcacaata gcagttgaaa caagaagcca cagacctagg atttcatgat
2161 ttcatttcaa ctgtttgcct tctactttta agttgctgat gaactcttaa tcaaatagca
2221 taagtttctg ggacctcagt tttatcattt tcaaaatgga gggaataata cctaagcctt
2281 cctgccgcaa cagtttttta tgctaatcag ggaggtcatt ttggtaaaat acttcttgaa
2341 gccgagcctc aagatgaagg caaagcacga aatgttattt tttaattatt atttatatat
2401 gtatttataa atatatttaa gataattata atatactata tttatgggaa ccccttcatc
2461 ctctgagtgt gaccaggcat cctccacaat agcagacagt gttttctggg ataagtaagt
2521 ttgatttcat taatacaggg cattttggtc caagttgtgc ttatcccata gccaggaaac
2581 tctgcattct agtacttggg agacctgtaa tcatataata aatgtacatt aattaccttg
2641 agccagtaat tggtccgatc tttgactctt ttgccattaa acttacctgg gcattcttgt

Fig. 3 (cont.)

2701 ttcaattcca cctgcaatca agtcctacaa gctaaaatta gatgaactca actttgacaa
2761 ccatgagacc actgttatca aaactttctt ttctggaatg taatcaatgt ttcttctagg
2821 ttctaaaaat tgtgatcaga ccataatgtt acattattat caacaatagt gattgataga
2881 gtgttatcag tcataactaa ataaagcttg caacaaaatt ctctgacaaa aaaaaaaaaa
2941 aaa Homo sapiens interleukin 2 (IL2), mRNA.
ACCESSION NM_000586
VERSION NM_000586.2 GI:28178860
1 cgaattcccc tatcacctaa gtgtgggcta atgtaacaaa gagggatttc acctacatcc
61 attcagtcag tctttggggg tttaaagaaa ttccaaagag tcatcagaag aggaaaaatg
121 aaggtaatgt tttttcagac aggtaaagtc tttgaaaata tgtgtaatat gtaaaacatt
181 ttgacacccc cataatattt ttccagaatt aacagtataa attgcatctc ttgttcaaga
241 gttccctatc actctcttta atcactactc acagtaacct caactcctgc cacaatgtac
301 aggatgcaac tcctgtcttg cattgcacta agtcttgcac ttgtcacaaa cagtgcacct
361 acttcaagtt ctacaaagaa aacacagcta caactggagc atttactgct ggatttacag
421 atgattttga atggaattaa taattacaag aatcccaaac tcaccaggat gctcacattt
481 aagttttaca tgcccaagaa ggccacagaa ctgaaacatc ttcagtgtct agaagaagaa
541 ctcaaacctc tggaggaagt gctaaattta gctcaaagca aaaactttca cttaagaccc
601 agggacttaa tcagcaatat caacgtaata gttctggaac taaagggatc tgaaacaaca
661 ttcatgtgtg aatatgctga tgagacagca accattgtag aatttctgaa cagatggatt
721 accttttgtc aaagcatcat ctcaacactg acttgataat taagtgcttc ccacttaaaa
781 catatcaggc cttctattta tttaaatatt taaattttat atttattgtt gaatgtatgg
841 tttgctacct attgtaacta ttattcttaa tcttaaaact ataaatatgg atcttttatg
901 attctttttg taagccctag gggctctaaa atggtttcac ttatttatcc caaaatattt
961 attattatgt tgaatgttaa atatagtatc tatgtagatt ggttagtaaa actatttaat
1021 aaatttgata aatataaaaa aaaaaaa Homo sapiens interleukin 3 (colony-stimulating factor, multiple) (IL3), mRNA.
ACCESSION NM_000588
VERSION NM_000588.3 GI:28416914
1 cagagcccca cgaaggacca gaacaagaca gagtgcctcc tgccgatcca aacatgagcc
61 gcctgcccgt cctgctcctg ctccaactcc tggtccgccc cggactccaa gctcccatga
121 cccagacaac gcccttgaag acaagctggg ttaactgctc taacatgatc gatgaaatta
181 taacacactt aaagcagcca cctttgcctt tgctggactt caacaacctc aatggggaag
241 accaagacat tctgatggaa aataaccttc gaaggccaaa cctggaggca ttcaacaggg
301 ctgtcaagag tttacagaac gcatcagcaa ttgagagcat tcttaaaaat ctcctgccat

Fig. 3 (cont.)

361 gtctgcccct ggccacggcc gcacccacgc gacatccaat ccatatcaag gacggtgact
421 ggaatgaatt ccggaggaaa ctgacgttct atctgaaaac ccttgagaat gcgcaggctc
481 aacagacgac tttgagcctc gcgatctttt gagtccaacg tccagctcgt tctctgggcc
541 ttctcaccac agagcctcgg gacatcaaaa acagcagaac ttctgaaacc tctgggtcat
601 ctctcacaca ttccaggacc agaagcattt cacctttcc tgcggcatca gatgaattgt
661 taattatcta atttctgaaa tgtgcagctc ccatttggcc ttgtgcggtt gtgttctcat
721 ttttatccca ttgagactat ttatttatgt atgtatgtat ttatttattt attgcctgga
781 gtgtgaactg tatttatttt agcagaggag ccatgtcctg ctgcttctgc aaaaaactca
841 gagtggggtg gggagcatgt tcatttgtac ctcgagtttt aaactggttc ctagggatgt
901 gtgagaataa actagactct gaac

//

Homo sapiens interleukin 4 (IL4), transcript variant 2, mRNA.

ACCESSION NM_172348

VERSION NM_172348.1 GI:27477091

1 ttctatgcaa agcaaaaagc cagcagcagc cccaagctga taagattaat ctaaagagca
61 aattatggtg taatttccta tgctgaaact ttgtagttaa tttttaaaa aggtttcatt
121 ttcctattgg tctgatttca caggaacatt ttacctgttt gtgaggcatt ttttctcctg
181 gaagagaggt gctgattggc cccaagtgac tgacaatctg gtgtaacgaa aatttccaat
241 gtaaactcat ttccctcgg tttcagcaat tttaaatcta tatatagaga tatctttgtc
301 agcattgcat cgttagcttc tcctgataaa ctaattgcct cacattgtca ctgcaaatcg
361 acacctatta atgggtctca cctcccaact gcttcccct ctgttcttcc tgctagcatg
421 tgccggcaac tttgtccacg gacacaagtg cgatatcacc ttacaggaga tcatcaaaac
481 tttgaacagc ctcacagagc agaagaacac aactgagaag gaaaccttct gcagggctgc
541 gactgtgctc cggcagttct acagccacca tgagaaggac actcgctgcc tgggtgcgac
601 tgcacagcag ttccacaggc acaagcagct gatccgattc ctgaaacggc tcgacaggaa
661 cctctggggc ctggcgggct tgaattcctg tcctgtgaag gaagccaacc agagtacgtt
721 ggaaaacttc ttggaaaggc taaagacgat catgagagag aaatattcaa agtgttcgag
781 ctgaatattt taatttatga gtttttgata gctttatttt ttaagtattt atatatttat
841 aactcatcat aaaataaagt atatatagaa tct

//

Homo sapiens interleukin 4 (IL4), transcript variant 1, mRNA.

ACCESSION NM_000589

VERSION NM_000589.2 GI:27477090

1 ttctatgcaa agcaaaaagc cagcagcagc cccaagctga taagattaat ctaaagagca
61 aattatggtg taatttccta tgctgaaact ttgtagttaa tttttaaaa aggtttcatt
121 ttcctattgg tctgatttca caggaacatt ttacctgttt gtgaggcatt ttttctcctg
181 gaagagaggt gctgattggc cccaagtgac tgacaatctg gtgtaacgaa aatttccaat
241 gtaaactcat ttccctcgg tttcagcaat tttaaatcta tatatagaga tatctttgtc

Fig. 3 (cont.)

301 agcattgcat cgttagcttc tcctgataaa ctaattgcct cacattgtca ctgcaaatcg
361 acacctatta atgggtctca cctcccaact gcttcccccct ctgttcttcc tgctagcatg
421 tgccggcaac tttgtccacg gacacaagtg cgatatcacc ttacaggaga tcatcaaaac
481 tttgaacagc ctcacagagc agaagactct gtgcaccgag ttgaccgtaa cagacatctt
541 tgctgcctcc aagaacacaa ctgagaagga aaccttctgc agggctgcga ctgtgctccg
601 gcagttctac agccaccatg agaaggacac tcgctgcctg ggtgcgactg cacagcagtt
661 ccacaggcac aagcagctga tccgattcct gaaacggctc gacaggaacc tctggggcct
721 ggcgggcttg aattcctgtc ctgtgaagga agccaaccag agtacgttgg aaaacttctt
781 ggaaaggcta aagacgatca tgagagagaa atattcaaag tgttcgagct gaatatttta
841 atttatgagt ttttgatagc tttatttttt aagtatttat atatttataa ctcatcataa
901 aataaagtat atatagaatc t Human interleukin 5 (IL-5) gene, complete cds.
ACCESSION J03478
VERSION J03478.1 GI:186338

1 atcctaatca agacccagt gaacagaact cgaccctgcc aaggcttggc atttccattt
61 caatcactgt cttcccacca gtattttcaa tttcttttaa gacagattaa tctagccaca
121 gtcatagtag aacatagccg atcttgaaaa aaaacattcc caatatttat gtattttagc
181 ataaaattct gtttagtggt ctaccttata ctttgtttg cacacatctt ttaagaggaa
241 gttaattttc tgattttaag aaatgcaaat gtggggcaat gatgtattaa cccaaagatt
301 ccttccgtaa tagaaaatgt ttttaaaggg gggaaacagg gatttttatt attaaaagat
361 aaaagtaaat ttatttttta agatataagg cattggaaac atttagtttc acgatatgcc
421 attattaggc attctctatc tgattgttag aaattattca tttcctcaaa gacagacaat
481 aaattgactg gggacgcagt cttgtactat gcactttctt tgccaaaggc aaacgcagaa
541 cgtttcagag ccatgaggat gcttctgcat ttgagtttgc tagctcttgg agctgcctac
601 gtgtatgcca tccccacaga aattcccaca agtgcattgg tgaaagagac cttggcactg
661 ctttctactc atcgaactct gctgatagcc aatgaggtaa ttttctttat gattcctaca
721 gtctgtaaag tgcataggta atcatttgtg atggttcctt tactatatat agagatctgt
781 tataaataat aagattctga gcacattagt acatgggtga taactacatc accagcaaac
841 attctgttaa aagttatgaa tgctggtgtg ctgtaaaaat gattgtattt cctttcctct
901 ccagactctg aggattcctg ttcctgtaca taaaaatgta agttaaatta tgattcagta
961 aaatgatggc atgaataagt aaatttcctg ttttaagctg taaatcatta gttatcattg
1021 gaactattta attttctata ttttgttttc atatgggtgg ctgtgaatgt ctgtacttat
1081 aaatatgagg aatgactttt tatcaagtag aatcctttaa acaagtggat taggctcttt
1141 ggtgatgttg ttagtttgcc ttcccaaaga gcatcgtgtc aggattcttt ccagaaggat
1201 tccacactga gtgagaggtg cgtgctagtc tccgtgcagt tctgactctt tctcactcta
1261 acgtgtttct gaaagtatta gcaactcaga attatatttt tagaaccatg atcagtagac
1321 attaaaatat ataacaaatg ccctatatta ataattctgc atacttaaat aattatgact

Fig. 3 (cont.)

1381 atatgatggt gtgtatgcat tgaatatgcc tggtcatatt aaaatgtaaa atatatagtt
1441 tattagtcta aatagaataa aactaccagc tagaactgta gaaacacatt gatatgagtt
1501 taatgtataa tgcattacac ttccaaaaca tttttttcca gttacataat taagttatat
1561 cctttataaa actcctcagt aatcatataa gcttcatcta ctttttgaaa attttatctt
1621 aatatgtggt ggtttgttgc ctagaaaaca aacaaaaaac tctttggaga agggaactca
1681 tgtaaatacc acaaaacaaa gcctaacttt gtggaccaaa attgttttaa taattatttt
1741 ttaattgatg aattaaaaag tatatatatt tattgtgtac aatatgatgt tttgaagtat
1801 gtatacattg cagaatggac aatggaccaa atttttatac cttgtcttga ttatttgcat
1861 tttaaaaatt ttcctcattt agcaccaact gtgcactgaa gaaatctttc agggaatagg
1921 cacactggag agtcaaactg tgcaaggggg tactgtggaa agactattca aaaacttgtc
1981 cttaataaag aaatacattg acggccaaaa agtaagttac acacattcaa tggaagctat
2041 atttgtcctg gctgtgccta tttctatgga attgacagtt tcctgtaata cctattgtca
2101 tttttctttt ttcacagaaa aagtgtggag aagaaagacg gagagtaaac caattcctag
2161 actacctgca agagtttctt ggtgtaatga acaccgagtg gataatagaa agttgagact
2221 aaactggttt gttgcagcca aagattttgg aggagaagga cattttactg cagtgagaat
2281 gagggccaag aaagagtcag gccttaattt tcaatataat ttaacttcag agggaaagta
2341 aatatttcag gcatactgac actttgccag aaagcataaa attcttaaaa tatatttcag
2401 atatcagaat cattgaagta ttttcctcca ggcaaaattg atatactttt ttcttattta
2461 acttaacatt ctgtaaaatg tctgttaact taatagtatt tatgaaatgg ttaagaattt
2521 ggtaaattag tatttattta atgttatgtt gtgttctaat aaaacaaaaa tagacaactg
2581 ttcaatttgc tgctggcctc tgtccttagc aatttgaagt tagcacagtc cattgagtac
2641 atgcccagtt tggaggaagg gtctgagcac atgtggctga gcatccccat ttctctggag
2701 aagtctcaag gttgcaaggc acaccagagg tggaagtgat ctagcaggac ttagtgggga
2761 tgtggggagc agggacacag gcaggaggtg aacctggttt tctctctaca gtatatccag
2821 aacctgggat ggtcgaaggg taaatggtag ggaataaatg aatgaatgtc gtttccaaga
2881 tgattgtaga actaaaatga gttgtaagct cccctggaag aagggatgtg gaacctgtaa
2941 ctaggttcct gcccagcctg tgagaagaat ttggcagatc atctcattgc cagtatagag
3001 aggaagccag aaaccctctc tgccaaggcc tgcaggggtt cttaccacct gaccctgcac
3061 cataacaaaa ggacagagag acatggtagg gcagtcccat tagaaagact gagttccgta
3121 ttcccggggc agggcagcac caggccgcac aacatccatt ctgcctgctt atggctatca
3181 gtagcatcac tagagattct tctgtttgag aaaacttctc tcaaggatcc

//

Homo sapiens interleukin 6 (interferon, beta 2) (IL6), mRNA.

ACCESSION NM_000600

VERSION NM_000600.1 GI:10834983

1 ttctgccctc gagcccaccg ggaacgaaag agaagctcta tctcgcctcc aggagcccag
61 ctatgaactc cttctccaca agcgccttcg gtccagttgc cttctccctg gggctgctcc
121 tggtgttgcc tgctgccttc cctgccccag taccccccagg agaagattcc aaagatgtag
181 ccgccccaca cagacagcca ctcacctctt cagaacgaat tgacaaacaa attcggtaca

Fig. 3 (cont.)

241 tcctcgacgg catctcagcc ctgagaaagg agacatgtaa caagagtaac atgtgtgaaa
301 gcagcaaaga ggcactggca gaaaacaacc tgaaccttcc aaagatggct gaaaaagatg
361 gatgcttcca atctggattc aatgaggaga cttgcctggt gaaaatcatc actggtcttt
421 tggagtttga ggtataccta gagtacctcc agaacagatt tgagagtagt gaggaacaag
481 ccagagctgt gcagatgagt acaaaagtcc tgatccagtt cctgcagaaa aaggcaaaga
541 atctagatgc aataaccacc cctgacccaa ccacaaatgc cagcctgctg acgaagctgc
601 aggcacagaa ccagtggctg caggacatga caactcatct cattctgcgc agctttaagg
661 agttcctgca gtccagcctg agggctcttc ggcaaatgta gcatgggcac ctcagattgt
721 tgttgttaat gggcattcct tcttctggtc agaaacctgt ccactgggca cagaacttat
781 gttgttctct atggagaact aaaagtatga gcgttaggac actattttaa ttatttttaa
841 tttattaata tttaaatatg tgaagctgag ttaatttatg taagtcatat ttatattttt
901 aagaagtacc acttgaaaca ttttatgtat tagttttgaa ataataatgg aaagtggcta
961 tgcagtttga atatcctttg tttcagagcc agatcatttc ttggaaagtg taggcttacc
1021 tcaaataaat ggctaactta tacatatttt taaagaaata tttatattgt atttatataa
1081 tgtataaatg gtttttatac caataaatgg cattttaaaa aattc Homo sapiens interleukin 7 (IL7), mRNA.

NM_000880

VERSION NM_000880.2 GI:28610152

1 acatccgcgg caacgcctcc ttggtgtcgt ccgcttccaa taacccagct tgcgtcctgc
61 acacttgtgg cttccgtgca cacattaaca actcatggtt ctagctccca gtcgccaagc
121 gttgccaagg cgttgagaga tcatctggga agtcttttac ccagaattgc tttgattcag
181 gccagctggt ttttcctgcg gtgattcgga aattcgcgaa ttcctctggt cctcatccag
241 gtgcgcggga agcaggtgcc caggagagag gggataatga agattccatg ctgatgatcc
301 caaagattga acctgcagac caagcgcaaa gtagaaactg aaagtacact gctggcggat
361 cctacggaag ttatggaaaa ggcaaagcgc agagccacgc cgtagtgtgt gccgcccccc
421 ttgggatgga tgaaactgca gtcgcggcgt gggtaagagg aaccagctgc agagatcacc
481 ctgcccaaca cagactcggc aactccgcgg aagaccaggg tcctgggagt gactatgggc
541 ggtgagagct tgctcctgct ccagttgcgg tcatcatgac tacgcccgcc tcccgcagac
601 catgttccat gtttctttta ggtatatctt tggacttcct cccctgatcc ttgttctgtt
661 gccagtagca tcatctgatt gtgatattga aggtaaagat ggcaaacaat atgagagtgt
721 tctaatggtc agcatcgatc aattattgga cagcatgaaa gaaattggta gcaattgcct
781 gaataatgaa tttaactttt ttaaaagaca tatctgtgat gctaataagg aaggtatgtt
841 tttattccgt gctgctcgca agttgaggca atttcttaaa atgaatagca ctggtgattt
901 tgatctccac ttattaaaag tttcagaagg cacaacaata ctgttgaact gcactggcca
961 ggttaaagga agaaaaccag ctgccctggg tgaagcccaa ccaacaaaga gtttggaaga
1021 aaataaatct ttaaaggaac agaaaaaact gaatgacttg tgtttcctaa agagactatt
1081 acaagagata aaaacttgtt ggaataaaat tttgatgggc actaaagaac actgaaaaat
1141 atggagtggc aatatagaaa cacgaacttt agctgcatcc tccaagaatc tatctgctta

Fig. 3 (cont.)

1201 tgcagttttt cagagtggaa tgcttcctag aagttactga atgcaccatg gtcaaaacgg
1261 attagggcat ttgagaaatg catattgtat tactagaaga tgaatacaaa caatggaaac
1321 tgaatgctcc agtcaacaaa ctatttctta tatatgtgaa catttatcaa tcagtataat
1381 tctgtactga tttttgtaag acaatccatg taaggtatca gttgcaataa tacttctcaa
1441 acctgtttaa atatttcaag acattaaatc tatgaagtat ataatggttt caaagattca
1501 aaattgacat tgctttactg tcaaaataat tttatggctc actatgaatc tattatactg
1561 tattaagagt gaaaattgtc ttcttctgtg ctggagatgt tttagagtta acaatgatat
1621 atggataatg ccggtgagaa taagagagtc ataaacctta agtaagcaac agcataacaa
1681 ggtccaagat acctaaaaga gatttcaaga gatttaatta atcatgaatg tgtaacacag
1741 tgccttcaat aaatggtata gcaaatgttt tgacatgaaa aaaggacaat ttcaaaaaaa
1801 taaaataaaa taaaaataaa ttcacctagt ctaaggatgc taaaccttag tactgagtta
1861 cattgtcatt tatatagatt ataacttgtc taaataagtt tgcaatttgg gagatatatt
1921 tttaagataa taatatatgt ttacctttta attaatgaaa tatctgtatt taattttgac
1981 actatatctg tatataaaat attttcatac agcattacaa attgcttact ttggaataca
2041 tttctccttt gataaaataa atgagctatg tattaacaaa aaaaaaaaaa aaaaaaaaaa
2101 aaaaaaaaaa aaaaaa Homo sapiens interleukin 8 (IL8), mRNA.
ACCESSION NM_000584
VERSION NM_000584.2 GI:28610153
1 ctccataagg cacaaacttt cagagacagc agagcacaca agcttctagg acaagagcca
61 ggaagaaacc accggaagga accatctcac tgtgtgtaaa catgacttcc aagctggccg
121 tggctctctt ggcagccttc ctgatttctg cagctctgtg tgaaggtgca gttttgccaa
181 ggagtgctaa agaacttaga tgtcagtgca taaagacata ctccaaacct ttccacccca
241 aatttatcaa agaactgaga gtgattgaga gtggaccaca ctgcgccaac acagaaatta
301 ttgtaaagct ttctgatgga agagagctct gtctggaccc caaggaaaac tgggtgcaga
361 gggttgtgga gaagtttttg aagagggctg agaattcata aaaaaattca ttctctgtgg
421 tatccaagaa tcagtgaaga tgccagtgaa acttcaagca aatctacttc aacacttcat
481 gtattgtgtg ggtctgttgt agggttgcca gatgcaatac aagattcctg gttaaatttg
541 aatttcagta aacaatgaat agtttttcat tgtaccatga aatatccaga acatacttat
601 atgtaaagta ttatttattt gaatctacaa aaaacaacaa ataattttta aatataagga
661 ttttcctaga tattgcacgg gagaatatac aaatagcaaa attgaggcca agggccaaga
721 gaatatccga actttaattt caggaattga atgggtttgc tagaatgtga tatttgaagc
781 atcacataaa aatgatggga caataaattt tgccataaag tcaaatttag ctggaaatcc
841 tggatttttt tctgttaaat ctggcaaccc tagtctgcta gccaggatcc acaagtcctt
901 gttccactgt gccttggttt ctcctttatt tctaagtgga aaaagtatta gccaccatct
961 tacctcacag tgatgttgtg aggacatgtg gaagcacttt aagttttttc atcataacat
1021 aaattatttt caagtgtaac ttattaacct atttattatt tatgtattta tttaagcatc
1081 aaatatttgt gcaagaattt ggaaaaatag aagatgaatc attgattgaa tagttataaa

Fig. 3 (cont.)

1141 gatgttatag taaatttatt ttattttaga tattaaatga tgttttatta gataaatttc
1201 aatcagggtt tttagattaa acaaacaaac aattgggtac ccagttaaat tttcatttca
1261 gataaacaac aaataatttt ttagtataag tacattattg tttatctgaa attttaattg
1321 aactaacaat cctagtttga tactcccagt cttgtcattg ccagctgtgt tggtagtgct
1381 gtgttgaatt acggaataat gagttagaac tattaaaaca gccaaaactc cacagtcaat
1441 attagtaatt tcttgctggt tgaaacttgt ttattatgta caaatagatt cttataatat
1501 tatttaaatg actgcatttt taaatacaag gctttatatt tttaacttta agatgttttt
1561 atgtgctctc caaatttttt ttactgtttc tgattgtatg gaaatataaa agtaaatatg
1621 aaacatttaa aatataattt gttgtcaaag taaaaaaaaa aaaaaa Homo sapiens interleukin 9 (IL9), mRNA.
ACCESSION NM_000590
VERSION NM_000590.1 GI:10834979
1 ccgctgtcaa gatgcttctg gccatggtcc ttacctctgc cctgctcctg tgctccgtgg
61 caggccaggg gtgtccaacc ttggcgggga tcctggacat caacttcctc atcaacaaga
121 tgcaggaaga tccagcttcc aagtgccact gcagtgctaa tgtgaccagt tgtctctgtt
181 tgggcattcc ctctgacaac tgcaccagac catgcttcag tgagagactg tctcagatga
241 ccaataccac catgcaaaca agatacccac tgattttcag tcgggtgaaa aaatcagttg
301 aagtactaaa gaacaacaag tgtccatatt tttcctgtga acagccatgc aaccaaacca
361 cggcaggcaa cgcgctgaca tttctgaaga gtcttctgga aattttccag aaagaaaaga
421 tgagagggat gagaggcaag atatgaagat gaaatattat ttatcctatt tattaaattt
481 aaaaagcttt ctctttaagt tgctacaatt taaaaatcaa gtaagctact ctaaatcagt
541 atcagttgtg attatttgtt taacattgta tgtctttatt ttgaaataaa t Homo sapiens interleukin 10 (IL10), mRNA.
ACCESSION NM_000572
VERSION NM_000572.2 GI:24430216
1 acacatcagg ggcttgctct tgcaaaacca aaccacaaga cagacttgca aaagaaggca
61 tgcacagctc agcactgctc tgttgcctgg tcctcctgac tggggtgagg gccagcccag
121 gccagggcac ccagtctgag aacagctgca cccacttccc aggcaacctg cctaacatgc
181 ttcgagatct ccgagatgcc ttcagcagag tgaagacttt ctttcaaatg aaggatcagc
241 tggacaactt gttgttaaag gagtccttgc tggaggactt taagggttac ctgggttgcc
301 aagccttgtc tgagatgatc cagttttacc tggaggaggt gatgccccaa gctgagaacc
361 aagacccaga catcaaggcg catgtgaact ccctggggga gaacctgaag accctcaggc
421 tgaggctacg gcgctgtcat cgatttcttc cctgtgaaaa caagagcaag gccgtggagc
481 aggtgaagaa tgcctttaat aagctccaag agaaaggcat ctacaaagcc atgagtgagt
541 ttgacatctt catcaactac atagaagcct acatgacaat gaagatacga aactgagaca
601 tcagggtggc gactctatag actctaggac ataaattaga ggtctccaaa atcggatctg

Fig. 3 (cont.)

661 gggctctggg atagctgacc cagccccttg agaaacctta ttgtacctct cttatagaat
721 atttattacc tctgatacct caaccccccat ttctatttat ttactgagct tctctgtgaa
781 cgatttagaa agaagcccaa tattataatt tttttcaata tttattattt tcacctgttt
841 ttaagctgtt tccatagggt gacacactat ggtatttgag tgttttaaga taaattataa
901 gttacataag ggaggaaaaa aaatgttctt tggggagcca acagaagctt ccattccaag
961 cctgaccacg ctttctagct gttgagctgt tttccctgac ctccctctaa tttatcttgt
1021 ctctgggctt ggggcttcct aactgctaca aatactctta ggaagagaaa ccagggagcc
1081 cctttgatga ttaattcacc ttccagtgtc tcggagggat tcccctaacc tcattcccca
1141 accacttcat tcttgaaagc tgtggccagc ttgttattta taacaaccta aatttggttc
1201 taggccgggc gcggtggctc acgcctgtaa tcccagcact ttgggaggct gaggcgggtg
1261 gatcacttga ggtcaggagt tcctaaccag cctggtcaac atggtgaaac cccgtctcta
1321 ctaaaaatac aaaaattagc cgggcatggt ggcgcgcacc tgtaatccca gctacttggg
1381 aggctgaggc aagagaattg cttgaaccca ggagatggaa gttgcagtga gctgatatca
1441 tgcccctgta ctccagcctg ggtgacagag caagactctg tctcaaaaaa taaaaataaa
1501 aataaatttg gttctaatag aactcagttt taactagaat ttattcaatt cctctgggaa
1561 tgttacattg tttgtctgtc ttcatagcag attttaattt tgaataaata aatgtatctt
1621 attcacatc Homo sapiens interleukin 12A (natural killer cell stimulatory
factor 1, cytotoxic lymphocyte maturation factor 1, p35) (IL12A),
mRNA.

1 tttcattttg ggccgagctg gaggcggcgg ggccgtcccg gaacggctgc ggccgggcac
61 cccgggagtt aatccgaaag cgccgcaagc cccgcgggcc ggccgcaccg cacgtgtcac
121 cgagaagctg atgtagagag agacacagaa ggagacagaa agcaagagac cagagtcccg
181 ggaaagtcct gccgcgcctc gggacaatta taaaaatgtg gccccctggg tcagcctccc
241 agccaccgcc ctcacctgcc gcggccacag gtctgcatcc agcggctcgc cctgtgtccc
301 tgcagtgccg gctcagcatg tgtccagcgc gcagcctcct ccttgtggct accctggtcc
361 tcctggacca cctcagtttg gccagaaacc tccccgtggc cactccagac ccaggaatgt
421 tcccatgcct tcaccactcc caaaacctgc tgagggccgt cagcaacatg ctccagaagg
481 ccagacaaac tctagaattt taccccttgca cttctgaaga gattgatcat gaagatatca
541 caaaagataa aaccagcaca gtggaggcct gtttaccatt ggaattaacc aagaatgaga
601 gttgcctaaa ttccagagag acctctttca taactaatgg gagttgcctg gcctccagaa
661 agacctcttt tatgatggcc ctgtgcctta gtagtattta tgaagacttg aagatgtacc
721 aggtggagtt caagaccatg aatgcaaagc ttctgatgga tcctaagagg cagatctttc
781 tagatcaaaa catgctggca gttattgatg agctgatgca ggccctgaat ttcaacagtg
841 agactgtgcc acaaaaatcc tcccttgaag aaccggattt ttataaaact aaaatcaagc
901 tctgcatact tcttcatgct ttcagaattc gggcagtgac tattgataga gtgatgagct
961 atctgaatgc ttcctaaaaa gcgaggtccc tccaaaccgt tgtcattttt ataaaacttt

Fig. 3 (cont.)

1021 gaaatgagga aactttgata ggatgtggat taagaactag ggaggggggaa agaaggatgg
1081 gactattaca tccacatgat acctctgatc aagtattttt gacatttact gtggataaat
1141 tgtttttaag ttttcatgaa tgaattgcta agaagggaaa atatccatcc tgaaggtgtt
1201 tttcattcac tttaatagaa gggcaaatat ttataagcta tttctgtacc aaagtgtttg
1261 tggaaacaaa catgtaagca taacttattt taaaatattt atttatataa cttggtaatc
1321 atgaaagcat ctgagctaac ttatatttat ttatgttata tttattaaat tatttatcaa
1381 gtgtatttga aaaatatttt taagtgttct aaaaataaaa gtattgaatt aaagtgaaaa
1441 aaaa Homo sapiens interleukin 20 (IL20), mRNA.
ACCESSION NM_018724
VERSION NM_018724.2 GI:31083165
1 ctttgaattc ctagctcctg tggtctccag atttcaggcc taagatgaaa gcctctagtc
61 ttgccttcag ccttctctct gctgcgtttt atctcctatg gactccttcc actggactga
121 agacactcaa tttgggaagc tgtgtgatcg ccacaaacct tcaggaaata cgaaatggat
181 tttctgagat acggggcagt gtgcaagcca aagatggaaa cattgacatc agaatcttaa
241 ggaggactga gtctttgcaa gacacaaagc ctgcgaatcg atgctgcctc ctgcgccatt
301 tgctaagact ctatctggac agggtattta aaaactacca gacccctgac cattatactc
361 tccggaagat cagcagcctc gccaattcct ttcttaccat caagaaggac ctccggctct
421 gtcatgccca catgacatgc cattgtgggg aggaagcaat gaagaaatac agccagattc
481 tgagtcactt tgaaaagctg gaacctcagg cagcagttgt gaaggctttg gggggaactag
541 acattcttct gcaatggatg gaggagacag aataggagga aagtgatgct gctgctaaga
601 atattcgagg tcaagagctc cagtcttcaa tacctgcaga ggaggcatga ccccaaacca
661 ccatctcttt actgtactag tcttgtgctg gtcacagtgt atcttattta tgcattactt
721 gcttccttgc atgattgtct ttatgcatcc ccaatcttaa ttgagaccat acttgtataa
781 gatttttgta atatctttct gctattggat atatttatta gttaatatat ttatttattt
841 tttgctattt aatgtattta ttttttact tggacatgaa actttaaaaa aattcacaga
901 ttatatttat aacctgacta gagca

Fig. 3 (cont.)

DEFINITION Kaposi's sarcoma-associated herpesvirus latent nuclear antigen gene, partial cds.

ACCESSION AF305694

VERSION AF305694.1 GI:11037007

1 agaccagatt tcccgaggat ggcgcccccg ggaatgcgcc tgaggtcggg acggagcacc
61 ggcgcgccct taacgagagg aagttgtagg aaacgaaaca ggtctccgga aagatgtgac
121 cttggcgatg acctacatct acaaccgcga aggaagcatg tcgccgactc cgtcgacggc
181 cgggaatgtg gaccccacac cttgcctata ccaggaagtc ccacagtgtt cacatccggg
241 ctgccagcat ttgtgtctag tcctacttta ccggtggctt ccattccttc acccgctccc
301 gcaacacctt tacctccacc ggcactctta ccccccgtaa ccacgtcttc ctccccaatc
361 cctccatccc atcctgtgtc tccggggacc acggatactc attctccatc tcctgcattg
421 ccacccacgc agtctccaga gtcttctcaa aggccaccgc tttcaagtcc tacaggaagg
481 ccagactctt caacacctat gcgtccgcca ccctcgcagc agactacacc tccacactca
541 cccacgactc ctccacccga gcctccctcc aagtcgtcac cagactcttt agctccgtct
601 accctgcgta gcctgagaaa aagaaggcta tcgtcccccc aaggtccctc tacactaaac
661 ccaatatgtc agtcgccccc agtctctccc cctagatgtg acttcgccaa ccgtagtgtg
721 taccccccat gggccacaga gtccccgatc tacgtgggat catccagcga tggcgatact
781 ccgccacgcc aaccgcctac atctcccatc tccataggat catcatcccc gtctgaggga
841 tcctcgggtg atgacacagc catgttggtg ctccttgcgg agattgcaga agaagcatcc
901 aagaatgaaa aagaatgttc cgaaaataat caggctggcg aggataatgg ggacaacgag
961 attagcaagg aaagtcaggt tgacaaggat gacaatgaca ataaggatga tgaggaggag
1021 caggagacag atgaggagga cgaggaggat gacgaggagg atgacgagga ggatgacgag
1081 gaggatgacg aggaggatga cgaggaggat gacgaggagg atgacgagga ggatgacgag
1141 gaggatgacg aggaggatga cgaggaggat gacgaggagg atgacgagga ggaggacgag
1201 gaggaggacg aggaggagga cgaggaggag gaggacgagg aggaggagga ggacgaggag
1261 gatgacgatg atgaggacaa tgaggacgag gaggatgacg aggaggagga caagaaggag
1321 gacgaggagg acgggggcga tggaaacaaa acgttgagca tccaaagttc acaacagcag
1381 caggagccac aacagcagga gccacagcag caggagccac aacagcagga gccacagcag
1441 caggagccac agcagcagga gcccctgcag gagccacaac agcaggagcc acagcagcag
1501 gagccacaac agcaggagcc acagcagcag gagcccctgc aggagccaca gcagcaggag
1561 ccacagcagc aggagccaca gcagcaggag ccacaacagc aggagccaca gcagcaggat
1621 gagcagcagc aggatgagca gcagcaggat gagcagcagc aggatgagca gcagcagcag
1681 gatgagcagc agcaggatga gcagcagcag gatgagcagc agcaggatga gcaggagcag
1741 caggatgagc agcagcagga tgagcagcag cagcaggatg aacaggagca gcaggaggag
1801 caggagcagc aggaggagca ggagcaggag ttagaggagc aggagcagga gttagaggag
1861 caggagcagg agttagagga gcaggagcag gagttagagg agcaggagca ggagttagag
1921 gagcaggagc aggagttaga ggagcaggag caggagttag aggagcagga gcaggagtta
1981 gaggagcagg agcaggagtt agatgagcag gagcaggagt tagaggagca ggagcaggag
2041 ttagaggagc aggagcagga gttagaggag caggagcagg agttagagga gcaggagcag
2101 gagttagagg agcaggagca ggagttagag gagcaggagc aggagttaga ggagcaggag

Fig. 3 (cont.)

2161 caggagttag aggagcagga gcaggagtta gaggagcagg agcaggagca ggagttagag
2221 gaggtggaag agcaagagca ggagcaggaa gagcaggaat tagaggaggt ggaggagcaa
2281 gagcaggagc aggaggagca ggaggagcag gagttagagg aggtggaaga gcaggaagag
2341 caggagttag aggaggtgga agagcaggaa gagcaggagt tagaggaggt ggaagagcag
2401 gagcagcagg gggtggaaca gcaggagcag gagacggtgg aagagcccat aatcttgcac
2461 gggtcgtcat ccgaggacga aatggaagtg gattaccctg ttgttagcac acatgaacaa
2521 attgccagta gcccaccagg agataataca ccagacgatg acccacaacc tggcccatct
2581 cgcgaatacc gctatgtact cagaacatca ccaccccaca gacctggagt tcgtatgagg
2641 cgcgttccag ttacccaccc aaaaaagcca catccaagat accaacaacc accggtccct
2701 tacagacaga tagatgattg tcctgcgaaa gctaggccac aacacatctt ttatagacgc
2761 tttttgggaa aggatggaag acgagatcca aagtgtcaat ggaagtttgc agtgattttt
2821 tggggcaatg acccatacgg acttaaaaaa ttatctcagg ccttccagtt tggaggagta
2881 aaggcaggcc ccgtgtcctg cttgccccac cctggaccag accagtcgcc cataacttat
2941 tgtgtatatg tgtattgtca gaacaaagac acaagtaaga aagtacaaat ggcccgccta
3001 gcctgggaag ctagtcaccc cctggcagga aacctacaat cttccatagt taagtttaaa
3061 aagcccctgc cattaaccca gccaggggaa aaccaaggtc ctggggactc tccacaggaa
3121 atgacat Human herpesvirus 8 ORF73 gene, complete cds.

ACCESSION AF360120

VERSION AF360120.1 GI:13936995

1 atggcgcccc cgggaatgcg cctgaggtcg ggacggagca ccggcgcgcc cttaacgaga
61 ggaagttgta ggaaacgaaa caggtctccg gaaagatgtc accttggcga tgacctacat
121 ctacaaccgc gaaggaagca tgtcgccgac tccgtcgacg gccgggaatg tggaccccac
181 accttgccta taccaggaag tcccacagtg ttcacatccg ggctgccagc atttgtgtct
241 agtcctactt taccggtggc tcccattcct tcacccgctc ccgcaacacc tttacctcca
301 ccggcactct taccccccgt aaccacgtct tcctccccaa tccctccatc ccatcctgtg
361 tctccgggga ccacggatac tcattctcca tctcctgcat tgccacccac gcagtctcca
421 gagtcttctc aaaggccacc gctttcaagt cctacaggaa ggccagactc ttcaacacct
481 atgcgtccgc caccctcgca gcagactaca cctccacact cacccacgac tcctccaccc
541 gagcctccct ccaagtcgtc accagactct ttagctccgt ctaccctgcg tagcctgaga
601 aaaagaaggc tatcgtcccc ccaaggtccc tctacactaa acccaatatg tcagtcgccc
661 ccagtctctc cccctagatg tgacttcgcc aaccgtagtg tgtacccccc atgggccaca
721 gagtccccga tctacgtggg atcatccagc gatggcgata ctccgccacg ccaaccgcct
781 acatctccca tctccatagg atcatcatcc ccgtctgagg gatcctgggg tgatgacaca
841 gccatgttgg tgctccttgc ggagattgca gaagaagcat ccaagaatga aaaagaatgt
901 tccgaaaata atcaggctgg cgaggataat ggggacaacg agattagcaa ggaaagtcag
961 gttgacaagg atgacaatga caataaggat gatgaggagg agcaggagac agatgaggag
1021 gacgaggagg atgacgagga ggatgacgag gaggatgacg aggaggatga cgaggaggat

Fig. 3 (cont.)

1081 gacgaggagg atgacgagga ggatgacgag gaggatgacg aggaggagga cgaggaggag
1141 gacgaggagg aggaggacga ggaggaggag gaggaggacg aggaggatga cgatgatgag
1201 gacaatgagg acgaggagga ggacaagaag gaggacgagg aggacggggg cgatggaaac
1261 aaaacgttga gcatccaaag ttcacaacag cagcaggagc cacagcagca ggagccacaa
1321 cagcaggagc cacagcagca ggagccacag cagcaggagc ccctgcagga gccacagcag
1381 caggagccac aacagcagga gccacaacag caggagccac aacagcagga gccacaacag
1441 caggagccac aacagcagga gccacagcag caggatgagc agcagcagga tgagcagcag
1501 caggatgagc agcagcagga tgagcagcag caggatgagc aggagcagca ggatgagcag
1561 cagcaggatg agcagcagca ggatgagcag cagcagcagg atgaacagga gcagcaggag
1621 gagcaggagc agcaggagga gcaggagcag caggaggagc aggagcagga gttagaggag
1681 caggagcagg agttagagga gcaggagcag gagttagagg agcaggagca ggagttagag
1741 gagcaggagc aggagttaga ggagcaggag caggagttag aggagcagga gcaggagtta
1801 gaggagcagg agcaggagtt agaggagcag gagcaggagt tagaggagca ggagcaggag
1861 ttagaggagc aggagcagga gttagaggag caggagcagg agttagagga gcaggagcag
1921 gagttagagg agcaggagca ggagttagag gagcaggagc aggagttaga ggagcaggag
1981 caggagttag aggagcagga gcaggagtta gaggagcagg agcaggagtt agaggagcag
2041 gagcaggagt tagaggagca ggagcaggag ttagaggagc aggagcagga gcaggagtta
2101 gaggaggtgg aagagcaaga gcaggagcag gaagagcagg aattagagga ggtggaggag
2161 caagagcagg agcaggagga gcaggaggag caggagttag aggaggtgga agagcaggaa
2221 gagcaggagt tagaggaggt ggaagagcag gaagagcagg agttagagga ggtggaagag
2281 caggagcagc agggggtgga acagcaggag caggagacgg tggaagagcc cataatcttg
2341 cacgggtcgt catccgagga cgaaatggaa gtggattacc ctgttgttag cacacatgaa
2401 caaattgcca gtagcccacc aggagataat acaccagacg atgacccaca acctggccca
2461 tctcgcgaat accgctatgt actcagaaca tcaccacccc acagacctgg agttcgtatg
2521 aggcgcgttc cagttaccca cccaaaaaag ccacatccaa gataccaaca accaccggtc
2581 ccttacagac agatagatga ttgtcctgcg aaagctaggc cacaacacat cttttataga
2641 cgctttttgg gaaaggatgg aagacgagat ccaaagtgtc aatggaagtt tgcagtgatt
2701 ttttggggca atgacccata cggacttaaa aaattatctc aggccttcca gtttggagga
2761 gtaaaggcag gccccgtgtc ctgcttgccc caccctggac cagaccagtc gcccataact
2821 tattgtgtat atgtgtattg tcagaacaaa gacacaagta agaaagtaca aatggcccgc
2881 ctagcctggg aagctagtca ccccctggca ggaaacctac aatcttccat agttaagttt
2941 aaaaagcccc tgccattaac ccagccaggg gaaaaccaag gtcctgggga ctctccacag
3001 gaaatgacat aa Kaposi's sarcoma-associated herpesvirus v-cyclin gene, complete cds.

ACCESSION U79416

VERSION U79416.1 GI:1711134

1 atggcaactg ccaataaccc gccctcggga cttctggatc ccacgctatg tgaggatcgg
61 atcttttaca atattcttga aattgagccg cgctttttaa cttctgactc tgtatttggg
121 tcctttcaac aatctcttac ttcgcatatg cgtaagttac tgggcacatg gatgttttca

Fig. 3 (cont.)

181 gtttgccagg aatacaacct agaacctaac gtggtcgcgt tggcccttaa tcttttggac
241 agactcctac ttataaagca ggtgtccaaa gaacactttc aaaagacagg gagcgcctgc
301 ctgttagtgg ccagtaagct cagaagcctc acgcctattt ctaccagttc actttgctat
361 gccgcggcag actccttttc ccgccaagaa cttatagacc aggagaaaga actccttgag
421 aagttggcgt ggcgaacaga ggcagtctta gcgacggacg taacttcctt cttgttactt
481 aaattgctgg ggggctccca acacctggac ttttggcacc acgaggtcga caccctgatt
541 acaaaagcct tagttgaccc aaagactggc tcattgcccg cctctattat cagcgctgca
601 ggctgtgcgc tgttggttcc tgccaacgtc attccgcagg atacccactc gggtggggta
661 gttcctcagc tggcaagcat attgggatgc gatgtttccg ttctacaggc ggcagtggaa
721 cagatcctaa catctgtttc ggactttgat ctgcgcattc tggacagcta ttaa

Fig. 3 (cont.)

Epstein-Barr virus nuclear antigen (EBNA1) mRNA, 5' end.

ACCESSION M13941

VERSION M13941.1 GI:330399

1 ttagagagtg gctgctacgc attagagacc actttgagcc acccacagta accacccagc
61 gccaatctgt ctacatagaa gaagaagagg atgaagacta agtcacaggc ttagccagta
121 acccagcact ggcgtgtgac gtggtgtaaa gttttgcctg aacctgtggt tgggcaggta
181 acttaggaag cgtttcttga gcttccctgg gatgagcgtt tgggagagct gattctgcag
241 cccagagagt agtctcaggg catcctctgg agcctgacct gtgatcgtcg catcatagac
301 cgccagtaga cctgggagca gattcaccgc cgcggccgtc tcctttaagt gtgaatcatg
361 tctgacgagg ggccaggtac aggacctgga aatggcctag gagagaaggg agacacatct
421 ggaccagaag gctccggcgg cagtggacct caaagaagag ggggtgataa ccatggacga
481 ggacggggaa gaggacgagg acgaggaggc ggaagaccag gagccccggg cggctcagga
541 tcagggccaa gacatag Epstein-Barr Virus LMP1 gene.

ACCESSION X66863 S48740

VERSION X66863.1 GI:59181

1 aatccgccac ctcattctga aattcccata tccccgtct gctgcttcgt cacccgccga
61 cccttagccc tctatccgcc tcacccgcct cccctacggt tacccacag ccttgcctca
121 cctgaacccc cctaaagcac agcctcccgc ctgccgacaa cgacctccca acgttgcgcg
181 ccctacgcct ctttgtgtgg attacactgc cgcttcccac aacactgctc actcccctt
241 gtgattgccg cactgccttt ccatttccct gtacgcttta ccaccgcatt cccacagctt
301 gcccctcggg gactcgcttt tctaacacaa acacacgctt tctacttcct cttttaacgc
361 ttacatgcac acacactacg cgctttcggg aaagcggcgc ccgtaccctg tccggcagac
421 cccgcaaatc cccccgggcc tccatcccca gaaacacgcg ttactctctc gtaggcggcc
481 tacataagcc tctgtcactg ctctgtcagc ttctttcctc agttgccttg ctcctgccac
541 actaccctga ccatggaacg cgaccttgag aggggcccac cgggcccgcc acggcccct
601 ctaggacccc ccctctcctc ttccataggc cttgctctcc ttctcctgct cttggcgcta
661 ctgttctggc tgtatatcgt tatgagtaac tggactggag gagcgctcct tgtcctctat
721 tcctttgctc tcatgcttat tattatcatt ctcatcatct ttatcaacag aagagacctt
781 ctctgtccac ttggaggcct tggtctactc ctactgatga gtaagtatta caccctttgc
841 cccccacccc ctttccctta cgcttccttc tctaacgcac tttctcctct ttccccagtc
901 accctcctac tcatcgctct ctggaatttg cacggacagg cattgtacct tggaattgtg
961 ctgttcatct ttggctgctt acttggtaag atctaacatt ccctaggact tatttaccac
1021 accctcacct ttccagccct aacactcttt tttcaacgca gtcttaggtc tctggatcta
1081 cttggagatt ctctggcggc ttggtgccac catctggcag cttttggcct tcatcctagc
1141 cttcttccta gccatcatcc tgcttattat tgctctctat ctacaacaaa actggtggac
1201 tctattggtt gatctccttt ggctcctcct gtttatggcc attttaatct ggatgtatta
1261 tcatggacca cgacacactg atgaacacca ccacgatgac tccctcccgc accctcaaca

Fig. 3 (cont.)

1321 agctaccgtc gattctagcc atgaatctga ctctaactcc aacgagggca gacaccacct
1381 gctcgtgagt ggggccggcg acggaccccc actctgctct caaaacctag gcgcacctgg
1441 aggtggtcct gacaatggcc cacaggaccc tgacaacact gatgacaatg gcccacagga
1501 ccctgacaac actgatgaca atggcccaca ggaccctgac aacactgatg acaatggccc
1561 acaggaccct gacaacactg atgacaatgg cccacaggac cctgacaaca ctgatgacaa
1621 tggcccacat gacccgctgc ctcataaccc tagcgactct gctggaaatg atggaggccc
1681 tccaaaattg acggaagagg ttgaaaacaa aggaggtgac cggggcccgc cttcgatgac
1741 agacggtggc ggcggtcatc cacaccttcc tacactgctt ttgggtactt ctggttccgg
1801 tggagatgat gacgaccccc acggcccagt tcagctaagc tactatgact aacctttctt
1861 tacttctagg cattaccatg tcataggctt gcctgactga ctctccctcc atttactggg
1921 aatgccttag ctaatcacct taactggcac acactccctt agccacactg tctgtctagg
1981 ctgaaaagcc acattcatat tctatttcaa aacaagggga aggaggacat a Epstein-Barr virus latent membrane protein 2A (LMP 2A) mRNA, complete cds.
ACCESSION M87778
VERSION M87778.1 GI:330384
1 ccaatgggcg cgggtccccc tagccccggc ggggatccgg atggggacga tggcggaaac
61 aactcccaat atccatctgc ttctggctct tctgggaaca cccccacccc accgaacgat
121 gaggaacgtg aatctaatga agagccccca ccgccttatg aggacctaga ttggggcaat
181 ggcgaccgtc actcggacta tcaaccacta ggaaaccaag atccaagttt gtacttggga
241 ttgcaacacg acgggaatga cgggctccct ccccctccct actctccacg ggatgactca
301 tctcaacaca tatacgaaga agcgggcaga ggaagtatga atccagtatg c
//
Epstein-Barr virus latent membrane protein 2A (LMP 2A) mRNA, complete cds.
ACCESSION M87777
VERSION M87777.1 GI:330382
1 actatggggt ccctagaagt gatgccaatg ggcgcgggtc cccctagccc cggcggggat
61 ccggatgggg acgatggcgg aaacaactcc caatatccat ctgcttctgg ctcttctggg
121 aacaccccca ccccaccgaa cgatgaggaa cgtgaatcta atgaagagcc cccaccgcct
181 tatgaggact cagattgggg caatggcgac cgtcactcgg actatcaacc actaggaaac
241 caagatccaa gtttgtactt gggattgcaa cacgacggga atgacgggct ccctccccct
301 ccctactctc cacgggatga ctcatctcaa cacatatacg aagaagcggg cagaggaagt
361 atgaatccag tatgcctgct tgtaattgtt gcgccctacc tgttttggct ggcggctatt
421 gccgcctcgt gtttcacggc ctcagttagt accgttgtga ccgccaccgg cttggccctc
481 tcacttttac tcttggcagc agtggccagc tcatatgccg ctgcacaaag gaaactgctg
541 acaccggtga cag

Fig. 3 (cont.)

Epstein-Barr virus (EBV) genome, strain B95-8.
ACCESSION V01555 J02070 K01729 K01730 V01554 X00498 X00499 X00784
VERSION V01555.1 GI:59074

1 agaattcgtc ttgctctatt caccettact tttcttcttg cccgttctct ttcttagtat
61 gaatccagta tgcctgcctg taattgttgc gccctacctc ttttggctgg cggctattgc
121 cgcctcgtgt ttcacggcct cagttagtac cgttgtgacc gccaccggct tggccctctc
181 acttctactc ttggcagcag tggccagctc atatgccgct gcacaaagga aactgctgac
241 accggtgaca gtgcttactg cggttgtcac ttgtgagtac acacgcacca tttacaatgc
301 atgatgttcg tgagattgat ctgtctctaa cagttcactt cctctgcttt tctcctcagt
361 ctttgcaatt tgcctaacat ggaggattga ggacccacct tttaattctc ttctgtttgc
421 attgctggcc gcagctggcg gactacaagg catttacggt tagtgtgcct ctgttatgaa
481 atgcaggttt gacttcatat gtatgccttg gcatgacgtc aactttactt ttatttcagt
541 tctggtgatg cttgtgctcc tgatactagc gtacagaagg agatggcgcc gtttgactgt
601 ttgtggcggc atcatgtttt tggcatgtgt acttgtcctc atcgtcgacg ctgttttgca
661 gctgagtccc ctccttggag ctgtaactgt ggtttccatg acgctgctgc tactggcttt
721 cgtcctctgg ctctcttcgc caggggggcct aggtactctt ggtgcagccc ttttaacatt
781 ggcagcaggt aagccacacg tgtgacattg cttgcctttt tgccacatgt tttctggaca
841 caggactaac catgccatct ctgattatag ctctggcact gctagcgtca ctgattttgg
901 gcacacttaa cttgactaca atgttccttc tcatgctcct atggacactt ggtaagtttt
961 cccttccttt aactcattac ttgttctttt gtaatcgcag ctctaacttg gcatctcttt
1021 tacagtggtt ctcctgattt gctcttcgtg ctcttcatgt ccactgagca agatccttct
1081 ggcacgactg ttcctatatg ctctcgcact cttgttgcta gcctccgcgc taatcgctgg
1141 tggcagtatt ttgcaaacaa acttcaagag tttaagcagc actgaattta tacccagtga
1201 gtatctattt gttactcctg tttagttgaa gaaaacaagc tattggattg taacacacat
1261 tttacgcttt gttccttaga tttgttctgc atgttattac tgattgtcgc tggcatactc
1321 ttcattcttg ctatcctgac cgaatggggc agtggaaata gaacatacgg tccagttttt
1381 atgtgcctcg gtggcctgct caccatggta gccggcgctg tgtggctgac ggtgatgtct
1441 aacacgcttt tgtctgcctg gattcttaca gcaggattcc tgattttcct cattggtaag
1501 tgtgacacca acaggtgttg ccttgttatg tcaccgttct gacacatgac ttacatgggt
1561 ttggcttttg taggctttgc cctctttggg gtcattagat gctgccgcta ctgctgctac
1621 tactgcctta cactggaaag tgaggagcgc ccaccgaccc catatcgcaa cactgtataa
1681 aggtaagtat tattaaattt tagagacact atcacgtgta acttgacgtg caaggatgga
1741 agagaggggc agggaaacgc aaatgccggt tgcccggtat gggggcccgt ttattatggt
1801 aaggctcttc gggcaagatg gagaggcaaa catacaggag gaaaggctat atgagctact
1861 ctctgaccca cgctccgcgc tcggcctaga cccggggccc ctgattgctg agaacctgct

Fig. 3 (cont.)

1921 gctagtggcg ctgcgtggca ccaacaacga tcccaggcct cagcgtcagg agagggccag
1981 agaactggcc ctcgttggca ttctactagg aaacggcgag cagggtgaac acttgggcac
2041 ggagagtgcc ctggaggcct caggcaacaa ctatgtgtat gcctacggac cagactggat
2101 ggcaaggcct tccacatggt ccgcggaaat ccagcaattc ctgcgactcc tgggcgccac
2161 gtacgtgctt cgcgtggaga tgggcaggca gtttggcttc gaggtgcata gaagccggcc
2221 ctccttccgt cagttccagg ccatcaatca ccttgtcctg tttgacaacg cccttcgcaa
2281 gtacgattcc ggccaggtgg cggcgggctt ccagagggcc cttctggtgg ccgggccaga
2341 gaccgctgac acgaggccgg acctccgcaa gctgaatgag tgggtgtttg gtggcagggc
2401 tgctggtggc agacagctgg ccgacgagct aaagatcgtg tccgcgctgc gagacactta
2461 ctcgggccac ttggtccttc agcccacgga gaccettgac acatggaagg tgttgagcag
2521 ggacacacga accgctcata gtttggagca cggattcatt catgccgcgg ggaccatcca
2581 ggccaactgc ccacagctgt ttatgagacg ccagcacccc ggcctctttc ccttcgttaa
2641 tgcaatagca tcatcgctgg gctggtacta ccagaccgcc accggccccg gagcagatgc
2701 cagggcggcg gcccggcgcc aacaggcctt tcagaccagg gcggcggctg aatgccatgc
2761 caaaagcggg gtgccggtcg tggccggctt ctacaggacc atcaacgcca cgctcaaggg
2821 aggagagggc ctacagccca ctatgtttaa cggggagctg ggggccatca agcaccaggc
2881 acttgacact gtgaggtatg actacggcca ctatctcata atgttggggc cattccagcc
2941 atggagcgga ctgacggccc ctccgtgccc ctacgccgaa agttcatggg cacaggcggc
3001 cgtgcagacg gccctcgagc tgttctcggc cctgtacccg gccccgtgca tctcgggcta
3061 cgcgcgcccc ccgggcccca gtgctgtgat cgagcatctg ggtccctag ttccaaaggg
3121 gggtctgctg ttgtttctgt ctcacctacc ggatgatgtt aaggacgggc tcggagaaat
3181 ggggccggcc agggccacgg gacctggaat gcagcagttt gtcagcagct acttcctcaa
3241 ccccgcctgt tccaacgtct tcattacagt gaggcagcga ggggagaaga tcaacggccg
3301 taccgtcctc caagcgctcg gacgcgcatg cgatatggca ggctgccagc actatgtgct
3361 gggctccacg gttcccctcg gtggactcaa ctttgtcaac gacctggcgt ccccggtttc
3421 caccgccgag atgatggatg atttctctcc cttcttcacc gtggagtttc ccccgattca
3481 agaggagggc gcaagttctc cggtaccctt agatgtggac gagagcatgg acatctctcc
3541 gtcttacgag ttgccctggc tctcgctgga gtcatgcctc acaagcatcc tgtcacaccc
3601 caccgtggga agcaaggagc acttggtcag gcacacggac agggtcagcg gaggacgcgt
3661 ggcacagcag cccggggtag gtcccctgga cctgccgctg gcggactacg ccttcgttgc
3721 ccacagtcag gtctggacca ggcccggtgg ggctcctccc ttgccctatc gtacctggga
3781 tcgaatgaca gagaagctgc ttgtctccgc aaaacccggc ggagagaacg ttaaggtttc
3841 aggtaccgtg attacattgg gagaacaggg gtacaaagtg tcgttggatc tgagggaggg
3901 aaccaggctg gcaatggctg aggcgctgct gaacgcagca tgtgccccaa tcttggatcc
3961 ggaagacgtc ttgctcaccc tgcatctaca cctggatccg cgccgggcag acaactcggc
4021 cgtgatggag gctatgacgg cggcgagtga ctacgcgcgt ggcctgggcg tgaagctgac
4081 ctttggctcg gcctcctgcc ccgagaccgg ctcgtccgcc tccaacttca tgaccgtggt
4141 ggcctctgtc tccgccccag gggaattctc gggtcctctg atcacgccag tgcttcagaa
4201 gacgggcagt ctcctgattg cggtgcgttg cggggatggc aagatccagg gagggtcgct

Fig. 3 (cont.)

4261 gtttgagcag ctctttagcg acgtggccac gaccccacgg gcacccgagg cgttgtctct
4321 gaagaatctc ttccgggcag tccagcagct ggtcaagagc ggcatcgtgc tgtcagggca
4381 tgacatcagc gacgggggcc tggtgacctg cctggtggag atggccctgg ccgggcagcg
4441 gggagtgacc atcactatgc cggtggcctc cgactacctc ccggagatgt ttgcagagca
4501 ccccggcctg gtgtttgagg tggaggagcg cagcgtgggt gaggtgctgc agaccctgcg
4561 ctccatgaac atgtacccgg cagtcctcgg tcgagtgggc gagcaaggtc cagatcaaat
4621 gtttgaggtg cagcacggcc cagagacggt gttgcgccag tcgctgcgcc tgctgctggg
4681 aacctggtca tcctttgcca gcgagcagta cgagtgcctg cgaccagatc ggattaaccg
4741 gtccatgcac gtgtccgact acggctataa cgaagcactg gcagtctccc cgttgacagg
4801 aaagaatctc agcccacgcc ggttggtgac agagcctgac ccacgatgtc aggtggccgt
4861 gctatgcgcc ccgggcacca ggggccatga aagcctcctg gcggccttca cgaatgccgg
4921 atgcctgtgc cgacgggtgt tctttcgcga ggttagggac aacacgttcc tcgacaagta
4981 cgtgggtctg gccatcggag gagttcatgg ggccagggac tctgccctgg caggccgtgc
5041 caccgtggcg ctgattaatc gtttccccgc cctgcgtgac gctattctaa agttcctcaa
5101 caggccagat acgttctcgg tggccttggg ggagctgggg gtgcaagttt tggctggcct
5161 gggggccgtg gggtcaacag ataatccacc cgcccctggc gtggaagtta atgtccagag
5221 atcacctctg attctggccc ccaacgcctc tggcatgttt gagtcccgct ggctgaacat
5281 tagcatcccg gcgaccacca gctctgtcat gctgcgtggc ctccggggct gcgtcctgcc
5341 ttgttgggtg caaggctcgt gcctgggcct gcaatttact aacctcggga tgccatatgt
5401 tttgcagaat gcccaccaga tcgcctgcca cttccacagc aatggcacgg atgcctggcg
5461 ctttgctatg aattatccaa gaaaccccac ggagcagggc aacattgcag ggctctgttc
5521 acgcgatggt cgtcatctgg ctctcctgtg tgacccctca ctttgtacag acttttggca
5581 atgggagcac attccccccg cctttgggca ccccacgggg tgctccccct ggacacttat
5641 gtttcaagca gctcacctat ggtcactcag gcacggtcgc ccctccgagt gaccagtcac
5701 cttccagact atgcatacac tgaatttagc ctgatattgt ccccctagcc ccgggcccag
5761 ccctcctcag aaaactctgc atggagaagc tggacgtgaa cctccccccc agacctgtgt
5821 gctgtattta caaacactac aataaaccca atgtgcaaat gtggtttgta tggctacttt
5881 gtgttcctaa aaaatgcaac aatagaagtg gaaaccctca gtcacgggac attaacctca
5941 accacaaaat gggggttgga gaaagtaacc acatatactg gagatgattc atgggctggg
6001 ggttcccgga caatacaccc atctggagtt caacctaatt acatggtaga taaattaaga
6061 gtccctcctc accactcgaa actatggcag acattctata agataacgag gagagatgag
6121 gtgagggcag aggacattgg gcaggtgtgg gccacggggc agctggccat atcccccgca
6181 ctacagaagt gtaagcaaag tgaagggctc ggaaggcagg cggggcctag caatgtcaca
6241 gctaaatgcc caccagggca cacactcaag cggggtctcg gagctcctag gtcagaccac
6301 gaaaggtcag cctgcaaggt ggatggcgtg ttttctgagg ttatccccgc tacgtgcagt
6361 gctgggtgat agagacccta gaatgtgtcg aaatgaccaa gcgtccccgc agcggggctc
6421 ccaacacggg ttcccagaga gggtaaaaga gggggccata aagcccaggg tgtaaaacac
6481 cgaccgcgcc accagatggc acacgtgggg gaaatgaggg ttagcatagg caaccccgc
6541 ctacacacca actatagcaa accccgcccc gtcacggtga cgtagtctgt cttgaggaga

Fig. 3 (cont.)

6601 tgtagacttg tagacactgc aaaacctcag gacctacgct gccctagagg ttttgctagg
6661 gaggagacgt gtgtggctgt agccacccgt cccgggtaca agtcccgggt ggtgaggacg
6721 gtgtctgtgg ttgtcttccc agactctgct ttctgccgtc ttcggtcaag taccagctgg
6781 tggtccgcat gttttgatcc aaacttttgt tttaggattt atgcatccat tatcccgcag
6841 ttccacctaa acggggctta acgttgcatc ccagaagatg cacgcttaac cccgcctaca
6901 accgtgacgt agctgtttac cagcatgtat agagttacgg ttcgctacat caaacaggac
6961 agccgttgcc ctagtggttt cggacacacc gccaacgctc agtgcggtgc taccgacccg
7021 aggtcaagtc ccgggggagg agaagagagg cttcccgcct agagcatttg caagtcagga
7081 ttctctaatc cctctgggag aagggtattc ggcttgtccg ctattttttt gtggctagtt
7141 ttgcacccac aacatgtaag ggcccgctac ccctacaaca caaaacaaac tatctcccct
7201 aaccatcctt ttgccaatca attctgtgac agggtttcct ggacacccag tcttagttca
7261 ggtagacacc cagttatgca gtgccaccaa ttccaaccat ttttaaacct cctggaattc
7321 tatcattaaa cggcatgcag gaaaaggaca agcagcgaaa attcacgccc ccttgggagg
7381 tggcggcata tgcaaaggat agcactccca ctctactact gggtatcata tgctgactgt
7441 atatgcatga ggatagcata tgctacccgg atacagatta ggatagcata tactacccag
7501 atatagatta ggatagcata tgctacccag atatagatta ggatagccta tgctacccag
7561 atataaatta ggatagcata tactacccag atatagatta ggatagcata tgctacccag
7621 atatagatta ggatagccta tgctacccag atatagatta ggatagcata tgctacccag
7681 atatagatta ggatagcata tgctatccag atatttgggt agtatatgct acccagatat
7741 aaattaggat agcatatact accctaatct ctattaggat agcatatgct acccggatac
7801 agattaggat agcatatact acccagatat agattaggat agcatatgct acccagatat
7861 agattaggat agcctatgct acccagatat aaattaggat agcatatact acccagatat
7921 agattaggat agcatatgct acccagatat agattaggat agcctatgct acccagatat
7981 agattaggat agcatatgct atccagatat ttgggtagta tatgctaccc atggcaacat
8041 tagcccaccg tgctctcagc gacctcgtga atatgaggac caacaaccct gtgcttggcg
8101 ctcaggcgca agtgtgtgta atttgtcctc cagatcgcag caatcgcgcc cctatcttgg
8161 cccgcccacc tacttatgca ggtattcccc ggggtgccat tagtggtttt gtgggcaagt
8221 ggtttgaccg cagtggttag cggggttaca atcagccaag ttattacacc cttattttac
8281 agtccaaaac cgcagggcgg cgtgtggggg ctgacgcgtg cccccactcc acaatttcaa
8341 aaaaaagagt ggccacttgt ctttgtttat gggccccatt ggcgtggagc cccgtttaat
8401 tttcgggggt gttagagaca accagtggag tccgctgctg tcggcgtcca ctctctttcc
8461 ccttgttaca aatagagtgt aacaacatgg ttcacctgtc ttggtccctg cctgggacac
8521 atcttaataa ccccagtatc atattgcact aggattatgt gttgcccata gccataaatt
8581 cgtgtgagat ggacatccag tctttacggc ttgtccccac cccatggatt tctattgtta
8641 aagatattca gaatgtttca ttcctacact agtatttatt gcccaagggg tttgtgaggg
8701 ttatattggt gtcatagcac aatgccacca ctgaaccccc cgtccaaatt ttattctggg
8761 ggcgtcacct gaaaccttgt tttcgagcac ctcacataca ccttactgtt cacaactcag
8821 cagttattct attagctaaa cgaaggagaa tgaagaagca ggcgaagatt caggagagtt
8881 cactgcccgc tccttgatct tcagccactg cccttgtgac taaaatggtt cactaccctc

Fig. 3 (cont.)

8941 gtggaatcct gaccccatgt aaataaaacc gtgacagctc atggggtggg agatatcgct
9001 gttccttagg accctttac taaccctaat tcgatagcat atgcttcccg ttgggtaaca
9061 tatgctattg aattagggtt agtctggata gtatatacta ctacccggga agcatatgct
9121 acccgtttag ggttaacaag gggccttat aaacactatt gctaatgccc tcttgagggt
9181 ccgcttatcg gtagctacac aggcccctct gattgacgtt ggtgtagcct cccgtagtct
9241 tcctgggccc ctgggaggta catgtccccc agcattggtg taagagcttc agccaagagt
9301 tacacataaa ggcaatgttg tgttgcagtc cacagactgc aaagtctgct ccaggatgaa
9361 agccactcag tgttggcaaa tgtgcacatc catttataag gatgtcaact acagtcagag
9421 aacccctttg tgtttggtcc ccccccgtgt cacatgtgga acagggccca gttggcaagt
9481 tgtaccaacc aactgaaggg attacatgca ctgccccgcg ggaaatacgt cctacccagg
9541 aacccgaaac agtgtttccc agaagctgta aaaatagaac gccctggaac tgccccactg
9601 tgcaatgcag cttttagcca tgccatgctc tataaatcac ttccctatct caggtaggcc
9661 tgcacacctt aggtatggag cgaaggttag tggtcactct gcagtgcctg gtgctgcttt
9721 acctggcacc tgagtgtgga ggtacagacc aatgtgacaa ttttccccaa atgttgaggg
9781 acctaagaga tgccttcagt cgtgttaaaa cctttttcca gacaaaggac gaggtagata
9841 accttttgct caaggagtct ctgctagagg actttaaggg ctaccttgga tgccaggccc
9901 tgtcagaaat gatccaattc tacctggagg aagtcatgcc acaggctgaa aaccaggacc
9961 ctgaagccaa agaccatgtc aattctttgg gtgaaaatct aaagacccta cggctccgcc
10021 tgcgcaggtg ccacaggttc ctgccgtgtg agaacaagag taaagctgtg gaacagataa
10081 aaaatgcctt taacaagctg caggaaaaag gaatttacaa agccatgagt gaatttgaca
10141 tttttattaa ctacatagaa gcatacatga caattaaagc caggtgataa ttccataccc
10201 tggaagcagg agatgggtgc atttcacccc aacccccccct ttcgactgtc atttacaata
10261 aaatgaaacc ttttattctt gattgcctct tgtgttcttg ccgcccaggt accttcctgt
10321 gttctcccca cgggaaaaag aatagcttct gcagaaggcc attgacgcaa gttttgcccg
10381 tggggattac ccgacccagc cacttacagc acatttgtt ctaggtccat cttaggagcc
10441 cgggccagca ttctatcagc ttaacgggaa gagaagtggg gagggcactc gcccactaac
10501 cttaacacct gcagcctaca aaagtacact agctgtttgc tctattcgcc actagagacc
10561 gccaagatgc gaaactacag gcccgggccc aggccttgca gggcagacgg ttaggctgac
10621 aaggggacaa gtgtggcagg tggcgggaa ggggcacaag aatgccggcg aaactggacc
10681 acggtccacc ccgccctcaa gcgtccggga gccgggcggc tcggctaagg agggcggcct
10741 tgcgaacaat tattagtagc taccaacaag ggcccccaga tgcccccccac cagtcacccg
10801 gccgtgtcca ctcacatatt ccactcttat ttttaaatta atgtgtccca attagaaacc
10861 caagcgcaga aattagttga gaggctagtg ttttaaacat gcaccctagg ccagccagag
10921 ataatgtcac aagattatca agttggtgta aacacgccgt gggaaaaaat ttatggttca
10981 gtgcgtcgag tgctatcttt ggaacagtag aaaattgaac cttgttggcg ggagaaggaa
11041 taacgcctta tctgggagga gcgacggatt atagccaata agagagctca agacgcaggg
11101 ctcgcaaagt atagtggccc cgtgggacct tagaggtgga gcaacgtcta aagtggtaat
11161 aacaccaggc ggggctgggc aaagggggtcc tacgggcggg attaattacg ccttgcttac
11221 gcaagctcag ttaattcgcc cacgacttga aaaatgtagc ccttaaccaa ttggcggccc

Fig. 3 (cont.)

11281 ctaaggggggg gactaaggtc ccactacaaa aactctgtgt tctgctgcaa attttagatc
11341 agatggcata gagacaagga caccgaagac ccccagagcc ctcatcgcag ggttcttacc
11401 atgcggccat gtaggcccac ttaacactac aagacctacg cctctccatt catcatgtaa
11461 cccacaaatc atctaaaccg taagtctaag ggcctcctga ggttttctca ggaggcccta
11521 atgtataatt aatcatgcat ttgattttaa aaaagtaggt tacactcatt ttaggccaga
11581 ctttatttgc agattaataa tttatgtgat tctccttccc tctaggactg aagaaacagc
11641 ctcctgcacg tgagcatgta tctgaaataa ttattatgtc ataagtgtaa tgattagaaa
11701 gtcataaacc cacttccctt tacatgaatc tgggcactga attttggggt acttctaaag
11761 actaacgtgt tcgatttcgg ggtcacttcc ccttttataa gtgtgtgaac agtgatttca
11821 gtaaaaccta agagatattt ggtgtcactt ccgcatttta agtttcagaa aattttaaaa
11881 ttaaaattga aatttctctc aaaataattc caatgaaaac ttcaaagaat cttatgtatg
11941 taattctttt gccccaaact gggcttcaga tgccttctat tgcactctca caaaaacatt
12001 ctggacacat gtgccagacg cctgggcctc taaggccctc gggtccccct ggaccccggc
12061 ctcagcaacc ctgctgctcc cctcctgcca ccccagcctc ccccctccc cgtccccctt
12121 cgctcctgtt cctcccccgg tccccagtag ggccgcctgc ccccctgcac ccagtacctg
12181 cccctcttgg ccacgcaccc cgggccaggc caccttagac ccggccaagc cccatccctg
12241 aagacccagc ggccattctc tctggtaacg agcagagaag aagtagaggc ccgcggccat
12301 tgggcccaga ttgagagacc agtccagggg cccgaggttg gagccagcgg gcacccgagg
12361 tcccagcacc cggtccctcc ggggggcaga gacaggcagg gcccccggc agctggcccc
12421 gaggaggcgc ccggagtggg gccggtcggc tgggctggcc gagcccgggt ctgggaggtc
12481 tggggtggcg agcctgctgt ctcaggaggg gcctggctcc gccgggtggc cctggggtaa
12541 gtctgggagg cagagggtcg gcctaggccc ggggaagtgg agggggatcg cccgggtctc
12601 tgttggcaga gtccgggcga tcctctgaga ccctccgggc ccggacggtc gccctcagcc
12661 ccccagacag accccagggt ctccaggcag ggtccggcat cttcaggggc agcaggctca
12721 ccaccacagg ccccccagac ccgggtctcg gccagccgag ccgaccggcc ccgcgcctgg
12781 cgcctcctcg gggccagccg ccggggttgg ttctgcccct ctctctgtcc ttcagaggaa
12841 ccagggacct cgggcacccc agagcccctc gggcccgcct ccaggcgccc tcctggtctc
12901 cgctcccctc tgagccccgt taaacccaaa gaatgtctga ggggagccac cctcggggcc
12961 caggccccag agtccagagg tcaggggcac ctcagggtgc ctcccgggt cccaggccag
13021 ccggagggac cccggcagcc cgggcggccc cagaggccgg ttcctcgccc cttccccggg
13081 cttcagagcc caggatgtcc cccagaaggg accctaggcg tcccctctcc tcccctccag
13141 gcccgagcct ctccctcgcg gagaggggcc tctttgggcc ctcaagtcca gccccaccga
13201 gacccgagtg gcccggatcc ccccaccggc ccttctctct gtccccctgc tcctctccaa
13261 ccttcgctcc accctagacc ccagcttctg gcctccccgg gtccaccagg ccagccggag
13321 ggaccccggc agcccgggcg agtcgccttc cctctcccct ggcctctcct tcccgcctcc
13381 cacccgagcc ccctcagctt gcctccccac cgggtccatc aggccggccg gagggacccc
13441 ggcggcccgg tgtcagtccc ccctgcagcc gcccagtctc tgcctccagg caagggcgcc
13501 agcttttctc cccccagcct gaggcccagt ctcctgtgca ctgtctgtaa agtccagcct
13561 cccacgcccg tccacggctc ccgggcccag cctcgtccac ccctccccac ggtggacagg

Fig. 3 (cont.)

13621 ccctctgtcc acccgggcca tccccgcccc cctgtgtcca ccccagtccc gtccaggggg
13681 gactttatgt gacccttggg cctggctccc catagactcc catgtaagcc tgcctcgagt
13741 aggtgcctcc agagcccctt ttgcccccct ggcggcccag cccgaccccc gggcgccccc
13801 aaactttgtc cagatgtcca ggggtccccg agggtgaggc ccagcccccct cccgcccctg
13861 tccactgccc cggtcccccc agaagccccc aaaagtagag gctcaggcca tgcgcgccct
13921 gtcaccaggc ctgccaaaga gccagatcta aggccgggag aggcagcccc aaagcgggtg
13981 cagtaacagg taatctctgg tagtgatttg gacccgaaat ctgacacttt agagctctgg
14041 aggactttaa aactctaaaa atcaaaactt tagaggcgaa tgggcgccat tttgtcccca
14101 cgcgcgcata atggcggacc taggcctaaa acccccagga agcgggtcta tggttggctg
14161 cgctgctgct atctttagag gggaaaagag gaataagccc ccagacaggg gagtgggctt
14221 gtttgtgact tcaccaaagg tcagggccca agggggttcg cgttgctagg ccaccttctc
14281 agtccagcgc gtttacgtaa gccagacagc agccaattgt cagttctagg gagggggacc
14341 actgcccctg gtataaagtg gtcctgcagc tatttctggt cgcatcagag cgccaggagt
14401 ccacacaaat gtaagagggg gtcttctacc tctccctagc cctccgcccc ctccaaggac
14461 tcgggcccag tttctaactt ttccccttcc ctccctcgtc ttgccctgcg cccggggcca
14521 ccttcatcac cgtcgctgac tccgccatcc aagcctaggg gagaccgaag tgaaggccct
14581 ggaccaaccc ggcccgggcc ccccggtatc gggccagagg taagtggact ttaatttttt
14641 ctgctaagcc caacactcca ccacacccag gcacacacta cacacaccca cccgtctcag
14701 ggtcccctcg gacagctcct aagaaggcac cggtcgccca gtcctaccag agggggccaa
14761 gaacccagac gagtccgtag aagggtcctc gtccagcaag aagaggaggt ggtaagcggt
14821 tcaccttcag ggtaagtaa cctgacctct ccagggctca cataaaggga ggcttagtat
14881 acatgcttct tgcttttcac aggaacctgg gggctagtct gggtgggatt aggctgcctc
14941 aagttgcatc agccagggct tcatgccctc ctcagttccc tagtccccgg gcttcaggcc
15001 ccctccgtcc ccgtcctcca gagacccggg cttcaggccc tgcctctcct gttacccttt
15061 tagaaccaca gcctggacac atgtgccaga cgccttggcc tctaaggccc tcgggtcccc
15121 ctggaccccg gcctcagcaa ccctgctgct cccctcctgc caccccagcc tcccccccctc
15181 cccgtccccc ttcgctcctg atcctccccc ggtccccagt agggccgcct gcccccctgc
15241 acccagtacc tgcccctctt ggccacgcac cccgggccag gccaccttag acccggccaa
15301 gccccatccc tgaagaccca gcggccattc tctctggtaa cgagcagaga agaagtagag
15361 gcccgcggcc attgggccca gattgagaga ccagtccagg ggcccgaggt tggagccagc
15421 gggcacccga ggtcccagca cccggtccct ccggggggca gagacaggca gggcccccccg
15481 gcagctggcc ccgaggaggc gcccggagtg gggccggtcg gctgggctgg ccgagcccgg
15541 gtctgggagg tctggggtgg cgagcctgct gtctcaggag gggcctggct ccgccgggtg
15601 gccctggggt aagtctggga ggcagagggt cggcctaggc ccggggaagt ggagggggat
15661 cgcccgggtc tctgttggca gagtccgggc gatcctctga gaccctccgg gcccggacgg
15721 tcgccctcag ccccccagac agaccccagg gtctccaggc agggtccggc atcttcaggg
15781 gcagcaggct caccaccaca ggcccccccag acccgggtct cggccagccg agccgaccgg
15841 ccccgcgcct ggcgcctcct cggggccagc cgccggggtt ggttctgccc ctctctctgt
15901 ccttcagagg aaccagggac ctcgggcacc ccagagcccc tcgggcccgc ctccaggcgc

Fig. 3 (cont.)

15961 cctcctggtc tccgctcccc tctgagcccc gttaaaccca aagaatgtct gaggggagcc
16021 accctcgggg cccaggcccc agagtccaga ggtcaggggc acctcagggt gcctccccgg
16081 gtcccaggcc agccggaggg accccggcag cccgggcggc cccagaggcc ggttcctcgc
16141 cccttccccg ggcttcagag cccaggatgt cccccagaag ggaccctagg cgtcccctct
16201 cctcccctcc aggcccgagc ctctccctcg cggagagggg cctctttggg ccctcaagtc
16261 cagccccacc gagacccgag tggcccggat ccccccaccg gcccttctct ctgtcccccct
16321 gctcctctcc aaccttcgct ccaccctaga ccccagcttc tggcctcccc gggtccacca
16381 ggccagccgg agggaccccg gcagcccggg cgagtcgcct tccctctccc ctggcctctc
16441 cttcccgcct cccacccgag ccccctcagc ttgcctcccc accgggtcca tcaggccggc
16501 cggagggacc ccggcggccc ggtgtcagtc ccccctgcag ccgcccagtc tctgcctcca
16561 ggcaagggcg ccagcttttc tccccccagc ctgaggccca gtctcctgtg cactgtctgt
16621 aaagtccagc ctcccacgcc cgtccacggc tcccgggccc agcctcgtcc acccctcccc
16681 acggtggaca ggccctctgt ccacccgggc catccccgcc cccctgtgtc caccccagtc
16741 ccgtccaggg gggactttat gtgacccttg ggcctggctc cccatagact cccatgtaag
16801 cctgcctcga gtaggtgcct ccagagcccc ttttgccccc ctggcggccc agcccgaccc
16861 ccgggcgccc ccaaactttg tccagatgtc caggggtccc cgagggtgag gcccagcccc
16921 ctcccgcccc tgtccactgc cccggtcccc ccagaagccc ccaaaagtag aggctcaggc
16981 catgcgcgcc ctgtcaccag gcctgccaaa gagccagatc taaggccggg agaggcagcc
17041 ccaaagcggg tgcagtaaca ggtaatctct ggtagtgatt tggacccgaa atctgacact
17101 ttagagctct ggaggacttt aaaactctaa aaatcaaaac tttagaggcg aatgggcgcc
17161 attttgtccc cacgcgcgca taatggcgga cctaggccta aaaccccccag gaagcgggtc
17221 tatggttggc tgcgctgctg ctatctttag aggggaaaag aggaataagc ccccagacag
17281 gggagtgggc ttgtttgtga cttcaccaaa ggtcagggcc caagggggtt cgcgttgcta
17341 ggccaccttc tcagtccagc gcgtttacgt aagccagaca gcagccaatt gtcagttcta
17401 gggaggggga ccactgcccc tggtataaag tggtcctgca gctatttctg gtcgcatcag
17461 agcgccagga gtccacacaa atgtaagagg gggtcttcta cctctcccta gccctccgcc
17521 ccctccaagg actcgggccc agtttctaac ttttcccctt ccctccctcg tcttgccctg
17581 cgcccggggc caccttcatc accgtcgctg actccgccat ccaagcctag gggagaccga
17641 agtgaaggcc ctggaccaac ccggcccggg ccccccggta tcgggccaga ggtaagtgga
17701 ctttaatttt ttctgctaag cccaacactc caccacaccc aggcacacac tacacacacc
17761 cacccgtctc agggtcccct cggacagctc ctaagaaggc accggtcgcc cagtcctacc
17821 agaggggggcc aagaacccag acgagtccgt agaagggtcc tcgtccagca agaagaggag
17881 gtggtaagcg gttcaccttc aggggtaagt aacctgacct ctccagggct cacataaagg
17941 gaggcttagt atacatgctt cttgcttttc acaggaacct gggggctagt ctgggtggga
18001 ttaggctgcc tcaagttgca tcagccaggg cttcatgccc tcctcagttc cctagtcccc
18061 gggcttcagg ccccctccgt ccccgtcctc cagagacccg ggcttcaggc cctgcctctc
18121 ctgttaccct tttagaacca cagcctggac acatgtgcca gacgccttgg cctctaaggc
18181 cctcgggtcc ccctggaccc cggcctcagc aaccctgctg ctcccctcct gccaccccag
18241 cctccccccc tccccgtccc ccttcgctcc tgatcctccc ccggtcccca gtagggccgc

Fig. 3 (cont.)

18301 ctgcccccct gcacccagta cctgcccctc ttggccacgc accccgggcc aggccacctt
18361 agacccggcc aagccccatc cctgaagacc cagcggccat tctctctggt aacgagcaga
18421 gaagaagtag aggcccgcgg ccattgggcc cagattgaga gaccagtcca ggggcccgag
18481 gttggagcca gcgggcaccc gaggtcccag cacccggtcc ctccgggggg cagagacagg
18541 cagggccccc cggcagctgg ccccgaggag gcgcccggag tggggccggt cggctgggct
18601 ggccgagccc gggtctggga ggtctggggt ggcgagcctg ctgtctcagg aggggcctgg
18661 ctccgccggg tggccctggg gtaagtctgg gaggcagagg gtcggcctag gcccggggaa
18721 gtggaggggg atcgcccggg tctctgttgg cagagtccgg gcgatcctct gagaccctcc
18781 gggcccggac ggtcgccctc agcccccag acagacccca gggtctccag gcagggtccg
18841 gcatcttcag gggcagcagg ctcaccacca caggcccccc agacccgggt ctcggccagc
18901 cgagccgacc ggccccgcgc ctggcgcctc ctcggggcca gccgccgggg ttggttctgc
18961 ccctctctct gtccttcaga ggaaccaggg acctcgggca ccccagagcc cctcgggccc
19021 gcctccaggc gccctcctgg tctccgctcc cctctgagcc ccgttaaacc caaagaatgt
19081 ctgaggggag ccaccctcgg ggcccaggcc ccagagtcca gaggtcaggg gcacctcagg
19141 gtgcctcccc gggtcccagg ccagccggag ggaccccggc agcccgggcg gccccagagg
19201 ccggttcctc gccccttccc cgggcttcag agcccaggat gtcccccaga agggacccta
19261 ggcgtcccct ctcctcccct ccaggcccga gcctctccct cgcggagagg ggcctctttg
19321 ggccctcaag tccagcccca ccgagacccg agtggcccgg atccccccac cggcccttct
19381 ctctgtcccc ctgctcctct ccaaccttcg ctccacccta gaccccagct tctggcctcc
19441 ccgggtccac caggccagcc ggagggaccc cggcagcccg ggcgagtcgc cttccctctc
19501 ccctggcctc tccttcccgc ctcccacccg agccccctca gcttgcctcc ccaccgggtc
19561 catcaggccg gccggaggga ccccggcggc ccggtgtcag tcccccctgc agccgcccag
19621 tctctgcctc caggcaaggg cgccagcttt tctcccccca gcctgaggcc cagtctcctg
19681 tgcactgtct gtaaagtcca gcctcccacg cccgtccacg gctcccgggc ccagcctcgt
19741 ccacccctcc ccacggtgga caggccctct gtccacccgg gccatccccg ccccccctgtg
19801 tccaccccag tcccgtccag gggggacttt atgtgaccct tgggcctggc tccccataga
19861 ctcccatgta agcctgcctc gagtaggtgc ctccagagcc ccttttgccc ccctggcggc
19921 ccagcccgac ccccgggcgc ccccaaactt tgtccagatg tccaggggtc cccgagggtg
19981 aggcccagcc ccctcccgcc cctgtccact gcccccggtcc ccccagaagc ccccaaaagt
20041 agaggctcag gccatgcgcg ccctgtcacc aggcctgcca aagagccaga tctaaggccg
20101 ggagaggcag ccccaaagcg ggtgcagtaa caggtaatct ctggtagtga tttggacccg
20161 aaatctgaca ctttagagct ctggaggact ttaaaactct aaaaatcaaa actttagagg
20221 cgaatgggcg ccattttgtc cccacgcgcg cataatggcg gacctaggcc taaaaccccc
20281 aggaagcggg tctatggttg gctgcgctgc tgctatcttt agaggggaaa agaggaataa
20341 gcccccagac aggggagtgg gcttgtttgt gacttcacca aaggtcaggg cccaaggggg
20401 ttcgcgttgc taggccacct tctcagtcca gcgcgtttac gtaagccaga cagcagccaa
20461 ttgtcagttc tagggagggg gaccactgcc cctggtataa agtggtcctg cagctatttc
20521 tggtcgcatc agagcgccag gagtccacac aaatgtaaga gggggtcttc tacctctccc
20581 tagccctccg ccccctccaa ggactcgggc ccagtttcta acttttcccc ttccctccct

Fig. 3 (cont.)

20641 cgtcttgccc tgcgcccggg gccaccttca tcaccgtcgc tgactccgcc atccaagcct
20701 aggggagacc gaagtgaagg ccctggacca acccggcccg ggcccccogg tatcgggcca
20761 gaggtaagtg gactttaatt ttttctgcta agcccaacac tccaccacac ccaggcacac
20821 actacacaca cccacccgtc tcagggtccc ctcggacagc tcctaagaag gcaccggtcg
20881 cccagtccta ccagaggggg ccaagaaccc agacgagtcc gtagaagggt cctcgtccag
20941 caagaagagg aggtggtaag cggttcacct tcaggggtaa gtaacctgac ctctccaggg
21001 ctcacataaa gggaggctta gtatacatgc ttcttgcttt tcacaggaac ctgggggcta
21061 gtctgggtgg gattaggctg cctcaagttg catcagccag ggcttcatgc cctcctcagt
21121 tccctagtcc ccgggcttca ggccccctcc gtccccgtcc tccagagacc cgggcttcag
21181 gccctgcctc tcctgttacc cttttagaac cacagcctgg acacatgtgc cagacgcctt
21241 ggcctctaag gccctcgggt ccccctggac cccggcctca gcaaccctgc tgctcccctc
21301 ctgccacccc agcctccccc cctccccgtc ccccttcgct cctgatcctc ccccggtccc
21361 cagtagggcc gcctgccccc ctgcacccag tacctgcccc tcttggccac gcaccccggg
21421 ccaggccacc ttagacccgg ccaagcccca tccctgaaga cccagcggcc attctctctg
21481 gtaacgagca gagaagaagt agaggcccgc ggccattggg cccagattga gagaccagtc
21541 caggggcccg aggttggagc cagcgggcac ccgaggtccc agcacccggt ccctccgggg
21601 ggcagagaca ggcagggccc cccggcagct ggccccgagg aggcgcccgg agtggggccg
21661 gtcggctggg ctggccgagc ccgggtctgg gaggtctggg gtggcgagcc tgctgtctca
21721 ggaggggcct ggctccgccg ggtggccctg gggtaagtct gggaggcaga gggtcggcct
21781 aggcccgggg aagtggaggg ggatcgcccg ggtctctgtt ggcagagtcc gggcgatcct
21841 ctgagaccct ccgggcccgg acggtcgccc tcagcccccc agacagaccc cagggtctcc
21901 aggcagggtc cggcatcttc aggggcagca ggctcaccac cacaggcccc ccagacccgg
21961 gtctcggcca gccgagccga ccggccccgc gcctggcgcc tcctcggggc cagccgccgg
22021 ggttggttct gccccctctct ctgtccttca gaggaaccag ggacctcggg caccccagag
22081 cccctcgggc ccgcctccag gcgccctcct ggtctccgct cccctctgag ccccgttaaa
22141 cccaaagaat gtctgagggg agccaccctc ggggcccagg ccccagagtc cagaggtcag
22201 gggcacctca gggtgcctcc ccgggtccca ggccagccgg agggaccccg gcagcccggg
22261 cggccccaga ggccggttcc tcgccccttc cccgggcttc agagcccagg atgtccccca
22321 gaagggaccc taggcgtccc ctctcctccc ctccaggccc gagcctctcc ctcgcggaga
22381 ggggcctctt tgggccctca agtccagccc caccgagacc cgagtggccc ggatcccccc
22441 accggccctt ctctctgtcc ccctgctcct ctccaacctt cgctccaccc tagaccccag
22501 cttctggcct ccccgggtcc accaggccag ccggagggac cccggcagcc cgggcgagtc
22561 gccttccctc tcccctggcc tctccttccc gcctcccacc cgagccccct cagcttgcct
22621 ccccaccggg tccatcaggc cggccggagg gaccccggcg gcccggtgtc agtccccccct
22681 gcagccgccc agtctctgcc tccaggcaag ggcgccagct tttctccccc cagcctgagg
22741 cccagtctcc tgtgcactgt ctgtaaagtc cagcctccca cgcccgtcca cggctcccgg
22801 gcccagcctc gtccacccct ccccacggtg gacaggccct ctgtccaccc gggccatccc
22861 cgcccccctg tgtccacccc agtcccgtcc aggggggact ttatgtgacc cttgggcctg
22921 gctccccata gactcccatg taagcctgcc tcgagtaggt gcctccagag cccctttgc

Fig. 3 (cont.)

22981 ccccctggcg gcccagcccg acccccgggc gcccccaaac tttgtccaga tgtccagggg
23041 tccccgaggg tgaggcccag ccccctcccg cccctgtcca ctgccccggt ccccccagaa
23101 gcccccaaaa gtagaggctc aggccatgcg cgccctgtca ccaggcctgc caaagagcca
23161 gatctaaggc cgggagaggc agccccaaag cgggtgcagt aacaggtaat ctctggtagt
23221 gatttggacc cgaaatctga cactttagag ctctggagga ctttaaaact ctaaaaatca
23281 aaactttaga ggcgaatggg cgccattttg tccccacgcg cgcataatgg cggacctagg
23341 cctaaaaccc ccaggaagcg ggtctatggt tggctgcgct gctgctatct ttagagggga
23401 aaagaggaat aagcccccag acaggggagt gggcttgttt gtgacttcac caaaggtcag
23461 ggcccaaggg ggttcgcgtt gctaggccac cttctcagtc cagcgcgttt acgtaagcca
23521 gacagcagcc aattgtcagt tctagggagg gggaccactg cccctggtat aaagtggtcc
23581 tgcagctatt tctggtcgca tcagagcgcc aggagtccac acaaatgtaa gagggggtct
23641 tctacctctc cctagccctc cgccccctcc aaggactcgg gcccagtttc taacttttcc
23701 ccttccctcc ctcgtcttgc cctgcgcccg gggccacctt catcaccgtc gctgactccg
23761 ccatccaagc ctaggggaga ccgaagtgaa ggccctggac caacccggcc cgggcccccc
23821 ggtatcgggc cagaggtaag tggactttaa ttttttctgc taagcccaac actccaccac
23881 acccaggcac acactacaca cacccacccg tctcagggtc ccctcggaca gctcctaaga
23941 aggcaccggt cgcccagtcc taccagaggg ggccaagaac ccagacgagt ccgtagaagg
24001 gtcctcgtcc agcaagaaga ggaggtggta agcggttcac cttcaggggt aagtaacctg
24061 acctctccag ggctcacata aagggaggct tagtatacat gcttcttgct tttcacagga
24121 acctgggggc tagtctgggt gggattaggc tgcctcaagt tgcatcagcc agggcttcat
24181 gccctcctca gttccctagt ccccgggctt caggccccct ccgtccccgt cctccagaga
24241 cccgggcttc aggccctgcc tctcctgtta cccttttaga accacagcct ggacacatgt
24301 gccagacgcc ttggcctcta aggccctcgg gtccccctgg accccggcct cagcaaccct
24361 gctgctcccc tcctgccacc ccagcctccc cccctccccg tccccccttcg ctcctgatcc
24421 tcccccggtc cccagtaggg ccgcctgccc ccctgcaccc agtacctgcc cctcttggcc
24481 acgcaccccg ggccaggcca ccttagaccc ggccaagccc catccctgaa gacccagcgg
24541 ccattctctc tggtaacgag cagagaagaa gtagaggccc gcggccattg ggcccagatt
24601 gagagaccag tccaggggcc cgaggttgga gccagcgggc acccgaggtc ccagcacccg
24661 gtccctccgg ggggcagaga caggcagggc cccccggcag ctggccccga ggaggcgccc
24721 ggagtggggc cggtcggctg ggctggccga gcccgggtct gggaggtctg gggtggcgag
24781 cctgctgtct caggaggggc ctggctccgc cgggtggccc tggggtaagt ctgggaggca
24841 gagggtcggc ctaggcccgg ggaagtggag ggggatcgcc cgggtctctg ttggcagagt
24901 ccgggcgatc ctctgagacc ctccgggccc ggacggtcgc cctcagcccc ccagacagac
24961 cccagggtct ccaggcaggg tccggcatct tcaggggcag caggctcacc accacaggcc
25021 ccccagaccc gggtctcggc cagccgagcc gaccggcccc gcgcctggcg cctcctcggg
25081 gccagccgcc ggggttggtt ctgcccctct ctctgtcctt cagaggaacc agggacctcg
25141 ggcaccccag agcccctcgg gcccgcctcc aggcgccctc ctggtctccg ctcccctctg
25201 agccccgtta aacccaaaga atgtctgagg ggagccaccc tcggggccca ggccccagag
25261 tccagaggtc aggggcacct cagggtgcct ccccgggtcc caggccagcc ggagggaccc

Fig. 3 (cont.)

25321 cggcagcccg ggcggcccca gaggccggtt cctcgcccct tccccgggct tcagagccca
25381 ggatgtcccc cagaagggac cctaggcgtc ccctctcctc ccctccaggc ccgagcctct
25441 ccctcgcgga gaggggcctc tttgggccct caagtccagc cccaccgaga cccgagtggc
25501 ccggatcccc ccaccggccc ttctctctgt ccccctgctc ctctccaacc ttcgctccac
25561 cctagacccc agcttctggc ctccccgggt ccaccaggcc agccggaggg accccggcag
25621 cccgggcgag tcgccttccc tctcccctgg cctctccttc ccgcctccca cccgagcccc
25681 ctcagcttgc ctccccaccg ggtccatcag gccggccgga gggaccccgg cggcccggtg
25741 tcagtccccc ctgcagccgc ccagtctctg cctccaggca agggcgccag cttttctccc
25801 cccagcctga ggcccagtct cctgtgcact gtctgtaaag tccagcctcc cacgcccgtc
25861 cacggctccc gggcccagcc tcgtccaccc ctccccacgg tggacaggcc ctctgtccac
25921 ccgggccatc cccgcccccc tgtgtccacc ccagtcccgt ccagggggga ctttatgtga
25981 cccttgggcc tggctcccca tagactccca tgtaagcctg cctcgagtag gtgcctccag
26041 agcccctttt gccccccctgg cggcccagcc cgacccccgg gcgcccccaa actttgtcca
26101 gatgtccagg ggtccccgag ggtgaggccc agccccctcc cgcccctgtc cactgccccg
26161 gtccccccag aagcccccaa aagtagaggc tcaggccatg cgcgccctgt caccaggcct
26221 gccaaagagc cagatctaag gccgggagag gcagccccaa agcgggtgca gtaacaggta
26281 atctctggta gtgatttgga cccgaaatct gacactttag agctctggag gactttaaaa
26341 ctctaaaaat caaaacttta gaggcgaatg ggcgccattt tgtccccacg cgcgcataat
26401 ggcggaccta ggcctaaaac ccccaggaag cgggtctatg gttggctgcg ctgctgctat
26461 ctttagaggg gaaaagagga ataagccccc agacagggga gtgggcttgt ttgtgacttc
26521 accaaaggtc agggcccaag ggggttcgcg ttgctaggcc accttctcag tccagcgcgt
26581 ttacgtaagc cagacagcag ccaattgtca gttctaggga gggggaccac tgcccctggt
26641 ataaagtggt cctgcagcta tttctggtcg catcagagcg ccaggagtcc acacaaatgt
26701 aagagggggt cttctacctc tccctagccc tccgcccccct ccaaggactc gggcccagtt
26761 tctaactttt ccccttccct ccctcgtctt gccctgcgcc cggggccacc ttcatcaccg
26821 tcgctgactc cgccatccaa gcctagggga gaccgaagtg aaggccctgg accaacccgg
26881 cccgggcccc ccggtatcgg gccagaggta agtggacttt aattttttct gctaagccca
26941 acactccacc acacccaggc acacactaca cacacccacc cgtctcaggg tcccctcgga
27001 cagctcctaa gaaggcaccg gtcgcccagt cctaccagag ggggccaaga acccagacga
27061 gtccgtagaa gggtcctcgt ccagcaagaa gaggaggtgg taagcggttc accttcaggg
27121 gtaagtaacc tgacctctcc agggctcaca taaagggagg cttagtatac atgcttcttg
27181 cttttcacag gaacctgggg gctagtctgg gtgggattag gctgcctcaa gttgcatcag
27241 ccagggcttc atgccctcct cagttcccta gtccccgggc ttcaggcccc ctccgtcccc
27301 gtcctccaga gacccgggct tcaggccctg cctctcctgt taccctttta gaaccacagc
27361 ctggacacat gtgccagacg ccttggcctc taaggccctc gggtccccct ggaccccggc
27421 ctcagcaacc ctgctgctcc cctcctgcca ccccagcctc cccccctccc cgtcccccctt
27481 cgctcctgat cctccccccgg tccccagtag ggccgcctgc cccccctgcac ccagtacctg
27541 cccctcttgg ccacgcaccc cgggccaggc caccttagac ccggccaagc cccatccctg
27601 aagacccagc ggccattctc tctggtaacg agcagagaag aagtagaggc ccgcggccat

Fig. 3 (cont.)

27661 tgggcccaga ttgagagacc agtccagggg cccgaggttg gagccagcgg gcacccgagg
27721 tcccagcacc cggtccctcc ggggggcaga gacaggcagg gcccccggc agctggcccc
27781 gaggaggcgc ccggagtggg gccggtcggc tgggctggcc gagcccgggt ctgggaggtc
27841 tggggtggcg agcctgctgt ctcaggaggg gcctggctcc gccgggtggc cctggggtaa
27901 gtctgggagg cagagggtcg gcctaggccc ggggaagtgg agggggatcg cccgggtctc
27961 tgttggcaga gtccgggcga tcctctgaga ccctccgggc ccggacggtc gccctcagcc
28021 ccccagacag accccagggt ctccaggcag ggtccggcat cttcaggggc agcaggctca
28081 ccaccacagg ccccccagac ccgggtctcg gccagccgag ccgaccggcc ccgcgcctgg
28141 cgcctcctcg gggccagccg ccggggttgg ttctgcccct ctctctgtcc ttcagaggaa
28201 ccagggacct cgggcacccc agagcccctc gggcccgcct ccaggcgccc tcctggtctc
28261 cgctcccctc tgagccccgt taaacccaaa gaatgtctga ggggagccac cctcggggcc
28321 caggccccag agtccagagg tcaggggcac ctcagggtgc ctccccgggt cccaggccag
28381 ccggagggac cccggcagcc cgggcggccc cagaggccgg ttcctcgccc cttccccggg
28441 cttcagagcc caggatgtcc cccagaaggg accctaggcg tcccctctcc tcccctccag
28501 gcccgagcct ctccctcgcg gagaggggcc tctttgggcc ctcaagtcca gccccaccga
28561 gacccgagtg gcccggatcc ccccaccggc ccttctctct gtccccctgc tcctctccaa
28621 ccttcgctcc accctagacc ccagcttctg gcctccccgg gtccaccagg ccagccggag
28681 ggaccccggc agcccgggcg agtcgccttc cctctcccct ggcctctcct tcccgcctcc
28741 cacccgagcc ccctcagctt gcctccccac cgggtccatc aggccggccg gagggacccc
28801 ggcggcccgg tgtcagtccc ccctgcagcc gcccagtctc tgcctccagg caagggcgcc
28861 agcttttctc cccccagcct gaggcccagt ctcctgtgca ctgtctgtaa agtccagcct
28921 cccacgcccg tccacggctc ccgggcccag cctcgtccac ccctccccac ggtggacagg
28981 ccctctgtcc acccgggcca tccccgcccc cctgtgtcca ccccagtccc gtccaggggg
29041 gactttatgt gacccttggg cctggctccc catagactcc catgtaagcc tgcctcgagt
29101 aggtgcctcc agagcccctt ttgccccccct ggcggcccag cccgaccccc gggcgccccc
29161 aaactttgtc cagatgtcca ggggtccccg agggtgaggc ccagccccct cccgcccctg
29221 tccactgccc cggtcccccc agaagccccc aaaagtagag gctcaggcca tgcgcgccct
29281 gtcaccaggc ctgccaaaga gccagatcta aggccgggag aggcagcccc aaagcgggtg
29341 cagtaacagg taatctctgg tagtgatttg gacccgaaat ctgacacttt agagctctgg
29401 aggactttaa aactctaaaa atcaaaactt tagaggcgaa tgggcgccat tttgtcccca
29461 cgcgcgcata atggcggacc taggcctaaa acccccagga agcgggtcta tggttggctg
29521 cgctgctgct atctttagag gggaaaagag gaataagccc ccagacaggg gagtgggctt
29581 gtttgtgact tcaccaaagg tcagggccca agggggttcg cgttgctagg ccaccttctc
29641 agtccagcgc gtttacgtaa gccagacagc agccaattgt cagttctagg gagggggacc
29701 actgcccctg gtataaagtg gtcctgcagc tatttctggt cgcatcagag cgccaggagt
29761 ccacacaaat gtaagagggg gtcttctacc tctccctagc cctccgcccc ctccaaggac
29821 tcgggcccag tttctaactt ttccccttcc ctccctcgtc ttgccctgcg cccggggcca
29881 ccttcatcac cgtcgctgac tccgccatcc aagcctaggg gagaccgaag tgaaggccct
29941 ggaccaaccc ggcccgggcc ccccggtatc gggccagagg taagtggact ttaatttttt

Fig. 3 (cont.)

30001 ctgctaagcc caacactcca ccacacccag gcacacacta cacacaccca cccgtctcag
30061 ggtcccctcg gacagctcct aagaaggcac cggtcgccca gtcctaccag agggggccaa
30121 gaacccagac gagtccgtag aagggtcctc gtccagcaag aagaggaggt ggtaagcggt
30181 tcaccttcag gggtaagtaa cctgacctct ccagggctca cataaaggga ggcttagtat
30241 acatgcttct tgcttttcac aggaacctgg gggctagtct gggtgggatt aggctgcctc
30301 aagttgcatc agccagggct tcatgccctc ctcagttccc tagtccccgg gcttcaggcc
30361 ccctccgtcc ccgtcctcca gagacccggg cttcaggccc tgcctctcct gttacccttt
30421 tagaaccaca gcctggacac atgtgccaga cgccttggcc tctaaggccc tcgggtcccc
30481 ctggaccccg gcctcagcaa ccctgctgct cccctcctgc caccccagcc tccccccctc
30541 cccgtccccc ttcgctcctg atcctccccc ggtccccagt agggccgcct gcccccctgc
30601 acccagtacc tgcccctctt ggccacgcac cccgggccag gccaccttag acccggccaa
30661 gccccatccc tgaagaccca gcggccattc tctctggtaa cgagcagaga agaagtagag
30721 gcccgcggcc attgggccca gattgagaga ccagtccagg ggcccgaggt tggagccagc
30781 gggcacccga ggtcccagca cccggtccct ccggggggca gagacaggca gggccccccg
30841 gcagctggcc ccgaggaggc gccccggagtg gggccggtcg gctgggctgg ccgagcccgg
30901 gtctgggagg tctggggtgg cgagcctgct gtctcaggag gggcctggct ccgccgggtg
30961 gccctggggt aagtctggga ggcagagggt cggcctaggc ccggggaagt ggagggggat
31021 cgcccgggtc tctgttggca gagtccgggc gatcctctga gaccctccgg gcccggacgg
31081 tcgccctcag ccccccagac agaccccagg gtctccaggc agggtccggc atcttcaggg
31141 gcagcaggct caccaccaca ggccccccag acccgggtct cggccagccg agccgaccgg
31201 ccccgcgcct ggcgcctcct cggggccagc cgccggggtt ggttctgccc ctctctctgt
31261 ccttcagagg aaccagggac ctcgggcacc ccagagcccc tcgggcccgc ctccaggcgc
31321 cctcctggtc tccgctcccc tctgagcccc gttaaaccca aagaatgtct gaggggagcc
31381 accctcgggg cccaggcccc agagtccaga ggtcaggggc acctcagggt gcctccccgg
31441 gtcccaggcc agccggaggg accccggcag cccgggcggc cccagaggcc ggttcctcgc
31501 cccttccccg ggcttcagag cccaggatgt cccccagaag ggaccctagg cgtcccctct
31561 cctcccctcc aggcccgagc ctctccctcg cggagagggg cctctttggg ccctcaagtc
31621 cagccccacc gagacccgag tggcccggat ccccccaccg gcccttctct ctgtccccct
31681 gctcctctcc aaccttcgct ccaccctaga ccccagcttc tggcctcccc gggtccacca
31741 ggccagccgg agggaccccg gcagcccggg cgagtcgcct tccctctccc ctggcctctc
31801 cttcccgcct cccacccgag ccccctcagc ttgcctcccc accgggtcca tcaggccggc
31861 cggagggacc ccggcggccc ggtgtcagtc ccccctgcag ccgcccagtc tctgcctcca
31921 ggcaagggcg ccagcttttc tccccccagc ctgaggccca gtctcctgtg cactgtctgt
31981 aaagtccagc ctcccacgcc cgtccacggc tcccgggccc agcctcgtcc acccctcccc
32041 acggtggaca ggccctctgt ccacccgggc catccccgcc cccctgtgtc caccccagtc
32101 ccgtccaggg gggactttat gtgacccttg ggcctggctc cccatagact cccatgtaag
32161 cctgcctcga gtaggtgcct ccagagcccc ttttgccccc ctggcggccc agcccgaccc
32221 ccgggcgccc ccaaactttg tccagatgtc caggggtccc cgagggtgag gcccagcccc
32281 ctcccgcccc tgtccactgc cccggtcccc ccagaagccc ccaaaagtag aggctcaggc

Fig. 3 (cont.)

32341 catgcgcgcc ctgtcaccag gcctgccaaa gagccagatc taaggccggg agaggcagcc
32401 ccaaagcggg tgcagtaaca ggtaatctct ggtagtgatt tggacccgaa atctgacact
32461 ttagagctct ggaggacttt aaaactctaa aaatcaaaac tttagaggcg aatgggcgcc
32521 atttgtccc cacgcgcgca taatggcgga cctaggccta aaaccccag gaagcgggtc
32581 tatggttggc tgcgctgctg ctatctttag aggggaaaag aggaataagc ccccagacag
32641 gggagtgggc ttgtttgtga cttcaccaaa ggtcagggcc caagggggtt cgcgttgcta
32701 ggccaccttc tcagtccagc gcgtttacgt aagccagaca gcagccaatt gtcagttcta
32761 gggagggga ccactgcccc tggtataaag tggtcctgca gctatttctg gtcgcatcag
32821 agcgccagga gtccacacaa atgtaagagg gggtcttcta cctctcccta gccctccgcc
32881 ccctccaagg actcgggccc agtttctaac ttttcccctt ccctccctcg tcttgccctg
32941 cgcccggggc caccttcatc accgtcgctg actccgccat ccaagcctag gggagaccga
33001 agtgaaggcc ctggaccaac ccggcccggg ccccccggta tcgggccaga ggtaagtgga
33061 ctttaatttt ttctgctaag cccaacactc caccacaccc aggcacacac tacacacacc
33121 cacccgtctc agggtcccct cggacagctc ctaagaaggc accggtcgcc cagtcctacc
33181 agaggggcc aagaacccag acgagtccgt agaagggtcc tcgtccagca agaagaggag
33241 gtggtaagcg gttcaccttc aggggtaagt aacctgacct ctccagggct cacataaagg
33301 gaggcttagt atacatgctt cttgcttttc acaggaacct gggggctagt ctgggtggga
33361 ttaggctgcc tcaagttgca tcagccaggg cttcatgccc tcctcagttc cctagtcccc
33421 gggcttcagg ccccctccgt ccccgtcctc cagagacccg ggcttcaggc cctgcctctc
33481 ctgttaccct tttagaacca cagcctggac acatgtgcca gacgccttgg cctctaaggc
33541 cctcgggtcc ccctggaccc cggcctcagc aaccctgctg ctcccctcct gccaccccag
33601 cctcccccc tccccgtccc ccttcgctcc tgatcctccc ccggtcccca gtagggccgc
33661 ctgcccccct gcacccagta cctgcccctc ttggccacgc accccgggcc aggccacctt
33721 agacccggcc aagccccatc cctgaagacc cagcggccat tctctctggt aacgagcaga
33781 gaagaagtag aggcccgcgg ccattgggcc cagattgaga gaccagtcca ggggcccgag
33841 gttggagcca gcgggcaccc gaggtcccag cacccggtcc ctccgggggg cagagacagg
33901 cagggccccc cggcagctgg ccccgaggag gcgcccggag tggggccggt cggctgggct
33961 ggccgagccc gggtctggga ggtctggggt ggcgagcctg ctgtctcagg aggggcctgg
34021 ctccgccggg tggccctggg gtaagtctgg gaggcagagg gtcggcctag gcccggggaa
34081 gtggaggggg atcgcccggg tctctgttgg cagagtccgg gcgatcctct gagaccctcc
34141 gggcccggac ggtcgccctc agcccccag acagacccca gggtctccag gcagggtccg
34201 gcatcttcag gggcagcagg ctcaccacca caggcccccc agacccgggt ctcggccagc
34261 cgagccgacc ggccccgcgc ctggcgcctc ctcggggcca gccgccgggg ttggttctgc
34321 ccctctctct gtccttcaga ggaaccaggg acctcgggca ccccagagcc cctcgggccc
34381 gcctccaggc gccctcctgg tctccgctcc cctctgagcc ccgttaaacc caaagaatgt
34441 ctgaggggag ccaccctcgg ggcccaggcc ccagagtcca gaggtcaggg gcacctcagg
34501 gtgcctcccc gggtcccagg ccagccggag ggaccccggc agcccgggcg gccccagagg
34561 ccggttcctc gccccttccc cgggcttcag agcccaggat gtcccccaga agggacccta
34621 ggcgtcccct ctcctcccct ccaggcccga gcctctccct cgcggagagg ggcctctttg

Fig. 3 (cont.)

34681 ggccctcaag tccagcccca ccgagacccg agtggcccgg atccccccac cggcccttct
34741 ctctgtcccc ctgctcctct ccaaccttcg ctccacccta gaccccagct tctggcctcc
34801 ccgggtccac caggccagcc ggagggaccc cggcagcccg ggcgagtcgc cttccctctc
34861 ccctggcctc tccttcccgc ctcccacccg agccccctca gcttgcctcc ccaccgggtc
34921 catcaggccg gccggaggga ccccggcggc ccggtgtcag tccccccctgc agccgcccag
34981 tctctgcctc caggcaaggg cgccagcttt tctcccccca gcctgaggcc cagtctcctg
35041 tgcactgtct gtaaagtcca gcctcccacg cccgtccacg gctcccgggc ccagcctcgt
35101 ccacccctcc ccacggtgga caggccctct gtccacccgg gccatccccg cccccctgtg
35161 tccaccccag tcccgtccag gggggacttt atgtgaccct tgggcctggc tccccataga
35221 ctcccatgta agcctgcctc gagtaggtgc ctccagagcc ccttttgccc ccctggcggc
35281 ccagcccgac ccccgggcgc ccccaaactt tgtccagatg tccaggggtc cccgagggtg
35341 aggcccagcc ccctcccgcc cctgtccact gccccggtcc ccccagaagc ccccaaaagt
35401 agaggctcag gccatgcgcg ccctgtcacc aggcctgcca aagagccaga tctaaggccg
35461 ggagaggcag ccccaaagcg ggtgcagtaa caggtaatct ctggtagtga tttggacccg
35521 aaatctgaca ctttagagct ctggaggact ttaaaactct aaaaatcaaa actttagagg
35581 cgaatgggcg ccattttgtc cccacgcgcg cataatggcg gacctaggcc taaaaccccc
35641 aggaagcggg tctatggttg gctgcgctgc tgctatcttt agaggggaaa agaggaataa
35701 gcccccagac aggggagtgg gcttgtttgt gacttcacca aaggtcaggg cccaaggggg
35761 ttcgcgttgc taggccacct tctcagtcca gcgcgtttac gtaagccaga cagcagccaa
35821 ttgtcagttc tagggagggg gaccactgcc cctggtataa agtggtcctg cagctatttc
35881 tggtcgcatc agagcgccag gagtccacac aaatgtaaga gggggtcttc tacctctccc
35941 tagccctccg ccccctccaa ggactcgggc ccagtttcta actttcccc ttccctccct
36001 cgtcttgccc tgcgcccggg gccaccttca tcaccgtcgc tgactccgcc atccaagcct
36061 aggggagacc gaagtgaagg ccctggacca acccggcccg ggccccccgg tatcgggcca
36121 gaggtaagtg gactttaatt ttttctgcta agcccaacac tccaccacac ccaggcacac
36181 actacacaca cccacccgtc tcagggtccc ctcggacagc tcctaagaag gcaccggtcg
36241 cccagtccta ccagaggggg ccaagaaccc agacgagtcc gtagaagggt cctcgtccag
36301 caagaagagg aggtggtaag cggttcacct tcaggggtaa gtaacctgac ctctccaggg
36361 ctcacataaa gggaggctta gtatacatgc ttcttgcttt tcacaggaac ctgggggcta
36421 gtctgggtgg gattaggctg cctcaagttg catcagccag ggcttcatgc cctcctcagt
36481 tccctagtcc ccgggcttca ggccccctcc gtccccgtcc tccagagacc cgggcttcag
36541 gccctgcctc tcctgttacc cttttagaac cacagcctgg acacatgtgc cagacgcctt
36601 ggcctctaag gccctcgggt ccccctggac cccggcctca gcaaccctgc tgctcccctc
36661 ctgccacccc agcctccccc cctccccgtc cccctcgct cctgatcctc ccccggtccc
36721 cagtagggcc gcctgccccc ctgcacccag tacctgcccc tcttggccac gcaccccggg
36781 ccaggccacc ttagacccgg ccaagcccca tccctgaaga cccagcggcc attctctctg
36841 gtaacgagca gagaagaagt agaggcccgc ggccattggg cccagattga gagaccagtc
36901 caggggcccg aggttggagc cagcgggcac ccgaggtccc agcacccggt ccctccgggg
36961 ggcagagaca ggcagggccc cccggcagct ggccccgagg aggcgcccgg agtggggccg

Fig. 3 (cont.)

37021 gtcggctggg ctggccgagc ccgggtctgg gaggtctggg gtggcgagcc tgctgtctca
37081 ggaggggcct ggctccgccg ggtggccctg gggtaagtct gggaggcaga gggtcggcct
37141 aggcccgggg aagtggaggg ggatcgcccg ggtctctgtt ggcagagtcc gggcgatcct
37201 ctgagaccct ccgggcccgg acggtcgccc tcagcccccc agacagaccc cagggtctcc
37261 aggcagggtc cggcatcttc aggggcagca ggctcaccac cacaggcccc ccagacccgg
37321 gtctcggcca gccgagccga ccggccccgc gcctggcgcc tcctcggggc cagccgccgg
37381 ggttggttct gcccctctct ctgtccttca gaggaaccag ggacctcggg caccccagag
37441 cccctcgggc ccgcctccag gcgccctcct ggtctccgct cccctctgag ccccgttaaa
37501 cccaaagaat gtctgagggg agccaccctc ggggcccagg ccccagagtc cagaggtcag
37561 gggcacctca gggtgcctcc ccgggtccca ggccagccgg agggaccccg gcagcccggg
37621 cggccccaga ggccggttcc tcgccccttc cccgggcttc agagcccagg atgtccccca
37681 gaagggaccc taggcgtccc ctctcctccc ctccaggccc gagcctctcc ctcgcggaga
37741 ggggcctctt tgggccctca agtccagccc caccgagacc cgagtggccc ggatcccccc
37801 accggccctt ctctctgtcc ccctgctcct ctccaacctt cgctccaccc tagaccccag
37861 cttctggcct ccccgggtcc accaggccag ccggagggac cccggcagcc cgggcgagtc
37921 gccttccctc tcccctggcc tctccttccc gcctcccacc cgagccccct cagcttgcct
37981 ccccaccggg tccatcaggc cggccggagg gaccccggcg gcccggtgtc agtccccccct
38041 gcagccgccc agtctctgcc tccaggcaag ggcgccagct tttctccccc cagcctgagg
38101 cccagtctcc tgtgcactgt ctgtaaagtc cagcctccca cgcccgtcca cggctcccgg
38161 gcccagcctc gtccacccct ccccacggtg gacaggccct ctgtccaccc gggccatccc
38221 cgcccccctg tgtccacccc agtcccgtcc agggggggact ttatgtgacc cttgggcctg
38281 gctccccata gactcccatg taagcctgcc tcgagtaggt gcctccagag ccccttttgc
38341 ccccctggcg gcccagcccg acccccgggc gcccccaaac tttgtccaga tgtccagggg
38401 tccccgaggg tgaggcccag ccccctcccg cccctgtcca ctgccccggt ccccccagaa
38461 gcccccaaaa gtagaggctc aggccatgcg cgccctgtca ccaggcctgc caaagagcca
38521 gatctaaggc cgggagaggc agccccaaag cgggtgcagt aacaggtaat ctctggtagt
38581 gatttggacc cgaaatctga cactttagag ctctggagga ctttaaaact ctaaaaatca
38641 aaactttaga ggcgaatggg cgccattttg tccccacgcg cgcataatgg cggacctagg
38701 cctaaaaccc ccaggaagcg ggtctatggt tggctgcgct gctgctatct ttagagggga
38761 aaagaggaat aagcccccag acaggggagt gggcttgttt gtgacttcac caaaggtcag
38821 ggcccaaggg ggttcgcgtt gctaggccac cttctcagtc cagcgcgttt acgtaagcca
38881 gacagcagcc aattgtcagt tctagggagg gggaccactg cccctggtat aaagtggtcc
38941 tgcagctatt tctggtcgca tcagagcgcc aggagtccac acaaatgtaa gagggggtct
39001 tctacctctc cctagccctc cgccccctcc aaggactcgg gcccagtttc taacttttcc
39061 ccttccctcc ctcgtcttgc cctgcgcccg gggccacctt catcaccgtc gctgactccg
39121 ccatccaagc ctaggggaga ccgaagtgaa ggccctggac caacccggcc cgggcccccc
39181 ggtatcgggc cagaggtaag tggactttaa ttttttctgc taagcccaac actccaccac
39241 acccaggcac acactacaca cacccacccg tctcagggtc ccctcggaca gctcctaaga
39301 aggcaccggt cgcccagtcc taccagaggg ggccaagaac ccagacgagt ccgtagaagg

Fig. 3 (cont.)

39361 gtcctcgtcc agcaagaaga ggaggtggta agcggttcac cttcaggggt aagtaacctg
39421 acctctccag ggctcacata aagggaggct tagtatacat gcttcttgct tttcacagga
39481 acctgggggc tagtctgggt gggattaggc tgcctcaagt tgcatcagcc agggcttcat
39541 gccctcctca gttccctagt ccccgggctt caggccccct ccgtccccgt cctccagaga
39601 cccgggcttc aggccctgcc tctcctgtta cccttttaga accacagcct ggacacatgt
39661 gccagacgcc ttggcctcta aggccctcgg gtcccccctgg accccggcct cagcaaccct
39721 gctgctcccc tcctgccacc ccagcctccc cccctccccg tccccccttcg ctcctgatcc
39781 tcccccggtc cccagtaggg ccgcctgccc ccctgcaccc agtacctgcc cctcttggcc
39841 acgcaccccg ggccaggcca ccttagaccc ggccaagccc catccctgaa gacccagcgg
39901 ccattctctc tggtaacgag cagagaagaa gtagaggccc gcggccattg ggcccagatt
39961 gagagaccag tccaggggcc cgaggttgga gccagcgggc acccgaggtc ccagcacccg
40021 gtccctccgg ggggcagaga caggcagggc cccccggcag ctggccccga ggaggcgccc
40081 ggagtggggc cggtcggctg ggctggccga gcccgggtct gggaggtctg gggtggcgag
40141 cctgctgtct caggaggggc ctggctccgc cgggtggccc tggggtaagt ctgggaggca
40201 gagggtcggc ctaggcccgg ggaagtggag ggggatcgcc cgggtctctg ttggcagagt
40261 ccgggcgatc ctctgagacc ctccgggccc ggacggtcgc cctcagcccc ccagacagac
40321 cccagggtct ccaggcaggg tccggcatct tcaggggcag caggctcacc accacaggcc
40381 ccccagaccc gggtctcggc cagccgagcc gaccggcccc gcgcctggcg cctcctcggg
40441 gccagccgcc ggggttggtt ctgcccctct ctctgtcctt cagaggaacc agggacctcg
40501 ggcaccccag agcccctcgg gcccgcctcc aggcgccctc ctggtctccg ctcccctctg
40561 agccccgtta aacccaaaga atgtctgagg ggagccaccc tcggggccca ggccccagag
40621 tccagaggtc aggggcacct cagggtgcct ccccgggtcc caggccagcc ggagggaccc
40681 cggcagcccg ggcggcccca gaggccggtt cctcgcccct tccccgggct tcagagccca
40741 ggatgtcccc cagaagggac cctaggcgtc ccctctcctc ccctccaggc ccgagcctct
40801 ccctcgcgga gaggggcctc tttgggccct caagtccagc cccaccgaga cccgagtggc
40861 ccggatcccc ccaccggccc ttctctctgt ccccctgctc ctctccaacc ttcgctccac
40921 cctagacccc agcttctggc ctccccgggt ccaccaggcc agccggaggg accccggcag
40981 cccgggcgag tcgccttccc tctcccctgg cctctccttc ccgcctccca cccgagcccc
41041 ctcagcttgc ctccccaccg ggtccatcag gccggccgga gggaccccgg cggcccggtg
41101 tcagtccccc ctgcagccgc ccagtctctg cctccaggca agggcgccag cttttctccc
41161 cccagcctga ggcccagtct cctgtgcact gtctgtaaag tccagcctcc cacgcccgtc
41221 cacggctccc gggcccagcc tcgtccaccc ctccccacgg tggacaggcc ctctgtccac
41281 ccgggccatc cccgcccccc tgtgtccacc ccagtcccgt ccagggggga ctttatgtga
41341 ccccttgggcc tggctcccca tagactccca tgtaagcctg cctcgagtag gtgcctccag
41401 agcccctttt gcccccctgg cggcccagcc cgaccccccgg gcgcccccaa actttgtcca
41461 gatgtccagg ggtccccgag ggtgaggccc agccccctcc cgcccctgtc cactgccccg
41521 gtccccccag aagcccccaa aagtagaggc tcaggccatg cgcgccctgt caccaggcct
41581 gccaaagagc cagatctaag gccgggagag gcagccccaa agcgggtgca gtaacaggta
41641 atctctggta gtgatttgga cccgaaatct gacactttag agctctggag gactttaaaa

Fig. 3 (cont.)

41701 ctctaaaaat caaaacttta gaggcgaatg ggcgccattt tgtccccacg cgcgcataat
41761 ggcggaccta ggcctaaaac ccccaggaag cgggtctatg gttggctgcg ctgctgctat
41821 ctttagaggg gaaaagagga ataagccccc agacagggga gtgggcttgt ttgtgacttc
41881 accaaaggtc agggcccaag ggggttcgcg ttgctaggcc accttctcag tccagcgcgt
41941 ttacgtaagc cagacagcag ccaattgtca gttctaggga gggggaccac tgcccctggt
42001 ataaagtggt cctgcagcta tttctggtcg catcagagcg ccaggagtcc acacaaatgt
42061 aagagggggt cttctacctc tccctagccc tccgcccccct ccaaggactc gggcccagtt
42121 tctaactttt ccccttccct ccctcgtctt gccctgcgcc cggggccacc ttcatcaccg
42181 tcgctgactc cgccatccaa gcctagggga gaccgaagtg aaggccctgg accaacccgg
42241 cccgggcccc ccggtatcgg gccagaggta agtggacttt aattttttct gctaagccca
42301 acactccacc acacccaggc acacactaca cacacccacc cgtctcaggg tcccctcgga
42361 cagctcctaa gaaggcaccg gtcgcccagt cctaccagag gggggccaaga acccagacga
42421 gtccgtagaa gggtcctcgt ccagcaagaa gaggaggtgg taagcggttc accttcaggg
42481 gtaagtaacc tgacctctcc agggctcaca taaagggagg cttagtatac atgcttcttg
42541 cttttcacag gaacctgggg gctagtctgg gtgggattag gctgcctcaa gttgcatcag
42601 ccagggcttc atgccctcct cagttcccta gtccccgggc ttcaggcccc ctccgtcccc
42661 gtcctccaga gacccgggct tcaggccctg cctctcctgt taccctttta gaaccacagc
42721 ctggacacat gtgccagacg ccttggcctc taaggccctc gggtccccct ggaccccggc
42781 ctcagcaacc ctgctgctcc cctcctgcca ccccagcctc cccccctccc cgtcccccctt
42841 cgctcctgat cctcccccgg tccccagtag ggccgcctgc ccccctgcac ccagtacctg
42901 cccctcttgg ccacgcaccc cgggccaggc caccttagac ccggccaagc cccatccctg
42961 aagacccagc ggccattctc tctggtaacg agcagagaag aagtagaggc ccgcggccat
43021 tgggcccaga ttgagagacc agtccagggg cccgaggttg gagccagcgg gcacccgagg
43081 tcccagcacc cggtccctcc ggggggcaga gacaggcagg gccccccggc agctggcccc
43141 gaggaggcgc ccggagtggg gccggtcggc tgggctggcc gagcccgggt ctgggaggtc
43201 tggggtggcg agcctgctgt ctcaggaggg gcctggctcc gccgggtggc cctggggtaa
43261 gtctgggagg cagagggtcg gcctaggccc ggggaagtgg agggggatcg cccgggtctc
43321 tgttggcaga gtccgggcga tcctctgaga ccctccgggc ccggacggtc gccctcagcc
43381 ccccagacag accccagggt ctccaggcag ggtccggcat cttcaggggc agcaggctca
43441 ccaccacagg cccccccagac ccgggtctcg gccagccgag ccgaccggcc ccgcgcctgg
43501 cgcctcctcg gggccagccg ccggggttgg ttctgcccct ctctctgtcc ttcagaggaa
43561 ccagggacct cgggcacccc agagcccctc gggcccgcct ccaggcgccc tcctggtctc
43621 cgctcccctc tgagccccgt taaacccaaa gaatgtctga ggggagccac cctcggggcc
43681 caggccccag agtccagagg tcaggggcac ctcagggtgc ctccccgggt cccaggccag
43741 ccggagggac cccggcagcc cgggcggccc cagaggccgg ttcctcgccc cttccccggg
43801 cttcagagcc caggatgtcc cccagaaggg accctaggcg tcccctctcc tcccctccag
43861 gcccgagcct ctccctcgcg gagaggggcc tctttgggcc ctcaagtcca gcccccaccga
43921 gacccgagtg gcccggatcc ccccaccggc ccttctctct gtccccctgc tcctctccaa
43981 ccttcgctcc accctagacc ccagcttctg gcctccccgg gtccaccagg ccagccggag

Fig. 3 (cont.)

44041 ggaccccggc agcccgggcg agtcgccttc cctctcccct ggcctctcct tcccgcctcc
44101 cacccgagcc ccctcagctt gcctccccac cgggtccatc aggccggccg gagggacccc
44161 ggcggcccgg tgtcagtccc ccctgcagcc gcccagtctc tgcctccagg caagggcgcc
44221 agctttctc cccccagcct gaggcccagt ctcctgtgca ctgtctgtaa agtccagcct
44281 cccacgcccg tccacggctc ccgggcccag cctcgtccac ccctccccac ggtggacagg
44341 ccctctgtcc acccgggcca tccccgcccc cctgtgtcca ccccagtccc gtccaggggg
44401 gactttatgt gacccttggg cctggctccc catagactcc catgtaagcc tgcctcgagt
44461 aggtgcctcc agagcccctt ttgcccccct ggcggcccag cccgaccccc gggcgccccc
44521 aaactttgtc cagatgtcca ggggtccccg agggtgaggc ccagcccccct cccgcccctg
44581 tccactgccc cggtcccccc agaagccccc aaaagtagag gctcaggcca tgcgcgccct
44641 gtcaccaggc ctgccaaaga gccagatcta aggccgggag aggcagcccc aaagcgggtg
44701 cagtaacagg taatctctgg tagtgatttg gacccgaaat ctgacacttt agagctctgg
44761 aggactttaa aactctaaaa atcaaaactt tagaggcgaa tgggcgccat tttgtcccca
44821 cgcgcgcata atggcggacc taggcctaaa accccccagga agcgggtcta tggttggctg
44881 cgctgctgct atctttagag gggaaaagag gaataagccc ccagacaggg gagtgggctt
44941 gtttgtgact tcaccaaagg tcagggccca agggggttcg cgttgctagg ccaccttctc
45001 agtccagcgc gtttacgtaa gccagacagc agccaattgt cagttctagg gagggggacc
45061 actgcccctg gtataaagtg gtcctgcagc tatttctggt cgcatcagag cgccaggagt
45121 ccacacaaat gtaagagggg gtcttctacc tctccctagc cctccgcccc ctccaaggac
45181 tcgggcccag tttctaactt ttccccttcc ctccctcgtc ttgccctgcg cccggggcca
45241 ccttcatcac cgtcgctgac tccgccatcc aagcctaggg gagaccgaag tgaaggccct
45301 ggaccaaccc ggcccgggcc ccccggtatc gggccagagg taagtggact ttaatttttt
45361 ctgctaagcc caacactcca ccacacccag gcacacacta cacacaccca cccgtctcag
45421 ggtcccctcg gacagctcct aagaaggcac cggtcgccca gtcctaccag agggggccaa
45481 gaacccagac gagtccgtag aagggtcctc gtccagcaag aagaggaggt ggtaagcggt
45541 tcaccttcag ggggtaagtaa cctgacctct ccagggctca cataaaggga ggcttagtat
45601 acatgcttct tgcttttcac aggaacctgg gggctagtct gggtgggatt aggctgcctc
45661 aagttgcatc agccagggct tcatgccctc ctcagttccc tagtccccgg gcttcaggcc
45721 ccctccgtcc ccgtcctcca gagacccggg cttcaggccc tgcctctcct gttacccttt
45781 tagaaccaca gcctggacac atgtgccaga cgccttggcc tctaaggccc tcgggtcccc
45841 ctggaccccg gcctcagcaa ccctgctgct cccctcctgc caccccagcc tcccccccctc
45901 cccgtccccc ttcgctcctg atcctccccc ggtccccagt agggccgcct gccccccctgc
45961 acccagtacc tgcccctctt ggccacgcac cccgggccag gccaccttag acccggccaa
46021 gccccatccc tgaagaccca gcggccattc tctctggtaa cgagcagaga agaagtagag
46081 gcccgcggcc attgggccca gattgagaga ccagtccagg ggcccgaggt tggagccagc
46141 gggcacccga ggtcccagca cccggtccct ccgggggggca gagacaggca gggccccccg
46201 gcagctggcc ccgaggaggc gcccggagtg gggccggtcg gctgggctgg ccgagcccgg
46261 gtctgggagg tctggggtgg cgagcctgct gtctcaggag gggcctggct ccgccgggtg
46321 gccctggggt aagtctggga ggcagagggt cggcctaggc ccggggaagt ggagggggat

Fig. 3 (cont.)

46381 cgcccgggtc tctgttggca gagtccgggc gatcctctga gaccctccgg gcccggacgg
46441 tcgccctcag ccccccagac agaccccagg gtctccaggc agggtccggc atcttcaggg
46501 gcagcaggct caccaccaca ggccccccag acccgggtct cggccagccg agccgaccgg
46561 ccccgcgcct ggcgcctcct cggggccagc cgccggggtt ggttctgccc ctctctctgt
46621 ccttcagagg aaccagggac ctcgggcacc ccagagcccc tcgggcccgc ctccaggcgc
46681 cctcctggtc tccgctcccc tctgagcccc gttaaaccca aagaatgtct gaggggagcc
46741 accctcgggg cccaggcccc agagtccaga ggtcaggggc acctcagggt gcctccccgg
46801 gtcccaggcc agccggaggg accccggcag cccgggcggc cccagaggcc ggttcctcgc
46861 cccttccccg ggcttcagag cccaggatgt cccccagaag ggaccctagg cgtcccctct
46921 cctcccctcc aggcccgagc ctctccctcg cggagagggg cctctttggg ccctcaagtc
46981 cagccccacc gagacccgag tggcccggat ccccccaccg gcccttctct ctgtcccccct
47041 gctcctctcc aaccttcgct ccaccctaga ccccagcttc tggcctcccc gggtccacca
47101 ggccagccgg agggaccccg gcagcccggg cgagtcgcct tccctctccc ctggcctctc
47161 cttcccgcct cccacccgag ccccctcagc ttgcctcccc accgggtcca tcaggccggc
47221 cggagggacc ccggcggccc ggtgtcagtc ccccctgcag ccgcccagtc tctgcctcca
47281 ggcaagggcg ccagcttttc tccccccagc ctgaggccca gtctcctgtg cactgtctgt
47341 aaagtccagc ctcccacgcc cgtccacggc tcccgggccc agcctcgtcc acccctcccc
47401 acggtggaca ggccctctgt ccacccgggc catccccgcc cccctgtgtc caccccagtc
47461 ccgtccaggg gggactttat gtgacccttg ggcctggctc cccatagact cccatgtaag
47521 cctgcctcga gtaggtgcct ccagagcccc ttttgccccc ctggcggccc agcccgaccc
47581 ccgggcgccc ccaaactttg tccagatgtc caggggtccc cgagggtgag gcccagcccc
47641 ctctcgccca agctgctttg attcctggga tatttttggg aatggtgtta actttctccc
47701 cttgtatttg ctattcaatc aacctgattc cccctgctca tacctccact tacaaccaag
47761 ccactacggc cacgtccccg gcctcccgct cgggtaagtg ctttttcatt tttagcccca
47821 gcccctcctc tataagttct aggcaaacct ccaatcacca gccaccttcc aatgtagtct
47881 cttagagagt ggctgctacg cattagagac cactttgagc caccccacagt aaccacccag
47941 cgccaatctg tctacataga agaagaagag gatgaagact aagtcacagg cttagccagg
48001 tgatttgtga atttcagttt atttactttc ttccaatcaa gctttcccag cctccgcttg
48061 ttaggtccta gttatgggtt ttccatgggg gacttagtat ccgttctatt agattaacgt
48121 gcaagacgct aaacttaacc aaggtcagcc aagggacgcg tgttatccca ggctgcccac
48181 cctgaggatt tccccccaaa atcctcctac cctctcttta tgccatgtgt gttgttggct
48241 tgtgttagtg ctatgtaatg cgttgccgcc aggtggcagc ctgtttatag atgtgcagta
48301 ccccttaatg ttaggtctgc tttagggctg ccaggtggcg caatctagga ttaattcacc
48361 tgtatccctt tccctccacc cgcagtaacc cagcactggc gtgtgacgtg gtgtaaagtt
48421 ttgcctgaac ctgtggttgg gcaggtacat gccaacaacc ttctaagcac ccgcgcttgt
48481 gttttgcttt atctgccgcc atcatgccta cattctatct tgcgttacat gggggacaaa
48541 catatcatct aattgttgac acggatagtc ttggaaaccc gtcactctca gtaattccct
48601 cgaatcccta ccaggaacaa ctgtcagaca ctccattaat tccactaaca atctttgttg
48661 gggaaaacac gggggtgccc ccaccactcc caccaccccc cccaccacca cccccaccac

Fig. 3 (cont.)

48721 ccccaccacc cccaccaccc ccaccacccc caccacctcc accaccttca ccaccacccc
48781 cgccccccacc acccccacca cctcagcgca gggatgcctg gacacaagag ccatcacctc
48841 ttgataggga tccgctagga tatgacgtcg ggcatggacc tctagcatct gctatgcgaa
48901 tgctttggat ggctaattat attgtaagac aatcacgggg tgaccggggc cttattttgc
48961 cacaaggccc acaaacagcc cctcaggcca ggttggtcca gccacatgtc ccccctctac
49021 gcccgacagc acccaccatt ttgtcacctc tgtcacaacc gaggcttacc cctccacaac
49081 cactcatgat gccaccaagg cctacccctc ctacccctct gccacctgca acactaacgg
49141 tgccaccaag gcctaccegt cctaccactc tgccacccac accactactc acggtactac
49201 aaaggcctac cgaacttcaa cccacaccat caccaccacg catgcatctc cctgtcttgc
49261 atgtgccaga ccaatcaatg caccctctta ctcatcaaag caccccaaat gatccagata
49321 gtccagaacc acggtccccg actgtatttt ataacattcc acctatgcca ttaccccct
49381 cacaattgcc accaccagca gcaccagcac agccacctcc aggggtcatc aacgaccaac
49441 aattacatca tctaccctcg gggccaccat ggtggccacc catctgcgac cccccgcaac
49501 cctctaagac tcaaggccag agccggggac agagcagggg gaggggcagg ggcaggggca
49561 ggggcagggg caagggcaag tccagggaca agcaacgcaa gcccggtgga ccttggagac
49621 cagagccaaa cacctccagt cctagcatgc ctgaactaag tccagtcctc ggtcttcatc
49681 agggacaagg ggctggggac tcaccaactc ctggcccatc caatgccgcc cccgtttgta
49741 gaaattcaca cacggcaacc cctaacgttt caccaataca tgaaccggag tcccataata
49801 gcccagaggc tcccattctc ttccccgatg attggtatcc tccatctata gaccccgcag
49861 acttagacga aagttgggat tacatttttg agacaacaga atctcctagc tcagatgaag
49921 attatgtgga gggacccagt aaaagacctc gcccctccat ccagtaaaaa cccttgccct
49981 ctccagcaac caatgtatcc caaataaatg ttacttcttt tgctcttaac cattgacacg
50041 cctgtcattc tatcaattaa acaagggaaa aaggtttagc tattccacca acacgacccc
50101 aaggaaggct tgccaaaatt ggtgccttgc tctcagcact ttgccagcaa cttatagcat
50161 ggtaggcagc tcaactcggc ccgtcttact gcccagccta ctctccactc ccagtccatg
50221 ttcgcactcc tatgcatttc ctgccctccc actttaccc cagtcccaac ccaaaaccac
50281 acacaacaca tagaattgtt agtttaaaca gtttattgat aggtggctgc ttttagccta
50341 attgtgtatt gctctcgttg ccaaaacctg ttgtaagggc cggcacccgc aacatgggga
50401 aaacataacc gccgccatcc catggggagg gtagaggcgg ttgacatgta ggtgagtagt
50461 gtaagaagca tggcgaagta gacaggttac ttttagagtg tagtgtacag ggccgggcgc
50521 aacagtgcca ccaacccggg gtctgagcat tccatgggca gcagggacac tgcactaccg
50581 ccaggtcctg gggcagccgg ggttcctggc gctccggggg cagccgggcg gccgccggtg
50641 ggtccgctgg gccgctgccc cgctccgggt ggggggtggc cccgctgggc accgctgcgc
50701 cgccgccagg tcctggggca gccggggttc ctggcgctcc gggggcagcc gggcggccgc
50761 cggtgggtcc gctgggccgc tgccccgctc cgggtggggg gtggccccgc tgggcaccgc
50821 tgcgccgccg ccaggtcctg gggcagccgg ggttcctggc gctccggggg cagccgggcg
50881 gccgccggtg ggtccgctgg gccgctgccc cgctccgggt ggggggtggc cccgctgggc
50941 accgctgcgc cgccgccagg tcctggggca gccggggttc ctggcgctcc gggggcagcc
51001 gggcggccgc cggtgggtcc gctgggccgc tgccccgctc cgggtggggg gtggccccgc

Fig. 3 (cont.)

51061 tgggcaccgc tgcgccgccg ccaggtcctg gggcagccgg ggttcctggc gctccggggg
51121 cagccgggcg gccgccggtg ggtccgctgg gccgctgccc cgctccgggt ggggggtggc
51181 cccgctgggc accgctgcgc cgccgccagg tcctggggca gccggggttc ctggcgctcc
51241 gggggcagcc gggcggccgc cggtgggtcc gctgggccgc tgccccgctc cgggtggggg
51301 gtggccccgc tgggcaccgc tgcgccgccg ccaggtcctg gggcagccgg ggttcctggc
51361 gctccggggg cagccgggcg gccgccggtg ggtccgctgg gccgctgccc cgctccgggt
51421 ggggggtggc cccgctgggc accgctgcgc cgccgccagg tcctggggca gccggggttc
51481 ctggcgctcc gggggcagcc gggcggccgc cggtgggtcc gctgggccgc tgccccgctc
51541 cgggtggggg gtggccccgc tgggcaccgc tgcgccgccg ccaggtcctg gggcagccgg
51601 ggttcctggc gctccggggg cagccgggcg gccgccggtg ggtccgctgg gccgctgccc
51661 cgctccgggt ggggggtggc cccgctgggc accgctgcgc cgccgccagg tcctggggca
51721 gccggggttc ctggcgctcc gggggcagcc gggcggccgc cggtgggtcc gctgggccgc
51781 tgccccgctc cgggtggggg gtggccccgc tgggcaccgc tgcgccgccg ccaggtcctg
51841 gggcagccgg ggttcctggc gctccggggg cagccgggcg gccgccggtg ggtccgctgg
51901 gccgctgccc cgctccgggt ggggggtggc cccgctgggc accgctgcgc cgccgccagg
51961 tcctggggca gccggggttc ctggcgctcc gggggcagcc gggcggccgc cggtgggtcc
52021 gctgggccgc tgccccgctc cgggtggggg gtggccccgc tgggcaccgc tgcgccgccg
52081 ccaggtcctg gggcagccgg ggttcctggc gctccactgc acctggaatg cagggtgggg
52141 gcgtggtccc ctggacccca gccccgccga tccctccccc agggcgtacc cggcttgcct
52201 ggttctgggg ctcctctggg ggtcgctgca tccgccggta gggttcgaat gggcgtggtc
52261 cgcttgctct gctggcccgg tacgcctgga ttgccggctg ggggctgggg tcccgggacg
52321 ccccctccct gctcccaccc ggttccctcc cccagggcgt gccccgcttg cctggtcctg
52381 gagctcatcc ggggatgctg catccgctag tccgacctgg gtgggtgcgg tccgctggcc
52441 ccaccctggg ggtagccgcc gggtctgctg gtccggtgca cctggaaggc aggggggggg
52501 gcagtgaggg aggggcgtgg tcctgggacc ccgcgccgac tggcaggggg tccccatggc
52561 acaggcctag gggtccaggg ggcagccgcg gcccagcgcg ccccgttcac gggggaggac
52621 cgcggccgag ccaccagggg cccggcgggg gtggggggtg cgctcccagg ccggaccctg
52681 gtgccaggca gggaccccgc gccacccgct tcatgggggg ggaggccgcc gcaaggacgc
52741 cgggccggct gggaggtgtg caccccccga gcgtctggac gacgctggcg agccgggccg
52801 gctcgccttc ttttatcctc tttttggggt ctctgtgtaa tactttaagg tttgctcagg
52861 agtgggggct tcttattggt taattcaggt gtgtcatttt agcccgttgg gtttcattaa
52921 ggtgtgtcac caggtgggtg gtacctggag gttattctat tgggataacg agaggaggag
52981 gggctagagg tccgcgagat ttggggtagg cggagcctca ggagggtccc ctccataggg
53041 ttgaaccagg agggggagga ttgggctccg ccccgatata cctagtgggt ggagcctaga
53101 ggtaggtatc catagggttc cattatcctg gaggtatcct aagctccgcc cctatatacc
53161 aggtgggtgg agctaggtag gattcagcta ggttcctact ggggtacccc cctaccctac
53221 cttaaggtgc gccacccttc ctccttccgt tttaatggta gaataaccta taggttatta
53281 acctagtggt ggaatagggt attgcagctg ggtatatacc tataggtata tagaacctag
53341 aggaagggaa ccctatagtg taatccctcc ccccctacc cccccctccc ttacggttgc

Fig. 3 (cont.)

53401 ctgagcccat cccccacccc agcaccccgg ggtgacgtgg caccccgcgt gccttactga
53461 cttgtcacct ttgcacattt ggtcagctga ccgatgctcg ccacttcctg ggtcatgacc
53521 tggcctgtgc cttgtcccgt ggacaatgtc cctccagcgt ggtggctgcc tttgggatgc
53581 atcactttga gccactaagc ccccgttgct cgccttgcct gcctcaccat gacacactaa
53641 gcccctgcta atccatgagc cccgccttta ggaagcacca cgtcccgggg acggaagggg
53701 acttggggtg attttctatg tgggggtgga aatatgagca agaataagga cggctcctta
53761 ttaacctgat cagccccgga gttgcctgtt tcatcactaa ccccgggcct gaagaggttg
53821 acaagaaggg tcaaggtttc gtctgtgtgt tgaagggcag gggctgttgg gtgcatctgg
53881 aacggcttac ctcgggtaac tgtttgccat taaaaggttg gggattaggt ttagcccctt
53941 tagctgccat ttcgaaccgg ggtgtgcaga tgcaggtctc cgggtgggca ggcagtacga
54001 gatgtcacgt tgtgttgtct ttcctcccac ccctgtcctg gctgtggcaa atgcgaccct
54061 catagagttg tgtttcaggt ctgtgtcctg ttttgcggtg ggttatttct tccctcagtg
54121 tttgccagct tatttcccca gttttcacgt actggggcct gtggacacct gagggagcgg
54181 ccgttggtgg gtatgtgttg gaattgctcc caccctcaat tttcgcttgc cttcttccct
54241 tgttaacctg atagcatagc ctctaggttt ccttgtaggt ctgtttgggt ttgttggttc
54301 acgtggtgct aacttgaatt ttttggtttt ctagttccct cttaattaca tttgtgccag
54361 atcttgtaga gcaagatggc ctattcaaca agggagatac tgttagccct gtgtatacgg
54421 gacagtcgtg tgcatggaaa tggtaccctg catcctgtgt tggagctagc agcaagagaa
54481 acacctctcc gcctttcgcc agaggacact gtagttctgc gttatcatgt gttgcttgag
54541 gagataattg aacgaaattc agagacattt acagaaactt ggaacagatt tataacacac
54601 accgaacatg tggatctgga ttttaactca gtatttttag agatatttca ccgtggagac
54661 ccaagccttg ggcgcgcgtt ggcctggatg gcctggtgca tgcatgcctg caggacattg
54721 tgttgtaacc agtctactcc ttactatgtt gtggacctgt cagttcgtgg gatgttagaa
54781 gccagcgaag gcctggatgg ttggattcat caacagggcg gctggtctac attaattgaa
54841 gacaacattc ctggatccag aaggtttagc tggactttgt ttcttgctgg actgactttg
54901 agtctgttag ttatatgtag ttatttattt atctccagag gaagacacta atctatacat
54961 tttctcagca ctttatatga atcagggtca ttgggcctgc ggggaactga gccagtagga
55021 tattaggcaa gggtgacaca gtgcccatgc attataattt aaccaaacag tggtcgtgag
55081 ttttaggccg gccatggggg cttacaagaa taacatgcca atgacccggc ccccactttt
55141 aaattctgtt gcagcagata gctgataccc aatgttatct tttgcggcag aaattgaaag
55201 tgctggccat atctacaatt gggtgtccta ggtgggatat acgcctgtgg tgttctaacg
55261 ggaagtgtgt aagcacacac gtaatttgca agcggtgctt cacgctcttc gttaaaataa
55321 cacaaggaca agatactaaa gaaataactg aggtgagtgt gggaagatgg gaatactatg
55381 tgttatgtta acgggtgaga gcctatactg cagcccagac tcggggggag gaggaaatgg
55441 taagagttat actctactta tctttttga cactacattt aactgttatg taacaatgtt
55501 tgcttatttt catgttcaat aaacgctatg ttaatgatga agaacctgtg ttctttggaa
55561 gtgggcccaa tggggtagta ggttttggga gggtgccgtg ctagatattt caactgccac
55621 agaccccatt ttgtcccacc tgttaccaca ttctaggtcc tgcatccagt gggccaggtg
55681 tctcaccatg gctctttcta ggtggatacc acagtccagg cccccaaggc taccgtgcta

Fig. 3 (cont.)

55741 attacctcct catgtccacc cccaccctgt gttactgtcg cctgattatc ctggcttagc
55801 agcctccaag ttttacaaga cgtcccattg ccctgccctt ggtccaagtc tcgccggttt
55861 tcagcagcct gttgtagcct gcccccaagt ttcgcaggtt tcccccatgc ttccacccgt
55921 taacccaata gcatgacagc caatccaaca cgaggcaagt tttaagagtt aaaagcaact
55981 actgtttatt ttccaaaatg agctgggtat agttgatgat ctgtaggcgc agctcatccc
56041 cacattccag gtccttgatg gcctcgtaga tggcatcttc gtcgacattg acagccttct
56101 catataccgt gtctctgggg ctgaccttta tacagaaggc gtcccctact aggtccacgg
56161 ccagctcgta ggtggggcct atgttttcac ataacagttt caagcaggtc tctgggatgt
56221 gaagggaggt gccctggagc aggagatgca tgattaggcg cccttttcca tttgtgctga
56281 agatggggca gatggtgcca caaaagtgtc cggtgaccag gtaagcgtag agaaggctgg
56341 gttgggaaag tccagccttt actgcactgg gagagctgct gagcagagac acatagaagg
56401 tcttgttggg tattatcttg tggacattgt tgaagaagga gagctgggtg gagctaaact
56461 cctgaggcac atgaacctgg gacctattga tgcagatctc gcagtgagac cccagagtca
56521 ggctgtggcc gaagggagac aggcgaaggc agcgcccggg ggagagagtg cacagtgaca
56581 gtgggagaaa cacggcctct gagacatgta tgggggtgtt catctcacgc agaaaatctt
56641 tgcccagctc aaagttggca gagattcccc tgaagaagtc ccgtagtgaa aaatgggatc
56701 tgtctacacc atgtctggtg tgccgggaac atattgatcg ggccacactg ccaacccttt
56761 ccattcttcc cagctctgag cgagattttc cacacctgga caccgacttc acgctatgcg
56821 ccgaggcctt tgaggccgtg tagtttctgt ggtgcggatg cattaggcgg cgcaatgcgg
56881 gatctgccgg tcgctgttgg cgtgcattca cggcatctgg ggtgaccggg gccatcgggt
56941 ttacttttca cacgtagacc tgggaagttt gataggactg taccaggtca aggccgtgga
57001 tgcgcaggac cacgtccagt tccttagtga catccacgag gattgttttg cccactctgg
57061 ccacttgtgt ggatttaaat atgtacacaa gcgtaattaa cgagtcacag accccctgtt
57121 ccagattctg accggctgca agcgctgcct taaaggcctg gaagctgggt gggtaaatct
57181 gaccaaacag cacgctcgga ttcgtgatgc tgtggttgat ggcacacagg gggtcgcaga
57241 acaggtgctt gtggaagtct tgcggggtgc acatctgcag ccaggcccct agcctggggc
57301 atggcacatc cagcagcgtg ttttgggtct tgatgaggaa cacgatcctg tctaggattt
57361 tgatgttgtt gccgaacgag tcaagaatca ggctcttgaa gcggtcaagg gtgtccttgg
57421 cgtccgggtg ggccccgagg ctctcgcaga gtgggcagat ggtccgtgag gcattcttgt
57481 gccttagtcc aaacatgggg gccaggaggc aggggccctg cgaatggtcg ccagcctccg
57541 gtctggtgat ggccagggcc aactccgcca gctcatcgcc gctgtattcc gcgtttaaac
57601 cgatagcatg gtggcctggc cccccgagca ggtccgtccc ctgccacgta cctaatagta
57661 gtccacagta gtcggccttg gttgtaattt caggagagag tcctcccttt tcggccctga
57721 gaaatggatg ctgaactcgg tttctggtag gcaggtggca gcacagggcg gtgtacaggc
57781 ccctgccgac gtcccctggg acatcctggg aatctttgca ggttctgggt ccagggaggg
57841 taagaaaagt gggggtggtt ctgggccaca tggacttgaa gcagaagttg gccggggact
57901 ggccggtgag gatggatttc agaaactcca atttgtagta gccgaggttg gcatttctaa
57961 tcatgtcaga agaggacaca gggaggaagc accggcaaat gtaaaagtga agctggatgt
58021 caatggcaag aatcctggag ggcatgaaga gggaatccaa ccccccggcc atggggaagt

Fig. 3 (cont.)

58081 attttatcag gatgtgtaaa aagtccatgc ctgtgatgag gctagagatc caggctcgtg
58141 gggcatttag acagtagtag cagagcaggg catagtcctc aaagaaggcc acgggggcat
58201 ctgagtgatt gaccagggtg tcgagcagat cacaaactcg gcaggtgctg gctggagaga
58261 gggactcgta ggtgtggacg agtggtgggt aggctatgcc ttcttccgcg ttggctggaa
58321 gataggagtg ggccatcaaa aggccgactg cctcgaactg gcttttcaga ttgtccacgg
58381 tccagggcac aaagtcctcc atctttggag ttctgcccgc gatctgtgcc acctctgtta
58441 cgccactcct cgtgaggggg cagctggaca gtctttttcc ggtcaggggg tttggctcgt
58501 ttgcgctcgt gactttgtga gccatgacac atctgggtgg caaggtgagg tcttctgggt
58561 ttttaatacc ggggtcggca ccagtttctg ggacaccgcc acaaggacaa ggtgggctag
58621 caagttctcg agtctacgaa gactccgggg gcagtctttt gagtttctcg cctatgatcc
58681 accccaatct cgcccccccta attgcgccat ctgcctacgc gaggctgaac ctcctgaatc
58741 actgcatctt tcttgaggcg tttaaagaag agaatagtgg ccagggcctc ggtggggtcc
58801 agcgtgaggt cttatttttg aaaagggata ttataaaaca ggtcattgct cggattgtgg
58861 cagccgatag caccctagat ctagtgaatc atggcgagcc cggaagagag gctcctagac
58921 gagctcaata acgtaattgt gtcatttctg tgtgactctg ggtctctgga agtggagaga
58981 tgctccgggg cgcatgtgtt ctccaggggc agctcccaac ccctctgcac cgtgaagctg
59041 cgccacggac agatttacca cctggagttt gtctacaagt tcctggcctt taagctgaag
59101 aactgcaact acccctcctc gccccgtgttt gtgatatcca acaacggcct ggccaccacc
59161 ctgaggtgct ttttgcacga gccgtcgggt ctcagatcgg gccagagcgg cccttgcctg
59221 ggtctctcaa cggatgttga cctaccaaag aactccatca ttatgctggg ccaggatgac
59281 ttcattaagt tcaaaagccc cctggtcttc cctgctgagc ttgatctcct gaaatctatg
59341 gtggtctgcc gggcctacat cacggaacac cggacgacga tgcagtttct ggtgtttcag
59401 gccgccaacg cccagaaggc ctcgcgggtc atggatatga ttagtgatat gtctcagcaa
59461 ctgtctcggt ctggtcaagt cgaggatacg ggcgccagag tcacaggtgg aggaggtccc
59521 aggcctggcg tcacgcactc ggggtgtctt ggggactcac acgttagggg gcgcggtggt
59581 tgggacttgg ataacttttc agaagctgag accgaagacg aggcgagtta cgctccttgg
59641 agggacaaag actcgtggtc ggaatccgag gcggcgccgt ggaagaagga actcgtgagg
59701 caccccatcc gcaggcaccg gacacgcgag actcgccgta tgcgcgggag ccattcacgg
59761 gtggaacacg tgccccccga gacccgggag acggtggtgg ggggagcatg gcgttattct
59821 tggcgcgcca caccttatct ggcacgggtg ctggctgtca cggccgtggc cctgctcctg
59881 atgtttctga ggtggacctg acgttgcagg cccttgggga gcgggggttc tccaggctcc
59941 tggatctggg gctggcctgc ctggatctga gctatgtgga aatgagggaa tttgtggttt
60001 ggggcaggcc cccagcttct gaggcggctg tggcctctac gccaggctcg cttttccgaa
60061 gccactcgtc cgcctactgg ttgtcggagg tggagaggcc cgggggcctt gtccgctggg
60121 ccaggtcaca gaccagcccc tcatccctga ccctcgcgcc ccatcttggc ccgtccctct
60181 tgtccctttc agtggtcacc ggtggtgggt gtggagccgt ggccttttgc aacgcctttt
60241 tcctagctta ttttttggtt gtgcggtctg ttttccccgc gttttccgat agaatagctg
60301 cctggatctg cgaccggtcc cctttctgcg aaaacacccg ggccgtggcc aggggttacc
60361 gaggcctcgt gaagaggttc ttggcattcg tgtttgagcg tagtagctat gacccccccct

Fig. 3 (cont.)

60421 tgttgaggca aaactctagg cctgtggagc gctgctttgc catcaagaat tatgtcccgg
60481 gcctggactc acaaagctgt gtgacggtcc cgagcttctc ccgctgggcc cagtctcacg
60541 ccagcgagct cgatccccgg gagattcgcg acagagttac accagcgact gcaccttcgt
60601 tcgtggctga tcatgcctcg gctctattgg cctccctcca gaagaaggcc tccgacaccc
60661 cctgtgggaa tcccattcag tggatgtggt accgcctgtt ggtaaactcg tgcctgagga
60721 gtgcccactg tcttctgcct atacctgccg tctctgaggg ggggagaaag acgggcgggg
60781 gcgtagggga ggagctcgtg ggggccgggg ggccctgcct gagccgggat gttttcgtgg
60841 cgatcgtaag ccgcaatgtt ctctcgtgtc tgctgaacgt gcctgccgcg ggtccccggg
60901 cctacaagtg tttcagatcc cacgcctcca gaccggtgtc tggcccggat taccctccct
60961 tggccgtgtt ttgcatggac tgcggttact gcttgaactt tggaaagcag acaggtgtag
61021 gaggcaggct caattccttt agacccactc tccagtttta tccccgtgac cagaaggaga
61081 agcatgtgct gacctgccat gccagcggcc gtgtgtactg ctccaactgc ggctctgcgg
61141 cggtgggctg ccagaggctg gctgagccac cgagcgcccg ctcgggctgg cggccccgaa
61201 tccgggcagt gctgccgcac aacgcggcct acgagctcga ccgtggctcc cgcctcttgg
61261 atgccatcat cccctgcttg ggacccgacc gcacttgcat gcggccggtg gtcctgcggg
61321 gggtgacggt caggcagctc ctgtatttaa ctttgcggac agaggccaga gccgtttgct
61381 ccatctgtca gcaacgccaa gctccagagg acgcccgcga cgagcctcac ctgttctcct
61441 cctgtttaga ggtagaattg ccacctggtg agcggtgtgc gggctgccgt ctctatcaga
61501 cgcgttatgg cacgccggct gcccaagccc accctccagg ggaggctgga ggcggatttt
61561 ccagacagtc ccctgcttcc taaatttcaa gagctgaacc agaataatct ccccaatgat
61621 gtttttcggg aggctcaaag aagttacctg gtatttctga catcccagtt ctgctacgaa
61681 gagtacgtgc agaggacttt tggggtgcct cggcgccaac gcgccataga caagaggcag
61741 agagccagtg tggctggggc tggtgctcat gcacaccttg gcgggtcatc cgccaccccc
61801 gtccagcagg ctcaggccgc cgcatccgct gggaccgggg ccttggcatc atcagcgccg
61861 tccacggccg tagcccagtc cgcgaccccc tctgtttctt catctattag cagcctccgg
61921 gccgcgactt cgggggcgac tgccgccgcc tccgccgccg cagccgtcga taccgggtca
61981 ggtggcgggg gacaacccca cgacaccgcc ccacgcgggg cacgtaagaa acagtagagg
62041 gcacgaaaca tggtgtatgc actttattaa taaacaatta cagatacaaa aacttgagtc
62101 tctcgaggtc tgcgatgagg cggtgggtgg aacgctccag cttgcggcga agctggctca
62161 cgaagcgaga cagtactcgg ctagcctgac taagggtgag gctataacgc aggtcctgtt
62221 ccggggcggc ggtggataga gaggaggggg atccggaggg gaccactagg tcgccggagg
62281 tcgaccctcc tgtcaccacc tccctgataa tgtcttcaat agacagaaat tgggtgacca
62341 ctgagggagt gttccacagt aatgttgtct ggtcgctaga tggcgcgggt gaggccacgc
62401 tttgcgaaaa cgaaagtgct tgaaaaggcg cgggatagcg tgcgctaccg gatggcgggt
62461 aatacatgct atccttacat tttggcattt tgggcagctg ggaggcggcg gatgggggtg
62521 cttctttcg cacggtgtat gtttggggac ccgcatgccg gtactgggat aggcgcacct
62581 cgggccgcgc gccaggctcc gagccggaat gcattggggg caatgggatt gcgggggatt
62641 gttgctgtct gctcctgaca gggagagaca cgcgcggcgg agatgcagcc gacggcgggg
62701 ccgcggtggg ctgcccccga ggacgggcgc cggccgccag cgcccccgtg gcctttggca

Fig. 3 (cont.)

62761 cgggcctggc acccaccgct ttaattgtgg gggtgggcag ggcagctgca tcttggggcc
62821 tttgtgcttg cgttttttgg gggcgcggtg ccaatgcacc aactggggtg tgcgccgggg
62881 cggccaagcc ggaccccagg gcgggtgcct gggggatggg aaagccggac ggcgcttctc
62941 ccgggtcgaa cgctggagta gcggaggctg ctgcgccggc ggccaccacg ggcgcacggg
63001 gtcgcagccc gacggccgtg gggaggcggg tggcggaggg ccgaatctcc gcggcttctt
63061 cccggccccc ctgctgtttc ttctcccgtt gcatgataga atggccatag ggtgggtcct
63121 gagaggaggc ttgtgtgtcc tggggctgga gcccaaaagt cgttaaagat gccgctgatg
63181 gtgtgggagc tatgcctccc gtcgactggc cgggcttgta gggggctgag ggtggataac
63241 tgggcttctg tgaaggcacc aaccctggaa tctggatggt atgtttcttc tgtgaccccg
63301 aggcagtcga tggtgtagag tgtggagaca atgtgtagac gatgggccct tgttcagaag
63361 cccagggact tgagggggggc tgttgtggtg ctggttgggg aaggagctcc agggaatctt
63421 tgggccatgg ccttggggag cttcccggag accggtctgg gctctcggaa gccctcgttt
63481 cggccccgaa atagggcctt gccatcaatc gggggcctgg gagagtgatg ggggcggcca
63541 atcccggggt aactgtcacg tcccgggggg aggaggtagg agacagccag tccctgggcc
63601 tgccaggggc caccttctct aagagggggc tctgtgggct gggagggcca gaggcctcag
63661 attcagcagt agtgctcccc ttttcccccct ggtccgtctc ccctcctccc aactgctgga
63721 gccggtcgga ggaggccggg gtgttatctg ctgactgaaa cccgtccccg ctgaccagtc
63781 cgtgccccac ccttgggggg aaaccggaga acagctcctg gacgttgcgt ggattcgggg
63841 gaagctggta tccaaccggc agtggaggat cttcgtgctc gtagaaggag gggttgagta
63901 catcggtcgg ccatcgtgag gccccggccg cgttaaagta gaactgcacg tccggcagat
63961 tgtgccgata ggtgaaacac ttccagatga tgtttttct gttggccagg atggccacgg
64021 tggggggcct ggcctcctta ggtttggcgg ccctggcctc ggtgagaagc tcgcgtagcc
64081 acacggcctg gcgtgcaaag atggacatct ctggctcgaa agactcggag tagccgtcca
64141 ggtcctgcag aaaattcagc gagatggtct ccaccaggga ccggaagggc tcagagtgcc
64201 cgtcgcagta gaggagggga gcaacgaccc tgacctgtcc cagggtcttc aggttaaaca
64261 gatattgaga ggagacaaag agagttaggg gccgaccgag gaaggccgcc gccacggccg
64321 cctcaaaaac ggagacgggg atggtgtcac cggagcccct cttaggaccg gtaatgggag
64381 tgccataagg cataagattt ctcagggccc ggccggtaac ggtgccgtag gaagacgggg
64441 tttcgcgggg gacctcgagt ccctccgccc tggggagctc ttctccgcgt gtataggcct
64501 gcttcacaaa gtcgcgcagg tagtcctgaa atgcgaccgg gccctccagc gggcgcaatg
64561 agtgccagag ctgctgaagg gcctcggggg cgaagcaccg gcgtgcgagg agcagcatgc
64621 aggctcgggc gcgggccgta ctttggttgt ggaccaggcc caagaactcg gggtgcggcc
64681 agagggcggc tcgggtatcc atctcctccc aggcgtcctg gaagaagatg aagccggtgg
64741 gtggaccggc gatgcggtgg cgggtgaggc ggcgcgcgtc ttccccgtcg ttgctgccgc
64801 gggtggttga gggcatgccc cccctcccgg aggctggact cctgaccagc ctgtaggtga
64861 ggaccgagtc cgacaggagg tctcccaaac ccccatctct cgctagagcc gagaccaggc
64921 cgagtcctgc gtagaacgat ggggcgccca ggaaggcggc agcgtaggcc ggatgtgtgc
64981 cgaccagcag cgccatcatc tcccgttgtt ccaatagaat aacttcccgg tctgtggccg
65041 gggctggata aggggggtga ttcctagagg cgatgagact ggcgtgcgct aaaagtgtca

Fig. 3 (cont.)

65101 tggccacaat ggggttgtct gccaggtctt ccatcagggc tttgggcgca gagacgtatt
65161 cccgaagcag ctccccggcg ttggactcca cgtcgggcca ggtgtcccag taggagtcgg
65221 cggcggcggc gctgaggcgg gcggaagcta cactggccag ggttcttctc ctcctctctt
65281 ggtcatcctg cgggggacca atagcttggg ggcgtccggc tggggtcagg gaaaaggcct
65341 ctgggttctc cagcacggtg ggcatgacat attccagaaa gttgtggtag acggggatgt
65401 agttgagcgg ctcctgggtg tctgcggaga cgtaggccgg gttaaggggg tcgcagggag
65461 actctgtttc cagccagagg gtgccggcgt atttcgccgg ccctgccgcc gccagaaatt
65521 gtgcccgccg ggtcggggct ccattgcccc atccagttgg tggtgccgaa atcgtgatga
65581 ggagggggcag gttgttggtc aagggatgct taacgaaaac ggtaggctgg gcggtctcgt
65641 aaaaagccag gaaactctgc ttggccgagg catagcgcag cagcttgtcc ttgaggaggg
65701 catactggga gccagccgag gccccaagcg ccaggcccct ggcagcctcc accacgatct
65761 tgagctggcg cgggtcggtg tggcccctgg cctgggtgac cagatcctgc agcgttccct
65821 gcagctggga ctcttcctgg gcctcctgga tgatggcctc cagtcgggag aggcgccttt
65881 tccagtctgc gacggtctcc ttgccccccg cgacccgctt ggggtccaac gtggccagag
65941 ccaacctcag ctcctccatg ccatccatgg agttctgggc catgccctcg acttccagga
66001 gccgtgttag ctcatgaatt tcaccgtcag ccgcagcggc taggttcagc caggcacccg
66061 cgccccccagc taaggccagg gctccttcgg aaagaccccg cacggcctcg cagatgcccc
66121 ggatccactt ggcggctgcc agggatttcc ggtagggcca tgagccgttc ccggccgctg
66181 cccgggccag ggcggcctcg aggggagcct ggacaggggc tttgggcggg gagggaagca
66241 ggctccggag ttcatcgtcg ggggcttcgt cgcgtgacct ggagaggacg gcctccagag
66301 ccgtgtgaaa gccccgccga gtgcttgccg ccatctcgtg ggccttcgcc atcagggtct
66361 ggctctcccg gacctgctct tccagcgccc ggacctcggc cgcctcggcc tcggtcagca
66421 gctccgagaa gaagtccccc gtggcctgga ggagatcgtc ccgctctcgc cttgtcagca
66481 gctggggctt cttaggccag agcgccgagt ccgaggccag cctgggcggg gcggttgcct
66541 gggggatagt tggaggagga ggcaggttag cctggcctgg gtcattagtg gcttcgggta
66601 gcgtccgatc cacgtactcg ctcacgatgg ccgtcagggc agcctcggct gctcgtcttt
66661 tttccagaag cccggccagc ccccgctcgt actccgcgta gggggcctcc agatccgtgt
66721 tgaccaccgc tgatttcatg tccggggact gcagggcctg gcgcgtctgc gcgagggccg
66781 aacggatggc atcggccgcc gtcctggcgc gaaagagggc cccggccgct tcctccgctc
66841 ctcgccctcc tcctccttct ttggcggtag ccgcgggggt ggcgggccaa gcgtccagtc
66901 tggccagagg gccggtctcg atatccgtga accagccggg ttccgcggcc tccattctct
66961 ccgccgcacc accatcgtcc acgagcaggg atcgcagtct ctccctcctc accctcgtta
67021 ttcccaatag catagcggca aggatctgtg tgagggagtc caagatgtcc gtgtttctgg
67081 ctactgccgc cgctgctgcc gcggctgagt ccgtattgtc tggcagcagg gaggccagca
67141 gggtgttcca gtcatcgggc gaagtgggag cgggctctgg gcgtgccccc agcgccttcc
67201 taattctggc ccaggcctca ttcgcctctc gcgctcgccg ctcctgcctc tccttgtctt
67261 cctgttctcg gagcttctcc ttttccttgc gcccggtctc cataagctgc cgcagcttct
67321 tctcatactg tcgcttgagc tctttgttgg gggcagtgtc cagaaaggcc tcgagctgtt
67381 cctcggtggc gggcttaaag ccttcggcct ccaggcgcca ggcctgcacc tccttctgtc

Fig. 3 (cont.)

67441 tgagctgatc gttgttgtta ttcttcaatt tctgcaggta acttaggaag cgtttcttga
67501 gcttccctgg gatgagcgtt tgggagagct gattctgcag cccagagagt agtctcaggg
67561 catcctctgg agcctgacct gtgatcgtcg catcatagac cgccagtaga cctgggagca
67621 gattcaccgc cgcggccgtc tcctttaagg tgctgtgagt agcaaaattc tgcaaggcca
67681 ctaggcgcgc tggctccagc gtcagccggt tgcccatctc gaatgtgtgc agggcctctg
67741 agaccatggg gtccaggatg cggtcaatgc catcctgcac ctcagggtca aggaccggca
67801 agtcacgata gaggtggtct atgctctcct cgaaggaggc aatgtagtta tcgatggtgt
67861 agaaggtgat ggatttcagg atgttcatca ggtacttttt ggagcgaaca atctgctgta
67921 tagtgtcacg taggcggatg tacgtggggt tctttgcggc cccgactatc gaccctgcat
67981 ttgcgatgta cttttctatg acggggatgg tgagggccgc ggtgtcggcc agcggtggcg
68041 tggcttcggg gttgtcgtgg ttggcgggtg tcgcagaggg agaggcggga gagatggggg
68101 cgcctggggc cgaggccaca ccggccaggc ccaacattgc ctcgatgtcg tccaggatgg
68161 tgcggaggcg cttttcgttt tctctggtgg tctcgagctc cttctgtttt ttcgcgactg
68221 tctcaaactc tggaaggggg gcaatgctgg ggtcgtcctc ctcaactcgc tccagggggcc
68281 aggggatacc gctcatatca ctaagggcgg tgcccaggta gaggagctcg cgatagtccc
68341 attcaatgga cgtgtaccgg atgtttagga gaggcaggga ggcgatgatc tggcatgtgt
68401 gccgcaggtg tgtcaggagg tcgtcaaaat ccatcactgt tgggaggctt gggtcctcaa
68461 ggtaggagag ataatcggag gccgccgagg ccaccttgtc cctgatgtcc gccgtacacc
68521 tgcgcacgtg cagggccgca ttcttggacc ggacggccac gttgtggaca aagggggggca
68581 ctgaggcggc gggaggggcc ccatactcta tcgctgtcaa cagcgccaaa aagcggacgt
68641 cctcctcatc taccccagcc tgttgtctgg ccacggccgt tcgggcggcc tccgccaggg
68701 ataggaggcg cttccagctt tcgtcgtcca ggaccaaggg gacgtccacg tgcgggcccc
68761 tgtagatgga attatcctcg ggttctcctc ctccttcccc cgcctcctga tctccgcccg
68821 agagcaggtc ggtcaggcgt ctgcgggccg cctccaggtc aaattttcca tcgtcgctct
68881 cggccagctg gggaatttca gccagcatct tagcaccggc atctacacgg accgcgtcct
68941 tcgtggccag ggacggcagg caggcctcca gctttgcggc caggtgctta tggaactctc
69001 ccgctcttcc cttgttttct gatagcatgt ttgcgaggtt ttggatgtta agttcggaag
69061 tgagcagttg ctccaggtcc agcgtgggga cctgcagatg tcccgaccag tcctttaaga
69121 attccagcag atttagcaca gacgatcggt ccctactcct tattagcccc tgctcgagga
69181 ccactgtcac aagaagatag tctatcatgc tcaaggcatc tgcctctggc acttcccggt
69241 tagaggccgg gtcgtagacg atggcctgtt cctggtaggt atgtccggct attctcgcaa
69301 tgttgctctc gaggggcaca aagtccatct caggagtctc tatgtcaaag gtggtctgat
69361 agtattggct cctggcggtg tccagtgtga tgggggacgt gggggcactg gatcccgatt
69421 ccaggctgtt ggagaacact tcatcttcga acatgtcttc atcctctgtg gtggggatat
69481 cggaggctaa gtcgctctcc gcttcttcag agtcggacat ggataggaaa ggctcctcta
69541 ggtcagacag gtagcggacg aggccagaac ccccagatgc atcatcccca aaggagggct
69601 gctgcccgaa gggaggtgat ggggatatct ccgttccagc cctgtcagcg gccgggggat
69661 ggttttttc tggttcgagt gtcgtggctg atggtgggag ctgctgagca ggaggaggag
69721 ccggggtagc tgatggcagg ggctgctgct gaggaggaag aggagaagga gcccgggcgg

Fig. 3 (cont.)

69781 ctgatggcgg gggctgctgc tgaggaagaa gtggagaagg agccggggcg gctgatggcg
69841 tgggctgctg ctgaggaaga agtggagaag gagccggggc ggctgattgc gggggctgct
69901 gctgagttgg aggaggagaa agagtcgtgg tggtgggggc tgctgctgca gtcggggaag
69961 gggatggggt ggtcagaggg atttttgggt tcgagggagc tgcctgtggc agagggatgg
70021 gtatttgcaa agggaggcga ggagatggag tgactgaagg agcgatagtt gagactggcg
70081 cggggtgggg tgtcggggag gcgggtggtg attggtgagg gatggggatt actggagggg
70141 gaaggcgagc tgctgaaggg gggcgatggg gcggaacgtg ggtgcgtggc agctgatcat
70201 cctctgtgtc agtggtggag gacagaggga ggcggcggcc ggaggtgggc ttcttgtggg
70261 ggctatcttt gcccaatccc tttttcctct tgggagtctg aggcgctgcg ccgctcgacg
70321 cccttggtgg cgtggaggga gcggggaccc cgggggtgtg acctaggccg gggatgggga
70381 tgaagagggg agggctggag gccggggccg cggaggccgg ggccgcggag gccggggccg
70441 cggaggccgg ggccgcggag gccggggccg cggaggccgg ggccgcagag gccggggccg
70501 cagaggccgg ggccgcagag gccggagacg acggcgggga gttggtcttt gcaggactat
70561 acctggcggc agggaatgag tcggatgtga aagatcgaga gggcagtggc ctgaggttat
70621 acggtattat tcgccgttca aacggtagca tgacgggagg gctgctatca gcaccgggcg
70681 tccccgccgc ctccccatca ctggacacaa gctcgggccc caccaggtca aagccgctgc
70741 cgttggcctc ataaaagtca tacacgccat agtgttccag cataaagatg cgggggtcct
70801 ctgtctcaaa ggcctcgggt agaaaataga gatgcacgca agtgtactgg gcccctggtg
70861 cccccacgta ctgcaggatg tcgtgcgcat aggtgctgac tctgacatgg gcgggggtgc
70921 ccggggccgc atccttctgg cagtgggggt caaacaagta gaaggagcca tctgtctcga
70981 tgatgatggc ccccgcgtag atgtcgcaga tgtagaggat gaactgggcc accccgttgt
71041 aactgccgtg caggacctcg gccagggact gaacaactgc cgagtttgcg atctgggcag
71101 ggaataggac gaggccaaag atctccgccg agcggtatat gtgcacgcgc ccaccgcccc
71161 tcaggaccac ggagctgggc acgtccgtca actgggccat ctcgtgcccc ttgaggatgc
71221 cgctctggcg catgagggca tccagccgcg ccccctcgtc caggacctcg tccagctcag
71281 ggcgggaggt caggggggcgg ccggccagga agctcttgac caggtagagg acgcagttgc
71341 tgacgcactg gatgccggca aagcggccaa acttgcagtg ggcctggttg cacgaggccg
71401 tgcctaggat gcggagggcc gagcctccac tcccgccccc gggggcattc acatccatgg
71461 tcctgattcc gcgcacgggg ccggttcccc gggtgcgctg gctttgcccc cagtcgccgt
71521 tactcatctt cggcggtggg gcggggagga cgccttgtcg cccccccttct ggtccggggt
71581 cttacgcggc tggcggcggc agccgccgag agataagggg ggtacgtgtg tgcctccgcc
71641 tctcctctgt ctgggccgcc gccgccgctt gccccgccttg aaggagaggg ggtagtccgc
71701 ggactgcgtc tgcgggggca ggaggtctca accttctggg ctcgggccgc ggtgtcgata
71761 tccgatggcc tttccctgtc ttcctcgtat gctccttctc ctcctcctcc cggcacgccc
71821 ctgagatctg cctcccctcc ctctccctcg tcctggtcgg aaaagtctga ggaggagaag
71881 gagaatgggg aggagtccaa aacggcacgc cacctgccgt ggggcggtgg tgacaggtcc
71941 cggctggccc ggcgcttgct cgcgttcctg ccgttaccca ggagaatggc cgcgagtttt
72001 ttggcgggga ggatgcggaa tggcgggggc gtttgtccca cgggtgaggg ggaatcgtcg
72061 gttagggccg gcacgaggtg gtgggtctgg acccgggccg tgcgagcaaa ggcggcgaga

Fig. 3 (cont.)

72121 accgaggggc ttctgggggt gactgtgatc tgttccggat ttaggtccat ggcgggtgtg
72181 tatgttttaa taggggtggt ctctggcgcg gcaggatgat ggtcgaggac gtccaccagg
72241 gccttgcaga tgctcttgcc tagatacagg atgtcgtcca tgctgagggg aggtggggtg
72301 tctgctcccc cctgcggaag ccgcctgggt gcggggatga agacaggtgg tgggcgggcg
72361 tctcgccgga ctatggcctc ggcacgctcg gcgtcgatgg cgggtggctg gaacaggcgg
72421 gcgaatgtgt aatcccggaa ccggtaggcg acgctgcgcc tgagggcgcc cgtcaggctg
72481 tatcccagct ccagggcgtg ctccacccgc tcgttgagct cctcgagatc cggacgcagg
72541 ggctcgctgg tgtgggccca gagggggtga tccgcgatgc cccggctctc cctgagggcc
72601 ggcaccagga ggcgccttct gagggtggcc gtgtcggccg tggccagggc ccacctggcg
72661 gcggcgtccc ggcacacatc ctggatgccc tccacgacgc tctttagcgt ctggaggtcc
72721 gtggagtagt ggcgggggga ggatgaaacg ctcttttcct tcaccgctac caccgcctcc
72781 tcctcctctt ccgtcgccag agggatctgc accctcccgg tctctgcgtc gtacaggagc
72841 gggcgggagc acagcctcca agctgccccc gtcaagcgcg agatgtcctc cgagagggtc
72901 tcacccgaga ccagaaagcg gcgggtggcc aggcccaacg actccgccgt cgtgctgtat
72961 ctcagggtga agaggagtga aaagagggag gtgggccagg caagcggtgg tgcttccgcc
73021 gcccgctctg aagctgagat agtctcggag atgatgcctg agacctctcg gacggcgtcc
73081 atgatcctaa ggactgcgtc gtgggacgac agccccccagg ggcccccgcc ctcttcgtct
73141 tctgcaccct cggctcctgc gtccccggcc ttgccttccc cctctaagtt gagggggcgc
73201 agtccgaccg cctgggggga ctccccaggc atcggagggg ccccgtcata gatctcccag
73261 acggtggcgt atatgagctc gagaggacgg cgggcccggg tcagctcggg ggaagggagg
73321 gccaggtcgc tgccgaagga gaccagccag cgcagggcgg ccagagagcg ggttttgggc
73381 agctcgttgg agaggacccg gcgaagggcg ggccagattt ggaactcgat gaaggcggcc
73441 gggaagaagg ggctgtggac ataggccgga tccgcgcgcg ccgtttggcc ggccctcagg
73501 gaccggcagt atgcctcgac gtctgtccgc ggggccgccg ccaccgctgc cgtccactgc
73561 cttcttccct gctcgccggg gagtaggggg ggcttacagg ggagggccgg agccggggcc
73621 ggggcctgcc acaggcggct gtagcggacc catagcagag acctgaggag ttcggatgaa
73681 aggtcccccg ccacctgctc atactcggcc gcgggagggg ggacgatgaa gatgcgcaga
73741 ggggttacgg cgtcccaagg gtccgccgcc gcccccacac ccacagccgt cgcggcgggg
73801 gcggcggcgg gcgtagaggg gccgctggtg cgccgggctc gtctgtccac ggcctcggcc
73861 tccgcccgca ggtaggccgc ccgggccaca cgggcgaagc ggctcgtggg gctcgcggtg
73921 ggcagcagtc ggaaaaagtg cagggcaaag cccgatagac tctctaggag ggcggcggtg
73981 gcctcgagcc acctccaccg cgagcgggac acccggggca cagaggccag catcatggcg
74041 tagtcccccg ccacggtctc gttgagcccg gccgagagca gaaccgtggc cacctgctcg
74101 atggcggctg gagagaagga tgcccggctc cccgccgcct cctgcacacg agcggccagg
74161 gcctccatct ctgccgccat cccggccagg aaggcctcga tgaccgagtc tgggacgccg
74221 taagtctggt cccagagcag ggcctcgtac acatagtcgt aaaagagggc ccctgagggc
74281 tccaaaagcc ggagccgggc ggcgtcaaag gccaggacgg gcacagccgc gacggggggc
74341 gtttgtcccc cgctggcctc cgcgtacacg cccaggatct ctaccgcccg ccgccggcc
74401 aggggcagcg aggccaccac gctggaaagt gactcggggc ggtgaaagag accaccaccg

Fig. 3 (cont.)

74461 ctttcttcac cctctccccc gccggccccg cccccactgt gctccaccag ctccacggcc
74521 atggccttga tgtccgcggc cgtgggctga ccctgccctg cagccgccca ggggtagcgg
74581 ttggtctccg cgtatacggt gaccagccat ctccccagcg tcgttttcgc cgcgttaaaa
74641 gcgtagaatg acagcccctc ccgcgggaag gcgtcccacc gggccagata agtgtcggcc
74701 accagctctt ccacgaaggc aaaggtggcc gttgggccag agaccgcgag cacctccccg
74761 ctgccctctt cgatgatgcg ccggtacgcg gccgccaggg cccgggtctc tgcgatgagc
74821 cgagagccgt ccagcggatc gtcggtggcc ggagaggctg tcgtgggggg cagtgaggat
74881 gccagcacgt ccagggccgc ctccagatgg ccgaggccga agctgcgcct ggaaaaggag
74941 gccgcccgga gtaggtagta ggcgtggtgg cggaggaccg ccgccgggta agcgtggccg
75001 ctcatgaggg tgagagtatt taaaaaatcg cgcaccagca ccggctgggc caaatccccc
75061 agtccaaaga tccccagctc cagaggcatc agcgcgcgca ggcgggcagc ggggtcgtcc
75121 ccagacagca gcaactgacg cgtcacgcgg gcgagccccc cgtccacctc tgccaggggt
75181 ggctgggcgt ctgcccctcc gctaccgccg ctgctgtcac tctccatagc ggacgccatg
75241 aaggtccagg ggtccgtcga tcgccgccgt ctgcaacgcc gaatcgcggg gctgctgccc
75301 cctccggccc ggcgtctaaa tatttcccgg gggtccgaat tcacgcggga cgttcgtggg
75361 ctggttgagg aacacgcgca ggcctcctcg ctgagtgcgg cggccgtctg gcgcgcaggg
75421 ctgctggccc cgggggaggt ggcggtcgcc gggggtggca gtggaggggg gagcttcagc
75481 tggtctgggt ggcggccgcc agtctttggg gactttctga tacacgccag ctccttcaac
75541 aacgccgagg ccactggaac gccccttttc caattcaagc agagtgaccc gttctcgggc
75601 gtcgacgcgg tattcactcc tctctccctg tttatcctaa tgaatcacgg ccggggtgta
75661 gccgcccggg tcgaggcagg tgggggcctg acgcggatgg ccaacctgct gtacgacagc
75721 cccgcaaccc tggctgacct ggtcccggac tttgggcggc tggtggccga ccgccgcttc
75781 cacaacttca tcaccccctgt gggccccctg gtggagaata taaagagcac ctatctgaat
75841 aaaatcacca cggtggtcca cgggcctgtg gtcagcaagg ccatccctcg cagcaccgtc
75901 aaggtgacgg tgccccagga ggcctttgtg gatctggacg cgtggctctc cggcggcgcc
75961 gggggtggcg gtggagtatg cttcgtcggg gggctgggcc tgcagccgtg ccccgccgat
76021 gcgcgcctct atgtcgctct gacctatgag gaagccgggc cgcggtttac gtttttccag
76081 tcgtcccgcg gccactgtca gatcatgaat atcttaagaa tttattactc accatccatc
76141 atgcaccgct atgctgtggt ccagccccta catatagagg agctaacctt cggggcggtt
76201 gcctgtctgg ggacatttag tgctactgac ggttggagga ggtctgcctt caattaccgt
76261 ggctctagcc tccccgtggt ggagattgac agcttttatt ccaacgtctc tgactgggag
76321 gtgattctct agacttaacg ggaggaaaca ggaggaggag ggggacaaga gcacaaaagt
76381 ggttcagtgg acacccacca cacagcatgg caacgaccag tcatgtcgag catgagctcc
76441 tctccaaatt gattgatgag ttaaaggtca aggccaactc agaccccgag gctgatgtcc
76501 tggccgggcg cctgctccac cgccttaagg ccgagtcagt tacacacaca gtagccgaat
76561 atctggaggt cttctctgac aaattctacg atgaggaatt cttccagatg caccgggatg
76621 agctggagac ccgagtctct gctttcgcgc agagcccggc ctacgagcgc atcgtctcca
76681 gcggctacct gtcggccctg cgctactatg acacctatct gtatgtgggg cgcagcggga
76741 agcaggagag tgtgcagcac ttttacatgc ggttagccgg cttctgtgcc tcaaccacct

Fig. 3 (cont.)

76801 gcctctacgc gggtctcagg gcagccctgc agcgggccag gccggagatt gagagtgaca
76861 tggaggtgtt tgattactac tttgagcacc taacctccca gacggtgtgc tgctccacgc
76921 cctttatgcg ctttgccggg gtggaaaact ccactctggc cagctgcatc ctcaccaccc
76981 ccgacctcag ctccgagtgg gacgtgaccc aggccctcta taggcacctg ggcgctacc
77041 tctttcagcg agccggggtg ggtgtagggg tgacgggggc tggccaggat gggaaacaca
77101 tcagcctcct gatgaggatg atcaacagcc acgtggagta ccacaactat ggctgcaaga
77161 ggccggtcag tgtggcggcc tacatggagc cctggcacag ccagattttc aagtttttgg
77221 aaacgaagct gccggagaac cacgagaggt gcccgggcat ctttacgggg ctctttgtcc
77281 ccgagctctt cttcaagctt tttagggaca cgccctggtc ggactggtac ctgtttgacc
77341 ccaaggacgc cggggacctg gagaggctct acggggagga gtttgagcgc gagtactatc
77401 ggctggtgac agcgggcaag ttttgtgggc gggtctccat caagtccctg atgttctcta
77461 tcgtcaactg cgccgtcaag gccggcagcc ccttcatcct tttgaaggag gcctgcaacg
77521 cccacttttg gcgcgacctg cagggcgagg ccatgaacgc cgccaacctg tgcgccgagg
77581 tgctgcagcc ctcgaggaag tctgtggcca cctgcaatct ggccaacatc tgcctcccgc
77641 gctgcctggt gaatgcgcct ctggcggtgc gggcacagcg ggccgacacg caggggggatg
77701 aactcctgct ggccctccct cgactctcag tcaccctacc tggagagggg gcagtcggtg
77761 atggattctc gctagcccgc ctcagagatg ccacccagtg tgccaccttt gtggtggcct
77821 gctccattct tcagggatcc cccacttatg attccaggga tatggcctcc atgggcctcg
77881 gggtgcaggg cctggccgat gtctttgcgg acctgggctg gcagtacact gaccctccct
77941 ctcgctcgtt aaacaaggaa atattcgaac atatgtactt tacggccctc tgcaccagta
78001 gtctgattgg acttcacacc aggaagattt ttccgggttt caaacagagc aagtatgccg
78061 gggggtggtt tcactggcac gattgggcag gaacagacct ttctattccc agggaaattt
78121 ggtctcgcct ctctgaacgc attgtgaggg atgggctttt caattcacag tttatcgccc
78181 tgatgcccac ctcaggctgt gcccaggtga cgggctgttc ggacgccttc taccccttct
78241 atgccaatgc gtccaccaag gtcaccaaca aggaggaggc ccttaggcca aaccggtctt
78301 tttggcgtca tgtgcgtctg gatgacaggg aagctttgaa tcttgtcggg ggccgtgtct
78361 cctgcctccc ggaggctctg cggcagcgct acctgcgttt ccaaacggcc tttgattaca
78421 accaggagga cctgattcag atgtcccggg acagggcccc ctttgtggac cagagccaat
78481 ctcacagcct gtttttgcgt gaggaagatg ccgcgcgggc cagcacgcta gccaacctac
78541 tggtgcgcag ctacgagctg ggcctgaaga ctatcatgta ctattgtcgc attgagaagg
78601 ccgccgatct gggggtgatg gagtgtaagg ccagcgcggc tctgtcggtg ccgcgggagg
78661 aacagaatga gcggagtccc gctgagcaga tgccgcctcg tcccatggaa ccggcgcagg
78721 ttgcggggcc ggttgacatc atgagcaagg gcccagggga gggaccaggt gggtggtgtg
78781 tgcccggggg attggaagtg tgctataagt accgtcagct cttctcagag gatgatctgt
78841 tggagactga cggttttact gaacgagcct gtgaatcttg ccaataaacg tttattgcca
78901 tgtccaagtt gttgtacgtg cgtgatcatg agggctttgc ctgcctaacg gtcgaaaccc
78961 accgcaaccg ctggttcgcg gctcacattg tcctcaccaa ggactgcggg tgtctcaagc
79021 tactcaatga gagggacttg gagttttaca agttcctctt tacgttcctg gccatggccg
79081 agaagcttgt gaactttaac attgatgaac tggtcaccag cttcgagagc cacgacattg

Fig. 3 (cont.)

79141 atcactacta caccgagcag aaggccatgg agaacgtcca cggggagact tatgctaaca
79201 ttttaaacat gctctttgat ggggacaggg cggcgatgaa cgcctacgca gaggccatca
79261 tggccgacga ggccctgcaa gccaagattt cctggctccg tgacaaggtg gcggccgccg
79321 tcaccctgcc ggagaagatt cttgtgttcc tgctgattga aggcatcttc ttcattagct
79381 ccttctacag catagccctg ctgcgggtcc ggggcctaat gcctggcatc tgcctggcca
79441 ataactacat aagtagggat gagctgctcc acacccgcgc tgcctccctg ttatacaata
79501 gcatgacagc caaggctgac cgaccaaggg ccacctggat ccaggagctg tttcgcactg
79561 cggtggaggt agagactgcc ttcatcgagg ctcgtggaga gggggttacc ttggtggatg
79621 tgcgagccat aaagcagttt ctggaggcca cggccgatcg catcctgggt gacattggtc
79681 aggctcccct gtatggcaca ccaccccccca aggactgccc gctcacctac atgactagca
79741 tcaagcaaac taatttcttt gagcaagaga gttccgatta caccatgctg gtggtagatg
79801 acctttgagt cagggtggct acttgctcag gtttctgggc ataaattctc ctgcctgcct
79861 ctgctctggt acgttggctt ctgctgctgc ttgtgatcat ggaaaccact cagactctcc
79921 gctttaagac caaggcccta gccgtcctgt ccaagtgcta tgaccatgcc cagactcatc
79981 tcaagggagg agtgctgcag gtaaaccttc tgtctgtaaa ctatggaggc ccccggctgg
80041 ccgccgtggc caacgcaggc acggccgggc taatcagctt cgaggtctcc cctgacgctg
80101 tggccgagtg gcagaatcac cagagcccag aggaggcccc ggccgccgtg tcatttagaa
80161 accttgccta cgggcgcacc tgtgtcctgg gcaaggagct gtttggctcg gctgtggagc
80221 aggcttccct gcaattttac aagcggccac aagggggttc ccggcctgaa tttgttaagc
80281 tcactatgga atatgatgat aaggtgtcca agagccacca cacctgcgcc ctgatgccct
80341 atatgccccc ggccagcgac aggctgagga acgagcagat gattgggcag gtgctgttga
80401 tgcccaagac ggcttcctcg ttgcagaagt gggcacgcca gcaaggctca ggcggcgtta
80461 aggtgacact caatccggat ctctacgtca ccacgtatac ttctggggag gcctgcctca
80521 ccctagacta caagcctctg agtgtggggc catacgaggc cttcactggc cctgtggcca
80581 aggctcagga cgtgggggcc gttgaggccc acgttgtctg ctcggtagca gcggactcgc
80641 tggcggcggc gcttagcctc tgccgcattc cggccgttag cgtgccaatc ttgaggtttt
80701 acaggtctgg catcatagct gtggtggccg gcctgctgac gtcagcgggg gacctgccgt
80761 tggatcttag tgttatttta tttaaccacg cctccgaaga ggcggccgcc agtacggcct
80821 ctgagccaga agataaaagt ccccgggtgc aaccactggg cacaggactc caacaacgcc
80881 ccagacatac ggtcagtcca tctccttcac ctccgccacc tcctaggacc cctacttggg
80941 agagtccggc aaggccagag acaccctcgc ctgccattcc cagccactcc agcaacaccg
81001 cactggagag gcctctggct gttcagctcg cgaggaaaag gacatcgtcg gaggccaggc
81061 agaagcagaa gcaccccaag aaagtgaagc aggcctttaa ccccctcatt taacaccatg
81121 ttctcgtgca agcagcacct gtccctgggg gcctgtgtct tctgtctcgg cctcctggcc
81181 agcacccccct tcatttggtg ctttgtcttt gccaacctgc tctctctgga gatcttctca
81241 ccgtggcaga cacacgtgta caggcttgga ttcccgacgg catgcctaat ggccgtcctc
81301 tggacgctgg tacccgccaa gcacgcggtg agggccgtca ctccagccat catgctgaat
81361 attgccagcg ccttgatctt cttctccctc agagtctact cgaccagcac gtgggtttct
81421 gccccctgtc tctttctggc caacctgcct ctcttatgcc tgtggccccg gctggccatc

Fig. 3 (cont.)

81481 gagattgttt acatctgccc ggctatacac caaaggttct ttgaacttgg gttgctcttg
81541 gcctgcacca tctttgccct gtccgtggtc tccagggccc tggaggtgtc ggctgtcttc
81601 atgtctccat ttttcatctt tctggctttg ggctctggaa gcctggccgg tgctcggcgt
81661 aaccagattt acacctcggg tctcgagcgg agacgcagca ttttctgcgc ccggggagat
81721 cattcggtgg catccctgaa ggagaccctc cataaatgcc cgtgggatct gctggccatc
81781 tctgccttga ccgttcttgt cgtctgtgtg atgattgtgt tgcatgtgca cgcagaggtg
81841 ttctttggac tctctagata cctgcccctc tttctctgtg gggcgatggc ctccgggggg
81901 ctgtacctgg gccattccag catcattgca tgtgtcatgg ccaccctctg caccctgaca
81961 tctgttgtgg tatatttcct ccatgaaacc cttggacccc tgggcaagac cgtgctgttt
82021 atctcaatct ttgtctatta ctttagcggg gtagcggccc tgagcgcagc tatgcgctac
82081 aagcttaaga agtttgtgaa cggacccctg gtccatctcc gtgtggtata catgtgctgt
82141 tttgtcttta ctttttgtga atatctgttg gtgacattca ttaaatccta acgaccggag
82201 tcctgtctct ttgtgttctt gggggacttg agttagctgt ctttcctctt attacattgg
82261 gctaacggga ggaaatgaac ccaggggtgg cagtggatgg ggtcatttat gggcaaaact
82321 cacaggacat gtttggggag ttagcattgg cgtcgggaaa cacagctctg gcagttataa
82381 ccgcaccagc taacaggaca tgtttggggg agttggcatt ggcgtcagga gacacggctc
82441 tgtcagttat caccgtacca tgagtgccat gtgtgtccag tgcctaatca ccgttcctca
82501 ttttgtgtgc ctcctcaaat gttccagaag tcggccacag gggaggtggc tgaattaggg
82561 ccttttccct cattccccca tgagacccac gtggcaggcc taggggctac attcgcctcc
82621 cacgtttccc ttcgcgtgag gcatccgata tgactgaatt ttcgcagtct cttttccctc
82681 ttcccttgtt attcccatag aattacagtg aggttacaca ggtggagatt cagtttaacc
82741 atttattgat ttaatccagg aacaaaaaac agtcctagtg acccagtgcc cggagagaga
82801 atggccctga caagtcggct gcatgatgca cttcggcagt cacgtgtgtg agtctccacg
82861 gcctctgtca aaagggagct tagcgtgcca gggttgtaat tcttgatgta gtggcccagg
82921 aattcaactt catcgtgtct ccgtctgcag ttggcgttaa tgtaggctgg ggctactgcc
82981 gcatatgctg ccaagagaca gaggggctgc ttcacatatg agctgctcag ggtctccacc
83041 accttgtttt gacgggccgt ggcacaggtg atgtagaaga gttgcttcac aaagttgtag
83101 tctcgcgtgt taggaaggaa gcagggtgcc agctctttga gcttggtcag gatcaccttg
83161 ctaagactca tggcgcaggc caggaggatg tcttccgcgg gagctagggg caggtcgccg
83221 tggtaggtga tctcctggag ccaaaagatg gtctcttcta gcatggccac cagggtgcag
83281 agccccgcgt tctggatcgc ctgcatgcgt gcatccagcc atgtgtcctt gttggttgac
83341 ttggtgaaaa actcacgtag tgtcttgtag ctcctgcgca gctcgtgtct gggttgcact
83401 ttctgccagg ctccaatctc tggatgggcg gccaccgcca gcatcgactg taggaacggg
83461 tcttggatgg gctctagggt cagagaggcc agggggctgg gcaaggtgac aaatgtaatc
83521 ttggagacag gcttaaccag actcatgtca aaccacggtt tgttcggcag gggcctctgg
83581 ctgcgttctt gcctcgcctg cttccttgtg ctcctgccgg cccctcgaga ttctgaccgg
83641 ggacctctgg ttgctctgtt gcttcgggga gctcttggag acctcggtgc tctaggcacc
83701 ctgggggccc ttggggctct gggcgctctt gctcccgggg gcaggtgtcg gcgcttgcca
83761 taactttcat cggtgcagcc atggacctct ccgcgtcgcc ttttgtggcc tctggtgtaa

Fig. 3 (cont.)

83821 gaggagttgc cagtctcctc cttctcgtcc tcgtccctgc acaggggtga gcgatgcaat
83881 gtgactgtct tgtcctgtag gtcccacttc tttctgggaa tcacaaacga tgccgaggta
83941 ggggttatga ccacgctgga gggccgtgca ggtatggcgt gggccggagt tggatcttca
84001 tcctcctcct ctgaggatga aatctctcca tctgtggagt gttcttcgct gccctccata
84061 gggtccagat cgcagtctgt gttggtgtct gagaccgctt cgagttccag aatgtggctc
84121 tctgcagagg ggagacaaaa ggtggagact gccttgagca cctctgtctc aggcaccgga
84181 tgccccggc tccacggccc cggccactgg ccggtgtagc ttcttacctg cgggatcctc
84241 gttggaggaa atgctgctag ttcgggagag tctctgagaa ggaaccatct tgtctgtctc
84301 tacgacgggc tagctgggat gtagtgctgt cttgactggc ctcagcccta tttatgattc
84361 tggaggcggg cacgctgatg gagaaatggg cggtcggttg attggcccca cagcgaccgg
84421 cgaagcactg actcatgaag gtgaccgtga tggcctgtga tgtgtagtag agtaccagaa
84481 acaccctcac attcttggag ctggccctgt gggtatgcct caggcacgca aagttcctgc
84541 cccgggcatg gcacacctga actaagtttg gcccggtttg ctcaaacgtg acatggagaa
84601 actgggggaa tttgtcttct ggcacagctg ttgccagggt gctcatgagc gagggccaga
84661 tgcaggagct gacccaggcg acgagatcca ggcccagatg tccctctatc atggcgcaga
84721 cattctccac ggtgggggc agggtctcgc gggtcctctg gattagatag tcacgcccat
84781 catccgcgat gtggtagcag aaggttttgg gggccggcca gccccacgtgc agtgagtgat
84841 gtaagaggtt ttgaatgttg agggcattct taacatagct gtgcttgtct tcctcttccg
84901 gatgacagac aaagaggcgc agctgccggc taagaccacc gcccctgtcc accttgtagg
84961 tatgcggcag ccggatgcac cgcccggcgt gatacacgcc gctgtcaaaa agcggggccc
85021 caatctcttt gatcttgtga cgcatgcggc gcaggcaggc cgttaggccc atgagcttct
85081 gcagcacaga cacaaaccct tgtactgcgc ttgttcccac aatagcatgg cctctaggta
85141 ggggggtgat gacgcgaaag cccagttttc ccgtgcatat gcaaaagggg agcacatctt
85201 ccatattatc cgggtcggcg ggtggacaag ctgatttgaa aaaatagact gggtgggccc
85261 tggacactgg acccaggcgg cgcatgaggc gcagtacctc acgccgcacg gtccggcaca
85321 ggtcatagat ttcctccagc gaccaggggg ccccccttgat ctttagatcc aggtccaaga
85381 ccaggttgca gaccggaagc cggggattaa agtattcatg ccgggagaca aagagctgct
85441 cgctcaggct gttctgtgaa tagtacactg gggtgtagga gagggccctg gtgagacacg
85501 tgtctgggag gcggcagttg gtcggggtgg agacgacctc cgccaggtgg gatgagaagg
85561 ggtcagcggc tgtcattaca aagtagtgcc tgtctgcaaa atggcagagg aagaccggta
85621 gccgctgcac ccttcgaagg acggtgggtg ggaggaattg ttccttggga ttccactggc
85681 cccggcaggt ggcctggccg gccaagcata gaaacccttg aagcgtgggg gggtatgtgg
85741 gaccctcatc cgcgtgccag cgcgcgagct ccaccagctc ccgggccacg tccacactga
85801 gcccggccca ggcccgcatg agtccgtcat cggggtcggg gtcccacgtg tatggggccg
85861 ggggctccat gcggattttc agctgctgga cacgcacatg ctcagccagg taagtctccc
85921 gggtgaagta ggtgcgcatg tgctccgcaa agcccctgtc caggagcgag gggagcacga
85981 cgcccccga aggcagacac ccaatttctc ccatgctcgt taactgagag tatcgcttaa
86041 aggttccctc gttgaagcac tgtgcgtggg ccaaatagac gtagcgcacg agatcggccg
86101 aggccagggg aaggcgcccc ctgtaggcgt ctatcgtcct tgccacagcg cggatctctc

Fig. 3 (cont.)

86161 gcgagtcccg ccgcagtttc tcgtgtgcaa agtgggcaaa agcctcggtc tgctccgccc
86221 atgccgagga gccaaagacc tcccccagct cggccaggga cgtgacggcg gccaggctct
86281 gaccagactc ggaagtaaat agctccgtga ggtgcgccag ggtctcaatc gtacaaggaa
86341 tgccccaaaa atagtaagca gccgtgacta gcacgaactg ggcctcgtgg gagccaaagg
86401 tgctaatgaa ccacctggcc gagatgttaa cgcggtagat gcggcgcaga cagcccacga
86461 tcttgggacg cagccacgcc acgcggcctc tggcatcccc ctgtggctgt ttcttagcgc
86521 tcagtgtgag cagttccacg aggggcgtga gcgagcgcag ggcccccgcg cgatctaggt
86581 aggtggatag acggtccgcg gtgagcggcg tgaggccgcg caggaagggg aaggcctcct
86641 ccgccggcag gtgcagcgtc agaaccaggc cgcagcggct ctgtgaggtc agccgcttct
86701 tgggcaggtg aagctgcagt tccacgagag aacccgccac gtggtggagg ggcgaggcgt
86761 tgtggcacaa acaaaacagg cggaagccct cgtcaggccg cgagaggatg gcatcgagga
86821 tggcctccgc aatgtcagtg tttgaggcca caagggcctt gatgacgacg ggggcggaca
86881 ttatttaaga ccgggaggcc ccaacggcgg gctaaacaga acgatggcct tctatctccc
86941 agactggtcg tgctgcgggc tctggctctt tggccggccc aggaatagat acagccagct
87001 ccctgaggag ccggagacct ttgagtgccc ggaccgctgg cgagccgaga tagatctggg
87061 cctgcccccct ggtgtgcagg tgggagattt gctaagaaat gagcagacga tgggctcact
87121 gagacaggtt tatttgctcg ctgttcaagc caatagcatc acggatcacc tgaagcgctt
87181 tgacgccgtc cgcgtccctg agagctgtcg tggggtggtg gaggcccagg tggccaagct
87241 tgaggccgtg cgctcagtca tctggaatac catgatctct ctggctgtaa gcggcatcga
87301 gatggacgag aatgggctca aggccctgct ggacaaacag gctggcgaca gcctggccct
87361 gatggagatg gagaaggtgg ccacggcgct caagatggac gagaccggtg cctgggcgca
87421 agagatctcg gccgttgtct catcggtgac cgccccctca gcctcggccc ctttcatcaa
87481 ctccgccttt gagcccgagg tgcccacccc cgtccttgca ccgcctcccg tggtgcggca
87541 gccggagcac tctgggccca cggagctcgc gttaacgtag caaccagact ccacaccaaa
87601 taaacatttt attggtaaaa caagggatat gaaggtgtca ttgacccgag gatccaaacc
87661 ccctcccctg tctcccctcg agcgcctcgc tcagcccact atcacccatg gccaggctcg
87721 gcacctcctc gaaggtgcag ctggcccacc taaagagaga tctggggcca aggacccccg
87781 cgtcactgtg gggctgtag aaggaggtga ggtggtgctt gtgaaggtaa acaagctgac
87841 agaagcgccg gtacttgtta aggaacacgg tctggtcact aaagttggtc aggctgacgt
87901 ccacccccacc ccggcgccac ctgcagggct tcactagaat accctgcatg gccaggcccg
87961 acctgccaaa gattgtcggc ctgtggtgag ggatagaagg ggggggcacg gtgagtgtca
88021 ctgagacggt ctgatggggg aagagggcca ggtcctttgg caaagagacg tccaggccca
88081 cgtccccggg gtactggggg tggttgatgg gacccttgtc ctcctccatc tggggggtgg
88141 catatctgaa ggcagccagg tggattttga gctccgatgg acgcagcgtg gagttgtagc
88201 gccgctgatt ctggaggatt agccggagtt cccccgtgta gccgggatcg atgatgccaa
88261 catgagacgt gaccggacgg gaggtgctgc ccccacagcat gagcccatga ccctcgggtg
88321 ggcgggcata gaggcctagg tccacagttg tggtcttcat cgggcgcagc aggatggtgg
88381 tcttgttgac caaggtgagc cgccctacac tagcctgctg gagcaacagc ttgtcattct
88441 ggaaggcgta gcgtatgtgt ggacaggcct ccatggtgat gatctaacag acagggacgg

Fig. 3 (cont.)

88501 cggcgctata tataagagcc caagacccgg ctctctttac tgcgaaatgg ggaaggtcct
88561 aagaaagccg tttgcaaagg ctgtgccact gctcttcctc gccgccacct ggcttctgac
88621 cggggtgctg ccggccggcg cttccagtcc cacaaacgcg gcggcggctt ccctgactga
88681 agcccaggac cagttctact cctacacatg taatgcggac acattctcgc cttctttgac
88741 cagctttgcc tccatctggg cacttctgac gcttgtctta gtcattatag cctcagccat
88801 ctacctgatg tacgtctgct ttaacaagtt tgtgaacacg ctgctgacgg attagatggg
88861 gatatttaaa aggggcagca atctcggctg tttgtacttc ttctctgctc gttaaaccaa
88921 tagcatgtca gctccacgca aagtcagatt gccttctgtt aaggctgttg acatgagcat
88981 ggaagacatg gccgcccgcc tggctcgcct ggagtctgag aataaggctc tgaagcaaca
89041 ggtcctcaga gggggtgcct gtgcctcgtc tacctctgtt ccttctgctc cagtgcctcc
89101 gcctgagccg cttacagctc gacagcgaga ggtaatgatt acgcaggcca cgggccgttt
89161 ggcgtctcag gctatgaaga agattgaaga caaggttcgg aaatctgttg acggtgtaac
89221 tacccgcaat gaaatggaaa atatattgca aaatctgacc ctccgcattc aagtatctat
89281 gttgggtgca aaaggccaac ccagccctgg tgagggaaca cgaccacgag aatcaaacga
89341 ccccaacgcc acccgacgtg cccgctcccg ctcccgggga cgtgaagcaa agaaagtgca
89401 aatttctgat taataaattt ttattgactt tatacatagg tctcggcgtc atcatatggt
89461 ggggtggtgt aggtatggga tgtagacaag ttacgcctaa aggcgcagtc cgccatgacc
89521 agcagcagca gaagggtcag cacagccaga gaggccccact gcagtactag catggagagg
89581 tttgagaatc tgggctggga cgttggcggg actggcacgg tggcttgggc tgtggtaacc
89641 ggtgggctcg taaaagtcca gcggggccgc agtttgctag aagtgctggg aggtagatag
89701 gtggtcgcat tgtatctcgg tcttggcgta gttgaatcac cgccgtaatc tgtggtgggc
89761 tctgtacttg tccgggctcc atgtcctgtg gtgtgctttc caccggtggt agaattggcc
89821 tttccacctg ttgaggtgac cgtgggaacc gccgtctttt ggccactggg ggcctggggc
89881 gacgttgcat tttgggggg cgtgcctttg gtgacattaa cctcccccgg ttttgtggat
89941 gtggaactgt ttccagggcc tgacgcttgg ctggtggtgc ctgggcgggg tgctggcgaa
90001 ctggtggaca catgatgtgt gctgatagag gctggtgtca cctgtgttat attttcacca
90061 cctgttgggt gagcggaggt tagtaaaggc atatgtgacg ttgaattgtc actggtggag
90121 gggctgagtg tctctgggtt tgaactgggt ctcagtgaca tggaagaggt tgaacttgaa
90181 gttatgttat gttggcctgt ggtaacagca ctggttgcat tttttggttg gctggtaact
90241 actggggtgg gacttgttcc tcctaaggtg tggttggtgg catttgcctg tggacttgtt
90301 tctcccacag tagggccggt ggcatttggg gttggggtag tcactgctga ggtggggctt
90361 gtttttccca aggtggggct ggtggcattt ggggttgggg tagtcactgc tgaggtgggg
90421 cttgtttttc ccaaggtggg gctggtggca tttggggttg gggtagtcac tgctgaggta
90481 ggacttgttt ttcccaaggt ggggctggtg gcatttgggg ttggggtagt cactgctggg
90541 gtggggctgg tggcatttgg ggttggggta gtcactgctg gggtggggct ggtggcattt
90601 ggggttgggg tagtcactgg tgaggtggag ctggtcatgt cgggggcctt actttctgtg
90661 ccgttgtccc atggagatgg acttggtgtc accggtgatg cgcctgacgt tgtgccggct
90721 ggtgttgggc tggtgacatc cgcggtggat acagtggggc ctgtgcttgc aggtgcggtg
90781 aggttggtag gcacgtgagt agagctgggt agacctgtcg ttgtattggg atcagcaaat

Fig. 3 (cont.)

90841 ccagttgtat tcaaggtagg ggaggtggtg gtgctctcgg gtgccttgga gaatataacc
90901 ttgtgggttg ttgtggtggc attggtagcc gttcgtgtga taatgagtgt cttgggggcc
90961 gtgccaagac ccgagacagt aatgtcaaat gtccgattgc tcgcaaatgc accagaaata
91021 ttttcacaac ccgaaggtgt ccccgaggtg agagtccatt tgcacttaaa gtcagtttca
91081 gtgttgtttg gccaggccca aaaggcagtc actgtaacat ttggcgagtt tgcgtcctca
91141 gaagtgacca ttggcactga ataggtagca ttgtcaccca catatgtgat gtctgtggtg
91201 tttgtcggca tgtcctgtga agctggaatc tcatcagaga acacaatgtt ggactgaatg
91261 cagtaatctc ccccgctcgc cttcggtcca ttcccagagt aaaacacgta caggatactg
91321 ttattgccaa gaaatcgtga cactggacgt ggtgtcagac gcaggctgta tgcatacccct
91381 gtaccaggta ttggggtggc cacgggactc gttgatgtga gaattccgcc gctgggaaca
91441 tggctctcgt atccactgca ggtgatgtta aatttgttgt ctccgggcag aacttgtgaa
91501 atttcgccat cctccataat acactcaata tctatctcat taccgagcat ttctgttttt
91561 acgctgaaat tcgagtcttg agctgacgtt ggcaaactta agggtagcgt gacatccagc
91621 ccctgtgccc tcactactgc cgttatattg gtagaattac agttatccca ctttatgtat
91681 ggcactgttt ctggtatcag gtacacgggg ttttgcattt ctgcatggtg gcaccacatg
91741 gttccaaaca catcttgaaa gtagacatct acagattcca ggcttacttg ttgctcctct
91801 ccggtggtga cgttaattgg aagcttctta gaccgcatag ttagagccaa ttctcctgca
91861 ccaaggagct ccagtagaaa gagattggtg gcattttctg agccaccaaa tgcacctcga
91921 ggttggtaga cagccttcgt atggggtgtc agctggccaa agtcaagatc aagttgatgc
91981 tttttgcccc cgacatcgaa attgatagtt acattgacat ctgccgtgca aacattgcat
92041 gtggggtaaa atgggaattc cggaatctca acattgaaaa aaccaggatc ttcacccgtg
92101 agatggatca ggctctggat ggtgtactga cacacaagca aggctgcctc cattgtctcg
92161 gcaccgattt ctaggcagca tcctctttaa taggtacaag gggggtgcgg tgttggtgag
92221 tcacactttt gttgcagaca aaatggacaa ggacaggccg ggtcccccgg ccctggatga
92281 caacatggaa gaagaagtcc catctacctc ggttgtgcag gaacaggtat cggcgggaga
92341 ttgggaaaat gtcctcatag agttatcaga tagcagctca gaaaaggaag cagaagatgc
92401 ccacctggag ccggcccaga agggtacgaa gagaaagcgg gtcgatcatg atgccggtgg
92461 gtcagctcca gcacgaccca tgctcccacc ccagccggat ctccctgggc gagaagccat
92521 tctccgcagg tttccactag atctaagaac acttcttcaa gcgattggag ccgcggctac
92581 ggtgagcatc cctatggcct aagtgtgtga tgtgtgtttt tacccatcac acaacaacaa
92641 ggtaagtaat ttgttgccgt tggtttcagc gcatcgacac acgagccata gaccagtttt
92701 tcggatccca gatttcaaat accgagatgt acataatgta tgccatggcc attcgacagg
92761 ccattagaga tcgtcggaga aatccagctt ctcgtagaga tcaggccaaa tggagactgc
92821 aaaccctggc cgccggatgg cctatgggtt accaggcata cagcagctgg atgtacagct
92881 acaccgatca ccagacgact cccacattcg tacatctcca ggcgacactt gggtgcacag
92941 gtggccgtag gtgtcacgtg accttttccg ccggcacctt taagctgccg cgatgtaccc
93001 ccggggatcg ccagtggttg tatgttcaga gctccgtggg taacattgta cagagctgta
93061 atccccgcta cagtatttc tttgactata tggctataca caggagcctc acgaaaatct
93121 gggaggaagt tttaacacct gaccagcgtg tttcatttat ggaattccta ggatttttgc

Fig. 3 (cont.)

93181 agagaacgga tttgtcctat atcaagagct ttgtcagcga tgccctgggc accactagta
93241 tccaaacacc gtggatcgat gacaatccta gcacggagac ggcacaggct tggaatgccg
93301 gctttctccg gggtcgtgcg tatgggatag acttgcttag aactgaaggg gaacatgtcg
93361 aaggtgctac cggtgaaacg cgagaagaaa gtgaggacac ggagagcgat ggagatgatg
93421 aagatcttcc ttgtatagtg tccagaggtg gacctaaggt caaacgaccc cctatattta
93481 taagacgtct gcacaggttg ctgctgatga gagcgggcaa acgaacagaa cagggcaagg
93541 aggtactgga aaaggcccgt gggagcactt atggcacacc taggccgcct gttccgaaac
93601 caagaccaga ggtcccacaa agcgacgaga cagctaccag tcacgggtcg gcgcaagtcc
93661 cagaaccccc aaccattcac ctagcagctc agggaatggc atacccatta catgaacaac
93721 acggcatggc cccgtgtccg gtagcacagg ccccacctac gcccttgccc cctgtatctc
93781 caggggatca actcccaggt gtttttagcg acgggcgagt ggcgtgtgca ccagtacccg
93841 ccccggctgg gcctattgtc cggccctggg agccatccct gacacaggct gcggggcagg
93901 cctttgcacc cgttagacca caacacatgc cagtagaacc cgtccctgtc ccgacagtgg
93961 cacttgagcg accagtttac cccaagccag ttcgtccggc acctcctaag attgctatgc
94021 agggccccgg ggaaacttct ggcattagac gcgcgcggga gcgttggagg cccgcacctt
94081 ggacgccaaa tccaccccgt tctcccagtc agatgtccgt gcgtgaccgt ctggctcgtt
94141 tgcgtgctga ggcacaggtc aaacaggcta gtgttgaggt gcagcccccc cagttgaccc
94201 aagtatcccc tcagcaacca atggaggggc cgttggtacc agagcagcag atgttccctg
94261 gtgccccctt tagccaggtt gctgatgtgg tccgggcacc tggggtaccg gcgatgcagc
94321 cacagtactt tgacctcccc ttaattcaac ccattagcca gggggcaccc gtggccccgt
94381 tgagggctag tatgggcccg gtacctccgg taccggcaac acagccacag tattttgaca
94441 tccccttaac tgaacccatt aaccaggggg catccgcggc ccattttctc cctcagcaac
94501 cgatggaggg gccgttggta cctgagcagt ggatgttccc aggtgccgcc ctgagccaga
94561 gtgttaggcc aggggtagcg cagtcacaat attttgacct ccccttaact caacccatta
94621 accatggggc acccgcagcc catttcctcc atcagccacc aatggagggg ccgtgggtac
94681 ccgagcagtg gatgttccaa ggtgccccccc ctagccaagg cactgacgtg gtccaacatc
94741 agctggatgc tttggggtat acactccatg gtcttaacca tcccggggtt cccgtgtctc
94801 ctgccgttaa ccaatatcat ctcagccagg ctgcctttgg gttacctatt gatgaggatg
94861 agagtggcga ggggtccgat acctccgagc cgtgtgaagc tcttgatttg tcaatccatg
94921 gcaggccctg ccctcaggcc cccgagtggc ctgttcaaga ggagggtggc caggatgcca
94981 ccgaggttct tgatttgtca atccatggca ggccccgccc tcggaccccc gagtggcctg
95041 ttcaagggga aggtggccaa aatgtcacag gccctgaaac tagaagggtg gtggtgtcag
95101 ctgttgttca catgtgtcag gatgacgagt ttccggatct acaagatcct ccagatgagg
95161 cctaagcaaa ggtgtagaag tgtgtccccc tccattccac ccactgataa tacgcccgac
95221 aataaagttg atgatattga attccacacc tgcttgtgtt tgtgatttta tttcatattc
95281 catgagagag acctcgcata tttgcagaag ggtcactgaa acatcttatc ttaaaacagt
95341 tacacctgaa taatgaagaa agcgtggctc agcagagcac agcaagccga tgccgggggg
95401 gcatctggct ccgaggaccc accagattat ggagatcaag gtaatgtgac acaggtggga
95461 tctgagccta tttcacctga gattggcccc tttgaactct ctgcggccag tgaggatgat

Fig. 3 (cont.)

95521 cctcaatctg ggccagtgga agagaattta gatgccgctg caagagagga agaggaacct
95581 catgagcagg agcacaatgg tggtgacgat cccttggatg tccatactcg ccagcctaga
95641 tttgtggatg tgaacccaac gcaggctcca gtgatccaac tagtccacgc tgtctatgat
95701 tccatgttgg taagaggcac ctagaacatt tccagatgtt tcgcttggat tttttggcca
95761 gtcttaattg attgtcattg gtttcagcaa tcggacctcc ggcccctagg cagtttattc
95821 cttgagcaaa acctgaacat cgaagaattt atatggatgt gcatgaccgt gcgtcacaga
95881 tgtcaggcca tcagaaaaaa accattacca attgttaagc agaggcgttg gaagctcctg
95941 tcatcttgca gatcctggcg tatgggttac cgcacgcata acctcaaagt aaacagtttt
96001 gagtcagggg gggacaatgt ccacccggtc cttgtgactg ctacgctagg atgtgatgag
96061 ggcacgcggc atgcaacaac gtacagtgct ggcattgtac agataccacg aatatcagac
96121 caaaaccaaa agatcgaaac agccttcctg atggcacgtc gtgctaggtc actttcggca
96181 gaaagatata ctttgttctt tgatttagta tcctccggaa acaccctgta tgctatatgg
96241 attgggctgg gcacgaaaaa ccgagtttca tttattgagt ttgtaggatg gttatgcaag
96301 aaggaccaca ctcatatacg cgaatggttc cgccagtgca ccgggagacc caaagcagcc
96361 aagccatggt taagagcgca tcctgtcgcc attccttatg atgatccgtt aacaaacgag
96421 gagattgatc tggcctatgc ccgcgggcag gccatgaata ttgaggctcc tagactgcca
96481 gatgatccta taattgttga ggatgacgac gaaagtgagg aaattgaagc tgaaagcgac
96541 gaggaggaag acaagagtgg aatggaatct cttaaaaata taccgcaaac actgccgtac
96601 aatccaacag tatacggcag gcccgcggtg tttgaccgaa agtcagatgc aaaatcaacc
96661 aaaaaatgca gggccatagt aactgacttt agtgtaatca aggccattga agaggaacac
96721 agaaagaaga aggcagccag aacagagcag ccaagagcca cgcctgaatc ccaggccccc
96781 acagtggtcc tccagcgacc acccacgcag caagagcctg gccccgtcgg cccactgagt
96841 gtccaggctc ggctggagcc atggcaacct ttgcctgggc cccaagtgac agcagttcta
96901 cttcacgaag aatccatgca gggtgtccaa gtacatggtt cgatgctaga ccttcttgaa
96961 aaagacgatg aagtcatgga gcagagggtt atggcaaccc tactgccacc agtaccacaa
97021 cagccccggg ctggcagaag aggcccttgt gtcttcaccg gtgacctagg catagagagt
97081 gatgagcccg cttcgacaga gccggttcat gatcagctac tgcctgcccc aggacctgac
97141 cctcttgaaa tccaaccact aacgtccccc accacgtctc aacttagcag ttcggcacca
97201 agctgcgcac aaactccatg gccggtggtt cagccaagtc agactccaga tgacccaacg
97261 aaacagtccc ggccaccgga aacagctgcc ccacgccagt ggccaatgcc cctgcgacct
97321 atccctatgc gccccttgcg gatgcagcca atcccattta atcatccagt gggacccact
97381 ccccatcaga cacctcaagt ggaaataaca ccatataagc ccacttgggc tcagataggg
97441 cacattccat atcagcctac accaacgggt cctgctacca tgctgttgcg ccagtgggca
97501 cccgccacca tgcagacacc accgagagcg cccactccca tgtcaccacc tgaggtgcca
97561 cccgttcccc ggcagaggcc tcggggggcg cccactccca cgccacctcc tcaggtgccg
97621 cccgttcccc ggcagaggcc tcggggggcg cccactccca cgccacctcc tcaggtgctg
97681 cccactccca tgcagctggc actaagggct cctgctggtc agcaggggcc gacaaagcaa
97741 attttgcgcc aattgttaac ggggggcgtc aagaaaggga gaccatcact taagttacag
97801 gccgcccttg agcgtcaagc cgctgcgggc tggcagcctt caccagggtc cggcaccagt

Fig. 3 (cont.)

97861 gacaagattg tgcaggcgcc tattttctac ccacccgttt tgcagcccat acaggttatg
97921 gggcaagggg gttccccaac ggccatggcc gcctcagcgg tgacacaggc acccacggaa
97981 tataccaggg aaaggagggg agtggggcct atgcctccca ccgatattcc gccgtctaaa
98041 cgagcgaaga tcgaggccta tacagagccc gagatgccgc acgggggggc ctcgcactct
98101 cccgtcgtta tcttggagaa tgtcggccag gggcaacagc agactctgga gtgcggagga
98161 actgctaaac aggaaaggga catgttgggg ctgggggaca ttgcagtttc ttccccttcc
98221 tcttctgaaa catcgaacga tgagtgattt cgcccatgta acaagaactg ggatgaaccc
98281 tggggcaaca gactgcgggg aggagggggg cagtgataag tcatgacaat tttagatgag
98341 gtagaaattt tgcatatttt cagacccacc atggaatcat ttgaaggaca gggggactct
98401 agacagtcac ccgacaatga gcggggagat aatgtacaga ctaccggcga gcatgatcag
98461 gaccctgggc cggggcctcc atccagtggg gcttctgaga gattggtacc agaagagtca
98521 tactcaagag atcagcaacc ttgggggcaa agcaggggtg atgaaaacag aggctggatg
98581 cagcgcatca ggcgaaggcg gagaagacgg gctgccttgt ccggccatct tttagacacg
98641 gaagacaatg tgccgccatg gttgcctcca cacgacatca caccatatac cgcaaggaat
98701 atcagggatg ctgcctgccg ggctgtcaag gtgagtatgc ctctaactgg gttcatgggg
98761 gccatctaag gcccacgtgt gacccatgtt tccattaatt ttagcaatcg cacctgcaag
98821 cgctatcaaa cctgatactc gatagtgggt tagacacaca acacatcttg tgcttcgtga
98881 tggcagccag gcagcgtctt caggacattc gacgtggacc cttggttgcg gagggcggtg
98941 tgggttggcg acattggctt ctaacatctc ccagccaatc ctggcccatg ggatatcgta
99001 cagcaacact acgcacatta actcccgtgc ctaacagggt tggggctgac agcatcatgt
99061 taactgccac atttggatgc caaaatgcgg cacgaactct aaacaccttc tctgccaccg
99121 tgtggacacc accccatgct ggaccaagag agcaagaaag atacgctcgg gaagccgagg
99181 tacgcttcct tcgtggtaaa tggcagaggc ggtaccgaag aatctatgat ttgatagaac
99241 tgtgtggctc tctgcaccac atctggcaaa acttgctcca gaccgaggag aacctttag
99301 atttcgtgcg tttcatgggt gtcatgtcca gctgcaataa tccagctgtg aattactggt
99361 ttcacaagac aatcggaaac tttaagccat attacccgtg gaatgcacca cctaatgaaa
99421 atccatatca cgcgcggaga ggcataaaag aacacgtaat ccagaacgca tttcgaaagg
99481 cacaaataca gggtttatca atgttagcaa cgggaggtga acccagaggt gatgctacta
99541 gtgaaacgag cagtgatgag gacaccggta gacagggttc ggacgtggag ctagagtcct
99601 cggacgatga gctgccatat atcgatccca atatggagcc ggttcagcag aggcccgtca
99661 tgtttgtgag ccgtgtgcct gcaaagaaac cgaggaaact gccttggccc acgcccaaga
99721 cgcacccagt gaagcgcaca aatgttaaga cctctgatag atctgataag gcagaagcac
99781 aaagcacccc tgaaaggccg ggcccttccg aacaatcatc agtgaccgtg gagcccgccc
99841 acccgacccc ggtggagatg ccaatggtga ttctccatca accacctcca gtgcccaaac
99901 cggttccagt caagcctacg ccaccgcctt cccgtaggag aaggggagcg tgtgttgtgt
99961 acgacgatga tgtcatagag gtgattgatg ttgaaaccac cgaagattca tcgtcagtgt
100021 cacagccaaa taagccacat cggaaacatc aagacggctt tcaacgttca ggccgacgtc
100081 aaaaacgagc cgcgcctccc accgtgagtc cttcggatac tgggcctcct gccgtggggc
100141 ctcctgccgc ggggcctcct gccgcggggc ctcctgccgc ggggcctcct gccgcggggc

Fig. 3 (cont.)

100201 ctcctgccgc ggggcctcct gccgcggggc ctcgcatact ggcgcctctt tccgctgggc
100261 ctcctgccgc ggggcctcac atagtgacgc ctccttccgc ccggcctcgt ataatggcgc
100321 ctcccgtcgt acgtatgttt atgagggagc gacagctccc ccagtccacc ggccgtaaac
100381 ctcagtgctt ctgggaaatg cgggctggtc gtgaaattac acaaatgcaa caagaaccaa
100441 gttcacacct gcagtccgcc actcagccta caacgcctcg cccatcatgg gcccccatcag
100501 tctgcgccct ctcggtgatg gatgctggta aggcccagcc catagaaagt tcacacttga
100561 gttccatgtc gcccacacag ccgatatcgc acgaagaaca accccggtat gaggatcctg
100621 acgctcctct ggatttaagt ttacatccag acgttgctgc tcaaccagct ccccaggctc
100681 cataccaggg ataccaggag ccgccggccc cccaggctcc ataccaggga taccaggagc
100741 cgccgccccc ccaggctcca taccagggat accaggagcc gccggcccac gggctccaat
100801 catcttcata tccaggatat gcgggtccct ggaccccaag gtctcaacat ccatgttata
100861 ggcacccctg ggcaccatgg tctcaagatc ctgtgcatgg gcacacccag ggtccatggg
100921 atcccagggc accacatctc ccacctcagt gggatggatc tgcaggacat ggccaggatc
100981 aggtctccca gttcccacat ctgcaatcgg agacaggccc accacgtctt caactttcat
101041 tggtgccact ggtctcatcc tctgcaccat catggtcatc tccccagccc cgagccccca
101101 tacgccccat tccaacaaga ttccccccctc cccctatgcc gttacaagat agcatggccg
101161 tggggtgtga ctcatcaggt acagcatgcc caagcatgcc ctttgccagt gattacagtc
101221 aaggtgcatt taccccactg gacattaatg ccaccacgcc aaaaaggcct cgagtagaag
101281 aaagttctca cggacctgcc cggtgttccc aagctactgc tgaagcacag gagattctca
101341 gtgacaattc tgagatctcc gtgttcccaa aggacgcgaa gcagactgac tacgatgcat
101401 ccactgaaag tgagctagat taaggggatc caaggtgacc cctgttagct atttgatctt
101461 tgactgacac ataaacatgg tttaaggaat gaacactcat ggtgtgagac tggaactgta
101521 ctaaatttgc tgacatatgt acaatgagag ccaaaaaattt gataaacctt aaaagtcccc
101581 ccatctaatg atgtccagtt cccttctccc accctgtaca ccccgaccca aagggactca
101641 atggcattca gatttctagt taccacaggt agaatatcgg gcgttggccc ataaaaataa
101701 gtgcatggat atagctctgc acaggcttgg aaacacccat tccaggtgtg cttctttttg
101761 gtgaaataaa aacagcatcc tttatatgaa aatgtgtatt ctctggtgtt gcagtatgta
101821 cagttagctt tggtatagtt ttggggtacc tgaaatgtgt gcagggtggg tgtccaatgt
101881 ggcagtttta cctctttgtc cccatactcc tgctcggccg tcttgttaaa gttaaccggc
101941 ggtggaggat ccaccggcca gacctctaca tttggtttgg gtacccaggt gatggccgcg
102001 gctgccaccc gccctcctcc tcttaccctg ggtggcaaaa agtatgccag gagtagaaca
102061 ataacaagtg cgatggcggt aaacaatggc accctcacct gcttaaatga aaccatggca
102121 accacttcaa agagagccga caggaagata tttattaata ttccattagt aaacgaggcg
102181 tgaagcaggc gtggtttcaa taacgggagt tagaaattta agagatcctc gtgtaaaaca
102241 tctggtgtcc gggggataat ggagtcaaca tccaggcttg ggcacatctg cttcaacagg
102301 aggcgcagcc tgtcattttc agatgatttg gcagcagcca cctgcggaca aaaatcaggc
102361 gtttagatgg ggcatttatg tttgggacgc tagccgcctg ggcattcgtg ttagtatata
102421 ctgacctcac ggtagtgctg cagcagttgc ttaaacttgg cccggcattt tctggaagcc
102481 acccgattct tgtatcgctt tatttctagt tcagaatcgc attcctccag ctgcgagcaa

Fig. 3 (cont.)

102541 gggaatgcgt tactacaagt ggtgcctagt cagttgaaac aagccccacc atccgctgcc
102601 gcccctccat gagccccacc gtccgctgcc gcccctcctt gagcccctcc ttaccgattc
102661 tggctgttgt ggtttccgtg tgcgtcgtgc cggggcagcc actggtgcag gctgtggaac
102721 accaatgtct gctagctgtt gtccttggtt agccccgggg caagcaaaca ccactgctgc
102781 tgctgtttga acagtagaat tgtctccagg ttgaggtgct tctcccccgg cttggttagt
102841 ctgttgattc tgggttatgt cggagactgg gaacagctga ggtgctgcat aagcttgata
102901 agcattctca ggagcaggct gaggggcaga aaaccacgac ccagtcggag cggttgaaac
102961 atgataggca gttagctggc cttgtggcag aggctctggc agcaccggcc acagcacaca
103021 aggcaaagga gcttgcgatg gccctcccag gtcctgatag actctggtag cttggtcaaa
103081 agcttgtaca aaaggcacct ggtatgggtc aggtgtaaat tttacatctt cagaagtcga
103141 gtttgggtcc atcatcttca gcaaagatag caaaggtggc cggcaaggtg caatgtttag
103201 tgagttacct gtctaacatc tcccctttaa agccaaggca ccagcctcct ctgtgatgtc
103261 atggtttggg acgtgctaaa tttaggtgtg tctatgaggt acattagcaa tgcctgtggc
103321 tcatgcatag tttctaaaag aggaggaggc agttttcaga agtgtctaaa ataagctggt
103381 gtcaaaaata gacagcccag ttgaaatatg catggcatgc agcagacatt catcatttag
103441 aaatgtatcc aagatttcat taagttcggg ggtcaggggg gagtccagat tcaaatcctc
103501 tgtcatggac tctagtgttg tggtcagttc gtccaaatgg ccacgagggg gcgggtggct
103561 caggtccatc tgtccacata tggctgcttc ctccttctgg ggaataacag tgtcagccat
103621 ctcccttagg gccttcacgg cctgactggt ttcttcatca gggtcctcca acagatgact
103681 tgcctcgggg gttactgcgg gggccgggtc aagtggctgg ggcaccgggg ctggcgttag
103741 ggatccgacc ggttcatgga caggtcctgt gggggtggga gccaaagagg caggcagggg
103801 ccggttggcc cacggggatc cgggtggatg gaagggcctg atcctctttg gctgacacac
103861 ctctcgcccc tcgaacacgt cagatatggc actgcccgct tccggctttg gcaggaacat
103921 accttcccgg ctatccctga ggcccttctt ccttttaacg ggaggaagaa aggtgggctt
103981 tgaggggtgg gggaatatgg gtctctcatc gctctcttgg tggaccgctg ctatccaagg
104041 ctgttcaggt tccgccgcgt tggaaggaca tggagtttga ccacggttgg gcctggatgt
104101 ccggcgcgac tttggggccc gcaggcgcgg ggcctcggcc ctggcctctt cccgctcgct
104161 ctgctcggtg tcactgttgc ccgagtcact gctgctggaa ctgctgtcac cgcagtcggc
104221 gctttgggca ccgggcttca ggggcatggt cgggctcggg agactttcga gttcatctgt
104281 aaaagcatga aactgtccgg actccgagta gcgggcctcg gtgtgagagg cacccccatc
104341 attccccatg agctcctcgt ccatcctgtc ggctccggac acgaggatag gagtttccac
104401 tgccttggac ttggttgaca gcaggcacgc gggaagcacg ccgctcacgt agctcctctg
104461 tccggcgtgg ctggagtagg aggcccgggg cagtgtctta atcagagccc tgacatcctt
104521 aacatcgtcc gtcagatggc ctgtcttgga cgagaccata gtctggaaca tctcctcgag
104581 gacgggatag gtgaacaccc acttgcaaaa ggccttgaac ttggagctta ggaggccttc
104641 cttctccatc ctgttcaggt gttccactac ctgcttgccg gaggccatga tggccgcgcg
104701 gtccacgccc agcaccttgc tgtaggtgta ggcccgcacc cgactgtgtt ttaggagctt
104761 gtacatagcg gtgcctatgg tggcaggaat catcacccgg ttgctggggg cctggatgaa
104821 gaatctgtca gtgaccacta tcaggtggtc taacacgtag cgcatcacta tagggcacgc

Fig. 3 (cont.)

104881 gatggaacat gcgtcgttgc cggcattctc agcccgtctt cttaccctgt tgtttcggag
104941 aatggcccaa aaattgcaga tgttgagcgt ggccattagc ccgcccccatt ctcgcccgtg
105001 ggccttggcc tcatttataa atgccttgca tatttgtag gatctcagag taatctccac
105061 actcccggct gtaaattcct tgttgaggac gttgcagtag tcagagacca gagagcccag
105121 ctgctttttg atttcaggag ttagcctcag aaagtcttcc aagccatcct ttttaggcct
105181 catggctagt agtaacagag gaaatgcccg accattaaaa tctttcctcc atgagcttta
105241 cctgaaacac tatcccgaag tgggggatgt ggtgcatcta ctgaacacca tcggggtcga
105301 ctgcgacctc ccacctagcc acccactcct gacagcccag agggggctgt tcctggcaag
105361 agtcttgcag gctgtacagc agcacaagct gctggaagac accatcgtcc ccaagatctt
105421 aaagaagctg gcttatttct tagagctgct aagctactac tcccccaagg atgaacagcg
105481 tgacatcgcc gaggttcttg accacctcaa gacgaatcgg gacctggggc tggacgacag
105541 actctgggcc ctgattagga aactgcgcca agacagacac catgcctctg taaatgtcct
105601 catgccagga agcgactaca cagccgtgtc gctgcagtac tacgacggca tctccatagg
105661 tatgaggaag gtaatcgcgg atgtctgccg cagtggctat gcctccatgc cctccatgac
105721 ggccacgcac aacctctccc accagctctt gatggcgtcc gggcccagtg aggaaccgtg
105781 cgcctggcgc gggttcttta accaggtcct cctctggact gtggccctct gcaagtttcg
105841 cagatgcatt tactataact acattcaggg atctatagcc accatctccc agcttctgca
105901 cctcgagatc aaggccctct gcagctggat aatatcccag gatggcatgc gcctctttca
105961 acacagcagg cctctcctca ccctctggga gagcgtggcc gcaaatcagg aggtcacgga
106021 tgccattacc ctgcctgact gcgctgaata catagaccta ctaaagcaca caaaacatgt
106081 cttagaaaac tgttctgcca tgcaatacaa ataaatttct cttacctgcg tctgtttgtg
106141 tagtgaggtg ttgtgtcctg tatggtattc tactttaaaa aggccggctg acatggatta
106201 ctggtctttt atgagccatt ggcatgggcg ggacaatcgc aatataaaac cctgaccatc
106261 acatggggca ttaggcgact ctgcatcagc atcgcttaag tatgagtggg cagcagagag
106321 gctcggttat tttggttcct gaacatctgg ctggggcatt aactaagctt atgagcgatt
106381 ttatcacagg acaagatgtc actctttctg gaggaaatat tgcagtcaaa attcgcgatg
106441 ctataaacca gaccccccggg ggtggtgatg tagctatact ttcttccctg tttgctttat
106501 ggaatgccct cccaacatct ggtagacaat cctccaggga cgatttaatc ccagccgccg
106561 tgcaggcctt aaccacggcc cacaacttat gtctgggtgt tattccaggt gagacctcac
106621 acaaggacac acccgagtca ttgctccggg ctatcgtgac gggtctccaa aaattgtggg
106681 tggattcgtg cggatgtcca gagtgcctac aatgtcttaa gggattgaag gcaattaagc
106741 ccggccttta tgaaatccct aggataatac cacacactaa gcagtgtagt cctgtcaatc
106801 tcctgaacat gttggtccac aagcttgtgg ctttacgtgg tcatgtgcag cttgcatacg
106861 acgcccgtgt cctgacgcct gactttcacg aaatccctga cctcgatgac tccgatgctg
106921 ttttcgcacg caccttattg gcagccttat ttcacctcaa tatgttcttt attctcaaag
106981 attacataac acaagactcc atgagcttga agcaggccct cagtggtcat tggatgtctg
107041 ccacgggcaa ccccctgcct gcagcaccgg aaaccctgcg agactacttg gaagctttcc
107101 gaaattcgga taatcacttt tatctcccga cgacagggcc tttaaacacc ttccaatttc
107161 ccgaagagct tctggggcgc gttgttgtta ttgattcctc tttgtgtgcc gccagtcacg

Fig. 3 (cont.)

107221 ttcaggacgt tatcacccat ggtgttgggg cgggtgttcc tcgtcctcgg ttttcggccc
107281 tgcctccggc cccatcccgc gagccccagc agacatgctc tcagttaacg agcagaggga
107341 atgaaagctc acggcgaaac ttgggccagc ccggggggac ctcccctgct gttcccccag
107401 tttgccccat cgtttccctg acggcctcag gggccaagca aaaccgcggg ggcatgggat
107461 ccttgcactt agccaagcct gaggaaacct cccccgccgt ctccccagta tgccccatcg
107521 cttccccagc ggcctccagg tccaagcagc actgcggggt cactggatcc tcacaggccg
107581 cacccagctt ttcttccgtt gccccagtag catctctgtc tggtgacctt gaagaggaag
107641 aggaggggtc ccgagaatcc ccatccctac cgtccagcaa aaagggggac gaggaatttg
107701 aggcctggct tgaggctcag gacgcaaatc ttgaggatgt tcagcgggag ttttccgggc
107761 tgcgagtaat tggtgatgag gacgaggatg gttcggagga tggggaattt tcagacctgg
107821 atctgtctga cagcgaccat gaaggggatg agggtggggg ggctgttgga gggggcagga
107881 gtctgcactc cctgtattca ctgagcgtcg tctaataaag atgtctattg atctctttta
107941 gtgtgaatca tgtctgacga ggggccaggt acaggacctg gaaatggcct aggagagaag
108001 ggagacacat ctggaccaga aggctccggc ggcagtggac ctcaaagaag agggggtgat
108061 aaccatggac gaggacgggg aagaggacga ggacgaggag gcggaagacc aggagccccg
108121 ggcggctcag gatcagggcc aagacataga gatggtgtcc ggagacccca aaaacgtcca
108181 agttgcattg gctgcaaagg gacccacggt ggaacaggag caggagcagg agcgggaggg
108241 gcaggagcag gaggggcagg agcaggagga ggggcaggag caggaggagg ggcaggaggg
108301 gcaggagggg caggaggggc aggagcagga ggaggggcag gagcaggagg aggggcagga
108361 ggggcaggag gggcaggagc aggaggaggg gcaggagcag gaggaggggc aggaggggca
108421 ggagcaggag gaggggcagg aggggcagga ggggcaggag caggaggagg ggcaggagca
108481 ggaggagggg caggaggggc aggagcagga ggaggggcag gaggggcagg aggggcagga
108541 gcaggaggag gggcaggagc aggaggggca ggaggggcag gaggggcagg agcaggaggg
108601 gcaggagcag gaggaggggc aggaggggca ggaggggcag gagcaggagg ggcaggagca
108661 ggaggggcag gagcaggagg ggcaggagca ggaggggcag gaggggcagg agcaggaggg
108721 gcaggagggg caggagcagg aggggcagga ggggcaggag caggaggagg ggcaggaggg
108781 gcaggagcag gaggaggggc aggaggggca ggagcaggag gggcaggagg ggcaggagca
108841 ggaggggcag gaggggcagg agcaggaggg gcaggagggg caggagcagg aggaggggca
108901 ggagcaggag gggcaggagc aggaggtgga ggccggggtc gaggaggcag tggaggccgg
108961 ggtcgaggag gtagtggagg ccggggtcga ggaggtagtg gaggccgccg gggtagagga
109021 cgtgaaagag ccaggggggg aagtcgtgaa agagccaggg ggagaggtcg tggacgtgga
109081 gaaaagaggc ccaggagtcc cagtagtcag tcatcatcat ccgggtctcc accgcgcagg
109141 ccccctccag gtagaaggcc atttttccac cctgtagggg aagccgatta ttttgaatac
109201 caccaagaag gtggcccaga tggtgagcct gacgtgcccc cgggagcgat agagcagggc
109261 cccgcagatg acccaggaga aggcccaagc actggacccc ggggtcaggg tgatggaggc
109321 aggcgcaaaa aaggagggtg gtttggaaag catcgtggtc aaggaggttc caacccgaaa
109381 tttgagaaca ttgcagaagg tttaagagct ctcctggcta ggagtcacgt agaaaggact
109441 accgacgaag gaacttgggt cgccggtgtg ttcgtatatg gaggtagtaa gacctcccctt
109501 tacaacctaa ggcgaggaac tgcccttgct attccacaat gtcgtcttac accattgagt

Fig. 3 (cont.)

109561 cgtctcccct ttggaatggc ccctggaccc ggcccacaac ctggcccgct aagggagtcc
109621 attgtctgtt atttcatggt ctttttacaa actcatatat ttgctgaggt tttgaaggat
109681 gcgattaagg accttgttat gacaaagccc gctcctacct gcaatatcag ggtgactgtg
109741 tgcagctttg acgatggagt agatttgcct ccctggtttc cacctatggt ggaaggggct
109801 gccgcggagg gtgatgacgg agatgacgga gatgaaggag gtgatggaga tgagggtgag
109861 gaagggcagg agtgatgtaa cttgttagga gacgccctca atcgtattaa aagccgtgta
109921 ttcccccgca ctaaagaata aatccccagt agacatcatg cgtgctgttg gtgtatttct
109981 ggccatctgt cttgtcacca ttttcgtcct cccaacatgg ggcaattggg catacccatg
110041 ttgtcacgtc actcagctcc gcgctcaaca ccttctcgcg ttggaaaaca ttagcgacat
110101 ttacctggtg agcaatcaga catgcgacgg ctttagcctg gcctccttaa attcacctaa
110161 gaatgggagc aaccagctgg tcatcagccg ctgcgcaaac ggactcaacg tggtctcctt
110221 ctttatctcc atcctgaagc gaagcagctc cgccctcacg ggccatctcc gtgagttgtt
110281 aaccaccctg gagactcttt acggttcatt ctcagtggaa gacctgtttg gtgccaactt
110341 aaacagatac gcatggcatc gcgggggcta gacctctggc tggatgagca cgtgtggaag
110401 aggaaacagg agattggtgt gaaaggagaa aatctgcttc tccccgactt atggctagat
110461 ttcctacaac tcagccccat cttccagcgc aagcttgctg ccgttattgc ctgtgtccga
110521 cgcctgcgga ctcaggccac cgtctaccca gaggaggaca tgtgcatggc ctgggcccgc
110581 ttttgcgacc cctctgatat taaggtggtt attttgggcc aggaccccta tcacgggggt
110641 caagcaaacg gcctggcatt cagcgtcgca tacggctttc cagttccccc cagcctgagg
110701 aacatctacg cggagctgca ccggagcctg ccggagtttt ctccccccaga tcacggctgt
110761 ctagacgcgt gggcctccca gggggtgttg ctactcaaca ccatcctgac cgtgcaaaag
110821 ggcaagcccg gctcgcacgc agacattggc tgggcgtggt ttactgacca cgtaatttca
110881 ttgctctctg agcggttaaa agcgtgcgtg tttatgctgt ggggtgcgaa ggcgggagac
110941 aaagcttcac taatcaactc caagaagcat ctggttctga cctctcagca tccctctccc
111001 ctggcccaga acagcacccg aaagagtgcc cagcagaagt tcctgggcaa caaccacttt
111061 gtcctcgcta acaacttttt gcgtgagaag gggctcggtg agatagattg gaggctgtag
111121 aggggtcatc actatggcca tgtttctgaa gtcgcgtggg gtccggtctt gcagggaccg
111181 gcgcctcttg tcggacgagg aggaagagac ttcacagagc agcagctaca ctctggggtc
111241 tcaggcctcc cagtctatcc aggaggagga cgtgagtgac actgatgagt ctgactactc
111301 agatgaagac gaggagattg atttggagga agagtacccc agtgacgaag acccatctga
111361 gggcagtgat agcgacccct cgtggcatcc ttcagattca gacgagtctg actacagcga
111421 gagcgacgag gatgaagcaa cccccggctc tcaggcctca cgatcttcaa gagtctcgcc
111481 atctacccaa cagtcttcag gtctgacacc cacgccttcg ttctcccgac cacgcacccg
111541 ggcacctccg aggccgccgg ctcccgcgcc ggtcagggga cgggcctcag cacctcccag
111601 gccaccagcc ccagttcagc aatccaccaa agacaagggt ccccatagac ctacgcgacc
111661 tgtacttaga ggcccagctc cacgccgccc ccctccacct tcaagtccca atacatacaa
111721 taaacacatg atggaaacca cccccccat taagggcaat aacaactaca attggccatg
111781 gctgtaaata aaatgtcata acctggagtc tgcatgtctg ttgttttatt cagtaaacca
111841 gtagtgcgcg tgagttcttt agggcatcca cgatgtagcc gctcgcgggg ttcccctccc

Fig. 3 (cont.)

111901 cagtgatcat ctcggatagg ggattcctgt ccatgaccac gcaattagag tgccgggccc
111961 gggacagcgc cacatacaca tggccgggtt tgatgtttct gtggctgccg aagcagatgg
112021 cgactttgtt tagggacaga ccctgggcct tggctatggt catggccagc tttgagctaa
112081 tgccatagtc acggatgctg cagaggttca gggacttgtc ctctatcgtc tcatacagtt
112141 tgttagtatt gtgttccagg cagcacacga agcctgcctc atccttgacc attagcctgg
112201 gcatgcgtga actgccagcg tcctgaggct gctgctttcc tcggatgcca aagaagacgt
112261 tgagatgcgt gtagcccaga agcgtgtagt tctcggtggt ggaggcgtag tccaggaggc
112321 cgtgaaggag aggctcgtct gaggtgaact ctatgttgtc gcgaatcagc atgttgttgg
112381 taaatgtgca gaaggggagg tccctgaact cccttccgcc atagcggacg gccacatcca
112441 ggcattgcct gaaataggcc ctgaggtcat tatatatgtt taacagggag cagagggggg
112501 cagaatttgc ggccggggga gccagtactc gggcatagaa gacagcggcg gggctccgct
112561 ccccatccca ggcaacctcc agcggcagtt cgcccagctc catcccagca gtcacctccg
112621 gatcccacgt acgcccgggc aggggcacag caccaagctc cgccacgtat tccccgtttt
112681 cacagagaga atgtcctccg tggctaaaag cgtagatgcc tccgtagatg agtcgggcca
112741 ggaagctgta gacatactcg ggctgctcat gcccgtgggc ctccacgaag ctgtccgcct
112801 cgagcgtgtc cataaagtcc ccgaaggtgc cggtatagcc acagatggac ttttggtct
112861 tgcagttgac cgacaccgag ctgtgcttga cgtaggtgac attgtaggtg accttgaccc
112921 gttcttcgtc ctgctcggtg cccaccggga ccatgtcttg gtcggcgaac tgcgagtagt
112981 taccgaggcg tgcataattc ttttggagcc aggtgtgggc cgtgaggccc ggaagcccga
113041 ccagggtctt gtactgggcc aggggatcga ggaagacctc gcactccacc gggcaggtaa
113101 acatggtcac cccgccccca tctcccccgg ttccccgcgc ggcacgcccc tgcccggcag
113161 tcttgagcgt ggcatggagg gtggtgagga aggtcttgac ctcggcgtgg gagaggaaga
113221 gccgggtcca gcccacgtac tgcgcggggt ccattatggc cgccctgggg acgacgaagc
113281 ggtcgacgta ggccaggatg tccggcgaga gctcgaggcc gtactcgagg gtcttcatga
113341 ggtgtccaaa ctggacgtcg gtgcagcgct tgttgttgat gaagagggcc cagttgcggg
113401 ccacgtccac gtaggtcgcg gccctggggt tgcccaccag gaaggtgagg atgttgtcgc
113461 actcgcgaat cttgtttacc tgggtctcgt ggctaaagga ggactgaaag gcgtctgtct
113521 gggtgggaga gcccacgcag acgatgcagg gaatgcggcc ccggcggtag agtggggtac
113581 gcagccaggc gttgaagaac cagtagcaaa agaccacggc tgttagaatg tgcacggaaa
113641 gcgttccagc ttcgtccacc acgatcacat tggtggtcca tagctgcccc tggtgcatgt
113701 ctctcaggac ctcaaaggcg gggccagaga ctcccgagta gagccccctg ggcttggttc
113761 gcctgaactc ggcggcaatg tcggagagta ccggccagta tttggccagg tcccgccgct
113821 ggagttcctc tagggcggcg tccgtagagc gaccatgact gctgacccgc tgcgtcatat
113881 ttatgtggcg gctcttgaac ccaaaggcgc tatagacggt tgggcagtag gctcggagtg
113941 tctgggagag gttctgtgcg gccacggttg tggctcccgt gaccaggcag tccatcgtgt
114001 ggtggaggca gctaacgctg gtgctcttgc cagccccccgc cgttcccgta attacatagg
114061 ctgaaaaggg caggaagggg ggctccgaga gctccgggtc aaactcgggg gagaacgtct
114121 ccatatccgg gagttgttgg acgcggcgcc tagccagggt ccctatcctc ctgactatac
114181 gcctcacgga ggcgtctgag gtcatgttca acatgaacgt ggacgagagc gcctctggcg

Fig. 3 (cont.)

114241 ccctcggctc ctcggccatt cctgttcacc ccacgccggc ctcggtccga ctttttgaga
114301 tcctgcaggg aaagtacgcc tacgtccagg gacagaccat ctacgccaac ctccgcaacc
114361 ccggagtctt ctcgaggcag gtgtttaccc atttgtttaa acgagccatc tctcattgca
114421 cgtacgatga cgtgctacat gactggaaca agttcgaggc ctgcatccag aagcgatggc
114481 cgagcgatga ctcgtgtgcg agccggtttc gtgagtccac cttcgagtcg tggtccacga
114541 ccatgaagct gaccgtgcgt gacctgctga ccaccaacat ctaccgagtg ctacacagcc
114601 gctccgtgct ctcctatgag cgttatgtgg actggatctg cgccaccggc atggtgcccg
114661 ccgttaagaa gcccataacc caagagctcc actccaagat aaagagcctg agggacaggt
114721 gcgtctgtcg ggaattgggg cacgagagga ccatcaggag tatcgggacg gaattatatg
114781 aggcaacgaa ggaaataata gagtcgctca actccacgtt catccccccag tttacggagg
114841 tgaccatcga gtaccttccg aggagcgacg agtatgtggc ctactactgt ggccgccgca
114901 tcaggctgca tgtgctcttc cccccggcca tctttgccgg aacggtgacc ttcgacagcc
114961 cggtgcagcg cctctaccag aacattttca tgtgctaccg cacgctggag catgccaaga
115021 tctgccagct cctgaacacg gcccctctca aggccatcgt gggccacggg gggcgagaca
115081 tgtacaagga catcctggcc catctggagc agaactcaca gcgcaaggac cccaagaagg
115141 agctgctgaa cctgctggtc aagctctcgg agaacaagac catcagcggg gtcacggacg
115201 tggtggagga gttcataacg gatgcctcca acaacctggt ggaccgcaac cgtctatttg
115261 gccagcccgg ggagacagct gcacagggcc taaagaaaaa ggtctccaac acggtggtca
115321 agtgtctgac tgatcagata aacgagcaat ttgaccagat taatggccta gagaaggaga
115381 gggagctcta tctaaagaag atccgctcca tggagtctca gctgcaggcc tccctgggtc
115441 ccggcggcaa caacccagcg gcgtcagccc ccgccgcagt tgcggcagaa gccgcgtctg
115501 tagatatact gacgggcagc accgcctccg caatcgaaaa gctgttcaac tcccccgtccg
115561 ccagcctggg tgccagggtg tctggtcaca atgaaagcat cctaaacagt ttcgtttctc
115621 aatacatccc cccttcgcgg gaaatgacta aggatctgac tgaactttgg gaaagcgagc
115681 tgtttaacac cttcaagtta acacccgtgg ttgataatca ggggcagcgt ctctacgtca
115741 gatactcgtc agacacgatc tctatattat tgggccccctt cacctatctg gtggcagagc
115801 tttcaccggt ggaactcgtg acagatgtct acgccaccct aggcatcgtg gagatcatcg
115861 acgagctcta ccggagcagt cgcctggcca tctacatcga ggacctcggt cgaaaatact
115921 gccccgcgag cgcgaccggg ggagatcatg gcatccggca agcaccatca gcccgggggg
115981 acacggagcc tgaccatgca aaaagtaagc ctgcgcgtga cccccccgcct ggtgctggaa
116041 gttaaccgcc ataacgccat ctgcgtggcc accaacgtcc ctgagttcta caatgccagg
116101 ggggacctta acatccgaga cctccgggcc cacgtcaagg cccggatgat ctcgtcccag
116161 ttttgcggct acgtcctcgt gagtctgctg gactccgagg accaggtcga ccacctcaac
116221 atattccccc acgtgttctc cgagaggatg atcctgtaca aacccaacaa tgtgaacctt
116281 atggagatgt gcgccctgct ctcgatgatt gagaatgcca agagcccctc cataggcctc
116341 tgccgggagg tgctgggtcg cctgaccctc ttgcactcca agtgcaacaa tctggactct
116401 ctgtttctgt acaatggggc caggacgctg ctgtccaccc tggtcaagta ccacgacctg
116461 gaggaggggg ctgccacccc cgggccgtgg aatgagggcc tgagtctctt taagctgcac
116521 aaggagctga agcgcgcccc atccgaagcc cgggacctca tgcagagcct ctttctgacc

Fig. 3 (cont.)

116581 tcggggaaga tggggtgcct ggccaggtca cccaaggatt actgcgcgga tctaaacaag
116641 gaggaagatg ccaactcggg cttcacattt aacctgtttt atcaagattc tttattgacc
116701 aagcatttcc agtgccagac cgtcctccag accttgagac gcaagtgcct cgggagtgac
116761 acggtctcaa aaataattcc ctagaataaa ctgagaacag tcatcagtaa atctgtctct
116821 cgcgtgattt ccataggaat ggtgtagccg gggtggaggg ccgatatcac atcaagcaga
116881 aaggccataa tctctcgaaa gtaggcggtg ggctgagac catgctcagt ggccgtctgg
116941 caggggggccg ggcgcgctcc gtccttgtcc aggagacaca cgtggcttcc agagaggcgc
117001 agcccagccc tccgcagccg ctgaagccag gctcgcggaa gagcccaaaa cctgtttcgg
117061 cgccgcccgg gggccagtct ccgggtcagg tcgcggacca gggtcaacag gtggtcgtgg
117121 gatggcgggg ccttgtctgc ctcgggtctc gccgctagtt ggtccagggt ccaggagaag
117181 gcttcgtgcc aaaccaaaaa gggccccgag tgctccctac atccacccac gtaaagatcc
117241 ccctgaaaga tggccatcag taggcacccg ggcccgcgtc gagccttcac ccgaatgtgt
117301 ctgcgggcca cggtggcctc tccacccatc acatcccggt cgagccggct ggcatcctcc
117361 gagtctttca cgccttgcag gaaagcctag gagatacagc aacagaaagc tattagccgg
117421 tggttccccc accatcattc ttcctgttaa cgggaagaat aagagttggg caaaccccgg
117481 gggccgcgct ctcccaccca gccccgcttc tcacctgtgc tagtggctcc tctgaaggat
117541 gggcggaggt tggtgccaca aagcccagga tgaactcgtc tgcataagcc caggtcagtc
117601 ctaggtcagc ggccgcgtgt aggagaaccc gggtgacggc ggtgtagagg cccccgagtg
117661 cccgtcgcgt gtctgaggtg ccatagcggt gaagggcccg cagccaggtt tgcgcgtccc
117721 gcgcctgccc tccgccatca ggcgttccca cgggggcgcc cctggcagag aggtggcagc
117781 gggccaattc gtagagccac caagtggcat cagcctcaag gatggctgtg gcctccgcgc
117841 gcccgaccac cgtcgtctcg tcctcccccc ctccctcgcc gccttcccgc gtgcaaacgt
117901 ggcgagggtt aatctccttt cgggtcgggg gccagatttg ttgtaggagc agcgagccgc
117961 gtcgttgccc tgaccgcgcg tcgaggccca ggagggcgtc tgccaggggc gtcccagaga
118021 ctcccaggtt caggtccagt agcaggagac cctcgctgtg tggcgcccgg tgccagaagg
118081 ccggcctcgc ccgtcccaca taatggatgg gcaggaaggg aaagcccggg acatagggct
118141 ggaaatctga gccccctggg cagagttcgg ggtccaggag gtagaagatg ggcttggtgc
118201 ctctgtggtt ggcgtagcag gaggcataga tactgcggag gaaggcgtag agcccgcccc
118261 cggccatact ccaagagttg acaagccagg actcgaatcc cccagccggc tcaagaattt
118321 tcaggctgac gcggtgccgt cgggcgtccc caccacggcc ggtggccccg tcggacgaca
118381 ccagatctac ttcataagtg accggtcgca ggatgtccct aaaggggacg ggagaggggt
118441 cgtcgggagt ctcggtggaa taggtgaaaa catccccacg cggtgtcctg atgtatacgt
118501 ccaactgtcc gggagactca gagtgcctct gagcatgggg gcatgtctgt tccccctcca
118561 tctcggaccc gaagccatca acaggtgggg gttgttggtc ccgcccatca tcccccgagc
118621 agctttggca gaccacctgt gctggaaaga gaggctggaa gatgaggccc tgctcatcct
118681 ccaccctggc ggcggacaag agtctgcggt ctcgggttct aaatgaaagg tcaaataggt
118741 ccttctcggc ggcatcggcg agcatagcaa tgagcccccc gctgcgcctg agctcccgct
118801 cccatcgcaa aaagttgagt tcggtagtcg agggcgcgtt gaccacgggg ggctccaggg
118861 agcctccaag cggcggctgg caggcctgca ccacgatcag agtctcaacg tcctcccttt

Fig. 3 (cont.)

118921 tgatgggcac gatgcccacg acccaaatcg cccaccaccg ccctgcggtc tgggtaacat
118981 tataaaaggt aaccgagctg acgcgggccc tgacgctctc cgcgggtgtt tccatcattg
119041 tttgagatct gaggaggact ggacccttta aaacatccgg tcacgccctt tgcaaattat
119101 ttaaaaggtg aatgctcaac tgagaccatc gcaatcatga agtcctccaa gaatgacacg
119161 ttcgtctata gaacgtgggt caaaacgctt gttgtgtact ttgtgatgtt tgtcatgtcg
119221 gcggtggtcc ccatcaccgc catgttcccc aacctggggt acccctgcta ctttaacgca
119281 ctggttgatt acggggcact taacctgacc aattacaacc tggcccacca cctgaccccc
119341 acgctctatc tggagccgcc ggagatgttt gtctacatca cactggtctt tatcgcggac
119401 tgcgtggctt tcatctacta cgcctgcggc gaggtggcgc taatcaaggc ccgaaaaaag
119461 gtctcgggtc ttacagacct ctcggcctgg gtctcggcag tgggctcccc aaccgtgctg
119521 tttttggcca tcctcaagct ctggtccata caggtcttca tccaggtcct ttcctacaag
119581 cacgtctttc tctcggcctt tgtgtacttt ttgcactttc tggcctcagt tctacacgcc
119641 tgcgcatgtg tgacccgctt ctccccggtc tgggtggtca aggcccagga caactctatt
119701 ccccaggaca ccttcttgtg gtgggtggtc ttctacctga agcccgtagt tacaaacctg
119761 tacctggggt gccttgccct ggagacgctg gtcttctcgc tcagcgtgtt cctggccctg
119821 ggcaacagct tttactttat ggtgggggac atggtgctgg gagccgtgaa cctcttcctc
119881 atcctgccca tcttctggta cattctgacg gaggtgtggc tggcctcctt cctgcggcac
119941 aactttggct tctactgcgg catgttcatc gcctccatca tcctgatcct gcccttggtc
120001 aggtacgagg ccgtctttgt ctccgccaag ctgcacacca ctgtggccat caatgtggcc
120061 atcataccta tcctgtgctc ggtggccatg ctcatcagga tatgccggat tttcaaaagc
120121 atgcgccagg gcactgacta tgtccctgtc tcggagacgg tggaactgga gctagagtca
120181 gagccgaggc ctaggccctc gcgcacgcca tcacccgggc gcaaccgccg ccgctcttct
120241 acgtcctcat cttcctccag gtcaaccagg agacagaggc ccgtctctac ccaagccctc
120301 gtctcctccg ttttaccgat gacgacggac agcgaggagg agatcttccc ctaatgcaat
120361 aaaaacttaa aacactgagg ttactttccc gtcattcttt cgggggaacg aggggaggcg
120421 ggaattgggt taagataggg gcgaagggtg ggggtgggtg caagaattgg ggctgggaat
120481 ggagagggga gtgggctagg tgccgacacc ggggtgccaa gataatggat tgagtaagca
120541 tggggctctg atcgggtccg ccgggttctc aggggtgtag tgggtgggca ttgcatattt
120601 ttgccgcggt gctgttgggc cttggactcg gggtgatcat ccgtaccatc acccgcaccc
120661 gcaccccagt ccacagccac cggccaaggt cctgggcctc ccaccaccgt tatgcctccc
120721 cctttaccca ttaattacaa gagatgttag tttggttttt tatttggcaa aaacagcaat
120781 tcatcatttt cagagtcctc atcatattcg agcccctcgt tggtttcccc gcaggccctc
120841 ccttcttcgg ccgctattag cttagtagtc tccaggttaa actcctcata gtcattatac
120901 aggttgatta ttcccccgtc cacgtcgcct atggagttga ctcgtcgtcg gcaaagagac
120961 cagagggcac ccatggcgcg gtgtcaaaag tattgtctgc gtacgctttc caggagccag
121021 ccgcggtgct caaggtctta cggatgacag agtccggcag gaccacgggt gtcaccagca
121081 ccgccacggg aatctccacc gaggcgtcca gaagcaggtc tgagccgagc gtgcaggtcg
121141 ccgggtctag aggcgaccgt tttcgaaaga aggccgtcac aatgttcacc cggggtgagc
121201 agtctctccc gggcttgcca cccccactgt ggcggacgta gtctccaaca attttgtatt

Fig. 3 (cont.)

121261 ggaggagcac ctggtagaag tagttgtgcc gtggattgat gaagatgttg actgggaccc
121321 ggtctttaat accaatgcgc cccgcatttt cgcttgggtc cgtcattacg tagagcatag
121381 actccacccc cctgttggca gctaggctgt ctgccaccag gtcatgaccg gggcccagtt
121441 tgcgcttacg gacatcttta agattccagg cctcatcctg cgtcaacaga tagtcaccct
121501 ccgagggcaa ccgccccatcc gggacgtact ccacggtagg acgagctata gaattgataa
121561 atctgataaa tgacctcttg catggcctct tgtaaagcgc agtgtaggat gggtagatgg
121621 ggtcaaattc tgacttggaa aagaggtact tgaagcggca cttaatctca taaatgcagc
121681 tccggtcggt gaacagtata aagtctccct gtgactccac attgacgcaa agatccagag
121741 acaccccaaa aatgccatcc gtgggactaa tcataaagcc aaattgacgg ttggcggatg
121801 cgtccccgca gatgagctta cagacaatgt ccttgaccgt gtcctcacac cgcaggccaa
121861 aggccacagg tcccccaaag tagtgatttg tggagatggg agctggctca aacaccttgg
121921 tgggtccatt cttaatggtg gagagcagct tggaagagga aattatgcca tttcgcaata
121981 tgtcccacat caggttctca gactgccccc tggtcatgga ctccacgtac gagcagagaa
122041 cagtcctctg ctcgtcggtg gcctcctgta gcccccagta aatggatttc agggagggac
122101 cgtccttgct gtcattctct tggactaacg aggagacaaa gtcacagaag ccagtttcac
122161 cagagaactc ttgtatttgt ttacagaggc aatagagata gacaaagcgc atggccggca
122221 tctgaggtgg acggtcaagg ttacggacaa aggcctcagt ctccggactg cggaggaagc
122281 gggcaaacgt gtaggaggtc atctcctcca tgggatcctc gagctcatcc acgtcggcca
122341 tctggaccaa agaagtcgtc tgccaagagt tcagctacca gacctggaag atgagggtgc
122401 tcaaaccgtg ggcgacagtt gaagaagtag ctctccttga acctcttttt aaggctccgg
122461 caccactgca agaattgact catatgctcc gccgtgacat ccacgcacgg actctcgcca
122521 cacgaggtca ggcccatgtc taagttcagg ttccacatct gcgacagcac ctccaacagc
122581 accacctttg gggctgcaaa ttgcaaaaag tagagcgggt cggatcggtc aaatcccatg
122641 tcagggttgg ggtaggggat tttgtgggtg gagtcagcga ggtgcatgat accatagagc
122701 agcgagtagc cgagcgactg cagatccagg cgaagggccg tctgcgcccc cacggggcca
122761 cacgccgagg ggtcagggat gtgcccagcc cccctcaaga tgtagcactt gctcaaaagg
122821 cagaggggct tataggtgtc cttggctata gaaaatggtt ccctctggca atagaggcga
122881 tagagctgcc ggcccttaga agactttagc cgcacatcca gcatcttgtt gcggtcgtgg
122941 agggaagcag tcccataatc agtcaggacc agcctaccca tgccccacat ggtgtctgtg
123001 aaatccacca ggatgttgct ggggctaatg tccgaatgga agaggccgca gtgccgattc
123061 agaaagtaaa cggcatcttt gaggccctga aagccccgca ccaggggctc aatactacca
123121 tcatgccagt ggccataatc ctggagactg catctgaact ggggcataaa cagggcgtgg
123181 caggacgtgc aggccgacag gtagtccacc agggccttgt cctgcccatc ctcggccgtg
123241 gccttcccaa tctgaatcat gtcacacacc atgagctcgt gatacagctc cgtcacagag
123301 tcatagagtt tgaccgtggc attatctgca tgtgcataca cggccccgta gctccccgc
123361 cccagcagat actcgcaggt aatggggagg tgatcacagc gcgtcatgtt ctccggcagc
123421 tttacataga gggtctccgt catgtcatca atgttggtca ccttcaggtg tttgtgctga
123481 aaggtgaagt aatcaatgac agtcaccttc cccaaaaagg cctgggtctc tcgagggggt
123541 tctggggaga cactcaactc gccactgctg gaggagttcg tcgggctcaa ctccgcagcc

Fig. 3 (cont.)

123601 atattcacat ccatgttcct caaatggctc gagggcctgt cgcagctcgt ctctggcctc
123661 aagctcctgc tcacggagct cctccacccg ctctagctgc ttgtagttga tttttggaaa
123721 ttgagtcttg gtcgcggtga ccaccctctg ataggtagaa attagctgtt tggactcaaa
123781 cgtctccctt gcgtggcgca gggactctaa ggcaccccga gcagatgtaa actgtgtttc
123841 aaacagagcg tggtccctcc caaatctgtc acgtgcgctc acagccgctc tcttttctac
123901 cgaggctctt agttgctggg ccaccagatc tcgcttagaa ctactcatct tcataagtca
123961 ccatgtccgc aactatggag cccagatcat acgtggggta gagtacggta gttccagtgg
124021 aggcttcccg gtaatttccc acagcgtcca ccatatatct ttctgcctct cccgttagaa
124081 ttaggcaagg atcatacgtg tccaccggcc ttttatactg agcgtttagg ttttgtttat
124141 gtagcaagca caaaaggcac acacgagtga tgcaaaaggg ttcctgaggc agcaggcaga
124201 gctgttttgc cattttattc aggcggctaa cgtcaaaggg aggagctata tcctcaccct
124261 tccagtcacg cacgtccaag tacagggcat acacacacct ggtgaggtgt gccaggaatg
124321 cctctatgtt ggcacatggt gtataaaccg cagtgggtag cagaataggg cccctttttgc
124381 cccgtgccgc agcgtaaacg cagtgacgct cttcgcagtg ggacctgggg ccgtagaaga
124441 gggcccacat ccaagggagt gggtcttcag gcaccaggga ggtccaggtt tgggagtggg
124501 ccaatatttg caaggcctga cctataacct catctttgtt ccaggccagc gcaattcgca
124561 taaggtcccc atcaaacacc tcaaaacaca gacccatgcc catttcaggc tgagagggct
124621 ccatccggct cgaccaacct tgtccaccaa actgccattc ttctggtaaa cgggggttga
124681 ggggcaagag ctccaaagcc aggctcgaga agtcatagtc atcctcggcc acacggccgg
124741 agctccgggc ctcgtgccag ggcctgttgt cctgggggag gatattggac acgagcagga
124801 agctcttgag tggcgtctcc accagcttaa attgctcggg cgtgtcctgg caggcctcca
124861 gtgccagttc cagacactgc ccatacctgc gggcgagcat cgggtcatcg ggcatatcgg
124921 ccttgaccgc gttgaacatg ctgtatgcct cgcagcgcgg ccgtctgacc gagaacctaa
124981 gaaacgccct tcagcaggac agcaccacgc aaggctgcct gggtgccgag accccgagta
125041 ttatgtacac aggggccaag tcagacaggt gggctcaccc tctggtgggc acaattcacg
125101 ccagtaattt atattgccca atgcttcgag catactgccg ccactatggc cccaggcccg
125161 tgtttgtagc ttctgatgaa tcattaccca tgttcggtgc gagccctgcc cttcacaccc
125221 cagtccaggt ccagatgtgc ctactaccag agctacgcga cacgttacag cgcctgctgc
125281 caccacccaa tcttgaagac tccgaggcct tgacggaatt caagaccagc gtgtcctctg
125341 cccgtgccat ccttgaggac cccaactttt tggagatgag agagtttgtc accagcctgg
125401 ccagcttcct gagtggtcag tacaagcaca agcccgcccg cctagaagca ttccagaaac
125461 aagtagtgtt acattctttt tattttctga tctcaatcaa atctttagag attacagaca
125521 ccatgtttga catctttcaa agtgctttcg gattggaaga aatgacgctg gagaagctgc
125581 acatttttaa gcaaaaagcc agcgtgtttc ttatccccag gcgccacggc aagacctgga
125641 tagtcgtggc catcatcagc ctcatcctct cgaatctctc caacgtgcaa ataggctacg
125701 tggctcacca gaaacatgtc gcgtccgccg ttttcactga aattattgac accttgacca
125761 agagcttcga ctccaagcgt gtagaggtca acaaggagac cagcaccatc acgtttaggc
125821 acagtgggaa aatctccagc accgtaatgt gtgccacctg cttcaataag aatgtaagac
125881 ctgacgtttc agtacttggc aattgtagag catagcccgg ctgtaaaggt cagaaaatcg

Fig. 3 (cont.)

125941 cagcagggtc caaggttgtg ctgtacatgg gacctctttc ccattagcaa gaaccccctg
126001 caggacacgt gacatgtccg ggtgcatttt gggtgggtta aatctcagtc ccaccacaaa
126061 gggggcatcc tccggtttga acatcagacc caacaaagcc cgatgcccag ttatgggtac
126121 gtagtcgttg ttcagggccg tgcatggcag cagacaagga caggtgccag atgtgcctgg
126181 gctatcgtcc tccgtccagc cacgcaggat gttcacgtgg gccccggcac catagcatgt
126241 cacacattcc ccgttatcac atctggttag caggttgata aaatgggtca gtgatggaaa
126301 ggttggcata ttggggcagc acatcagcat gtccatgtta acgaaaaaca tgtacagggc
126361 cccttctgca taccaggcac cacccccgtcc cagtgggatg atctccgagg gtgtgatatc
126421 ttgcagttct tctactgttt taacggcggt tgaggtggta aagacgtggg ccgtggtcag
126481 atctgtgcag gtgactacag ggttacccct aatctccaca ggcaccgcct cacccactgc
126541 atctgagaat accccaaagt acatgagagt caggctgtgt ggcccctgga ctgccttagt
126601 gaagagaacc tcgggcctgg ccacggtggc tagggttcca ttgatgtaga cggtcacata
126661 ggtgggcttc ttcttgggct tcagcacaat gagggtaaca ttcatgtagg ttttaggagg
126721 tccggctatc tgaggcacgt acacagctga cacggcggtt gtggccgtat agactttcat
126781 ctggggcgta gaggcatcgc tcagcaccca gaggcactcc ttgttgagga acttgcgaag
126841 ctgttcccgg ctactgttcg cggcggatgc catgacgtgc cagaatatat cccctctcct
126901 cgggggtgag tgccaattgg cctttaataa caaagccccc aggcagcacc aaaaatgcct
126961 gcccgtccga tgtggtggcc aggtggacgc agtgcccgtc agttccaagg gctactagct
127021 gggaagcagc cccaaccagc ccacccgggg gcctggagtc gatcacctta ccccaggccg
127081 aggccccttc ctcatacagc gggtggctat ctatccatag gcaggcatcc ggcgtctttg
127141 gtgcattgga gatagtagct ttcacccaac aactttccca actaacccgt gtctggacag
127201 tgaagaacgc ttccctgatc aggtctgaat ttttatagat acgggagtag gaggtgggaa
127261 taacaactgg gatttcttgt tgtgctgtcc aggcctgcat ggccagtttt tccctgaagc
127321 tagcagaaat tctgagggcc actgaaatga ggaagcgaaa ctccctctct ggagctccca
127381 aaattgaaac ctcagcaaga tctgttgctg gggaggcatg ggtgacagct gtcatcctgt
127441 gcagtctgcc ctgggcactc agctctggat atgtgacaac atagagagcg tgggggctaa
127501 aaatatgagc aattcccctg accagggccc tggactcacg aatggcccga cgggtcttag
127561 agaaagaaac aggcaccctc gagagtgccc ccgacccgac ccccacagtg ccgccagtcc
127621 ctgctcggcc tccgccgcct tccccaccgg cgctgccccg gatgttgctg gggttctcga
127681 gggctgggtg gtgcttggac acagaggtct cagcagccgc cttggtctcg gccccggccc
127741 taagtctgag ccccaggcaa agggccggac tcccagcgtg gcccaacctc tgctcccctc
127801 tattctcctc ttgcgttatc tccaatagaa tttgcttgag gtcatacgtt ttagggtgct
127861 cgacctgggc cgcggccacc ggcatatgct ctatacccgc ccctccgggg ggcccaggat
127921 ctataggtat gggctgcata gccgcagcag actcctggac cccagaggcc tctctgataa
127981 gatgcccgtc ggtcagagcc cttttggccc cctcaaagag agacaggtaa taaatctgta
128041 gctccccaac cagccctcct tcatcgtaaa atcgaagggc ggccacgtgg aaggggttgt
128101 agagctctgg aaggccctca tcgcagtaca ctggcacact ggtaaacgtg ccccgatggc
128161 taggccgtcc gggcagcatg ccccgagcag caaacacgcg gcagaccctc gtgagacccg
128221 tccggtcact gaagagagtc tggcaccagg ccccctcgca gtttggcacg cgattggggc

Fig. 3 (cont.)

128281 aaagctctgc cataaccgtg tcgggaacaa ataggtgcac gaggaggggg gtcccgaggc
128341 cactcaacac ttggttgtca atgtggacat ccatagctct ctcatgcgtt tggctacagc
128401 atcatagcgc ttgtttctgg tggatttaaa taacagggcc ccgtagacag tctttgtga
128461 gtaaatagag atgatgacat ggatgtagag actgaggacc acatccacca ccttctcgga
128521 ggaggccccc ctaaacagca tcaggcagca agggaacaca aaggaaacca gggccgggat
128581 gtgaggcctc agcgccccct cctgatcaaa gagggcctcg ctgacccccgg agatgacatt
128641 ctcattcaga aagtagtgat agaggtgatt gaccacagtc ttaaccaggc cctggacttg
128701 ttcaggctcc cacttgtccc gctggtcctg tgtgtcttgt cggatctcgg tccagggcct
128761 cagcgccggc tggaaatgcg gccccatgta gttgcctgta agggcgcaca ccactccctc
128821 atgggtctca atcagggtgc actcgctgga tccatcacat acgtggtact cgccacagcc
128881 ccagcaggca aacacggagg ccatgctctc aggtaacggg agatggaact ccagcttact
128941 atacgagcac aggtggcgag gattgggctc atccgtgccc ccctcccccc gcgggaggct
129001 caatcggcct tggtctgaca ttccaccccg gccaggtcca ggagggtgca aatattctcc
129061 aggcgctgca cctcagagac ctcctgctca aagagacctc ccaccgccac gtagacgcgg
129121 gccaccgtcc ggggaaggtc agtggggtcc cagctcagca attctccaaa ttctctctcc
129181 ccaatagtgc ctcgcttctt atcctgtctt tcagagcatc cgggggcaga catttcacct
129241 cttgtttgtg gacgaggcta actttatcaa gaaggaggcc ctgccggcga tcctgggctt
129301 tatgcttcag aaggatgcca agattatctt catctcgtct gtgaactcgg ctgaccaggc
129361 caccagcttt ctttataagc tgaaggatgc tcaggagcgg ctgctgaacg tggtaagtta
129421 tgtgtgtcag gagcatcggc aagattttga catgcaggac agcatggtct catgcccctg
129481 ctttcgcctg cacatcccgt cctacatcac catggacagc aacatccgag caaccaccaa
129541 cctctttctg gacggggcct ttagcaccga gctgatgggt gacacctcct cgctgagcca
129601 gggtagcctg agccgcactg tgcgtgacga tgccatcaac cagctggagc tctgccgggt
129661 tgacaccctc aacccccgag tagccggacg cctagcctcc tccctctacg tgtacgttga
129721 tccggcctat accaacaaca catccgcatc aggcaccgga atcgccgccg tgactcacga
129781 cagggcggac cctaacaggg tcatcgtcct gggcctggaa cacttcttcc tcaaggacct
129841 aacaggggac gctgccctcc agatcgccac ctgcgtcgtg gccctcgtct cctcgatcgt
129901 caccctgcac ccccacttgg aggaggtgaa ggtagccgtg gagggcaaca gcagtcagga
129961 ctctgcggtg gccattgcct caatcattgg ggaatcctgc cccctcccct gcgccttcgt
130021 gcacaccaag gacaagacgt ccagcctgca gtggcccatg tacctcctga ctaatgagaa
130081 gtccaaggcc tttgagaggc tcatctacgc agtgaacacg gccagccttt ctgccagtca
130141 ggtcaccgtc tccaacacca tccagctctc cttcgatccg gtcctctatc tcatctccca
130201 gatcagggcc atcaagccca tccctctccg cgacggtacc tacacctaca ccggcaagca
130261 gcgcaacctc tctgacgacg tgctggttgc gctagtcatg gctcattttc tcgcaacaac
130321 acagaagcac acgttcaaga aagttcatta aactttattg actacaccag tcccttgtaa
130381 agcgacgggt ctcgcgtgac ggcattcgtg agcagggctt cgtccagggg cttgttcttg
130441 gcggacatca ttagcccagc cgcaaatatc agaattagca tcagaaaagt gagccccaca
130501 aacaccagtg tccagagagg aagaccgtaa gataaagatg gctgcctctc atctggaacg
130561 gtgggaagct cagcagttgt ttttgtggca ttggacgtcc ctttggagga cagcgtgggg

Fig. 3 (cont.)

130621 gccaaggtgg tagcgttggt aatacgggta gtagcactgg tggtggagga ggacctggtg
130681 gtgacattgc tagtcacacc cgtggaggtt cctgttccgg cctcggtggc agtgatgttc
130741 tgtgcagtaa ccttagtggt gacattgatg gtggatgcgt tggaagttgt tgggactggt
130801 gtgacagttg tcccagtgaa tgtcaccgtg gttgtgttgg tgctcagaat agcagttgtg
130861 gttatagggg cgctagtcgt ggtcaaggtc gtagactggt ttgtgctagg acccgatgcc
130921 gacggtgatg gtgtagtcac agccgttgtg cctgtcacgt tccccgccga ggccgtcgaa
130981 ctgccactag atgtccaaat aaggcttgtc tcacagatga gtatcatggc cataacagcg
131041 cctgccttgt ctctggcgtg tgccatcgcg tctggacgca gaaggcctcc cggcctcttt
131101 tatagctagt ctccacaccc aatactctac tgaaccatca catacatgac ctcctcgagg
131161 tatgcaggga atgagcggtc cgtgagccgg tcaacacgac attgcttccg tttcatgcct
131221 ccagctgccc ctgaccagtt aggacccttg acggatgtct ttaacggcgc ggtgcagttg
131281 gtcaccaatg acggcctaaa ggccaacaca tccttgaagc agggcgtagg aatggtacca
131341 aactcggggc ccacccccatc aaagacataa tatgtctcat agtggcagtg atgatgcatc
131401 accaccacag cactcgccag gaccctctgc atatcttgta caaggcgcct ttcaactcgg
131461 ccactggctc tggtgacgtt aaatgtcctg ttcctattag tcacagcctg tagatttggg
131521 cacccagact caaaaagtgc agctacatga agggcagccg cctcaaatcc accatgaccc
131581 ccatggctgt ccgtgttgtt ggggtaataa gtcacattgt taatgaccac ggccgggata
131641 agggtgtaaa ccttgcagaa tggattggtc ggacacccat aagacagggg caccccaaaa
131701 tcacgcccct taccccgaag caccttggcc cccaccggca taaagctggg caaaaagagt
131761 gggttaaaac caaaggcgag tagggccagg aacgccaaat agcagcagta atagatgaaa
131821 acaaagctca gcatgaaaca gcgtggaggc tcagctaggg tctctgcctc tccatcatag
131881 acatcttcct tgaatctcat tctctcaccg catacctcgc tcttcatcca ggagggggcc
131941 atggctgcca ttctaccagt taacgaggag agagagagta ggtccgcgga aattggtgcc
132001 cctctctgcc ctcctgacga ggccatggtg tcatccatct ccgcagtccg ttcttcagct
132061 ttggcattgg tccgggtccg ggtggtctga ttttgattct gatcctgggt attggtcttg
132121 gtctctcctc ccccattggc atggattggc ataggtgggt gtggctcagg ctcaggttcc
132181 ggccctggga cggcagcagc cgccgggacg gtgaagtcgt ggaaggtaga ggcccgtccc
132241 tcccgaggtc gtggggccgg agccttataa aagacttcca ccctctcccc gctggccaag
132301 acacgccgct cgtggaccac gccatcttcc tcccggctga ttgtgtggct gacggtgccg
132361 tgttccaccg ccacttgttc atcgaccatg gtaccccctt tatcttaacc agcaagtggc
132421 cgtcagggtc tcttgagagt atgccgctgt ggccaagcga ggccccaaat taaatagtga
132481 tgccaaagac tgtaggtagg tcatcatcac acgcatgcgt gataaatcat ccgccactga
132541 caggtcatcc aggtctatcc gggctatctc atccggcacc atttcctgga agagattcaa
132601 gaggtcgtga tgctcatgcc ggataaggcc tcggaccagg cgcatactgg ccctgggcag
132661 cagggtcacc atgatgcaaa agtagagact cagattgtcc agcagggcca agccaagggg
132721 ccctggcacc tccgggaggg ccaactcgta gtggtgcccc aggtatgaaa cagagccaag
132781 atgcatgtgt acatcgagca tgtctgcgtt cccgggagcc tgcatgacaa cccgggagta
132841 cacgttaaac aggagaatct tctgcagcac ctcctctgct atgggcgtag gcagcaccat
132901 ggggaaaaca atgtccacat cattggactc taacttcacg gtggcatgct ctcgtccaaa

Fig. 3 (cont.)

132961 taccgggggc ataacactga ggctcccggt cccatgccac tggaaaaagg gctggtactt
133021 gttcttaatg gcgtaggtct gacctggaac aatcttggtg agtatcaaac tgtccacgct
133081 aacctcatcc agcacggcca gggtgcaatc agacaggtag ttgtacatgg acacgtagtc
133141 cgggaccgtc tctagagagt acacctgacc caagcccaat ccctgcacat tctgcgtccc
133201 gtgagtggaa gccaggggta agatgcagcc aatcctctgt tgcatcttgg caatctcatc
133261 ggtatacaga cgagaggaga gagacactac cactttcaaa tccatcttta ttgacaatta
133321 tcaaaaaacc accttatttc caaactttaa tattcttcgt accggcgcca cctcttcaat
133381 tatatagtgt ccgtaatgga tgggggcgtg ggtctgtttg acagacataa actcatcgat
133441 gagtgcccgg gaggaggctg agagtgcggg gaatgcctcc tgcagaaagc tgcagggctg
133501 ctccagaaac acgtcagtgc cagcaatcac tacaaactgc acctctgtgt tgctggtggc
133561 tgggtgccct ccaagtcgct ggctgtactc gttgaccatg ttgtagagtc ccctgttgtt
133621 gcgcagaagc tcctccttgt tgaaaaatgc ccggcagggg ctgtagaggc ccgggacggc
133681 cgtctggcga taggaggagt tgtacatgat gtcacccaga gaacccagct gagatgccca
133741 gggattcaca gtgctccggt attcataggc ggcatccggg cgagaatggt catagatgag
133801 cccctcggca acctcctgat tgtagttttc acaggagacc acacaggcgg cccgtcccct
133861 tggagagttg gacttttgaa aataagccac gtctgccgtg accggtgtta cgataatctc
133921 acaggtggcc tgctggccgt ggcagagtcc tggagctcca ttaacattag tcatacctgc
133981 caggtatgtc ctggggtccc gaagcagcgt cccattgcgc tgagcgccca ccttggcctt
134041 gatgtagtca ttgacttgct ggttgccaaa ggcctcggcc ggaaagacgc taaagaagtc
134101 ttgggtgtgg atacccatgt cagtagtgat ggccgccacc ctggccggag tcatggtcga
134161 gctataacta agcccggtgt cgatggaggc catctcgtga tgcacctcaa aggttaccgc
134221 gtccaccctg gcctcccggc ggctaacatt tggggtccca atgaacatgg atgttgaggc
134281 cctggagcta aacaatatgt tttcagagag gatctcatcg gtcctgacca cggtcatggc
134341 cacccctggg tggatcttga gcttggcctg ggcaatatag gccatggggg acatcttgat
134401 gtgcatggcg gtcattccac tgattgaaac gagggaagga agacattcgg ccgcgtattt
134461 gcccatgggc gagcggtgcc actcccggta ctctgcaaag agctgctctg gccggttgaa
134521 ggcttccacg gcccgctgct gaggattgcg cataacaaag gtggcaacat cctggtgcat
134581 ggtggcagcc actcgcgggt ccccgtaaaa catatggaaa ggaatggcgt gaaagagaca
134641 ctgggtgacg gcccgggtcc tctcggagaa ggcaaaggcc accagcccgt tcaccaaaac
134701 agtctgctct gtccgcttgt cggcgggatt cggggccagc tgctgcgtaa cgtcattgtc
134761 caccgacaca cgcacggcac gggtgaaagt ggggcaggtc atgaatgagg cgctgaggtc
134821 cctgatcatg cccacggtgg ggcggaggtc ggagatctcc agcagatccc tgagcgtccc
134881 attctccaaa ttgtcgagga tgtcctcgtc cctggtaaaa tggtggctga aggctggccc
134941 gttgtaggcc agggtctggg ccacgtgctg aaagtccacc ccgaggccgc acatgtgggc
135001 attggtgcag gttgggagga aaacgtagta aaagatcttt tccagcacat ccgcatgccc
135061 ctcatctaca taagggccta ggtgcagacg gaaatcgtgg tcgtggtctc cgttaacccg
135121 gtagccgtac aaggccacaa attgggcagc catctcatcc atgtttccaa ccctctcaat
135181 aaactggggc gcggccaggg tgtcagcgta aacctcattt ccgataataa tctgggggc
135241 ccggtcacta acggtgagaa gatgggtgaa aatgtctgtg taggccaccg gggggagcag

Fig. 3 (cont.)

135301 gttagggtcc aggagagcgc agacatactg acccacgctc tcatccccca caacatctga
135361 cccggccagg cgcatcaggg cctgctctag ggctataagt tccccataga tttttctata
135421 catggaatag gcctccttgg agatggcgtt atttcccagg tggcggcaga tgaacttgat
135481 catggaaaag ctgttcacaa aggcaagcct ccctgaccgt tcccagtagg tgttgatgca
135541 cagggacacc aaaggcacgt tcatgacaaa cttttcctca aacccgtgga tcatagcctc
135601 gactacgtag aagaaggctg gataggcagt gtcataggca gtatcctgca cagtctcaat
135661 aacggcctga tccaccacgt gggccagaga tgtggcggtc tcaaactgct gcccccgggc
135721 ctcttggaat gcagctgggg ccaggggagt cggcaggtta cccaccatta gccggtgcac
135781 agccctgtgc ctggccctct ccccggcatc cctgccaatg taaatatcat aaagggggtg
135841 cagctccagc cgcagcaggt cataattgga cgggtggagg aagtcttcgg tgggcagccc
135901 gcacttgaga gctatatctg tcacgggggc tgcatacttg ttatcataga actcgtccac
135961 aataacaagc acattcatgt gattgggcct cctgtgttgc agggagtagg tctcgcgcct
136021 gtctcgcggg gccggggccg cgttgaggct gtttagggta tgggcgggtg tgtggagtcg
136081 ggggtgacag agaaccttga gagcattctg taggttaaac gcgaggagaa ggttattctt
136141 gtttacgatc catgcctcca ccggtagctg ctgtgtgggg ttgtccagca ttttgatggc
136201 ggcggaggtc gtgtacttgg gattgggcat aaacaggccc actgggaaat agtagctgta
136261 ctgcattctt ctgttgaggg ggtatgggga ctgagtgtca ttgtacatct tttgcaggct
136321 ttccacggcc accgcgtggt tgcccagctt gatgacggcg gctgagatcg gcacccgggg
136381 ctgatcctcg acccctgcgg ccacagccgg caggtcagac ttggtgcttc cggctttttc
136441 cggtgagtcc acgatcctag ccatgaaatg ctcaaacgta cgcatcacgc gcccgtagct
136501 cacggcagtg accaggttct ccccccgtac cacaaaagaa gcatagctcg agggccccat
136561 aatctggttg tcggcctcct cacccaggaa ggtcaagagc tggcgcagaa cgttgtcggt
136621 gacaataaac accccccccca ctggctctcc cccctggcg gtcgtgtagg tactgacccc
136681 cttgagcacg ctctccccgg acacggccgc taccatctca gagagacggc ttcgcacgta
136741 ctgagaaaac ccggagccca tgttctcggc ccggtccagg aagaaggagt gctccagcag
136801 atgcctcttg aacatggcaa tgaggtcaga cttgacagtc ttggagaacc ccctctcagt
136861 gaaggtggga tccgccaggg tctgcaggat aaacatggga ggggcatggc gaagcttcac
136921 actcaggacg gtgttaatga ggcccctctc cagggcatcg accccaaact gtagggccga
136981 ggccacggtc ttgacagccc ccacgtactc tgcgtactcg accggggtct cggggatact
137041 atgcaggatc tccagatcca gcatggacag ttccatttcc gtactaatgt ggtgtttgtg
137101 gcaatttttg accacaatga atgtccgctg cttgctgggt ctccttccgt ccccgtgagc
137161 aatggtgggg acggagattc gaaattgaat cttgccatcc gtcatacgac tcaggtcttt
137221 gaattccgtg ttcacacagg acacggccag tgccgtctcc aggaagcgaa catattggat
137281 ggcgttcgtg tagaccccga gtagcacctc aaacttgatg cccgcctctc tggcatcctt
137341 gcccaccagc aggtcaaagc tatgaaacaa cccctcagcc gctgactgcc gcaggttcga
137401 gagcaggtcg gcatccaccg tcagataggg gaagggtctg ttttccacac cctcatttga
137461 ggccatgaca caaggtaaga gggagatggg gggaggtctc gagggcttct cttcacagct
137521 gggtctcttt tacgccctgg cctgcaaccg cagcccaccc acacttcccg aggatgctac
137581 ccttctaatc aaatggttgg acacggccct gggcagggag gccacctttt acgcgtgtcg

Fig. 3 (cont.)

137641 ggctatgcgt cggcttctac tcggcgttat ccgaatgaat gactgccagg agctgccacc
137701 cggtttaata attctgagtc cgggcaccgt ccctggcccc cttggagtcc agagtctgga
137761 gcatacagac tgcgaaatat ggtcctctgc ccaccctgac cacgctgccc acctcccggt
137821 gcccagggtc atcacataca ccgactgccc gggttccata aacacgagct caatgtttcg
137881 ccttatcatc cgctacttgt ctcatcacca atttgagcgc tgcttcgagc agttctgccg
137941 cgtggtcccg cgtcggcttc ctagggacct gtaagcgaaa ctctgcaaag atgctggctc
138001 atctgaatca ggttaccagg atcccccccct gtccgccctt cagcgggcgg gaggccagac
138061 tcaagttcca cttcttctcc tggagcacat tcatgctgtc atggccaaac aatgccacac
138121 tccgggagat caggacgagg gccgccacca acctcaccca ccacccacat ctagtggata
138181 ctctgtacca cgcctctccg cagaccccat ttctgacacg cagcggtgct ctataccgct
138241 tcgtcacctg ttgcaactgc accctgccca atatctccat ccagcagtgc aaggccgggg
138301 acagaccggg ggacctggag atcattctac agagtaacgg cggagggagg cccgcgagct
138361 tccagttccc ctcctcccca actggctccc tattgcgatg catagttgct gcgtccctgc
138421 tgccggaggt gtccgtgggg caccaggagc tgtctccgct gcggtccaga agccagggag
138481 ggcagacgga tgtcaggtcg ggcccggacc cggcccggag actggtggcc ctcctgcgaa
138541 gggaagatgg ggcacctaaa gaccccccctc tgggaccgtt tggacacccc cgggggcccg
138601 gcccggccaa gagcgaagac gaggagtctg agcgtcgaga cgcccctcca cccccgctcg
138661 attccagctt ccaagcttcc cggttggtgc ccgtggggcc tgggtttcgc ctgctcgtgt
138721 tcaacaccaa tcgggtgatc aacactaaat tggtgtgctc agagcccctg gtgaagatgc
138781 gagtttgcaa tgtcccccgc ctcatcaaca actttgtagc ccgcaagtac gtggtgaaag
138841 agacggcgtt caccgtcagt ctattcttta cggacggggt gggggccaac ctagccatca
138901 atgtcaatat cagtggcacc tatctgagct tcctattggc catgacgtca ctgcggtgct
138961 tcctgcctgt ggaggctatt tatcccgcgg ccgtgtcaaa ctggaactcg actctagatc
139021 tccatgggct ggaaaatcag agcctagtca gagagaaccg aagcggggtc ttttggacta
139081 ccaactttcc ctcggtggtg tcctgccggg acggtctcaa cgtgtcctgg tttaaggccg
139141 caactgccac catatctcga gtgcacgggc agacattgga gcagcacctg atccgtgaaa
139201 tcacccccat cgtgacgcat cgagaggcaa aaatctcccg gattaaaaac cggctcttta
139261 ccctgctaga gctacgcaat cggagtcaga ttcaagtgct gcacaagcgt ttcctggaag
139321 gcctgctaga ctgcgcctcc ctcctgcgcc tggatcccag ctgtatcaac cgaatcgcct
139381 ccgagggcct gtttgatttc tccaagagaa gcatcgccca ctccaaaaac cgacacgagt
139441 gcgcgcttct gggtcacaga cattcggcga acgtgacaaa gctggtggta aacgagcgca
139501 agacccgcct ggacatactg ggccgtaacg ctaacttttt aacgaggtgt aagcatcagg
139561 ttaatctaag acagtcacct attttcctga ccctcctgag gcacatccgc cgacgtctgg
139621 gcctgggccg tgcttccgta aaacgagaga ttacccttct cctggcccac ctgcgcaaaa
139681 agacagcccc catccactgc cgtgatgctc aagtgtaagc agcccggggc ccgcttcatt
139741 cacggggccg tgcacctgcc atcgggacag attgtcttcc acaccatcca cagcccccact
139801 cttgcctcgg cgctgggact gcctggggaa aatgtaccca tcccggccct cttccgtgcc
139861 tcgggcctca acgtccgtga gagcctaccc atgaccaaca tgagggcacc gatcatctcg
139921 ctggctcgcc tcatcctggc ccccaacccc tatatcctag agggacagct gacggtgggc

Fig. 3 (cont.)

139981 atgacacagg acaacggcat tcccgtgctt tttgccaggc ctgtcattga ggtaaaaagc
140041 gggcctgagt ccaacattaa agcctcctcg caacttatga tagcagaaga ctcctgcctg
140101 aatcagatcg ccccctttc cgcatcagag caccccgcct tctccatggt tgagtccgta
140161 aaacgagtcc gggtcgatga gggagcaaac acccggcgca ccatccggga tattctggag
140221 atccccgtga ctgtgctctc atccctgcaa ctgtctccca ccaagtccat cctgaaaaag
140281 gcaccggagc ccccacctcc ggagccccaa gccaccttcg atgccacccc ctatgcccgc
140341 atcttttacg acatcgggcg acaggtgccc aagctgggca atgcccccgc cgcgcaggtc
140401 agcaacgtgc tcatcgccaa ccgctcccac aactctctaa ggctggtgcc caatccggac
140461 ttgctgcctc tccagcattt gtacctcaag cacgtagtgc taaagagtct gaatctggag
140521 aatatagtgc aggactttga ggccatcttc acctccccgt ctgataccat cagtgaggct
140581 gaaaccaagg cctttgagaa gctggtggag caagccaaaa acaccgtaga gaacatagtc
140641 ttttgcctca acagcatctg ttccacctct acactcccag atgtcgtccc cgatgtcaat
140701 aacccaaaca ttagcctggc tctagagaag tattttctca tgttccctcc ctcaggcacc
140761 attatgagaa atgtcagatt cgccaccccc atcgtccggc tcttgtgcca aggggctgag
140821 cttggcacca tggcacagtt tctaggaaag tacatcaagg tcaagaagga aactggaatg
140881 tacacactgg tcaagcttta ttacctgctg cgcatctaaa ggaaaaacat aacaatcttg
140941 tgaaccagaa agatacccag agcaaaagca ataaagtaca ggattattgc caaaacaacg
141001 tgtgctcttt cttcatacag gcccgcaatt tccatgacag tcccgttggt ggtcagcagc
141061 agatagtgaa cgtggaggtt gtcaaaatca aagtagttgg agctcaagat ggagttttgg
141121 acttcctggg aggtgatgta ggttgtagtt tccaggcctt ccttttcatc ataactgagc
141181 agggcaaagc cacaaaaaat gcaggatttc tgcgtcctgg taaaattctg gatctttgga
141241 atctggcggg gctccccagc cacagcaccc tgcgaacatt tattcattat aacgggggag
141301 agaaagagag agctgctgag ataggtggtg ctggcctcgt atagcgccga gcctcggacc
141361 tcacggtcac tagagattat gaatgtcaca ttgatgagcg ggataatcat cagaactttg
141421 tcgagcctgt ccacgcattt gtaggcgggg agatgccacg catccctgtc ttctcgctcc
141481 aaagagagcc gcccaagaaa cccatccaca gcatttgaaa cggccgcctg gtccagcgtt
141541 gcctcctggg gggccatgct cagcagcttg tctcgtgtga ggtcaaatcg taggctgagg
141601 tagcacggtg agaagagccc gctctctgtc cccagggcta gcccccgcaa aacctcccca
141661 atctctaggg ccgagcacag ggcggtggac agcagttggt atagggcaag gttgggcccc
141721 tgggtagtca cgttcagccg caactcgcgt agcaccacgt ggctgccgat aaacagggtc
141781 tctctcatca cggtatgcag gggctggaaa agggggtggc ggttgtaggc cgagagaagc
141841 acagatgtgg cgcctccaat gaggccactg taaaccccgg ccttggggta gccgacggtg
141901 gctaacctca gcgcgtactc ctgtttctca gtagtcaggt gacccagctc ctccatcttg
141961 accgtggcca tcagcatggc ggccaagcgc tccagcccgt aggattgcat gcccttgaca
142021 gtggccccat aacatatgcc gatgatgtct ttcaggacag tcagctcaaa gaagctcttg
142081 gccaaccagc ggaggtccac gcagccattg ccagtctcac ccacagcatg acccacctta
142141 aagaaggcca cagaaacctc aaacatggta gtcagcgttt ccgtgtccag ttccggctcc
142201 cggcagcctc ccttcatctc cagcaggacc agtttctgga gaacgtagcg agcgtagctg
142261 gcggctgtca tggtgacggc tcgggaaaac atatccttca ggttgggtac aaagtagttg

Fig. 3 (cont.)

142321 tgaaagttgg cataatgcac aaaggttgta acaatcacca gggaatagtc cccgctttgg
142381 gcactggtta aggatgggta actaaaaggc cccctcagat ccggcaggtc cttcgtcttg
142441 ccaaagacca ggctcaacac atgctcatct cccttctcgg tcactcgctt gtaggtgccc
142501 atcagaaatt tagaagtcat ggcccccgtg tactgaaact tgtccccgtt gatggacagg
142561 gccacataag acaagtgaca gcgcagctga taaaagacat agctgtgtgg ccgcgtgttg
142621 ggcagcatgg tgccaatata gtagaagagc tgcttctcaa ggggggcact aagcatgcag
142681 gcaggggaat tcaggccgct aatgactccg ggatggacct tagatgcatc cacttgcatg
142741 gatccttcag agacagcagg gatatcgaca ggctcggcca gcgcaatacc aagggtacca
142801 gacgtcttgt aaattaactt gtagcggtta agcatagacg ccaaatcttc ggtgacattt
142861 gcctctctcc acagcgcctc tgggctaagg cctgggacct ttgccatcag ttcggtccat
142921 gggatggtgt aatgcgaagc atgcccctct atgtccaggt gcagcttaac ctcgctgagg
142981 ctggcagccc ccacctccca tagcaacacc aggcaaaaaa cacagagcaa ctgcatccta
143041 gtcccgattt cccctctcaa aatcagagat caccttgctc agaccagccc aatcgaaaaa
143101 ctgagatcgt attgccggat tcttcaatgc ctgcatgtaa atctccgtcc agcatccagg
143161 taaatcgtcc tgaaactctg agaggtccac aagcacaaac tgaaggtagg ctagcgttcg
143221 ggtgaacgca agacaaactt ccaacaacac cgcgtcggct cggaaaggct gtatgacttc
143281 cttaagtaca ctaaagatgc tgttcttata cagcttctcg gccacaccac ttcgaattat
143341 gggggtgtgg ctttgatgac atactgtcgt gattgttgtt agaccggcac ataccttcac
143401 aatgtcctcg ggggcaaaat actgtgttag gagccaggca cagtaaacgg cgtgatatgc
143461 atcgttgaca ctcttcaggt agccagcatc cagtcctgac tcatgtttcc tccctcgctt
143521 cttcaggcgg cgcatgttct cctccacgtt taacttcatc cagactatgg tgtcccccgg
143581 gtctgcggta aacgtggcca aaacttgaat aaagtcacta taggagagaa gctggctccg
143641 gagcagcatt agagggaaaa ccacggaggc cgacagcaaa tggcgatcat gcaaaatcca
143701 acaatccagg ggcgcgactg acctggcacc agactcggta accagcaagc tccgcttcct
143761 agaggccaag actctgaaag gggtggtaaa tttcatctgg catgctaaaa cctcagccga
143821 cgtgtcttcc cttccatgcc tcgcccgagt cacattcttg tgcatggcct taatggcatt
143881 ttcatacaca tgagtccagt accgcatcgg ttcagggact acaatggtca ggtccccaaa
143941 gacagccttc aaatgattca gcatagtagt ctttcccaca ccagggggcac cttccaaaaa
144001 tagggaacag gcaggtttga ttactggtac atgatttgtt aggtgggtca caattggaac
144061 ccgcatgctc tccttcctct gagccttggc ctggcgggtg tcttgggcat catccagatt
144121 cagaacattc atcacactcc cacttagccg cttcagctgg gcagcatgct tggataactt
144181 actaaactcg cgcccatggg cggccaggtg ttcgaagaga ccagaaggct taccccttgcc
144241 accattcttt tgttttaacg cggaatgaga agagggcctg cggaaattag actcatcctc
144301 agactcacag tcagatttgt catcgagccc aaggccggcc aggccctcct caaagccttt
144361 ctggtacatg aagctccggc tcgtggagtc cgcacctcct tctgtgcacg aagttttgcg
144421 gaaccaggag aaggggtctg gcgtcttgct ggggccacac tcccggctac ggggcttcgg
144481 ggtaggggca gtaggctttt ggtgtgcggg tgctggtggc tgggctcccc tgggcagggt
144541 aaaggggcac gatgtgtgcc ggctacccgg agagtttcca gtattagatg tcacggcagc
144601 ctgggtccgg cacggcaccc tctccccaga cagtccggtc ggagccatca agggggggcca

Fig. 3 (cont.)

144661 gtgggtgggc acctggtaga ggccgtcgtc atcttcctca cctgcccctg agtcactacc
144721 ggttggggta agaactgagg gggcaaagtc atcaatctca gcgtaaaagt tttcgtgtct
144781 ttcgttttca ggggactcat cctcctgaca ttttcgccag ccgccgggcg ggccggcctc
144841 ctttcctgga aatccagcca tggatcccac ccggggtctg tgtgccctct ccacacacga
144901 cctggcaaaa tttcacagtc ttccccccggc tagaaaggcg gcaggtaagc gagcgcacct
144961 tcggtgttac tccaagctgc tctctcttaa gagctgggag caactggcct cttttttgtc
145021 tctgccccccg ggacccacgt ttacagactt tagactattt ttcgaagtca ccctgggtcg
145081 gagaatcgca gattgcgttg tggtagctct gcagccttat ccccggtgtt atattgtaga
145141 atttaagacg gccatgagca acacggccaa cccgcaaagc gttactcgca aggcacagag
145201 gctagagggc accgcccagt tgtgtgactg tgccaatttt cttcgcacgt cctgcccccc
145261 cgtgctgggc agtcagggcc tggaagtctt ggcggcgttg gtatttaaaa accagcgatc
145321 cctgagaacg ctccaggtag agtttccagc cctgggccaa aagaccctcc ccacctccac
145381 caccggcctg ctaaacctcc tctcccgctg gcaggatggc gctctccggg cacgtcttga
145441 tagaccccgc ccgactgccc agggacacag gccccgaact catgtgggcc ccaagccttc
145501 gcaactcact gcgcgtgtcc cccgaagcgc tcgagctggc agagcgggag gccgaaaggg
145561 ccaggtcgga gcggtgggac aggtgtgccc aggtgctcaa aaataggctg ctccgcgtgg
145621 agctggacgg catcatgcgt gaccacctgg ccagggcgga ggagatccgc caggacctgg
145681 atgctgtagt ggccttctct gatggcctgg agagcatgca ggtcaggtcc ccctccacgg
145741 gagggcgctc tgcgccagcc ccgccctccc catccccagc ccagccgttc actcggctca
145801 ccgggaacgc ccagtatgca gtctcaatct ctcccacgga cccccctctg atggtggccg
145861 gcagcctggc tcaaacgctg cttggtaatc tgtacgggaa catcaaccag tgggtaccgt
145921 ccttcggacc ctggtacagg accatgtcgg ctaatgccat gcagcggcgc gtgttcccta
145981 agcagctgag gggcaacctg aactttacca actccgtctc cctaaagctg atgacagaag
146041 tggtggcggt gcttgagggc accacccagg actttttctc agacgtcagg cacctgccag
146101 acctccaggc tgccctgatc ctctcggtgg cctacctgct actccagggg ggctcctcac
146161 accagcagcg ccccctccct gcctcacggg aagagctgct ggagctgggc ccggagagcc
146221 tagagaaaat catcgccgac ctcaaggcca agtcacccgg cggaaatttt atgattttaa
146281 caagcggaaa caaggaagcg cgccagtcaa tagcccctct caaccgacag gcggcatatc
146341 cacccggcac attcgcggac aataagattt acaacctgtt tgtgggagcg ggactactgc
146401 ccacgacggc cgcgctgaac gtgcccgggg cggcgggtcg ggaccgggac ctggtgtacc
146461 ggatcgccaa ccagatcttt ggggaggatg tgcccccctt ctcatctcac cagtggaacc
146521 tgcgcgtagg tttagccgca ctcgaggccc tgatgctcgt ctacacgctc tgcgagaccg
146581 ccaacctggc cgaggcggcc acccggcgtc tacacctatc gtccctgctc ccccaggcaa
146641 tgcagcggcg caagcctgcc atggcgtcag ctggtatgcc gggcgcctat ccagtccaga
146701 cgcttttccg ccacggggag ctcttccgct tcatctgggc ccactacgtg aggcccacgg
146761 tggcggcaga cccccaggcc tccatcagct ctcttttccc cgggctggtt ttgctggccc
146821 tggagctgaa gttgatggat gggcaggctc cctcccatta tgccataaac ctgaccggac
146881 aaaagtttga caccctcttt gagattatca accagaagct tttatttcac gacccggctg
146941 ccatgctggc ggcgcgcaca cagctgcgtc tagccttcga ggacggcgtc ggtgttgccc

Fig. 3 (cont.)

147001 tggggcgccc ctcgcccatg cttgcggcgc gggagatcct ggagcgtcag ttctcagcct
147061 cggatgacta cgaccggctg tacttcctga cgctgggcta cctggcctcc ccggtggccc
147121 caagctgagc cagttcctcg cactggagtg ggtcattggc aaaaaggtaa ataaactcat
147181 cgcacggggg ttttgcctcc ttctcgtctc ttgtttcggg taggggagta aggccgctgc
147241 caggccgcca tgctcagggc cacggcgtgc cagaggccct cgtagtcgtg cgcatccgag
147301 aggatggcac ggtccagaag cagatagccg gccaggcaga ggaaggccac aaagaggggg
147361 cgaaggcgtg cccgaacccg ggtttcatgc tcgtctgcac cccagtggac aaggcagtag
147421 aggacaccca ccaccaggcg gttagggagg acactgccaa ggttgaagag cagatttccg
147481 tcagccaggg tgacctggct caggtccggc gccctgcgag tccaagctgc gcccacacac
147541 atgcacagac ggcccctgtg acatcaggcc ggtcatgcaa aaacagacaa agagaccgtg
147601 agcggttacc ggggcgcagg gcctctgccg ggaagcccac ccgggccagg gcccggtaaa
147661 gcaggtacca gtattcatcc ggcaccttgc gtgccaacac acgattcgtg cggtttccag
147721 tatttatcac ggcttcccgc cacaggtaaa agttaacact tagggtcagc agcttggtca
147781 gggataggtg caaaaacctg agctcgtcct cgcgcagagc gcaaagcggc cagttcttta
147841 gcatcttcag gaggagcccg tgaatcccag gtgtcattcg cgcgtcatcc ccgcgcaccc
147901 ccagtcccat taacatagcg ggcacaatgg tgcaggcacc gtctgtatac gtctgcggct
147961 tcgtggagcg cccggacgcc ccacccaagg acgcctgcct tcacctggat cccctcaccg
148021 tcaagagcca gctccctctg aagaagccct tgccactcac ggtggaacac ctgccggatg
148081 ctccggtcgg ctcagtcttt ggcctttacc agagccgagc gggtctcttt agcgcagcct
148141 cgattacctc tggggacttc ctgtccctgc tggactcaat ttaccacgat tgcgatattg
148201 cacagagtca gcgcctgccc ctccctcgag aacccaaggt ggaggctctg cacgcctggc
148261 tcccctcact gtcactggcc tccctccacc cagacatacc ccaaaccacc gcagatggag
148321 gcaagctgtc cttctttgac cacgtgtcta tctgtgccct gggtcgtcgg cgcggcacca
148381 cggcagtcta cggtacagac cttgcgtggg tcctgaagca ctttagtgac ctggaaccgt
148441 ctatcgccgc ccagattgag aatgacgcca atgccgcaaa gcgtgaatcc ggatgcccgg
148501 aagaccaccc tctgcccctc acgaagctca tagctaaggc aatcgatgct ggatttctga
148561 gaaaccgcgt ggagactctg aggcaggaca ggggtgtggc caatatccca gccgagtcgt
148621 atttaaaggc cagcgacgcc ccggacctac aaaagccgga caaggcactt cagagcccac
148681 caccggcctc cacagaccca gccaccatgc tatcaggtaa cgcaggagaa ggagcaacag
148741 cctgcggagg ttcggccgcc gcgggccagg acctcatcag cgtccccccgc aacaccttta
148801 tgacactgct tcagaccaac ctggacaaca aaccgccgag gcagaccccg ctaccctacg
148861 cggccccgct gcccccccttt tcccaccagg caatagccac cgcgccttcc tacggtcctg
148921 gggccggagc ggtcgccccg gccggcggct actttacctc cccaggaggt tactacgccg
148981 ggcccgcggg cggggacccg ggtgccttct tggcgatgga cgctcacacc taccaccccc
149041 acccacaccc ccctccggcc tactttggct tgccgggcct ctttggcccc cctccacccg
149101 tgcctcctta ctacggatcc cacttgcggg cagactacgt ccccgctccc tcgcgatcca
149161 acaagcggaa aagagacccc gaggaggatg aagaaggcgg ggggctattc ccgggggagg
149221 acgccaccct ctaccgcaag gacatagcgg gcctctccaa gagtgtgaat gagttacagc
149281 acacgctaca ggccctgcgc cgggagacgc tgtcctacgg ccacaccgga gtcggatact

Fig. 3 (cont.)

149341 gcccccagca gggcccctgc tacacccact cggggcctta cggatttcag cctcatcaaa
149401 gctacgaagt gcccagatac gtccctcatc cgcccccacc accaacttct caccaggcag
149461 ctcaggcgca gcctccaccc ccgggcacac aggcccccga agcccactgt gtggccgagt
149521 ccacgatccc tgaggcggga gcagccggga actctggacc ccgggaggac accaaccctc
149581 agcagcccac caccgagggc caccaccgcg gaaagaaact ggtgcaggcc tctgcgtccg
149641 gagtggctca gtctaaggag cccaccaccc ccaaggccaa gtctgtgtca gcccacctca
149701 agtccatctt ttgcgaggaa ttgctgaata aacgcgtggc ttgaaagtaa actttattgc
149761 gtgttagtac ctgtccattc acaggggtat ccagcccttg cgccgcctcc cccagcccgc
149821 cagccacccc agacaggaga tgataatgat gaggagcacc ggagccacca cagcacaagt
149881 gattaggagc agggcccagt gcacccaggt ggtcttaggg cgccagggat cgattggaaa
149941 agggcccagg gtcactggct tatgcgtggg acgtttagaa acaggccgcc tatggggcct
150001 gtgactggtg cttgtggtgt gggagactaa tgtggtgggg gctatggtag tggctgggat
150061 aacagtaaga tgcatacgct gagtgagggt ccggttggca tggtattggt cgtcttcttc
150121 ccctgcagag taattgcagt ggaccccgga ggccacactg caatttctca gtgtcacatt
150181 gcacgtgtag taacctgcat gcgcaagggt cacattgggg attatcagag agacggaggt
150241 gttggagtca tttacccatt ctagggtaag gctataattg taaccccegt tagttatatg
150301 agttccgttg ttggaagtag ctacggccaa gggcagttgt ccatccccgg gagtgtatcc
150361 ccggcccaac tcgatccgag agaccgactc attgctagga acgctgcagg tgagattcac
150421 tctagcacct gcatgggcgg tgacattttc aaatttaacc agatctgaga aaaatgcaca
150481 aacagacccc acacagcagc acaatagaag cactaaatga gtcattccta aactgtcagt
150541 tttaaaactc cctgcttctc aggcctaaat atgtggtggg gtgtgcttag gatcactttc
150601 atattctgca acaacagcca tacccggaag aggagctgcc ggttgccatt tttcaagctg
150661 ctaaaccacg agtggcagca ggcctaagaa gctcctcagc aacatggaga cctcgaaggg
150721 aaactggcag gagcagggag tcacgtaggc actagcctct tcatgtgagg taagagatcg
150781 ctaaaaatgg gatcagggta tgtaaaccga gttttgcggg ggatggtgag ccagacacgg
150841 cgggtggggg aaggagctga cacgattgag tagaaagggc caaaaataca ccagctataa
150901 ggaattgctc aggccaaagt tgttcctcag gtggctttag gcctaatgta ggcaattgcg
150961 tgcctagaac attgctaatg tgccctgggt ttcctgcctt catgcaaata ttctacctcc
151021 cccggcctgg tgcaaaatgt ctgcctcaga atactaacag ctaatccaag ctaacattct
151081 atcagtaaac gggcagaaaa ctgataagga ccgcggagtt tggccctccg cggtgtccgg
151141 tggtcctcac acgtgccctc cccccgggcc gatggctgag gccccggaata tgcaagtgca
151201 tctttctaac cagtaggggc ctccacctag gtgctttgtt aatctttagt gggaactagt
151261 gggagtgctg tgcctcgggt acccctatcc tataggtcct accggagctc cttgtcttga
151321 taatccctgt aaacacacac cacctaagaa caaggcattg ttaacctttg gtggaaccta
151381 gtgttagtgt tgtgctgtaa ataagtgtcc agcgcaccac tagtcaccag gtgtcaccgg
151441 aggctacttg cctcagtgcc acttttacct tctcaaatct atacgggggg gggggggggct
151501 ctgtaacatt tggtgggacc tgatgctgct ggtgtgctgt aaataagtgc ctagcacatc
151561 acgtaggcac caggtgtcac cagggctact tgcctcggca tctcctcacc ggagaagggg
151621 ttaacaaacc cgtggggggt cttagtggaa gtgacgtgct gtgaatacag gtccatagca

Fig. 3 (cont.)

151681 ccgctatcca ctatgtctcg cccgggctat atgtcgcctt acctccccta tatagtcacg
151741 accccaccga accaggcatg atgtagaata aaattttatg catcatcttc taatctgtgc
151801 cgcttggagg gaaacatgac cacctgaagt ctgttaacca ggtcagtggt tttgtttcct
151861 tgatagagac acaaggactg ccagccccat tggggagggg gggtgggtac gggagagttt
151921 gggctcgttt aaacaaagtc tcatctgatg ctctgtggca cctcaaggtg aatatagctg
151981 cccatcgacg tatcgctgga aaccggtggg ccagggcctc gtaggccgag acgggcagcc
152041 ggagcttgtg gtactgtccc tccggcaggt ggagtgggac acagttagag aacattagtc
152101 ctctggtccc tatctccacc cgccaggcct gtgtgtcagt ttgcagggcc atcctcgcac
152161 tcaggtggac tggctaggca cccttctgaa gtatctggcg gtgactgtca cctggttctt
152221 gagagagtcc ataaaatggc tgaagctcca ggcgtatagt ataatgagca acagggccaa
152281 acaggcggcg gggcctgggt agtagcgggc aacgagagac tctgtgcaat caaaccccag
152341 gctcccggcc tcacccagga agagcagcgg cagggacagc ataaaccagg agaaggcgca
152401 aatgagtccg gtgaaggtga cgttgcatat caggcgcggc ttccttccga attttgtgcg
152461 caaaagtttc cagatgatga taactgtgag gaggacgatc aggactgccg ccagtaggta
152521 gcagccggct ttcagtcctt ggacggccgt gtgcatgcct ttggtggggc cttccctgca
152581 catgttgggg cctctgttga gattggcgtc ggggcccatg gtaatgagga ggatgataat
152641 cagcaggagt accagacaaa acacgcccat caggtacagg cacacatttc tgtgggaggt
152701 tctcttgggc gttcggctga acaatgctag ggtcttctcc aacgccatac ccaagtgagt
152761 ccatacggag cacatcaggc ccaagaacat catgttctgg gtcaaaaggc agagaccggt
152821 agacgagaac tcctgaatca tttttcccag cacccagagc agcagttcta tgagaagagc
152881 tatcagccag acatccattc ggtgaaccaa ttttcttaca aagatgataa acaagatgcc
152941 agccagtgtt agcagaatca gcaggacgag cagcaggctt gtcatgccgc tgaggaaggc
153001 gctgtaggat ttagtgcacg catcttccgt tgcattgacg gaagtcatgt tggccaccag
153061 ggtccccacg gtggacccgg gggccatggt ggagagcatc ttgctggtca gagccagact
153121 gggtggtgtc tgcagcaaaa gaggaacttg cccaggcagt cagttatttt gcatgccacc
153181 tccctgcctg gtggacttcc agactatttt ctgcattcgc ccttgcgtgt ccattgttgc
153241 aaggagcgat ttggagaaaa taaactgtga gtttcacaga tccacgggcc acgctcccct
153301 gggggcttca tgatcccacc gcctttcccg atgatgatga caaccgcggc tgtctgaagc
153361 ggctgacgaa atcggttgag attctgatga gaggcttggg ggggtctttg ccctcaaggc
153421 gaggctcctt ctcctaggaa tgccgagccc cctgcactag cttcgctcca ctggggatct
153481 ttgccagcct tcatactaga ttcagcgatc ccccggttgg gaatcttcgc cagccccccg
153541 tcctgctatc ccgctcgtcg ccgcgcctcc catgctaagg gcccccttcc tttcccttga
153601 ctttggggat attcggagtc tgctctcgcc gctctcttct ctcgtttaaa cgagagaata
153661 gtagtagggt ccagtctcag gccccctcac tttgggtctt agaatggtgg ccgggctgta
153721 aaattctgga ggacggagag ggcggccccg gagttgttat caaagaggca ctggaggatg
153781 ttggccgctc cttggagcag cttgtcgaaa taatgatcca cggccacggg aacgccgtgc
153841 cgctcggcgt aggccgggtc ctcggccatc tccgtctttc tcgccccctt cactcccccc
153901 ttgggctcca caaagacgta ctggatgcgg tcgtggatct ggggcagttc ctcgttgcgc
153961 tcgacgaact tctggtagac ggccaggtga ggcatctggg tgctcttgta ggctgagagc

Fig. 3 (cont.)

154021 ttgcggctga gctccgttga aaagcagagc tcccccatgg ggaccctgcc ttcacggagg
154081 tctgtgtagg cctggtttag gatgtcaatg acgggcaaaa agcccacagg tagcccttgt
154141 gtaaatgact cttggaaggg ccggtgggag aggaggctgg ccgcctcctt tacccgggca
154201 tccgccagca ccaggtcgag cacgcgccgg cagcgtgtct gcacaaactt gcaggccgtc
154261 ttccggacga gctccacccc cttcatcagg gtcttgccgt ccgtcagcac ccccacatat
154321 ctcttctttg taatcagcat caggcaggag aaggtcttct cggcctccag ggagatgggg
154381 gccacaaaca ggctccgggt ggtgtgggcg gccagggcat cggcaaagcg cagggtctcg
154441 ctctctgaaa acccccggca ctcgataaac agcgagtccg tgtccccgta gatgactcga
154501 agctggccct cggggttgag gggcgcccag gcgtccgggg agggggccag ggcctgcagg
154561 ttggcggggc tcagggcctc cacgaaggcc ttggcccgct ccaacatcgt gcggccctgc
154621 agcgtcaccg tctcggcgat ggagaggcag ggaaagaggc cgttggccac cccggtgaag
154681 ccgtagacgg cgttgcacgt gcacttgatg gccagctgct gcttgtcgag gatggtcctt
154741 tggcgcggat cctcgcaggc cgccagcagc ttcttgatgg ccttgcgctt ggccagccag
154801 gaggtcaaca gactagccaa gaaggactcg tgcacgtgct tctttacaaa gtggtagacg
154861 ccccccgtga gcctgaagga ctcatagtct tctcccgggc gcaggccggc tagcctgtgc
154921 tcttctcccg gcgttatcat ggtagaataa cagagattat gagcctgaat gatgctcggg
154981 tagaggctgg caaagtccac caccagaacc ggggagttgt agaatccgga caggggctgg
155041 atgacggtgg ccccctggta gccgtcccgg tcagaggccg agggcatggg caggataaag
155101 ttttcctttt gggcggccgc caggaggcag gagaacacgc ggatctgctg cccatcgtcc
155161 agcacccgcc tgcaggggat gtgagcgatc ttggcaatct ctgccacctc cacgtggatc
155221 acgaaatggt ttagcagatc catgaccagg gccgagtcct gcacgcagta catgccgagc
155281 cgcctgcgcc cctcggggcc cgctgcaaag aggcgaggaa tctccttgta atgcacatcc
155341 tccttcttgg cccccagtag gtgcctggct actgtgtcca gcttgtagtc tgagaggctg
155401 agcttgtccc ggcacacggc gtacatgtcg atggggatga ggccggtgat gcggaccttg
155461 gtgttggccc gcaagaagcc cttgcccgca tcatggggtc gcctgacctc gcagacgccc
155521 ccagccctaa ttttgcccag agaggctggg ttgatgctgt agatgtgcct ggctctgtcc
155581 agaatgtagg gccagtcaaa gttggccacg ttgtagccgg tcacaatctc cacgctgagg
155641 tctctgatga gctggaagaa ggcgtagagc atgtccagct ccgatgggaa ctcgtagacc
155701 tcaacccccct ctatgtcttc gcaggtgccc agcgtcagca ggatgcgcct atagcgcccg
155761 gcctcctccc ctgtcgacca gaggacgcag gatatctgca ggatcaggtc agcctcgttg
155821 gtggccgtgg ggaagccctc ctcccccaga cactcgatat cgaaggccag ggcctggtag
155881 gagggccagg agctgtcttc acgccggacc gagaggtcgc ccacctcaca gtcgtactcg
155941 agctcggcgt acgagtcccg gtgctggagg cgggggatgg cgcggcggca gctgtaccag
156001 ccaaaggtga caaagtcatt gtccaggaca aagcggcgcg tggcatccac gttggcctca
156061 aagatccgac acccgtgctt gtcttgcagc cacgtggcca cgtgacacac actgttggga
156121 tgggagaggg tgatcttgtg gtagtcgccg gcatggttgc cgtagcccat aatggaacgg
156181 cgcgtgacct tctccaccga gacccggcag gggtcctgc ggtcgaaggt gctggccttg
156241 agggcgctga ggactgcaaa ctccacgtcc agaccctgag gcgcgctggc gtagaagtag
156301 gcctgctgcc caaacacgtt cacacacacg ctggccccat cggccttgcg ccggcccagt

Fig. 3 (cont.)

156361 agcttgatga cgatgccaca tggcaccaca tacccctgtt tatccgatgg aatgacggcg
156421 catttctcgt gcgtgtacac cgtctcgagt atgtcgtaga catggaagtc cagagggctt
156481 ccgtgggtgt ctgcctccgg ccttgccgtg ccctcttggg cacgctggcg ccaccacatg
156541 ccctttccat cctcgtcacc ccccaccacc gtcagggagt cttggtagaa gcacaggggg
156601 ggctgaggcc cccgcacatc caccacccct gcggcgcctg gtgtctggaa acacttggga
156661 atgagacgca ggtactcctt gtcaggcttt ttcagaaggc ctttattagg tcttaggaaa
156721 gggttataga agagtccccc agacatggtt aaaactcagt ctctgcctcc ccaagcagtg
156781 cggcggcggt ctctggatcg tgatagcgtc ttctgcgtag gcctggaaaa cggtccctgg
156841 ctgcctgcaa tgctctgctg gccactgagg gtccggccgc cctctgagct gctctctttt
156901 gctcctggtt ttgctcatgc agcgctaaca tgatggcttg taattctgtc ttactaatgg
156961 gattaatgcc tggaccctca ccagaggcat gttgctgagc gagctcgtcg atcccggggt
157021 agagcatctg caccggctgc tgcgacatct ggcgcgtgcg cctcgtgagg gaaataacca
157081 ggatcaccac ccccgccacc aggaccagaa tgagcatgcc gccgaagggg tttttgaaga
157141 aggagatgaa accagagacc aggctgctaa acaaaccccc caccgtgctg actaggttgg
157201 tgatggactg acccacgcta cccagactgt ccataagttc ccccaggccg tccacgaatt
157261 gatttcttcc gtttgacact gcattgtcca aatccttccg caggccggcg atgttttgcg
157321 cctggaagtt gtactcccgg aagatgccct ccaggtcaaa gacgttggag gcacgctgtt
157381 cgtcccgtga gtacagctcc agggaggcaa agtcaatgtt ctcgatgagg gaggtgttta
157441 gtgagatgaa ggtctgcagg gtggcaatgc cgtccagctc gatggtttta aagtggtggt
157501 agtcgttgta gacgtggatc tcgttgccgg actggaagta gtactggctg gtcgcctggc
157561 acacctccgt catctttttt gtgaggaaga tctcgttgtc ggtgcccagc tgtccctcgt
157621 aggtcttggt gtcgttgata aagctgaagg acaccagggg gcgcgagtag cacatggtct
157681 cggagccagg gaccctcatg ctcttgcgca gggtgacggt ggcctggtta acgggcacgc
157741 actgggagac tgagatgaca tcccccaggc gcttggccgc caccgcctta ccgtagatgc
157801 tggacatgac ggtggttgga ttaatcttgg ttagttctct cagcaccatg ttctgcctct
157861 tctgctccag gcaccaggcc cgcgcaaggt ctcccagcat gcggttgatc tggcggcgca
157921 gggagtcgta ggcaaattgg atctggacgg tggcgggatt gttgagggtg cccagggact
157981 tcccgggggc cgtgggggc accggtgtgg tggcgttccc cgcatcccgc ctccgacgcc
158041 tcagaacggc ggcgggggtg ctcccgcggg ccgcggatgg ggctgggggc gatggactgc
158101 tggggggtga ggaagtcgga gtggtaagct ccgtcaggtt cttgacggtg gccaacgagc
158161 gcggggtcag aggtagccaa gctaataaca atcctccgct cgttataaaa tatgtaatgg
158221 cttcctggcc cttcgtgtaa cgatcctgga cggcctcgta cttctcatgc atggtcttgt
158281 tcacctgctc ttcgatgcac ttgaaggcgt ccgggagctc tatgcccacg gttgtgttgg
158341 tcacgaagct agaggtgccc tcgtcagtca caaaatgtat tgacttccct gtttctgtgg
158401 cgatggtcga gtcaaaggtt tgccagtgtt gaagcgggca gtaggctgtc ctgttctcga
158461 gcttccaaga tagcgtgtaa gtgcccttgt ccaggaaggc tcggcgttcg ccttgcgggt
158521 tcgtccctcg gttgtcgtag tccactatct tgtagttagt tctcacgtgg aaggagtctg
158581 cccgctcatg gaaggtttcc ttatttttcc cgtcatagaa aggggacatt tccacagtct
158641 gcccggtggt ggtcacaaag aagtcgaagg ggctgttgga cttggccatc atgtcagtta

Fig. 3 (cont.)

158701 tcaggcagtt gacggtagtt cttgttctgt aagtccatat caaccacccg ggggcgtcat
158761 agagctccgt ctggctggcg tagcggcgca ccccgttggc caggcccccg gtgggcttta
158821 ggttgacggt gatgttaact ccgtcgcggt ctacatacac gcgcgtcagc ccatcttttg
158881 tcatcttgac cgcgttgtag cactggtaga tggtatccat ctggtcagtt tcgtagctgt
158941 caacggagaa cttctcctcg tgccggttgg tcacggagtc cgcgtaccag ccattgtaga
159001 tgagaatgtt ggtcactatc ttggtgtagg agcggacctt aaacgagtag ggaataatgt
159061 tgtctttaaa caccatcaac aggccctccg tgtgattctc ccgcgtgcca aacgagggac
159121 actggatgtc cgaggagaag cggaacaggt cgccgtggct ggagagctcg cagactcgga
159181 aaggaaagct ggtttgctga cgcgtggcgg taggctgcac cgtggtggcg gggggtgcgg
159241 gctgctctgg ggtctgcgca ccgagacggc acgccagggc ggctagcagc acgaccacgc
159301 ttagcaccct acgccgagtc atctctcatt tggaggtgca ggtagagaag ggcatataga
159361 tccttaaata cccacccct gcccttatac agaagaatta gggggcggtc agagtcgtac
159421 gtgaggtaaa gcccatccgg gggcagggcc tggccggggc tgaccgcgtc cgcccggcgc
159481 aggatcaagg accgccccca ggtcttgttg tagagggaca cggttaggac ggcctcgcgc
159541 agcgcccggc acagaatttg ctggctagat gccagtgagc ccccgggtac gctgtagaag
159601 ctgttgaagg aggtctctat ccagtcgctc ggctcgatgc ctggccatat cagggaagtc
159661 aggaatgcct tctggtgggg cagcgtacct gcggcgtcac agcagcgagc cagggccacg
159721 ttgctgggtg ggggaaagag cccgctctcc tccgccaggg gccccgtgat gaaggtgtac
159781 aggctgtgcg tcagcgcgtg caggtgctcc gagctcaggg tctgggtaaa caggtgtgtt
159841 ttgatgtact tggaattctc aaaggcggca ccctcgccgg cgcgcctgtc ctcccaggga
159901 cccgagacga aggcccgtct gtagaggaag tggttgcgca tgcgggccag ctcccagtag
159961 accacgtccc cccagacgcg caggcacagg gtctcggtca gggtctcgct ctgttgcgcc
160021 aggcaggact gcagcttggc cagaccctcg gtggccacct ggcgcaggta ctgctccttg
160081 cgcttgagcg cgtccgagag ggcgccggac gggccgggct ctcgtgcccc agccggccgg
160141 ggcacctccg ggctctcccg ggacgcctcc tcctcgcctc ggcccaaccg ctgcatggct
160201 cggttgagcc gcgtgtacag ctcgttcctc ttttgcagga tggcccggta ctgggggtgc
160261 gccgtgaagg cggcggcgca gtccgccttc agcgcctcca ccgcgtcgcc cgaggagctg
160321 tagaccccgc cgcagaagag ccgctccgtg gccccgggag ccacggcgtc aaacaggtga
160381 gtcagccttg cccccgccag cgcctcctcg caggcccccc gcaccagggc caggcgacgc
160441 tcccgggcaa acagggcaga gaggcgggaa tggccgccac cctccccctg ccccgttgca
160501 ccgatagcat ggccgccaga gttccaatag aggagctccg agagctccgc cacctccggg
160561 ggcactgtcg agaagacgtt gtaggtgtcc agcgctctgg tcgccccctc tgcctccggc
160621 cgccccgggc ccgggaccgc gccctcctct gggccgcccg gcctcgcctt ctcctcagcc
160681 tccaacaggt gcccgagccc cgcctggcgg acttcattct caaacagtcc cgagaccggc
160741 tccggattca ccggcaccgc caggtggtta caggagacgt gggtcccctc tgccgtggaa
160801 gggttgccgt ggttgggcag aaccatcagc tcgcccacac agcgccagca gggcacagag
160861 gtgatgtaga ggcgcgggtc tgggatggga cttacgcccc gaaagcggcc cagcagatcc
160921 agggcccgtt ccaggctctc cagccccatg gtgtgagaca tgcaataaaa cacgctattg
160981 attctcttca ttaaaatctc tatgtcattt attaggcaca aacttacatc gactttatgc

Fig. 3 (cont.)

161041 cccccgtaaa actccacaga gtacgcgact gagggggtac ggagaggcgg gacccgggta
161101 ccctttctac caggggcgag cagcgcggca gaggcctctc tcgagttctc tagcaggtgc
161161 accagctcca gggacagggc gctgcatgca cggtcattct gccgtctcaa acggggaagg
161221 aggatggcct ccagctcggc cagcaggccg gcgttgcgca ccaccgcagc cacgtccaga
161281 ctccgggggt ccagccgggt gcacacgctc agctcaaccg ccagggcgta cacctggctg
161341 tacgccgccg ccagcagccc cgacatcgcc gccccagggg tctctagacc tcgagtccgg
161401 ggagaacggt ggccagacgg cgcttgcgtc tgccccccgga gccctgccct cctccaccca
161461 gcagcagccc ggccgaggcc tgcgacgcgg tgctgaccgg ctcggccacg ctgataaagt
161521 tgtcctgggc tgccccgggc ccacccccaca ctccctccag aaagtcccga gcggcctccg
161581 ccgtccactc tatcccgctg gaggcaatgg tcgccagggt ttctaggacg ctgtccgcca
161641 ggacggagaa gcggcccaat aagtactccg cgtcgtccct agtcagcgag gcgcatgcct
161701 cgcccatggc atccacaagg ttgcacacca catcaaacac acagtcttcc tcctgttttt
161761 gtgatataat ggcctccagg ccagccctga tgttctcaat ctcatatgtg gtcgcggctt
161821 gggtccggcg cttcacggtc aaccctaggg tgggggtggc aaagacaaac ttcttccgca
161881 tggaagagcc cccggcctgc ttgcgcagcc cagccccggg ggcctgcagc aggttcctgt
161941 ccacgccccg gcccataaag tatcccaggt tcccggcctg gaatatctgg ttgttgccgt
162001 tgaccccccgt gtacttgttg atggtcactg gcagcgtgac aaccggacgg gccttgcaga
162061 cctggctaag acagtctgtg gccgcgcaga ccaccgtggt cgcagtaagg gaggaggtgg
162121 cctccgcgta ggccgctgcc gactccaccg cccgcgtgcc cagtacgtgg gggtagtcac
162181 gggcgggcac cgactgcgtc ctcggcacca gtccctgaat caggctgatg tagaactggg
162241 tctggccgca cgccttcagg atggcgttgt tgagcctctg cttggcgtaa gtgaccaggt
162301 tgccaggcac cacatctatg acgttgctct cttcgtgggc ccgggagccc ccgtccacaa
162361 agagggccag gtcagagtac tcctccgcgc tggccccgct ggggacaggg accgagcgcc
162421 gcctggaaaa gttgtgccac aggtacaggc ttgagagctt agtgtccggg aatagggtct
162481 tgtggtaggt gttgaggaat ttcatgtagg gcccgttgat gatgtagttc tccctcctgg
162541 tagtggactt gatgaagctg ttctggaggg cggcattctc cccgtgaag accaccctgt
162601 tcttgatctt gatgttcctg gggcacagca tcagcacctt ggacatgcgc acaggcagcc
162661 gccggccgta cacccggccc tgcagggccg cgtccaggtc tggcaggtcg caggtgggct
162721 ccccatgcac caccttggcc tccttggccg tgaggacccc cttgtcgatg gccaggctcc
162781 taaagttggt gcacagcgtc tggtagtgac cctttagcca ctctgggggg ctctggccaa
162841 gcccggggtt gtcattctca tagcacatac agatgggcag ggagatgtcc tgcaggatgg
162901 tcagcagtga gcggtaaaac agctgggtga agatggggca ggcgggctgc gcaaaggggt
162961 tgcacgagta ctgcatcacg tggtagcagc tcttgaccag gtccttgtag gtgatgttgt
163021 tcttggccat gctgttcata aactggacca cttcggcgtc caccgccgca tccacgtcct
163081 tgaacatctt gacaaagtca cgcgggccat ggggctcctt ctctagcttt ccttcagcgt
163141 ctatgcccag ccgagacagc cgctccagca ggttctggtt cagctgccag taggtgtagc
163201 ggggctcgtc gtccggccgc tgcccgtcgt cctccttatc gatgaagttg agaaagttgc
163261 ccaaaaagtc cgtctcgttg taggagcccg aggcccccga gatcacatag gggtccctcc
163321 gctgcgtgga catgacgggg gggaagcggt ccctcagcct aaagaagagc gtgttcaggc

Fig. 3 (cont.)

163381 acacggccgg ggcccggccc tcgcagagcg agcacatggg actggcggcc gcccccgcca
163441 cgtagctgcc cgtctccggc accggggtca gagagctctt ctgtccctgg caaaactgca
163501 ggtagtaggc atagcgggca agaaggttgg gcgagaagga ggccgcatag accaggtgct
163561 ccacagcgta gtttcccgga ccgttggttc cggtcacgtc tggcccaccc cagcccgaga
163621 agcagggtcg gcggcagggg tcccaggtcc cctcctgcag ggtccccagg ccgtgggtca
163681 tgtagaaact gttaaagaga ctctccttgc cctgaccggt tgacttcgag acccccgaga
163741 cgtagaggac ggaattggtg gcaaagatct gcgtggacac gtgggggccc aggctggcat
163801 tatatcggtg taacgcagcc acacgggcct ctggaccctc acagtcggca aacaggggcc
163861 acgagtcgta gttgaggctg gccggggtct cgtgcgaggc ctccagcatg gcgggtgcgt
163921 agctcaccgc cagctcgcat gccgcgctgt ccacaatcat taaggctccc gagtccgggt
163981 gactgatggt tgaggctggg aactccttga ggggggccac cttggccacc ttggcctggt
164041 cctgcaggct ctgcttctcc agcagctcca ccagcttgcc cacccgtcgg acgcgcagcg
164101 cctgcgccag cccggtgtac agcgcctcgt gcatgcagcg gctgaggtcc gagttgtaaa
164161 actggcggag ctggggcacg ccctctggga acacctcctt gtcgtagagc gggaccctaa
164221 cgctcgcaga ctgccccacc gctacctcct gttttaacga tggaatggcc accaggtttc
164281 cgctgtagag tcgctccttg aaggcctcgg ttattgccac cgcccccagg taggcagagg
164341 gatctagccc ttcggggaag aagtcccccg gcttggagct ttccctcggt agggcgctgt
164401 aggcgtcgta cccaaacacc tccctggtct cgccacagag ggcctcgaga cccggcccct
164461 caaagatggg gggaaccata tggcattgt ggaacacgta gatgtccctg tgataggagg
164521 tagcgcgtag gagcccgcag ttggggtcgg gcctcctgtg cagagccttg acattgatgc
164581 tgaagcccgg ctccacggtg atgccgcaaa ggagcggcac cgtcaggcac ctgtggcccg
164641 cgtagccggt ccccagtgtg gccacctccc taagagggta ggtggccagg gggtaaaagt
164701 agatgtagcc gcacggaccc ggctggctct ggctgcccag attatcctcg ctagtctgtg
164761 caccctgcat gatgcccaag gtatcgcccc ggcctcccag tcccacatta aatgttacac
164821 tttactcatc acgcaacacc cactgtttat tcatttacaa agatttcagg aagtcagtca
164881 ggctggccag ggcccacgtc acggggaact gacgtctcag cgatcttggc atgccgccca
164941 gcctcgcaaa ccagagtctg cgatagaggg ccaggtagtg ggcgattgcc cccagcacga
165001 aggcggcgct cttgtggtca tccaggtagt ttcgcaccgc aaacaccact gtgtagcaca
165061 gcaccaccct gagccgcgac cagtagtcgt agtggtcgtt gtacactgcg cgcaggacgc
165121 tgatgatgag ccgtacgtgc gtgtctttgc ccccgatgtc ggctgtcctg caggccagct
165181 ccgcgtacag cttcctatcc ttcctcaggg aggccttgat gagccggcag aggaccaggg
165241 ctggcaaagg caggtctttc tcatcccggg tgaacaccgc gtacatggcc ctgaacatga
165301 ggtagctgga ctcagccacc ttgtcgtccg gcggcgaggg cgcgacccac gcctcgaccg
165361 gggtcctcac aaacacagaa tctgtagact tggctggcct catggtctcg tcaggccagc
165421 tcacgggctt caggcttata tgataaaatg ggcgtggcag aatagtataa gacgcgaggc
165481 ctgggtgagg agagtccaga gcaatggcca ggttcatcgc tcagctcctc ctgttggcct
165541 cctgtgtggc cgccggccag gctgtcaccg ctttcttggg tgagcgagtc accctgacct
165601 cctactggag gagggtgagc ctcggtccag agattgaggt cagctggttt aaactgggcc
165661 caggagagga gcaggtgctt attgggcgca tgcaccacga tgtcatcttt atagagtggc

Fig. 3 (cont.)

165721 ctttcagggg cttctttgat atccacagaa gtgccaacac cttcttttta gtagtcaccg
165781 ctgccaacat ctcccatgac ggcaactacc tgtgccgcat gaaactgggc gagaccgagg
165841 tcaccaagca ggaacacctg agcgtggtga agcctctaac gctgtctgtc cactccgaaa
165901 ggtctcagtt cccagacttc tctgtcctta ctgtgacatg caccgtgaat gcatttcccc
165961 atccccacgt ccagtggctc atgcccgagg gcgtggagcc cgcaccaact gcggcaaatg
166021 gcggtgttat gaaggaaaag gatgggagcc tctctgttgc tgttgacctg tcacttccca
166081 agccctggca cctgccagtg acctgcgttg ggaaaaatga caaggaggaa gcccacgggg
166141 tttatgtttc tggatacttg tcgcaataaa cgcacttgcc tatttcacct tgttttagtg
166201 tggcattggg ggggtggcat tgcgggtgga tagcctcgcg actcgtggga aaatgggcgg
166261 aagggcaccg tgggaaaata gttccaggtg acagcagcag tgtgtgaaga ttgtcacagc
166321 tgctggtttg gagaaaacgg gggtgggcgg tgatcaggga gaacaattcc ccggggacac
166381 ctgcacgaga cccctgggct ctcaggaact ccgcccaggt cttgccaatt ggggtgatcc
166441 tgtagcgccg cggtttcagc atcacaggtt attttgcctg aagcttgctg gggcgtaaat
166501 ccctctcgcc ttgtttctca gagagcattt caggccggtt ttgcagtcgc tgctgcagct
166561 atggggtccc tagaaatggt gccaatgggc gcgggtcccc ctagccccgg cggggatccg
166621 gatgggtacg atggcggaaa caactcccaa tatccatctg cttctggctc ttctgggaac
166681 acccccaccc caccgaacga tgaggaacgt gaatctaatg aagagccccc accgccttat
166741 gaggacccat attggggcaa tggcgaccgt cactcggact atcaaccact aggaacccaa
166801 gatcaaagtc tgtacttggg attgcaacac gacgggaatg acgggctccc tccccctccc
166861 tactctccac gggatgactc atctcaacac atatacgaag aagcgggcag aggaaggtaa
166921 gagtgccatc tatctgtact tttatttatt gcatcacaag tcacatcaat aataagggcg
166981 ccatctagcg ggagatgtta tccacaccat cccaattcac atctcaggga caacaggtca
167041 aagttctttg ttgacacccc cagcgctggc tccagggggt ggaagcgttg gatgcagtcc
167101 tccgcatcgg ggcggacgcc tcctcccaac gcgtttctgc ggatcagtcg ctggctggtg
167161 ggcatcggag tcggtgggcg gtcctccacg gggacacgct ccttcttggc cttgttcttt
167221 gacctttgg acattcttct gaaggaacgg cggagagtag cgtagaatcc agccagtggt
167281 ctacccggtc gcatggtggc ttcttagatg aggagcaggc ataaaagtcc aaacaggaca
167341 cagagtacca ccaggagtag tcttagtctg ctgacgtctg ggtcctcggg gcaggggtgg
167401 ctaggcctgg tctccgtaga agagccgggc aggccgcagg cagaggactg ctgctctagc
167461 aaagcacgct ccaggacgtg taccatctcg agagtgaggc acagctgttt tcgtggactt
167521 ttatacagta aggacaagga aagaaggcca gaggaatgtg gaaagatgag cgaggacagg
167581 tgtggaggtt ttgggctagc tcttagtttc tgggtgtgag agagggatta aagtgcttat
167641 gcgcaaagaa tgtgtcaaca acaggtgttc ctgcctctgc tggcatgagt taggtgtggc
167701 ttgggctgaa tccaaatgtg tattggcaca agatggaaag caaagttgct ggagttactg
167761 ggtgggagac agggatgtat gtggtccccc gctggtatgc cagtaccctg tggaagtaag
167821 gggcctcatc tgcctggtag ttgtgttgtg cagaggtctg atgtgtgtag gaggggtggg
167881 ttcaacgcag gggcgttggt ggcggagtct ggcaacgccc gggtccttgc tacctgtgtg
167941 gtgtgttaag ggctgggtaa aggtgtctgc caattctcgc atgtcctcct ttccccttgt
168001 tttgaaatag aatatgaatg tggcttttca gcctagacag acagtgtggc taagggagtg

Fig. 3 (cont.)

168061 tgtgccagtt aaggtgatta gctaaggcat tcccagtaaa tggagggaga gtcagtcagg
168121 caagcctatg acatggtaat gcctagaagt aaagaaaggt tagtcatagt agcttagctg
168181 aactgggccg tgggggtcgt catcatctcc accggaacca gaagaaccca aaagcagcgt
168241 aggaaggtgt ggatcaccgc cgccatggcc ggaatcatga ctatgaccgc cgcctccgtc
168301 tgtcatcaaa ggcgggccct ggtcacctcc tttgtttca acctcttccg tcaattgtgg
168361 agggcctcca tcatttccag cagagtcgct agggctatga ggcagcgggt catgtgggcc
168421 attgtcatca gtgttgtcag ggtcctgtgg gccattgtca tcagtgttgt cagggtcctg
168481 aggcagcggg tcatgtgggc cattgtcatc agtgttgtca gggtcctgtg ggccattgtc
168541 atcagtgttg tcagggtcct gtgggccatt gtcaggacca cctccaggtg cgcctaggtt
168601 ttgagagcag agtgggggtc cgtcgccggc tccactcacg agcaggtggt gtctgccctc
168661 gttggagtta gagtcagatt catggccaga atcatcggta gcttgttgag ggtgcgggag
168721 ggagtcatcg tggtggtgtt catcactgtg tcgttgtcca tggtaataca tccagattaa
168781 aatcgccaga aacaggagga gccaaaggag atcaaccaat agagtccacc agttttgttg
168841 tagatagaga gcaataatga gcaggatgag gtctaggaag aaggctagga agaaggccaa
168901 aagctgccag atggtggcac caagtcgcca gagcatctcc aataagtaga tccagatacc
168961 taagactgcg ttgaaaaaag agtgttaggg ttggaaaagt gggggtgtgg taaataattc
169021 ctagggaatg ttagatctta ccaagtaagc acccgaagat gaacagcaca attccaagga
169081 acaatgcctg tccgtgcaaa ttccagagag cgatgagcag gagggtgact ggggaaagag
169141 gagaaagtgc gttagagaag gaagagtaag ggaaaggggg tgtggggcaa agggtgtaat
169201 acttactcat cagtaggagt atacaaaggg ctccaagtgg acagagaagg tctcttctga
169261 agataaagat gatcaaaatt ataattataa gcatgagagc aaaggaatag aggacaagga
169321 gggctcctcc agtccagtca ctcataacga tgtacagcca aaacagtagc gccaagagga
169381 ggagaaggag agcaaggcct agggaagagg agaggggggg tcctcgaggg ggccgtcgcg
169441 ggcccggtgg gcccctctca aggtcgtgtt ccatcctcag ggcagtgtgt caggagcaag
169501 gcagttgagg aaagaagggg gcagagcagt gtgagaggct tatgtagggc ggctacgtca
169561 gagtaacgcg tgtttcttgg gatgtaggcc cggggggatt tgcggggtct gccggaggca
169621 gtacgggtac agatttcccg aaagcggcgg tgtgtgtgtg catgtaagcg tagaaagggg
169681 aagtagaaag cgtgtgtttg tgttagaaaa gcgggtcccc ggggggcaag ctgtgggaat
169741 gcggtggcca agtgcaacag gaaatggaaa ggcagtgcgg caatcagaag ggggagtgcg
169801 tagtgttgtg ggaagcggca gtgtaatctg cacaaagagg cgcggggcgc gcaacgttgg
169861 gaggtcgttg gcggcaggcg ggaggccgtg ctttaggggg gttcaggtga ggcaaggctg
169921 tggggtaacc gtaggggagg cgggtgaggc ggctaagagg gctaagggtc ggcgggtgac
169981 gaagcagcag acggcggata tgggaatttc agaatgaggt ggcggattca ggcgaaaagg
170041 gtgtgggctg tgcgagtgtc atgaggcagg cgcggaaagt cgctgcggct tgctggggca
170101 tggggggccg cgcattcctg gaaaaagtgg agggggcgtg gccttccccc gcggcccccc
170161 agcccccccg cacagagcgg cgctacggcg ggcgggcggc ggggggtcgg ggtccgcggg
170221 ctccgggggc tgcgggcggt ggatggcggc ggacgttccg gggatcgggg gggtcggggg
170281 gcgccgcgcg ggcgcagcca tgcgtgaccg tgatgagggg gcagggtcgc agggggtgtg
170341 tctggtgggg gcgggagcgg ggggcggcgc gggagcctgc acgccgttgg agggtagaat

Fig. 3 (cont.)

170401 gacaggggggc ggggacagag aggcggtcgc gcccccggcc gcgccagcca agccccccaag
170461 gggggcgggg agcgggcaat ggagcgtgac gaagggcccc agggctgacc ccggcaaacg
170521 tgacccgggg ctccggggtg acccagccaa gcgtgaccaa ggggcccgtg ggtgacacag
170581 gcaaccctga caaaggcccc ccaggaaaga cccccggggg gcatcggggg gtggggcatg
170641 gggggccgcg cattcctgga aaaagtggag ggggcgtggc cttcccccgc ggcccccccag
170701 cccccccgca cagagcggcg ctacggcggg cgggcggcgg ggggtcgggg tccgcgggct
170761 ccgggggctg cgggcggtgg atggcggcgg acgttccggg gatcgggggg gtcgggggggc
170821 gccgcgcggg cgcagccatg cgtgaccgtg atgagggggc agggtcgcag gggggtgtgtc
170881 tggtgggggc gggagcgggg ggcggcgcgg gagcctgcac gccgttggag ggtagaatga
170941 caggggggcgg ggacagagag gcggtcgcgc cccccggccgc gccagccaag cccccaaggg
171001 gggcggggag cgggcaatgg agcgtgacga agggccccag ggctgacccc ggcaaacgtg
171061 acccggggct ccggggtgac ccagccaagc gtgaccaagg ggcccgtggg tgacacaggc
171121 aaccctgaca aaggcccccc aggaaagacc cccgtggggc atggggggcc gcgcattcct
171181 ggaaaaagtg gaggggggcgt ggccttcccc cgcggccccc cagccccccc gcacagagcg
171241 gcgctacggc gggcgggcgg cgggggggtcg gggtccgcgg gctccggggg ctgcgggcgg
171301 tggatggcgg cggacgttcc ggggatcggg ggggtcgggg ggcgccgcgc gggcgcagcc
171361 atgcgtgacc gtgatgaggg ggcagggtcg cagggggtgt gtctggtggg ggcgggagcg
171421 gggggcggcg cgggagcctg cacgccgttg gagggtagaa tgacaggggg cggggacaga
171481 gaggcggtcg cgcccccggc cgcgccagcc aagcccccaa ggggggcggg gagcgggcaa
171541 tggagcgtga cgaagggccc cagggctgac cccggcaaac gtgacccggg gctccggggt
171601 gacccagcca agcgtgacca aggggcccgt gggtgacaca ggcaaccctg acaaaggccc
171661 cccaggaaag acccccgggg ggcatcgggg ggtggggcat ggggggccgc gcattcctgg
171721 aaaaagtgga gggggcgtgg ccttcccccg cggcccccca gcccccccgc acagagcggc
171781 gctacggcgg gcgggcggcg gggggtcggg gtccgcgggc tccgggggct gcgggcggtg
171841 gatggcggcg gacgttccgg ggatcggggg ggtcgggggg cgccgcgcgg gcgcagccat
171901 gcgtgaccgt gatgaggggg cagggtcgca gggggtgtgt ctggtggggg cgggagcggg
171961 gggcggcgcg ggagcctgca cgccgttgga gggtagaatg acaggggggcg gggacagaga
172021 ggcggtcgcg ccccccggccg cgccagccaa gcccccaagg ggggcgggga gcgggcaatg
172081 gagcgtgacg aagggcccca gggctgaccc cggcaaacgt gacccggggc tccggggtga
172141 cccagccaag cgtgaccaag gggcccgtgg gtgacacagg caaccctgac aaaggccccc
172201 caggaaagac cccccgggggg catcgggggg ggtgttggcg ggggcatggg ggggtcggat
172261 ttcgccctta ttgccctgtt t

Fig. 3 (cont.)

Human herpesvirus 8, genome

Accession: NC_003409

1 tactaatttt caaaggcggg gttctgccag gcatagtctt tttttctggc ggcccttgtg
61 taaacctgtc tttcagacct tgttggacat cctgtacaat caagatgttc ctgtatgttg
121 tctgcagtct ggcggtttgc tttcgaggac tattaagcct ttctctgcta tcgtctccaa
181 atttgtgccc tggagtgatt tcaacgcctt acacgttgac ctgtctgtct aatgcatcct
241 tgccaatatc ctggtattgc aacaatactc ggcttttgcg actgacggag agaagagtca
301 ttcttgacac cattgcctgc aattttactt gtgtggaaca atctgggcat cgacagagca
361 tttggattac atggcgtgca caacctgtct tacaaacctt gtgtgcacag ccatcaaaca
421 cagtcacttg tggtcagcat gttactttgt attgttctac ctctggaaat aatgttaccg
481 tttggcatct accaaacgga cgaaatgaaa ccgtgtcaca aactaaatac tataatttta
541 cgctgatgag ccaaactgag gggtgttata cttgttctaa cgggctgtcg tctcgcctgt
601 caaatcgtat atgtttttgg gcgcgttgtg ccaatataac tccagaaact catactgtat
661 ctgtcagcag tactacaggc tttagaacat tgagtactaa tagcttagtg aagataatcc
721 atgcaaccac acgtgatgta gttgtagtga aagaagcaaa atctacacat tttcatattg
781 aagtgcattt tcttgtattt atgacactcg tagctctgat aggaaccatg tgtggtatct
841 taggaactat tatctttgcc cattgtcaaa aacaacgtga ctcaaacaaa acagtgccac
901 aacaattgca ggattattat tccctacacg atttgtgcac ggaagactat acgcaaccag
961 tggattggta ctgacattca ggtaagataa tctaaatatt ctctataaca taattgtaat
1021 gtgttttatg tttatagcta caaatgtttt atgcaaaata cattttatga ggtcggatac
1081 ttattaaaag cattgtctta agtacattaa aaggacattg tataaccgtg ctacttacag
1141 catggccttt ttaagacaaa cactgtggat tttatggaca tttaccatgg ttattggcca
1201 ggacaatgaa aagtgttccc aaaaaacctt aattggatat agacttaaaa tgtctcgtga
1261 cggtgacatt gcagttggag aaacagtgga attacgttgt agatctggat acactactta
1321 tgcccgcaat ataacagcaa catgtttaca aggtgggacg tggtctgaac caacggcaac
1381 atgtaacaaa aagtcctgtc caaacccagg tgaaatacaa aatggaaagg ttatatttca
1441 tggtggacaa gatgccttaa aatatggggc aaacatttca tatgtttgta atgaaggata
1501 ttttttggtt ggtcgagaat acgtgcgata ttgtatgatt ggagcatctg gccaaatggc
1561 gtggtcatct tctcctcctt tttgtgaaaa agaaaagtgt cacagaccga aaatcaaaaa
1621 tggagatttt aagcctgata aagattatta tgagtataat gatgcagttc attttgaatg
1681 taatgaagga tatactctag ttggaccaca ttccattgca tgtgcagtta ataacacgtg
1741 gacatctaac atgccaacct gtgaactcgc aggctgtaaa tttccatcgg tgactcatgg
1801 ttatccaatc caaggttttt ctcttactta taaacataag caaagtgtta cttttgcatg
1861 caatgatgga tttgttctca gaggatcccc cacaattacg tgtaacgtta ctgaatggga
1921 cccaccactt cctaagtgtg ttttggaaga tatagatgat ccaaacaatt caaatcctgg
1981 acgtttgcat ccaacaccca atgaaaaacc aaatggtaat gtctttcaac gctcaaacta
2041 tacagaacct ccaacaaagc ctgaagacac ccatacagca gctacttgtg ataccaactg
2101 tgaacagcca cctaaaatcc tgccaacatc cgaaggtttt aatgagacta ccacatctaa

Fig. 3 (cont.)

2161 tacaattaca aaacaattag aggatgagaa aactatatcc cagccaaata cacatattac
2221 atctgcctta acatccatga aagcgaaagg taactttacc aacaagacca ataactctac
2281 tgatctacat atagcgtcta cacccacttc ccaagatgat gctacgcctt caatacctag
2341 tgtacagaca cccaattata atactaacgc accgacacgt acactaacgt ctctccatat
2401 tgaagaaggc ccatccaatt ctactacttc agaaaaggcc acttcctcta ctctctcaca
2461 caactcacac aaaaatgaca ccggaggcat atacacaaca ttaaacaaaa caacacagtt
2521 gccatccact aataaaccta caaacagtca agccaagagt tccactaagc cacgcgttga
2581 gacacacaat aaaacaacca gtaatcctgc catttcttta acagattctg cagatgtgcc
2641 tcagagaccg cgagaaccaa cactccctcc cattttcagg ccaccggcgt ctaaaaatcg
2701 ctatctggaa aagcaactag ttattggact actaaccgct gtcgccctaa cgtgtggact
2761 gattacctta tttcactatc tgttctttcg ttagcctaga acttgctcca gtgttagaca
2821 gggctatgat tgcttctcca cgctgtccac cttaacactt cccaataaca aatccggtat
2881 gcagcagcgt gacactacta atgtaaccta aaaaatgtgc atgtggtatg tattgtacta
2941 aagataccga ccaatacaag acaactaata ttaaccatag tgtgcgtttc tttgtataaa
3001 atacgcgtgt gggaaagcga cagaaggggg cggcgtttcc atatgaggcc aagtgcattg
3061 gctattttag ggcggtgac cacgcactat agtgcgcggt gtggcagaaa attcacaccg
3121 tatataaaca aggaaagggg actctgcgcg cttaagcgcc aagccattat acacacgggt
3181 tttttgttgt cttggccaat cgtgtctcca tggcgctaaa gggaccacaa accctcgagg
3241 aaaatattgg gtctgcggcc cccactggtc cctgcgggta cctctatgcc tatctgacac
3301 acaacttccc catagggga gcctccctgc tgggcaatgg ctacccggag gcaaaagtat
3361 tttcactacc tcttttgcac gggctcacag tggaatccga tttcccctta aacgtaaagg
3421 cggtgcacaa gaaaatcgat gcaaccacag cttctgtgaa attaacttca taccacaggg
3481 aggccatcgt ctttcataat actcacttat ttcagccaat ctttcaagga aagggactgg
3541 aaaagttatg tcgagagagc cgagagctgt ttggattttc aacgtttgtt gagcaacaac
3601 acaaagggac gctctggagc ccagaggcat gccctcagct accctgcgcg aatgagattt
3661 ttatggcggt catagttaca gagggattca aggagagact gtacggcggc aaactggtgc
3721 ccgtgccctc tcagacaacg cccgtacaca ttggggaaca ccaggcgttc aagataccct
3781 tgtatgacga ggatctgttt ggtccaagtc gcgcccaaga actatgtagg ttttacaacc
3841 ccgatatcag tagataccta catgactcca tattcactgg aatagcacag gctctaaggg
3901 taaaggacgt tagcacggtc atccaagcct cagaaaggca atttgtgcac gaccaataca
3961 agataccaaa gctggtccaa gccaaggact tcccccagtg tgcttccagg ggaaccgacg
4021 ggtctaccct aatggtgata gacagtctgg tggctgaact tggtatgagt tatggtctgt
4081 cctttattga gggaccccag gatagctgcg aggttctaaa ttatgacacg tggcccatct
4141 ttgaaaactg cgagacgcca gatgcccgcc ttcgtgcact agaagtttgg cacgcagagc
4201 aggccttgca tattggcgcc cagctgtttg cggccaactc tgtgctctac ctgaccagag
4261 tggcaaagct gcctcagaag aatcagagag gagacgccaa catgtacaac tcattctacc
4321 tacagcatgg cctgggatac ctctcagagg caacagtaaa ggaaaatgga gcctctgcct
4381 tcaagggcgt gccagtgtct gcactggatg ggtcatctta caccctccag cacctggcct
4441 acgcgtcctc tttctcccca catctcctgg caaggatgtg ttactatctg cagttcttgc

Fig. 3 (cont.)

4501 cccaccataa aaacaccaac agtcagtcat acaatgtggt ggactacgtg ggcaccgcgg
4561 cacctagtca aatgtgtgac ctgtgtcagg ggcaatgtcc agctgtatgc atcaacacgc
4621 tgttttacag gatgaaggac aggttcccac ctgttctgtc aaacgttaag agagacccat
4681 atgtgatcac gggcacagcg ggaacgtaca atgacctaga gattctcgga aactttgcca
4741 ccttcaggga gagagaggag gaggggaatc ctgtggaaga tgctccaaag tatacatatt
4801 ggcaactatg ccagaatata accgagaagc tagcgtccat gggcatctcg gagggcggcg
4861 atgccctaag aaccctcatt gtggacatcc ccagcttcgt caaagtgttc aaggggatag
4921 acagcacggt agaggcagag ctcctaaagt ttattaactg catgatcaaa aacaattaca
4981 acttcagaga gaacatcaaa tccgtccatc acatccttca gtttgcatgc aacgtatact
5041 ggcaggcgcc gtgcccggtt tttctgaccc tttactacaa gtcactgctg acggtcatac
5101 aggacatatg tctgacgtca tgtatgatgt acgagcagga caacccggcc gtgggaattg
5161 taccatccga gtggcttaaa atgcactttc agacaatgtg gaccaacttc aagggtgcct
5221 gcttcgacaa aggagcaatc acgggcgggg aactaaaaat agtccaccag tccatgttct
5281 gtgacctctt tgacaccgac gctgccatag gagggatgtt tgcacccgct cggatgcagg
5341 tcaggatagc cagagcaatg ctcatggttc caaaaaccat aaaaataaaa aacaggatca
5401 tcttttccaa ctccaccgga gcagagtcga tccaggcagg ttttatgaag ccggccagcc
5461 aaagggattc atacatcgtc ggaggaccct acatgaaatt cctaaacgcc ctgcacaaaa
5521 cactttttcc ttccacaaaa acttctgccc tgtacttgtg gcataagatt ggccagacca
5581 caaaaaatcc catactacca ggtgtctcgg gggaacacct aacggagtta tgtaattatg
5641 taaaggcaag tagccaggct ttcgaagaga taaatgtttt ggaccttgtg ccagacaccc
5701 tgacatcata tgcgaaaata aaactaaaca gttccattct ccgggcttgc ggacagacac
5761 agttttatgc aactactctc tcttgccttt cgccagtgac tcagctggtt ccggccgagg
5821 agtacccccca cgtactgggg ccagtggggt tgtcatctcc agatgaatac agggcaaaag
5881 tcgccggcag gtctgtaacc attgtacagt caacactgaa gcaagctgtt tccaccaacg
5941 gacgactccg gcctatcatt accgtgccac tggtggtcaa caaatataca gggagcaacg
6001 ggaacacaaa cgtctttcac tgtgcaaacc tgggatactt ctcggggaga ggggtggaca
6061 gaaatctcag gccagaaagc gtccccttta aaaagaataa tgtcagctct atgctaagaa
6121 aacgccacgt gattatgacc cccctggtag acaggctggt aaagagaata gttggcatca
6181 actctgggga attcgaggca gaagcggtta agagaagtgt gcagaatgtc ctggaagaca
6241 gagataaccc aaacctgccg aagacagttg tattagagtt ggttaagcca cctcggtgga
6301 gctcctgtgc aagtctcaca gaggaggacg tgatttacta cctgggccct tatgccgtac
6361 ttggggacga ggtcctgtca ttactgagca cagtgggcca ggcgggggtg ccatggacgg
6421 ccgagggtgt ggcctcggtc atccaggaca taatagatga ttgcgagtta cagtttgtgg
6481 gcccagaaga gccttgcctt atccaaggac agtcggtagt ggaggagctt tttccgtccc
6541 cgggcgtccc aagcctgaca gtgggtaaaa aacgaaaaat cgcatccctg ctctctgacc
6601 tggatttgta gttgtgtacc cgtaacgatg gcaaaggaac tggcggcggt ctatgccgat
6661 gtgtcagccc tagccatgga cctctgtctt cttagttacg cagacccggc aacactggac
6721 actaaaagtc tggccctcac tacagggaag tttcagagcc ttcacggcac actactcccc
6781 ctcctcagac gacaaaacgc acacgaatgc tcaggtctgt cactagaatt ggagcacttt

Fig. 3 (cont.)

6841 tggaaaacgt ggctgatgct ctggccacgt tgggagtgtg cactagcaga aaactgtctc
6901 cagaagagca tttttccctc ctgcatttgg acacaacatg caacaagcaa ccggagcgtt
6961 aggtttaatt tttacggaaa ttgggccttg gagttaaagc tgtcactaat aaacgacgtt
7021 gaaattttct ttaaacgtct tagtagcgtt ttttattgta taggatcggg cagtgctctg
7081 gagggtttag gggaggtatt gcgtttcgtt gggaagctga ggggtatctc acccgtacct
7141 gggccggacc tatatgtctc aaatctgccc tgcctagaat gccttcagga agtgtgtctg
7201 actcccaacc agggcaccag tctgcaggcc atgctcccag acacggcctg cagtcacata
7261 tgtacccccg catgcggtga gcctgtccgg ggcctctttg agaacgagct aaaacagctc
7321 gggcttcaaa cccctgagtc catacctact accccctgtc agtcccgggt aaggcaagat
7381 gatgaaatca gacagagctc tctaatggcg gtaggagatc accacatttt cggagaggtg
7441 accagatctg tcctggaaat ctcaaacctg atctattgga gctctggcca ctcggatgcc
7501 acctgcgacg gagacagaga ctgctctcac ctggcctcgc tgtttactca cgaggctgac
7561 atgcataaaa ggcgcgtcga cctggccgga tgcttgggcg aacgcggcac gcccaaacac
7621 ttttttgact gctttcgccc agactcccta gaaacccttt tctgtggtgg tctttttagc
7681 tccgtggagg acaccataga aagtctccaa aaggactgct cttctgcctt ctaccaacag
7741 gtaaactaca ctactgcact gcaaaaacag aacgagtttt acgtccgact cagcaaactg
7801 ctggcagctg gtcagctaaa tttgggcaaa tgttccactg aaagttgcca atccgaggcc
7861 cgtaggcagc tggtaggtgg gggcaaacca gaggaagtgc tgagggatgc aaaacaccgg
7921 caagaactat accttcagaa agtggcacgc gacggtttta aaaaactctc tgattgtata
7981 agacaccagg gccacatcct gtctcagacc ctgggtctaa gactgtgggg gtctgtcatc
8041 tacaacgagg catctgccct acaaaaccac tttttacaca gagcacagtt catatccctc
8101 ccctggcagg acctgacggt cgactgtcca acgcggtttg aaaattctaa atatatcaaa
8161 aattctctgt actgccagcg tctggggcgg gaacacgtag agatcctgac actggagttc
8221 tacaaactta tcacgggccc gctgtcaaag cgacatactt tatttcccag tcctccaaat
8281 gtgacgctgg ctcagtgctt cgaggctgcg ggcatgcttc cccatcaaaa gatgatggta
8341 tcagagatga tctggcccag catagagccg aaggactgga tagagcccaa cttcaaccag
8401 ttctatagct ttgagaatca agacataaac catctgcaaa agagagcttg ggaatatatc
8461 agagagctgg tattatcggt ttctctgtac aacagaactt gggagaggga gctaaaaata
8521 cttctcacgc ctcagggctc accggggttt gaggaaccga aacccgcagg actcacaacg
8581 gggctgtacc taacatttga gacatctgcg cccttggtgt tggtggataa aaaatatggc
8641 tggatattta aagacctgta cgcccttctg taccaccacc tgcaactgag caaccacaat
8701 gactcccagg tctagattgg ccaccctggg gactgtcatc ctgttggtct gcttttgcgc
8761 aggcgcggcg cactcgaggg gtgacacctt tcagacgtcc agttccccca cacccccagg
8821 atcttcctct aaggccccca ccaaacctgg tgaggaagca tctggtccta agagtgtgga
8881 cttttaccag ttcagagtgt gtagtgcatc gatcaccggg gagctttttc ggttcaacct
8941 ggagcagacg tgcccagaca ccaaagacaa gtaccaccaa gaaggaattt tactggtgta
9001 caaaaaaaac atagtgcctc atatctttaa ggtgcggcgc tataggaaaa ttgccacctc
9061 tgtcacggtc tacagggggct tgacagagtc cgccatcacc aacaagtatg aactcccgag
9121 acccgtgcca ctctatgaga taagccacat ggacagcacc tatcagtgct ttagttccat

Fig. 3 (cont.)

9181 gaaggtaaat gtcaacgggg tagaaaacac atttactgac agagacgatg ttaacaccac
9241 agtattcctc caaccagtag aggggcttac ggataacatt caaaggtact ttagccagcc
9301 ggtcatctac gcggaacccg gctggtttcc cggcatatac agagttagga ccactgtcaa
9361 ttgcgagata gtggacatga tagccaggtc tgctgaacca tacaattact ttgtcacgtc
9421 actgggtgac acggtggaag tctccccttt ttgctataac gaatcctcat gcagcacaac
9481 ccccagcaac aaaaatggcc ttagcgtcca agtagttctc aaccacactg tggtcacgta
9541 ctctgacaga ggaaccagtc ccactcccca aaacaggatc tttgtggaaa cgggagcgta
9601 cacgctttcg tgggcctccg agagcaagac cacggccgtg tgtccgctgg cactgtggaa
9661 aaccttcccg cgctccatcc agactaccca cgaggacagc ttccactttg tggccaacga
9721 gatcacggcc accttcacgg ctcctctaac gccagtggcc aactttaccg acacgtactc
9781 ttgtctgacc tcggatatca acaccacgct aaacgccagc aaggccaaac tggcgagcac
9841 tcacgtccct aacgggacgg tccagtactt ccacacaaca ggcggactct atttggtctg
9901 gcagcccatg tccgcgatta acctgactca cgctcagggc gacagcggga accccacgtc
9961 atcgccgccc ccctccgcat cccccatgac cacctctgcc agccgcagaa agagacggtc
10021 agccagtacc gctgctgccg gcggcggggg gtccacggac aacctgtctt acacgcagct
10081 gcagtttgcc tacgacaaac tgcgggatgg cattaatcag gtgttagaag aactctccag
10141 ggcatggtgt cgcgagcagg tcagggacaa cctaatgtgg tacgagctca gtaaaatcaa
10201 ccccaccagc gttatgacag ccatctacgg tcgacctgta tccgccaagt tcgtaggaga
10261 cgccatttcc gtgaccgagt gcattaacgt ggaccagagc tccgtaaaca tccacaagag
10321 cctcagaacc aatagtaagg acgtgtgtta cgcgcgcccc ctggtgacgt ttaagttttt
10381 gaacagttcc aacctattca ccggccagct gggcgcgcgc aatgagataa tactgaccaa
10441 caaccaggtg gaaacctgca aagacacctg cgaacactac ttcatcaccc gcaacgagac
10501 tctggtgtat aaggactacg cgtacctgcg cactataaac accactgaca tatccaccct
10561 gaacactttt atcgccctga atctatcctt tattcaaaac atagacttca aggccatcga
10621 gctgtacagc agtgcagaga aacgactcgc gagtagcgtg tttgacctgg agacgatgtt
10681 cagggagtac aactactaca cacatcgtct cgcgggtttg cgcgaggatc tggacaacac
10741 catagatatg aacaaggagc gcttcgtaag ggacttgtcg gagatagtgg cggacctggg
10801 tggcatcgga aaaacggtgg tgaacgtggc cagcagcgtg gtcactctat gtggctcatt
10861 ggttaccgga ttcataaatt ttattaaaca ccccctaggt ggcatgctga tgatcattat
10921 cgttatagca atcatcctga tcatttttat gctcagtcgc cgcaccaata ccatagccca
10981 ggcgccggtg aagatgatct accccgacgt agatcgcagg gcacctccta gcggcggagc
11041 cccaacacgg gaggaaatca aaaacatcct gctgggaatg caccagctac aacaagagga
11101 gaggcagaag gcggatgatc tgaaaaaaag tacaccctcg gtgtttcagc gtaccgcaaa
11161 cggccttcgt cagcgtctga gaggatataa acctctgact caatcgctag acatcagtcc
11221 ggaaacgggg gagtgacagt ggattcgagg ttattgtttg atgtaaattt aggaaacacg
11281 gcccgcctct gaagcaccac atacagactg cagttatcaa ccctactcgt tgcacacaga
11341 cacaaattac cgtccgcaga tcatggattt tttcaatcca tttatcgacc caactcgcgg
11401 aggcccgaga aacactgtga ggcaacccac gccgtcacag tcgccaactg tcccctcgga
11461 gacaagagta tgcaggctta taccggcctg tttccaaacc ccggggcgac ccggcgtggt

Fig. 3 (cont.)

11521 tgccgtggac accacatttc cacccaccta cttccagggc cccaagcggg gagaagtatt
11581 cgcgggagag actgggtcta tctggaaaac aaggcgcgga caggcacgca atgctcctat
11641 gtcgcacctc atattccacg tatacgacat cgtggagacc acctacacgg ccgaccgctg
11701 cgaggacgtg ccatttagct tccagactga tatcattccc agcggcaccg tcctcaagct
11761 gctcggcaga acactagatg gcgccagtgt ctgcgtgaac gtttcaggc agcgctgcta
11821 cttctacaca ctagcacccc agggggtaaa cctgacccac gtcctccagc aggccctcca
11881 ggctggcttc ggtcgcgcat cctgcggctt ctccaccgag ccggtcagaa aaaaaatctt
11941 gcgcgcgtac gacacacaac aatatgctgt gcaaaaaata accctgtcat ccagtccgat
12001 gatgcgaacg cttagcgacc gcctaacaac ctgtgggtgc gaggtgtttg agtccaatgt
12061 ggacgccatt aggcgcttcg tgctggacca cgggttctcg acattcgggt ggtacgagtg
12121 cagcaatccg gccccccgca cccaggccag agactcttgg acggaactgg agtttgactg
12181 cagctgggag gacctaaagt ttatcccgga gaggacggag tggcccccat actcaatcct
12241 atcctttgat atagaatgta tgggcgagaa gggttttccc aacgcgactc aagacgagga
12301 catgattata caaatctcgt gtgttttaca cacagtcggc aacgataaac cgtacacccg
12361 catgctactg ggcctgggga catgcgaccc ccttcctggg gtggaggtct ttgagtttcc
12421 ttcggagtac gacatgctgg ccgccttcct cagcatgctc cgcgattaca atgtggagtt
12481 tataacgggg tacaacatag caaactttga ccttccatac atcatagccc gggcaactca
12541 ggtgtacgac ttcaagctgc aggacttcac caaaataaaa actgggtccg tgtttgaggt
12601 ccaccaaccc agaggcggtt ccgatggggg caacttcatg aggtcccagt caaaggtcaa
12661 aatatcgggg atcgtcccca tagacatgta ccaggtttgc agggaaaagc tgagtctgtc
12721 agactacaag ctggacacag tggctaagca atgcctcggt cgacaaaaag atgacatctc
12781 atacaaggac ataccccgc ttttaaatc tgggcctgat ggtcgcgcaa aggtgggaaa
12841 ctactgtgtt attgactcgg tcctggttat ggatcttctg ctacggtttc agacccatgt
12901 tgagatctcg gaaatagcca agctggccaa gatccccacc cgtagggtac tgacggacgg
12961 ccaacagatc agggtatttt cctgcctctt ggaggctgct gccacggaag gttacattct
13021 ccccgtccca aaaggagacg cggttagcgg gtatcagggg gccactgtaa taagcccctc
13081 tccgggattc tatgacgacc ccgtactcgt ggtggatttt gccagcttgt accccagtat
13141 catccaagcg cacaacttgt gctactccac actgataccc ggcgattcgc tccacctgca
13201 cccacacctc tccccggacg actacgaaac ctttgtcctc agcggaggtc cggtccactt
13261 tgtaaaaaaa cacaaaaggg agtcccttct tgccaagctt ctgacggtat ggctcgcgaa
13321 gagaaaagaa ataagaaaga ccctggcatc atgcacggac cccgcactga aaactattct
13381 agacaaacaa caactggcca tcaaggttac ctgcaacgcc gtttacggct tcacgggcgt
13441 tgcctctggc atactgcctt gcctaaacat agcggagacc gtgacactac aagggcgaaa
13501 gatgctggag agatctcagg cctttgtaga ggccatctcg ccggaacgcc tagcgggtct
13561 cctgcggagg ccaatagacg tctcacccga cgcccgattc aaggtcatat acggcgacac
13621 tgactctctt ttcatatgct gcatgggttt caacatggac agcgtgtcag acttcgcgga
13681 ggagctagcg tcaatcacca ccaacacgct gtttcgtagc cccatcaagc tggaggctga
13741 aaagatcttc aagtgccttc tgctcctgac taaaaagaga tacgtggggg tactcagtga
13801 cgacaaggtt ctgatgaagg gcgtagacct cattaggaaa acagcctgtc gttttgtcca

Fig. 3 (cont.)

13861 ggaaaagagc agtcaggtcc tggacctcat actgcgggag ccgagcgtca aggccgcggc
13921 caagcttatt tcggggcagg cgacagactg ggtgtacagg gaagggctcc cagaggggtt
13981 cgtcaagata attcaagtgc tcaacgcgag ccaccgggaa ctgtgcgaac gcagcgtacc
14041 agtagacaaa ctgacgttta ccaccgagct aagccgcccg ctggcggact acaagacgca
14101 aaacctcccg cacctgaccg tgtaccaaaa gctacaagct agacaggagg agcttccaca
14161 gatacacgac agaatcccct acgtgttcgt cgacgcccca ggtagcctgc gctccgagct
14221 ggcagagcac cccgagtacg ttaagcagca cggactgcgc gtggcggtgg acctgtactt
14281 cgacaagctg gtacacgcgg tagccaacat catccaatgc ctcttccaga acaacacgtc
14341 ggcaaccgta gctatgttgt ataacttttt agacattccc gtgacttttc ccacgcccta
14401 gtgactcaga cgcggaaaca gcgcctagaa agtttcctct tgcgctatgt gggacaacta
14461 gagtccaacc tggcaagcag tggagcaaga cgccagacag ccgatctcga aaaaaataat
14521 gcagacagag gcaacgttca tcctaggtga ctgggagata acggtgtcta actgccggtt
14581 tacttgcagc agcctaacat gtggcccccct ttacagatct agcggcgact acacgcggct
14641 aagaatcccc ttctctctgg atcgactaat acgtgaccat gccatctttg ggctagtgcc
14701 aaatattgag gatctgttaa cccatgggtc atgcgtcgcc gtagtggccg acgcaaacgc
14761 cacaggcggc aacgcgcgac gcatcgtcgc gcctggcgtg ataaacaatt tttcagaacc
14821 catcggcatt tgggtacgcg gccctccgcc gcaaacgcgc aaggaagcta ttaagttctg
14881 catatttttt gtcagtcccc tgccccccgcg ggagatgacc acatatgtgt tcaagggcgg
14941 cgatttgcct cccggagcag aggaacccga aacactacac tccgccgagg cacccctacc
15001 gtcgcgcgag acgctggtaa ctggacagct gcgatccacc tcgccgcgaa cgtatacggg
15061 atactttcac agtcctgtcc cgctctcttt tttggacctc ctgacattcg agtccattgg
15121 gtgtgacaac gtggaaggtg accccgagca attgacaccc aagtacttga cgttcacgca
15181 gacgggagaa agactttgca aagtaaccgt ttacaacacc cattcgacag catgcaagaa
15241 ggcccgtgtt cgtttcgtct acagaccgac gccgtccgcc cgtcagcttg tcatgggtca
15301 ggcttcaccc ctcataacaa cccctctggg agccagggta ttcgcagtct atccagactg
15361 tgagaaaact atcccacctc aggaaaccac caccctgagg attcaattgc tgttcgagca
15421 gcatggtgcc aacgccggag actgcgcctt tgtcatcatg gggctcgccc gtgaaacaaa
15481 gtttgtctca tttcccgcag tactccttcc gggcaagcac gaacacctta ttgtattcaa
15541 cccacagaca catcctctga ccattcaacg ggacacaata gtgggcgtgg caatggcttg
15601 ctatatccac cccggtaagg cagccagcca ggcaccatac agcttctacg actgcaagga
15661 agagagctgg cacgtggggc tcttccagat caaacgcgga ccgggagggg tctgtacacc
15721 accttgccac gtagcgatta gggccgaccg ccacgaggaa cccatgcaat cgtgactgtc
15781 cgagcacata tggcgcagga gtcagagcag tgctcccgtg cgtttgcagt gtgcagtagt
15841 aaacgacagc tcgggcgcgg cgagcccgtg tgggattccg tcattcaccc gagccacatc
15901 gtcatctcta atcgagtacc cctcttacta agagaacagc acatatgtct cccttcgtgc
15961 cccagcgtcg gccagatcct ccacagagcc taccccaact ttacatttga caacacgcac
16021 cgcaagcagc aaacggagac ctacactgca ttctacgctt ttggggacca aaataacaag
16081 gttaggatct tgcccactgt tgtggaaagc tcctcgagcg tgctgatttt tagactgcgt
16141 gcatcggtct ctgcgaacat cgccgtggga gggctcaaaa taataatact tgctctcacc

Fig. 3 (cont.)

16201 ctggtgcatg cccaaggagt gtacctgcgt tgcggtaagg acctttctac accacactgc
16261 gcaccggcta ttgttcagcg tgaggtgctg agcagcgggt ttgagccgca gtttaccgta
16321 actggcattc cagtgacatc ctcgaactta aaccaatgct actttctggt aagaaagcca
16381 aaaagccggc tggcaaagcc gtttgcacgc ctgtccgcgg agacgactga ggagtgtcgc
16441 gtcaggtcta tccgccttgg gaagacacac ctgcggatat cggtgactgc gcctgcgcag
16501 gaaacgcccg tctgggggct cgtgaccacg agcttcagcc ttaccccccac cgcaccgctg
16561 gcctttgatc gtaacccgta caatcacgag acatttgcct gtaatgccaa gcactacatc
16621 ccagtcatct acagcggacc aaaaattacg ctggccccgc gcggccgcca ggtagtctgg
16681 cacaacaaca gctacacgtc ctccctgcca tgcaaagtca cagccatcgt gtcaaaccac
16741 tgctgtaact gtgacatatt tttagaggac tcggaatggc gcccaaacaa gccagcaccc
16801 ctgaaactgg tgaacacgag tgatcatccc gtcatattgg agccggacac acacattgga
16861 aacgccctct tcatcatcgc acccaaggcc cgaggtttac gcagactgac tcgcttaacc
16921 acaaaaacca ttgaacttcc tggcggggta aagatagaca gcaggaaatt acaaacattc
16981 agaaaaatgt atgttgccac cggacgcagt taggtgtccg gttcccaccc acacatttgt
17041 ctttattgct ttcaaataaa acggtgttct gtcaacctcc tccgggctca ctagtattgt
17101 gttcccatac gcgcctgtcg ccccaggatc aacacttcgt cccctatcca ccctaataca
17161 taacacacac aaagacatag tgactgtaga cagttaatct ttattgtcta gacacgcaaa
17221 gtatattagt gttataagaa attttatgtc acgtcgctct ttacttatcg tggacgtcag
17281 gagtcacgtc tgggatagag tccaaaacac gcaccgcttg acctgcaaac ttttccattg
17341 cactcagaac ataaaacgaa gcaaagtgtc tcacccaata cttaagtccc tgaagcctcc
17401 ctaatagacc gcggtcaaat ttgggtggac tgtagtgcgt cttagtcagc ttattgagct
17461 cttcctgtat gtcccatcct aaggtcttcg tcagaagctc catgacgtcc acgtttatca
17521 ctgattttcc aaactccgtc gttaaaaact taaacaacac ctcgaattca aaaaagccat
17581 cggcgagctt tttaaggcag ctagtctcat taaatcctat taacccgcag tgatcagtat
17641 cgttgatggc tggtagtttc agatgaaaaa tagcagcggg ctctagaata cccttgcaga
17701 tgccggtacg gtaacagagg tcgcggaagc attcatcgat cacccatagc atccaattga
17761 gtctctgaat gagaagatcc ttttcaaact cgggggcgtc cggcaacttg ccccgcgttc
17821 cagataccag cagtgaaccg accagcaaga gagaccacaa cttgaaccag cacatggctg
17881 ctaacgcggc atacactagc cggtggtgcc cgagcgggag ttacgaagtc tcactgaagg
17941 gcggggtcgc gggtcggggc cgctccaaat caggcaacgc cgtatccgaa ctctgagtca
18001 cttttatgta ggtctcaaac atgtaaaaga taccacgttc ttgaaaaacc ctctcttgct
18061 cgccaggctt ggggttcacg cgggcatacg cagccaagct atcatgcgag agaaacacgt
18121 cacacgcaaa gtcatgtaaa acccgggtta aaaatagcct aactggccag gggccagtga
18181 gcgcctcccg gtacaagtcc ccacccccga tgacccaaac cttgtcaatt tgctgtgcta
18241 gctctgggct tctcgccaac ccaagcgcgg catcgagcga actcgccaaa aagtgagcac
18301 cagggggcgg ggtttctaac gtgcgactta gaaccacatt gattctaccc gccaatggtc
18361 gacagcccgc gggaatcgaa agccatgtgc gccgccccat aacaaccatg ttttgttttc
18421 caggggcaca gtcggtagtc agctgtcgaa aacgcctcat gtctccccgc aatgcaggcc
18481 acgggagaca tctgtttttt ccgatcccga gtttggtatc aaccgcaact acacagtaaa

Fig. 3 (cont.)

18541 gtgtaggatc catgccgcga gggtataggt aaacaccacc aaccacacag tgtgctctta
18601 tatactttta atgaaacata agggcagacg aaacagccga acgtttccta atcacgccca
18661 tggaaccata gccaccccca ggcaaaccct gtggaaggat atcaactaga gaggagggtc
18721 cagccttatt atggcaggag acactataag ccccatcgcc cgactgggca ccaacataac
18781 cgccacagta agtggcccta taccgctcag cgcccaagtt gttacagtca cacccaaccg
18841 cggttggctc tacattgtca tcacgtccat cattatgtgt tggttctccc gcttccttgt
18901 accctgcagc ttcatccacg gattcttctg agtcgcgatg cacaggagcg ccatccgcgg
18961 ggccatcttg gtcgcctgga gctgccccg cggggccatt ttggtcgcct ggagctgccc
19021 ccgcgggccc ctcctcgtcc tggttatccc cacggggaag aatttcctga agctcgatct
19081 cctctactgc acactctggt gatgtcggcc gaggtctata tggaaacact tcaacccgcg
19141 tgtttacagc agcgtatgcc cgccccacgt ggcgcatcat gtggaaaaac gcacccaacc
19201 caaaaacgac aaacaattgg taaaacacga aaaaaacgta gtacgcggct gcagcgacgt
19261 gatctatctc tgggtcatga ccgcccacta tatatagcca aacccacgtc gcagcggcaa
19321 ggccagcggc ccccaatgtc ataatgaaaa taaaaacaat cagttccaga ccctcctggt
19381 aagtcagccg aggcaatagc gtcatttcgc gcaagggtcg ccagaccacg cgcgtgttgt
19441 atacgacgcc acatatctga caggccgtgt ttctagagat agtgagccag gtgcttaaac
19501 aacttctatg gacgttctcg agctctcctg tgcatccaca ggctctaaat ctctcatttc
19561 cgagctcctc gttgcaaatc cagcagacag gaacatcctc atcttccata tcctgagaga
19621 gaacccacaa taaaacatgg cattaacccc tgcaacaagt gaccgtacca gggcacgcgt
19681 ccaggcaacc ggggtccccc tcgttggtct atacaattcc atgactacct actggtaatg
19741 ctacagccac tcactgtaca agccggttaa ctgggaggcg acgctggcgt ggtatcggcc
19801 aactgaaaca caccactcca ctccaaacac ttatgtactt tgtggctcgg ctttattgta
19861 acagccaaga ggggcgtttg tggctcagct ttattgtaac agccaagagg gacgtatgtg
19921 gctatctcac aaaaagtcac cgattcatgt agacaacccg ctcccacgaa ttcggttttt
19981 aaaaagccct cacgtataca gacgggccac taaatacgca catgagcggg catcctgttt
20041 ccgccttgac gcccaccact ctgaccgcac gctaaacatc gccctacctg ctatactgcc
20101 atttccatac gaatggtagg atgcgggcag tagtccacca gtctaaaatc atcaggtgta
20161 aactcttcca tggaagaaac agaccggagt atctccaggc gcggaaaggg acgtggagtg
20221 cgcgtcagct gcagccgtag tggctctata tgcgttttgt agatgtgggc atctcccaac
20281 gtgtgaataa actccccggg tctaagacca gtaacatgag caagcatata agttaagagg
20341 gaatagctgg caatgttaaa aggaactccc aaacccatgt ctcccgacct ctgatacagc
20401 tgacaggaaa gctcaccgtc agctacataa aattgacata acaagtgaca gggcggaagc
20461 gccatcaacg acaagtccgc cgggttccac gcacacataa tgattcttct atcgtgcgga
20521 ttatttttta ttaaatccac aatgtacgac aattggtcaa acccctggcc tgtatagtca
20581 gcatccgcgt ccacgtacgc cgccccaaag tgcctccact ggaaaccgta aacaggtccc
20641 aaatccccct cccttctgtg cgccaggccg cgcccggcca ggaactccct ggagccattt
20701 ttgtcccata tcttgactcc tgttcttgaa agctccctgg agtcagtact ccccttcaga
20761 aaccaaagca gctcttgcac tacgcctcgc caaaacaccc gctttgtggt tagtaaggga
20821 aagtggtccc gcagactata cctggcctgc atgccaaata gagagagggt gcctatgccg

Fig. 3 (cont.)

20881 gtgcggtcga gtcgatcgct gccacggcac aaaatttccc tcaactgcct gagatactga
20941 agttcctcgt ggggcgtctc agccccagtt acctcatgct gaatcgaaca agggtcaacc
21001 tcgggggcca aagccaagac gccaggcttt tgacagaagc gaaacccccct ggcacggaat
21061 aactttttgg cgacatacaa gcttaaaggt acaaacggaa acatgataga tcctggaagt
21121 ttgtgaagcc ctgtgcccgg agagacaccc ctcaactcgc agtgctcgga gacctacatg
21181 tatactcagg ctcttctata aaccctcccc aaaagtttat aaaacaccgt acgtaataca
21241 cattactcac agttcccacg gtgacgccca aacccatgca cacgggcgtg atcgatacca
21301 gaaaacatca caagaacaaa aagtgtgtgt ctgacattca catttatttt tacaagacaa
21361 ttttgtgcag tagagttgtg ccttccgaca ccccgcgccg ttcgctgttc tcctgtaatt
21421 gggagatccc actccttggc aggcacgttt cacgaaacgc tcttgtctcg ctggccttag
21481 acttgtggac ccaacatggg tatcgttaga gatccgtcgc gtaaatgcgc agctggcaaa
21541 gcattcttca gcgagcagtg actggtaatt gctgcatcag cttcttcacc cagtctttcg
21601 atttgtcggc acacacctgg cgaccacgct ttgtcaaaaa tatcacaccc ggcttgctgc
21661 acagttggga ggtggggtac cagctggaca gaagcacctg tggtaatggt cttttctggt
21721 aaccgagaca gcacttgtcc ggtctatgcc aggacgctcc cagcgtgtcc ccagattgca
21781 aacaaagcaa ggcagtcagc acagcgacga gcaggatgcc cttggtgtcc ataactcccc
21841 tcgtgtgtcc tcgtgtaaat gcgaaacggc gatgttaggt caggcgcggt aaacagctca
21901 actcggttca aaacacgtac gtgatgtagt gctggttcta cgacgcctac ctgtaaactc
21961 caggatcctg ggcttttatt acgaaggcca acaccccaaa aaatccacgc ccccgtgacc
22021 gcaggggcgg ttactaacga cggttacagg tccctcccga gccacgcacc tgccatgtaa
22081 cctgcaaggt aaccagacaa acatctagga agcgtaaata tccccaggta ggagaagtat
22141 tgcatatgtc acagactcaa cacacacggg ccgttacgca acggctaggg gcataaccct
22201 ttaccggcgc gaagcgctac gcgcttcgcg agaggtatct ccgtgtgctt ctccatcaga
22261 agacgcgtgc gccgcttcgc aggcgacccg catactttcc gcccccgagtg cgttacaaaa
22321 atgactgcct tctggcgaca atacacggtg gacgtccagt accacccgca tatcagctta
22381 tccggtggca atctggcact ggacagggaa ttctcgcaac aatccgaggc catgatggtg
22441 gcaggaccgc tggccgcaca tagctcaatc acggccaccc agaagagcag ccccaaatgt
22501 gcgcgcaaca cccagcacat gctccacata cagttctggc gccacaacga tgatgcgcaa
22561 aggggtgcat taccctaaat cccagcctag ttataaatta ttgaagccca ggcgaccagg
22621 ggtcgccgcg ctttcctcc ccaaacgcga cgataaagac cagcgttgcc aaatgtaact
22681 tatgtataac ccaaaatatt gcgcatcgat aaggtttgcc aaaacacccg aaagtacaca
22741 cacaaaaaaa cagcaacaag acgctcacta gacattcacc ccttccccca cccccgaaaa
22801 caaaacaact tgacacaggg gaaacaccag gggcggcgga ggttgtcaat agtgtccagt
22861 atttcgttag acgcgggttc ttggacccga tgtcccaggt cattaaagtc tcaaatggga
22921 ttaaaggatc atagttccca ggtttaatac tccaagctat cccagaacag gaccccggca
22981 gaaccccgct taacagcacc aaatccactt gcggtcccag aaaaggtcgc cgaggtggca
23041 aggtgactga aaaggtcata gagaggacac cggtcccatt tcccacggtc caaaaatcca
23101 gcgcgcccca ccggctttcc gagaacttcg gcaaagctaa tttgcatgcg ctaatccttt
23161 tatgtgcata aattatgtag atgaggagtc gcgcatgcgc agaaaaattc agagcgcccg

Fig. 3 (cont.)

23221 ggtgcacggg gtcacctcca ggtcacgccg ctaggtggga ccgtgagcga ctcgaaaaat
23281 tataattttt ggccatttca tgggcgccgc catcttgaat ttgctaatcc cccataatcc
23341 tctgccccgc tcccattggt ccgccggccc gtcaatcaaa gttttccgag ccgccattgg
23401 cccatccggc cgaccaatcc cgttcgagct aggcgaccgc gccattccat tggacgcccc
23461 agccgtcaat caaattcgga ggcctcccat tggcccctat ccctagaact cccaagctga
23521 ttggcccaga gcgggaacca atcagcgatt agagttttgt tttgattttt cctatatata
23581 tatatataat cctttaatcc tagcgcagct gagtcatcgc agcccctatt ccagtaggta
23641 tacccagctg ggtaatccag taggtatacc caggtgggtg aacccagctg ggtataccca
23701 gctgcaattc tataattaaa caaggtagaa accaacgggg tcctcaggtg gtatttccgg
23761 aagcattacc aaataaggca acctcagctg ggaataccag cggactaccc ccaactgtat
23821 tcaaccctcc tttgttttcc ggaagtatat ccatttatgg aaatcagctg ggtcactcta
23881 ctgggttatt ctttataata gggcccgatg agtcatgggg ttgggatttt tctactaggt
23941 cgtttcggtg gatgggtgcc aggattatag gggccctgtc cacggggttg ttcggtggcg
24001 gggggggggc tagtgagtca cgggcctgga atctcgcctc tgggtggttt cggtagatgg
24061 gggccgggag gatggggccc cgcccaccgc tggcgcgccc cagaacatgg gtggctaacg
24121 cctacatggg cagcttgtcc tacggttacg cccatttgag acgggttaac caactgttac
24181 acccccttcgc cgggaacgct ataaaaacga gggacagcag cccccccctcg cgcactgcgc
24241 gcgcggcggc acgtgggacg gatctcttgg atttacccgt aacgaggagc cccggcagca
24301 ccccaggagc cccggcagca ccccaggagc cccggcagca ccccaggagc cccggcagca
24361 ccccaggagc cccggcagca ccccaggagc cccggcagca ccccaggagc cccggcagca
24421 ccccaggagc cccggcagca ccccaggagc cccggcagca ccccaggagc cccggcagca
24481 ccccaggagc cccggcagca ccccaggagc cccggcagca ccccaggagc cccggcagca
24541 ccccaggagc cccggcagca ccccaggagc cccggcagca ccccaggagc cccggcagca
24601 ccccaggagc cccggcgcgc caccctcccc ggagggggat cccggcgcgc caccctcccc
24661 ggagggggat cccggcgcgc caccctcccc ggagggggat cccggcgcgc caccctcccc
24721 ggagggggat cccggcgcgc caccctcccc ggagggggat cccggcgcgc caccctcccc
24781 ggagggggat cccggcgcgc caccctcccc ggagggggat cccggcgcgc caccctcccc
24841 ggagggggat cccggcgcgc caccctcccc ggagggggat cccggcgcgc caccctcccc
24901 ggcaacaacc tgttgccatg tatggcgatt tgtatcagtc acaagcacac aacccctgct
24961 agtattaatg gtgtttaaaa cgttctacac gtacggcgga ccgcatccgt cgcaagcacg
25021 cgcatataac ccccaaatgc accatgatga gaagcacagc cacgcgtcaa aaaactttaa
25081 aaacatcgtt atccaatatc attaaaaacc acaccgaaat ttacacaggt agcacgtcac
25141 cgtgttagtg tcacccactg tacacaaggc gtgtcgtata tgtagtatag gtatttgatg
25201 aggcggaagc atatcccgct tccagcgaac ggaaataaga atcatccgtt ccagcattta
25261 ttcaaagagg gcacagagga ttcacattgt ttagagagag tttttcttag tcaccattcc
25321 atacttgggc agtattggcc tacgatttgg gcgacgtttc aggctggtct attctccgtc
25381 cacttttccc cggctattct gtcccagcat aggctcttga aataaacaat gtttaccgag
25441 taaaaggttc cactcaccct catttgtcgt tgcacccatc cccccttgc ttaatcaccc
25501 gaaaactaga ggacacggat ggaaaacata tcgcacgcgg gttgtttgaa agtcaacagc

Fig. 3 (cont.)

25561 tacttgtttt taatgaggac agatttgggc acaggccaga gggtaaagcc ctacgtgtgc
25621 gcgggggggg gggtgtatac gctgcgaaaa cctgcacggt gcataacacc cagggcgtca
25681 cgtcacatat ctctgtgcac ccaagtggtt gttcaaccgt tgttttttgg atgatttttc
25741 cgcaccggct tttttgtggg cgcgcatagg tcggtacgcg ctgtccccct aagtcccgca
25801 cggtcgttcg ggcccccgtc cggctcgtct ccggatgaac cgtcacgttc tttgtctcca
25861 gaggcgacgt ctccttcaga tgactcgtcc gtgggctcct cgtccgtccc gcccgcgggt
25921 ccgacaagga ccgtcaattc gatgttatct tcgttcgcgg ttggccggcg cggccgtcgg
25981 tatggcagta cggtcacccg ggtgttattt gccgcgtata atgccctcac agtgccactt
26041 acgcggcata tgccgccaaa tgcaaacaca ataaatattt ggtaaaaccc aaagaagcag
26101 agaaaaccga gcacggcccc gggggagaat gttcccgcag gagcagttag gatgaccagg
26161 agcgtccagg tgcacaacgc cacgccgaca agcccagcca ccaccacaga catcagcaga
26221 aacagttcaa aaatttcttg gcgctccatc tccggccaca ggttaaggcg actacgccac
26281 tgcgtgcgcg tgcggtatat aacgcgacac atttgacagg ccgtgtttcg agacactgtt
26341 agccaagtgc ttaaacactg cgggtggacg acatccagct ctccggtaca ggcgcagggg
26401 tgtatgccct cgttccccac ctcttcccta catatccagc agatgggtcc ctctacaccc
26461 tcttctacgt ccttagacgc catctctgca gctggggtgg aagtctgaaa aagggaaagg
26521 ggaggtgagc agagtgccca gttagtctcc gacccgccgt ccgccctact gtcgctatcc
26581 cgccttgaca gatgtctaac gtattcacgg acgccacatg tgtgtctatt ttcctacatc
26641 caggctttcc ctggaaaact gtcacaaccc accctgcttt agctctacat ctgtattttt
26701 gtttacgcac aggatcaacg cttcgtgccc gtccaccccc gcgctctccg cctgtgtttg
26761 gaggttttat gagtggttag ttctaggcag ctccggacaa gttgtccaaa acacggcgcg
26821 ccccgccctt ccttccctcc ggatccgccc acaccggacc tatgaaataa gggacacgcg
26881 tcatcactag ttatgagaga aaaaccacaa cagctttatt ggaaaacacc tgagtggatc
26941 ccccaccccc cgcgtacgac aggcgtttct gtggtgcgct tctgggaaaa acgtttttcc
27001 cccatttctt cctcgacagg tcttctaagg tagataaatc cccccccttt gcgcgtctcc
27061 tagaatggcc taggcgcacg atggcgttgt cgcctcgagc agttgggccg cagtgatatc
27121 ttcaactttc gaccgtctaa gctatggcag gcagccgctg catcagctgc ctaacccagt
27181 ttttggaagg gtctgcgcag atctgacgcc ctcgcttggt cagcaaaata actccgggtt
27241 ttgggcacgc tggggacgtg ggataccact cttttagaat ttggacgggc ggtgggtgct
27301 gctggaaccc gtagcagcag ctattaggcg tgtacgacac gagtgacccc gcgctttctg
27361 tgggcgtcag gtaaaacgtg gcaagcagta cgctaacgca gcataaaacg tggacggggg
27421 ccatctggag gtgccaagtt cgcaacagtc taaagaaaac cgtaaaggct atttggggtt
27481 tctgttctgt cagatgtaac gccgagttcc ttatatgctt acctgattct ggtctcacct
27541 gtttatttat agtggcgtat gctaaccgcc agcttacatg cgggataagt tggcctaact
27601 caccaaaaac gggttgcaga caaaagtgat tgttggggcg cttacttaga aggtgtgagg
27661 gtttctaaga aaccccgcca acgcccggaa accgcatgcg ttccagtcgg tgcggcctgc
27721 gccggcgtcg ctgtggcgcc tttgtgggct ttgagttctg tcattaagcc aggtttccat
27781 tgccacccgg gcgaaaacaa gccgggtagt ttcaggggtc atctggcgat cagtgtacca
27841 tattcccacg acccatcaac accgctgctt gaggcgtgtc tctgtatgtg tcaccggaga

Fig. 3 (cont.)

27901 ctgcatgtat cgtgcatatc tgtattgtgc gcttgcgcgg agacaacata ccgacgacca
27961 agtcaggggt cacctccagt gcacgccgct aggtgggacc gtgggcgagc cgaaataatt
28021 atatattttt ttggcacggt tgtgagcaac gccatcgtga gttggttaat accctctaaa
28081 cgcatagtct ttttttattt gtcaaccaac cagtcaatca cctgtcatcg ccgctcagaa
28141 gcacacgtct tcggccaatg ccgtgttggc gggtttgacc acggttactg ataggtagac
28201 gagtccgaca atcacacacg tccgccagcg atttgcagcg cagctaaaat cgcgtggccg
28261 ggttggtaga agcaaattat ccaatggtcg tgtttgggtt tgttttgggg ttatctacat
28321 attatattcc ttatcccgac tggttgcgga agtattcgca gcttggctac tctgctcgat
28381 taccccgtga ataactgggc ggggggtgac ccaacatagt gattcggtag atttgggga
28441 ctggatgaac attaatgaaa gtttattaat gttcatccgt attgtgtata tgtaatttgg
28501 tttccatatt tggtaggagt atggagtttt cttatggatt attaagggtc agcttgaagg
28561 atgatgttaa tgacataaag ggcgtggct tccaaaaatg ggtggctaac ctgtccaaaa
28621 tatgggaaca ctggagataa aaggggccag cttgagtcag tttagcactg ggactgccca
28681 gtcaccttgg ctgccgcttc acctatggat tttgtgctcg ctgcttgcct tcttgccgct
28741 tctggttttc attggtgccg ccgattgtgg gttgattgcg tcgcttttgg caatataccc
28801 atcctggctt tcggctaggt tttccgtcct actttccca cattggcctg agagctgtag
28861 tacaaaaaac accgcgcggt ctggagctct ccataagccc gcagaacaaa agctgcgatt
28921 tgcccaaaaa ccttgccatg gcaactatac agtcacccct tgcgggttat tgcattggat
28981 tcaatctcca ggccagttgt agcccccttt tatgatatgc gaggatactt aacgtgtctg
29041 aatgtggaat ataatgtgaa aggaaagcag cgcccactgg tgtatcagaa cagtggtgca
29101 ctacctatct gctcattcgt tgtttcggtt ctgtgtttgt ctgattctta gatagtgttg
29161 aggtaattct agaaagcgga ttgagtgtaa atcgggccac tttgccctaa atgtgacaat
29221 ctggatgtgt atcttattgg tgcgttgtga agcatttaa aatgcgtttt agattgtatc
29281 aggctagtgc tgtaatggtg tgtttatttt tccagtgtaa gcaagtcgat ttgaatgaca
29341 taggcgacaa agtgaggtgg catttgtcag aagtttcaaa gtcgtgtaag aacattggac
29401 taaagtggtg tgcggcagct gggagcgctc tttcaatgtt aatgttttaa tgtgtatgtt
29461 gtgttggaag ttccaggcta atatttgatg ttttgctagg ttgactaacg atgttttctt
29521 gtaggtgaaa gcgttgtgta acaatgataa cggtgttttg gctgggtttt tccttgttcg
29581 caccggacac ctccagtgac cagacggcaa ggtttttatc ccagtgtata ttggaaaaac
29641 atgttatact tttgacaatt taacgtgcct agagctcaaa ttaaactaat accataacgt
29701 aatgcaactt acaacataaa taaaggtcaa tgtttaatcc atatttcctg acttgtgtct
29761 tgacttgcgt cgattgggat gggggtgtgg gatgggggtg tgggatgggg gtgtgggatg
29821 ggggtgtggg atgggggtgt gggatggggg tgtgggatgg gggtgtggga tgggggtgtg
29881 ggatgggggt gtgggatggg ggtgtgggat gggggtgtgg gatgggggtg tgggatgggg
29941 gtaaatgaca atgggggtaa atgacaatgg ggcgcttggt gacacatttg ccccaccgtc
30001 gcctgcccgg aaccagcttg gtgatgtgct gtctggctct caggtgcact ttatgcaaag
30061 cagttgaggc gcattagata tataaaactt gggtacacac ccttggtgct gtgcgcgtgc
30121 tatgtgccct ggtgaccgtc cacaatggac gaggacgttt tgcctggaga ggtgttggcc
30181 attgaaggga tattcatggc ctgtggatta aacgaacctg agtacctgta ccatcctttg

Fig. 3 (cont.)

30241 ctcagcccta ttaagctata catcacaggc ttaatgcgag acaaggagtc tttattcgag
30301 gccatgttgg ctaatgtgag atttcacagc accaccggta taaaccagct tgggttgagc
30361 atgctgcagg ttagcggcga tggaaacatg aactggggc gagccctggc tatactgacc
30421 tttggcagtt ttgtggccca gaagttatcc aacgaacctc acctgcgaga ctttgctttg
30481 gccgttttac ctgtatatgc gtatgaagca atcggacccc agtggtttcg cgctcgcgga
30541 ggctggcgag gcctgaaggc gtattgtaca caggtgctta ccagaagaag gggacggaga
30601 atgacagcgc tattgggaag cattgcatta ttggccacta tattggcagc ggtcgcgatg
30661 agcaggagat aacgcgtaat tcgaggtccc cggaagagta gagggttgca tgttatacaa
30721 acaacataaa cattaaatga acattgttca aaacgtatgt ttattttttt tcaaacaggg
30781 gagtagggta ggaagggtac gtctaatacg taactgttcg ctactgcttg ttcaggagct
30841 cctcgcagaa catcttgcga attttagatt ttggactaga gcgactgctg gcttcaacgc
30901 ggttcgatgt agggttcggc gtaggagcgt ctttctccac cgccgcgcat ggtgtatgcg
30961 tggtctccgg tgcctgttgt tggatgctct gcgtgctgga ggcgggggtg ggttcagcgg
31021 gtggtgcgcc aactaccgcg agtcctgtag agactggcgg gtggctcaca tgtggctgag
31081 caaaaaggat gggcgccgct tgctggaact gaccgtgtgg cgcctgcacg taaatgggtg
31141 ggtgtacgta ggttcctccg tgctccttca ttgtcgggaa ttgacacggg accgctgaat
31201 tggcgtgggg cctgtagtgt ggatctactg cggctgctgc tgcagaggag gacggcggtg
31261 gccctgcgtg ccaaccgttc agtttcatct ctttgagttc agactgtatt tccgctatgt
31321 tctttgacat ggacaagata tccttgtgat acgccggctc ctctcctgga aagaggtgtc
31381 cttcgtcgtc ctctgcgccg cgcttgcgct tccccgtcct atatccaggc agctgtggcg
31441 agtaatacca tggatcgtat gggttcttgt aagcgtagcc gtatggtggc gctgggtttg
31501 aaacatacga aggtaggtga tggtcggtgg ggaacatctg gccccccacac cccattaggc
31561 ctggccctga aagtgtatgt gacatttttg ccgctgtggt cttcattcca tcgatgctgc
31621 tttgtagcat gctcaggaag gcggatttgg ggatggatat gatatcctct tgaccagagc
31681 tgttcatggc tggtctgggt ggtgtgacgg cttggatgcc gaccgggaat tggctggcct
31741 ttaaatacgc cgggctcaat atgctggcca cacctctgtc agttttcaat aggtcgaggc
31801 ggtcccgtat gaagctggca tctatagctt ttgccattaa ggtctccagg ggactgacga
31861 aatttggtgt ggaaaggtcc tccagcctgc agctacttac gtgctggagg atgtgggcgc
31921 gctccgactt agatactgat gagaatctgg aaaccaccca ctcggcgtcg tgtccgtaca
31981 cggccactgt gccgcgtcgg cgccccaggg cgcatagtga tacgtgttga aacacgggac
32041 cgctgggagt ctgggataac tcgcggggat gtatagacga taaagacagc cccgggagcc
32101 acgtgtggag tatctccaac agtggttcct tagggagatt tttcacgggg gctctggcca
32161 cgtgggaggt gtccgccagc ctggatgcca gctctaggaa ggctggcgac gtgatggctc
32221 cggtgcagaa aataccgtgg gacacttgaa atagacccag tgtccagccc acttctgtct
32281 ctggtaggtg ttcgattgtt attggaaggg gttctgtgac tgggagataa tccgtcacct
32341 gatccggatc gagatagagc tcttgctcca gcttggggca ggacacaaca tctacaaacc
32401 ctccgacgta caggccctgt gccatgctcg gaaaatacgt gtgtgagacc gagccgctga
32461 gcccggggct taggaggctc atgtggcgct ttttgcaaaa taagaattta aatacattcc
32521 acgcccaaga gctgcgtttt attcatttgg ttctctgcag gatgtacaat ttcggtctaa

Fig. 3 (cont.)

32581 atgtgtacct gttaagggag gctactgcca atgccgggac ctacgacgag gtggtcctgg
32641 gacgcaaggt tcctgcggag gtgtggaagc tcgtgtacga tgggctcgag gagatgggcg
32701 tgtcaagtga gatgctgctg tgtgaggcat accgggacag cctctggatg cacttgaacg
32761 ataaggtggg gctcttgagg ggcctggcga attatctgtt tcaccggcta ggggtcaccc
32821 acgacgttcg catcgccccg gaaaacctgg tggacggaaa ctttttgttt aatctgggaa
32881 gtgtgctccc ctgcaggctg ctccttgcgg cgggctactg cctcgccttt tggggcagcg
32941 atgaacacga acgctgggtg cgcttcttcg cccagaagct tttcatttgc tacctgatag
33001 tctccgggcg tcttatgcca cagaggtctc tgctagtttg ggccagcgaa acgggctatc
33061 ccggtccggt ggaggcagtc tgtcgcgaca tccgctccat gtacggcata cgaacgtatg
33121 cggtctcggg ttatcttccg gctccgtccg aagcgcagct ggcctacctt ggtgcgttta
33181 acaacaacgc ggtttaaacg accgcgagga ccaccggcag gcagccaaga accataaagt
33241 acgctctatc gtagtcatcg ccgccgccaa actgggactt gataatctcc tggagaaggg
33301 tgggtgggga tgggtgtgaa agcaggacgt ccaggccctc ttctgttgcc aggcggaggg
33361 ctgttctcgc ctggagcagc gccagtggat ctcggaatgt aagctgctgg ttcaggattt
33421 cgaatatctc attaaaccta ctgcctgtca gatttacaaa tggtccgggt tgtttgtggg
33481 acacggtcga tcgcgcctcg agggcggcca gtattatgcc agggaagatg aaggacacgg
33541 gggcgtttgg attagcctgc agtgtgggga ttatgtagtg ctccgatatg aacgaaaata
33601 gctggcccct tttcagcatg gggcgtttg gatccggtag ggcaccgggc tgaaatttgg
33661 gtcccagcag ggataccagg ttcaagcggc ggtttgggtg ccctcgcgcg acttgcccaa
33721 actccagcaa tccatacgcg aggataaaca cctccagcgc aacaatcccc gctcgcaggt
33781 tccactggta tgcggaaaat ggtggtatat cggacccaaa catggcgctc gtaatggcga
33841 ataccaagtc catggcgggc gctgtccctg gcgcgcccgt acccttgttg tggggaaata
33901 atccagcctt agccatcatt gcgtgaagct tgtggcgctg gaagaaggct gtcggatagc
33961 ggctctcctt attgagaggc gccagcgagg cgcgctcctg ggggtttgag tatgtgaagc
34021 tgaagtcccc aggaccgctt tcctgtttta gctgagtgat tagcaggtct agcttttgag
34081 gcaggtctgc taacaggtca tcgggagtag cgggcagttg cctggatgtc ttttgacaaa
34141 agtacgcgtt gacgaggcaa agcgcggcct gggtgtccgt gagatgcctg gcgtcggcga
34201 aaaagtcagc ggtggtcgag gcgaccgtcg tcagggtgtg agagatgagt ttgagcgatg
34261 tggaattctg aaagttaaca gtccccttta gttctttagg gaagacgcgc cgctgcatgg
34321 cgttgtccgt gaggctgatg aaccacggcc caaaggatgg caaccactga ttctggttca
34381 tgtacagggt gggcatgagc tcgccgcgca ggtccctgtc aacggagaag tgagggtccc
34441 cggggacgat cgccacggtg aagttacggt ggctggcctg cggggggggat gtcactaagg
34501 gaggctcatg ggaacggctt tggggcatgt ctatgttgtc agaccatgtc atgttgccta
34561 tcatctgttt caccgcgtcg atatctgcgt taatgacgcg gacgcgtgag tcatggacct
34621 gaacaagccg gtccagctct agggaaagca ggtgtgcctt tgtctttcgt tctcgatttc
34681 gcacgagttg gctgcgcagt ccaagggcga cccttcttgt ttcttccatg gtgggcttgt
34741 gaataaacag cacgttttcc gggtgtgggg cccagaatct tcccgcctct gtccatcttc
34801 ggttttttgg gtaccttaga taggaccttt ctgatgtcag cattttctct agcagtgaga
34861 aaggcgcaca attttccttc ggtggtgtgc accggcgtgg gaaacgcccc gggtgattca

Fig. 3 (cont.)

34921 gagtatactg tctttagtgt tttctgattc ttaaatatca gcaggggcgt gatagtccac
34981 gcctcggtac ccggaggggc cgagtgagcg atgtaatgga tcgagtcgga gagttggcac
35041 aggccttgag ctcgctgtga cgttctcacg gtgttggttg ggatcagctg gtgactcaga
35101 caagtcttga gctctacaac gtaacatacg ggctgatgcc cacccgatac cagaattacg
35161 cagtcggcaa ttctgtgccc tagagtcacc tcaaagaata atctgtggtg tccaagggga
35221 gggttctggg gccggctact tagaaaccgc catagatcgg gcagggtgga gtacttgagg
35281 agccggcggt aggtggccag gtgggcccgg ttacctgctc ttttgcgtgc tgctggaagc
35341 ctgctcaggg atttcttaac ctcggcctcg gttggacgta ccatggcaga aggcggtttt
35401 ggagcggact cggtggggcg cggcggagaa aaggcctctg tgactagggg aggcaggtgg
35461 gacttgggga gctcggacga cgaatcaagc acctccacaa ccagcacgga tatggacgac
35521 ctccctgagg agaggaaacc actaacggga aagtctgtaa aaacctcgta catatacgac
35581 gtgcccaccg tcccgactag caagccgtgg catttaatgc acgacaactc cctctacgca
35641 acgcctaggt ttccgcccag acctctcata cggcaccctt ccgaaaaagg cagcattttt
35701 gccagtcggt tgtcagcgac tgacgacgac tcgggagact acgcgccaat ggatcgcttc
35761 gccttccaga gccccagggt gtgtggtcgc cctccccttc cgcctccaaa tcacccacct
35821 ccggcaacta ggccggcaga cgcgtcaatg ggggacgtgg gctgggcgga tctgcaggga
35881 ctcaagagga ccccaaaggg atttttaaaa acatctacca aggggggcag tctcaaagcc
35941 cgtggacgcg atgtaggtga ccgtctcagg gacggcggct ttgcctttag tcctaggggc
36001 gtgaaatctg ccatagggca aaacattaaa tcatggttgg ggatcggaga atcatcggcg
36061 actgctgtcc ccgtcaccac gcagcttatg gtaccggtgc acctcattag aacgcctgtg
36121 accgtggact acaggaatgt ttatttgctt tacttagagg gggtaatggg tgtgggcaaa
36181 tcaacgctgg tcaacgccgt gtgcgggatc ttgccccagg agagagtgac aagttttccc
36241 gagcccatgg tgtactggac gagggcattt acagattgtt acaaggaaat ttcccacctg
36301 atgaagtctg gtaaggcggg agacccgctg acgtctgcca aaatatactc atgccaaaac
36361 aagttttcgc tcccc ttccg gacgaacgcc accgctatcc tgcgaatgat gcagccctgg
36421 aacgttgggg gtgggtctgg gaggggcact cactggtgcg tctttgatag gcatctcctc
36481 tccccagcag tggtgttccc tctcatgcac ctgaagcacg gccgcctatc ttttgatcac
36541 ttctttcaat tactttccat ctttagagcc acagaaggcg acgtggtcgc cattctcacc
36601 ctctccagcg ccgagtcgtt gcggcgggtc agggcgaggg gaagaaagaa cgacgggacg
36661 gtggagcaaa actacatcag agaattggcg tgggcttatc acgccgtgta ctgttcatgg
36721 atcatgttgc agtacatcac tgtggagcag atggtacaac tatgcgtaca aaccacaaat
36781 attccggaaa tctgcttccg cagcgtgcgc ctggcacaca aggaggaaac tttgaaaaac
36841 cttcacgagc agagcatgct acctatgatc accggtgtac tggatcccgt gagacatcat
36901 cccgtcgtga tcgagctttg cttttgtttc ttcacagagc tgagaaaatt acaatttatc
36961 gtagccgacg cggataagtt ccacgacgac gtatgcggcc tgtggaccga aatctacagg
37021 cagatcctgt ccaatccggc tattaaaccc agggccatca actggccagc attagagagc
37081 cagtctaaag cagttaatca cctagaggag acatgcaggg tctagccttc ttggcggccc
37141 ttgcatgctg gcgatgcata tcgttgacat gtggagccac tggcgcgttg ccgacaacgg
37201 cgacgacaat aacccgctcc gccacgcagc tcatcaatgg gagaaccaac ctctccatag

Fig. 3 (cont.)

37261 aactggaatt caacggcact agttttttc taaattggca aaatctgttg aatgtgatca
37321 cggagccggc cctgacagag ttgtggacct ccgccgaagt cgccgaggac ctcagggtaa
37381 ctctgaaaaa gaggcaaagt cttttttcc ccaacaagac agttgtgatc tctggagacg
37441 gccatcgcta tacgtgcgag gtgccgacgt cgtcgcaaac ttataacatc accaagggct
37501 ttaactatag cgctctgccc gggcaccttg gcggatttgg gatcaacgcg cgtctggtac
37561 tgggtgatat cttcgcatca aaatggtcgc tattcgcgag ggacacccca gagtatcggg
37621 tgttttaccc aatgattgtc atggccgtca agttttccat atccattggc aacaacgagt
37681 ccggcgtagc gctctatgga gtggtgtcgg aagatttcgt ggtcgtcacg ctccacaaca
37741 ggtccaaaga ggctaacgag acggcgtccc atcttctgtt cggtctcccg gattcactgc
37801 catctctgaa gggccatgcc acctatgatg aactcacgtt cgcccgaaac gcaaaatatg
37861 cgctagtggc gatcctgcct aaagattctt accagacact ccttacagag aattacactc
37921 gcatatttct gaacatgacg gagtcgacgc ccctcgagtt cacgcggacg atccagacta
37981 ggatcgtatc aatcgaggcc aggcgcgcct gcgcagctca agaggcggcg ccggacatat
38041 tcttggtgtt gtttcagatg ttggtggcac actttcttgt tgcgcggggc attaccgagc
38101 accgatttgt ggaggtggac tgcgtgtgtc ggcagtatgc ggaactgtat tttctccgcc
38161 gcatctcgcg tctgtgcatg cccacgttca ccactgtcgg gtataaccac accacccttg
38221 gcgctgtggc cgccacacaa atagctcgcg tgtccgccac gaagttggcc agtttgcccc
38281 gctcttccca ggaaacagtg ctggccatgg tccagcttgg cgcccgtgat ggcgccgtcc
38341 cttcctccat tctggagggc attgctatgg tcgtcgaaca tatgtatacc gcctacactt
38401 atgtgtacac actcggcgat actgaaagaa aattaatgtt ggacatacac acggtcctca
38461 ccgacagctg cccgcccaaa gactccggag tatcagaaaa gctactgaga acatatttga
38521 tgttcacatc aatgtgtacc aacatagagc tgggcgaaat gatcgcccgc ttttccaaac
38581 cggacagcct taacatctat agggcattct ccccctgctt tctaggacta aggtacgatt
38641 tgcatccagc caagttgcgc gccgaggcgc cgcagtcgtc cgctctgacg cggactgccg
38701 ttgccagagg aacatcggga ttcgcagaat tgctccacgc gctgcacctc gatagcttaa
38761 atttaattcc ggcgattaac tgttcaaaga ttacagccga caagataata gctacggtac
38821 ccttgcctca cgtcacgtat atcatcagtt ccgaagcact ctcgaacgct gttgtctacg
38881 aggtgtcgga gatcttcctc aagagtgcca tgtttatatc tgctatcaaa cccgattgct
38941 ccggctttaa cttttctcag attgataggc acattcccat agtctacaac atcagcacac
39001 caagaagagg ttgccccctt tgtgactctg taatcatgag ctacgatgag agcgatggcc
39061 tgcagtctct catgtatgtc actaatgaaa gggtgcagac caacctcttt ttagataagt
39121 cacctttctt tgataataac aacctacaca ttcattattt gtggctgagg gacaacggga
39181 ccgtagtgga gataaggggc atgtatagaa gacgcgcagc cagtgctttg tttctaattc
39241 tctcttttat tgggttctcg ggggttatct actttcttta cagactgttt tccatccttt
39301 attagacggt caataaagcg tagattttta aaaggtttcc tgtgcattct ttttgtatgg
39361 gcatatactt ggcaagaaat ccgagcacct cagaaagtgg attgccgtca catatcagtt
39421 cgaccacccc tgcacctagc catgcggcgc tttgacggtc tttggggcta cacatcataa
39481 agtacttttc catggcttct ataagcacct tggaacaatc tgggggttgg cgaatgggtt
39541 ccctaaacgg gaaatcctct atggtattca ggcagaagac cgcgtcctcc acccgacgtt

Fig. 3 (cont.)

39601 tgagtctttc tagcagagcg ccgaagaact cccgctcgtg tgttttcgca ggggcaagtt
39661 ctgcgccgta cagcgatgag aaacacgaca cgatgttttc cagcccccatg ctgcgcagca
39721 acacgtgctt caggaacagg tgttgtagcc ggttcagttt tagcttgggt agaaaagtta
39781 tcgagttgtt agcacgctcc atgatggtaa cggtgttgaa gtcacagacc gggctttctc
39841 cgagtctcgg ccgcctgagt ccaatcatgt agaacataga cgcggcctcg ttgtctgtgt
39901 taagtgacac gatatcccgt tcgcaaacct gtgcgatgtt gtgtttcagt atagatctgg
39961 tctgaccggc acggggtgtt atggggtgac gcggtaaagg cgactctggg tcaaacacct
40021 ttatgcggtt ggcggcctcg tcgatgacga cacgcttgtt cgcggcgtgt atggggacgc
40081 gacggcatcc cgctggcaga tctataatct taaagttggt ataagactgg tcgctcgtta
40141 tggccagccg gcactccggt agtatctgcg tgtcctcgaa ttcgtggccg cgtacgactg
40201 gcttggagtg caggtaaacg ccaagagatg cggtctcttc gcctacgcac aagtggcttc
40261 ttaacgcgta ggggtgcggt gagagcatga tccgtagcaa cgatagttcc gggtgcctag
40321 ccgcgtagag tggcagggta gacgagtccg gagtcccaaa cttttcgaac aacagtggca
40381 tcgggacttc aggattagag actcccacca tggccgccac cgccggagag gtcaagacgt
40441 gaaacacgcg ctcgcctgtc gacaggcgcg ccgcgccctc tactagacta gccttcacgt
40501 ccggaactcg taacatagct tagaccagcg gacggacgca acgtacgtgg ggatcggctg
40561 gcggtgtctg ctcgttggac gcggccgttc ggtggcgcca gtgcaggcct agtttgcgaa
40621 tggcgtgacg gacaatttgt ggctttagag cggcgaaccg atgacccgtg gtggcgacga
40681 acgaaatgaa gtttgcattg cggcccaact cgtctagcct ggtcttcttg tttcgggcat
40741 agattttcgg gattaggtta cactttttat atcccagtac tgcgcactcg tgtttgcttt
40801 tagtgtgact gattatcttc tttgagaagt caaacaggcc ccgggcggcg gctcgcctaa
40861 tgcaagccac gtcaagcctg agaaacgaac agcattccac cagacactcc aggaaccttt
40921 tgtgtagcgt ctgtatttgg gaacggtttc tgtgctcaag tagggagaat attctatttt
40981 tgtttccgtc gatgcgcgcg tgctggtccg tgagaatggg cgccagctcg tggcgaatct
41041 gttccacaag aggctgcccg tacactttag aaatcgtggc tgtcgcggcc ttaaaccagg
41101 acacgtttag cccatccttg ctggagacca cagatggaaa gtttgtggtc caaaatacgt
41161 tttttcgccc cattctcacc atgtactggt tttccagtcc gtgcaggtcc aacgtggagt
41221 tccaatttgc tatcgataca ggaaatatgt gcctgattgg cagaaagcat ttcagcgtac
41281 ccattgcgaa gagaaagtgc agcatgtccc cactgatgtt gatgtttatt gcggtgcctt
41341 gacacatgtt gtcggaaaaa aacacgctta tggtaaaaga aggttccttt acggagtact
41401 ttcgtataac aaaattgttg gtcaatctgg ggatgtttaa aatagtcttt tgcagggtgt
41461 taggaacgtg gcagcttatc ttagtgttaa tcaccatgtt ggtgttgaat atggtgatct
41521 tgaagttttc caaactgacg tgttttgtgg gttccagcat gtctgacact gtagagctgc
41581 ccagagtccg cgcgtccgtg gccgcgtatc gttggaagca cgcctgcaaa tttcctttca
41641 tggctgctcg ccggtctttc ggcgcgtacc ggattcttga aagcgtcgcc gccaggagac
41701 gcggtgtctc gtgggtgcct aaaaagtttg cgcaggggtg cagtccgctg cacgagtggc
41761 cgatgcagtc tgccactgcc atacacatga cgagtctgta gatggccggt gtgcccggat
41821 acactagata gtaggtacaa tctggggtac tgacgaccac cctgtatggc tttggtccgg
41881 ggtccttgcg ttggattttt acgtgcagac gggacacgag ctggtttaga gccagctgaa

Fig. 3 (cont.)

41941 agcccaccag atcccgtccg ttaaccttga cgtcctggtg cttactctgt ttcgacaggt
42001 tcttcagcac ggtgggcagt cgctctacgt tgtgagcgat ggcacggcgc agcgagacca
42061 gctctccgtg ccaccccac gtggccatga agctgctgat gttaaacttt aaaaaatgta
42121 gctgtgcgtc tggggatgcg ggtggcatta ttgaaaacga gagatgcttc aggctctcca
42181 ggagtgcaaa ataattttga tagattgtgg gttgtagact atggggcaac accgccagaa
42241 acgcatgaaa acactgttcg aactcccaga actccaggta cctgcacact atcctgaaca
42301 tggctttgta acatatggtg cacgttagta gcgcgggaag atacagcgag cgtagctccc
42361 tgaattcgca gggtttatca caatcatcgg taagttccca tgatcccacc gcaggtaggt
42421 agttgtcggt gtctatctgt ccgcgcgtaa acactccacc accgtcaatt attaaacctt
42481 cgccgctgta ccgtcgaccc acttttccca aaagagtccc ttcttgatgt ataaaagggt
42541 ggaggcgttc ccccaggagt agtctgcgta tcgctctgca ggcgaaaaag gtgggctcgg
42601 gctgcatcat cttatcaaga ccttctaagg tcagctctgc ctgcaggtgc gagttggtgg
42661 ccagacagca gaatatttcc agctgtgatt cccaagtcgc ttgataacac gtggtctgcg
42721 gactcgtcgt cagggaggcg ctcggtggca gtagtagggg gccctcgagc gctgccatgg
42781 aggcgacctt ggagcaacga cctttcccgt acctcgccac ggaggccaac ctcctaacgc
42841 agattaagga gtcggctgcc gacggactct tcaagagctt tcagctattg ctcggcaagg
42901 acgccagaga aggcagtgtc cgtttcgaag cgctactggg cgtatatacc aatgtggtgg
42961 agtttgttaa gtttctggag accgccctcg ccgccgcttg cgtcaatacc gagttcaagg
43021 acctgcggag aatgatagat ggaaaaatac agtttaaaat ttcaatgccc actattgccc
43081 acggagacgg gaggaggccc aacaagcaga gacagtatat cgtcatgaag gcttgcaata
43141 agcaccacat cggtgcggag attgagcttg cggccgcaga catcgagctt ctcttcgccg
43201 agaaagagac gcccttggac ttcacagagt acgcgggtgc catcaagacg attacgtcgg
43261 ctttgcagtt tggtatggac gccctagaac gggggttagt ggacacggtt ctcgcagtta
43321 aacttcggca cgctccaccc gtctttattt taaagacgct gggcgatccc gtctactctg
43381 agaggggcct caaaaaggcc gtcaagtctg acatggtatc catgttcaag gcacacctca
43441 tagaacattc attttttcta gataaggccg agctcatgac aagggggaag cagtatgtcc
43501 taaccatgct ctccgacatg ctggccgcgg tgtgcgagga taccgtcttt aagggtgtca
43561 gcacgtacac cacggcctct gggcagcagg tggccggcgt cctggagacg acggacagcg
43621 tcatgagacg gctgatgaac ctgctggggc aagtggaaag tgccatgtcc gggcccgcgg
43681 cctacgccag ctacgttgtc aggggtgcca acctcgtcac cgccgttagc tacggaaggg
43741 cgatgagaaa ctttgaacag tttatggcac gcatagtgga ccatcccaac gctctgccgt
43801 ctgtggaagg tgacaaggcc gctctggcgg acggacacga cgagattcag agaacccgca
43861 tcgccgcctc tctcgtcaag ataggggata agtttgtggc cattgaaagt ttgcagcgca
43921 tgtacaacga gactcagttt ccctgcccac tgaaccggcg catccagtac acctatttct
43981 tccctgttgg ccttcacctt cccgtgcccc gctactcgac atccgtctca gtcaggggcg
44041 tagaatcccc ggccatccag tcgaccgaga cgtgggtggt taataaaaac aacgtgcctc
44101 tttgcttcgg ttaccaaaac gccctcaaaa gcatatgcca ccctcgaatg cacaacccca
44161 cccagtcagc ccaggcacta aaccaagctt ttcccgatcc cgacggggga catgggtacg
44221 gtctcaggta tgagcagacg ccaaacatga acctattcag aacgttccac cagtattaca

Fig. 3 (cont.)

44281 tggggaaaaa cgtggcattt gttcccgatg tggcccaaaa agcgctcgta accacggagg
44341 atctactgca cccaacctct caccgtctcc tcagattgga ggtccacccc ttctttgatt
44401 tttttgtgca cccctgtcct ggagcgagag gatcgtaccg cgccacccac agaacaatgg
44461 ttggaaatat accacaaccg ctcgctccaa gggagtttca ggaaagtaga ggggcgcagt
44521 tcgacgctgt gacgaatatg acacacgtca tagaccagct aactattgac gtcatacagg
44581 agacggcatt tgaccccgcg tatcccctgt tctgctatgt aatcgaagca atgattcacg
44641 gacaggaaga aaaattcgtg atgaacatgc ccctcattgc cctggtcatt caaacctact
44701 gggtcaactc gggaaaactg gcgtttgtga acagttatca catggttaga ttcatctgta
44761 cgcatatggg gaatggaagc atccctaagg aggcgcacgg ccactaccgg aaaatcttag
44821 gcgagctcat cgcccttgag caggcgcttc tcaagctcgc gggacacgag acggtgggtc
44881 ggacgccgat cacacatctg gtttcggctc tcctcgaccc gcatctgctg cctccctttg
44941 cctaccacga tgtctttacg gatcttatgc agaagtcatc cagacaaccc ataatcaaga
45001 tcggggatca aaactacgac aaccctcaaa atagggcgac attcatcaac ctcaggggtc
45061 gcatggagga cctagtcaat aaccttgtta acatttacca gacaagggtc aatgaggacc
45121 atgacgagag acacgtcctg gacgtggcgc ccctggacga gaatgactac aaccccggtcc
45181 tcgagaagct attctactat gttttaatgc cggtgtgcag taacggccac atgtgcggta
45241 tgggggtcga ctatcaaaac gtggccctga cgctgactta caacggcccc gtctttgcgg
45301 acgtcgtgaa cgcacaggat gatattctac tgcacctgga gaacggaacc ttgaaggaca
45361 ttctgcaggc aggcgacata cgcccgacgg tggacatgat cagggtgctg tgcacctcgt
45421 ttctgacgtg ccctttcgtc acccaggccg ctcgcgtgat cacaaagcgg gacccggccc
45481 agagttttgc cacgcacgaa tacgggaagg atgtggcgca gaccgtgctt gttaatggct
45541 ttggtgcgtt cgcggtggcg gaccgctctc gcgaggcggc ggagactatg ttttatccgg
45601 taccctttaa caagctctac gctgacccgt tggtggctgc cacactgcat ccgctcctgg
45661 caaactatgt caccaggctc cccaaccaga gaaacgcggt ggtctttaac gtgccatcca
45721 atctcatggc agaatatgag gaatggcaca agtcgcccgt cgcggcgtat gccgcgtctt
45781 gtcaggccac cccgggcgcc attagcgcca tggtgagcat gcaccaaaaa ctatctgccc
45841 ccagtttcat ttgccaggca aaacaccgca tgcaccctgg ttttgccatg acagtcgtca
45901 ggacggacga ggttctagca gagcacatcc tatactgctc cagggcgtcg acatccatgt
45961 ttgtgggctt gccttcggtg gtacggcgcg aggtacgttc ggacgcggtg acttttgaaa
46021 ttacccacga gatcgcttcc ctgcacaccg cacttggcta ctcatcagtc atcgccccgg
46081 cccacgtggc cgccataact acagacatgg gagtacattg tcaggacctc tttatgattt
46141 tcccagggga cgcgtatcag gaccgccagc tgcatgacta tatcaaaatg aaagcgggcg
46201 tgcaaaccgg ctcaccggga aacagaatgg atcacgtggg atacactgct ggggttcctc
46261 gctgcgagaa cctgcccggt ttgagtcatg gtcagctggc aacctgcgag ataattccca
46321 cgccggtcac atctgacgtt gcctatttcc agaccccag caacccccgg gggcgtgcgg
46381 cgtgcgtggt gtcgtgtgat gcttacagta acgaaagcgc agagcgtttg ctctacgacc
46441 attcaatacc agaccccgcg tacgaatgcc ggtccaccaa caacccgtgg gcttcgcagc
46501 gtggctccct cggcgacgtg ctatacaata tcacctttcg ccagactgcg ctgccgggca
46561 tgtacagtcc ttgtcggcag ttcttccaca aggaagacat tatgcggtac aataggggggt

Fig. 3 (cont.)

46621 tgtacacttt ggttaatgag tattctgcca ggcttgctgg ggccccgcc accagcacta
46681 cagacctcca gtacgtcgtg gtcaacggta cagacgtgtt tttggaccag ccttgccata
46741 tgctgcagga ggcctatccc acgctcgccg ccagccacag agttatgctt gacgagtaca
46801 tgtcaaacaa gcagacacac gccccagtac acatgggcca gtatctcatt gaagaggtgg
46861 cgccgatgaa gagactatta aagctcggaa acaaggtggt gtattagcta accettctag
46921 cgttggctag tcatggcact cgacaagagt atagtggtta acttcacctc cagactcttc
46981 gctgatgaac tggccgccct tcagtcaaaa atagggagcg tactgccgct cggagattgc
47041 caccgtttac aaaatataca ggcattgggc ctggggtgcg tatgctcacg tgagacatct
47101 ccggactaca tccaaattat gcagtatcta tccaagtgca cactcgctgt cctggaggag
47161 gttcgcccgg acagcctgcg cctaacgcgg atggatccct ctgacaacct tcagataaaa
47221 aacgtatatg ccccctttt tcagtgggac agcaacaccc agctagcagt gctaccccca
47281 tttttagcc gaaaggattc caccattgtg ctcgaatcca acggatttga cctcgtgttc
47341 cccatggtcg tgccgcagca actggggcac gctattctgc agcagctgtt ggtgtaccac
47401 atctactcca aaatatcggc cggggccccg gatgatgtaa atatggcgga acttgatcta
47461 tataccacca atgtgtcatt tatggggcgc acatatcgtc tggacgtaga caacacggat
47521 ccacgtactg ccctgcgagt gcttgacgat ctgtccatgt acctttgtat cctatcagcc
47581 ttggttccca gggggtgtct ccgtctgctc acggcgctcg tgcggcacga caggcatcct
47641 ctgacagagg tgtttgaggg ggtggtgcca gatgaggtga ccaggataga tctcgaccag
47701 ttgagcgtcc cagatgacat caccaggatg cgcgtcatgt tctcctatct tcagagtctc
47761 agttctatat ttaatcttgg ccccagactg cacgtgtatg cctactcggc agagactttg
47821 gcggcctcct gttggtattc cccacgctaa cgatttgaag cgggggggg gtatggcgtc
47881 atctgatatt ctgtcggttg caaggacgga tgacggctcc gtctgtgaag tctccctgcg
47941 tggaggtagg aaaaaaacta ccgtctacct gccggacact gaaccctggg tggtagagac
48001 cgacgccatc aaagacgcct tcctcagcga cgggatcgtg gatatggctc gaaagcttca
48061 tcgtggtgcc ctgccctcaa attctcacaa cggcttgagg atggtgcttt tttgttattg
48121 ttacttgcaa aattgtgtgt acctagccct gtttctgtgc ccccttaatc cttacttggt
48181 aactccctca agcattgagt ttgccgagcc cgttgtggca cctgaggtgc tcttcccaca
48241 cccggctgag atgtctcgcg gttgcgatga cgcgatttc tgtaaactgc cctataccgt
48301 gcctataatc aacaccacgt ttggacgcat ttacccgaac tctacacgcg agccggacgg
48361 caggcctacg gattactcca tggcccttag aagggctttt gcagttatgg ttaacacgtc
48421 atgtgcagga gtgacattgt gccgcggaga aactcagacc gcatcccgta accacactga
48481 gtgggaaaat ctgctggcta tgttttctgt gattatctat gccttagatc acaactgtca
48541 cccggaagca ctgtctatcg cgagcggcat ctttgacgag cgtgactatg gattattcat
48601 ctctcagccc cggagcgtgc cctcgcctac cccttgcgac gtgtcgtggg aagatatcta
48661 caacgggact tacctagctc ggcctggaaa ctgtgacccc tggcccaatc tatccacccc
48721 tcccttgatt ctaaatttta aataaaggtg tgtcactggt tacaccacga ttaaaaacca
48781 ctcactgaga tgtcttttta accgctaagg gattataccg ggatttaaaa ccgcccactg
48841 attttttac gctaagagtt gggtgcttgg ggggttttgc attgctctgt tgtaaactat
48901 atataagtta aaccaaaatt cgcagggaga caaggtgacg gtggtgagaa ctcagttgag

Fig. 3 (cont.)

48961 agtcagagaa tacagtgcta atcagggtag atgagcatga cttccccgtc tccagtcacc
49021 ggaggaatgg tggacggctc cgtcctggtg cgaatggcca ccaagcctcc cgtgattggt
49081 cttataacag tgctcttcct cctagtcata ggcgcctgcg tctactgctg cattcgcgtg
49141 ttcctggcgg ctcgactgtg gcgcgccacc ccactaggca gggccaccgt ggcgtatcag
49201 gtccttcgca ccctgggacc gcaggccggg tcacatgcac cgccgacggt gggcatagct
49261 acccaggagc cctaccgtac aatatacatg ccagattaga acggggtgtg tgctataatg
49321 gatggctatg ggggggctgt agataattga gcgctgtgct tttattgtgg ggatatgggc
49381 ttgtacatgt gtctatcatc ggtagccata aaatgggcca tgacaactgc cacaagtaag
49441 tcgtccgaca tgtgcttttg cttggcgctg tatgactgcc ctccatccct aagcgggacg
49501 cacttgatcg cgcggacctg ttctaccagg taggtcaccg ggtcaaatga tattttgatg
49561 gtgttggaca ccaccgtctg gctggcgctc agggtgccgg agttcagagc gtagatgaat
49621 gtctcaaacg cggaggattt ctcgcctccc aacatgtaaa ttggccactg cagggcgctg
49681 ctcttgtcag tatagtgtag aaaatgtatg gggagcgggc atatttcgtt aaggacggtt
49741 gcaatggcca ccccagaatc ttggctgctg ttgccttcga ccgccgcgtt cacgcgctca
49801 attgtggggt ggagcacagc gatcgcctta atcatcgtgc atgcgcagga cgctatctcg
49861 taagcagctg cgccagtgag gtcgcgcagg aagaaatgct ccatgcccaa tatgaggctt
49921 ctggtgggag tctgagtact cgtgacaacg gcgcccacgc cagtaccgga cgcctccgtg
49981 ttgttcgtat acgcggggtc gatgtaaaca aacagctgtt ttccaaggca cttctgaacc
50041 tgctgggcgg tggtgtctac ccgacacatg tcaaactgtg tcagcgctgc gtcacccacc
50101 acgcggtaaa gcgtagcatt tgacgacgct gctccctcgc ccattagttc ggtgtcgaat
50161 gccccctcca taaagaggtt ggtggtggtt ttgatggatt cgtcgatggt gatgtacgtc
50221 ggaatgtgca gtctgtaaca aggacaggac actagtgcgt cttgcaggtg gaaatcttcg
50281 cggtggtccg cacacacgta actgaccaca ttcagcatct tttcctgggc gttcctgagg
50341 ttaagcagga aactcgtgga gcggtctgac gagttcacgg atgatataaa tataagcttg
50401 gcgtctttct gaagcatgaa acccagaata gccggcagtg catccttttt aataaaattc
50461 gcctcgtcta cgtagagcag gttaaaggtc tgtccccgaa tgctctgcag acacggaaag
50521 acacaaaaga ggggctcata agcggctaac agtaaaggag aggaggcgaa cagtgcgtgg
50581 ctcttgttct tgggaataaa agggggcgtg tgtgccgatc gtatgggtga gccagtggat
50641 cctggacatg tggtgaatga gaaagatttt gaggagtgtg aacaattttt cagtcaaccc
50701 cttagggagc aagtggtcgc gggggtcagg gcactcgacg gcctcggtct cgctgactct
50761 ctatgtcaca aaacagaaag actctgcctg ctgatggacc tggtgggcac ggagtgcttt
50821 gcgagggtgt gccgcctaga caccggtgcg aaatgaagag tgtggcgagt cccttatgtc
50881 agttccacgg cgtgttttgc ctgtaccagt gtcgccagtg cctggcatac cacgtgtgtg
50941 atgggggcgc cgaatgcgtt ctcctgcata cgccggagag cgtcatctgc gaactaacgg
51001 gtaactgcat gctcggcaac attcaagagg gccagttttt agggccggta ccgtatcgga
51061 ctttggataa ccaggttgac agggacgcat atcacgggat gctagcgtgt ctgaaacggg
51121 acattgtgcg gtatttgcag acatggccgg acaccaccgt aatcgtgcag gaaatagccc
51181 tgggggacgg cgtcaccgac accatctcgg ccattataga tgaaacattc ggtgagtgtc
51241 ttcccgtact gggggaggcc caaggcgggt acgccatggt ctgtagcatg tatctgcacg

Fig. 3 (cont.)

51301 ttatcgtctc catctattcg acaaaaacgg tgtacaacag tatgctattt aaatgcacaa
51361 agaataaaaa gtacgactgc attgccaagc gggtgcggac aaaatggatg cgcatgctat
51421 caacgaaaga tacgtaggtc ctcgctgcca ccgtttggcc cacgtggtgc tgcctaggac
51481 ctttctgctg catcacgcca tacccctgga gcccgagatc atcttttcca cctacacccg
51541 gttcagccgg tcgccagggt catcccgccg gttggtggtg tgtgggaaac gtgtcctgcc
51601 aggggaggaa aaccaacttg cgtcttcacc ttctggcttg gcgcttagcc tgcctctgtt
51661 ttcccacgat gggaactttc atccatttga catctcggta ctgcgcattt cctgccctgg
51721 ttctaatctt agtcttactg tcagatttct ctatctatct ctggtggtgg ctatgggggc
51781 gggacggaat aatgcgcgga gtccgaccgt tgacggggta tcgccgccag agggcgccgt
51841 agcccaccct ttggaggaac tgcagaggct ggcgcgtgct acgccggacc cggcactcac
51901 ccgtggaccg ttgcaggtcc tgaccggcct tctccgcgca gggtcagacg gagaccgcgc
51961 cactcaccac atggcgctcg aggctccggg aaccgtgcgt ggagaaagcc tagacccgcc
52021 tgtttcacag aaggggccag cgcgcacacg ccacaggcca ccccccgtgc gactgagctt
52081 caaccccgtc aatgccgatg tacccgctac ctggcgagac gccactaacg tgtactcggg
52141 tgctccctac tatgtgtgtg tttacgaacg cggtggccgt caggaagacg actggctgcc
52201 gataccactg agcttcccag aagagcccgt gcccccgcca ccgggcttag tgttcatgga
52261 cgacttgttc attaacacga agcagtgcga ctttgtggac acgctagagg ccgcctgtcg
52321 cacgcaaggc tacacgttga gacagcgcgt gcctgtcgcc attcctcgcg acgcggaaat
52381 cgcagacgca gttaaatcgc actttttaga ggcgtgccta gtgttacggg ggctggcttc
52441 ggaggctagt gcctggataa gagctgccac gtccccgccc cttggccgcc acgcctgctg
52501 gatggacgtg ttaggattat gggaaagccg cccccacact ctaggtttgg agttacgcgg
52561 cgtaaactgt ggcggcacgg acggtgactg gttagagatt ttaaaacagc ccgatgtgca
52621 aaagacagtc agcgggagtc ttgtggcatg cgtgatcgtc acacccgcat tggaagcctg
52681 gcttgtgtta cctgggggtt ttgctattaa aggccgctat agggcgtcga aggaggatct
52741 ggtgttcatt cgaggccgct atggctagcc ggaggcgcaa acttcggaat ttcctaaaca
52801 aggaatgcat atggactgtt aacccaatgt caggggacca tatcaaggtc tttaacgcct
52861 gcacctctat ctcgccggtg tatgaccctg agctggtaac cagctacgca ctgagcgtgc
52921 ctgcttacaa tgtgtctgtg gctatcttgc tgcataaagt catgggaccg tgtgtggctg
52981 tgggaattaa cggagaaatg atcatgtacg tcgtaagcca gtgtgtttct gtgcggcccg
53041 tcccggggcg cgatggtatg gcgctcatct actttggaca gtttctggag gaagcatccg
53101 gactgagatt tccctacatt gctccgccgc cgtcgcgcga acacgtacct gacctgacca
53161 gacaagaatt agttcatacc tcccaggtgg tgcgccgcgg cgacctgacc aattgcacta
53221 tgggtctcga attcaggaat gtgaaccctt ttgtttggct cgggggcgga tcggtgtggc
53281 tgctgttctt gggcgtggac tacatggcgt tctgtccggg tgtcgacgga atgccgtcgt
53341 tggcaagagt ggccgccctg cttaccaggt gcgaccaccc agactgtgtc cactgccatg
53401 gactccgtgg acacgttaat gtatttcgtg ggtactgttc tgcgcagtcg ccgggtctat
53461 ctaacatctg tccctgtatc aaatcatgtg ggaccgggaa tggagtgact agggtcactg
53521 gaaacagaaa ttttctgggt cttctgttcg atcccattgt ccagagcagg gtaacagctc
53581 tgaagataac tagccaccca acccccacgc acgtcgagaa tgtgctaaca ggagtgctcg

Fig. 3 (cont.)

53641 acgacggcac cttggtgccg tccgtccaag gcaccctggg tcctcttacg aatgtctgac
53701 tacttcagcc gcttgctgat atatgagtgt aaaaaactta aggccctggg cttacgttct
53761 tattgaagca tgttgcgcac atcagcgagc tggaccgtcc tccgggtcgc gtgtagatta
53821 tggttccgtt ctccttcttg atgtttaaat ttttgggggg gaaccaccga caaagcgtct
53881 ttatgatttc cgcgaacacg gagttggcta cgtgcttttg gtgggctacg tacccaatgt
53941 taatgttctc tacggatgcc agtagcatgc tgatgatcgc caccactatc catgtctttc
54001 cgtgtctcct tggtattagg aatacgcttg ccttttgctt aaacgtctgt aaaacactgt
54061 ttggagtttc aaataaaccg aagtactgct taaacaatcc aaacaactgg tgcgtctttt
54121 gtggggcctt gattgaaacc aaaaagaaaa aagtgtgcat tactagctgc tgttggaagg
54181 gctccagcca gtgcaccccg ggaacgtaac agccgttcag aaaggacgaa aggttaacca
54241 gaaaagcctg aagttcgcgg tagacagagc aggcgtgcag ggagtcgtgt gtttttctgg
54301 ccgcctggta ctcgaccagt tgatcggccg tggagacgtg cgcgtcctcg cgcacacacc
54361 gcatctgcaa gtatgttgat agggactcca ataggcgcgg ctttgcgggg acgttgtcct
54421 cggacggtct gggggttccc acgtcgggat ttgctgacgt gggcgtggcg ggatggtgcc
54481 gtgtgcagta tgtttccagg accgaactgt atgagtttat tctgtgcacc acgccaataa
54541 aagggtgcgc catccgtgcc gttttgggac agtgtcgcgt gaatgtcggg gcactcagtt
54601 cccacctctc tccggcgtct ttggcggtct cctgcaggtt ggcggcaagg cgctccctgt
54661 gacggctgag cagcatgttt gctttgagct cgctcgtgtc cgagggtgac ccggaggtga
54721 ccagtaggta cgtcaagggc gtacaacttg ccctggacct tagcgagaac acacctggac
54781 aatttaagtt gatagaaact cccctgaaca gcttcctctt ggtttccaac gtgatgcccg
54841 aggtccagcc aatctgcagt ggccggccgg ccttgcggcc agactttagt aatctccact
54901 tgcctagact ggagaagctc cagagagtcc tcgggcaggg tttcggggcg gcgggtgagg
54961 aaatcgcact ggacccgtct cacgtagaaa cacacgaaaa gggccaggtg ttctacaacc
55021 actatgctac cgaggagtgg acgtgggctt tgactctgaa taaggatgcg ctccttcggg
55081 aggctgtaga tggcctgtgt gaccccggaa cttggaaggg tcttcttcct gacgaccccc
55141 ttccgttgct atggctgctg ttcaacggac ccgcctcttt ttgtcgggcc gactgttgcc
55201 tgtacaagca gcactgcggt tacccgggcc cggtgctact tccaggtcac atgtacgctc
55261 ccaaacggga tcttttgtcg ttcgttaatc atgccctgaa gtacaccaag tttctatacg
55321 gagatttttc cgggacatgg gcggcggctt gccgcccgcc attcgctact tctcggatac
55381 aaagggtagt gagtcagatg aaaatcatag atgcttccga cacttacatt tcccacacct
55441 gcctcttgtg tcacatatat cagcaaaata gcataattgc gggtcagggg acccacgtgg
55501 gtggaatcct actgttgagt ggaaaaggga cccagtatat aacaggcaat gttcagaccc
55561 aaaggtgtcc aactacgggc gactatctaa tcatcccatc gtatgacata ccggcgatca
55621 tcaccatgat caaggagaat ggactcaacc aactctaaaa gagagtttat taagtcggct
55681 ctggaggcca acatcaacag gagggcagct gtatcgctat ttgatcgttt tgggggtagc
55741 agcgccgtgt ttgagaagca gtttcaggac gcacagcatg ccgtcagggc ccacggtgca
55801 ctgaagcgcg aagccgagct cgggactctg gtacgcaagg cgggccagag gtttgaggcg
55861 ctgaaaaggg aacggtcaat tttgcgccag ccgcgcgacc tcccacgggt cgccgacatt
55921 gacgccctgg tcgacgccgt cgcggacctc aaagaagagg tggccgtgcg cctagatgcg

Fig. 3 (cont.)

55981 ctggaagaga atggagagga gacccccact cactcctctt cggagatcaa ggacacaatc
56041 gtcaggtgga ggcttgacga tttgcccccg gtgtgccctg aaactcccta aggctacccg
56101 gatttcagag agaccctggg cgtccacatg gcagctgaat cagcatatac aggtgtccaa
56161 gactaaaaag gccaccgcgt atcttaaagc gccccgtgaa tgggggcagt gcacgcacca
56221 ggatccagac tggtccaagc gtctgggtcg tggcgccttt ggcataatcg tccctatctc
56281 cgaggatctg tgtgtgaagc agtttgatag ccgccgggag tttttctacg aggcaattgc
56341 caacgacctg atgcaggcca cccgagagag gtaccccatg cattctggtg gatctagact
56401 gctaggattc gtgcagcctt gcataccctg tagatcgatt gtgtatccta gaatgaagtg
56461 caacctgctg cagctggact ggagtcaggt caacctgagt gtcatggcgg cggagttcac
56521 cggcctaatg gcggcggtgt cctttctaaa cagatactgt ggcatggtgc actgcgacgt
56581 tagtccagac aatattttgg ccacaggaga cctaacgccc atgaaccccg ggaggctggt
56641 ccttaccgat ttcggttccg ttgcgctaca ctctgggagc aagtggacta accttgtggt
56701 gacctctaac ctggggttta agcaacactg ctacgacttc agggtgccac ccaaactcat
56761 ttgtaagcat ctctataagc cgtcttgcgt cctcttccag tgttacctat ccagtctcgg
56821 taagatgcac gcgcaggtat tggaccaacc gtaccctatc agccctaaca tgggactgac
56881 catcgacatg tcctcgttgg gctacactct gctgacatgc ctggaactct atctcgatct
56941 gccgctaaac aaccctctga agttcttggg ttcagccacc agagacggac gccccgaacc
57001 catgtactac ttgggcttca tgattcccag ggtggtgatg actcagatcc tgtccgctgt
57061 gtggaccatg acgcttgacc tgggactaga ttgcaccggc aaagcccagg cgattcccat
57121 gcgacaggag caccagctgg cgtttcagaa gcagtgctat ttatataaag ccaaccaaaa
57181 ggcagagtcg ttagcgaact gctccgataa gctaaactgc cccatgttaa agtctctcgt
57241 tagaaagcta ctagagcgag actttttcaa ccatggaggc cacccccaca cccgcggact
57301 tgttttctga agactatctg gttgacaccc tggatgggtt aacagtggat gaccaacagg
57361 ctgtcctcgc aagcttgagc ttttcaaagt ttctaaagca cgccaaggtt cgagactggt
57421 gcgcacaggc caagatccaa cccagcatgc ctgcgctgcg catggcttac aactatttcc
57481 tttttcaaa agtgggcgag tttattggta gtgaggatgt gtgtaacttt ttcgtggacc
57541 gtgtgtttgg tggtgtcagg ttactggacg tggccagcgt gtacgccgcc tgttcgcaaa
57601 tgaacgcaca tcagcggcac cacatctgct gtctagtgga gagggccact agtagtcaga
57661 gtctgaaccc cgtgtgggac gccctgcgag acggaattat atcttcatcc aagtttcact
57721 gggcagttaa acaacagaac acttcaaaaa agatattcag cccatggcct ataacgaaca
57781 accactttgt cgcgggcccg cttgcctttg ggctgcggtg cgaggaggtg gtgaaaacgt
57841 tgctggccac ccttttgcac ccggacgaga caaattgtct cgattatggg tttatgcaga
57901 gtccgcaaaa tggaatattt ggcgtgtcgc tggatttcgc ggcgaacgtc aaaactgaca
57961 ccgagggtcg tctacagttt gaccctaact gtaaagtgta tgaaataaaa tgcaggttca
58021 agtacacctt tgcgaaaatg gagtgtgacc ccatatacgc cgcgtatcag cggctgtacg
58081 aggcacccgg aaagctggca ctgaaggact tcttctatag catttccaag cctgcggttg
58141 agtacgtggg acttggaaaa ctgcccagtg aatctgatta cttggtggct tatgatcagg
58201 aatgggaggc gtgtcctcgc aaaaagagga aattaacgcc ccttcacaat cttattaggg
58261 agtgtatttt gcacaactcg accacggagt ctgacgtcta cgtacttact gatcctcaag

Fig. 3 (cont.)

58321 atactcgggg tcaaatcagt attaaagccc gcttcaaagc caacctcttc gtgaacgtcc
58381 gtcacagcta cttttatcag gtattgctgc agagttcgat cgtcgaggag tacattggcc
58441 tagatagcgg cattcctcgc ctcggatcac cgaaatacta catcgccacc ggcttcttca
58501 gaaagcgggg ctatcaggat cctgtcaact gtaccatcgg tggcgatgct ttagacccgc
58561 acgtggagat tcctacgctg ctaatcgtaa cccccgtcta ctttccccga ggcgcaaagc
58621 atcgtctgct tcaccaagct gccaactttt ggtcaagaag tgcgaaggac acctttccat
58681 atatcaaatg ggatttctcc tatctatctg caaacgtccc tcacagcccg tagacgtgga
58741 cggggaaccg ctcgacgtag tcgtggacta tgaccccatt cgcgtttcag aaaagggcat
58801 gttgcttgag caatcgcaat ccccatatcc cgcattaaaa aagaagaaaa aaaataaaga
58861 agcaatttat taagcaaaca gtatggtttt ctgtacgtat tttattccgt ggtgggtgaa
58921 aaataacggg ggatggagga agagggatgg gtttataatg ccaatatatc agctaaatga
58981 atatcatttg cgtttcgtcg atttcactgt cactttcatg gtcggactgg tattgggtcc
59041 tcggggcggg cgtcgatatg tccttcactt tggcgcgggc tctggtcttt gctgggaggg
59101 gcggcggttt ctggtgaaca gtcggagttc tatcgaccgt cggcgccgac gtcgccagag
59161 gcatgtatgc cgcactcggc gtacagagtc cccagtcgct ccttataacg cgtataacga
59221 tggctaggat gcacagtata gggatacagg agatattgat agccactatg tagtggagat
59281 tagcctgcac gaacgcgttt tcatacctga tgacaggcag cagtagaatc agataaccca
59341 ccaatactcc cacgtaaaag cctacctgcc gtctcataaa ctttaccagg aaaaattccg
59401 tgtttatgta ccacacgacc gtcaaggcta ggaacatgtt caccgcacca aaaatggcgt
59461 ctgacacgag cacgtaaaag ctgttgccaa cggccatcat ggtgctcaat gaaaacagca
59521 gcatttccaa ggcggttgtt gataggtaca ggttgacgca gaccggtttc caccgagtca
59581 gcagtgactc catcatggta ttatcaggta cgtgctgttc caggagaggt atttcccact
59641 gggcggagtt acatgttatc agtgactgga tgtgggcaaa ggatatgcaa aaatgaatgc
59701 agtagacaaa ggctgccata agtacgtgtt tatatgacag aacatggata aacagttgca
59761 tgctccacat ccttaagatg gcgacataaa gcacgctatg tgatccaagt agcgctatcc
59821 aggattgcat gctcatcatg gtagtggcgt gaacatgctt ggcccgatat acggccaccg
59881 ccgcgagaca gtagtatact atggcaatgc cgtccacgat aaaagtccaa aatatgtaca
59941 ccagcatctc tggtttctct aaaaacaggg tcggggtgag gtgcttcgct gagttgcgca
60001 ccgtgaggtt tagcgcgctg tagtttacca gattgttgaa gtagcagggg aaaccaaggc
60061 cctcgtacgt ggcggccatg ggcacgactg cagagcaaat gtacataatt acagccacaa
60121 acaacagctt gacccaggag gacatgagaa aacggtcgct ctttgaagcg cgcatgtttc
60181 tcggtctttt taactttcgc caggcggcgc tgcggcggga gagccaatct gatgccactg
60241 cctatcgcgg ttgactttta aatacgcgcc ccgggcagaa gccagaggta gtcgactcat
60301 tgactcaatg gcaacgagcg aagaaacggc ggccggttat gtcatcggtg tctactttca
60361 cagcgttcac gtccactgcc gcattattgt ctggcaggtt aattttctac ccctggaccc
60421 aaacgacggg gagactgaat gctactttgt ggtggacacg ctgacgaaag aggcgatgga
60481 gcgcatgccc gaaatccagg aatgcgtccc gtctattact gaacacgccc gtgacctggc
60541 gatctgggag ttggcgctgc gactgcagaa tcagacgatc gtcaaggccg tccggacagc
60601 gtcgcttccg gtggttctaa ttatgactgt gggtcgcata gtgaatgatg tgattccctg

Fig. 3 (cont.)

60661 ccccaacgtc agaacaccca gaccactagc ctgtgcttac ctacactgtg aggcgacggt
60721 gacctttgag gtcccactaa ccgggcccgc ggcgtccacc ggaacgtggc acagctctat
60781 ctatagggaa tgtgcgatct cggctatcga gatatgcttg aagaccagtc gaggcatata
60841 ctcctgccag tcgaacgagg cccctgaggc caagagggaa aagcgaggtt tagacatatc
60901 agatgtgttt gtctgtctca cgtatgatat ccctatcgca gggcgggtcc tttctctgct
60961 ggtgccccac gcgcccgctt ttcacgtctt atggatcaat gaggacagca agtggaacgg
61021 ggcagccgtc gaatttttca gagccctaca ccataagctg ttcagtgaac gcaatggtat
61081 aaccccctctg tggttgtacg tgttcccggg agctgtggaa gagggcacag cctttgcgcc
61141 attacttccc gcattccctt gcataccttt gcggtatggg tcgcctacct ctctggacag
61201 ggcgtccgtg cagtgggacc tatttgaacc gcacatcctg acccactttg acgggataaa
61261 gcgaacttct ttggcagata cagtgtttgg gtacgactcc ctggccattt caagggaatg
61321 tgaagatcag tatgtgtggc ccacgcctgt cactgacatt aatattaatt tgtgcacgga
61381 tagtgacact atggccatcg ttagagaacc atccggtctg gtggccgtga atctagaagc
61441 cctgttgcgc accgactccg tattatcgcg ggtctcgtcc attgtctcac tcgatacgct
61501 cttggacctt tccaccccgg agtgccgtag gagcgtggag cttagataca actcactttt
61561 gtcgactgta ttatcatggt ccacctctag ggtcacaaa tgggccgcaa tcgtgaagtg
61621 gaagttattt ttcctcgtcc aagctttgga gcctgaggtg agacctactg tccctgcttg
61681 aagcggagag ggggtggtgc gagttggcag ttgacgggtt tgtgatagct ggagtgctga
61741 ccacggcaca ggacccatta actttcctat gtgtttattt ttagcaatgg tctccagaat
61801 tcaaggatct caaaagggcc tgccagatgg ccgggtttac tctgaagggg gggacttcgg
61861 gggatcttgt attctcatcg catgcgaact tgctcttttc aacctcgatg ggatatttcc
61921 tccatgcagg cagtccaagg tcgacagcgg ggacgggggg tgagcctaac ccacgtcaca
61981 tcaccggacc agacactgag ggaaatgggg aacacagaaa ctcccccaac ctctgcggct
62041 ttgttacctg gctgcaaagc ttaaccacat gcattgaacg agccctaaac atgcctcccg
62101 acacttcctg gctgcagctg atagaggaag tgataccccct gtattttcat aggcgaagac
62161 aaacatcatt ctggctcatc cccctatcgc actgtgaagg gatcccagta tgcccccctt
62221 taccatttga ctgcctagca ccaaggctgt ttatagtaac aaagtccgga cccatgtgtt
62281 accgggcagg cttttcgctt cctgtggatg ttaattacct gttctattta gagcagactc
62341 tgaaagctgt ccggcaagtt agcccacagg aacacaaccc ccaagacgca aaggaaatga
62401 ctctacagct agaggcctgg accaggcttt tatctttatt ttgaaaaaag ggaaacaatg
62461 gggggtttga aaagggtgca cattttcaga tattttaaaa cttcattgtt ctccaggtgc
62521 ttggtaaaga tggtatcaca ataaaaaatg tttactgggt ccgcgcaggt ttgtttgtca
62581 tcttcattct ctccactaga ctccagttta aaagactcta gataaatggg tttcattagt
62641 cccccatgg gggttgaagc gtcgcctatc gccttatgaa gcttaaacat aacgagtggg
62701 gtggccctga aatgatcgtc cacggacagc tcgtaaacaa aggcggccgt ggcagtcaac
62761 gtctctatac cgtgcatgac gaaggccgcg tccatccccg gcgtcctctc atgtgtcttt
62821 ctggcgcgac aaataataga tctcaaaaac gttggtgaca tgtctcgaca gttctcgagc
62881 atcgataaca ggcagcagag ctcggttatg ccgggagatg taggtctaag gaggcacact
62941 cgctcttgga acacgtgagg gtgtaggtct atgtgggtca ccatgtcttc gtgctccacc

Fig. 3 (cont.)

63001 aggcacacca ccgtaaatcc cacaaagttg ggcgaggaca ggcgagattt cacgtgctcc
63061 ctgagacacg ctatatctaa gtggcccatc acggacattt tgggggtatt gcttccaacc
63121 agtgcgttgt ttttcctatg cacttccagg acaaggcggg gcaccacagg gtgggggtat
63181 acgggacagg cctcttctga ctcgcgagtc ttcggggcat gagtactcat tggcactcca
63241 gtcagtctcg ccagggccct ttccagggac attctcgaag ggtggtgtaa ctagacagta
63301 tttctgtccc acgtcggtta tatacacaaa gagtctgcta gtctgatata aataggccgc
63361 gatgtcctgc aagctggagg atacgaagga gtgactaatg agctccatct gaagcaggtc
63421 cgcgatcaca tacgtgaatg gaccaagcag gatggatatg gtgtcctgag aataggtgac
63481 gctgagccgc tgcccttggt tgtcaacaac gggagccagc ttgtaggttt gaaacatctc
63541 gctttcccac aggttcgtga gatctttcat gctttctctc actgggggta tgtaagaaga
63601 gaaaaagcta tttagcacgg cactgcccga tgggatatgg gaagacgtta gctgcagaga
63661 ggggtcctgt aaacgtccca gagattgaaa tgtgttggcg gtcagcagat tcacactccc
63721 gggacccttt gcgtcaccgg gctgttggtg tgacagctgt gtctcaatac attttagcct
63781 cttcatgcag agctccctct ccttttcaag ttgagttatt gtgtcaaatt gttcgtttat
63841 ctggttggtg agacacttga aaacgctgtt ggacacctgg cgcctgagcc cctgagtggt
63901 cgtctcttgg cctgtgccga atagtttatt cttgtctact atgttttggg acacgtcggt
63961 gacaaagtcc tccacgacgt cggtgacacc gctcactgtc ttgttttctg ccagtttcat
64021 gagcaggttg aggagctctc gcttggggtc tgttctctga gaggcctgct ccaggtgggt
64081 catgatgtct ttgtacacat tgttacaggc gcttccaacg agggccttgg tgggggctgt
64141 gttcaggagc tggcaaagtt ttgcgtgctc tgccgtccgg tgacagctca taatgctggt
64201 atacatcctc tgaatggggc tgtcaaagat cacccgccca gccaagatgg cgggcatagt
64261 aatcacctcc acatgaaccc ttttctgctt atacaatccc acgaaagtgt ttttaacaca
64321 gtcatagtct atgctcacct ctgagtagcc cggaatatag agggcgctta aactagacac
64381 caggttgcta atctcctgag tcacgctggt gagtatccgg cctatggttt tttcaccaga
64441 ggccagacgc tggcaatctt tcatcagctg ttcctggata gagttaacca gcttgtggtc
64501 gggtgtgtgc ttgacgactg gtaccattcc taccgtgacc acccagtcta cgtatctctc
64561 atacgagagc tgtgtcttgg cgtagaggac ccggttgatg gcattgagaa gcaggtggtc
64621 taatgtcatg cgcatagtct gggcccagga gtcgaaggtt gaccttctgt aagaccccca
64681 ctgtgcttcc ttttctggcc acctggtttt tgctgaggac tcgtatgtcc tccagtcgga
64741 caagacgtgg tcgtagctac agttggccaa tgcattcttg tacaggtgga taaatagctg
64801 tctgaaaaaa acacccgggt ttcgcaggct gcagtgtaga gtctgacctc tgacataaga
64861 atacttgcct tgcaggatct caaagaggga gatggacagc tcggaagggt gcactgatat
64921 ggacgagccc agccccgggt tcatcctcaa catgacatcg gatgccaaag tcaggagcgt
64981 agtggaacag attgacaggt tgtcaaatat cactacctcg cccccggaga tgggctggta
65041 tgacctagag ttcgatccac tggaagacga aggccccttt ctgccgtttt cggcatacgt
65101 aataacgggg actgcaggag cggggaaaag caccagcgta tccgccctac atcagaatct
65161 caactgccta attacggggg ctacagtggt agcggcacag aatctttcca gggctttaaa
65221 gtcctactgt cccactatat accacgcctt cggattcaag agcagacaca ttaatatctg
65281 ccagaggaaa gtgcccaagg taactcagtc ctccatcgag caactccaga gatacgagct

Fig. 3 (cont.)

65341 ggctaggtac tggccaactg tcaccgatat tattcgagaa tttatgcgca agaaacaaaa
65401 ggggcagtat agctccctct ctcaaagcgc tttcagactc ctttgccgta tgggtggagc
65461 caatttgtgg acgagtaaca ttatcgtgat agacgaagct ggaaccctct cgtcccatat
65521 tttgacggcc gtggtgttct tctattggtt ttacaacagt tggctggaca ccccgctata
65581 cagaaatggt gccgtgcctt gcatagtctg cgtggggtct cccacccaga cggacgcctt
65641 tcagtcggtc ttcaaccaca cgcagcagag aaacgagata tctgcctgtg ataatgtgct
65701 caccttccta ttgggaaaac gtgaggttgc agattatatt aggctggacg agaattgggc
65761 cctatttata aacaataagc gctgtacgga tccccagttt ggtcacttgc tgaagacctt
65821 agaatataat ctagacatat caccagagtt aatggactat atagataggt ttgtggttcc
65881 gaagagtaag attctggacc cgctcgagta tgcagggtgg acaagactct tcatctcaca
65941 ccaggaggtg aagtcttttc tggcaacgct gcacacctgc ctgtcgagta ataaggatgc
66001 tgtgtccaca aagcttttca cctgcccagt ggtctgtgag gtgtttacag agccatttga
66061 ggagtacaaa cgggcggtag gcctcacaca catgactccc atagaatggg taacaaaaaa
66121 tcttttcagg ctaagtaact actcgcagtt tgctgatcag gacatggctg tggttgggac
66181 ctatatcaca gacgcgtcca cacagatcac cttcgccact aaatttgtca aaaacagcta
66241 tgctaccctt actggaaaga ccaaaaaatg tatatgcggg tttcacgggt cataccaaag
66301 attcaagtcc atcctagacg gggagctatt tatcgaaagt cattcgcacg ataaccccgc
66361 ttatgtgtac agtttcctta gtaccctgct atataatgcc atgtactcat tttacgcgca
66421 cggggtgaag caggggcatg aagaattcct cagggacctc agggaactgc cggtgtctca
66481 agagctgatc tctgagatga gctccgagga cgttctgggg caggaggggg acacagatgc
66541 cttctacctc accgccagcc tcccaccatc ccccacccac gcggctcttc caacactggt
66601 ggcctattac tccggggcca aggaactatt ctgcaacagg ctggccctgg cacgccgaca
66661 ctttggtgac gagttcctcc actccgattt ttcaacgttt acggtgaaca tcgtggtgcg
66721 agatggcgtg gactttgtgt ccacttcccc cgggctccac ggtctagtgg catacgcatc
66781 cactatagac acctatataa tccagggata tacgttcctc ccagtgagat tcggccgtcc
66841 aggaggacag cgcctcagcg aggacctgcg cagaaagatg ccctccatag ttgtccagga
66901 ctcatcgggg ttcattgcct gcctggaaaa taacgtcacc aagatgacag agaccctcga
66961 aggtggcgac gtgtttaaca tatgttgtgc aggggactac ggtatcagtt ctaatctggc
67021 tatgaccata gtgaaggcac agggggtttc actaagtagg gtggccatat cgttcggcaa
67081 ccaccgcaat atcagagcca gtctagtgta tgtgggtgta tccagggcca tcgacgctcg
67141 ttacctggta atggacagta atccccttaa gctaatggac cgcggtgacg cccagtcccc
67201 atcctcaaag tacatcatca aagccctatg caaccccaag actactctga tctactgacc
67261 cgtacccctc tcttaggaca ctgatgtgtt tgggaataaa gcatgagact tgacacctat
67321 aatggtctgt attgacacca ttcttttatt tatcagtcca gccacggcca gttatatgca
67381 ccgtttccac acaggggtgg cgtggaggcc aggatgcggg ttgggtcgct gcacctggac
67441 cccgcggtag ttgtgcttcc tgatgaaatc gagtgggcgg aagtactggg agattgggtt
67501 gggaggtgac cctttgtgct cgacggagac acgatcacgc tcacggcgga cgagggctcc
67561 tcgtctgtgt cactccccga ggatataatt atcacggacg ccactgcttt gcggcttaag
67621 tttggttgtc tctggcagcg caccacatcc tcgctaccag aggaggcggt agactgcctt

Fig. 3 (cont.)

67681 ttgcgcttct ggcccacgtc catgagcccg attctctgac tcaatacttc cccttggtct
67741 tctccgtcct cctcggacga gggtggctgg tgggaaaaat ggcgcgcgtc ggtaaacgcg
67801 gcctcattgt tcacgtccgg agagttggaa ctgtcatcgc tatcagagtc cgatgtcagg
67861 tcgacgatcg cggtgggtgc ggcgcgcagg gggcgccacg agggcccttc atcagggtcg
67921 ctgtatggtg aactttgtgt tccaggtaca ctatttctgg aagcaggtga aagtccgtat
67981 gccccggtcc cagtgtatgc cgccatcggt tccaggatag caaccccctc gtcgtctgaa
68041 ggtgagagcc cagcagggga aaatccgtca tcctgactaa cccatcccat ggacgcctcg
68101 gactccgccg tgtccgttga actgcgcacg cggccccgcta ccactgctac cggtttgggc
68161 gtatgggccc gtctggccag aggcctcggg cgcaagtgag ataaaggttg aaaaaagtct
68221 gcagggtacc cctctggctc gtcttcctcc tgaacatcgt cattttcttc ttcatcttca
68281 tcttcctcat cctcgtcata ttcagattcg ccgctcgact gatccgggga tatctgtaga
68341 tccagagggg ttgctggcgg cgatggcgtg tcctcggcga agacgtcgtc tggggcagac
68401 atatctatca ccgtgggtcc agcatagccg cgcggcctgc caaatcctgg aagtgatgaa
68461 agaggtggag gtgggaatat gaacttcacg gggggtcgtc tgcgaggcgc tccttcaatt
68521 ggaagcattc tctcttcatc gtgtgtgcta gacgaggtcc tcacaaacat cgccatggcc
68581 ttgtacgggg ttgaccgcta ggggcggaaa tttacaaagc acacgagtta ttgcctttac
68641 tgctccaaca ggccccagtc cacagtctca cgccggtggc gagtcaaata gtcgttggct
68701 aggttaaagt gattacagcc ctggaaccga ggccatcgcg agtgtcggcc accaagagag
68761 gccagcggag atggatgctg ggccgtaagc accaggtgtt tctgtgcgtt tatgagcgga
68821 gttctgtcaa tggccttgcg cccccacagg agaaaaacgc aatgttctaa ctttgaggat
68881 atgctactga tgatgaaact cgtgaaccaa tcccagccaa gtccctcgtg tgagccggcc
68941 ctccccttct ccaccgtcaa aactgtgttt agtagcaaca caccctggcg agcccagctg
69001 tcgaggcacc cgtgggaagg agtactgaaa ttggggacgg aagcctctag ctctctaaag
69061 atgcttctca aactgggtgg aacctgacat tgcggatcca cactaaacgc caggccagta
69121 gcttggccct tgtggtacgg gtcctggcct aagatcacca ctttaatatc ctctggatcg
69181 cagcagtggg accaccacat cagcttgtcc tgtgggggat acactgtggt ggttagccta
69241 agttcccgaa tctgtctgag cagcgagagc agtttctgtt tcagaaatga tgagaggctc
69301 agaaaggaaa tccacttagg tgccagtaac agatcccggt cgtccacccc ctgactgatg
69361 gatagggtgc ccctaaagac cgtctgttgc aaccatgcgt ccatgttgaa cttattttcc
69421 cttttgacct gcgtgcgctc tccggctgct gcttttagcc cgagtctgac ttccgctaac
69481 agaacctgtc cggttcatgg cctttcccac gcttattata attatgttta cgttgtgaat
69541 agagctatct gcagtggtcg cgttaaaacc tacagtatag gccgtcaaac ttcgttgtaa
69601 ataccacaac aacctcaggt tttcctgcga cgcccaggac cccaatcttc gaacgaccgc
69661 gactaaaaat gacctcagat taaacccatt cacgcatgtt tccacggtaa tgtcgcctgt
69721 tttgcttcgc agcttggcta tacagacccc gttgcagtga ttcggatcgg cgaagtggat
69781 agagtggacc gcaaagaaca acggcagggt agaggctgcc gatgcctgaa ttgcgcaaca
69841 tggtaaggcg acgtatgcgt gagatgtgac caatagggtg gtccacagga cggcaaatag
69901 cgcaaagatc cccatggggc aaatccgggt ttcacccttg tgttgcctgg ttcggtgctc
69961 cccagggagc ccccttccgt aatatctgtt ttatatagtg agggttcacg catgcgcgag

Fig. 3 (cont.)

70021 tcccgactaa tgaggacaat tactgaaatt gaccttttcg cgacacgggg gtgaggtcta
70081 tttcccacga catacttccg cggaaaaata cccacgctcc ttaatttccg tgggaagacg
70141 atgggggaaa tgtggcatta cctgacacgg tttcaatcat actcatcgtc ggagctgtca
70201 cacgtctggc tgagattttc taaaaagtca tccaatgaat catcggaatc atcagcacac
70261 tctagaacta ctccatatgc cggggtgcgc gggggtcccg agtagtgcac gtcgccatcg
70321 ggagacacag atgatgggtt tgaaatgtcc atacgggccg tgtgcacaag ggtcacgtcc
70381 ccatccccaa cacaaggacc tttagatacc ctctcccggc atgtgcgcgt atccgggcaa
70441 gcaagctggt gttctggatt ccaaacgtgc ccagcggtac ccaaaatcgc cagggcgtgt
70501 tttattattt ccacaggaac cggtttctct aattgcatca ccagggtatc caaaagccgg
70561 gcttccacgt tgatccggct taccgacagt tctttccagg gtttcctggt ggggcgcggc
70621 agctgactca aaaaggtcac tgcctctgcc catgggcggg tgggtgacag tccgccatac
70681 tcttccagga cactggccat gcatgactcc aaccgtctca cgtccgaggt aatgtgctct
70741 atgaagatgt ggtagagcca gcagacgttc aaacacgatg aaatcaagct aagctcccgc
70801 cggaactcca catccacaaa ggggtattgc tccggtgtct gtattaggtc tggaatagaa
70861 aactcagaaa aagacactga cccaccaagg agaacctggc gtcttgcaaa gttgatgagc
70921 cccgcagaaa gaatgtgtct cccgtgggac aaagagcttg ggggggcaga gatggcgcta
70981 cagtgggtga tttcttctac cacggtcata cattggtggc acccacaggc ctgttccagt
71041 atcagcataa atctatcttt gcagtcatcc cagatcaaag tcatgtcaga tgctgttgcc
71101 tggcattttg cccgcatgta catttcctgt cccacatatt ttaacatctg taatactgga
71161 agtagattca gtctggtgtt gagccccccc ggggaagcca gcgtatgctt caggaccacc
71221 agggacgcta agaaccccgg gtgtccgcgc tccggaaaca gacctctgag aatacgctcg
71281 gtcttgacga aacccgatgt ggtaccgaat gccacaatct gtgccctcca gctctcacaa
71341 ttttcatctc caatacccgg aattgggata cacacctcca tgttcagtca catgtacgct
71401 agggtctccc cacccaaccc ccataggacc cagctacagc ttatcctcca ctaaatacca
71461 ggcagctacc ggcgactcat taagccccgc ccagaaacca gtagctgggt ggcaatgaca
71521 cgtccccttt aaaaagtcaa ccttactccg caaggggtag tctgttgtga gaatactgtc
71581 caggcagcca caaaaatggc gcaagatgac aaggtaaaga tcgacctttt tattgtatac
71641 tgaacaatgc gtgtttacaa tggtgtaggt gggagcagag ttcgccaagc tctacgtccg
71701 aacagtcggg tgtcagggct cttattaagt gttcggtgta cttgaccaaa gccgcggaac
71761 ctaggttggg tctgtacagg tcgtaccagg caaaaaagga tcgggcggtg cttttcagga
71821 gagttaggga cgtgctgatt atgtggacaa gcttctgctc gtaaatgcac cgctggtaca
71881 tctgaacgac agctgtccaa aaaaaacaaa ggttcagctg cacgttaaaa tctgtatcct
71941 gaaagtcctc gtaaatgaca gtttctacca agaaaaactt ttttaccacg ctggccatcc
72001 actgaaagga gggagcacac gtcccgttgt gcgttgttag gatatcccta acttcggagc
72061 ggagacggcc ggacgctccc acaaaatggg agaggcacca ctctgtgcag tccgcggtct
72121 ggggttctga ttccaggggc gccgtgtggg ggtattggag agtcaaaact ctgggcagtc
72181 ccttaatgag ctctctctca aaacctatgc agccagcgtc cactagtggc agcatgccgt
72241 taataacacc ccttatcttg tcgttgccaa gtttgtacaa ctgctgcagg gaataagcca
72301 aattcgccct agccgcggga accaggtacg gctcgctttg tcggtgctgg accaatatct

Fig. 3 (cont.)

72361 gaatggtctt tgcaaggtat agggtcttct caacgtttag agcgggtacg tggcagtctg
72421 gattgagggt ggcgacggac agggtatcta actcctgaag tatctgatcc caggacgggt
72481 aatgatacct aaacagatgg ttgaacaggt gatctttaag ggccttctc gatgtcattg
72541 taaaaactat gacacgccac tctctcctta gggtaagaag cttcggcggt cctgtgtgga
72601 aagcttcgtc ggcctctcgg acgaactgaa ggcccaactc taccagtgtg tgctccttat
72661 aaatgacgca tacgaaacaa tctacgatcc cagtgaccta aatagagtgg tggaagatgt
72721 gtgcattcgg attatgaaag aatgttccaa gcttggtgcg ctatgtggtc tgtttacaga
72781 cattaacatg tttaaccttt tctgcttttt tcgtgcctct cgaatgagga ccaaaggcgc
72841 ggccgggtac aacgtgccat gcgcagaggc atcccaaggc attattcgga tcctcacgga
72901 gaggatctta ttctgcacag aaaaggcatt tctgacagcc gcatgcagcg gggtgagcct
72961 gcctccagcc atatgtaagc tactacacga aatatacact gaaatgaagg ccaaatgcct
73021 gggggcctgg aggcgactcg tctgcaatcg gaggcccatt atgatattaa cctcttccct
73081 actgaagctc tacaacacgt acgataccgc cgggctgctc tctgagcagt ccagggccct
73141 ctgccttttg gttttccaac cggtctacct tccgaggatt atggcgccgc tggagatcat
73201 gaccaagggt cagctcgccc ctgaaaactt ttacagcatc accggttctg ctgagaaacg
73261 ccggccaatt accaccggca aggtcactgg actgtcctat ccaggaagcg gtctcatgcc
73321 agaatcttta attttgccaa tcctggagcc aggactgttg ccggcttcca tggtagacct
73381 cagcgatgtg ctggcaaaac ccgccgttat tctgagcgcc cctgccctga gccagtttgt
73441 cattagcaaa ccccatccca acatgccgca caccgtcagc atcatcccct ttaacccatc
73501 gggtacagac ccggcgttta ttagtacgtg gcaggccgcg tcacagaata tggtgtacaa
73561 cacatccacc gcgcccttaa aaccggccac cggtagttca cagacggtgt cagtcaaggc
73621 ggttgctcaa ggggccgtga ttactgcgac aacggtgccg caggcaatgc cagcgcgggg
73681 taccggaggg gagttgcctg taatgtcagc gtccactcct gcaagagatc aggtcgctgc
73741 atgttttgtc gcagagaaca ccggagattc tcccgacaac ccgagctctt tcctgacgtc
73801 atgtcaccct tgcgatccga acacggttat agtggcccag caatttcaac caccgcaatg
73861 cgttacgttg ttgcaggtta cctgtgcccc ctcttcgaca ccaccccccg attcaacagt
73921 ccgggccccg gtggtgcagt tgccaacagt agtccctctg ccggccagcg cgttcctccc
73981 ggcgctcgcc caaccagaag cctcgggcga agagcttccg ggcggtcatg acggagacca
74041 aggtgtgccg tgtagagatt caacggcggc ggctacggcg gcagaggcga caacacccaa
74101 acgaaagcag agaagcaaag agaggagctc aaagaagcgt aaggctttga ccgtgccaga
74161 agccgacacc acgccatcga ccacgacacc tggtacctct ttgggatcaa ttaccacccc
74221 ccaggatgtg cacgccacgg atgtcgccac gtctgaggga ccatcggagg cacaaccccc
74281 gctactgtcg ttaccccccgc cactggacgt agatcagagt ctattcgccc tgttagacga
74341 agcgggccct gaaacatggg atgtcgggtc gcctctctcc cccactgacg acgcgctgtt
74401 gtccagtatt ctgcaaggac tgtaccagct ggacacgcca ccgcctctgc ggtcaccctc
74461 ccccgcttcc ttcggcccgg agtctccggc ggatataccg tcaccttctg gtggagagta
74521 tacgcaactg caaccggtca gggcgacctc ggcgacgccc gctaacgagg tacaggagtc
74581 cggcacactg taccagctgc accaatggcg taattacttc cgagactgaa gtgttcgcaa
74641 gggcgtctgt gcctgcgtta acttcccagg cagtttattt ttaacagttt ggtgcaaagt

Fig. 3 (cont.)

74701 ggagttaacc tacagattct acttaaaata gctcattttc tcacgaatct ggttgattgt
74761 gactatttgt gaaacaataa tgattaaagg gggtggtatt tcctccgttg tcgactataa
74821 cctggcgtgt aaacgtgtaa ccctgccaaa tgcccagaat gaaggacata cctactaaga
74881 gttccccggg aacggacaat tctgagaaag atgaagctgt cattgaggaa gatctaagcc
74941 tcaacgggca accatttttt acggacaata ctgacggtgg ggaaaacgaa gtctcttgga
75001 caagctcgct gttgtcaacc tacgtaggtt gccagccccc ggccataccg gtctgtgaaa
75061 cggtcattga ccttacagcg ccttcccaaa gtggcgcgcc cggtgacgaa catctgccat
75121 gctcactgaa tgcagaaact aaattccaca tccccgatcc ttcctggacg ctctctcaca
75181 caccaccaag aggaccacac atttcgcaac agcttccaac tcgcagatcc aagaggcgac
75241 tacatagaaa gtttgaagag gaacgcttat gcactaaggc caaacagggc gcaggtcgcc
75301 ccgtgcctgc gtctgtagtt aaggtaggga acatcacccc ccattatggg gaagaactga
75361 caaggggtga cgccgtccca gccgccccta taacaccccc ctccccgcgc gttcaacgcc
75421 cagcacagcc cacacatgtc ctgttttctc ctgtttttgt ctctttaaag gccgaagtat
75481 gtgatcagtc acattctccc acgcgaaagc aaggcagata cggccgcgtg tcatcgaaag
75541 catacacaag acagctgcag caggtataga cgggaaacag gtgtctatct tggccggctg
75601 gttactcaaa tgggaacaat ggcgccacct tgctgtcttt gtaggcatta gaagaaaagg
75661 atgcacaact atgtttccta gcggcgagat tggaggcaca taaggaacag attattttcc
75721 ttcgcgacat gctgatgcga atgtgccagc agccagcgtc gccaacggac gcgccactcc
75781 caccatgttg aagcttggtt gtgccgtcgt ccgggagaac catgccagac tttgtgtggt
75841 aagaaggaat tgttatccgg cagcaatatt aaagggaccc aagttaatcc cttaatcctc
75901 tgggattaat aaccatgagt tccacacaga ttcgcacaga aatccctgtg gcgctcctaa
75961 tcctatgcct ttgtctggtg gcgtgccatg ccaattgtcc cacgtatcgt tcgcatttgg
76021 gattctggca agagggttgg agtggacagg tttatcagga ctggctaggc aggatgaact
76081 gttcctacga gaatatgacg gccctagagg ccgtctccct aaacgggacc agactagcag
76141 ctggatctcc gtcgagtgag tatccaaatg tctccgtatc tgttgaagat acgtctgcct
76201 ctgggtctgg agaagatgca atagatgaat cggggtcggg ggaggaagag cgtcccgtga
76261 cctcccacgt gacttttatg acacaaagcg tccaggccac cacagaactg accgatgcct
76321 taatatcagc cttttcaggt gtattacacg tttcaactgt aatccctcgc aattgggtaa
76381 accgtcggtg tgtagggata aagcgtaacc ttacgttctg tctcatctac aggatcatat
76441 tcatctgggg aaccatccag gaccacgcga attcgcgtat caccggtcgc agaaaacggc
76501 agaaatagtg gtgctagtaa ccgtgtgcca ttttctgcca ccactacaac gactagagga
76561 agagacgcgc actacaatgc agaaatacgg acccatcttt acatactatg ggctgtgggt
76621 ttattgctgg gacttgtcct tatactttac ctgtgcgttc cacgatgccg gcgtaagaaa
76681 ccctacatag tgtaacacaa aaccataaaa gtaaataaac gtgtttattg ttcacatgat
76741 aaagagtggt actctttact ggtttggggg ttgggttgtg gcgtggtggc tggtccgcgg
76801 ttcagtcatc aacccccgcc cgtgttgtcg aggctcctct tcgtcgcctg ttattggcac
76861 caggaggcgg tttagcggtg cccccgtctg acatgcagac gtcgattcta agcgaaagtc
76921 ccttcagggc atcgtccact tgcttttgtg ttacaacctt gctgaatatt gtcctgaccc
76981 tggcttcgat tttcttagcg gccgccgcac tcagtgcacc cacagtagcg gtaagctgcg

Fig. 3 (cont.)

77041 cttccttctc ggtggccgtc agaggccgat ctctcggatc ggcagtggat cccagtgctt
77101 tccgaagctc ccgattctcc acagtcaatt ggcttatctt tgcggttagg tcttccatcg
77161 taaggtcctt tttgggtctg cccctgggcg cggccatgtc aggtacgcgt agatgtacgt
77221 gttggtgatg ctcacaacaa aagcccaaat ccctccttta tacccagctt taaatacttt
77281 attgaaaaac catagctttc gtcagcgctt gtgcgagtaa tcacatgcca gtctatgcat
77341 ggaccacctc gtccacaaac ttgaaaaaac aaagatatac cagatagaaa aatgtggcca
77401 cgacgactag taacgcgtta atcaaggccc agacgctaga aaagctagaa agggaggggc
77461 taaaactatc cgcggaacaa gcaacgtcat agaatcctgg ggtagtgact gatgtgggac
77521 cgggcgaagg cctggcgctg agcccagccg tactgggact agaacgctct gtagatgatg
77581 cgacacctgt cgagttggcc gtaacccagc agtgacctag tatcgaggcc acaaataaag
77641 ccagggccac cgtggacgct gtcattatga acaaccgccg aggctccaag ccgtctatcc
77701 aacgttccgc gttcgcctct tatatacact ctgcaatgca gtccgactct gcccctctac
77761 ccagggtgga atatgtgttc gaaacaagca aatttagaat gacgtcgaga gcaaatgaag
77821 ccagactcag actgacaaat gagtgtccga tactggtgag accccacgag ccgttcatca
77881 tgcccaccgg aatacacttc acgcgaaccc ctagctgcgc tttcatcctg accggagaga
77941 ccgacaagga tgtattttgc cacacgggcc taatcgacgg aggctaccgc ggggagatac
78001 aggttatttt actcaacaag aggaagtacc ctgtgacgct gtatcgcggg gagctcaaca
78061 tctgcctgtc tgctttcaat tacgtgctac ctccgttgag ggacgtatca ttcttaaccc
78121 cccctatgta tgcaaacgac gccggatttg acgtgatggt gatgcactct atggttatcc
78181 ctcctactac tgaccaaccg ttcatgatat atctaggagt ggagacccca ggcccccctg
78241 aaccccacgt ggctctagca ttggggcgat ccggtctagc atctaggggt atagttatag
78301 acgttagtga gtggggaccg cgaggattgc agctgaagtt ttataactac tcggggcagc
78361 cgtggctggc gcagcccggt agccgcatat gccagattgt gtttgtggaa cgcagacaca
78421 tcctcaaggg cttcaaaaag tgcttgcgcc ataggaagct agctcctggc gtccgtttcc
78481 gggaggctcg agtgcatttt cgcgaggata caaatagcgt ccgaaaacat acccacgaag
78541 acaaccccgt ccacgaaccc aacgtagcca ccgcttccgc tgacattcgt ggaaccaagg
78601 ggctggggtc gtctgggttt tagagccgcc gccaaatgcg gccagtttat tagggcgatt
78661 cgatcccgca acccacagca tccccccaaat aaaaaaacga gtgtacacag ccaatgtttt
78721 tattattgtt cgattcatta ctggtaccag agaataaagc caacctatgt cgaacctatc
78781 gcgctttctg tcgtctcttc cagggttgac gaaggccggg gagggattga cgaatgcatc
78841 gcggaaacgg acgggtcttc ggtgggtggc ttgggtaaag ttgcctccgg ctggcgcgta
78901 acggcaggcg tgagaggcaa tacagaagtg ggttccgaca aggagtggct gatctcagag
78961 gcccatatta ccgagtcgtc tgacgccata gcagtcgcca gtttttccat ctccatgagc
79021 gaaacgcatt ccccggccct tttgtttaag agggactgga gcgcactgtc gtccacggta
79081 atctcgccga ccgccaaggc cagcattgtg ttccacacga cgttctgaat agactgcagt
79141 tttttcacct gggttttcac ggtctcctgg cagcccgccg gaattttagc cacgtcaaaa
79201 cgcttcaggt agtctgtgat cttgtttgac tgtacagcca gaaggtaggt ctggtgcagc
79261 gccgtcgtgc caaggttcga ctggacaacg tcacccagac acactccggg ggggaggccc
79321 aaatctatct cttgccgcca gcgctctgga cagccttcca gagggtcacc gaggcgcttg

Fig. 3 (cont.)

79381 taagcgtggt tgccgcgtcc aaaaaggttt ataccgcaac acgtccaggt gtaccatgga
79441 gacgacatac cgccgcgagg cgctgacagt aagggttatt ttttgtacga gtggcgacag
79501 cgccgagacg atcgccgacg tccttacggg ggccccaacg tcagcgtcct tcttttctgt
79561 actccacgac cttttttatt cccagatact cgcccccagg gtaaccctaa aattgtgcct
79621 ccccgcacgg cgtcctggca acggcacaag gtgttcgccc gtgttggtcc tacgtactga
79681 cgcatcagtg gcctcggggt tccttggcgg ccggccactg gaggcgtccg acattaaata
79741 tatgctgctc agcgaccaga ccgcggggtt gttcaagccg ctgttggaga taatcggtgg
79801 cgcgcgcgca ccaccaaatc aggacgcgtg cactttccag agccaggtgg cctggctcag
79861 aacgaaattt gttaccgcat tgagaaaact ttacaagatg actccctcac cctactggat
79921 gctgtctgca tttggcgctc aggaagccca gttcgtcctg accagctcat tctatttttt
79981 tgaacacact gtggtctgta ccacagagac agtttctcac ctgtctagac tgttttcgcc
80041 tcaacaggga cagacgctgg tttccgttac cagccacgag gagctggggc agctatacgg
80101 cacttcccct ttcaggcggc gcgtccccgc gttcgtcgct tatgtaaaag agaaattagc
80161 gagagacagt ctggagacgg aggccatcga ccgcaccata gaccagatca ggggcaaact
80221 catgctgtct aaccaggacc tggtccattt catatatatc tccttttatc agtgcctcaa
80281 caaacgggcg ttcctgcgct actctagaca gacgtcctct tcaagtgctc taagggagct
80341 gggggaagac cctcaattgt gtggcgccct acacggggag tttcgtgacc acgtccagtc
80401 ctactaccac aaaaaaacct acctatccac ttacatagac attcggtacg tgggtggcgt
80461 attaccagac ggctattttg gcgggagtct tgtaggcgag cggtgcgttt attggtgcgg
80521 gcagtcaaag gacacggcca gcctgttggc caccattagc caacaggtgc cgcacctgag
80581 gttgcaaaac gagttcgctg gcatgctaga cgtggccgca ctgcgaggtt ccgatgacgg
80641 tcagtttaaa gagggccttt tctcccacag tcaagcccta cccctgtaca ggtgcgagtt
80701 tctgggcaag cagtttttca caatgcttca ggaagacggc ctagagcgat actgggagca
80761 aagtgtgata tttccaggcg accaggactg ggatatgtta tctgacaaag acctcaccta
80821 ccgaattttt taccatgacc tcagcctatc gctgccaaca ctgaaggaac agctccttgt
80881 ttcaagacac gaatacttca accctcgctt gccagtgtat agatgggtat tagactttga
80941 cctgcccgtc tgccgcgaca ttgacaggac attcgaggag gtgcactctc tctgttgttc
81001 cctgcgtgag gccatactcg acatcattca actccttgga ccagtggatc ctcgaacaca
81061 cccagtatat tttttcaaat cagcctgtcc accggacgag tggcgcggcg aagacgtcgc
81121 cagcaccagc ttctgtcggt gtcatgacaa actgggtatg cgtattatcg tcccgttccc
81181 agaaggagta tgcgtcgttg ggtcggagcc catggtggca ctcactggca ttctaaacag
81241 gacgataaag cttgatccgg agctggtcca cagattcccg tcaatacaaa aaaagggggg
81301 ccctttcgac tgtggcatat acggccgagg acgaagcgtc cggcttcccc actgttacaa
81361 ggtgggctta gtgggggaac tctgccgcct actgaagata ctagtctgtc accccgcccc
81421 caacggcaag gcgcagtacg tgcggcgcgc ctttacgctt cgcgaactgc tccatcactc
81481 cccgggccac agcgccggtc atgtcggccg aatcatctat agcatcatgg atcgcaatga
81541 gaatttttta gaaaacaaga ccattagcta tctgccggcc aaaatacctc acatctttca
81601 gcggatagag accctatccg gtcgttcaat agaggactgg ctacactcgg ccgtttggga
81661 taaagcatac gacactatat gtaaattttt cccagatgaa aaagcacaac agttttctca

Fig. 3 (cont.)

81721 cgttgcattt acgcaacaag gggaaaacat catccagtta agaccccgtc agggaagaca
81781 cttcctctgc atcaaccata atcataaaaa caagtcaaaa acagtccgtg tattccttac
81841 ccttcattcc attagggtga gcgaagtcac ggtaacactt atgagtcagt gttttgccag
81901 caagtgtaac aataatgttc ccacggccca tttttcgttt gtggtaccag tgggactggc
81961 cagttaatcc cactatataa cctggctgcc aggttcccaa aatagcccgc ggcatacggc
82021 tcacttcccc ccacattccc cccgtgcaca atataagaac caaaggacat ggtacaagca
82081 atgatagaca tggacattat gaagggcatc ctagagggta agtcctcgtc tacaacagac
82141 ttttcccatt tctaacgtat cgtgctatct tcgtcgcccg gcggaccatc cccccacccc
82201 tcatttatcg cgtttgatat tacagactct gtgtcctcct ctgagtttga cgaatcgagg
82261 gacgacgaga cggacgcacc gacactggaa gacgagcaat tgtccgaacc cgccgagcct
82321 ccggcagacg agcgcatccg tggtacccag tcggcccagg gaatcccacc ccccctgggc
82381 cgcatcccaa aaaaatctca aggtcgttct caactgcgca gtgagatcca gttttgctcc
82441 ccactgtctc gacccaggtc cccctcacca gtaaacaggt acggtaaaaa aatcaagttt
82501 ggaaccgccg gtcaaaacac acgtcctccc cctgaaaagc gtcctcggcg cagaccacgc
82561 gaccgcctac aatacggcag aacaacacgg ggcggacagt gtcgcgctgc accgaagcga
82621 gcgacccgcc gtccgcaggt caattgccag cggcaggatg acgacgtcag acagggtgtg
82681 tctgacgccg taaagaaact cagactccct gcgagcatga taattgacgg tgagagcccc
82741 cgcttcgacg actcgatcat cccccgccac catggcgcat gtttcaatgt cttcattccc
82801 gccccaccat cccacgtccc ggaggtgttt acggacaggg atatcaccgc tctcataaga
82861 gcaggggggca aagacgacga actcataaac aaaaaaatca gcgcaaaaaa gattgaccac
82921 ctccacagac agatgctgtc ttttgtgacc agccgccata atcaagcgta ctgggtgagt
82981 tgccgtcgag aaaccgcagc cgccggaggc ctgcaaacgc ttggggcttt cgtggaggaa
83041 caaatgacgt gggcccagac ggttgtgcgc cacggggggt ggtttgatga gaaggacata
83101 gatataattt tggacaccgc aatatttgtc tgcaatgcgt ttgttaccag atttagatta
83161 cttcatcttt cctgcgtttt tgacaagcag agcgagctag cactgatcaa acaggtggca
83221 tatttggtag cgatgggaaa ccgcttagta gaggcatgta accttcttgg cgaggtcaag
83281 cttaacttca ggggagggct gctcttggcc tttgtcctaa ctatcccagg catgcagagt
83341 cgcagaagta tttctgcgcg cggacaggag ctgtttagaa cacttctgga atactacagg
83401 ccaggggatg tgatggggct actaaacgtg atagtaatgg aacatcacag cttgtgcaga
83461 aacagtgaat gtgcagcggc aacccgggcc gcaatggggt cggccaaatt taacaagggt
83521 ttattctttt atccactttc ttaaggattg ccaaacccca tggcagagtg tctcccgtat
83581 tccatgtaac tcacgtagcc tttctctaat aaacaagcta cctgcaaact atacacaaat
83641 gaaatgagtc aggcgtggtc tcttctctac cgtgaatcgc accttaaaca caacaccaga
83701 ccgccaccag gtggcaccca acatccatta tggaaaaacc ccgcgccacc ttccgccacg
83761 tggagccaac aaacaagaca cacccgccaa tgttttggtc tctttattga tatgatatac
83821 tccctcccat aacaatacgg tgtaggcatt ttgtattatt tattgcatgg catcccataa
83881 cggcttcggc attatttcga gtacgacgca ggcgtctgag aaattactgc acctcgccgc
83941 aaagtctcgc ggggacgggg cgtggggctc taacttgcca accgccaccg gtttccccag
84001 ccacagcttc accaaaggac acgtcacgtg agagggtgct ggtaacggtg aatttgccaa

Fig. 3 (cont.)

84061 ccccaccaga aatgtattcg ggttaaatat cctcgtcggt tttccctggg gcagcaagag
84121 ggggccggag tcaggcggaa cggtatttcc aataaagtgc acgggcccgt tatgataaca
84181 tacgcaaaat atgccattac aagagctagt cagcagaatg cctttgcac atgcgtccag
84241 cgtatcgcat agctcccgct tggctatctc gcaggccagg tttggcacat tgggtagcca
84301 tacctggccc ggagacccca ctgcacagta atgaactgcg gggtccctac gcaaggccga
84361 tgagattcga cagcccgact ggcttgtcgt cagtaactca tgaacctgtt cgccattata
84421 atacatcctg ataaacaacc gaccccagtc aatgacggcc tcctgaccct ctgccgtcgt
84481 acaagatggc acgggcgtta caatctcgcc tggcaagcac tgccccgggg aaaaaaatcc
84541 ctcttgcaag agacgtgcca tattgttaaa atcgtggacg gctccggcca cgactccaca
84601 ttccacgcat tgttcttcct ccggtttacg tactctaaag accagaaaat ggtgtccatc
84661 ctgagaaatg cctttgccaa tctcttgtaa accccgcgtc ctgcgtagcg cggcaagcat
84721 tcgcctgcgc cccctggtgc ctttaaacga ggcgtccacg ggcatgttac ccctttcgcg
84781 gatatacaca acacccaatt ccccgtctct gcgccattca aaacaggggt ccgcgagggg
84841 cgtaactggt atacggaagc gggtgcgctc ttcgtcttcc cactctactc cgggaaattt
84901 tccactgttg acttgacata ctatccaatc cttgattgac gctttcccct cactggcacc
84961 ggtagatatt cttagttgtc gtgtccggct ccactccgtt atcgcagcca ccacagcctg
85021 ccgtgtaata tcgcctgcgg ctgcagaacc cccggtcccg gagggtcctt ctcccggtga
85081 ctccgacctg gatggttcat cgcaaggagc cccggagcca gatgttcccg gtgacccttg
85141 tgacaaacaa ggttttttgg gtatcgcccc aggcgcccca aaagggttcg gtctttggcc
85201 tgggtccatt gtcccgcaac cagactagct cgcgccgcaa tgtccagtgg taagcacagc
85261 tatgccgggg agccaccggc catcagatat agagaggcga caggctctct atatatcacg
85321 gctaggtggc tgacatatta gtgggcctag ccgcagaatt gcctgggtag tcaaaaacca
85381 gcgtttctca aattaaccga aactacattt ttctatttta agtacgggat acaaagcagg
85441 gtctgaggca atctgccgcc ctccaccccc acccaccata cccaaaaaag atatgtcaga
85501 aagagcactc tacctattaa ctcgtggaga aacatcatac aaaatctgta cattattttt
85561 aatactttaa tttgtgcagg tttcttcacc ccacacctgc tttttgtctg gtacaaaaaa
85621 ccactgcagg gtcccgccta tagccaactc ctaagcgggt tttttgctaa agcacttttt
85681 tagactgtcc cagaaaccac atagcttcct tttcactcat ttgaaaaaca gcccccgccca
85741 actgcctgga gaattttcca ccccctctac catttcgcgc ctttaccgct ggtgcgaaat
85801 ctagccatcc tatcaccgcg gatccgctgg accaatatac cacgcccact tttcgtaatc
85861 agcaaccctc tacgcctaca cccctatgac tgaatataac ccccaacaag gctatgaaat
85921 catgaatggt aactgtctgg acaccaatct tccgcggggt ggcggcagtg cgacgcaagt
85981 atccacaata aatggtgcaa taattggcga aatgtcgtgt ctggtttatt tggactacaa
86041 gattacatcc ggttttataa ttcacatata tgatcaatgt agactatccc aaatggagcc
86101 tataaaaatt ttaacagtca agggtacatt ttggaaattt tctgtagatg ccggggatgc
86161 gccgaaaaat accgtcccgc acgtcactgg gttgacgctc agcggtgtct gtgggattgc
86221 ggctgtggtt gccaggtatc gcgcggtgtt gaacagctgc tgcggaactc tggggctaaa
86281 gcttcggagg atgcgttcat agcgggaatt tggattacca aaccaccagc cttccacttg
86341 agtggcgttt ctggagtata ttccagacat cgagcaaaat attgggaatc cgtggccaag

Fig. 3 (cont.)

86401 gccttcaaaa actcggttca aaatctccat ttgctcgggt gaggggactg taagacgcgg
86461 tatgcgaagc agttctggta cgaaactctg acataggtgc cccaacgtat ccccaacagg
86521 ccagctacat aacattgcct cgcccgcgtc accttcgcgt ctcagagttc cacgaaggtt
86581 cccatacaca aagatttcca caacaaaaga cacccgctga ctatcagggg gatcaaaaaa
86641 catctttgaa ggtggctttt cgggaccgga gtggctaacg ggcgtacgcc gcccgtgcgg
86701 ggacctggac ctcgggcgcc gcctatccgt ggcctgtctg gttgaggagc tcggttcctc
86761 ctgcagctca gacaaaatgt tacccaaccc ttcttcccac gtacatatat cctctccttg
86821 aaggttcgag agcgtaagag ggagacccaa aggcggcggc actaaagatt gttctggtcc
86881 ataacccccc actgcatatc tatctccagc atatgtacta acaagtggaa ctctgggcct
86941 ttcgccacta cccgggcaca cacactcccg ccgctccagc tctgtcggta aatgcgaaac
87001 ctcggggttc acagcgggct ccggtgcaga ataaagcacc gtaggttgga aaacgcgcgg
87061 cccactgaca ggtaggggcg tggatgctac agtggtagat ggggtatcgg aatccccagt
87121 gaggtcaata atctccactt cgagggcacc agaactagtt gtcacgcgtc tgtatccagt
87181 cgccatgttg tccccctggc agacgtacgg tattccagac gaggatggct cctgtcgctc
87241 tgccacctct ggggtgggtg gtgcgccggc ggagggcgtg gccgacgcgc caccctgcgt
87301 gtgggaaaga ccctggtttg gagcgcctcc actagaccac ggaatccaaa gcggtgtgcg
87361 aacttccggc accacggcgt gaccaactgg tgggtgccaa acaggcgcgc gtatgggtcg
87421 cgtagctggc ggttctgcca atggactcca attgtaacat gatggtttcg catacccggg
87481 cgcgggggcg ctgggcggtt gaggttcgaa gggatacacc cgctcactcg cagcaccctg
87541 aggagcccgg ccttctgtag atgccccgca agcgccttcg gcaccggttt cccggcgggg
87601 aagccacgcg cgagcacatt ggccgctttg ggggagcaat ccctgtggcg ccagaggtgc
87661 accctggctg aactcaccga caaatgttcc cgcttgggcg tgcggcggaa tccaactggg
87721 ggcagcagga ttcagctggc tgctaggaat ccccgtatat gtccaacggg gggaaagggg
87781 atcaaattgg cccgtggttg gcggatgcac tttctccggg agaccagacg cgccctgagg
87841 ccaccatccc gtgacaggaa gatctcccca tggaaaacac gcaggtatcc acggggacgt
87901 agatggcagc ctagacccat cgcgcatggg aggggctagt tgccccgtat cccccggcgt
87961 ctgtgcgacg ccggagaccc ctgacacagt accggcaagc cgtgtttcgt gctgcggctt
88021 gggcggcgcc gtgcccggta ggcctgcacc agatgagtga gggtctgaag ggccggtcag
88081 cgttgatgga gcaggcggat ctccgggaac ccgccacgta aaggacgagg cctgcgtaac
88141 ttgtcgcgtc ccagaggacc ccatacctga ggtagatgcg ccctcattca ctggtatcca
88201 cacggagcag gcagccttct gttcagtcgt tatatcgcca acattgtaat agcggttcga
88261 tttccgaggg cgacccctca gccccgatgg cgccttaggg ggagcaggtg ctgcagcccc
88321 tgcctcctcg tagctttgtt ctctaagtaa aaggcacgag agttaacgtg gttagggtac
88381 ctaaagtatt tcccgccgac accaacgcat caaacctcac acccccttcc ccgagttaca
88441 tacctagtgt cactgcgtcg cgtagccgtg gtttgcattg ggggggacaa cagacactga
88501 ataaatcgct gcagtttttc aggaccatac gcggccccat agcaatacgt acagttttta
88561 aacggcgttc gcaccaactg ccatactacg tagctaccac caaatgtgtc gctgtaccgt
88621 aaatcgttcc gcacgacggc cctcctggtt ccacgcaaca gtctcccaaa acgtccatac
88681 accgtctgtc ccacgacagg cgatggtccg tagactctat cacactcctc atcaaatgca

Fig. 3 (cont.)

88741 tggtacaccg aataccagcc aggcgggata tcgctgccgg caggcagggg cgcgggggct
88801 gcaaaaagaa ggttgttcct atcaaaccag gaaaaatagg gaaacttatt gttttcaagg
88861 gcatcaataa tccataacgt ggcccattct gagccaccgg ctttaggcat ggtccgacac
88921 agaaaccgat cggcgttcgt ctttgaggca cagtcccgac tgagccttat agtgcccccc
88981 ttcttgctat gaaaaaaacc cacgaccgtt acgcaaattt gaggagctac tcacctaaaa
89041 gtagctcctt tgacaaatgt cctggtttta taccaattgt tcacaatgac atattgtgct
89101 ggcggaaaca ggtgtcccga tgtatcctcg gcaagtaagc accattacca tgtgccatca
89161 tattgtgtgg cacaaaaaaa gcaacttttc acgcacgcag cataagaccc gagccagtcg
89221 cgccctccat cgcgcctgcg aattttccca ccacccaata ttgtggcaga tctttcttat
89281 gtatatgtgg ttacaaacac cacgcccctt aagctgtcct ctctcccaag gggactagat
89341 tataacagtg acatacgaaa ccgagacgct ctcaaatgct ttctatttta tttatcgatt
89401 ccgggttaac ataatcacag gtagctataa aatccccatc ctcttgacct ggtaaccctg
89461 gcttgaggtt tcctctgtta tcaaacaaac ctgaccacaa ctgtacagag aaaagtgggt
89521 gaaatgtagt gtttatttta tcctcacact ttcacttaac cacagcccgt caaaccacag
89581 ggaccctgtt ggctgactat tagtcatcac atgtaactga acgcaatctg agcttgatga
89641 cgagggggac catatcgaac tgttctgccg acgttgggtc acctccgatg aacacagttg
89701 ttttttaat gtgctcatgt ccctgtatgc gatattgtgc cacattaaaa acatccagaa
89761 cagccctaga tgacagtccg cagatcacac caaacttctt tggaggatta tttccatgat
89821 ataatacggt agacttgcac aaattcttaa cataaatgcc agatcggaga gaaactatca
89881 caagacccga agcaaacgag cgcagcacgg ccgccagcag gttaacgtct cctggccctg
89941 tgttattgtc gtcaggtttg ggcaacaaaa ctcttaaccc tttgcgcgaa tgcaagcaag
90001 agtggctaat gtctgccagt gggttctggg aacatagaat aaacaccttt cgttccactt
90061 ccaaagacat tgcagggcgg ccaaaataaa acacttccac accaagccta tcggttatca
90121 ttactggcgg ccgtgccact ctataatatg cggatctaag cttcctgtgg cgaatgcgcc
90181 tcgtggtagg cctctcgtgt ctccgtggcc catcatccca taaaaattcg ccaacaactg
90241 gccggcgtct ggacgccggc ggcagtccag caccatcatc gacttcttcg tcacttatct
90301 ccaacacata ttcccctgct acattctggg cctcgagtgc cccagctaag tacacatcct
90361 ctacacccgc cccgacagcc gaggcggcga ttgagccctc tgttaccacg ccgcttgcat
90421 ccgtgtcgcc tccgggctgt gatgttgcga taacatcctc tgggatgcca agcagatcaa
90481 agaggtcttc atcgcacatc gccctcatta gcatgtccat ctcctgtccc acgtggtaca
90541 tcaatgcaca tgcagattct ttatcaagca gtgtgaggtc atcttcaacg ttgtctgtgt
90601 gcaccgttgt ttcatcggcc ggggggggct gcgagtcgct atgacgcgtc gagggtcctt
90661 cgtctccaga gccaggagag tcggcattgg catcatcaac tggctgaacc ccagacgcac
90721 tatggcgcgt cgatggtccc tcgtctccag agtcctcaga ttccgcgccc gtctgcgtga
90781 ccggcacatc gcaaaaggct gggtgatcct cctcactgga atccgagttt tcacccacaa
90841 atggcctaca gaaaaaaaaa caaatatgtc aaccggacta gggtggccaa accatttgcc
90901 ccacccctcc ccactctttc cccaggggac acatcttacc ttggtcttct ccgatgcttc
90961 tcgagccgta cactgtgttg atacaaaatt tcccatagtg atgacccact gtgtaggtga
91021 gtcctggcat gaacgcacca ccagcattcc tttacctcgg cacacaggag gcgccacctt

Fig. 3 (cont.)

91081 ctacaattaa ttccctgtac gacctcgtac tcttcacctg gcaagcgtct aaggcgccgc
91141 gacgtggtac atatttccc aaaagccgta atcggcgagc ccagtaaatc tctgggatgc
91201 aggcccttcg ataggcattc cctcttaaaa tcaatgaaaa actgtaggct atccagagga
91261 attacgtcat tacgggcagc cggagcaaga aatgttccag tagatctatc tagccacttg
91321 accaaaggat atttatcaga gtccaaagca cctacaataa actcagaaat ccaggtaagc
91381 ctgcgtcccg ccatgttgac ctgtcagaat ggtctgcctc cgagcattac cccacctcaa
91441 cagaagtaat ctactacgca aaccacaaca tgcttcctgc agctttaacc ttcagtcacg
91501 ggtcaaaaag cattgcctgt attagacaca tgtgtttctc actatgaatc gtgctctcca
91561 gcgctggcaa gaacatctgg ggtgatgctg ccccggacca gctttgaaac agggtattgc
91621 atgcataatg aagcccacat gtttgtctta ctttactaac ctcattacct tgcattgcag
91681 gggacacccc cttgccttgg cagctgagtg aatcccaacc gcctaggaaa aaaataacca
91741 ctcagacttt attttgcagc cacacggtgg cgctaacctt taatgatgtc ccactcagtg
91801 agtttggcca ctcccaagcc cacatgggcc tactataaca ggaaacatag aagttgcgga
91861 tagagcctgg tttctaacgg caatgatatt tatagtgcaa aacggagggc ggtaagacaa
91921 agggaggtac ccggacagag tgacaagaag acttgtcaaa attttagtct ctgtggtaaa
91981 atggggcaag gtaaatgtgc aaaatgactg gatagtgatc cgagtcatat tcaggcgacg
92041 gccggcggcc cagaaacagg gacgcgtacc gggacccttc aggttctcga ttatgtcgct
92101 ccacgtcaaa agcttgttgg atctcgtggc ggtgggacag gggcctacat ttgcctattc
92161 ttcttcgcga tgcatttcca acaaagtatg ctgggtattc caataatccc ttcagaaaaa
92221 tgcccatgtt tgtaccgatg gccacaactc ccatggaaaa cctgtccagc gtctgttcca
92281 aagttcggtt tgcgtccaca ctacagtggg ccgttctggg aagtaagcat ttatacgggg
92341 gtaccgtctg acatatgtgt tcaggggagg cctctgggac ttgggagcaa ataacgatgc
92401 cccccgttaa atcaaagtgg gtcttcacct tttctccgaa ataatacact tccaccacta
92461 ggggcacaag cttgtcaccc actttgtaaa tagcctgttt cttactcagg tatgctgcca
92521 cggattgggt ggcggttaag accttgggcc tcatgtcgct tccataccag taaaatgtct
92581 ggtcagcttt ctcttggtcc tcgacgtccc ggtcatcacg acacaacggt ggaatacaat
92641 caataaaatc atccacattg tcggaagctt ggaaagatga acccatgaca gaggccccag
92701 gtgccgaact ctcaagggga tgcgtggcgg gaagtactga gacactctcc gtggacccct
92761 cctcacctcc ctccgactgc atcgggccct gagggctcgc agtttcacac agaagttcac
92821 tcaggtcgcc taagtcagga agctcctggc ctgaacccat gacagaggcc ccaggtgccg
92881 aactctcaag ggatgcgtg gcgggaagta ctgagacact ctccgtggac ccctcctcac
92941 ctccctccga ctgcatcggg ccctgagggc tcgcagtttc acacagaagt tcacccaggt
93001 cgcctaagtc aggaagctcc tggccaacat ctgacaagag atctaacaaa cacccctcaa
93061 tgtgatccac catcggtagg caatcatcca gcccactgac atgactgggg acggggcctt
93121 ctggggaaaa tggggtttgc gactgtccag caggcggcgc taataagcct tgtgtctcat
93181 gtggaaaaat aacaggagaa ggtaaacccc ccgttggcaa acatagatcc gtcggggtgt
93241 gcacgtgtaa tgggccctgc acctggctcg tggagggacg cggggaatcc ggagctaata
93301 agctcgatga ctgaccagat gacccaaacc ccgacggttc tggctcttca aaaaacaaac
93361 tgtgcatatc cctccctaca aaaccctgag cccccaccca aagttcgttt tcgctgtcac

Fig. 3 (cont.)

93421 tcgattccgt atcttcgctc tgtgaccgtg atgaaacttc agctgcggag gatgttgtgg
93481 gcgtggcgac tgccgccgcc tgtttcctgg cggcctccct aaacaaaagt taattacaca
93541 aaggtaagtc tgagtgacat ctccaatttc ccgtgatgcc cgctgcacgt acatcccgcc
93601 gcccacacaa cccaccgccc agtacatcaa ccatcctacc tctgggcttt ttttctaagg
93661 ctccttctaa gtgccttttc tctgtgtttg tcatcatggg gatagatccc aaacaatgct
93721 tttagcatgt ttttcatggc tggttcctgc gtcaagtaca caagacatcc ttcacatccc
93781 ttgtatggcc taggtgtcat aatccagcgg ttgagtttca tttttccctt atagatggta
93841 aagggcctct cctgtctggc tcgattggcg gtccttaata gccgtccaaa gcagcccagg
93901 ccagtctcag tctccgggat ttctggcagc ccgtgcctac gtcgctcctc caaaaatgcc
93961 tcatagaagt catcgaagcc ttctggcatt ctctcccgcc ggtttcgacc cggcacggtg
94021 aatattctct tttgttcatc caaccaccct accccccaga agcgtccact gtctaaagca
94081 tctataataa agtccgtgag ccattccgac tccgtgtagc gaggcatctt tttaggcaaa
94141 agccacgaca caaaacacct tttccgtggg cgactttctc gccacaacta gctggacccc
94201 aacccccactg gcacgtagac tctgtgccat ctaacaacaa aactcaatat atgcagctca
94261 acaccgcccc ccccagccgg ttgtcgggct gcggaaactt gtggttagaa ctcactacgg
94321 aaaagggaac caatgcagtt gaactactgg cacacaccca taacccggga cagcacccag
94381 gcactgtcca ccctctaata caagcggcct ttggacgcga gggaggggtg tcatggtcaa
94441 caaaccaaga aaaacacatg tattattcaa ttagccaaca actttattta ttaccgacag
94501 gagacatgag atacataaat ttccaaccgt gcatagggcc aataccatct gtggagcgtt
94561 aagtgccctg tggagttttc gcctaattag ctgaatctcg accccccattg cggccagcat
94621 gctcacgagg aataggcagc agaggcagga cctaactagg agcatatccg gacctgatcc
94681 aagtatgtgc accaaggtga gcaacactgc cgccaaaggc aggagaacaa atagcgctcg
94741 tcgggaggcg acggatacgc ccacgcatga cagtaaccca acataaaata gcgtcatata
94801 cttatccagg ccaatcagga ccggagtcag caggccgatc gaggccgtcg atatcagggt
94861 ggccagcagt aaggtcacaa acacgacaac ctcgcgccta cagtaggccc aggcctggaa
94921 cactgaatag gtgatgtact tcccgggcat gatgaatatg gccctcctcc tttgcattcc
94981 ggccctgatg tacacatgct gttccaggtg cctaaatgcc aaaagtcccc cgaccaagaa
95041 gacaatgaag ggcagccaga aaacgccgga cacaaagacc ttcttaaaca acagaaggta
95101 gtacaccata aatgctccgc agaagcccag ctcatagtac ctgtgtacta ttggcggcgc
95161 ctgatacacc gccgttgcgg tggctagcgg ataaggtaac agcagtaaac agttaagtac
95221 gcacagaccc ggtatgaagg gcacacgaga aaatgtaaac ccagaaaagg ccgcgcaaac
95281 tacagcagca aacactgctg acgcgcagat ccattccagc ctccggtcca gctgtttttg
95341 cgccgcaggg cacagacaca tgcatatcag ggccaagtgc gtgactggca gcgaccagaa
95401 aaacacggcc gtgatctctg tggtaaagag tgtgaacgag tacagggcct tgaagataaa
95461 acaccacaga aagggggtcg ccgccaacgt cccgctcaga taactgaaga gcgacagagc
95521 gcgctcactg tccaggcggc acatggtgtc aaatcagggg gttaaatgtg gttttgggca
95581 ccttcccacg atccctggac tggctcgagt ctgagcgcct cttgtgaggc ctctttgtgc
95641 tgtccttagt tggcgccgct ggggggcagc tggtgacaga ggcagcgtcc tcagaggcgt
95701 cctccagcgg cccaaaggga ccaactggtg tgagaggggg agaatccgga gactccaatt

Fig. 3 (cont.)

95761 ccggctgcct cctggagtcc ggtatagaat cgggaacctt ttgcgaagac tcgcctccct
95821 cggcagacac agatcggttt acctctaaaa gtaggacact taactttacg tcacctgatt
95881 ggcagccagt gggcacacct tccacttcta atatttcgtt ggagtgccaa atcagcccgg
95941 gggtaaacca acccgggact ttacacagtc tcagggcggc gattaaggac tccaggctaa
96001 cccggctcag ggcgtcggtg tgcaccacgc ccacatccac cgacttcttc cccttcagac
96061 catcccagcc agaaacgggt ttggtttctg gcttgaaatc aatgatcttg ctcacgccac
96121 caagagaaaa tgtcacgatc gacagcgtct cgctgacaga cacagtcacc gtttggtcct
96181 cttttgtttt ttgctgcctt agccacttaa gtaggaatgc acccgttttg ccacagagga
96241 gaagcctggt ggtcctacca ccggcttcca tccgatcgtg gaaaggtagg atacccttt
96301 ggtccaccac gcttttgtgc acggtggagg tgaggttgtc cccgtaggaa atggtggtcc
96361 tgacgaactg cggttgggcc cccgtatcgc atgcctcccc ctttcgataa aaggctatgc
96421 cagcgtcgag tacattcgca ccgaatagct cacgcgtgtg cgtgaagccg ctaccgacgg
96481 acgtattcct gaagctgaag ctaacgtctc cactgccttc cgtgtgtccc accaggggcg
96541 taagggcatt ctttattctt aaccccagaa cgccagctgt ccccacgctg gacagcacac
96601 tgagggttgg cgtgcaagcc gatccgtgca cttgcactac tccggtttta gtggcactct
96661 taatgtgttc attgaccctc ctgattttag acaggagggt cacgtccacc ctgaccccat
96721 agtgaaaatc cacaggcatg attgcggccg tagacgcaca gagaaatcac aggaaagctg
96781 cgcgcacact gggtgatctg gagacgatag actgccttaa atagaacttt taggggaggt
96841 ggaagtgtgc gacatggaca ggttaacctt cacaaatcgt cagtcacaca cgtggtgtaa
96901 tcagaattgt ctcgctcaaa aaaattcaca gccttgaaac tgccggtgta tgagaggggg
96961 cacgcttctg gcggaggcgt gccaaatatg ggaggaacga aaatatcacg cagaatcctg
97021 tcagcggtgg cttccaggaa cctccggatg tccaccacgt taacaagcgt caccccggcc
97081 gccttggcct ggataaaccg aatctcaata ttcactgcct ccctgaacag cgcctggacc
97141 tctgcgtgac tgggtttttc ctgtatctcc accatagtgt tgtacaacat actggcggcc
97201 ttggtgtgca gcagctcgtc cctggaaatg taatcgttgg caaggcacac cccgggcatg
97261 atgcctcgca ccctgcacaa actgatagag tagaaggagc taataaagta tatcccctcc
97321 acaatcaaaa acatcagaat cttctgagct ttggtggtcg ccttacgcac cctggagtga
97381 agccactcca gcttctcgca aagggcgggg tccaaaatga tcttggcagc atatgctaga
97441 agttcgcctc gactgttgtt gaaaaatatc ttcaagatat tggcatacac gacaccgtgg
97501 atattctcca tggcaacctg ttcggcataa tagtgggcca cgtcgtggct gttaaaattt
97561 gtgacaaggt cctcaatgtt aaagttaact aggcgttcgg ccattcccaa aaacgtaaac
97621 aaaaatctat aaaagtcctt gtcggcatcg ctgagctggt gcacgtggga aacatcaagg
97681 tgcaggggta tctggctagg aaaccatcgg ttctgccaag tctcgcgcgt tagcgccaaa
97741 aatccgtcgt gatcgcttgt atacagaaat cgatcaactg aatccattgg cctcacccgg
97801 cttgcagaga cctacctact gacagaccag gcactcgggg tctgccgcgc aggactcctc
97861 ctccgggttt ttaggtccgg gtaaccacgc cccatcttgt ttcatcccag agtgaggcgg
97921 tgaccctgga tctgccaggc actgaagagc cgtcagacta gattgcttct gaaccctaca
97981 gtagtacatg agggttttta gaccaagcct gtatccatgt agcagcaggt ccctaagata
98041 gctcgcattc ctgactctgt cctccttgag gaagaagctc atggactggc tctggtctac

Fig. 3 (cont.)

98101 aaacggcgcc ctggcacgag ccctgtccag tagcttaaat ggacagtaat caaaggctgt
98161 taggaatacc ctatatcttt ccctgtgatg cttggggaac gtggaaacgt ccccaccata
98221 ctgtctaacc acccgaaggt cgtcggggag aaccttctta aaaaaagtca cattgggcct
98281 caacacctct tctttattgg tgaccttgga agatatatta gcaaaaaagg ggtacacaga
98341 ctcggcatag ccagttactt gcgaggtccc agccgtcggc atcaccgcca gaaactgaga
98401 attgaatatg ccatgctcgg caatgctctt tcccaacgcg tcccagcgat ggcgtggtac
98461 aaacgaagca tcctccccct cccatgtttg ccaatgaaac ctgcccttgg cgaagttact
98521 gacctcccag ccatgaaatg ggacaccctg tccctccaaa acaaggttgt gactagtctc
98581 caccgcggtg tagtacatag actggaatat attcttgtct aactcagcgc tctcagcatc
98641 gaggtacccg taccccaatt ccgcaaacac atccgccaac ccctgaacac caatccccat
98701 agacctctcc ttttgacctc gctcgacccc cggtgttgga tgggaaccac ccagaatgca
98761 ggcgttgatg acgaggactg ccacccttac tgcgtcgccc aaggcctcaa aacaaaaaaa
98821 cggcctgttg gcgtccgtgg tgccaaccct cgcgctttca acagttctca gacactttgg
98881 aaggcagata tttgccaggt tgcacaccga agtgtttctt cctggcagtt ggactatctc
98941 tgcacacaag tttgagcagt taatggccat gccctgagtg tcggtccagt ggtgttcatt
99001 gagcgcttct tttaaaagca cgtacggtga gcctgtcttt atgatggtgt ggataagagt
99061 gaacatcata gacttcaacg gcatgcaact aacgtacttt ccagcccgca ccaggcgctc
99121 gtattcgtta tcgaacgcag caccgtatag cttaatcaaa ttgggggcgg tggctggatc
99181 gaacaaatac cataacttgg atgggtcctt ttcatacatc ctgaaaaaca atgttgggat
99241 gcacacgccc tgaaagagac tgtgacatct gtcgggattc tccggtagtt tggcgttcaa
99301 aaaatcacag atttgactgt gccagagttc catgtatgcg ctcgcgccaa cgggcctgat
99361 gttattgtca ttgaaataat gaacctgggc atccaccagt ttgaggcaac tggctatgtt
99421 cttttggtgg gagaatgacg taacatccag acccacgcct gacttactgg ccagcaacgg
99481 actcatatcg tggtacaggg cgtccaaagt acccgactca ttcatcatgg agggctgcag
99541 aataaaacag ctggcgagtt gtccgccttc gactccagct gagcgcagta ttggcgtggc
99601 gcagcacacg tgctgcgcag cgaggtagcc aaaaacgtac tccactatag ccatctcaga
99661 tacagactta gcgtcctcaa taaggtcccg cgccaaccaa tacaggcatt catgctctaa
99721 gcactgacag gcaacaaaca cggaaaccct cataaacatt tgcgccacgc tttcatagac
99781 aggctctgtc cccatggtcc ttaggacgta agtatcatac aacctcacgg ccgataggta
99841 gccacagtta agtgtgtcct cgtaagcttt ggaccgtctg taggcgcaca acatatcttc
99901 caaggcatca atgttctttt gaataaacga ttccacccga tgtcccaaca cgcctcgaaa
99961 aatcccaaga tactgcttga gagtcgctgg gcacctagcc tccataattt ggtgccacag
100021 ccgccccgcc atggcattgg cccgcacgtc ccacccgacc ctaaccttta gaaagtctat
100081 gagagattgg gcacacatat caaaatccga caattgtccc gcagacacct gagacccgcg
100141 tcgctctggt gggacagctc ccaagtgaac ctgacaaaat gtccggacag acatgacctt
100201 acagaaacac agtccagggg ccacacgcgg cctcaaagtt cgcaaacacc agtacaggca
100261 aggacgtgcc cttcacgttc agactttggt gcaccggatg agaatcaaag ggaactgtgc
100321 ccagcgtaca aaccgcccca aaaacaagcc gatttatata cagctcgtgc ctcagctgaa
100381 tatacttggt ccggattaca tccgtaaagt gatcctttat catggccaca acctccgcaa

Fig. 3 (cont.)

100441 agcccttccc agactggaaa aacgtcagcg ccatagatgg tctctggttc acacggagat
100501 aaaccaacga ggcataaata gtaacgttta ggcctgccgg ttcccggcgc tggaccatgg
100561 gacatgactc atccaaatca actagcatat cacaagggag ggtcaagcct acgtgtgcac
100621 ggggctcgtc ccgggccaac ccaactccct tcatggcgga ggtgaccttg gtcacgaagg
100681 tactgtggac actctggacc attggaccta ctggggtaag gagggtatga aactccccag
100741 tgtccatgag ttcactcaag ttagggatga aatccgccag gccggatcca cttccgtacc
100801 acacaccggc cactttgtga gtctgtggcg cttttgccgc ttccattcca gagagcataa
100861 acagggacgt gggtgttagc agcatatcca tagacgagcc gttgtcctcc tgcttgaatg
100921 aaaataaaaa ggttcccaga ggctcctggg gactaaaggt ctgtgaatac acgaggaaat
100981 ctccataggt cggctgccta aacggcgcct gccgcaaggc ctcatgcagc gagccaaccg
101041 tgggtcgtgt ggacgccgca tatttagaga gtaaatcccg cacccccctg gcaaactccg
101101 gtcctctagt gagggatacc cggtgagttg gtggaggtaa aagacccaac acttgcctac
101161 ccaggcgagc cgcatttca gcctgcacct tcatatccac gccggcaatg gacggcacag
101221 acgctcttga aaagcttacc aaaggcctga gtgggggagg cgggagcctt caccagacaa
101281 agctgttgat ggaatttcaa ctccgaggac tgccggtgcc tgccctctta aacagcagca
101341 caacagagca gtttttaaat actgttgccc aactgccgac ggacctatca aaatttatac
101401 gcgactatcg cgtgttcgca ctggttcgcg cggcgtattt tttagaaccc ccttctagca
101461 tcgacccccct tgaggcagcg cgcgctcttg gacgcctggt tgatatatta tcatcacaac
101521 caccgcagaa caccgcaccg gcgcagccac ccacctccga cgacaccctg aataactgta
101581 cattgctcaa actactagcc cactacgcgg atcagatagc aggtttcaaa acccccgctc
101641 tccctcccgt gccacctgga atcatcggcc tgttcacatg cgtggaacag atgtaccacg
101701 catgttttca gaaatactgg gcagctgcac tacccccaat gtggatactg acatacgacc
101761 ctcccacttc tccgttacag gactggctta tagtcgccta tggtaacaag gaaggactgc
101821 tactcccctc tggcataccc tcggaggagg tgttagccaa aacattagta acagaacacc
101881 acgagttgtt cgtatcgcgg tcgaattcga ccgagaccgc cgtcaccatg cccgtatcca
101941 aagaacgcgc cctcgccatc taccgggtgt tcgccaaggg tgaggtggtg gcggaaaata
102001 ctcccattct tgccttcacc gacgtggaac tatccacact caaaccccac tatctgttca
102061 tctatgattt tatcatagag gcattatgca agagctacac atactcatgc acccaggccc
102121 gcctggaatc ctttttgagc cgaggtatag acttcatgac tgacctaggt cagtacctag
102181 ataccgctac tagcggcaag cagcagctga cgcacagcca aataaaggaa atcaaataca
102241 ggctgctaag ctgcggtctc tcggcttccg cgtgtgatgt tttcagaact gtgatcatga
102301 ccctcccata tcgaccgacc cccaacctcg ctaacctgtc cacgtttatg gggatggttc
102361 accaactgac catgttcgga cactatttct accggtgcct gggcagctac agtcccaccg
102421 gcttggcctt cacagaattg caaaagatac tgacacgcgc cagcgcggag caaacggaac
102481 gtaacccgtg gagacatccg ggtatctcgg acattccact gcgttggaaa atatcgcgtg
102541 ctctagcatt cttcgtccct ccggcccccca taaacacttt gcagcgcgtg tacgccgcgc
102601 tgccctcgca actcatgcgg gccatcttcg agatctcggt caagaccaca tggggaggcg
102661 ccgtaccggc aaacctggcg cgcgacattg acacaggacc gaacacacaa catatctcct
102721 ccacaccacc gcccaccctc aaggatgttg agacatactg tcaaggtctg cgggtgggag

Fig. 3 (cont.)

102781 acacggagta cgatgaggac attgtgagaa gcccgctctt tgcagacgcg tttaccaaga
102841 gtcacttgtt gcctatactg cgcgaggttc tggaaaaccg cctgcagaaa aacagagctc
102901 tgtttcagat aagatggctg ataatatttg ctgccgaggc ggcaaccggg ctcatccctg
102961 ccaggcgccc gctagccaga gcctacttcc acatcatgga cattctggag gagagacatt
103021 cccaagacgc cctatacaac cttttggact gtatccagga gctcttcacc cacatcaggc
103081 aggctgttcc agacgcacag tgtccgcacg cctttctaca gtccctgttc gtctttcaat
103141 tccgcccttt cgtactcaaa caccagcagg gtgtaacctt gtttctagat ggcttgcaga
103201 catccctccc cccggtgata agtctggcca accttggaga caagctgtgt cgtctcgagt
103261 tcgagtacga cagcgagggc gacttcgtgc gcgtgccagt tgcaccgcca gaacaaccac
103321 cgcacgtaca tctgtcgcat ttcaagaaga caatacagac catcgaacag gccaccaggg
103381 aggccaccgt agccatgaca acaatcgcaa agccaatata ccccgcctac atccggttac
103441 tgcagcggct agaatatctt aacagactca accaccacat tctcaggatt cccttcccac
103501 aggacgccct ttctgaactc caggaaacct acctggcggc gtttgcacgg ttgacaaaat
103561 tggcagcgga cgcagcaaac acttgtagct actccctcac caagtacttt ggagttttat
103621 tccaacacca gctggtcccc acggccatcg ttaaaaaact gctacatttc gacgaggcta
103681 aagataccac agaagccttt ttacagagcc tggcacaacc cgtagtgcag ggacaacggc
103741 agggggcggc tggcgggtcg ggtgtcctga cgcagaaaga acttgagctc ttgaacaaaa
103801 taaacccaca gtttacagac gctcaggcta acattcctcc atctattaaa cgttcatatt
103861 caaataaata tgacgtccct gaggtctcag tcgactggga aacgtactcc cggtctgcct
103921 tcgaggcacc ggacgacgaa ctccgttttg tcccactgac gctggcaggc ctccggaaac
103981 tgtttgtcga atagaggcca tggcagccca gcctctgtac atggagggaa tggcctccac
104041 ccaccaagct aactgtatat tcggagaaca tgctggatcc cagtgcctca gcaactgcgt
104101 catgtacctg gcgtccagct attataacag cgaaaccccc ctcgtcgaca gagccagcct
104161 ggacgatgta cttgaacagg gcatgaggct ggacctcctc ctacgaaaat ctggcatgct
104221 gggatttaga caatatgccc aacttcatca catccccgga ttcctccgca cagacgactg
104281 ggccaccaag atcttccagt ctccagagtt ttatgggctc atcggacagg acgcggccat
104341 ccgcgagcca ttcatcgagt ccttgaggtc ggttttgagt cgaaactacg cgggcacggt
104401 acagtacctg atcattatct gccagtccaa agccggagca atcgtcgtca aggacaaaac
104461 gtattacatg tttgaccccc actgcatacc aaacatcccc aacagtcctg cacacgtcat
104521 aaagactaac gacgttggcg ttttattacc gtacatagcc acacatgaca ctgaatacac
104581 cgggtgcttc ctttacttta tcccacatga ctacatcagc ccagagcact acatcgcaaa
104641 ccactaccgc accattgtgt tcgaagaact ccacgggccc agaatggata tctcccgcgg
104701 ggtggaatca tgctccatca ccgaaatcac gtccccttct gtatcccccg cgcctagtga
104761 ggcaccattg cgcagggact ccacccaatc acaagacgaa acgcgcccgc gcagacctcg
104821 cgtcgtcatt cctccttacg atccgacaga ccgcccacga ccgcctcacc aagaccgccc
104881 gccagagcag gcagcgggat acggtggaaa caaaggacgc ggcggtaaca aaggacgcgg
104941 cggaaagacg ggacgtggcg gaaatgaagg acgcggtggc caccagccac cagacgagca
105001 ccagcccccca cacatcaccg cggaacacat ggaccagtcc gacggacaag gcgccgatgg
105061 agacatggat agtacacccg caaatggtga gacatccgtt acggaaaccc cgggccccga

Fig. 3 (cont.)

105121 acccaatccc ccagcacggc ctgacagaga gccaccgccc actccccggg cgaccccagg
105181 cgccacagcg ctgctctctg acctaactgc cacaagaggg cagaaacgca aattttcctc
105241 gcttaaagaa tcttatccca tcgacagccc accctctgac gacgatgatg tgtcccagcc
105301 ctcccaacaa acggctccgg atactgaaga tatttggatt gacgacccac tcacaccctt
105361 gtacccacta acggatacac catctttcga cataacggcg gacgtcacac ccgacaacac
105421 ccaccccgag aaagcagcgg acggggactt taccaacaag accacaagca cggatgcgga
105481 caggtatgcc agcgccagtc aggaatcgct gggcaccctg gtctcgccat acgattttac
105541 aaacttggat acactgctgg cagagctggg ccggttggga acggcacagc ctatccctgt
105601 aatcgtggac agactaacat cgcgaccttt tcgagaagcc agcgctctac aggctatgga
105661 taggatacta acacacgtgg tcctagaata cggtctggtt tcgggttaca gcacagctgc
105721 cccatccaaa tgcacccacg tcctccagtt tttcattttg tggggcgaaa aactcggcat
105781 accaacggag gacgcaaaga cgctcctgga aagcgcactg gagatccccg caatgtgcga
105841 gatcgtccaa cagggccggt tgaaggagcc cacgttctcc cgccacatta taagcaagct
105901 aaacccctgc ttggaatccc tacacgccac tagtcgtcag gacttcaagt ccctgataca
105961 ggcattcaac gccgaaggga ttaggatcgc ctcgcgtgag agggagacgt ccatggccga
106021 actgatagaa acgataaccg cccgccttaa accaaatttt aacattgtct gtgcccgcca
106081 ggacgcacaa accattcaag acggcgtcgg tctcctcagg gccgaggtta acaagagaaa
106141 cgcacagata gcccaggagg ctgcgtattt tgagaatata atcacggccc tctccacatt
106201 ccaaccacct ccccaatcgc aacagacgtt cgaagtgctg ccggacctca aactgcgcac
106261 gctcgtggag cacctgaccc tggttgaggc gcaggtgaca acgcaaacgg tggaaagtct
106321 acaggcatac ctacagagcg ctgccactgc tgagcatcac cttaccaacg tgcccaacgt
106381 ccacagtata ctgtctaaca tatccaacac tctaaaagtt atagattatg taattccaaa
106441 atttataata aacaccgata cactggcccc atataaacag cagttttcat atctgggggg
106501 tgaactggca tctatgttct cccttgactg gcctcacgca cctgcagagg cggtagagcc
106561 actacccgtg ctgacttctc tgcgaggtaa aatcgcagag gcgctgacgc gtcaagaaaa
106621 caaaaacgct gtagatcaaa ttctaaccga cgccgaaggc ctccttaaga acattaccga
106681 tccaaacggc gcacacttcc acgcccaggc cgtatcaatt ccagtgttag aaaactacgt
106741 acataacgcg ggggtccttc tcaagggcga aaagagcgag aggttctccc ggctgaagac
106801 cgccatccaa aacctggtat cctccgaatc atttatcacc gtgaccctac acagtacaaa
106861 ccttggaaac ctagttacca acgtaccaaa acttggtgag gcgttcaccg gggcccgca
106921 cctcctgaca agcccgtccg tgagacagtc cctttccacc ctgtgcacaa ccctgctgcg
106981 agatgccctg gacgccctgg aaaaaaagga tccggccctt cttggtgagg ggaccacgtt
107041 ggcgctggag acactcctag gatacgggtc ggtgcaggac tacaaggaga cggtacagat
107101 aatatccagc cttgtgggca tccaaaaatt agtcagggac cagggcgcgg acaagtgggc
107161 cactgccgtg acaaggctaa ctgacctcaa atcaactctg gccacgaccg ccatcgagac
107221 ggctacgaaa cggaaactat acagattgat ccaaagggac ctcaaagagg ctcaaaaaca
107281 cgagaccaat cgggccatgg aggaatggaa gcagaaagta ctggctcttg acaatgcgtc
107341 tccggaacgt gtcgccaccc tcctgcaaca ggctcccacc gcgaaggcta gagagtttgc
107401 agagaagcac ttcaaaatac tactccccgt acccgcggac gcccccgtcc aagcgtctcc

Fig. 3 (cont.)

107461 aacgccgatg gaatacagcg ccagccccct cccggaccca aaggatatag acagagctac
107521 atccatccac ggggaacagg cgtggaagaa gatacagcag gcgttcaagg atttcaactt
107581 cgccgtcctg cggcccgctg actgggatgc cctggcagcg gagtaccaac gccgtggttc
107641 gccccttccg gcggccgtgg gtccagcgct ctcagggttc ctggagacga tcctagggac
107701 gctgaacgac atctacatgg ataagctccg ctcctttctg cccgacgcgc agccttttca
107761 ggcgccgccc ttcgactggc taacgccgta tcaggaccaa gtcagctttt tcttgcgcac
107821 catagggctg ccgctggtgc gagcgctggc cgacaagatc agcgtgcagg cactgaggct
107881 tagccacgcg ctccagtccg gcgatttgca gcaggccacg gtgggcacgc ccctggagct
107941 ccctgccaca gagtacgcgc gcatcgcctc caacatgaag tccgtgttca acgaccacgg
108001 acttcaggtg cgatcagagg tcgcggatta tgtggaggcc caacgagccg acgcacacac
108061 gccacacgtc ccacgtccaa agatacaggc accaaagact ctgattccac atccggacgc
108121 aatcgtcgcg gacggactac ccgcctttct taagacgtcc ctactgcagc aagaggccaa
108181 acttctggcg ctacagcggg cggacttcga gtcgctcgag agcgacatgc gcgccgcaga
108241 ggcccagaga aaagcatcgc gcgaggaaac ccagcgcaaa atggcacacg ccatcactca
108301 gctcttacag caggcaccca gtgcgatctc ggggcgcccg ctatccttac aggacccggt
108361 gggcttcctc gagggcatca tatacgacaa ggtcctggag cgcgaatcct acgagacggg
108421 tctcgaggga ctgtcctggc tcgagcagac catcaagtcc atcaccgtat acgctcccgt
108481 agaggagaag caaagaatgc acgtgctgct ggacgaggtg aaaaagcagc gagcaaacac
108541 tgagaccgct ctcgagctag aggccgcggc tacgcacggc gacgacgcta gactcctgca
108601 gcgagcggtc gatgagctgt caccgttgcg cgttaagggg gggaaggccg cggtggaatc
108661 ctggcggcag aaaatccaaa ccctgaaatc cctggtacag gaagcggagc aggccggcct
108721 cctgttggcc accatagaca cggtggccgg ccaggcccag gagaccatat caccatccac
108781 actccaggga ctgtaccaac agggacagga ggccatggcg gccattaagc ggtttaggga
108841 ctcgccccag ctagctggcc tgcaggaaaa gctggccgag ctacagcagt acgtcaagta
108901 caagaagcag tatctggaac actttgaggc cacccaaagc gtagtgttta cagcctttcc
108961 gctcacacag gaggttacga tcccagccct gcattacgcg ggacctttcg acaacttgga
109021 gcggctctca cgatacctac acatcggcca gacgcagccg gctccgggac agtggctcct
109081 gacacttccc acattcgacc ccacgcgccc ggcctgcgtc ccagccggcg gccacgaacc
109141 cccgttgcac agacaggtgg tgttctccag ctttttggag gcccagatcc gattagcgtt
109201 gtccgtagcg ggccccgtgc ctggacgggg tctgcccgga acaccgcaga tccgaagggg
109261 cgtggaggct gccgcttgtt tcctccacca gtgggacgag atatctcgcc tccttccaga
109321 ggtactggac accttttccc acaacgcgcc ccttcccgca gagtcttcct ccaatgcttt
109381 cctggccatg tgcgtattga cgcaccttgt ctacctagct gggcgcgccg tcttgggccc
109441 acgggagccg gagcacgccg ccccggacgc gtacccaagg gaggtggcgc tggccccgcg
109501 cgacctgacc taccttctac tggccatgtg gccatcttgg atctcggcaa ttttgaaaca
109561 gccttcgcac gcggaggcgg cgcacgcatg tcttgtcacg ctgccaacaa tgctcaaggc
109621 tgtgccgtac ctcacgctgg aagcctcagc tggaccactg ccggcggaca tgcgccactt
109681 cgccacgcca gaagcgcgtc tgtttttccc cgcgcgatgg caccacgtca acgtgcagga
109741 gaaactgtgg ctgcgtaatg attttatgtc gctgtgtcac cgttccccgg ggcgcgcgcg

Fig. 3 (cont.)

109801 catagccgtc ttggtgtggg ccgtcacttg cctagatcct gaggtaataa ggcagctgtg
109861 gtccaccttg cggcccctta ctgcggatga atccgacacg gcttctggac tgctgcgggt
109921 gctagtagaa atggagtttg gtccgccgcc caagacgccg cggcgggagg cggtggcgcc
109981 cggcgcaaca ctgccaccgt acccctacgg ccttgccacc ggcgagcgcc tggtcggcca
110041 ggcgcaggaa cgctctggcg gcgctggcaa gatgccggtg tccgggtttg agatagtttt
110101 aggcgcactg ctgttccgcg cccccctacg cattttcagc accgcatcaa cccacaggat
110161 ctcagatttc gagggcggtt tccagatact gactcctctc ctggactgtt gcccagatcg
110221 cgagccattc gcctccctgg ccgccgcacc acgaaggacg gtgccactgg gagacccgtg
110281 cgccaacatt cacacccccg aagagataca gatctttgcg cgtcaagccg cctggcttca
110341 atataccttc gcaaattacc agatccccag caccgacaac ccgataccga tcgttgtgct
110401 aaacgctaac aataaccttg aaaacagcta catccctcgc gatcgcaaag cggacccgct
110461 acgaccattc tatgtagtcc ctctgaagcc gcagggtaga tggcctgaaa taatgaccac
110521 agcaacaacc ccctgccgcc taccgacatc gccagaagag gcgggatcac agttcgccag
110581 actccttcag agccaggtga gcgccacatg gtctgacatc ttctccaggg ttcccgagcg
110641 cctcgctccc aatgcgcctc agaagagttc ccagacaatg tcagaaatcc acgaggtcgc
110701 cgccacgccg ccactcacaa tcaccccaaa taaaccgacc ggaacccctc acgtctcccc
110761 ggaggctgat ccaataacag aacgcaaacg cggacagcag ccgaagattg tcgcggacaa
110821 catgcctagt cgtattctcc cgtcgctacc gaccccgaaa cccagagagc ctagaatcac
110881 gctaccccac gcactgcccg ttatatcacc cccagcacat cgcccgtcgc ctataccgca
110941 tctgccagca ccgcaggtaa cggagcccaa aggggttctc caaagcaaac gtggaactct
111001 cgtgctgcgg cccgccgcgg tcattgaccc acggaagccc gtctcggcac cgatcacgcg
111061 atatgagagg acggcgctcc agcccccccg gactgagggc gaaggccggc gccctcccga
111121 cacgcaaccc gtcactttaa cctttcgtct cccacctacc gcacccactc ccgcaactgc
111181 agccctagaa accaaaacaa ctcccccatc cacgccccca cacgccatag acattagccc
111241 accacagaca cctcccatgt ccacctcacc tcacgcgaga gacacaagcc cccccgcaga
111301 aaagcgggcc gcacccgtca ttcgagtaat ggcgcccacg caaccgtcgg gagaggcaag
111361 agtcaagcga gtggagatcg aacagggcct ttccacacgc aatgaagccc ctccccttga
111421 acgctcgaat cacgccgtgc ccgccgttac cccaaggcgc accgtagccc gcgaaatcag
111481 gatcccgccg gagataaagg cgggttggga cactgcaccg gacattcctc tgccccacag
111541 ctccccggag tcatccccac cgacttcccc ccagcctatc cgcgtggatg ataaatcgcc
111601 tcttcccaac ctcgtagaga gatacgcgcg gggtttcctg gacacgccct ctgtagaggt
111661 gatgtccctg gaaaatcagg acatcgccgt ggaccccgga ctgctaaccc gccggattcc
111721 atccgtggtg cccatgcccc atccaattat gtggtcaccc atagtaccca tcagtttaca
111781 aaacacagac atagacactg caaagataac actgattagt tttattagac gcatcaaaca
111841 aaaagtggcc gccctatcgg cgtccctggc ggagacggtt gacagaataa agaagtggta
111901 cttgtgactc cacggttgtc caatcgttgc ctatttcttt ttgccagagg ggggtttcct
111961 cgcgtcggcc accgcggggg cggccgtttc cgtcgtggat gagagggttg tgagaatgtc
112021 tgacgccggc gacaatgaat ggggaccaga ggacagggtg gttatactgc ttcccgagac
112081 ccccagtgag tcctggcccc cgggcgtggt gccggatgca gggcctggcc tcgaaggcac

Fig. 3 (cont.)

112141 ggtgaacgtc cccgcgtcgt aagccgacgc cgcggaaact cggtcagcgc gctcgcgcgg
112201 tttctgatcc ctaagggtct gcagatgatc ccgcctttga attccaccca tcctcctcag
112261 ataggcctca taataatgat gggcaattaa gaacacgaga tagtgtctct tttgcacgag
112321 gtattcggcc tgcgacatat ttccctgatc cagggtattc atgcgagcca ccaggggatg
112381 gtgagcgtag tcatgatcca gtcgctcctg gatcacgggg tctctcacct taaagttgga
112441 catcttccac acaggcgggc gaaatagcct caggaggaac acttcccgca acagaactcc
112501 agcagctgtg aggtgagctg aagcagtccg cgcacgtcac ggtgctttaa tagggcagcc
112561 tcgcagtcgg gcgtcccaag gcaaggcact acaaaactga cagtttgatc taggtctcga
112621 atggcaaggg ccgcgttgtt agctagaaca gccctgatta cgacgcgtgc tagggtcccg
112681 cgtccggtaa tatcgcacag gggatacacc ctcatatgtt cgctgccaca gtaagaacag
112741 tagatcctcc ccgtggtcgc acagatggtg aactgcttct ctttcctgtc cctgctgaaa
112801 aacacgttgg tgggaggaaa attgacagta tgaaacttgc ccctgccaaa gttaagacag
112861 tgtccacact ccatgcacac aaccgcccga gcgcaacgcg cccgcttggc aagggccgcg
112921 cgggccacgc gagaacagat gacgggtatg gacacgcagg gggagagaac attgtatgcc
112981 agaagcctcc tgccaaggtt ccgcacgaga ccaggtccct cctgctcgca ggcgggcagc
113041 actacgtggc gggacttaat aaggctcaaa aaacacagtg acccaagcat ggcgtcgaac
113101 gggttaccgc agggaaccgt aggggcgacg cgctccaagg cctcccggag gccggtatct
113161 gccgccccta tcccgagccc gttaccgtct tcggtcgcag ccacaccgcg acgggtgtgc
113221 gagggcacct ccaggagggg acgacgcggc aacggcccat gccacttctt ccttagccag
113281 ggtagcgacg gtgggggctt cgaacagcag gtcactaacg gaaagcgaga gcaaagcgcc
113341 aacagcttgc agagttgggc acaggccttg gaaaatggaa gcgacaggta ttttgcccat
113401 acgtggcgcg gtatcgccct agcatggtcg gcggcctggg cacgggacag cgtcaccaca
113461 acccatacgt gggcgccaag cagctgctgc gccgcacaaa tctgcgcctg tttggcgacg
113521 gtgtctgagc cagcgcgcaa cacggcgatc gcctgcgcca gcgacgggcg gtccaacagg
113581 tgcctggccc aggagggcat gtttccctgg aaaccccgct ccccgaatat gacaaaagcc
113641 acatattcct ccactggcac gccattctcg ccctcgaaca cgcggtgggc cgtcagctgg
113701 gcctcatcca aaccaaacca agacacaaga aagcgatccc agcgctgatc cagggccatg
113761 accttctcac cagcgcgacc gcacggccta agctccactg aaaggcgccc agaatccgca
113821 ccgtcctacc cccctggccc gcccaatata ccgctgtgac gtctgatgta caggcccgcg
113881 cgtcgcggcc gttggtggga aaaccggcac caccctgtgc ggccgaatcc gccacggggg
113941 ctgccagaca gtacactgtc tccagcagcg acttcagtct cttgtgactt ttgggcgtca
114001 ccaccaaaaa ttgcaaaacc tgcctgtagt ccgtgaagta ggtacggcat attaccatgg
114061 agttgtacac gcccaggttc tttgagaaca ccaggctcgc cttgaacttt gtaaagtcat
114121 cctgccccag cacgacagac gtatttttgg caaggtatac gtccgactcc acgggaagga
114181 cgtgcccaaa ctgggacacg gcgtcgcttg gtcggcacag aaagcacttc agggttgtgg
114241 aaaggccatt attcgatata acaaagcagg gagagaacgg gtagtgcatc tcctccagga
114301 ggtgcgccca aaacttatac acaaactcta agtggtacac gcaaccgtgc tgcattctaa
114361 ccgtacatat ggcggtagca ccgcccttag cataaactgg ggccccgtcg atgcaccgtt
114421 ccaaatccag ggactgacca gactgtccca agtatgagga taccacccga cacagttcgt

Fig. 3 (cont.)

114481 ccactacacg cttaccaacg acactcatgg cgacagcggg gtggggctgg caaggccccc
114541 aaagcgcgac acccgcagtc aatcagggcc gtgcccgcgc ctcggagaat acggcgtccg
114601 tgctcacgat cttgcgcagg acctgcctta ccgtgtccac cttgctctcc aacaccagag
114661 tatgatcgca ggctgcaggc tgtgcccgct ggacgagaaa ggtttttaaa tactgacagt
114721 agttgatggc gttcaatcta caatagatcg tgggaaataa aatttgcatg tcacgaggca
114781 gaagctggtc agacgcgtac tccatgttgg gttccacggg gaggggaaca cacgccccaa
114841 gacacgacgg cgcacatagg gagcggagca aacaattgat tcaaatattt gactccgcag
114901 cgagccggtt tgcagagtgg tcacctgccc tgctccacac ccaccccccgc gtctcttcca
114961 actctcaact cacgatccag ggaaaccacc gtccagtggc catgtttgtt ccctggcaac
115021 tcggtacaat tacccgtcac cgagatgagc tccaaaaact actggcagcc tccctgctcc
115081 cggagcaccc ggaggagagc ctcggtaacc ccataatgac acagattcac cagtcgctcc
115141 aaccatcttc cccctgcagg gtctgtcagc tcctatttc tctggtccgc gattcgtcca
115201 cccccatggg tttcttcgag gactatgcct gcctctgctt cttctgtcta tacgccccac
115261 actgctggac ctcgaccatg gcggcagcgg cagacctgtg cgagatcatg catctgcact
115321 ttccagaaga ggaggcgaca tacgggctat tcggaccggg tcgccttatg ggtatcgact
115381 tgcagctgca cttctttgtt caaaagtgct ttaagaccac cgccgccgaa aaaatactgg
115441 gaatatccaa cctgcaattt ttaaaatcag aattcatccg gggcatgctc acaggcacca
115501 tcacctgcaa cttctgcttc aaaacgtcct ggcccaggac agacaaggag gaggccaccg
115561 gccccacccc atgctgccag attacagaca ccaccaccgc acccgcgagc ggcataccgg
115621 aactagcccg ggccacattc tgcggcgcaa gtcgccccac aaagcccagc ctacttcccg
115681 cgctaataga tatctggtcc acgagctcag agctccttga cgagccgcgc cctcgactga
115741 tcgcaagcga catgagtgaa ctcaaatccg tggtcgcatc ccacgatccg ttcttctctc
115801 ccccgcttca ggcagacacc tcacagggtc catgtctgat gcacccaacc ctggggctac
115861 gatacaaaaa cgggactgca tccgtctgcc tcctctgcga gtgccttgcg gcacacccag
115921 aggcacccaa ggcgctgcag acccttcagt gcgaggtaat gggccatata gaaaacaacg
115981 taaagctggt agacagaatt gcctttgtgt tggacaaccc attcgccatg ccatatgtat
116041 cagatccgct acttagagag ctgatccggg gctgtacccc acaggaaatt cacaagcacc
116101 tgttctgcga cccgctgtgc gccctcaatg ctaaggtggt gtcagaggac gtactattcc
116161 gcctgcccag ggagcaggag tataaaaagc tcagggcatc cgcggccgcc ggacagctcc
116221 tcgatgccaa caccctgttc gactgcgagg tcgtgcagac tttggtcttt ctctttaagg
116281 gtctccaaaa cgccagggtg gggaaaacca cctcactaga cattattcgg gagctaaccg
116341 cacaactaaa aagacaccgc ctagacctgg cccacccctc acagacgtca cacttgtacg
116401 cttgagctgg tcccgggcct tcgcacccca tccaccgatg ccgaaatcag tgtccagcca
116461 catcagcttg gcgacctcaa ccggtcgcag tggaccgcga gacatcagaa gatgcttgtc
116521 atcccgcctg cggtcggtcc cgcccggggc gcgaagcgcc agcgtcagca gcaagcacag
116581 aaacggcctt cgcaagttta tctcagacaa ggtatttttt agcatcctat cgcacagaca
116641 cgagctagga gtggactttc tccgtgagat ggagaccccg atatgcacct ccaaaacagt
116701 aatgctgccc ctagacctgt ctaccgtcgc acccggccgc tgcgtctccc tctctccgtt
116761 tggacactcc tcaaacatgg ggttccagtg cgctctgtgc ccatccacag aaaatcccac

Fig. 3 (cont.)

116821 cgttgcccaa ggctcccggc ctcagacaat ggtgggcgat gcgctcaaaa aaaataacga
116881 gctatgctcg gtagcgctgg ccttttatca ccacgcagac aaagtgatcc aacacaagac
116941 gtttacccta tcactcctca gtcactccat ggatgtggtt cggcagagct tcctgcagcc
117001 tggtctactg tacgctaacc tggtcctaaa aacctttggg cacgatcccc tacccatctt
117061 cactaccaac aacggcatgc taacaatgtg catccttttt aaaacccggg cactacatct
117121 gggagaaact gcgcttaggc tgcttatgga taacctcccc aactacaaga tatcggcgga
117181 ctgctgcaga cagtcctacg tggtcaagtt tgtcccaacg cacccggaca ccgcaagcat
117241 tgcagtgcag gtacacacca tatgcgaagc ggttgcggcg ctagactgca ccgacgagat
117301 gcgggatgac attcaaaagg gaaccgcact tgtcaacgcc ctataacctc acatgtagcc
117361 tgtcacccca gctcctattg caactgacca tgttcaggtg gtaataaagt cattaaacga
117421 caaagtgatt cttttaatct gtttattgtt tttgaacatg tggcacacgc tgcaatgtac
117481 tgccatgaaa ggtggttcta tatccaccac ttggcgtctg ccgaagtcag tgccacaatt
117541 tcattaacaa acaaggtcaa tacattgtga gggagtgttt tttgccatgg taccattcgt
117601 gtggtttggg agagcggacg ccatttgcgt gcaaaatgtg ctttgctgga ggccaacttc
117661 cgtcgcgctg gttgatgcgc ggcacattgt gtcaaccagg gcaccctccc ccaccgagtg
117721 ctttaatgcg gagaggaatg gtggcctggt tgacaccgcg tgccggccat ctgaactgtg
117781 actgtgttat gagccacggg tatgccctcg atacgcctgc tcttcagcat tgtatgtgtt
117841 taatgttgtg cttggtgcaa ccgtgattgt gtttttgtat tttattttac tgacactctt
117901 tgggagggca cgctagcttc agtgcgcgcc cgttgcaact cgtgtcctga atgctacggg
117961 gccacgctgg ccactcgggg ggacaacact aatcgccaac agacaaacga gtggtggtat
118021 cgccccaagc ctccagcgcc acccatttag taacacatcc gggacatgaa ctgccacaaa
118081 caccgttaag cctctatcca tgcattggga ttggagtgag gagggaggag ggcaccaggt
118141 tcccggggag gagggcacca ggttcccggg gaggagggca ccaggttccc ggggaggagg
118201 gcaccaggtt cccggggagg agggcaccag gttcccgggg aggagggcac caggttcccg
118261 gggaggaggg caccaggttc ccggggagga gggcaccagg ttcccgggga ggagggcacc
118321 aggttcccgg ggaggagggc accaggttcc cggggaggag ggcaccaggt tcccggggag
118381 gagggcacca ggttcccggg gaggagggca ccaggttccc ggggaggagg ctggggtgcg
118441 ccgcgccggg ttcctggggt gcgccgcgcc gggttcctgg ggtgcgccgc gccgggttcc
118501 tggggtgcgc cgcgccgggt tcctggggtg cgccgcgccg ggttcctggg gtgcgccgcg
118561 ccgggttcct ggggtgcgcc gcgccgggtt cctggggtgc ggggtgcggg ggaccgcgcc
118621 ggggtactgc agggttcgca gggttcgggg gtactacctg gtttcctggg gtgtgccagg
118681 acgggttcct ggggtgccac cgctcctcga tacgtgtaaa tccaagagat ccgtcctccg
118741 tgccgccgcg cgcgtaatgc gcgagggggg tcggtctccc ctcttcttta tagcgtttcc
118801 tgcgaagggg gcgtaaccgt aggacaaact gcttatgtag ggttagcca cccatttccc
118861 ggggccgcgc cagaggtgag cgtggaccta gcatcccgct cccatttacc gaaaccaccc
118921 agaggcgaga ttccagggcc gtgactcact agctcccctc ccatcgaaca accacgcttg
118981 gctaacacgg ctggagtggc ggtgggcggg gcccctataa tcctggcccc catctactga
119041 aacgacccag tagaaaaatc ccaaccccat gactcatcag gccctattat atagaatatc
119101 ccagtagagt gacccagctg gtttccataa atggatatac ttccggaaaa cgaaggaggg

Fig. 3 (cont.)

119161 ttgaatacag ttgggggtag tccgctggta ttcccagctg aggttgcctt atttggtaat
119221 gcttccggaa ataccacctg agtaccccat tggtttatac cttgtttaat tgtagaatta
119281 cagctggatt tacccagccg ggtttacgca gctgcgtata cccagctgtg tttacgcagc
119341 ggggtttacg cagctgggta gacccagctg ggtataccta ctggaatagg ggctgcgatg
119401 actcagctgc gctaggatta aaggattata tatatatata taggaaaaat caaaacaaaa
119461 ctctaatcgc tgattggttc ccgctctggg ccaatcagct tgggagttct agggataggg
119521 gccaatggga ggcctccgaa tttgattgac ggctggggcg tccaatggaa tggcgcggtc
119581 gcctagctcg aacgggattg gtcggccgga tgggccaatg gcggctcgga aaactttgat
119641 tgacgggccg gcggaccaat gggagcgggg cagaggatta tgggggatta gcaaattcaa
119701 gatggcggcg cccatgaaat ggccaaaaat tataattttt cgagtcgctc acggtcccac
119761 ctagcggcgt gacctggagg tgaccccgtg cacccgggcg ctctgaattt ttctgcgcat
119821 gcgcgactcc tcatctacat aatttatgca cataaaagga ttagcgcatg caaattagtc
119881 agatagcagg gccatccaca ctttatgttg gccgcgtgcc aggcgccggc gtgggcgccg
119941 cgcgcgtgct ctctcagtcg cgcctagctg cttccaacag acaaaagcgg ggcgttagtg
120001 agggagtgcg cgcgctgcgc tgacttggcc gatttccagt gcatgctttg tcaccccagc
120061 gcgagaatgg aattttcatt attgagcaat ttgggcaccc tgggcacgat aaccatacat
120121 ggatacacgg gttccaaata tgcaaagtag acactaaggt accatttggc atatttggac
120181 gtcctgggca ggttagctac ccaccagaat atatgggact ctgggcagga tagccaccca
120241 caattgtttt gcgcccctct ttggccaggg gaccaaggtc gtatggttcg cgctacacta
120301 agcccgaacg ttcagctttg cgtgctttcg acgtccaggc ggctggcaca cgggccgtga
120361 gcgccagcaa catgggatca tggtagtaag atacagcata aatccccgtc cggtggcgct
120421 caacgccaat atgcgcggct gcgtggtatc tcatcggtgg gcacgcgtac ggtggtctca
120481 tgggtattgg acttgtaggc gaggggaggc gcatacgaca aaaattgccg ccgtgaaggt
120541 cgggaacccg cccgcgcttc cgcaaggcac ggggccgcat cggacacagg ctaagcatta
120601 aggatcataa caccgcccta gaaatgttta agctgtgacc aaagcgaacc tcgcatgagg
120661 catacgcgag cgtggaggta ggattcccaa ggctattgag agacggtggg tgaaatgatg
120721 aagaacacac agaacaataa cgggcgacta gataaaaaga ctcgctcaac agcccgaaaa
120781 ccatcagccc gaccgccgat ggattaggtg ctgctggaca agtctttcta aacccgcgca
120841 gggtttgtgt cgatccagac gcttacgaac gcccgcttta aaaacactat tcataattaa
120901 cagaagttga caccagcccg cagttaccca accttctatt tttttggagt gttgacaagt
120961 ttccatcgcc cgtttggcgt ttcccgcatg gtgtcaaatt agtgacgcac cctccccccg
121021 tcactatggg tttaccctga tttagtaagt aaaactgccg cccccgccca ctcatttttt
121081 taccctgtta tttgctgtat ttacatctac ggaccccctt ttggtgagat tgccgtggtt
121141 ctaaataacg ttgtggtttt cggacccttt cagggaccaa atcttttacg tgttgccaag
121201 gtagcatttg ctggacccgc ataggttttt gtggcaccag gttatggtct tatgagcggg
121261 cttgaccggc aagttccagg catcctaagt gcttgatgta gacccttagg gcaccaggga
121321 ctacctaggt caaactcccc cttagtcatg acgccgtgcc cacgaggttt gagaggcgta
121381 gacatccgtg tcgactgctg gacggaggta gtataatcag ctaggcctca gtattctatg
121441 taacaaatga atgccctaga gtactgcggt ttagctagtt atactgcccg gttccaccag

Fig. 3 (cont.)

121501 gcggcgttgt ggccacgggc ggttcgtcgc ttggacctgg aggggtgtca cattctgtga
121561 ccgcgacgtt gacgttagac acacgtcgct gccgtcctca gaatgtgata gcccatcaca
121621 ggcattgtag ctgttgcgtt ggttgggagt ttggggacca aatttctata attggtgtca
121681 ccgcggcagc tctagccctg gaagatctgg aagcttgctt caatggctca gatcgacccg
121741 gactacagtt agcgaagtag acccattata atcttaatct taaatctggt tgacggactt
121801 tcgcgccggg aacacgcagg tggcagcgga tgtgttttgc ccaaacacga gggttgcagg
121861 aaacaggtgc tgccggggat tatgtacagc ttacacccag tttcctgtaa tcgcccgcat
121921 ccggccgtcc tgggcagcac cgcaccctgc gtaaacaacc gcgtactttt tcctcctccc
121981 cccaccccca catccttcct cccaccctgc cagtccaacc cgcttcctgt tttattcgcc
122041 ttcaaacaga agcacgcatt ctaatgattc ttacaaaact tgttagtgtt tattaaatca
122101 gatacataca ttctacggac caaaaattag caacagcttg ttatctatgg tgtatggcga
122161 tagtgttggg agtgtgatgg gccggaaagg tgaaggccca ttagggtttg cacttggcgc
122221 tgtaggtcta ctcttgacaa agatctaagc attgacatta gggcatccac gtcagtggga
122281 cccagtaggt ctaagttttc catacagtac acccagtgta agaatgtctg tggtgtgctg
122341 cgagacccta tagtgtcctt gcttaaaaat atcaaagacc taatatccct cgcacacagc
122401 tccccgtcta cgtggagaac agtgagctga taagggctga aataactcat tgtgcccgct
122461 aggtggcgct ctaaaaaacg cgggtctaag tgaagcaggt cgcgcaagag gtctctgcga
122521 cctgcacgaa acagacattc cgctaacagg ggaaacgtta acctgccctc ctcctttaaa
122581 gctctaagag ctccaattaa ttgggccagt gtgggttgag gtatgaacac gtttaggagg
122641 aacaatacca cttccctgtc atccgtgccc agtttccgcg ccacctcaca gagaacctcg
122701 taagtggcca tggtgccggc ttgtatatgt gaaggcaccg atgtggaaaa acaaaggaaa
122761 atttattttt ccgccctaaa caaaatcaca agcttaatag ctgtccagaa tgcgcagatc
122821 aaagtccgaa acagatgtta ggatctgttc cactgccgcc tgtagaacgg aaacatcgca
122881 tcccaatatg cttgccagct gaggaactac cccacccgag tgggtatcct gcggaatgac
122941 gttggcagga accaacagcg cacagcctgc agcgctgata atagaggcgg gcaatgagcc
123001 agtctttggg tcaactaagg cttttgtaat cagggtgttg acctcgtggt gccaaaagtc
123061 caggtgttgg gagcccccca gcaatttaag taacaagaag gaagtgacgt ccgtcgctaa
123121 gactgcctct gttcgccacg ccaacttctc aaggagttct ttctcctggt ctataagttc
123181 ttggcgggaa aaggagtctg ccgcggcata gcaaagtgaa ctggtagaaa taggcgtgag
123241 gcttctgagc ttactggcca ctaacaggca ggcgctccct gtcttttgaa agtgttcttt
123301 ggacacctgc tttataagta ggagtctgtc caaaagatta agggccaacg cgaccacgtt
123361 aggttctagg ttgtattcct ggcaaactga aaacatccat gtgcccagta acttacgcat
123421 atgcgaagta agagattgtt gaaaggtccc aaatacagag tcagaagtta aaaagcgcgg
123481 ctcaatttca agaatattgt aaaagatccg atcctcacat agcgtgggat ccagaagtcc
123541 cgagggcggg ttattggcag ttgccatata gagtggcgag cgtatgtggc ctacctgtag
123601 agcctggagt ttcagggtgc tctgtcaggt tctcccatcg acgacgctgg gccgcgagag
123661 tacgctagcc gttgtccgtg tgttcagttg aggtagatgg gtcgtgagaa cactgccccc
123721 cacacacacc agcacccatg gcgccaaatg caagtgcgga gcggcgacgg tggcttctag
123781 ggaggaaaaa gggggagagg tgtggctttt atgtcatttc ctgtggagag tccccaggac

Fig. 3 (cont.)

123841 cttggttttc ccctggctgg gttaatggca ggggcttttt aaacttaact atggaagatt
123901 gtaggtttcc tgccaggggg tgactagctt cccaggctag gcgggccatt tgtactttct
123961 tacttgtgtc tttgttctga caatacacat atacacaata agttatgggc gactggtctg
124021 gtccagggtg gggcaagcag gacacggggc ctgcctttac tcctccaaac tggaaggcct
124081 gagataattt tttaagtccg tatgggtcat tgccccaaaa aatcactgca aacttccatt
124141 gacactttgg atctcgtctt ccatcctttc ccaaaaagcg tctataaaag atgtgttgtg
124201 gcctagcttt cgcaggacaa tcatctatct gtctgtaagg gaccggtggt tgttggtatc
124261 ttggatgtgg cttttttggg tgggtaactg gaacgcgcct catacgaact ccaggtctgt
124321 ggggtggtga tgttctgagt acatagcggt attcgcgaga tgggccaggt tgtgggtcat
124381 cgtctggtgt attatctcct ggtgggctac tggcaatttg ttcatgtgtg ctaacaacag
124441 ggtaatccac ttccatttcg tcctcggatg acgacccgtg caagattatg ggctcttcca
124501 ccgtctcctg ctcctgctgt tccaccccct gctgctcctg ctcttccacc tcctctaact
124561 cctgctgctc ctgctcttcc acctcctcta actcctgctc ttcctgctct tccacctcct
124621 ctaactcctg ctcttcctgc tcttccacct cctctaactc ctgctcctcc tgctcctcct
124681 gctcctgctc ttgctcctcc acctcctcta attcctgctc ttcctgctcc tgctcttgct
124741 cttccacctc ctgctcttgc tcttccacct cctgctcctc taactcctgc tcctgctcct
124801 ctaactcctg ctcctgctcc tctaactcct gctcctgctc ctctaactcc tgctcctgct
124861 cctctaactc ctgctcctgc tcctctaact cctgctcctg ctcctctaac tcctgctcct
124921 gctcctctaa ctcctgctcc tgctcctcta actcctgctc ctgatcctct aactcctgct
124981 cctgctcctc taactcctgc tcctgctcct cctgctgctc ctgctcctcc tgctgctcct
125041 gttcatcctg ctgctgctgc tcatcctgct gctgctgctc atcctgctgc tgctgctcat
125101 cctgctgctg ctgctcatcc tgctgctgct gctcatcctg ctgctgctca tcctgctgct
125161 cctgctcatc ctgctgctcc tgctcatcct gctgctcctg ctcatcctgc tgctgctcat
125221 cctgctgctg ctcatcctgc tgctgctcat cctgctgctg ctcatcctgc tgctgctcat
125281 cctgctgctg ctcatcctgc tgctgctcat cctgctgctg ctcatcctgc tgctgctcat
125341 cctgctgctg ctcatcctgc tgctgctcat cctgctgctg ctcatcctgc tgctgctcat
125401 cctgctgctg ctcatcctgc tgctgctcat cctgctgctg ctcatcctgc tgctgctcat
125461 cctgctgctg ctcatcctgc tgctgctcat cctgctgctg ctcatcctgc tgctgtggct
125521 cccgctgctg tggctcccgc tgctgtggct cccgctgctg tggctcccgc tgctgtggct
125581 cccgctgctg tggctcccgc tgctgtggct cccgctgctg gggctcccgc tgctgtggct
125641 cccgctgctg tggctcctgc tgctgtggct cctgctgctg tggctcctgc tgctgtggct
125701 cctgctgctg tggctcctgc tgctgtggct cctgctgctg tggctcctgc tgctgtggct
125761 cctgctgctg tggctcctgc tgttgtggct cctgctgttg tggctcctgc aggggctcct
125821 gctgctgtgg ctcctgctgt tgtggctcct gcaggggctc ctgctgctgt ggctcctgct
125881 gctgtggctc ctgctgttgt ggctcctgca ggggctcctg ctgctgtggc tcctgctgct
125941 gtggctcctg ctgttgtggc tcctgctgct gttgtgaact ttggatgctc aacgttttgt
126001 ttccatcgcc cccgtcctcc tcgtcctcct tcttgtcctc ctcctcgtca tcctcctcgt
126061 cctcattgtc ctcatcatcg tcatcctcct cgtcctcctc ctcctcgtcc tcctcctcgt
126121 cctcctcctc gtcctcctcc tcgtcatcct cctcgtcatc ctcctcgtca tcctcctcgt

Fig. 3 (cont.)

126181 catcctcctc gtcatcctcc tcgtcatcct cctcgtcatc ctcctcgtca tcctcctcgt
126241 catcctcctc gtcatcctcc tcgtcatcct cctcgtcctc ctcatctgtc tcctgctcct
126301 cctcatcatc cttattgtca ttgtcatcct tgtcaacctg actttccttg ctaatctcgt
126361 tgtccccatt atcctcgcca gcctgattat tttcggaaca ttctttttca ttcttggatg
126421 cttcttctgc aatctccgca aggagcacca acatggctgt gtcatcaccc caggatccct
126481 cagacgggga tgatgatcct atggagatgg gagatgtagg cggttggcgt ggcggagtat
126541 cgccatcgct ggatgatccc acgtagatcg gggactctgt ggcccatggg gggtacacac
126601 tacggttggc gaagtcacat ctagggggag agactggggg cgactgacat attgggttta
126661 gtgtagaggg accttggggg gacgatagcc ttctttttct caggctacgc agggtagacg
126721 gagctaaaga gtctggtgac gacttggagg gaggctcggg tggaggagtc gtgggtgagt
126781 gtggaggtgt agtctgctgc gagggtggcg gacgcatagg tgttgaagag tctggccttc
126841 ctgtaggact tgaaagcggt ggcctttgag aagactctgg agactgcgtg ggtggcaatg
126901 caggagatgg agaatgagta tccgtggtcc ccggagacac aggatgggat ggagggattg
126961 gggaggaaga cgtggttacg gggggtaaga gtgccggtgg aggtaaaggt gttgcgggag
127021 cgggtgaagg aatgggagcc accggtaaag taggactaga cacaaatgct ggcagcccgg
127081 atgtgaacac tgtgggactt ccaggtatag gcaaggtgtg gggtccacat tcccggccgt
127141 cgatggagtc ggcgacatgc ttccttcgcg gttgtagatg taggtcatcg ccaaggtcac
127201 atctttccgg agacctgttt cgtttcctac aacttcctct cgttaagggc gcgccggtgc
127261 tccgtcccga cctcaggcgc attcccgggg gcgccatcct cgggaaatct ggtctgacaa
127321 ccaaagtaaa attatggagg cggtggcagt atattcacat tatgcaatac ccgtagtgac
127381 cacaaggggg agctctcaga caattaagcg gttacacaca gtagcaggct gcagtaccgc
127441 ccatggccac aggatgtaga tcgcagacac tgaaacgctg aaacacagca ttaagctgca
127501 ataccgccga tggccaccag atggcacgcg ccgccagcaa atttaagtcc tggtggctca
127561 cctgccaggt aaacaaggtt aaagtgggtt tgctggcctt gcgttgccat ggatgctacc
127621 taggcaagtc cagatatata atccgggcgt gagaaacaga aacggccaat aacccatgtt
127681 tttcgaaaac caccacacac cttaacacaa atcatgtaca cctggtatta ctatttccca
127741 cacatcttat agcatttcaa agataagggt gccttacggg ccgcccgaaa caagtgggcg
127801 ggcgctactc actgtttata agtcagccgg accaagctgc tgctcttggg gacgtgactg
127861 cttcgtggcg cagctgcctc caaatgatac acacattttt tgattgtccc gggcgccgcg
127921 tagtggaggg cggagttata tcaagctact ttctgattgg tgccccaggc aggactgcca
127981 taaaaactga agaaggcgtg tctgctttgc agaatttacc ccccactgtg ctcccggttg
128041 ctggcaccgg ttcagtggtc cgacctgtcg tctgtgctcc cccgtggacg acgccgagtg
128101 cctctcgggg gtccatgtct agcctcttca tttcattacc ttgggtggcg ttcatctggc
128161 tagccctcct tggcgcggtt gggggtgccc gcgttcaggg gcccatgcgg ggctctgctg
128221 ccctcacctg cgccatcacg ccccgtgctg acatagttag cgttacctgg caaaaaaggc
128281 agctccccgg tcccgtaaac gtcgccacgt acagccattc atatggggtg gtggttcaga
128341 cccagtaccg ccacaaggca aatataacct gtcctgggct ttggaactct acccttgtta
128401 tccataacct tgcagtggat gatgagggct gttacctgtg tatctttaac tcatttggtg
128461 gccggcaggt gtcatgcaca gcctgcctgg aagtgacatc tccccctact ggacacgtgc

Fig. 3 (cont.)

128521 aggtaaatag cacagaagac gcagacaccg tcacctgttt ggcaactggt cgcccacccc
128581 ccaatgtcac ctgggccgca ccctggaaca acgcctcttc tacccaggag cagttcactg
128641 acagtgatgg tcttacagtt gcgtggagga ccgtgaggct gccgcgtggg gataatacca
128701 ccccaagtga gggaatatgt ctcatcacct ggggaaatga gagcatatca atcccggctt
128761 ctattcaagg ccccttggcc catgaccttc ccgcggccca gggaactctt gccggggttg
128821 ccattactct ggtgggccta tttgggatat tcgcattaca tcattgccgc cgcaagcagg
128881 gcggtgcatc acctacttca gatgacatgg accccctatc cacccagtga ctagatggac
128941 accccgtgaa ccgtcgtgct tacccacccc cttctgattc tgacagacaa cactactatg
129001 tcccaaagac tgttttttac agcccgatgg cccttcaggc ctccttgagt gtctagctgg
129061 tcccgtggtc attgtgtggt ttggcagtca cttccccatt ttggtgtcgc gttttgggtt
129121 ttgccctgcc cccagccaac gtggatcata ttctttcccg tcaggggagt gacaagctat
129181 aggacagaaa ggtcacctgg cccaaacgga ggatcctagg tgggtgtgca tttattagac
129241 gttggtgtgt tgaaggacgg atcaggcggg gaggaggggg tgggggagac ttactgcagc
129301 actaggttag gttgaaagcc ggggtaaaag gcgtggctaa acaacaccta tactacttgt
129361 tattgtaggc catggcggcc gaggatttcc taaccatctt cttagatgat gatgaatcct
129421 ggaatgaaac tctaaatatg agcggatatg actactctgg aaacttcagc ctagaagtga
129481 gcgtgtgtga gatgaccacc gtggtgcctt acacgtggaa cgttggaata ctctctctga
129541 ttttcctcat aaatgttctt ggaaatggat tggtcaccta cattttttgc aagcaccgat
129601 cgcgggcagg agcgatagat atactgctcc tgggtatctg cctaaactcg ctgtgtctta
129661 gcatatctct attggcagaa gtgttgatgt ttttgtttcc caatatcatc tccacaggct
129721 tgtgcagact tgaaattttt ttttactatt tatatgtcta cttggatatc ttcagtgttg
129781 tgtgcgtcag tctagtgagg tacctcctgg tggcatattc tacgcgttcc tggcccaaga
129841 agcagtccct cggatgggta ctgacatccg ctgcactgtt aattgcattg gtgctgtcgg
129901 gggatgcctg tcgacacagg agcagggtgg tcgaccccggt cagcaagcag gccatgtgtt
129961 atgagaacgc gggaaacatg actgcagact ggcgactgca tgtcagaacc gtgtcagtta
130021 ctgcaggttt cctgttaccc ctggccctcc ttattctgtt ttatgctctc acctggtgtg
130081 tggtgaggag gacaaagctg caagccaggc ggaaggtaag gggggtgatt gttgctgtgg
130141 tgctgctgtt ttttgtgttt tgcttccctt accacgtact aaatctactg gacactctgc
130201 taaggcgacg ctggatccgg gacagctgct atacgcgggg gttgataaac gtgggtctgg
130261 cagtaacctc gttactgcag gcactgtaca gcgccgtggt tcccctgata tactcctgcc
130321 tgggatccct ctttaggcag aggatgtacg gtctcttcca aagcctcagg cagtctttca
130381 tgtccggcgc caccacgtag cccgcggatg tctacgtgcc cttccccctt aatttaatct
130441 agcctcccgt tcccatgatg cagagaggcg aatttggttt gtacacagat gtgactatgt
130501 atttgtttta ttatgcgatt aaatgagggg tctgatccca aaagcaatgt ttagtggtgg
130561 tcgttgatct tcttgacgct ccataggtag attgactgga acgccatggc ccacggggac
130621 atggacaggg gtgttaggtc tggtggaaca tgctgccact gccacggatg gaacatcaga
130681 gatgggtcta tgatcagggc agcgtgtcgc ccgtcactgg atgtaagtcc ggccaccgtg
130741 gagttgcctg tggggtttct gggatagtgt ctggctggca gggtctcatc cgcggcattt
130801 ccatggtagg tgagggttat ctcgcctcgc tgtctcagta tgtactcgag ggcgtcctgc

Fig. 3 (cont.)

130861 tcgtaccgga cccccaggta ctctccctgg gcccagctgg gcagcaccgt cccccgcaac
130921 actcggagga aaacgctctt agtgttctga gggatctgta tgtttagcca gtggctgtca
130981 tacagcttgg acacgttggt ctccaggttt accgcccagc gctggggtgg tgtgggtccg
131041 tacgtgtatg gtgaggattc cgaccggccc actacaccca gggccaccag cagctggaag
131101 cccacctcgc cacagcagat ggagaatgtg tcgggtctgt ttagaaactc tgtcagggtg
131161 gaggcacagg tagggtcgtt acacagcgcc aggacccatc ccctggcgct ggcgtagctg
131221 gcctggcagc ctgttctgag acatgtaatc agaccagaga accccgacaa ggactgtcct
131281 cgtttaagct cttccacagt caccgtggcc acctcaaagc ccgtgttctg caacgcggcc
131341 atgagcgcgt acggggcact gctcccaggc agcaccaacg cggccacacg gcgcggggag
131401 gtggggcacg aaaacaggcg cagctgactc ccaaggcaca tggcccttag gctgcccagg
131461 tgatgctcca gacgacccag gtccttcctg tgcatgtcct ccagtgggtg caggggaggc
131521 gtcaccaggt tccacatttc gtcagaaaag gaggtccatg agacttgcaa ggaagtcagg
131581 gtctcttgaa acacaactgt ctcgttctgc aaaaccgtga cgttgttgcc ttgtccctcg
131641 gggccaacgg tgcccagtgg gtgtgccacg cagcggtagt ccctggccgc ccgcagcacc
131701 tctgacaagt gtacctgggg cacctcaacc agtgccccag gggtctctga aaccataagt
131761 tcgagcgggt tagggtgggc gggtagtgag agctgcagtc ccctgcagcc ggccagggcc
131821 atctcgattg cagatgggag aagccctccg tcccctatgt cgtgcccaga tacaatgagc
131881 ctcttggaca tcaggtactt aacaagcatg aacaggctgg cgaccgtgga cgggttcaga
131941 gggggtattg ggtgcctgga tgccaggaag ttgtgctcga aggtggaccc ggctatgaga
132001 cagctctgat tcacggccag gtataccagg gcgttgcctt cgacctttac gtccggggtg
132061 accctgtatc tggatccctt gacctcggcc cagctggtaa acaccaccga gttgaaggga
132121 aggacctcca ccgtttcttg ctgttgtgtg atgcgcacat ggcgctccga aagcgtcgga
132181 gagctggcag ccgaggagat ggacagtgcc actcccagct cccggcagaa ttccttgcag
132241 gcgaagaggc actcctgtag gaggccggct tggtggtcct ctggactcca cgccacggcg
132301 ccagttagca ctacgtcctg gagcttggac acgggactga acatgaggtt ggtgagagcc
132361 tcggtgatgg cataggtggc cccggtggat acattagtag ccatcttgta ggcctgctcc
132421 cccatggcca ttgcctgacc cctccacgct ggcactggaa gcagctcctg gggcagggcc
132481 ttcacccagg tctcgaagtc cttgtgtagg aggttggcca tggacggagt gatggcctcc
132541 accgtgtcgg gcactctggg cgccaccctc tcggccagca tggacgagtg cagcaccagg
132601 tggtagtctg aaaccggtat gtccaggggt cccacgccag cctgttgggc gatgaggccg
132661 ttggagcatc ggtccatgtg tcgcgtaaag aactccttgc tgccaaccgt cgagtggcga
132721 agtaactggt ggattgtgga gccggtggca aaaaggcccc agtcaacatc ctcggggtgc
132781 cccgagacgc ggacaccatc ggacagcgcc agccaggggg acggggggt ggacgacggc
132841 tggtctacag agaagaccct cgtggtctcc ccggtcaggt cgtctactat tctgatgcct
132901 gggtgctccg aggtcctccc gaggaccgtt acctggcacg cgcacaggcg cgcggcgcgc
132961 tgcagtacct ccaacggggt ctcgcccaga tccccaggca ccgcgcccga ctctgccacc
133021 accgcaaaca ccagggagca atacacgttg agaaagtgct ctgccaccgc cgccttcacg
133081 gcatccggac cggccgcggg atccgcaggc aggtgggtgc gcacctcgtc gggtagcttg
133141 gagacaaaca gctccaggcc ggtccgcggc gccagcgcct gcaggtgcct caccaccggg

Fig. 3 (cont.)

133201 gccgggtcat gcgatctgtt tagtccggag aagatagggc ccttggcaag ccgctggacc
133261 agcttcaggg tctccaagat gcgcaccgca ttgtcggagc tgtcgcgata gaggttaggg
133321 taggtgtccg gtccatccgt gggctcaaac ctgcccagac acaccactgt ctgctggggg
133381 atcatccttc tcagggagat gcattctttg gaagtagtgg tagagatgga gcagactgcc
133441 agggcgttgc caggagtggt ggcgatggtg cgcaccgttt ttaagaaacc ccccagggtg
133501 gggactcccg ctccctgcag catctcggcc tgctgtacgc ccttggcgaa tatgcgacgg
133561 aatcggctgt gcgcacgggg tcccagggcc ggttcggtgg catacaggcc ggtgagggcc
133621 ccctgtgtct gtccgcctgg aaacagggtg ctgtgaaaca gcaggttgcc aaggccgcga
133681 atacccctct gcacgctgct gtggacgtgg gtgtacgctc cgtggatccc gaacgcctgt
133741 ctggcacagt tccagggcca ccgttccatg gtgcatcttc ccggtatcac aaagtacctg
133801 gccacgttat aattgtcccc ggttgaagcc tgcaccgcca gcggtagcag gtctgccccc
133861 agggatatca taacagcctg cataatgaca tcatcttcaa tgtgtggcct agccacgggc
133921 tggggaccct cgggcacttc caaccccctcg tacggtacca ggtcggtatt ttgtgtaaat
133981 gccctgataa actgaggtgg gtgtggttct agcagggtct gtgtgatttt ggacaccagg
134041 tgcctgccca cttccactct agcccactcc tgcaatccta gctcttgcag cagaactgca
134101 agctctgttg acaatgttgt gggccggtgg tgcatgtttg gcccgtagcc aaaggataca
134161 acacgctcgc tcccccgtgg cacagaccgc ctgatgacat ggggatatcc aaggagcggt
134221 gacagcacag cgagcaccgt ctgtatttcc acatcccgtc tctctcgctc ctccctcgaa
134281 gtgggaggtc ttcggaaagt tatccatagc agatagtagc ctccggtgcc accgggtacg
134341 agagtgagtg tgcccgtacg gcttgtataa aagttcacaa aagcttcctc atccgcggtg
134401 agatcactct ccaaccacag cccagtgacg tcgtaggcca tgcctagagg gcgcaccgcc
134461 cccggggaca ccctctgtag tcaggctgcc gagaaacccg cgagatctct ggggagtagg
134521 aagaaactta gaatccccaa atatgtcgca gtcacaggtt gtcgggcaga gtctgtttcc
134581 gctttcatgg gatccacagt tacttgtagc catgtcacta acctcaaata ctcaaaaaaa
134641 gctatcgatg gaaaaatgct gtggtcctag gttagtccgt gggaaacaaa acttcctcat
134701 acacttcatc tgcaggctga aatggtggcg gatccagact ccttacacca cagttgctca
134761 cattagagat acctgattgg ttaatacaag cggacgcacg cgttggtgga ggcgtgttgt
134821 cgcccaagat actagcatag gtgactgtgc gttcgctatg tagttgctgc atttcaagtt
134881 gggtcgttac ttctgtgttg caaaccctta ctggagataa tgccatgtct gttgtggaac
134941 ttaaaatacg cgagtgtata acatttctag atggtagagg tggtaaacgg cgagctaaat
135001 gattaacatc gggacatatc ctgcctgcat gagcatgtgg tgtgtcgtgt ggtgtatata
135061 ttggtaatct tgttgttaca ttgttgaacg acacaagtct gctctctcgg tagagataac
135121 ccaccagtac ggcttggcca gtacctaata agaaaaaata aaatcgttaa tctctgtttt
135181 tatgtggcgc tggtgttcca attataaata aaaacacaac tcacttaata tcacaattac
135241 acaaatcagt cctgaagtaa cacctgtagt ccaaccgtca gtgtagagca ggactaactt
135301 aacacagcat ccagcacatg tccatgctaa ggaaataaac caaagttatg tttcggtttg
135361 ctttatgacc agggagctgc tacccaggta caaaaaatcc ttacccaaaa atagaaacag
135421 gaagccacca gagagtgaag ctttgtgaaa gctttgccag cagaagaaac aatataataa
135481 aaagccacag cctgctagta atgttatact ccctgtaaat aaaaaatatg gacagtaata

Fig. 3 (cont.)

135541 atttatgaca cccaataagt atgtggaaaa aatgtaatgt aaaccactat actggtaaaa
135601 acataccttc gttattggtg tcttgttcgc gctttataaa cagtatccct attgttgtgg
135661 ttagtgtaac caacactcct ccttgtaaaa gtaaaaatga cataagcccc ttagttgatc
135721 caatccaatg tcgtttcatt gttataaaca agccggtcat acctgtaata aagttattca
135781 ttacaaaatg ttataatagt attggtaatg tttagttaag ataatgtaaa cttcacagta
135841 gtcatatacc aatatgtatg cagcttatgc atcctgcgat gattacagaa aggcatgaat
135901 gggaaacgca aaaaaaggcc ggtgttgcct tgagtatacc tgtagtaaaa aataaataat
135961 attgttggtt gcaatgctta ggtgcaagca gacataattg catagcagta aaaaccagac
136021 ttaccaccac atattgcaaa cacacatgca gcgagcttga gacaaggccc attatctgtt
136081 gcaaagatat gtataaaaaa aacaagcaac aatgtccata atggcaaaaa aaactggcaa
136141 tgtgtccagt tgttgtaaat ctgcaatccc attgagaata taagtaccaa caccataaca
136201 atgcacagta atccgctatc aatagtgcat ttaacgactc ttaatgttcc accaagtgat
136261 agaatggctg aaaaacacat acaggggaat tacgtttttt taaaaaattg gaaatattag
136321 atacataatt tttatttaat aaaaaacctt tagtaaaact taccagtaat tatagacaat
136381 aaacttataa tacaaacaca aacagtactc aaagtacttt gagtagagaa actccaactg
136441 gcaaaggcaa tacatcctaa aacaaaagac aaatacacga gacatttaaa caatgtatac
136501 ttagaaagaa ataagttaaa catttaaaaa atgtaactta ccaacaatta tagatggtcc
136561 aatgggaggg gaagcttgaa aacgttgttt ttttgactgc acatatatgt tgttattgta
136621 caaaaaagtt ggtagtaaac acttatgtta ctgagcaaaa atatggtgtt ttgtaaattt
136681 atagttaaaa gacaaaacat aatagacaaa cacccacaac atgttataag tgctgcaaac
136741 caagtacccc acaggtattt tttgtaattc attgtagaca aaaagcccaa ggcccaaaaa
136801 tgaagtggac aaaagaaata tgtaattaag tgtagttgga caaggaatta tatagctgga
136861 tgagttagtt ttgcacagaa ccagacatcc tatttttgtt tggaaaccta aaatccggat
136921 gaagggctta taaaatggca cagctgcaaa aagctgataa tgtaacactg catcctggtg
136981 tttttgattg tagcggaaaa atgtaataaa ttttacagac agttttgcct actgagaaca
137041 tgttgaaaaa aaggcactaa gggctttttt gccaaaggaa aaatgccccc gtggggttag
137101 gggaaagggg ggatggggtg atgggggaat ggtgggaaag gggggatggg gtgatggggg
137161 aatggtggga aaggggtgat ggggtgatgg gggaatgggg ggaaaggggg aatgggggga
137221 aagggggaat ggggggaaag ggggaatggg gggaaagggg ggatgggggg aaagggggaa
137281 tgggggggaaa gggggaatgg ggggaaaggg gggatggggg gaaaggggga atggggggaa
137341 agggggatg gggggaaacg ggggatgggg ggaaaggggg gatggggggg aaagggggga
137401 tgggggggaa aggggggatg ggggggaaag gggggatggg ggggaaaggg gggatgggga
137461 aggggggggg gagggggaag ggggtgaagg gggaaggggg gaggcgaa

Fig. 3 (cont.)

Human gene for granulocyte-macrophage colony stimulating factor
(GM-CSF).
ACCESSION X03021
VERSION X03021.1 GI:31858
Miyatake,S., Otsuka,T., Yokota,T., Lee,F. and Arai,K.
TITLE Structure of the chromosomal gene for granulocyte-macrophage colony stimulating factor: comparison of the mouse and human genes
JOURNAL EMBO J. 4 (10), 2561-2568 (1985)

1 ttctcagagt ggctgcagtc tcgctgctgg atgtgcacat ggtggtcatt ccctctgctc
61 acaggggcag gggtcccccc ttactggact gaggttgccc cctgctccag gtcctgggtg
121 ggagcccatg tgaactgtca gtggggcagg tctgtgagag ctcccctcac actcaagtct
181 ctctcacagt ggccagagaa gaggaaggct ggagtcagaa tgaggcacca gggcgggcat
241 agcctgccca aaggcccctg ggattacagg caggatgggg agccctatct aagtgtctcc
301 cacgccccac cccagccatt ccaggccagg aagtccaaac tgtgcccctc agagggaggg
361 ggcagcctca ggcccattca gactgcccag ggagggctgg agagccctca ggaaggcggg
421 tgggtgggct gtcggttctt ggaaaggttc attaatgaaa acccccaagc ctgaccacct
481 agggaaaagg ctcaccgttc ccatgtgtgg ctgataaggg ccaggagatt ccacagttca
541 ggtagttccc ccgcctccct ggcattttgt ggtcaccatt aatcatttcc tctgtgtatt
601 taagagctct tttgccagtg agcccagcta cacagagaga aaggctaaag ttctctggag
661 gatgtggctg cagagcctgc tgctcttggg cactgtggcc tgcagcatct ctgcacccgc
721 ccgctcgccc agccccagca cgcagccctg ggagcatgtg aatgccatcc aggaggcccg
781 gcgtctcctg aacctgagta gagacactgc tgctgagatg gtaagtgaga gaatgtgggc
841 ctgtgctagg caccagtggc cctgactggc cacgcctgtc agcttgataa catgacattt
901 tccttttcta cagaatgaaa cagtagaagt catctcagaa atgtttgacc tccaggtaag
961 atgcttctct ctgacatagc tttccagaag cccctgccct ggggtggagg tggggactcc
1021 attttagatg gcaccacaca gggttgtcca ctttctctcc agtcagctgg ctgcaggagg
1081 agggggtagc aactgggtgc tcaagaggct gctggccgtg cccctatggc agtcacatga
1141 gctcctttat cagctgagcg gccatgggca gacctagcat tcaatggcca ggagtcacca
1201 ggggacaggt ggtaaagtgg gggtcacttc atgagacagg agctgtgggt ttggggcgct
1261 cactgtgccc cgagaccaag tcctgttgag acagtgctga ctacagagag gcacagaggg
1321 gtttcaggaa caacccttgc ccacccagca ggtccaggtg aggcccccacc cccctctccc
1381 tgaatgatgg ggtgagagtc acctccttcc ctaaggctgg gctcctctcc aggtgccgct
1441 gagggtggcc tgggcggggc agtgagaagg gcaggttcgt gcctgccatg gacagggcag
1501 ggtctatgac tggacccagc ctgtgcccct cccaagccct actcctgggg gctgggggca
1561 gcagcaaaaa ggagtggtgg agagttcttg taccactgtg ggcacttggc cactgctcac
1621 cgacgaacga cattttccac aggagccgac ctgcctacag acccgcctgg agctgtacaa
1681 gcagggcctg cggggcagcc tcaccaagct caagggcccc ttgaccatga tggccagcca
1741 ctacaagcag cactgccctc caaccccggt gagtgcctac ggcagggcct ccagcaggaa
1801 tgtcttaatc tagggggtgg ggtcgacatg gggagagatc tatggctgtg gctgttcagg

Fig. 3 (cont.)

1861 accccagggg gtttctgtgc caacagttat gtaatgatta gccctccaga gaggaggcag
1921 acagcccatt tcatcccaag gagtcagagc cacagagcgc tgaagcccac agtgctcccc
1981 agcaggagct gctcctatcc tggtcattat tgtcattacg gttaatgagg tcagaggtga
2041 gggcaaaccc aaggaaactt ggggcctgcc caaggcccag aggaagtgcc caggcccaag
2101 tgccaccttc tggcaggact ttcctctggc cccacatggg gtgcttgaat tgcagaggat
2161 caaggaaggg aggctacttg gaatggacaa ggacctcagg cactccttcc tgcgggaagg
2221 gagcaaagtt tgtggccttg actccactcc ttctgggtgc ccagagacga cctcagccca
2281 gctgccctgc tctgccctgg gaccaaaaag gcaggcgttt gactgcccag aaggccaacc
2341 tcaggctggc acttaagtca ggcccttgac tctggctgcc actggcagag ctatgcactc
2401 cttggggaac acgtgggtgg cagcagcgtc acctgaccca ggtcagtggg tgtgtcctgg
2461 agtgggcctc ctggcctctg agttctaaga ggcagtagag aaacatgctg gtgcttcctt
2521 cccccacgtt acccacttgc ctggactcaa gtgtttttta tttttctttt tttaaaggaa
2581 acttcctgtg caacccagat tatcaccttt gaaagtttca aagagaacct gaaggacttt
2641 ctgcttgtca tcccctttga ctgctgggag ccagtccagg agtgagaccg gccagatgag
2701 gctggccaag ccggggagct gctctctcat gaaacaagag ctagaaactc aggatggtca
2761 tcttggaggg accaaggggt gggccacagc catggtggga gtggcctgga cctgccctgg
2821 gcacactgac cctgatacag gcatggcaga agaatgggaa tattttatac tgacagaaat
2881 cagtaatatt tatatattta tatttttaaa atatttattt atttatttat ttaagttcat
2941 attccatatt tattcaagat gttttaccgt aataattatt attaaaaata tgcttctact
3001 tgtccagtgt tctagtttgt ttttaaccat gagcaaatgc cat

Fig. 3 (cont.)

SEQUENCE LISTING

<160> NUMBER OF SEQ ID NOS: 60

<210> SEQ ID NO 1
<211> LENGTH: 876
<212> TYPE: DNA
<213> ORGANISM: homo sapien

<400> SEQUENCE: 1
agaacctaga gcccaaggtt cagagtcacc catctcagca agcccagaag tatctgcaat 60
atctacgatg gcctcgccct ttgctttact gatggtcctg gtggtgctca gctgcaagtc 120
aagctgctct ctgggctgtg atctccctga gacccacagc ctggataaca ggaggacctt 180
gatgctcctg gcacaaatga gcagaatctc tccttcctcc tgtctgatgg acagacatga 240
ctttggattt ccccaggagg agtttgatgg caaccagttc cagaaggctc cagccatctc 300
tgtcctccat gagctgatcc agcagatctt caacctcttt accacaaaag attcatctgc 360
tgcttgggat gaggacctcc tagacaaatt ctgcaccgaa ctctaccagc agctgaatga 420
cttggaagcc tgtgtgatgc aggaggagag ggtgggagaa actcccctga tgaatgcgga 480
ctccatcttg gctgtgaaga aatacttccg aagaatcact ctctatctga cagagaagaa 540
atacagccct tgtgcctggg aggttgtcag agcagaaatc atgagatccc tctctttatc 600
aacaaacttg caagaaagat taaggaggaa ggaataacat ctggtccaac atgaaaacaa 660
ttcttattga ctcatacacc aggtcacgct ttcatgaatt ctgtcatttc aaagactctc 720
acccctgcta taactatgac catgctgata aactgattta tctatttaaa tatttattta 780
actattcata agatttaaat tatttttgtt catataacgt catgtgcacc tttacactgt 840
ggttagtgta ataaaacatg ttccttatat ttactc 876

<210> SEQ ID NO 2
<211> LENGTH: 1142
<212> TYPE: DNA
<213> ORGANISM: homo sapien

<400> SEQUENCE: 2
gagaacctgg agcctaaggt ttaggctcac ccatttcaac cagtctagca gcatctgcaa 60
catctacaat ggccttgacc tttgctttac tggtggccct cctggtgctc agctgcaagt 120
caagctgctc tgtgggctgt gatctgcctc aaacccacag cctgggtagc aggaggacct 180
tgatgctcct ggcacagatg aggagaatct ctcttttctc ctgcttgaag gacagacatg 240
actttggatt tccccaggag gagtttggca accagttcca aaaggctgaa accatccctg 300
tcctccatga gatgatccag cagatcttca atctcttcag cacaaaggac tcatctgctg 360
cttgggatga gaccctccta gacaaattct acactgaact ctaccagcag ctgaatgacc 420
tggaagcctg tgtgatacag ggggtggggg tgacagagac tcccctgatg aaggaggact 480
ccattctggc tgtgaggaaa tacttccaaa gaatcactct ctatctgaaa gagaagaaat 540
acagcccttg tgcctgggag gttgtcagag cagaaatcat gagatctttt tctttgtcaa 600
caaacttgca agaaagttta agaagtaagg aatgaaaact ggttcaacat ggaaatgatt 660

```
ttcattgatt cgtatgccag ctcacctttt tatgatctgc catttcaaag actcatgttt    720

ctgctatgac catgacacga tttaaatctt ttcaaatgtt tttaggagta ttaatcaaca    780

ttgtattcag ctcttaaggc actagtccct tacagaggac catgctgact gatccattat    840

ctatttaaat atttttaaaa tattatttat ttaactattt ataaaacaac ttatttttgt    900

tcatattatg tcatgtgcac ctttgcacag tggttaatgt aataaaatgt gttctttgta    960

tttggtaaat ttattttgtg ttgttcattg aacttttgct atggaacttt tgtacttgtt   1020

tattctttaa aatgaaattc caagcctaat tgtgcaacct gattacagaa taactggtac   1080

acttcatttg tccatcaata ttatattcaa gatataagta aaaataaact ttctgtaaac   1140

ca                                                                  1142
```

<210> SEQ ID NO 3
<211> LENGTH: 1193
<212> TYPE: DNA
<213> ORGANISM: Homo Sapien

<400> SEQUENCE: 3

```
tgaagatcag ctattagaag agaaagatca gttaagtcct ttggacctga tcagcttgat     60

acaagaacta ctgatttcaa cttctttggc ttaattctct cggaaacgat gaaatataca    120

agttatatct tggcttttca gctctgcatc gttttgggtt ctcttggctg ttactgccag    180

gacccatatg taaaagaagc agaaaacctt aagaaatatt ttaatgcagg tcattcagat    240

gtagcggata atggaactct tttcttaggc attttgaaga attggaaaga ggagagtgac    300

agaaaaataa tgcagagcca aattgtctcc ttttacttca aacttttttaa aaactttaaa    360

gatgaccaga gcatccaaaa gagtgtggag accatcaagg aagacatgaa tgtcaagttt    420

ttcaatagca acaaaaagaa acgagatgac ttcgaaaagc tgactaatta ttcggtaact    480

gacttgaatg tccaacgcaa agcaatacat gaactcatcc aagtgatggc tgaactgtcg    540

ccagcagcta aaacagggaa gcgaaaaagg agtcagatgc tgtttcaagg tcgaagagca    600

tcccagtaat ggttgtcctg cctgcaatat ttgaatttta aatctaaatc tatttattaa    660

tatttaacat tatttatatg gggaatatat ttttagactc atcaatcaaa taagtattta    720

taatagcaac ttttgtgtaa tgaaaatgaa tatctattaa tatatgtatt atttataatt    780

cctatatcct gtgactgtct cacttaatcc tttgttttct gactaattag gcaaggctat    840

gtgattacaa ggctttatct caggggccaa ctaggcagcc aacctaagca agatcccatg    900

ggttgtgtgt ttatttcact tgatgataca atgaacactt ataagtgaag tgatactatc    960

cagttactgc cggtttgaaa atatgcctgc aatctgagcc agtgctttaa tggcatgtca   1020

gacagaactt gaatgtgtca ggtgaccctg atgaaaacat agcatctcag gagatttcat   1080

gcctggtgct tccaaatatt gttgacaact gtgactgtac ccaaatggaa agtaactcat   1140

ttgttaaaat tatcaatatc taatatatat gaataaagtg taagttcaca act          1193
```

<210> SEQ ID NO 4
<211> LENGTH: 7896
<212> TYPE: DNA
<213> ORGANISM: Human papillomavirus type 59

<400> SEQUENCE: 4

```
gttaagaccg aaaacggtgc atataaaggt agttgaaaag aaaagggcaa cggcatggca     60

cgctttgagg atcctacaca acgaccatac aaactgcctg atttgagcac aacattgaat    120

attcctctgc atgatattcg catcaattgt gtgttttgca aaggggaact gcaagaaaga    180
```

-continued

```
gaggtatttg aatttgcttt taatgactta tttatagtgt atagagactg tacaccgtat    240
gcagcgtgtc tgaaatgcat ttcattttat gcaagagtaa gagaattaag atattataga    300
gattccgtgt atggagaaac attagaggct gaaaccaaga caccgttaca tgagctgctg    360
atacgctgtt atagatgcct aaaacctcta tgtccaacag ataaattaaa gcatataact    420
gaaaaaagaa gattccataa tatagctgga atatatacag gacagtgtcg tgggtgtcgg    480
acccgagcaa gacacctaag acagcaacga caagcgcgta gtgaaacact ggtgtaaaac    540
aatgcatgga ccaaaagcaa cactttgtga cattgtttta gatttggaac cacaaaatta    600
tgaggaagtt gaccttgtgt gctacgagca attacctgac tccgactccg agaatgaaaa    660
agatgaacca gatggagtta atcatccttt gctactagct agacgagctg aaccacagcg    720
tcacaacatt gtgtgtgtgt gttgtaagtg taataatcaa cttcagctag tagtagaaac    780
ctcgcaagac ggattgcgag ccttacagca gctgtttatg gacacactat cctttgtgtg    840
tcctttgtgt gcagcaaacc agtaacctgc aatggccgat tcggaaggta cagatgggga    900
agggacgggg tgcaatggat ggtttttgt gcaggcaata gtagataaaa aaacaggtga    960
caaaatttca gatgacgagg atgaaaatgc aacagataca ggttcagact tggtagattt   1020
tattgatgat accacaacaa tttgtgtaca ggcagagcgc gagacagcac aggccttgtt   1080
taatgtgcag gaagcccaaa gggatgcacg ggaaatgcat gttttaaaac gaaagtttgg   1140
gtgcagtata gaaaacagta gtgagaaagc ggcggcagga aaaaaagcta agtcaccatt   1200
acaagaaata tcagtaaatg ttaaccaccc aaaagtaaaa agaaggttaa taacagtgcc   1260
agacagcggc tatggctatt ctgaagtgga aatgctcgag actcaggtaa ccgtggagaa   1320
tactggaaat ggggatagca atggcagtgt ttgtagcgac agtcaaatag actgtagcga   1380
cagcagtaac atggatgttg aaaacatagt tccaacatcc cccactaatc aattgttaca   1440
gttattacat agcaaaaata agaaagcagc tatgtatgca aaatttaaag aattgtatgg   1500
gttatcattt caagatttgg ttaggacatt taaaagtgac agaactacct gtagcgattg   1560
ggtaaccgcc atttttggtg ttaatccaac tgtagcagaa ggatttaaaa cattaataca   1620
accctatgtg ctatatgcac atatacaatg cttagattgt gcatggggag tagtaatatt   1680
agcattatta agatataaat gtggaaaaaa tagaataaca gttgcaaaag gacttagcac   1740
attactacat gtaccagata cgtgcatgtt aattgaacca cccaaattgc gtagtggtgt   1800
tgcagcacta tattggtaca gaacaggaat gtccaatatt agtgaagtta taggggaaac   1860
gcccgaatgg atacaaagac taacaattat acaacatgga gttgatgata gcgtgtttga   1920
cctgtcagaa atgatacaat gggcgtttga taatgaccta acagatgaaa gtgatattgc   1980
atatgaatat gcattaatag cagatagtaa tagtaacgcc gctgcatttt taaaaagcaa   2040
ctgccaggca aaatacctaa aagattgtgc agttatgtgt aggcattata aaagagcaca   2100
aaaaagacaa atgagtatgt cacagtggat aaaatggaga tgtgataaaa tagaagaggg   2160
gggagattgg aaacccatag tacaattttt aagatatcaa ggagtagaat ttataacgtt   2220
tttatgtgca ttaaaagatt ttttaaaagg taccccaaaa agaaattgca ttgtgctgtg   2280
tgggccagca aatacaggca agtcatactt tggaatgagc ctgctacatt ttttacaagg   2340
aactgtaatt tcacatgtaa attcaaatag tcacttttgg ctagaacctt taacagatcg   2400
taaattagct atgctagacg atgcaacaga tagttgttgg acatattttg atacatatat   2460
gcgaaatgct ttggatggca atcctataag tgtagataga aagcataggc acctagtaca   2520
aattaaatgt ccaccaatgc ttattacatc aaatacaaat ccagttacag ataacaggtg   2580
```

-continued

```
gccatattta aatagcagat taatggtatt taaatttcca aacaaattgc catttgacaa   2640
aaatagaaat ccagtatata caattaatga cagaaactgg aaatgttttt ttgaaaggac   2700
gtggtgcaga ttagatttga acgaggaaga ggaagatgca gacagtgatg gacacccttt   2760
cgcagcgttt aagtgtgtta caggatcaaa tattagaaca ttatgaaaac gatagtaaag   2820
acattaatga acacataaac tattggaaac tggtgcgtat ggaaaatgta attttatttg   2880
cagcaagaga gaacaatata catacattaa accaccaggt ggtgccaacg tttttggtgt   2940
ctaaaaacaa ggcatgtgaa gctattgaac tgcagtcaaa ccgtacttcc actgtaatgc   3000
cctgtttttt aaaacatttt ttaggtgctg tttgccatag ttcttggcat gtttcttgca   3060
ttgtccattg ctcattttta aactcagttt gtgccaaact ctctaacgcc atctgcagca   3120
aggaaaacac aatgcattac acaagctgga catttatata ttatgtaaat gatgtaggac   3180
agtggtgtaa aaccacagga aatgtggact tttggggact atattataaa gtggaagagg   3240
aacaggtgta ctatgtaaaa tttatacatg atgccaaaaa atatgggact acagacaagt   3300
gggaagtgca ttataatggc aaggttattg attgttatga ctctatgtgc agtaccagtg   3360
acgagcaagt atccactgct ggatcttctg agcaactatc atacccctcc gcaacgcccc   3420
ccgaagccac gtacttgggc ccccaaacgt ggaaccgtca gacgaagact ggaaagcgac   3480
caagacagtg tggatacaca cagcaccctc agtctaccag cgtgtcagtg gactactgtg   3540
acaacccagt cgtccgtttg catccaggca acaacccgcg acggcacatc ccttgcagta   3600
acactacgcc tataatacac ttaaaaggtg acaaaaatgg ccttaagtgt ttaaggtata   3660
gattaagaaa agtacactgg ttatttgaaa atatttcctc tacctggcat tggacaggaa   3720
acagaggatc agccaaaaca ggcattttaa cattaacata tacaagcgaa acacaacgca   3780
atgaattttt agatactgta aaaattccta atagtgtaca aatacatgtt gggtatatga   3840
gtgtgtaatg gttgttatgc aaatgtaaca caagccaata ctgctgctat attgtatagc   3900
tgaggaaatg ataacccttg tatttgtgtg ttgtgtttgt gtttgcttgt gtgtgtgttg   3960
caatgtcccg cttctgcaat ctgtctatat gtgtgcatat acatggttac tagtatttgt   4020
gtatattgtg gttatcacct cctcatatga gtgtttttta ctatatatat tgttttttat   4080
aattccactg ttactactat atgcccatgc aatactgtcc atacaataat tgctgtatat   4140
tgtaaattac attgcactgt attgtacagt atattttaaa cacattatta tttttgttag   4200
gtgttggttt tgttacattt ataataaaac atggtttccc atcgtgctgc tcgtcgtaaa   4260
cgtgcctcag caacagactt atataaaact tgcaagcagg caggtacatg cccttctgat   4320
gttattaata aagttgaagg tacaacttta gctgataaaa tattgcagtg gaccagccta   4380
ggaatatttt taggtggact aggtattggt actggatctg gtaccggtgg cagaacaggg   4440
tacatacctt tagggggcg tacaaacact atagtagatg tatcgcctgc taaaccacca   4500
gtagttattg aacctgttgg acctacagat ccatctatag ttacattagt tgaggattct   4560
agtgttataa catctggagc ccctgcccca acatttacag gtacttcagg atttgaaata   4620
tctacctcta gtacaacaac accagctgtt ttggatataa ccccaacctc ttctgttcaa   4680
attagtagct ctagttttat aaatcctgca tttacagacc cttctgtcat tgaggttccc   4740
caaacaggtg aaatttctgg taatatatta attagtaccc ctacctctgg tgcacatggc   4800
tatgaagaaa ttccaatgca aacgtttgct acggaaggta ctggtttgga acccattagc   4860
agtacccca atccaacagt acgtcgtgtg gctggaccta gattgtacag tagggctaat   4920
caacaagttc gggtgtctaa cgctgacttt ttaacacgtc catccacatt tgttacatat   4980
```

-continued

```
gataaccctg cttatgatcc aattgatact acattaactt ttgacccctc atcagaggtt   5040
ccagacccgg actttatgga tatagttcgt ttgcataggc ctgcattaac atccagacgc   5100
agcactgtaa ggtttagtag gctaggacaa cgggcaacca tgtttacccg tagtggtaaa   5160
caaattgggg cccgtgtaca tttttatcat gatataagcc ctataccaca tgctgaagat   5220
attgaattgc aacctcttgt ttcttcccag gctgctactg atgatatata tgatatatat   5280
gcagatatta cagatgaagc acctactagt actgccaaca ctgcatttac aattcctaaa   5340
tcttcttttc aaagtttgtc attaacacgg tcggcatcta gcaccttttc aaatgtaact   5400
gttcctttgg ctactgcctg ggatgttcct gtaaatacag gacccgatat agttttacct   5460
aatactaata ttgttgaacc cacttattct actacaccct ttaccaccat acagtctatt   5520
aatatagaag gcacaaatta ttttttatgg cctatatatt attttttacc tcgtaaacgt   5580
aaacgtgttc cctatttttt tacagatggc tctatggcgt tctagtgaca acaaggtgta   5640
tctacctcca ccttcggtag ctaaggttgt cagcactgat gagtatgtca cccgtaccag   5700
tattttctac cacgcaggca gttccagact tcttacagtt ggacatccat attttaaagt   5760
acctaaaggt ggtaatggta gacaggatgt tcctaaggtg tctgcatatc aatacagagt   5820
atttagggtt aagttacctg atcccaataa atttggcctt ccagataaca cagtatatga   5880
tcctaactct caacgcttgg tctgggcctg tgtaggtgtt gaaatcggtc ggggccaacc   5940
tttaggggta ggactcagtg gtcatccatt atataataaa ttggatgaca ctgaaaactc   6000
tcatgtagca tctgctgttg ataccaaaga tacacgtgat aatgtatctg tggattataa   6060
acaaactcag ctgtgtatta ttggctgtgt acctgccatt ggagaacact ggacaaaggg   6120
cactgcttgt aagcctacta ctgtggttca gggcgattgt cctccactag aattaataaa   6180
tacaccaatt gaagatggtg atatggtaga cacaggatat ggggctatgg actttaaatt   6240
gttgcaggat aacaaaagtg aagtaccatt ggatatttgt cagtctattt gtaaatatcc   6300
tgattattta caaatgtcag cagatgctta tggagacagt atgttttttt gtttaaggcg   6360
agaacaggtt tttgccagac atttttggaa tagatctggt actatgggtg atcaacttcc   6420
tgaatcacta tatattaaag gtactgacat acgtgccaac ccaggcagtt atttatattc   6480
cccttcccca agtgggtctg tggttacttc tgattcacaa ttatttaata aaccatattg   6540
gctgcacaag gctcagggtt taaacaatgg tatatgttgg cacaatcaat tgtttttaac   6600
agttgtagat actactcgca gcaccaatct ttctgtgtgt gcttctacta cttcttctat   6660
tcctaatgta tacacaccta ccagttttaa agaatatgcc agacatgtgg aggaatttga   6720
tttgcagttt atatttcaac tgtgtaaaat aacattaact acagaggtaa tgtcatacat   6780
tcataatatg aataccacta ttttggagga ttggaatttt ggtgttacac cacctcctac   6840
tgctagttta gttgacacat accgttttgt tcaatctgct gctgtaactt gtcaaaagga   6900
caccgcaccg ccagttaaac aggaccctta tgacaaacta aagttttggc ctgtagatct   6960
taaggaaagg ttttctgcag atcttgatca gtttcctttg ggacgtaaat ttttattgca   7020
attaggagct agacctaagc ccactatagg cccacgcaaa cgtgcagcgc ctgcccctac   7080
ctctacccca tcaccaaaac gtgttaagcg tcgcaagtct tccagaaaat agtgttgttt   7140
gttatgtgtt tgtatgtgtg catgttgtat gttttgtatt gtttgcctgt ttgtatgttg   7200
tgtatatgta catgtttgtt tgtctgctgt atgtgtgtat ttgtttttgt acataataaa   7260
gtatgcatga cagtttcatg tgtggttgca cccaatgagt aaggtactgt ccctttattg   7320
tttctttgtc cttattacac attattacac attgccctac ttacataggt gtgtttgttc   7380
```

cttcattttg tcctgaatgt ccagttttgc atttgcacat tatatggcgt ccattttatc 7440
ctttaaatcc tccattttgc tgtgcaaccg ttttcggtta ccttggttta accttacctt 7500
tttgaacaat taatctgttt aaacatcagc aaaacagtta atccccatct tgtttcctcc 7560
tacacgccta gactactaac acaacttaca aacgccaaat agttagtcat catcctgtcc 7620
aggtgcactc taacaatact tgcataactt tggtggcgcc cttgttaata aaacagcttt 7680
taggcacata ttttcactgt ttttactact ttaattgcat aattggcttg caaaactact 7740
gtgcaatcca agaatgtgtc tataatttat tgtaaaaaac atgactaagg tttttgtcat 7800
tgttaagcaa ccgaaaaagg tcgggcaagt acatgcacac tttctactta ttactttta 7860 caatcatagt aataaaaaag ggtgtaaccg aaaacg 7896

<210> SEQ ID NO 5
<211> LENGTH: 222
<212> TYPE: DNA
<213> ORGANISM: Human papillomavirus type 59

<400> SEQUENCE: 5
atgataaccc ttgtatttgt gtgttgtgtt tgtgtttgct tgtgtgtgtg ttgcaatgtc 60
ccgcttctgc aatctgtcta tatgtgtgca tatacatggt tactagtatt tgtgtatatt 120
gtggttatca cctcctcata tgagtgtttt ttactatata tattgttttt tataattcca 180
ctgttactac tatatgccca tgcaatactg tccatacaat aa 222

<210> SEQ ID NO 6
<211> LENGTH: 483
<212> TYPE: DNA
<213> ORGANISM: Human papillomavirus type 59

<400> SEQUENCE: 6
atggcacgct ttgaggatcc tacacaacga ccatacaaac tgcctgattt gagcacaaca 60
ttgaatattc ctctgcatga tattcgcatc aattgtgtgt tttgcaaagg ggaactgcaa 120
gaaagagagg tatttgaatt tgcttttaat gacttattta tagtgtatag agactgtaca 180
ccgtatgcag cgtgtctgaa atgcatttca ttttatgcaa gagtaagaga attaagatat 240
tatagagatt ccgtgtatgg agaaacatta gaggctgaaa ccaagacacc gttacatgag 300
ctgctgatac gctgttatag atgcctaaaa cctctatgtc caacagataa attaaagcat 360
ataactgaaa aaagaagatt ccataatata gctggaatat atacaggaca gtgtcgtggg 420
tgtcggaccc gagcaagaca cctaagacag caacgacaag cgcgtagtga aacactggtg 480
taa 483

<210> SEQ ID NO 7
<211> LENGTH: 324
<212> TYPE: DNA
<213> ORGANISM: Human papillomavirus type 59

<400> SEQUENCE: 7
atgcatggac caaaagcaac actttgtgac attgttttag atttggaacc acaaaattat 60
gaggaagttg accttgtgtg ctacgagcaa ttacctgact ccgactccga gaatgaaaaa 120
gatgaaccag atggagttaa tcatcctttg ctactagcta gacgagctga accacagcgt 180
cacaacattg tgtgtgtgtg ttgtaagtgt aataatcaac ttcagctagt agtagaaacc 240
tcgcaagacg gattgcgagc cttacagcag ctgtttatgg acacactatc ctttgtgtgt 300
cctttgtgtg cagcaaacca gtaa 324

<210> SEQ ID NO 8
<211> LENGTH: 7880
<212> TYPE: DNA
<213> ORGANISM: Human papilloma virus type 13

<400> SEQUENCE: 8
gtttctaaca atcttaagtt taaaaaatag gtgggaccga aaacggtttt aaccgaaaac 60
ggtgatatat aaaccagccc aaaaattgag caagcggggc ataatggaaa gtgcaaatgc 120
ctccacgcct gcaaaaacta tagaccagtt gtgcaaggag tgcaaccttt ctatgcacag 180
cttgcaaatt ctatgcgtgt tctgcaggaa aaccctgtcc acggcagagg tttatgcatt 240
tcagtataag agtttatata tagtgtggcg aggacagttt ccatttgcgg cttgtgcatg 300
ctgcttagaa atacaaggaa agattaacca gtttaggcat tttgacttcg cgggatttgc 360
tgtaacagtt gaagaagaca caaagcagtc aattttggat gtgctaattc gctgctattt 420
atgccacaaa ccattgtgtg aagtggagaa actaagacat attttgcaga aggcacgatt 480
tattaaatta aacagcagtt ggaaaggccg ctgttttcat tgctggtcat catgcatgga 540
aaatatccta ccttaaaaga cattgtttta gagctgactc ctgaccctgt aggtctacat 600
tgcaatgagc aattagacag ctcagaagac gaggtggacg aacaagccac gcaagccacg 660
caagccacgc aacatagcac actattacaa tgctaccaaa tactaacgtc ctgtagtaaa 720
tgttgtagca acgtccggct ggtggtggag tgtacaggac ctgacattca cgacctacac 780
gacctactgc tgggcacgct gaatatagtg tgccctttgt gtgcaccaaa aagctaacca 840
cgatggcaga ggatacaggt actaataatg aggggacggg atgctcagga tggtttttag 900
tagaggctgt agtagaacga acaactgggc aacaaatatc agatgatgag gatgaaacag 960
tggaagatag tgggttggat atggtggatt tcatagatga cagacctatt acacacaatt 1020
ccgtggaagc acaggcattg ttaaacgagc aggaggcgga tgctcattat gcggctgtgc 1080
aggacctaaa acgaaagtat ttaggcagtc catatgttag tcccctagga catgttgaac 1140
agtcagtgga ctgtgatata agtcctcgat tggacgctat aaaattaagt agaaattcta 1200
aaaaagtaaa gcgacggctg tttcaatcaa gggaaataac ggacagtgga tatggctatt 1260
ctgaagtgga agctgaaacg caggtagaga gaaatggcga accggaaaat gattgtgggg 1320
gtggtggaca cggaagggac aaagaggggg agggacaggt gcacacggaa gtgcacacag 1380
gcagccagat agaagagcac acagggacca cgcgggtgtt agaactcctt aaatgtaagg 1440
atgtaagggc tacattgtat ggtaagttta aagactgtta tgggttatca tttacagatt 1500
taattagacc atttaaaagt gataaaacaa catgtgggga ctgggtggtt gcagcatttg 1560
gtatacatca tagtgtatca gaggcatttg aaaagttaat gcagccatta acaacatata 1620
tgcatataca atggcttaca aatgcatggg ggatggtatt gttagtatta ataagattta 1680
aagtaaataa aagtagatgc acagtggcgc gaacactggc aacctttctt aatattcctg 1740
aggaccacat gttaattgaa cctcccaaaa tacaaagcag tgtggcagca ttatactggt 1800
ttagaacagg tatttctaat gctagtatag taactggtga aacaccagaa tggataaaaa 1860
ggcaaacaat tgtagagcat ggacttgcag ataatcaatt taaattaact gaaatggtgc 1920
agtgggcata tgataatgat ttttgtgatg aaagcgaaat agcatttgaa tatgcacaac 1980
gaggagattt tgattcaaat gccagggcat ttttaaatag taattgtcag gcaaaatatg 2040
taaaagattg tgcaacaatg tgcaagcatt ataaaaatgc agaaatgaaa aaaatgtcta 2100
tgaaacaatg gataacatat agaagtaaaa aaatagagga agcaggaaat tggaaaccaa 2160

-continued

```
tagtacaatt tttaaggcat caaaatatag aatttattcc atttttaagt aaattaaaat   2220
tgtggcttca tggcacgcca aagaaaaact gtattgcaat agtggggcca ccagatacag   2280
gcaaatcatg tttttgcatg agcttaatta agtttttagg gggcacagta attagttatg   2340
taaattcaag tagccatttt tggctgcagc cattatgtaa tgcaaaggta gctttgctag   2400
atgatgcaac gcagtcatgc tgggtatata tggacacata catgagaaat ttattagatg   2460
gcaatccaat gagcattgat agaaaacata agtctttagc attaataaaa tgtccgccat   2520
tattagtaac atctaatgta gacattacca aagatgacaa atataaatat ttgtatagta   2580
gagtaacaac acttacattt ccaaatccat tccctttga cagaaatggg aatgcagtat   2640
atgagttgtc tgatgcaaac tggaaatgtt tttttacaag attgtcagca agcctagata   2700
tacaggactc tgaggacgag gacgatggag acaatagcca agcatttaga tgcgtgccag   2760
gaacagttgt tagaactgta tgaagaaaat agtaatgaac ttaaaaaaca tatacaacat   2820
tggaaatgct taaggtacga aagtgtactc ttacacaaag cacgccaaat gggcctaagc   2880
cacattggat tacaagtggt gccaccattg acagtatcac aagctaaggg acatgaggca   2940
attgaaatgc aaatgacttt agagacatta ctagagtctg agtttggtat ggaaccatgg   3000
actttacaag atacaagtcg tgaaatgtgg ctaacacccc caaaacgctg ttttaagaaa   3060
cagggacaaa ctgtggaagt aaaatatgac tgtaatacag acaatagaat ggattatgtg   3120
tcgtggacat acatatatgt gtttgacaca gataaatgga caaaggtgaa aggaatggta   3180
gattataaag ggttgtacta catacatgga aatttgaaaa catattattt agagtttgaa   3240
aaggaggcta aaaaatatgg ggaaacgtta caatgggaag tatgtattgg cagcacagtc   3300
atatgttctc ctgcatctgt atctagtact gtacaagaag tatccattgc tgggcctgct   3360
tcatactcca ccaccacctc cacacaggcc tccaccgcag tgtcctgcag cgcctcggaa   3420
gaatgtgtgc aagcgccgcc ttgtaaacga caacgaggac cttcacgtcc cattggaaac   3480
ccccagaaca cacaaagcat tgtgtgtgtc acagactacg acaccctgga cagtgcaaac   3540
aacaacatca acgttaacca ttacaacaat aacaaaggac gggacaacag ttactgtgca   3600
gctacaccta tagttcaatt acaaggtgac tctaattgtc taaagtgttt tcgatataga   3660
ttacatgaaa aatataaaga tttatttttg ttagcatcat ctacatggca ttggaccgcc   3720
cctaataatt cacaaaaaca tgcactggta accttaacct atgtaaatga acaacaaaga   3780
caagactttt taaaaactgt aaaaatacct ccaaccataa cacataaact aggttttatg   3840
tcattgcaat tgttataaca gcatatattg tatgtaaata tttgttgtgt gtgtgtatat   3900
attgtaaatg gaatttatac ctgtggatgt tagtacacag gcaaccagca agtcattact   3960
gccacttgta attgcactta cagtgtgtgt agttagcatt ataacaatat tgtgcatatc   4020
agagttcttg gtgtacacaa acgttttagt actaacatta attttatatg tacttttgtg   4080
gcttttacta acaactccct tgcaattcta tttactaacc ctgtctcttt gctttcttcc   4140
tgcgttgtgt gtacaccaat atattttaca aacacaagaa taactataca caatgttaac   4200
ctgtactttt gatgatggtg acacatggtt gctattatgg ttaattttat catttattgt   4260
agccattcta gggttactgt tgctgtatat aagaactgga catatgcatt gccagtgctg   4320
gagtaaataa gtggttttat attttgtgtg tattcattta attatggcac atagtagggc   4380
tcgcagacgc aaacgcgctt cagctacaca actatatcaa acttgtaagg cttctggaac   4440
atgtcctcct gatgttatac caaaggttga acaaaacact cttgcagata aaatattaaa   4500
gtggggcagt ttaggagtat tttttggggg gcttggcatt ggcacaggct ctggtactgg   4560
```

-continued

```
cggtaggact ggctatgtac cagtaggatc caccccacgc cctgccatat caactgggcc   4620
tactgcacgt cctcctattg ttgttgatac tgttgggcct acagaccctt ctattgtatc   4680
tttggtagag gaatcagcta ttattaattc tggagtacct gaccctttgc ctcccgttca   4740
tggggggtttt gaaatcacca catctcaatc agccactcca gcaatattgg atgtgtctgt   4800
tacaacacaa aacactacgt ccacaagtat atttagaaat cctgtttttt cagaaccttc   4860
tattacacaa tctcaacctt ctattgaaag tggtgcacac gtgtttatat cgccatctac   4920
tatttcccct cattctacag aagacattcc tttagataca tttattgtat cttcctcaga   4980
tagtaatcct gcatcaagca cccctgttcc agcaactgtt gcacgtccac gtctaggcct   5040
ttacagtagg gccttacatc aagtacaggt tactgatcct gccttttat cgtcgcccca   5100
acgccttata acctttgata accctacata tgaaggtgaa gatataagtt tgcagtttgc   5160
acacaatacc attcatgaac cccctgatga ggcatttatg gatattataa gactacatag   5220
gccagccata acatcacggc gtggtcttgt taggtttagt agaattggtc agagggggtc   5280
tatgtatact cgaagcggca agcatatagg tggaagggtc catttcttta aggatatttc   5340
tcctatatct gcagctgcag aagaaataga attacacccc cttgtggctg ctgcacagga   5400
tcacagtggt ttgtttgata tttatgcaga acctgaccct gaccctgtgg ctgtaaacac   5460
ctctgggtca ttgtcttctg cctccacacc atttgcacaa tcttctttgt cttccgcccc   5520
atggggtaat actactgttc ctctttcact accaggtgat atatttatac agcctggtcc   5580
tgacataaca ttcccaactg cacctacagt aacgccttat aatcctgtta cgcctgcttt   5640
acctacaggt cctgttttta ttactgcttc tggattttat ttatatccta catggtattt   5700
tacacgcaaa cgccgtaaac gtgtttcctt gtttttaca gatgtggcgg cctagtgaca   5760
acaaactata tgtgcctcct cccgcccctg tatcaaaagt aattactacg gatgcctatg   5820
ttacacgtac caacatattt tatcatgcta gcagttctag actacttgca gtgggaaatc   5880
cttattttcc tattaagaaa caaaacaaaa ctgttgtccc taaggtatct ggttatcagt   5940
ttagggtatt taaagttgta ttacctgacc ctaataaatt tgccctgcct gacacatcta   6000
tatttgactc aactagtcaa cgcttagtgt gggcctgtac aggtttagag gttggtaggg   6060
gtcaaccctt aggtgttggt attagtggtc atccattatt aaataaatat gatgatgtgg   6120
aaaattctgc aagttatgct gccaatcctg gtcaggataa tagggttaat gtggccatgg   6180
actataaaca aacacagtta tgtttagtgg gctgtgcacc tcctttaggt gaacattggg   6240
gacagggcaa gcaatgtact ggtgtaaatg tacaacctgg agattgccct cctttagaat   6300
taattagtag tgtaattcag gatggtgaca tggtggatac aggatttgga gccatgaatt   6360
ttgcggaatt gcaatctaat aaatctgatg tgccactaga catatgcacg tccacatgca   6420
aatatcctga ctatttacaa atggctgcgg atccttatgg agacagatta tttttttatc   6480
tgcgaaagga acaaatgttt gcaaggcatt tctttaacag ggcaggctct gttggtgaac   6540
aaatcccagc agaattatat gttaagggta gtaatacact ttctaatagt atttactata   6600
atactcccag tggctctctt gtgtcttctg aggcccagtt gtttaataaa ccttattggt   6660
tacaaaaggc ccagggacac aataatggta tatgttgggg caatcacttg tttgttactg   6720
tagttgatac tacacgcagt actaacatga ctgtgtgtgc agccactaca tcatctcttt   6780
cagacacata taaggccaca gaatataaac agtacatgcg acatgtagaa gaatttgatt   6840
tacaatttat ttttcaattg tgcactatta aattaactgc agaggttatg tcatatattc   6900
atactatgaa tcctacaatt ctagaagact ggaactttgg gctatctccc cctcctaatg   6960
```

```
gaacattaga agacacatat agatatgtac aatctcaggc cataacgtgt caaaagccta   7020

cacctgataa agaaaaacag gatccgtatg cgggtcttag tttttgggag gttaatctta   7080

aggaaaagtt ttctagtgaa ctagatcagt atccccttgg cagaaagttt ttattacaaa   7140

caggcgttca gtctaggtcc cctattcgtg taggtaggaa acgtgctgca tctacatcta   7200

ctgccacacc tactacacgt aaaaaagcta aaaggaaata atagtttgtt tatgattgtg   7260

tatgtatgtc acgtttgttt gtactgtatg tatgttgtgt actgtatgtg taatgttgta   7320

tgtatgtgca tgttacttat taaagaatgt gtgtgtgtgt ttgtatgcaa taaatctaat   7380

ctgtggtgtc ctgttccacc ctatgagtaa gtggtatgtt gtgtctcgtg tggtgttttg   7440

tatactatac tataacatta gtgcaaccat tttgtaactt ttcttacatt ttacgtctcc   7500

atattaagtg caaccgattt cggttgctat tgtttctgcg accgatttgt tgcagcacgc   7560

tgtttatata atcttaccta ccgcctgcca aaattatcca ccgcttgcca aaatcaccca   7620

cacacctggc gttgctaggg cgcggttata tatatttact aaatcttact aatctttcta   7680

tcactcattt tacctttata acaatacttt tgcttttcaa gtacattttt gtacttacta   7740

gccaatgcct gaaaggtttt ttggctacca gcactacatt tttgtacagt taatgttaca   7800

tgtataaaat gagtaaccta aggtcacaca cctgcaaacc ggtatcggtt aaaacacacc   7860

ctctatagtt ccttataatt                                               7880
```

<210> SEQ ID NO 9
<211> LENGTH: 276
<212> TYPE: DNA
<213> ORGANISM: Human papilloma virus type 13

<400> SEQUENCE: 9

```
atggaattta tacctgtgga tgttagtaca caggcaacca gcaagtcatt actgccactt     60

gtaattgcac ttacagtgtg tgtagttagc attataacaa tattgtgcat atcagagttc    120

ttggtgtaca caaacgtttt agtactaaca ttaattttat atgtactttt gtggctttta    180

ctaacaactc ccttgcaatt ctatttacta accctgtctc tttgctttct tcctgcgttg    240

tgtgtacacc aatatatttt acaaacacaa gaataa                              276
```

<210> SEQ ID NO 10
<211> LENGTH: 453
<212> TYPE: DNA
<213> ORGANISM: Human papillomavirus type 13

<400> SEQUENCE: 10

```
atggaaagtg caaatgcctc cacgcctgca aaaactatag accagttgtg caaggagtgc     60

aacctttcta tgcacagctt gcaaattcta tgcgtgttct gcaggaaaac cctgtccacg    120

gcagaggttt atgcatttca gtataagagt ttatatatag tgtggcgagg acagtttcca    180

tttgcggctt gtgcatgctg cttagaaata caaggaaaga ttaaccagtt taggcatttt    240

gacttcgcgg gatttgctgt aacagttgaa gaagacacaa agcagtcaat tttggatgtg    300

ctaattcgct gctatttatg ccacaaacca ttgtgtgaag tggagaaact aagacatatt    360

ttgcagaagg cacgatttat taaattaaac agcagttgga aaggccgctg ttttcattgc    420

tggtcatcat gcatggaaaa tatcctacct taa                                 453
```

<210> SEQ ID NO 11
<211> LENGTH: 306
<212> TYPE: DNA
<213> ORGANISM: Human papillomavirus type 13

<400> SEQUENCE: 11
atgcatggaa aatatcctac cttaaaagac attgttttag agctgactcc tgaccctgta 60
ggtctacatt gcaatgagca attagacagc tcagaagacg aggtggacga acaagccacg 120
caagccacgc aagccacgca acatagcaca ctattacaat gctaccaaat actaacgtcc 180
tgtagtaaat gttgtagcaa cgtccggctg gtggtggagt gtacaggacc tgacattcac 240
gacctacacg acctactgct gggcacgctg aatatagtgt gccctttgtg tgcaccaaaa 300
agctaa 306

<210> SEQ ID NO 12
<211> LENGTH: 1342
<212> TYPE: DNA
<213> ORGANISM: Homo sapiens erythropoietin

<400> SEQUENCE: 12
cccggagccg gaccggggcc accgcgcccg ctctgctccg acaccgcgcc ccctggacag 60
ccgccctctc ctccaggccc gtggggctgg ccctgcaccg ccgagcttcc cgggatgagg 120
gcccccggtg tggtcacccg gcgcgcccca ggtcgctgag ggaccccggc caggcgcgga 180
gatgggggtg cacgaatgtc ctgcctggct gtggcttctc ctgtccctgc tgtcgctccc 240
tctgggcctc ccagtcctgg gcgccccacc acgcctcatc tgtgacagcc gagtcctgga 300
gaggtacctc ttggaggcca aggaggccga gaatatcacg acgggctgtg ctgaacactg 360
cagcttgaat gagaatatca ctgtcccaga caccaaagtt aatttctatg cctggaagag 420
gatggaggtc gggcagcagg ccgtagaagt ctggcagggc ctggccctgc tgtcggaagc 480
tgtcctgcgg ggccaggccc tgttggtcaa ctcttcccag ccgtgggagc ccctgcagct 540
gcatgtggat aaagccgtca gtggccttcg cagcctcacc actctgcttc gggctctgcg 600
agcccagaag gaagccatct cccctccaga tgcggcctca gctgctccac tccgaacaat 660
cactgctgac actttccgca aactcttccg agtctactcc aatttcctcc ggggaaagct 720
gaagctgtac acaggggagg cctgcaggac aggggacaga tgaccaggtg tgtccacctg 780
ggcatatcca ccacctccct caccaacatt gcttgtgcca caccctcccc cgccactcct 840
gaaccccgtc gaggggctct cagctcagcg ccagcctgtc ccatggacac tccagtgcca 900
gcaatgacat ctcaggggcc agaggaactg tccagagagc aactctgaga tctaaggatg 960
tcacagggcc aacttgaggg cccagagcag gaagcattca gagagcagct ttaaactcag 1020
ggacagagcc atgctgggaa gacgcctgag ctcactcggc accctgcaaa atttgatgcc 1080
aggacacgct ttggaggcga tttacctgtt ttcgcaccta ccatcaggga caggatgacc 1140
tggagaactt aggtggcaag ctgtgacttc tccaggtctc acgggcatgg gcactccctt 1200
ggtggcaaga gcccccttga caccggggtg gtgggaacca tgaagacagg atgggggctg 1260
gcctctggct ctcatggggt ccaagttttg tgtattcttc aacctcattg acaagaactg 1320
aaaccaccaa aaaaaaaaaa aa 1342

<210> SEQ ID NO 13
<211> LENGTH: 1152
<212> TYPE: DNA
<213> ORGANISM: Mus musculus

<400> SEQUENCE: 13
gaattcgcgg ccgcgtcgac attctgggga cgtcggtcgg ggttcttaga agaggagatg 60
acttttcaca gtcactgagg ctcgtgcagg aagcctgggg gagcaggagg cggaaaccga 120
cccacatcaa gggcggcagg gccgggcggc ggggtacagg ggttgggggg gaaggggctg 180
cagggtatga gcccgagacc tgccctcctg tcacttccaa gaacctgtca caggcatgag 240
gggtccccgg cagagatgac agtgctggcg ccagcctgga gcccaaattc ctccctgttg 300
ctgctgttgc tgctgctgag tccttgcctg cgggggacac ctgactgtta cttcagccac 360
agtcccatct cctccaactt caaagtgaag tttagagagt tgactgacca cctgcttaaa 420
gattacccag tcactgtggc cgtcaatctt caggacgaga agcactgcaa ggccttgtgg 480
agcctcttcc tagcccagcg ctggatagag caactgaaga ctgtggcagg gtctaagatg 540
caaacgcttc tggaggacgt caacaccgag atacattttg tcacctcatg taccttccag 600
cccctaccag aatgtctgcg attcgtccag accaacatct cccacctcct gaaggacacc 660
tgcacacagc tgcttggtct gaagccctgt atcgggaagg cctgccagaa tttctctcgg 720
tgcctggagg tgcagtgcca gccggactcc tccaccctgc tgcccccaag gagtcccata 780
gccctagaag ccacggagct cccagagcct cggcccaggc agctgttgct cctgctgctg 840
ctgctgctgc ctctcacact ggtgctgctg gcagccgcct ggggccttcg ctggcaaagg 900
gcaagaagga ggggggagct ccaccctggg gtgcccctcc cctcccatcc ctaggatgcg 960
agccttgtgc atcgttgact cagccagggt cttatctcga tgaggtctca atatgttgcc 1020
caaactgact ttgaaaacct cgatgcacct tcctgcccca caaacttcca aacagctggg 1080
cttacgggca tgctatatac aacaaggctt tcttttcttc tttcttggtg ctagagttgg 1140
gaaccaaaac aa 1152

<210> SEQ ID NO 14
<211> LENGTH: 2475
<212> TYPE: DNA
<213> ORGANISM: Homo sapiens

<400> SEQUENCE: 14
agccgctctc cgcatcccag gacagcggtg cggccctcgg ccggggcgcc cactccgcag 60
cacccagcga gcgagcgagc gagcgagggc ggccgacgcg cccggccggg acccagctgc 120
ccgtatgacc gcgccgggcg ccgccgggcg ctgccctccc acgacatggc tgggctccct 180
gctgttgttg gtctgtctcc tggcgagcag gagtatcacc gaggaggtgt cggagtactg 240
tagccacatg attgggagtg gacacctgca gtctctgcag cggctgattg acagtcagat 300
ggagacctcg tgccaaatta catttgagtt tgtagaccag gaacagttga aagatccagt 360
gtgctacctt aagaaggcat ttctcctggt acaagacata atggaggaca ccatgcgctt 420
cagagataac acccccaatg ccatcgccat tgtgcagctg caggaactct ctttgaggct 480
gaagagctgc ttcaccaagg attatgaaga gcatgacaag gcctgcgtcc gaactttcta 540
tgagacacct ctccagttgc tggagaaggt caagaatgtc tttaatgaaa caaagaatct 600
ccttgacaag gactggaata ttttcagcaa gaactgcaac aacagctttg ctgaatgctc 660
cagccaagat gtggtgacca agcctgattg caactgcctg taccccaaag ccatccctag 720
cagtgacccg gcctctgtct cccctcatca gcccctcgcc ccctccatgg cccctgtggc 780
tggcttgacc tgggaggact ctgagggaac tgagggcagc tccctcttgc ctggtgagca 840
gcccctgcac acagtggatc caggcagtgc caagcagcgg ccacccagga gcacctgcca 900
gagctttgag ccgccagaga ccccagttgt caaggacagc accatcggtg gctcaccaca 960
gcctcgcccc tctgtcgggg ccttcaaccc cgggatggag gatattcttg actctgcaat 1020
gggcactaat tgggtcccag aagaagcctc tggagaggcc agtgagattc ccgtacccca 1080

-continued agggacagag ctttcccccct ccaggccagg agggggcagc atgcagacag agcccgccag 1140
acccagcaac ttcctctcag catcttctcc actccctgca tcagcaaagg gccaacagcc 1200
ggcagatgta actggtaccg ccttgcccag ggtgggcccc gtgaggccca ctggccagga 1260
ctggaatcac accccccaga agacagacca tccatctgcc ctgctcagag accccccgga 1320
gccaggctct cccaggatct catcaccgcg cccccagggc ctcagcaacc cctccaccct 1380
ctctgctcag ccacagcttt ccagaagcca ctcctcgggc agcgtgctgc cccttgggga 1440
gctggagggc aggaggagca ccagggatcg gaggagcccc gcagagccag aaggaggacc 1500
agcaagtgaa ggggcagcca ggcccctgcc ccgttttaac tccgttcctt tgactgacac 1560
acatgagagg cagtccgagg gatcctccag cccgcagctc caggagtctg tcttccacct 1620
gctggtgccc agtgtcatcc tggtcttgct ggccgtcgga ggcctcttgt tctacaggtg 1680
gaggcggcgg agccatcaag agcctcagag agcggattct cccttggagc aaccagaggg 1740
cagccccctc actcaggatg acagacaggt ggaactgcca gtgtagaggg aattctaaga 1800
cccctcacca tcctggacac tctcgtttgt caatgtccct ctgaaaatgt gacgcccagc 1860
cccggacaca gtactccaga tgttgtctga ccagctcaga gagagtacag tgggactgtt 1920
accttccttg atatggacag tattcttcta tttgtgcaga ttaagattgc attagttttt 1980
ttcttaacaa ctgcatcata ctgttgtcat atgttgagcc tgtggtctat aaaaccccta 2040
gttccatttc ccataaactt ctgtcaagcc agaccatctc taccctgtac ttggacaact 2100
taactttttt aaccaaagtg cagtttatgt tcacctttgt taaagccacc ttgtggtttc 2160
tgcccatcac ctgaacctac tgaagttgtg tgaaatccta attctgtcat ctccgtagcc 2220
ctcccagttg tgcctcctgc acattgatga gtgcctgctg ttgtctttgc ccatgttgtt 2280
gatgtagctg tgaccctatt gttcctcacc cctgcccccc gccaacccca gctggcccac 2340
ctcttccccc tcccacccaa gcccacagcc agcccatcag gaagccttcc tggcttctcc 2400
acaaccttct gactgtcttt tcagtcatgc cccctgctct tttgtatttg gctaatagta 2460
tatcaatttg cactt 2475

<210> SEQ ID NO 15
<211> LENGTH: 1531
<212> TYPE: DNA
<213> ORGANISM: Homo Sapiens

<400> SEQUENCE: 15
cggagcctgc agcccagccc cacccagacc catggctgga cctgccaccc agagccccat 60
gaagctgatg gccctgcagc tgctgctgtg gcacagtgca ctctggacag tgcaggaagc 120 caccccccctg ggccctgcca gctccctgcc ccagagcttc ctgctcaagt gcttagagca 180
agtgaggaag atccagggcg atggcgcagc gctccaggag aagctggtga gtgagtgtgc 240
cacctacaag ctgtgccacc ccgaggagct ggtgctgctc ggacactctc tgggcatccc 300
ctgggctccc ctgagcagct gccccagcca ggccctgcag ctggcaggct gcttgagcca 360
actccatagc ggccttttcc tctaccaggg gctcctgcag gccctggaag ggatctcccc 420
cgagttgggt cccaccttgg acacactgca gctggacgtc gccgactttg ccaccaccat 480
ctggcagcag atggaagaac tgggaatggc ccctgccctg cagcccaccc agggtgccat 540
gccggccttc gcctctgctt tccagcgccg ggcaggaggg gtcctggttg cctcccatct 600
gcagagcttc ctggaggtgt cgtaccgcgt tctacgccac cttgcccagc cctgagccaa 660
gccctcccca tcccatgtat ttatctctat ttaatattta tgtctattta agcctcatat 720

```
ttaaagacag ggaagagcag aacggagccc caggcctctg tgtccttccc tgcatttctg     780
agtttcattc tcctgcctgt agcagtgaga aaaagctcct gtcctcccat cccctggact     840
gggaggtaga taggtaaata ccaagtattt attactatga ctgctcccca gccctggctc     900
tgcaatgggc actgggatga gccgctgtga gcccctggtc ctgagggtcc ccacctggga     960
cccttgagag tatcaggtct cccacgtggg agacaagaaa tccctgttta atatttaaac    1020
agcagtgttc cccatctggg tccttgcacc cctcactctg gcctcagccg actgcacagc    1080
ggcccctgca tccccttggc tgtgaggccc ctggacaagc agaggtggcc agagctggga    1140
ggcatggccc tggggtccca cgaatttgct ggggaatctc gtttttcttc ttaagacttt    1200
tgggacatgg tttgactccc gaacatcacc gacgcgtctc ctgtttttct gggtggcctc    1260
gggacacctg ccctgccccc acgagggtca ggactgtgac tctttttagg gccaggcagg    1320
tgcctggaca tttgccttgc tggacgggga ctggggatgt gggagggagc agacaggagg    1380
aatcatgtca ggcctgtgtg tgaaaggaag ctccactgtc accctccacc tcttcacccc    1440
ccactcacca gtgtcccctc cactgtcaca ttgtaactga acttcaggat aataaagtgt    1500
ttgcctccaa aaaaaaaaaa aaaaaaaaaa a                                   1531
```

<210> SEQ ID NO 16
<211> LENGTH: 2960
<212> TYPE: DNA
<213> ORGANISM: Homo sapiens

<400> SEQUENCE: 16

```
ctgccgcttc caggcgtcta tcagcggctc agcctttgtt cagctgttct gttcaaacac      60
tctggggcca ttcaggcctg ggtggggcag cgggaggaag ggagtttgag gggggcaagg     120
cgacgtcaaa ggaggatcag agattccaca atttcacaaa actttcgcaa acagcttttt     180
gttccaaccc ccctgcattg tcttggacac caaatttgca taaatcctgg gaagttatta     240
ctaagcctta gtcgtggccc caggtaattt cctcccaggc ctccatgggg ttatgtataa     300
agggcccccct agagctgggc cccaaaacag cccggagcct gcagcccagc cccacccaga     360
cccatggctg gacctgccac ccagagcccc atgaagctga tgggtgagtg tcttggccca     420
ggatgggaga gccgcctgcc ctggcatggg agggaggctg gtgtgacaga ggggctgggg     480
atccccgttc tgggaatggg gattaaaggc acccagtgtc cccgagaggg cctcaggtgg     540
tagggaacag catgtctcct gagcccgctc tgtccccagc cctgcagctg ctgctgtggc     600
acagtgcact ctggacagtg caggaagcca ccccctggg ccctgccagc tccctgcccc     660
agagcttcct gctcaagtgc ttagagcaag tgaggaagat ccagggcgat ggcgcagcgc     720
tccaggagaa gctggtgagt gaggtgggtg agagggctgt ggagggaagc ccggtgggga     780
gagctaaggg ggatggaact gcagggccaa catcctctgg aagggacatg ggagaatatt     840
aggagcagtg gagctgggga aggctgggaa gggacttggg gaggaggacc ttggtgggga     900
cagtgctcgg gagggctggc tgggatggga gtggaggcat cacattcagg agaaagggca     960
agggccccctg tgagatcaga gagtgggggt gcagggcaga gaggaactga acagcctggc    1020
aggacatgga gggagggggaa agaccagaga gtcggggagg acccgggaag gagcggcgac    1080
ccggccacgg cgagtctcac tcagcatcct tccatcccca gtgtgccacc tacaagctgt    1140
gccaccccga ggagctggtg ctgctcggac actctctggg catcccctgg gctcccctga    1200
gcagctgccc cagccaggcc ctgcagctgg tgagtgtcag gaaaggataa ggctaatgag    1260
gagggggaag gagaggagga acacccatgg gctcccccat gtctccaggt tccaagctgg    1320
```

```
gggcctgacg tatctcaggc agcaccccct aactcttccg ctctgtctca caggcaggct   1380
gcttgagcca actccatagc ggccttttcc tctaccaggg gctcctgcag gccctggaag   1440
ggatctcccc cgagttgggt cccaccttgg acacactgca gctggacgtc gccgactttg   1500
ccaccaccat ctggcagcag gtgagccttg ttgggcaggg tggccaaggt cgtgctggca   1560
ttctgggcac cacagccggg cctgtgtatg ggccctgtcc atgctgtcag cccccagcat   1620
ttcctcattt gtaataacgc ccactcagaa gggcccaacc actgatcaca gctttccccc   1680
acagatggaa gaactgggaa tggcccctgc cctgcagccc acccagggtg ccatgccggc   1740
cttcgcctct gctttccagc gccgggcagg aggggtcctg gttgcctccc atctgcagag   1800
cttcctggag gtgtcgtacc gcgttctacg ccaccttgcc cagccctgag ccaagccctc   1860
cccatcccat gtatttatct ctatttaata tttatgtcta tttaagcctc atatttaaag   1920
acagggaaga gcagaacgga gccccaggcc tctgtgtcct tccctgcatt tctgagtttc   1980
attctcctgc ctgtagcagt gagaaaaagc tcctgtcctc ccatcccctg gactgggagg   2040
tagataggta aataccaagt atttattact atgactgctc cccagccctg gctctgcaat   2100
gggcactggg atgagccgct gtgagcccct ggtcctgagg gtccccacct gggacccttg   2160
agagtatcag gtctcccacg tgggagacaa gaaatccctg tttaatattt aaacagcagt   2220
gttccccatc tgggtccttg caccccctcac tctggcctca gccgactgca cagcggcccc   2280
tgcatcccct tggctgtgag gcccctggac aagcagaggt ggccagagct gggaggcatg   2340
gccctggggt cccacgaatt tgctggggaa tctcgttttt cttcttaaga cttttgggac   2400
atggtttgac tcccgaacat caccgacgtg tctcctgttt ttctgggtgg cctcgggaca   2460
cctgccctgc ccccacgagg gtcaggactg tgactctttt tagggccagg caggtgcctg   2520
gacatttgcc ttgctggatg gggactgggg atgtgggagg gagcagacag gaggaatcat   2580
gtcaggcctg tgtgtgaaag gaagctccac tgtcaccctc cacctcttca ccccccactc   2640
accagtgtcc cctccactgt cacattgtaa ctgaacttca ggataataaa gtgtttgcct   2700
ccagtcacgt ccttcctcct tcttgagtcc agctggtgcc tggccagggg ctggggaggt   2760
ggctgaaggg tgggagaggc cagagggagg tcggggagga ggtctgggga ggaggtccag   2820
ggaggaggag gaaagttctc aagttcgtct gacattcatt ccgttagcac atatttatct   2880
gagcacctac tctgtgcaga cgctgggcta agtgctgggg acacagcagg gaacaaggca   2940
gacatggaat ctgcactcga                                                2960
```

<210> SEQ ID NO 17
<211> LENGTH: 3221
<212> TYPE: DNA
<213> ORGANISM: Homo Sapiens

<400> SEQUENCE: 17

```
ccgagatgtt cccagcacag ccccatgtga gagctccctg gctccgggcc cagtatctgg     60
aatgcaggct ccagccaaat gcattctctt ctacgggatc tgggaacttc caaagctgcc    120
tcctcagagt gggaatttcc actcacttct ctcacgccag cactgacctc ccagcggggg    180
agggcatctt ttcttgacag agcagaagtg ggaggcagac agctgtcact ttccagaaga    240
ctttcttttc tgattcatac ccttcacctt ccctgtgttt actgtctgat atatgcaaag    300
gccaagtcac tttccagaga tgacaactcc ttcctgaagt agagacatgc ttccaacact    360
cagaagccta tgtgaacact cagccagcaa agctgggaag tttttctctg tgaccatggg    420
ctaattggtc tccttctctg gattgtggct ttatcagata aaaacaagtg gtcatgccac    480
```

```
aggatgtcta taagcccatt gattctggga ttctatgagt gatgctgata tgactaagcc    540
aggagagact tatttaaaga tctcagcatc tttcagcttg ttaacctaga gaaaacccga    600
agcatgactg gattataaag ggaaattgaa tgcggtccac caagttcatg gtaaaggatg    660
cactaacaga ttagagagag gtttcccctg atatgaggaa aacttcttgg aagatgaggt    720
gagatggcct aggaagaaat tcctacacaa aattgcacag tctctagtcc tggaaacatt    780
ttattcattg gataagaatg gattgaggca tgagcagagg actgagacaa acacagagaa    840
gtttcaacac tggttgggga gaaaaggagt aactagtgag attcaggcag aacaagaata    900
aggctcctca agaggcacaa gcaaagcagg gctcgagttg atttgttctc tcttcatcct    960
gctttttgta attccaccag agtctgaaat gaccactcca tagagtctct gctctgggat   1020
tctccaggaa accaatatcc atcatgagac atcaagtcta gtcccaggaa gaagagattc   1080
tggaatggaa acatcctggg tgggagtctc agcacatcta ctattctgtc tgagttactg   1140
gacaaataac ttcagtttta acctaacgaa agctgggttg gttggaggac tgggcaggca   1200
gcgctggaaa gtatgtcagc accatacctg actccctgaa tgcactcaac aatgccatta   1260
ctgaccactt actagaaata aaacagtcat ttgttgaata caacccgttt ctttttacaa   1320
gtgtagtgaa aagtgttttc tttcaagaaa ccccatgcat ttatagacat tgcctcagtg   1380
accctttatg aaagaagtca ctagtctttg tatgcccatt gggcaagggc accgcaaggc   1440
tcagaaggag gaggcagtgg gctaggagaa tggagagatc agaattttaa actcagccca   1500
gccattaaca tgcctcaagt actcctatca tatttgtaag agacaacagt tcactgaaat   1560
gaattctaag gtctttgggt ttttatcagt gtgcttctgt agtttctgag gaaatctaag   1620
gcacaactga ggaatgaagt caggctttcc aattcccgaa atactcctcc actgcttact   1680
catgtccctt ggaaattaag aaggaagcca ggagaatagc tgccataacc agggatgaac   1740
ttcttgtcca ctgctgcctg ctatgctagc aacagcctcc taactcataa tgacttagcc   1800
atgaggaatg tttctagatt ctcctttagc tgtctgccca tttggaagat gctgaggaca   1860
gagagaggac ccaagcaggc aactagttgg aggacttgta cacgtttcct tccagcagta   1920
tgtcagagag gtgagcagcc cactggggac agggctgcct gggttctgtg ctcgagggga   1980
ccttgagcag gctatttaac ccttctgtgc ctcagttgcc tgatctataa catgaaaatt   2040
agcaatccct actagataaa gttggggaat ttacagagtt aatatttgta aaggtctgag   2100
aatattcctg gcagagtaag cactctgtga gtatgacact ggcatttctt ctgcagcact   2160
acatgctgtc tatgcctttg tccaagtctg aaaccctaga actcttagaa ttcagttcaa   2220
tgtttacaca atcctacagt tctgctaggc ttctatgatg ctactattct gcatttgaat   2280
gagcaaatgg atttaatgca ttgtcaggga gccggccaaa gcttgagagc tccttcctgg   2340
ctgggaggcc ccttggaatg tggcctgaag gtaagctggc agcgagcctg acatgctttc   2400
atctagtttc ctcgcttcct tccttttctg cagttttcgc ttcacagaaa gcagaatcct   2460
taaaaataac cctcttagtt cacatctgtg gtcagtctgg gcttaatggc accccatcct   2520
ccccatttgc tcatttggtc tcagcagtga atggaaaaag tgtctcgtcc tgaccccctg   2580
cttccctttc ctacttcctg gaaatccaca ggatgctgca tttgctcagc agatttaaca   2640
gcccacttat cactcatgga agatccctcc tcctgcttga ctccgccctc tctccctctg   2700
cccgctttca ataagaggca gagacagcag ccagaggaac cgagaggctg agactaaccc   2760
agaaacatcc aattctcaaa ctgaagctcg cactctcgcc tccagcatga aagtctctgc   2820
cgcccttctg tgcctgctgc tcatagcagc caccttcatt ccccaagggc tcgctcagcc   2880
```

aggtaaggcc ccctcttctt ctccttgaac cacattgtct tctctctgag ttatcatgga 2940
ccatccaagc agacgtggta cccacagtct tgctttaacg ctacttttcc aagataaggt 3000
gactcagaaa aggacaaggg gtgagcccaa ccacacagct gctgctcggc agagcctgaa 3060
ctagaattcc agctgtgaac cccaaatcca gctccttcca ggattccagc tctgggaaca 3120
cactcagcgc agttactccc ccagctgctt ccagcagagt ttggggatca gggtaatcaa 3180
agagagggtg ggtgtgtagg ctgtttccag acacgctgga g 3221

<210> SEQ ID NO 18
<211> LENGTH: 561
<212> TYPE: DNA
<213> ORGANISM: Homo Sapiens

<400> SEQUENCE: 18
accacagtgg tgtccgagaa gtcaggcacg tagctcagcg gcggccgcgg cgcgtgcgtc 60
tgtgcctctg cgcgggtctc ctggtccttc tgccatcatg ccgatgttca tcgtaaacac 120
caacgtgccc cgcgcctccg tgccggacgg gttcctctcc gagctcaccc agcagctggc 180
gcaggccacc ggcaagcccc cccagtacat cgcggtgcac gtggtcccgg accagctcat 240
ggccttcggc ggctccagcg agccgtgcgc gctctgcagc ctgcacagca tcggcaagat 300
cggcggcgcg cagaaccgct cctacagcaa gctgctgtgc ggcctgctgg ccgagcgcct 360
gcgcatcagc ccggacaggg tctacatcaa ctattacgac atgaacgcgg ccaatgtggg 420
ctggaacaac tccaccttcg cctaagagcc gcagggaccc acgctgtctg cgctggctcc 480
acccgggaac ccgccgcacg ctgtgttcta ggcccgccca ccccaacctt ctggtgggga 540
gaaataaacg gtttagagac t 561

<210> SEQ ID NO 19
<211> LENGTH: 2156
<212> TYPE: DNA
<213> ORGANISM: Homo Sapiens

<400> SEQUENCE: 19
ggcacgagcc cagaaacaaa gacttcacgg acaaagtccc ttggaaccag agagaagccg 60
ggatggaaac tccaaacacc acagaggact atgacacgac cacagagttt gactatgggg 120
atgcaactcc gtgccagaag gtgaacgaga gggcctttgg ggcccaactg ctgccccctc 180
tgtactcctt ggtatttgtc attggcctgg ttggaaacat cctggtggtc ctggtccttg 240
tgcaatacaa gaggctaaaa aacatgacca gcatctacct cctgaacctg gccatttctg 300
acctgctctt cctgttcacg cttcccttct ggatcgacta caagttgaag gatgactggg 360
tttttggtga tgccatgtgt aagatcctct ctgggtttta ttacacaggc ttgtacagcg 420
agatcttttt catcatcctg ctgacgattg acaggtacct ggccatcgtc cacgccgtgt 480
ttgccttgcg ggcacggacc gtcacttttg gtgtcatcac cagcatcatc atttgggccc 540
tggccatctt ggcttccatg ccaggcttat acttttccaa gacccaatgg gaattcactc 600
accacacctg cagccttcac tttcctcacg aaagcctacg agagtggaag ctgtttcagg 660
ctctgaaact gaacctcttt gggctggtat tgcctttgtt ggtcatgatc atctgctaca 720
cagggattat aaagattctg ctaagacgac caaatgagaa gaaatccaaa gctgtccgtt 780
tgatttttgt catcatgatc atcttttttc tcttttggac cccctacaat ttgactatac 840
ttatttctgt tttccaagac ttcctgttca cccatgagtg tgagcagagc agacatttgg 900
acctggctgt gcaagtgacg gaggtgatcg cctacacgca ctgctgtgtc aacccagtga 960
tctacgcctt cgttggtgag aggttccgga agtacctgcg gcagttgttc cacaggcgtg 1020
tggctgtgca cctggttaaa tggctcccct tcctctccgt ggacaggctg gagagggtca 1080
gctccacatc tccctccaca ggggagcatg aactctctgc tgggttctga ctcagaccat 1140
aggaggccaa cccaaaataa gcaggcgtga cctgccaggc acactgagcc agcagcctgg 1200
ctctcccagc caggttctga ctcttggcac agcatggagt cacagccact tgggatagag 1260
agggaatgta atggtggcct ggggcttctg aggcttctgg ggcttcagtc ttttccatga 1320
acttctcccc tggtagaaag aagatgaatg agcaaaacca aatattccag agactgggac 1380
taagtgtacc agagaagggc ttggactcaa gcaagatttc agatttgtga ccattagcat 1440
ttgtcaacaa agtcacccac ttcccactat tgcttgcaca aaccaattaa acccagtagt 1500
ggtgactgtg ggctccattc aaagtgagct cctaagccat gggagacact gatgtatgag 1560
gaatttctgt tcttccatca cctccccccc cccgccaccc tcccactgcc aagaacttgg 1620
aaatagtgat ttccacagtg actccactct gagtcccaga gccaatcagt agccagcatc 1680
tgcctcccct tcactcccac cgcaggattt gggctcttgg aatcctgggg aacatagaac 1740
tcatgacgga agagttgaga cctaacgaga aatagaaatg ggggaactac tgctggcagt 1800
ggaactaaga aagcccttag gaagaatttt tatatccact aaaatcaaac aattcaggga 1860
gtgggctaag cacgggccat atgaataaca tggtgtgctt cttaaaatag ccataaaggg 1920
gagggactca tcatttccat ttacccttct tttctgacta tttttcagaa tctctcttct 1980
tttcaagttg ggtgatatgt tggtagattc taatggcttt attgcagcga ttaataacag 2040
gcaaaaggaa gcagggttgg tttcccttct ttttgttctt catctaagcc ttctggtttt 2100
atgggtcaga gttccgactg ccatcttgga cttgtcagca aaaaaaaaaa aaaaaa 2156

<210> SEQ ID NO 20
<211> LENGTH: 638
<212> TYPE: DNA
<213> ORGANISM: Mus musculus

<400> SEQUENCE: 20
gcttctgaag cttctgggcc ctgcagtccc agctctgtgc aaacctaacc ccgagcaaca 60
ccatgaagct ctgcgtgtct gccctctctc tcctcttgct cgtggctgcc ttctgtgctc 120
cagggttctc agcaccaatg ggctctgacc ctcccacttc ctgctgtttc tcttacacct 180
cccggcagct tcacagaagc tttgtgatgg attactatga gaccagcagt ctttgctcca 240
agccagctgt ggtattcctg accaaaagag gcagacagat ctgtgctaac cccagtgagc 300
cctgggtcac tgagtacatg agtgacttgg agttgaactg agcagctcca gcggcagggc 360
aggaggagcc acttcaggag aggcctcctc agccctgatg cttctcactg agaagcgtcc 420
ttgctcctca cgttcagatt tcctgcccct cttcttaatt taaatctctg tgtagacttt 480
gttttgtttt tttgggggag tattatttct attatttatg ttttagttat aggacgcgtg 540
tctcccatgg agatggtcca ccattgctgt ttctctgcta ttgtggatat gactgtgaaa 600
ttgatttcat gcattttcat aataaatctt tctttaag 638

<210> SEQ ID NO 21
<211> LENGTH: 764
<212> TYPE: DNA
<213> ORGANISM: Homo sapiens

<400> SEQUENCE: 21
atgtgctgta ccaagagttt gctcctggct gctttgatgt cagtgctgct actccacctc 60
tgcggcgaat cagaagcagc aagcaacttt gactgctgtc ttggatacac agaccgtatt 120
cttcatccta aatttattgt gggcttcaca cggcagctgg ccaatgaagg ctgtgacatc 180
aatgctatca tctttcacac aaagaaaaag ttgtctgtgt gcgcaaatcc aaaacagact 240
tgggtgaaat atattgtgcg tctcctcagt aaaaaagtca agaacatgta aaaactgtgg 300
cttttctgga atggaattgg acatagccca agaacagaaa gaaccttgct ggggttggag 360
gtttcacttg cacatcatgg agggtttagt gcttatctaa tttgtgcctc actggacttg 420
tccaattaat gaagttgatt catattgcat catagtttgc tttgtttaag catcacatta 480
aagttaaact gtattttatg ttatttatag ctgtaggttt tctgtgttta gctatttaat 540 actaatttc cataagctat tttggtttag tgcaaagtat aaaattatat ttgggggga 600 ataagattat atggactttt ttgcaagcaa caagctattt tttaaaamma actatttaac 660
attcttttgt ttatattgtt ttgtctccta aattgttgta attgcattat aaaataagaa 720
aaatattaat aagacaaata ttgaaaataa agaaacaaaa agtt 764

<210> SEQ ID NO 22
<211> LENGTH: 545
<212> TYPE: DNA
<213> ORGANISM: Homo sapiens

<400> SEQUENCE: 22
atggccctgc tactggccct cagcctgctg gttctctgga cttccccagc cccaactctg 60
agtggcacca atgatgctga agactgctgc ctgtctgtga cccagaaacc catccctggg 120
tacatcgtga ggaacttcca ctaccttctc atcaaggatg gctgcagggt gcctgctgta 180
gtgttcacca cactgagggg ccgccagctc tgtgcacccc cagaccagcc ctgggtagaa 240
cgcatcatcc agagactgca gaggacctca gccaagatga agcgccgcag cagttaacct 300
atgaccgtgc agagggagcc cggagtccga gtcaagcatt gtgaattatt acctaacctg 360
gggaaccgag gaccagaagg aaggaccagg cttccagctc ctctgcacca gacctgacca 420
gccaggacag ggcctggggt gtgtgtgagt gtgagtgtga gcgagagggt gagtgtggtc 480
tagagtaaag ctgctccacc cccagattgc aatgctacca ataaagccgc ctggtgttta 540
caact 545

<210> SEQ ID NO 23
<211> LENGTH: 4037
<212> TYPE: DNA
<213> ORGANISM: Homo sapiens

<400> SEQUENCE: 23
gagctccgtt gggagtccca tgtttcttta tggcataatg ggtgagaaca cagacttgga 60
agccaaacca cctgaatttg aaccccagtt ccatttacca actgtcaaaa gcttaggctt 120
tgattctaag cctgtttcct caactgctgt tctaaagatt aaataggcta atattcataa 180
ggcaactggg acagtggctt gtgtgtatag caaccattat ataagtgaat tatctactga 240
gcaccacagc acttcttcac tccatggtgt ggtgaccaga atggagatga gacagagaac 300
tgcaggttct gcttcgagtt taagttagga tttcccttga ccaatgagac ctgacttgga 360
ggagtcctgg cctcattcca ttaccccaaa caccctctag tctctagatg aacagatcct 420
gaatgtccag gccccacgtg gcctgttcta aggcctgaga tggaattgga tacaggacac 480
atccagcctt gagatctttt gctaagtgtg acacagtgcc cccagccctg tgctcatgtt 540
catgcctagg gaaaggcttc tatcaaaaga gttgaacttc ttcccactgg ggatggaaga 600

-continued

```
ccatttcctc ccttaaacct tggctctccc tgcttccttc aggccaccaa caacacatgt    660
gcaggatatg aaattgctga ggcatcactg ctttcctact tcccttccaa gtctcagctc    720
ccttatttta aaaaatattt ggcctcaatg atcatttctc aacaattcct caccgcagga    780
gcctctgaag ctcccaccag gccagctctc ctcccacaac agcttcccac agcatgaaga    840
tctccgtggc tgccattccc ttcttcctcc tcatcaccat cgccctaggg accaagactg    900
aatcctcctc acgtgagtgc aatgccttgt cttccttcca acctagagcc tgcagggaaa    960
taagcaggag tgaggttggg gctcagggga agaccaggag cagggactca gaaaggaggg   1020
ctggtatctt cttgaaattg tgtgtatagc aacattatat aaatgaatta tctactgagc   1080
accacagcac ttcaccccat ggtgtggtga gcaggatgga gatgagactt aggactgtag   1140
gttctgctta agagtttaag ttgggatctt ccagccttga ccaatgagac ttgacttggg   1200
agactccagg cttcattcca ctaccccaaa tgccctctag tctccaaata aacagatcct   1260
gaatctccag gcctcacatg gccttgatct cttatcattg ccccccagga ccagtccccc   1320
cttgccctca aggacatgga gtgagaccag cctgcctctc tactccctca atttctctct   1380
ctttgccgct aagcaaaaga gtggcccacc ccatttgggg tatatttcct cagggagatt   1440
aggagcagtg tcttgagccc ctcaagggca tttttctatt ggcctcctga ggtttgggcc   1500
cagcctgctt ccagcgtcac ctgtgcccag tgagtgcagc attgcttggg tatgggctgg   1560
ggggaaacac gacagtgtgg ggtccatcct aggccccctt ttctcagctg atttcttaga   1620
ataagctgcc tttagagata accaaaacta tttatcactc ttccatttta cctactctcc   1680
ttttcagaaa ctgggggaa accgaaggtt gttaaaatac agctaaagtt ggtgggtatg   1740
tgcacagttt gacttgccct ctccgatgtc atttgtcagc tcagaggaac aaggtgggag   1800
agtataggag ctctgactgg gtctcaggaa acaggggccc cttatgccgt tctttggatc   1860
gtgaggatgc tgcctggaat ggagctggaa aacaggatga gacccttcca cccagacatc   1920
tggccaccct cagtgacctc tgaggccatt gtgatgcaca tccatgattc tatgaagcag   1980
ggtcacataa catgcacaca cctgatttct ccactccata accacaacat gtgcctgttt   2040
gtacagggct cttggcctac aatgtccttc ctgctacctc tataattcaa gcttggggtg   2100
gctgctgtca ccttgcttct cctataaaag ccatgaaact tctcaatcag aaaatagatg   2160
aaaaaatcac ccaatccagt gatttttaaa actttttaga ccacaaaacc ttttcttcaa   2220
gcaatatctt ccacagaggc ccaatatgta aaacagaaaa aatgggttga gtagggtaca   2280
agacaccact ctcaaatgca gcaaggcctc cacaatagtc cctgaggccc ccagagctca   2340
gtgtaaaaac cactgatgca gtccaagggc ctcatttaca gaggagggaa caggggggaaa   2400
gtaaaatggc cacagtacac aggaagcaca ggcaaggtta ggttaggatt tgggtgccct   2460
gactctgtgg cctttgtcct tggggcttgc tgtgggcatc ctgctctctc tgcaggttgt   2520
cggttcaatg gggacatggg cagggtggag cactaggagg ggctgggttt gcattcccaa   2580
atggcatgtc tccaaatccc tattgggatt tcttccaaat attcctccta tttggagcac   2640
ctttcccgaa taaggcatga aggctgcatg atattggcca agtccctagc cttctctgcc   2700
agtcggcccc cagagatggt gtaagaagat ctgagtgtgc tgctcttcaa tcctggagtt   2760
gaaagtcatc caccagtctt tccaagaggg gttgaagaaa aggaggaagg gtgattgatg   2820
atgagggagg agaaaaagaa gagcccagga gtaccatgga gaaggagaag agaagatgag   2880
gaaagcctac tctcccctcc aagttctgag ggctgtctc ctccttcctt ccctcctcca   2940
tgccctcagc ttgcaggagc agccaatggt atggccttta acaaggggcc cctcctcagc   3000
```

atctgatgct ctctcctcag ggggacctta ccacccctca gagtgctgct tcacctacac 3060
tacctacaag atcccgcgtc agcggattat ggattactat gagaccaaca gccagtgctc 3120
caagcccgga attgtgtagg tggtacacac acatcacact ggggggagag ggagccagca 3180
gggcctcctg gagggaagca gggagtggtg gtggaatggg gacccccagc gtacctccca 3240
ggtgtgacta catggggaga ggcagctgag ggcaatctg agcgctttct ggctggagcc 3300
tgcaggagcc atggggaaac tgaccccatg gatggggaga tgacagagaa gggagaagaa 3360
ggcaagaggg cacttcctca gggggacaca gagactagat gggtctaggg gtcctaggaa 3420
ccgaagagta tgtctcagag aggagactgg ctctaagctg cctctgtgga agaaaggaaa 3480
agcagtatag gtcaggtggg gaatttagga gggagggaag atgggctgtc tcttccggcc 3540
actgggcccc tcggtttgtg atccttctcc ctcttgctcc acagcttcat caccaaaagg 3600
ggccattccg tctgtaccaa ccccagtgac aagtgggtcc aggactatat caaggacatg 3660
aaggagaact gagtgaccca gaaggggtgg cgaaggcaca gctcagagac ataaagagaa 3720
gatgccaagg ccccctcctc cacccaccgc taactctcag ccccagtcac cctcttggag 3780
cttccctgct ttgaattaaa gaccactcat gctcttccct ggcctcattc ctttctacgg 3840
gatttactca ttggccatgc actgaggaca ccagggtgtg gcaccctcgg catcaagcct 3900
cgctctgcag aagttttggt ggagcctggt acaaaaaata ggtcaggcct gcaatgcagg 3960
tagtgagaag cagaaagtga gaaagaaaag cagtgtaaag accgtctcct cctcagcagc 4020
aacagtagca gaccccg 4037

<210> SEQ ID NO 24
<211> LENGTH: 481
<212> TYPE: DNA
<213> ORGANISM: Homo sapiens

<400> SEQUENCE: 24
agcctctgaa gctcccacca ggccagctct cctcccacaa cagcttccca cagcatgaag 60
atctccgtgg ctgccattcc cttcttcctc ctcatcacca tcgccctagg gaccaagact 120
gaatcctcct cacggggacc ttaccacccc tcagagtgct gcttcaccta cactacctac 180
aagatcccgc gtcagcggat tatggattac tatgagacca acagccagtg ctccaagccc 240
ggaattgtct tcatcaccaa aaggggccat tccgtctgta ccaaccccag tgacaagtgg 300
gtccaggact atatcaagga catgaaggag aactgagtga cccagaaggg gtggcgaagg 360
cacagctcag agacataaag agaagatgcc aaggcccccct cctccaccca cccctaactc 420
tcagccccag tcaccctctt ggagcttccc tgctttgaat taaagaccac tcatgctctt 480
c 481

<210> SEQ ID NO 25
<211> LENGTH: 360
<212> TYPE: DNA
<213> ORGANISM: Homo sapiens

<400> SEQUENCE: 25
atggcaggcc tgatgaccat agtaaccagc cttctgttcc ttggtgtctg tgcccaccac 60
atcatcccta cgggctctgt ggtcataccc tctccctgct gcatgttctt tgtttccaag 120
agaattcctg agaaccgagt ggtcagctac cagctgtcca gcaggagcac atgcctcaag 180
ggaggagtga tcttcaccac caagaagggc cagcagttct gtggcgaccc caagcaggag 240
tgggtccaga ggtacatgaa gaacctggac gccaagcaga agaaggcttc cctagggcc 300 agggcagtgg ctgtcaaggg ccctgtccag agatatcctg gcaaccaaac cacctgctaa 360

<210> SEQ ID NO 26
<211> LENGTH: 492
<212> TYPE: DNA
<213> ORGANISM: Mus musculus

<400> SEQUENCE: 26
gaagaccttc acctcagctt ttggtaccat gaggtcactt cagatgctgc tcctggctgc 60
tctgcttctg ggacttttc tgcagcatgc cagagctgct cgagccacca atgtaggccg 120
agagtgctgc ctggattact tcaaaggggc cattcctatc aggaagttgg tgagctggta 180
taagacctca gtggagtgtt ccagggatgc catcgtgttt ctgactgtcc agggcaagct 240
catctgtgca gaccccaaag acaaacatgt gaagaaggcc atcagattgg tgaaaaaccc 300
aaggccgtga ccttcccgct gaggcatttg gagacgccag ggctgctgtc catggtttca 360
acataaagcg gcctgtgacc agcagagccc aagagcagcc acagagcaga agtccctgtt 420
ccctttttta tggactctta tgcactacag gcgaacacaa aaaaaagcaa cggaataaag 480
ccttcctccc tc 492

<210> SEQ ID NO 27
<211> LENGTH: 3460
<212> TYPE: DNA
<213> ORGANISM: Homo sapiens

<400> SEQUENCE: 27
aagaaagtca ttggtagctt gatggggatg gtattgaatc tataagttac cttgggcagt 60
atggccatat tcacgatatt gatttttcct acccatgagc atggaatatt cttccatttg 120
tttgtatcct cttttatttc attgagcagt ggtttgtagt tctccttgaa gaggtccttc 180
atgtcccttg taagttggat tcctaggtat tttattctct ttgaagcaat tgtgaatggg 240
agttcactca tgatttggct ctctgtttgt ttgttattgg tgtataagaa tgcttgtgat 300
ttttgtgcat tgattttgta tcctgagact ttgctgaagt tgcttatcag cttaaggaga 360
ttttgggctg agaccatggg gttttctaga tatacaatta tgtaatttgc aaatagggac 420
aatttgactt cctcttttcc taattgaata ccctttattt ccttctcctg cctaattgtc 480
ctggccattg gagaggagga gcatctccca gacagctgcg tgcctcagag aagccagcct 540
cgctaacccc tcaagcccag gggatgagac cctcctgaat cgctgctcta ttttggctgg 600
agccacagct ccctccaccg cggggcgggg ctaaaatgtc ctccccctta agggagcagg 660
cagctcctcc cagccaccca ccccaccaat tcccatcctc ccgccccct ccaccaaccc 720 cttctttcca cactgccccc tgagttcagg gaatttcccc agcatcccaa agcttgagtt 780
tcctgccagt cgggagggat gaatgcagat aaagggagtg cagaaggcac gaggaaacca 840
aagtgctctg tatcctccag tctccgcgcc tccacccagc tcaggaaccc gcgaaccctc 900
tcttgaccac tatgagcctc ccgtccagcc gcgcggcccg tgtcccgggt ccttcgggct 960
ccttgtgcgc gctgctcgcg ctgctgctcc tgctgacgcc gccggggccc ctcgccagcg 1020
gtgagagctc ctggcactgg ggtgcatccc agcctctgcg gggccgctgc gttccaggga 1080
actctcccag caacctgccc tataaaaatg tctttcttcc ccagctggtc ctgtctctgc 1140
tgtgctgaca gagctgcgtt gcacttgttt acgcgttacg ctgagagtaa accccaaaac 1200
gattggtaaa ctgcaggtgt tccccgcagg cccgcagtgc tccaaggtgg aagtggtgta 1260
agttctcctg tgttgctgtg tccactgtga cttaggcaag tcctccagcc tgggtcgtca 1320
acctttgtgg ctcatgggtg catcctcttt ttctttactt cagagcctcc ctgaagaacg 1380
ggaagcaagt ttgtctggac ccggaagccc cttttctaaa gaaagtcatc cagaaaattt 1440
tggacaggta tttgtccctt tgatctttgt ggtgttttaa tatcttctat ggaaagcata 1500
tacttcacaa tgtccttatt ctctctgtag gatttagact atgcttagaa ttataaggtt 1560
gttaagaaga ataaggaaac ttttttttctg gaatgttctg ggtaaacctt tatcaccaat 1620
cttacatgcc tgaacaatta cacagagctc attactgaca tctatttttt gtctgctctt 1680
tgcttttatt gatttttttc ccccaccaaa cgcttttgaa aaccaaatgt agcatacaag 1740
agtgtgggaa ttggttatac taatataact cttttctcaa cagtggaaac aagaaaaact 1800
gagtaacaaa aaagaccatg catcataaaa ttgcccagtc ttcagcggag cagttttctg 1860
gagatccctg gacccagtaa gaataagaag gaagggttgg tttttttcca ttttctacat 1920
ggattcccta ctttgaagag tgtgggggaa agcctacgct tctccctgaa gtttacagct 1980
cagctaatga agtactaata tagtatttcc actatttact gttattttac ctgataagtt 2040
attgaaccct ttggcaattg accatattgt gagcaaagaa tcactggtta ttagtctttc 2100
aatgaatatt gaattgaaga taactattgt atttctatca tacattcctt aaagtcttac 2160
cgaaaaggct gtggatttcg tatggaaata atgttttatt agtgtgctgt tgagggaggt 2220
atcctgttgt tcttactcac tcttctcata aaataggaaa tattttagtt ctgtttcttg 2280
gggaatatgt tactctttac cctaggatgc tatttaagtt gtactgtatt agaacactgg 2340
gtgtgtcata ccgttatctg tgcagaatat atttccttat tcagaatttc taaaaattta 2400
agttctgtaa gggctaatat attctcttcc tatggtttta gacgtttgat gtcttcttag 2460
tatggcataa tgtcatgatt tactcattaa actttgattt tgtatgctat tttttcacta 2520
taggatgact ataattctgg tcactaaata tacactttag atagatgaag aagcccaaaa 2580
acagataaat tcctgattgc taatttacat agaaatgtat tctcttggtt ttttaaataa 2640
aagcaaaatt aacaatgatc tgtgctctga aagttttgaa aatatatttg aacaatttga 2700
atataaattc atcatttagt cctcaaaata tatacagcat tgctaagatt ttcagatatc 2760
tattgtggat cttttaaagg ttttgaccat tttgttatga ggaattatac atgtatcaca 2820
ttcactatat taaaattgca cttttatttt ttcctgtgtg tcatgttggt ttttggtact 2880
tgtattgtca tttggagaaa caataaaaga tttctaaacc actgatgttg tttctccttc 2940
ttatacagtt actatttatc tttaattcta cattattcaa aatattacct ctgctcttct 3000
ctggctggca gagaggccct cattacccaa taccattgca ttggttcaac ttttctccat 3060
gttcagcccc cttccagtta ctccttcaca gcaccaatag cctctggggt ctttagaaaa 3120
cacaaatagg ataagatttt cctatctaaa ttcttaaatg gctccctgtt tcctagacat 3180
gaaataaaag ttgctaaaca tgatgaatga ggttctgtct catctcactc ctgatcatcg 3240
gtacttcaac ttcccttgtg cctcacattc actatagtca ggcgttcagt tccctaacta 3300
ggcatgttct ttccccaggc tcatgacttt gtatttgcta gggtctctac ctggaaagca 3360
tttacgtttt cctgcgtata agaggaggct tattcatcct tcagaactca gttcaagcaa 3420
tatctccttc gtgaattttc cttggcacac tcagcaaagc 3460

<210> SEQ ID NO 28
<211> LENGTH: 254
<212> TYPE: DNA
<213> ORGANISM: Homo Sapiens

<400> SEQUENCE: 28

-continued

```
ggtcctgtct ctgctgtgct cacggagctg cgttgcactt gtttacgcgt tacgctgaga     60

gtaaacccca aaacgattgg taaactgcag gtgttccccg caggcccgca gtgctccaag    120

gtggaagtgg tagcctccct gaagaacggg aagcaagttt gtctggaccc ggaagcccct    180

tttctaaaga aagtcatcca gaaaattttg gacagtggaa acaagaaaaa ctgagtaaca    240

gtcgacgcgg ccgc                                                      254


<210> SEQ ID NO 29
<211> LENGTH: 393
<212> TYPE: DNA
<213> ORGANISM: Homo sapiens

<400> SEQUENCE: 29

tcccacctct caggtggtat cttcagcgca ggctgccact cagcccccct ccagggatct     60

ggggcagaag gcgaatatcc cagagtctca gagtccacag gagttactct gaagggcgag    120

ccgcgggctg catcagtgga cccccacacc ccacccgcac cccaagcgct ccaccctggg    180

ggcggggccg tcgccttcct tccggactcg ggatcgatct ggaactccgg gaatttccct    240

ggcccggggg ctccgccctt tccagcccca accatgcata aaaggggttc gcggatctcg    300

gagagccaca gagcccgggc cgcaggcacc tcctcgccag ctcttccgct cctctcacag    360

ccgccagacc cgcctgctga gccccatggc ccg                                 393


<210> SEQ ID NO 30
<211> LENGTH: 374
<212> TYPE: DNA
<213> ORGANISM: Homo sapiens

<400> SEQUENCE: 30

cgcctcctcg caggcggtta tctcggtatc tctgagagcg gcgggctctc gctcccgctc     60

cagggattcg gggcagaaag agaacatccc acagttggcg ggagttacgc aagacagtca    120

gacccggacg tcactcgtga gtgccccgac ccccctccac cccagaggcg gggccatcgc    180

cttccttccg aactcgggat cgatctggag ctccgggaat ttccctggcc cgggactccg    240

gctttccagc cccaaccatg cataaaaggg gttcgccgtt ctcggagagc cacagagccc    300

gggccacagg cagctccttg ccagctctcc tcctcgcaca gccgctcgaa ccgcctgctg    360

agccccatgg cccg                                                      374


<210> SEQ ID NO 31
<211> LENGTH: 1064
<212> TYPE: DNA
<213> ORGANISM: Homo sapiens
<220> FEATURE:
<221> NAME/KEY: misc_feature
<222> LOCATION: (27)..(27)
<223> OTHER INFORMATION: n is a, c, g, t or u
<220> FEATURE:
<221> NAME/KEY: misc_feature
<222> LOCATION: (766)..(766)
<223> OTHER INFORMATION: n is a, c, g, t or u

<400> SEQUENCE: 31

cacagccggg tcgcaggcac ctccccngcc agctctcccg cattctgcac agcttcccga     60

cgcgtctgct gagccccatg gcccacgcca cgctctccgc cgcccccagc aatccccggc    120

tcctgcgggt ggcgctgctg ctcctgctcc tggtgggcag ccggcgcgca gcaggagcgt    180

ccgtggtcac tgaactgcgc tgccagtgct tgcagacact gcagggaatt cacctcaaga    240

acatccaaag tgtgaatgta aggtcccccg gaccccactg cgcccaaacc gaagtcatag    300
```

-continued

```
ccacactcaa gaatgggaag aaagcttgtc tcaaccccgc atcccccatg gttcagaaaa    360
tcatcgaaaa gatactgaac aaggggagca ccaactgaca ggagagaagt aagaagctta    420
tcagcgtatc attgacactt cctgcagggt ggtccctgcc cttaccagag ctgaaaatga    480
aaaagagaac agcagctttc tagggacagc tggaaaggga cttaatgtgt ttgactattt    540
cttacgaggg ttctacttat ttatgtattt atttttgaaa gcttgtattt taatatttta    600
catgctgtta tttaaagatg tgagtgtgtt tcatcaaaca tagctcagtc ctgattattt    660
aattggaata tgatgggttt taaatgtgtc attaaactaa tatttagtgg gagaccataa    720
tgtgtcagcc accttgataa atgacagggt ggggaactgg agggtngggg gattgaaatg    780
caagcaatta gtggatcact gttagggtaa gggaatgtat gtacacatct attttttata    840
cttttttttt taaaaaagaa tgtcagttgt tatttattca aattatctca cattatgtgt    900
tcaacatttt tatgctgaag tttcccttag acattttatg tcttgcttgt agggcataat    960
gccttgttta atgtccattc tgcagcgttt ctctttccct tggaaaagag aatttatcat   1020
tactgttaca tttgtacaaa tgacatgata ataaaagttt tatg                    1064
```

<210> SEQ ID NO 32
<211> LENGTH: 2177
<212> TYPE: DNA
<213> ORGANISM: Homo Sapiens

<400> SEQUENCE: 32

```
gaattctcag taagcggact taccaaagta ggtgatctgt aggggagtta acaaaattca     60
gtggtccttt caggccactg acttcaagtg gcaagagaca agggtctctt gttatcatgt    120
tatcttggct tccaaagctg gttgaagtcc agagattcat aaagtcattc aagaaaccta    180
gaatgacctg cctgcaagaa gacaggaagg actttcagtt tatagcaatt caaacatgaa    240
taacatttcc tgattaatag taataataat tagaaaggat tgactttcag aaatttttct    300
caaatcaagg ctcctgttac tttggttcca ccttttctct ctagaaggag aggaggagca    360
tctcccagat gctgcgtgct ccagaaaagc cggcatccct agcccgctct ggcacaggcc    420
atgaggcgct gctgaatcct gctgaatagc tactcccttc tagctggagc cacagctccc    480
tccaccgcgg aacagggtta caacgtccct ctcggtagag gtgcacgcag ctcctcctgg    540
ccaccctccc caccagttcc cattgtctgg ccccccctccc ccaacctctt ctttccacac    600
tgccccatga gttcagggaa tttccccagc atcccaaagc ttgagtttcc tgtcagtggg    660
gagagatgag tgtagataaa aggagtgcag aaggaacgag gaagccacag tgctccggat    720
cctccaatct tcgctcctcc aatctccgct cctccaccca gttcaggaac ccgcgaccgc    780
tcgcagcgct ctcttgacca ctatgagcct cctgtccagc cgcgcggccc gtgtccccgg    840
tccttcgagc tccttgtgcg cgctgttggt gctgctgctg ctgctgacgc agccagggcc    900
catcgccagc ggtgagagcg catggcgcgc gggacgcact cgcactcggg cacagaggtg    960
catcccagcc tctgcggggt cgctgcgttc cagggaactc tcccagcaac ctgccctata   1020
aagggtgtct ctctttcttc cccagctggt cctgccgctg ctgtgttgag agagctgcgt   1080
tgcgtttgtt tacagaccac gcaaggagtt catcccaaaa tgatcagtaa tctgcaagtg   1140
ttcgccatag gcccacagtg ctccaaggtg gaagtggtgt aagttctgtg ctgctgtgtc   1200
cgctgtgacc ttggcaagag agaaatcccg cagcctgggt cttcaacctt ggtatctcat   1260
gagtgtatct tctttttctt tccttcagag cctccctgaa gaacgggaag gaaatttgtc   1320
ttgatccaga agccccttt ctaaagaaag tcatccagaa aattttggac gggtacttgt   1380
```

cactttgatc tttgtggttt ctaaatctga tctagggaga ccatagactt cacaaggtct 1440
ttattctctg tacgatttaa gtaacacttt tcatgtttag aattaaaagg ttgttgaatt 1500
gggaaagttt ttctggattg tcctgggaaa atataccaat cttacatgta attacttgag 1560
caattacaca cagcttgtca ctaagttatg tttttgttt acccattgct tttattgatt 1620
tttgtattct cctttttac caaacatcat aaacgctgag ttttgacaag ggtggagtag 1680
aaaggagtgt gaaaaatggt taaactaata taacattttt ctcaacagtg gaaacaagga 1740
aaactgatta agagaaatga gcacgcatgg aaaagtttcc cagtcttcag cagagaagtt 1800
ttctggaggt ctctgaaccc agggaagaca agaaggaaag attttgttgt tgtttgttta 1860 tttgttttc cagtagttag ctttcttcct ggattcctca ctttgaagag tgtgaggaaa 1920
acctatgttt gccgcttaag ctttcagctc agctaatgaa gtgtttagca tagtacctct 1980
gctatttgct gttattttat ctgctatgct attgaagttt tggcaattga ctatagtgtg 2040
agccaggaat cactggctgt taatctttca aagtgtcttg aattgtaggt gactattata 2100
tttccaagaa atattcctta agatattaac tgagaaggct gtggatttaa tgtggaaatg 2160
atgtttcata agaattc 2177

<210> SEQ ID NO 33
<211> LENGTH: 554
<212> TYPE: DNA
<213> ORGANISM: Rattus norvegicus

<400> SEQUENCE: 33
tttcctaaat aaatatgacc accaagaaca tgttctctga agacattctc agccttgact 60
ccagcacggt gacttaatag agctcggctc tgccatgaag tccgttgctc tattcctcat 120
gggcatcatc ttcctggatc actgtggagt tcgaggaacc ctagtgataa ggaatcagcg 180
atgctcctgc atcagcacca gccaaggcac attccactac aaatccctca aagacctcaa 240
acagtttgcc ccaagcccta actgcaacaa aactgaaatc atcgctacac tgaagaacgg 300
agatcaaacc tgcctagacc cagattcagc aagggtgaag aagctgatga aagaatggga 360
gaaaaagatc agccaaaaga aaaagcaaaa gagggggaaa aaccatcaaa ggagcaagaa 420
aacccgaaaa gctaaaacac cccaccatcc ggagtcaaag aagactgcat aagagaccac 480
tttaccaaca agcgctctgc atctaaacgg cttttagatc atactaaaac gccttccctt 540
taatacacaa ctcg 554

<210> SEQ ID NO 34
<211> LENGTH: 514
<212> TYPE: DNA
<213> ORGANISM: Rattus norvegicus

<400> SEQUENCE: 34
atcaccagag ccacagcaga gagctgcagc tgccgctgag atgaacagga cgggcatggc 60
cgtagccctg gctatgatca tctgggccac aacggttcca ggcttcgtta tgttcaaagg 120
ggggcgctgt ctttgcatcg accgcggagt gaaagtggtc aaaatggcag caatcaagga 180
agtttctgta atttacccga gtaacggctg tgacaaagtt gaagtgattg ttaccctgaa 240
ggctcataaa ggacaaaggt gcctggaccc cacatccaag caagctcgcc tcataatgca 300
gacaatacaa aaaaagaatt ttttaaggcg ccagaacatg tgatgggccc tcaaattcga 360
gctctgtgcc aagaagctga ccctctcctg tcttggaata tgcatccgtt ttgccagatt 420
gcagaactcg ctaggaggtc ggatacctct aaactattct gcttggctat gaaaatattt 480

-continued atctcgaaga gtcatgtgtc tctgtgtgtg caca 514

<210> SEQ ID NO 35
<211> LENGTH: 3524
<212> TYPE: DNA
<213> ORGANISM: Homo Sapiens

<400> SEQUENCE: 35
tctccgtcag ccgcattgcc cgctcggcgt ccggcccccg acccgtgctc gtccgcccgc 60
ccgcccgccc gcccgcgcca tgaacgccaa ggtcgtggtc gtgctggtcc tcgtgctgac 120
cgcgctctgc ctcagcgacg ggaagcccgt cagcctgagc tacagatgcc catgccgatt 180
cttcgaaagc catgttgcca gagccaacgt caagcatctc aaaattctca acactccaaa 240
ctgtgccctt cagattgtag cccggctgaa gaacaacaac agacaagtgt gcattgaccc 300
gaagctaaag tggattcagg agtacctgga gaaagcttta aacaagaggt tcaagatgtg 360
agagggtcag acgcctgagg aacccttaca gtaggagccc agctctgaaa ccagtgttag 420
ggaagggcct gccacagcct cccctgccag ggcagggccc caggcattgc caagggcttt 480
gttttgcaca ctttgccata ttttcaccat ttgattatgt agcaaaatac atgacattta 540
tttttcattt agtttgatta ttcagtgtca ctggcgacac gtagcagctt agactaaggc 600
cattattgta cttgccttat tagagtgtct ttccacggag ccactcctct gactcagggc 660
tcctgggttt tgtattctct gagctgtgca ggtggggaga ctgggctgag ggagcctggc 720
cccatggtca gccctagggt ggagagccac caagagggac gcctgggggt gccaggacca 780
gtcaacctgg gcaaagccta gtgaaggctt ctctctgtgg gatgggatgg tggagggcca 840
catgggaggc tcaccccctt ctccatccac atgggagccg ggtctgcctc ttctgggagg 900
gcagcagggc taccctgagc tgaggcagca gtgtgaggcc agggcagagt gagacccagc 960
cctcatcccg agcacctcca catcctccac gttctgctca tcattctctg tctcatccat 1020
catcatgtgt gtccacgact gtctccatgg ccccgcaaaa ggactctcag gaccaaagct 1080
ttcatgtaaa ctgtgcacca agcaggaaat gaaaatgtct tgtgttacct gaaaacactg 1140
tgcacatctg tgtcttgtgt ggaatattgt ccattgtcca atcctatgtt tttgttcaaa 1200
gccagcgtcc tcctctgtga ccaatgtctt gatgcatgca ctgttccccc tgtgcagccg 1260
ctgagcgagg agatgctcct tgggcccttt gagtgcagtc ctgatcagag ccgtggtcct 1320
ttggggtgaa ctaccttggt tcccccactg atcacaaaaa catggtgggt ccatgggcag 1380
agcccaaggg aattcggtgt gcaccagggt tgaccccaga ggattgctgc cccatcagtg 1440
ctccctcaca tgtcagtacc ttcaaactag ggccaagccc agcactgctt gaggaaaaca 1500
agcattcaca acttgttttt ggtttttaaa acccagtcca caaaataacc aatcctggac 1560
atgaagattc tttcccaatt cacatctaac ctcatcttct tcaccatttg gcaatgccat 1620
catctcctgc cttcctcctg ggccctctct gctctgcgtg tcacctgtgc ttcgggccct 1680
tcccacagga catttctcta agagaacaat gtgctatgtg aagagtaagt caacctgcct 1740
gacatttgga gtgttcccct cccactgagg gcagtcgata gagctgtatt aagccactta 1800
aaatgttcac ttttgacaaa ggcaagcact tgtgggtttt tgttttgttt ttcattcagt 1860
cttacgaata cttttgccct ttgattaaag actccagtta aaaaaaattt taatgaagaa 1920
agtggaaaac aaggaagtca aagcaaggaa actatgtaac atgtaggaag taggaagtaa 1980
attatagtga tgtaatcttg aattgtaact gttcgtgaat ttaataatct gtagggtaat 2040
tagtaacatg tgttaagtat tttcataagt atttcaaatt ggagcttcat ggcagaaggc 2100

```
aaacccatca acaaaaattg tcccttaaac aaaaattaaa atcctcaatc cagctatgtt   2160
atattgaaaa aatagagcct gagggatctt tactagttat aaagatacag aactctttca   2220
aaacctttg aaattaacct ctcactatac cagtataatt gagttttcag tggggcagtc    2280
attatccagg taatccaaga tattttaaaa tctgtcacgt agaacttgga tgtacctgcc   2340
cccaatccat gaaccaagac cattgaattc ttggttgagg aaacaaacat gaccctaaat   2400
cttgactaca gtcaggaaag gaatcatttc tatttctcct ccatgggaga aaatagataa   2460
gagtagaaac tgcagggaaa attatttgca taacaattcc tctactaaca atcagctcct   2520
tcctggagac tgcccagcta aagcaatatg catttaaata cagtcttcca tttgcaaggg   2580
aaaagtctct tgtaatccga atctcttttt gctttcgaac tgctagtcaa gtgcgtccac   2640
gagctgttta ctagggatcc ctcatctgtc cctccgggac ctggtgctgc ctctacctga   2700
cactcccttg ggctccctgt aacctcttca gaggccctcg ctgccagctc tgtatcagga   2760
cccagaggaa ggggccagag gctcgttgac tggctgtgtg ttgggattga gtctgtgcca   2820
cgtgtatgtg ctgtggtgtg tccccctctg tccaggcact gagataccag cgaggaggct   2880
ccagagggca ctctgcttgt tattagagat tacctcctga gaaaaaagct tccgcttgga   2940
gcagaggggc tgaatagcag aaggttgcac ctcccccaac cttagatgtt ctaagtcttt   3000
ccattggatc tcattggacc cttccatggt gtgatcgtct gactggtgtt atcaccgtgg   3060
gctccctgac tgggagttga tcgcctttcc caggtgctac acccttttcc agctggatga   3120
gaatttgagt gctctgatcc ctctacagag cttccctgac tcattctgaa ggagccccat   3180
tcctgggaaa tattccctag aaacttccaa atcccctaag cagaccactg ataaaaccat   3240
gtagaaaatt tgttattttg caacctcgct ggactctcag tctctgagca gtgaatgatt   3300
cagtgttaaa tgtgatgaat actgtatttt gtattgtttc aagtgcatct cccagataat   3360
gtgaaaatgg tccaggagaa ggccaattcc tatacgcagc gtgctttaaa aaataaataa   3420
gaaacaactc tttgagaaac aacaatttct actttgaagt cataccaatg aaaaaatgta   3480
tatgcactta taattttcct aataaagttc tgtactcaaa tgta                    3524
```

<210> SEQ ID NO 36
<211> LENGTH: 2140
<212> TYPE: DNA
<213> ORGANISM: Homo sapiens

<400> SEQUENCE: 36

```
ccgacctaga acccgcccgc tgcctgccac gctgccactg ccgcttcctc tataaaggga     60
cctgagcgtc cgggcccagg ggctccgcac agcaggtgag gctctcctgc cccatctcct    120
tgggctgccc gtgcttcgtg ctttggacta ccgccccgca gtgtcctgcc ctctgcctgg    180
gcctcggtcc ctcctgcacc tgctgcctgg atccccggcc tgcctgggcc tgggccttgg    240
tgggtttggt tttggtttcc ttctctgtct ctgactctcc atctgtcagt ctcattgtct    300
ctgtcacaca ttctctgttt ctgccatgat tcctctctgt tcccttcctg tctctctctg    360
tctccctctg ctcaccttgg ggtttctctg actgcatctt gtccccttct ctgtcgatct    420
ctctctcggg ggtcgggggg tgctgtctcc cagggcggga ggtctgtctt ccgccgcgtg    480
ccccgccccg ctcactgtct ctctctctct ctctctttct ctgcaggttc tccccatgac    540
accacctgaa cgtctcttcc tcccaagggt gtgtggcacc accctacacc tcctccttct    600
ggggctgctg ctggttctgc tgcctggggc ccaggtgagg cagcaggaga atgggggctg    660
ctggggtggc tcagccaaac cttgagccct agagcccccc tcaactctgt tctcccctag    720
```

gggctccctg gtgttggcct cacaccttca gctgcccaga ctgcccgtca gcaccccaag 780
atgcatcttg cccacagcac cctcaaacct gctgctcacc tcattggtaa acatccacct 840
gacctcccag acatgtcccc accagctctc ctcctacccc tgcctcagga acccaagcat 900
ccacccctct cccccaactt cccccacgct aaaaaaaaca gagggagccc actcctatgc 960
ctccccctgc catcccccag gaactcagtt gttcagtgcc cacttcctca gggattgaga 1020
cctctgatcc agacccctga tctcccaccc ccatccccta tggctcttcc taggagaccc 1080
cagcaagcag aactcactgc tctggagagc aaacacggac cgtgccttcc tccaggatgg 1140
tttctccttg agcaacaatt ctctcctggt ccccaccagt ggcatctact tcgtctactc 1200
ccaggtggtc ttctctggga aagcctactc tcccaaggcc ccctcctccc cactctacct 1260
ggcccatgag gtccagctct tctcctccca gtaccccttc catgtgcctc tcctcagctc 1320
ccagaagatg gtgtatccag ggctgcagga accctggctg cactcgatgt accacggggc 1380
tgcgttccag ctcacccagg gagaccagct atccacccac acagatggca tcccccacct 1440
agtcctcagc cctagtactg tcttctttgg agccttcgct ctgtagaact tggaaaaatc 1500
cagaaagaaa aaataattga tttcaagacc ttctccccat tctgcctcca ttctgaccat 1560
ttcaggggtc gtcaccacct ctcctttggc cattccaaca gctcaagtct tccctgatca 1620
agtcaccgga gctttcaaag aaggaattct aggcatccca ggggaccaca cctccctgaa 1680
ccatccctga tgtctgtctg gctgaggatt tcaagcctgc ctaggaattc ccagcccaaa 1740
gctgttggtc ttgtccacca gctaggtggg gcctagatcc acacacagag gaagagcagg 1800
cacatggagg agcttggggg atgactagag gcagggaggg gactatttat gaaggcaaaa 1860
aaattaaatt atttatttat ggaggatgga gagaggggaa taatagaaga acatccaagg 1920
agaaacagag acaggcccaa gagatgaaga gtgagagggc atgcgcacaa ggctgaccaa 1980
gagagaaaga agtaggcatg agggatcaca gggccccaga aggcagggaa aggctctgaa 2040
agccagctgc cgaccagagc cccacacgga ggcatctgca ccctcgatga agcccaataa 2100
acctcttttc tctgaaatgc tgtctgcttg tgtgtgtgtg 2140

<210> SEQ ID NO 37
<211> LENGTH: 1498
<212> TYPE: DNA
<213> ORGANISM: Homo Sapiens

<400> SEQUENCE: 37
accaaacctc ttcgaggcac aaggcacaac aggctgctct gggattctct tcagccaatc 60
ttcattgctc aagtgtctga agcagccatg gcagaagtac ctgagctcgc cagtgaaatg 120
atggcttatt acagtggcaa tgaggatgac ttgttctttg aagctgatgg ccctaaacag 180
atgaagtgct ccttccagga cctggacctc tgccctctgg atggcggcat ccagctacga 240
atctccgacc accactacag caagggcttc aggcaggccg cgtcagttgt tgtggccatg 300
gacaagctga ggaagatgct ggttccctgc ccacagacct tccaggagaa tgacctgagc 360
accttctttc ccttcatctt tgaagaagaa cctatcttct tcgacacatg ggataacgag 420
gcttatgtgc acgatgcacc tgtacgatca ctgaactgca cgctccggga ctcacagcaa 480
aaaagcttgg tgatgtctgg tccatatgaa ctgaaagctc tccacctcca gggacaggat 540
atggagcaac aagtggtgtt ctccatgtcc tttgtacaag gagaagaaag taatgacaaa 600
atacctgtgg ccttgggcct caaggaaaag aatctgtacc tgtcctgcgt gttgaaagat 660
gataagccca ctctacagct ggagagtgta gatcccaaaa attacccaaa gaagaagatg 720
gaaaagcgat ttgtcttcaa caagatagaa atcaataaca agctggaatt tgagtctgcc 780
cagttcccca actggtacat cagcacctct caagcagaaa acatgcccgt cttcctggga 840
gggaccaaag gcggccagga tataactgac ttcaccatgc aatttgtgtc ttcctaaaga 900
gagctgtacc cagagagtcc tgtgctgaat gtggactcaa tccctagggc tggcagaaag 960
ggaacagaaa ggtttttgag tacggctata gcctggactt tcctgttgtc tacaccaatg 1020
cccaactgcc tgccttaggg tagtgctaag aggatctcct gtccatcagc caggacagtc 1080
agctctctcc tttcagggcc aatccccagc ccttttgttg agccaggcct ctctcacctc 1140
tcctactcac ttaaagcccg cctgacagaa accacggcca catttggttc taagaaaccc 1200
tctgtcattc gctcccacat tctgatgagc aaccgcttcc ctatttattt atttatttgt 1260
ttgtttgttt tattcattgg tctaatttat tcaaaggggg caagaagtag cagtgtctgt 1320
aaaagagcct agtttttaat agctatggaa tcaattcaat ttggactggt gtgctctctt 1380
taaatcaagt cctttaatta agactgaaaa tatataagct cagattattt aaatgggaat 1440
atttataaat gagcaaatat catactgttc aatggttctg aaataaactt cactgaag 1498

<210> SEQ ID NO 38
<211> LENGTH: 2943
<212> TYPE: DNA
<213> ORGANISM: Homo Sapiens

<400> SEQUENCE: 38
accaggcaac accattgaag gctcatatgt aaaaatccat gccttccttt ctcccaatct 60
ccattcccaa acttagccac tggcttctgg ctgaggcctt acgcatacct cccggggctt 120
gcacacacct tcttctacag aagacacacc ttgggcatat cctacagaag accaggcttc 180
tctctggtcc ttggtagagg gctactttac tgtaacaggg ccagggtgga gagttctctc 240
ctgaagctcc atcccctcta taggaaatgt gttgacaata ttcagaagag taagaggatc 300
aagacttctt tgtgctcaaa taccactgtt ctcttctcta ccctgcccta accaggagct 360
tgtcacccca aactctgagg tgatttatgc cttaatcaag caaacttccc tcttcagaaa 420
agatggctca ttttccctca aaagttgcca ggagctgcca agtattctgc caattcaccc 480
tggagcacaa tcaacaaatt cagccagaac acaactacag ctactattag aactattatt 540
attaataaat tcctctccaa atctagcccc ttgacttcgg atttcacgat ttctcccttc 600
ctcctagaaa cttgataagt ttcccgcgct tccctttttc taagactaca tgtttgtcat 660
cttataaagc aaaggggtga ataaatgaac caaatcaata acttctggaa tatctgcaaa 720
caacaataat atcagctatg ccatctttca ctattttagc cagtatcgag ttgaatgaac 780
atagaaaaat acaaaactga attcttccct gtaaattccc cgttttgacg acgcacttgt 840
agccacgtag ccacgcctac ttaagacaat tacaaaaggc gaagaagact gactcaggct 900
taagctgcca gccagagagg gagtcatttc attggcgttt gagtcagcaa agaagtcaag 960
atggccaaag ttccagacat gtttgaagac ctgaagaact gttacagtga aaatgaagaa 1020
gacagttcct ccattgatca tctgtctctg aatcagaaat ccttctatca tgtaagctat 1080
ggcccactcc atgaaggctg catggatcaa tctgtgtctc tgagtatctc tgaaacctct 1140
aaaacatcca agcttacctt caaggagagc atggtggtag tagcaaccaa cgggaaggtt 1200
ctgaagaaga gacggttgag tttaagccaa tccatcactg atgatgacct ggaggccatc 1260
gccaatgact cagaggaaga aatcatcaag cctaggtcag caccttttag cttcctgagc 1320
aatgtgaaat acaactttat gaggatcatc aaatacgaat tcatcctgaa tgacgccctc 1380

-continued aatcaaagta taattcgagc caatgatcag tacctcacgg ctgctgcatt acataatctg 1440
gatgaagcag tgaaatttga catgggtgct tataagtcat caaaggatga tgctaaaatt 1500
accgtgattc taagaatctc aaaaactcaa ttgtatgtga ctgcccaaga tgaagaccaa 1560
ccagtgctgc tgaaggagat gcctgagata cccaaaacca tcacaggtag tgagaccaac 1620
ctcctcttct tctgggaaac tcacggcact aagaactatt tcacatcagt tgcccatcca 1680
aacttgttta ttgccacaaa gcaagactac tgggtgtgct tggcaggggg gccaccctct 1740
atcactgact ttcagatact ggaaaaccag gcgtaggtct ggagtctcac ttgtctcact 1800
tgtgcagtgt tgacagttca tatgtaccat gtacatgaag aagctaaatc ctttactgtt 1860
agtcatttgc tgagcatgta ctgagccttg taattctaaa tgaatgttta cactctttgt 1920
aagagtggaa ccaacactaa catataatgt tgttatttaa agaacaccct atattttgca 1980
tagtaccaat cattttaatt attattcttc ataacaattt taggaggacc agagctactg 2040
actatggcta ccaaaaagac tctacccata ttacagatgg gcaaattaag gcataagaaa 2100
actaagaaat atgcacaata gcagttgaaa caagaagcca cagacctagg atttcatgat 2160
ttcatttcaa ctgtttgcct tctactttta agttgctgat gaactcttaa tcaaatagca 2220
taagtttctg ggacctcagt tttatcattt tcaaaatgga gggaataata cctaagcctt 2280
cctgccgcaa cagtttttta tgctaatcag ggaggtcatt ttggtaaaat acttcttgaa 2340
gccgagcctc aagatgaagg caaagcacga aatgttattt tttaattatt atttatatat 2400
gtatttataa atatatttaa gataattata atatactata tttatgggaa ccccttcatc 2460
ctctgagtgt gaccaggcat cctccacaat agcagacagt gttttctggg ataagtaagt 2520
ttgatttcat taatacaggg cattttggtc caagttgtgc ttatcccata gccaggaaac 2580
tctgcattct agtacttggg agacctgtaa tcatataata aatgtacatt aattaccttg 2640
agccagtaat tggtccgatc tttgactctt ttgccattaa acttacctgg gcattcttgt 2700
ttcaattcca cctgcaatca agtcctacaa gctaaaatta gatgaactca actttgacaa 2760
ccatgagacc actgttatca aaactttctt ttctggaatg taatcaatgt ttcttctagg 2820
ttctaaaaat tgtgatcaga ccataatgtt acattattat caacaatagt gattgataga 2880
gtgttatcag tcataactaa ataaagcttg caacaaaatt ctctgacaaa aaaaaaaaaa 2940
aaa 2943

<210> SEQ ID NO 39
<211> LENGTH: 1047
<212> TYPE: DNA
<213> ORGANISM: Homo sapiens

<400> SEQUENCE: 39
cgaattcccc tatcacctaa gtgtgggcta atgtaacaaa gagggatttc acctacatcc 60
attcagtcag tctttggggg tttaaagaaa ttccaaagag tcatcagaag aggaaaaatg 120
aaggtaatgt tttttcagac aggtaaagtc tttgaaaata tgtgtaatat gtaaaacatt 180
ttgacacccc cataatattt ttccagaatt aacagtataa attgcatctc ttgttcaaga 240
gttccctatc actctcttta atcactactc acagtaacct caactcctgc cacaatgtac 300
aggatgcaac tcctgtcttg cattgcacta agtcttgcac ttgtcacaaa cagtgcacct 360
acttcaagtt ctacaaagaa aacacagcta caactggagc atttactgct ggatttacag 420
atgattttga atggaattaa taattacaag aatcccaaac tcaccaggat gctcacattt 480
aagttttaca tgcccaagaa ggccacagaa ctgaaacatc ttcagtgtct agaagaagaa 540
ctcaaacctc tggaggaagt gctaaattta gctcaaagca aaaactttca cttaagaccc 600
agggacttaa tcagcaatat caacgtaata gttctggaac taaagggatc tgaaacaaca 660
ttcatgtgtg aatatgctga tgagacagca accattgtag aatttctgaa cagatggatt 720
accttttgtc aaagcatcat ctcaacactg acttgataat taagtgcttc ccacttaaaa 780
catatcaggc cttctattta tttaaatatt taaattttat atttattgtt gaatgtatgg 840
tttgctacct attgtaacta ttattcttaa tcttaaaact ataaatatgg atcttttatg 900 attcttttg taagccctag gggctctaaa atggtttcac ttatttatcc caaaatattt 960
attattatgt tgaatgttaa atatagtatc tatgtagatt ggttagtaaa actatttaat 1020
aaatttgata aatataaaaa aaaaaaa 1047

<210> SEQ ID NO 40
<211> LENGTH: 924
<212> TYPE: DNA
<213> ORGANISM: Homo sapiens

<400> SEQUENCE: 40
cagagcccca cgaaggacca gaacaagaca gagtgcctcc tgccgatcca aacatgagcc 60
gcctgcccgt cctgctcctg ctccaactcc tggtccgccc cggactccaa gctcccatga 120
cccagacaac gcccttgaag acaagctggg ttaactgctc taacatgatc gatgaaatta 180
taacacactt aaagcagcca cctttgcctt tgctggactt caacaacctc aatggggaag 240
accaagacat tctgatggaa aataaccttc gaaggccaaa cctggaggca ttcaacaggg 300
ctgtcaagag tttacagaac gcatcagcaa ttgagagcat tcttaaaaat ctcctgccat 360
gtctgcccct ggccacggcc gcacccacgc gacatccaat ccatatcaag gacggtgact 420
ggaatgaatt ccggaggaaa ctgacgttct atctgaaaac ccttgagaat gcgcaggctc 480
aacagacgac tttgagcctc gcgatctttt gagtccaacg tccagctcgt tctctgggcc 540
ttctcaccac agagcctcgg gacatcaaaa acagcagaac ttctgaaacc tctgggtcat 600
ctctcacaca ttccaggacc agaagcattt caccttttcc tgcggcatca gatgaattgt 660
taattatcta atttctgaaa tgtgcagctc ccatttggcc ttgtgcggtt gtgttctcat 720
ttttatccca ttgagactat ttatttatgt atgtatgtat ttatttattt attgcctgga 780
gtgtgaactg tatttatttt agcagaggag ccatgtcctg ctgcttctgc aaaaaactca 840
gagtggggtg ggagcatgt tcatttgtac ctcgagtttt aaactggttc ctagggatgt 900
gtgagaataa actagactct gaac 924

<210> SEQ ID NO 41
<211> LENGTH: 873
<212> TYPE: DNA
<213> ORGANISM: Homo sapiens

<400> SEQUENCE: 41
ttctatgcaa agcaaaaagc cagcagcagc cccaagctga taagattaat ctaaagagca 60
aattatggtg taatttccta tgctgaaact ttgtagttaa ttttttaaaa aggtttcatt 120
ttcctattgg tctgatttca caggaacatt ttacctgttt gtgaggcatt ttttctcctg 180
gaagagaggt gctgattggc cccaagtgac tgacaatctg gtgtaacgaa aatttccaat 240
gtaaactcat tttccctcgg tttcagcaat tttaaatcta tatatagaga tatctttgtc 300
agcattgcat cgttagcttc tcctgataaa ctaattgcct cacattgtca ctgcaaatcg 360
acacctatta atgggtctca cctcccaact gcttccccct ctgttcttcc tgctagcatg 420
tgccggcaac tttgtccacg gacacaagtg cgatatcacc ttacaggaga tcatcaaaac 480
tttgaacagc ctcacagagc agaagaacac aactgagaag gaaaccttct gcagggctgc 540
gactgtgctc cggcagttct acagccacca tgagaaggac actcgctgcc tgggtgcgac 600
tgcacagcag ttccacaggc acaagcagct gatccgattc ctgaaacggc tcgacaggaa 660
cctctggggc ctggcgggct tgaattcctg tcctgtgaag gaagccaacc agagtacgtt 720
ggaaaacttc ttggaaaggc taaagacgat catgagagag aaatattcaa agtgttcgag 780
ctgaatattt taatttatga gtttttgata gctttatttt ttaagtattt atatatttat 840
aactcatcat aaaataaagt atatatagaa tct 873

<210> SEQ ID NO 42
<211> LENGTH: 921
<212> TYPE: DNA
<213> ORGANISM: Homo sapiens

<400> SEQUENCE: 42
ttctatgcaa agcaaaaagc cagcagcagc cccaagctga taagattaat ctaaagagca 60
aattatggtg taatttccta tgctgaaact ttgtagttaa ttttttaaaa aggtttcatt 120
ttcctattgg tctgatttca caggaacatt ttacctgttt gtgaggcatt ttttctcctg 180
gaagagaggt gctgattggc cccaagtgac tgacaatctg gtgtaacgaa aatttccaat 240
gtaaactcat tttccctcgg tttcagcaat tttaaatcta tatatagaga tatctttgtc 300
agcattgcat cgttagcttc tcctgataaa ctaattgcct cacattgtca ctgcaaatcg 360
acacctatta atgggtctca cctcccaact gcttccccct ctgttcttcc tgctagcatg 420
tgccggcaac tttgtccacg gacacaagtg cgatatcacc ttacaggaga tcatcaaaac 480
tttgaacagc ctcacagagc agaagactct gtgcaccgag ttgaccgtaa cagacatctt 540
tgctgcctcc aagaacacaa ctgagaagga aaccttctgc agggctgcga ctgtgctccg 600
gcagttctac agccaccatg agaaggacac tcgctgcctg ggtgcgactg cacagcagtt 660
ccacaggcac aagcagctga tccgattcct gaaacggctc gacaggaacc tctggggcct 720
ggcgggcttg aattcctgtc ctgtgaagga agccaaccag agtacgttgg aaaacttctt 780
ggaaaggcta aagacgatca tgagagagaa atattcaaag tgttcgagct gaatatttta 840
atttatgagt tttgatagc tttatttttt aagtatttat atatttataa ctcatcataa 900
aataaagtat atatagaatc t 921

<210> SEQ ID NO 43
<211> LENGTH: 3230
<212> TYPE: DNA
<213> ORGANISM: Homo sapiens

<400> SEQUENCE: 43
atcctaatca agaccccagt gaacagaact cgaccctgcc aaggcttggc atttccattt 60
caatcactgt cttcccacca gtattttcaa tttcttttaa gacagattaa tctagccaca 120
gtcatagtag aacatagccg atcttgaaaa aaaacattcc caatatttat gtattttagc 180
ataaaattct gtttagtggt ctaccttata ctttgttttg cacacatctt ttaagaggaa 240
gttaattttc tgattttaag aaatgcaaat gtggggcaat gatgtattaa cccaaagatt 300
ccttccgtaa tagaaaatgt ttttaaaggg gggaaacagg gatttttatt attaaaagat 360
aaaagtaaat ttatttttta agatataagg cattggaaac atttagtttc acgatatgcc 420
attattaggc attctctatc tgattgttag aaattattca tttcctcaaa gacagacaat 480

```
aaattgactg gggacgcagt cttgtactat gcactttctt tgccaaaggc aaacgcagaa    540
cgtttcagag ccatgaggat gcttctgcat ttgagtttgc tagctcttgg agctgcctac    600
gtgtatgcca tccccacaga aattcccaca agtgcattgg tgaaagagac cttggcactg    660
ctttctactc atcgaactct gctgatagcc aatgaggtaa ttttctttat gattcctaca    720
gtctgtaaag tgcataggta atcatttgtg atggttcctt tactatatat agagatctgt    780
tataaataat aagattctga gcacattagt acatgggtga taactacatc accagcaaac    840
attctgttaa aagttatgaa tgctggtgtg ctgtaaaaat gattgtattt cctttcctct    900
ccagactctg aggattcctg ttcctgtaca taaaaatgta agttaaatta tgattcagta    960
aaatgatggc atgaataagt aaatttcctg ttttaagctg taaatcatta gttatcattg   1020
gaactattta attttctata ttttgttttc atatgggtgg ctgtgaatgt ctgtacttat   1080
aaatatgagg aatgactttt tatcaagtag aatcctttaa acaagtggat taggctcttt   1140
ggtgatgttg ttagtttgcc ttcccaaaga gcatcgtgtc aggattcttt ccagaaggat   1200
tccacactga gtgagaggtg cgtgctagtc tccgtgcagt tctgactctt tctcactcta   1260
acgtgtttct gaaagtatta gcaactcaga attatatttt tagaaccatg atcagtagac   1320
attaaaatat ataacaaatg ccctatatta ataattctgc atacttaaat aattatgact   1380
atatgatggt gtgtatgcat tgaatatgcc tggtcatatt aaaatgtaaa atatatagtt   1440
tattagtcta aatagaataa aactaccagc tagaactgta gaaacacatt gatatgagtt   1500
taatgtataa tgcattacac ttccaaaaca tttttttcca gttacataat taagttatat   1560
cctttataaa actcctcagt aatcatataa gcttcatcta ctttttgaaa attttatctt   1620
aatatgtggt ggtttgttgc ctagaaaaca aacaaaaaac tctttggaga agggaactca   1680
tgtaaatacc acaaaacaaa gcctaacttt gtggaccaaa attgttttaa taattatttt   1740
ttaattgatg aattaaaaag tatatatatt tattgtgtac aatatgatgt tttgaagtat   1800
gtatacattg cagaatggac aatggaccaa atttttatac cttgtcttga ttatttgcat   1860
tttaaaaatt ttcctcattt agcaccaact gtgcactgaa gaaatctttc agggaatagg   1920
cacactggag agtcaaactg tgcaaggggg tactgtggaa agactattca aaaacttgtc   1980
cttaataaag aaatacattg acggccaaaa agtaagttac acacattcaa tggaagctat   2040
atttgtcctg gctgtgccta tttctatgga attgacagtt tcctgtaata cctattgtca   2100
tttttctttt ttcacagaaa aagtgtggag aagaaagacg gagagtaaac caattcctag   2160
actacctgca agagtttctt ggtgtaatga acaccgagtg gataatagaa agttgagact   2220
aaactggttt gttgcagcca aagattttgg aggagaagga cattttactg cagtgagaat   2280
gagggccaag aaagagtcag gccttaattt tcaatataat ttaacttcag agggaaagta   2340
aatatttcag gcatactgac actttgccag aaagcataaa attcttaaaa tatatttcag   2400
atatcagaat cattgaagta ttttcctcca ggcaaaattg atatactttt ttcttattta   2460
acttaacatt ctgtaaaatg tctgttaact taatagtatt tatgaaatgg ttaagaattt   2520
ggtaaattag tatttattta atgttatgtt gtgttctaat aaaacaaaaa tagacaactg   2580
ttcaatttgc tgctggcctc tgtccttagc aatttgaagt tagcacagtc cattgagtac   2640
atgcccagtt tggaggaagg gtctgagcac atgtggctga gcatccccat ttctctggag   2700
aagtctcaag gttgcaaggc acaccagagg tggaagtgat ctagcaggac ttagtgggga   2760
tgtggggagc agggacacag gcaggaggtg aacctggttt tctctctaca gtatatccag   2820
aacctgggat ggtcgaaggg taaatggtag ggaataaatg aatgaatgtc gtttccaaga   2880
```

```
tgattgtaga actaaaatga gttgtaagct cccctggaag aagggatgtg gaacctgtaa   2940
ctaggttcct gcccagcctg tgagaagaat ttggcagatc atctcattgc cagtatagag   3000
aggaagccag aaaccctctc tgccaaggcc tgcaggggtt cttaccacct gaccctgcac   3060
cataacaaaa ggacagagag acatggtagg gcagtcccat tagaaagact gagttccgta   3120
ttcccggggc agggcagcac caggccgcac aacatccatt ctgcctgctt atggctatca   3180
gtagcatcac tagagattct tctgtttgag aaaacttctc tcaaggatcc              3230
```

<210> SEQ ID NO 44
<211> LENGTH: 1125
<212> TYPE: DNA
<213> ORGANISM: Homo sapiens

<400> SEQUENCE: 44

```
ttctgccctc gagcccaccg ggaacgaaag agaagctcta tctcgcctcc aggagcccag     60
ctatgaactc cttctccaca agcgccttcg gtccagttgc cttctccctg ggctgctcc     120
tggtgttgcc tgctgccttc cctgccccag tacccccagg agaagattcc aaagatgtag    180
ccgccccaca cagacagcca ctcacctctt cagaacgaat tgacaaacaa attcggtaca    240
tcctcgacgg catctcagcc ctgagaaagg agacatgtaa caagagtaac atgtgtgaaa    300
gcagcaaaga ggcactggca gaaaacaacc tgaaccttcc aaagatggct gaaaaagatg    360
gatgcttcca atctggattc aatgaggaga cttgcctggt gaaaatcatc actggtcttt    420
tggagtttga ggtataccta gagtacctcc agaacagatt tgagagtagt gaggaacaag    480
ccagagctgt gcagatgagt acaaaagtcc tgatccagtt cctgcagaaa aaggcaaaga    540
atctagatgc aataaccacc cctgacccaa ccacaaatgc cagcctgctg acgaagctgc    600
aggcacagaa ccagtggctg caggacatga caactcatct cattctgcgc agctttaagg    660
agttcctgca gtccagcctg agggctcttc ggcaaatgta gcatgggcac ctcagattgt    720
tgttgttaat gggcattcct tcttctggtc agaaacctgt ccactgggca cagaacttat    780
gttgttctct atggagaact aaaagtatga gcgttaggac actattttaa ttatttttaa    840
tttattaata tttaaatatg tgaagctgag ttaatttatg taagtcatat ttatattttt    900
aagaagtacc acttgaaaca ttttatgtat tagttttgaa ataataatgg aaagtggcta    960
tgcagtttga atatcctttg tttcagagcc agatcatttc ttggaaagtg taggcttacc   1020
tcaaataaat ggctaactta tacatatttt taaagaaata tttatattgt atttatataa   1080
tgtataaatg gtttttatac caataaatgg cattttaaaa aattc                   1125
```

<210> SEQ ID NO 45
<211> LENGTH: 2116
<212> TYPE: DNA
<213> ORGANISM: Homo sapiens

<400> SEQUENCE: 45

```
acatccgcgg caacgcctcc ttggtgtcgt ccgcttccaa taacccagct tgcgtcctgc     60
acacttgtgg cttccgtgca cacattaaca actcatggtt ctagctccca gtcgccaagc    120
gttgccaagg cgttgagaga tcatctggga agtcttttac ccagaattgc tttgattcag    180
gccagctggt ttttcctgcg gtgattcgga aattcgcgaa ttcctctggt cctcatccag    240
gtgcgcggga agcaggtgcc caggagagag gggataatga agattccatg ctgatgatcc    300
caaagattga acctgcagac caagcgcaaa gtagaaactg aaagtacact gctggcggat    360
cctacggaag ttatggaaaa ggcaaagcgc agagccacgc cgtagtgtgt gccgcccccc    420
```

```
ttgggatgga tgaaactgca gtcgcggcgt gggtaagagg aaccagctgc agagatcacc    480
ctgcccaaca cagactcggc aactccgcgg aagaccaggg tcctgggagt gactatgggc    540
ggtgagagct tgctcctgct ccagttgcgg tcatcatgac tacgcccgcc tcccgcagac    600
catgttccat gtttctttta ggtatatctt tggacttcct cccctgatcc ttgttctgtt    660
gccagtagca tcatctgatt gtgatattga aggtaaagat ggcaaacaat atgagagtgt    720
tctaatggtc agcatcgatc aattattgga cagcatgaaa gaaattggta gcaattgcct    780
gaataatgaa tttaactttt ttaaaagaca tatctgtgat gctaataagg aaggtatgtt    840
tttattccgt gctgctcgca agttgaggca atttcttaaa atgaatagca ctggtgattt    900
tgatctccac ttattaaaag tttcagaagg cacaacaata ctgttgaact gcactggcca    960
ggttaaagga agaaaaccag ctgccctggg tgaagcccaa ccaacaaaga gtttggaaga   1020
aaataaatct ttaaaggaac agaaaaaact gaatgacttg tgtttcctaa agagactatt   1080
acaagagata aaaacttgtt ggaataaaat tttgatgggc actaaagaac actgaaaaat   1140
atggagtggc aatatagaaa cacgaacttt agctgcatcc tccaagaatc tatctgctta   1200
tgcagttttt cagagtggaa tgcttcctag aagttactga atgcaccatg gtcaaaacgg   1260
attagggcat ttgagaaatg catattgtat tactagaaga tgaatacaaa caatggaaac   1320
tgaatgctcc agtcaacaaa ctatttctta tatatgtgaa catttatcaa tcagtataat   1380
tctgtactga tttttgtaag acaatccatg taaggtatca gttgcaataa tacttctcaa   1440
acctgtttaa atatttcaag acattaaatc tatgaagtat ataatggttt caaagattca   1500
aaattgacat tgctttactg tcaaaataat tttatggctc actatgaatc tattatactg   1560
tattaagagt gaaaattgtc ttcttctgtg ctggagatgt tttagagtta acaatgatat   1620
atggataatg ccggtgagaa taagagagtc ataaacctta agtaagcaac agcataacaa   1680
ggtccaagat acctaaaaga gatttcaaga gatttaatta atcatgaatg tgtaacacag   1740
tgccttcaat aaatggtata gcaaatgttt tgacatgaaa aaaggacaat ttcaaaaaaa   1800
taaaataaaa taaaaataaa ttcacctagt ctaaggatgc taaaccttag tactgagtta   1860
cattgtcatt tatatagatt ataacttgtc taaataagtt tgcaatttgg gagatatatt   1920
tttaagataa taatatatgt ttacctttta attaatgaaa tatctgtatt taattttgac   1980
actatatctg tatataaaat attttcatac agcattacaa attgcttact ttggaataca   2040
tttctccttt gataaaataa atgagctatg tattaacaaa aaaaaaaaaa aaaaaaaaaa   2100
aaaaaaaaaa aaaaaa                                                   2116
```

```
<210> SEQ ID NO 46
<211> LENGTH: 1666
<212> TYPE: DNA
<213> ORGANISM: Homo sapiens

<400> SEQUENCE: 46
```

```
ctccataagg cacaaacttt cagagacagc agagcacaca agcttctagg acaagagcca     60
ggaagaaacc accggaagga accatctcac tgtgtgtaaa catgacttcc aagctggccg    120
tggctctctt ggcagccttc ctgatttctg cagctctgtg tgaaggtgca gttttgccaa    180
ggagtgctaa agaacttaga tgtcagtgca taaagacata ctccaaacct ttccacccca    240
aatttatcaa agaactgaga gtgattgaga gtggaccaca ctgcgccaac acagaaatta    300
ttgtaaagct ttctgatgga agagagctct gtctggaccc caaggaaaac tgggtgcaga    360
gggttgtgga gaagtttttg aagagggctg agaattcata aaaaaattca ttctctgtgg    420
```

tatccaagaa tcagtgaaga tgccagtgaa acttcaagca aatctacttc aacacttcat 480
gtattgtgtg ggtctgttgt agggttgcca gatgcaatac aagattcctg gttaaatttg 540
aatttcagta aacaatgaat agtttttcat tgtaccatga aatatccaga acatacttat 600
atgtaaagta ttatttattt gaatctacaa aaaacaacaa ataattttta aatataagga 660
ttttcctaga tattgcacgg gagaatatac aaatagcaaa attgaggcca agggccaaga 720
gaatatccga actttaattt caggaattga atgggtttgc tagaatgtga tatttgaagc 780
atcacataaa aatgatggga caataaattt tgccataaag tcaaatttag ctggaaatcc 840
tggatttttt tctgttaaat ctggcaaccc tagtctgcta gccaggatcc acaagtcctt 900
gttccactgt gccttggttt ctcctttatt tctaagtgga aaaagtatta gccaccatct 960
tacctcacag tgatgttgtg aggacatgtg gaagcacttt aagtttttc atcataacat 1020 aaattatttt caagtgtaac ttattaacct atttattatt tatgtattta tttaagcatc 1080
aaatatttgt gcaagaattt ggaaaaatag aagatgaatc attgattgaa tagttataaa 1140
gatgttatag taaatttatt ttattttaga tattaaatga tgttttatta gataaatttc 1200
aatcagggtt tttagattaa acaaacaaac aattgggtac ccagttaaat tttcatttca 1260
gataaacaac aaataatttt ttagtataag tacattattg tttatctgaa attttaattg 1320
aactaacaat cctagtttga tactcccagt cttgtcattg ccagctgtgt tggtagtgct 1380
gtgttgaatt acggaataat gagttagaac tattaaaaca gccaaaactc cacagtcaat 1440
attagtaatt tcttgctggt tgaaacttgt ttattatgta caaatagatt cttataatat 1500
tatttaaatg actgcatttt taaatacaag gctttatatt tttaacttta agatgttttt 1560
atgtgctctc caaatttttt ttactgtttc tgattgtatg gaaatataaa agtaaatatg 1620
aaacatttaa aatataattt gttgtcaaag taaaaaaaaa aaaaaa 1666

<210> SEQ ID NO 47
<211> LENGTH: 591
<212> TYPE: DNA
<213> ORGANISM: Homo sapiens

<400> SEQUENCE: 47
ccgctgtcaa gatgcttctg gccatggtcc ttacctctgc cctgctcctg tgctccgtgg 60
caggccaggg gtgtccaacc ttggcgggga tcctggacat caacttcctc atcaacaaga 120
tgcaggaaga tccagcttcc aagtgccact gcagtgctaa tgtgaccagt tgtctctgtt 180
tgggcattcc ctctgacaac tgcaccagac catgcttcag tgagagactg tctcagatga 240
ccaataccac catgcaaaca agatacccac tgattttcag tcgggtgaaa aaatcagttg 300
aagtactaaa gaacaacaag tgtccatatt tttcctgtga acagccatgc aaccaaacca 360
cggcaggcaa cgcgctgaca tttctgaaga gtcttctgga aattttccag aaagaaaaga 420
tgagagggat gagaggcaag atatgaagat gaaatattat ttatcctatt tattaaattt 480
aaaaagcttt ctctttaagt tgctacaatt taaaaatcaa gtaagctact ctaaatcagt 540
atcagttgtg attatttgtt taacattgta tgtctttatt ttgaaataaa t 591

<210> SEQ ID NO 48
<211> LENGTH: 1629
<212> TYPE: DNA
<213> ORGANISM: Homo sapiens

<400> SEQUENCE: 48
acacatcagg ggcttgctct tgcaaaacca aaccacaaga cagacttgca aaagaaggca 60
tgcacagctc agcactgctc tgttgcctgg tcctcctgac tggggtgagg gccagcccag 120
gccagggcac ccagtctgag aacagctgca cccacttccc aggcaacctg cctaacatgc 180
ttcgagatct ccgagatgcc ttcagcagag tgaagacttt ctttcaaatg aaggatcagc 240
tggacaactt gttgttaaag gagtccttgc tggaggactt taagggttac ctgggttgcc 300
aagccttgtc tgagatgatc cagttttacc tggaggaggt gatgccccaa gctgagaacc 360
aagacccaga catcaaggcg catgtgaact ccctgggggga gaacctgaag accctcaggc 420
tgaggctacg gcgctgtcat cgatttcttc cctgtgaaaa caagagcaag gccgtggagc 480
aggtgaagaa tgcctttaat aagctccaag agaaaggcat ctacaaagcc atgagtgagt 540
ttgacatctt catcaactac atagaagcct acatgacaat gaagatacga aactgagaca 600
tcagggtggc gactctatag actctaggac ataaattaga ggtctccaaa atcggatctg 660
gggctctggg atagctgacc cagccccttg agaaacctta ttgtacctct cttatagaat 720
atttattacc tctgatacct caacccccat ttctatttat ttactgagct tctctgtgaa 780
cgatttagaa agaagcccaa tattataatt tttttcaata tttattattt tcacctgttt 840
ttaagctgtt tccatagggt gacacactat ggtatttgag tgttttaaga taaattataa 900
gttacataag ggaggaaaaa aaatgttctt tggggagcca acagaagctt ccattccaag 960
cctgaccacg ctttctagct gttgagctgt ttccctgac ctccctctaa tttatcttgt 1020
ctctgggctt ggggcttcct aactgctaca aatactctta ggaagagaaa ccagggagcc 1080
cctttgatga ttaattcacc ttccagtgtc tcggagggat tcccctaacc tcattcccca 1140
accacttcat tcttgaaagc tgtggccagc ttgttattta taacaaccta aatttggttc 1200
taggccgggc gcggtggctc acgcctgtaa tcccagcact ttgggaggct gaggcgggtg 1260
gatcacttga ggtcaggagt tcctaaccag cctggtcaac atggtgaaac cccgtctcta 1320
ctaaaaatac aaaaattagc cgggcatggt ggcgcgcacc tgtaatccca gctacttggg 1380
aggctgaggc aagagaattg cttgaaccca ggagatggaa gttgcagtga gctgatatca 1440
tgcccctgta ctccagcctg ggtgacagag caagactctg tctcaaaaaa taaaaataaa 1500
aataaatttg gttctaatag aactcagttt taactagaat ttattcaatt cctctgggaa 1560
tgttacattg tttgtctgtc ttcatagcag attttaattt tgaataaata aatgtatctt 1620
attcacatc 1629

<210> SEQ ID NO 49
<211> LENGTH: 1444
<212> TYPE: DNA
<213> ORGANISM: Homo sapiens

<400> SEQUENCE: 49
tttcattttg ggccgagctg gaggcggcgg ggccgtcccg gaacggctgc ggccgggcac 60
cccgggagtt aatccgaaag cgccgcaagc cccgcgggcc ggccgcaccg cacgtgtcac 120
cgagaagctg atgtagagag agacacagaa ggagacagaa agcaagagac cagagtcccg 180
ggaaagtcct gccgcgcctc gggacaatta taaaaatgtg gccccctggg tcagcctccc 240
agccaccgcc ctcacctgcc gcggccacag gtctgcatcc agcggctcgc cctgtgtccc 300
tgcagtgccg gctcagcatg tgtccagcgc gcagcctcct ccttgtggct accctggtcc 360
tcctggacca cctcagtttg gccagaaacc tccccgtggc cactccagac ccaggaatgt 420
tcccatgcct tcaccactcc caaaacctgc tgagggccgt cagcaacatg ctccagaagg 480
ccagacaaac tctagaattt taccttgca cttctgaaga gattgatcat gaagatatca 540
caaaagataa aaccagcaca gtggaggcct gtttaccatt ggaattaacc aagaatgaga 600
gttgcctaaa ttccagagag acctctttca taactaatgg gagttgcctg gcctccagaa 660
agacctcttt tatgatggcc ctgtgcctta gtagtattta tgaagacttg aagatgtacc 720
aggtggagtt caagaccatg aatgcaaagc ttctgatgga tcctaagagg cagatctttc 780
tagatcaaaa catgctggca gttattgatg agctgatgca ggccctgaat ttcaacagtg 840
agactgtgcc acaaaaatcc tcccttgaag aaccggattt ttataaaact aaaatcaagc 900
tctgcatact tcttcatgct ttcagaattc gggcagtgac tattgataga gtgatgagct 960
atctgaatgc ttcctaaaaa gcgaggtccc tccaaaccgt tgtcattttt ataaaacttt 1020
gaaatgagga aactttgata ggatgtggat taagaactag ggaggggggaa agaaggatgg 1080 gactattaca tccacatgat acctctgatc aagtattttt gacatttact gtggataaat 1140
tgtttttaag ttttcatgaa tgaattgcta agaagggaaa atatccatcc tgaaggtgtt 1200
tttcattcac tttaatagaa gggcaaatat ttataagcta tttctgtacc aaagtgtttg 1260
tggaaacaaa catgtaagca taacttattt taaaatattt atttatataa cttggtaatc 1320
atgaaagcat ctgagctaac ttatatttat ttatgttata tttattaaat tatttatcaa 1380
gtgtatttga aaaatatttt taagtgttct aaaaataaaa gtattgaatt aaagtgaaaa 1440
aaaa 1444

<210> SEQ ID NO 50
<211> LENGTH: 925
<212> TYPE: DNA
<213> ORGANISM: Homo sapiens

<400> SEQUENCE: 50
ctttgaattc ctagctcctg tggtctccag atttcaggcc taagatgaaa gcctctagtc 60
ttgccttcag ccttctctct gctgcgtttt atctcctatg gactccttcc actggactga 120
agacactcaa tttgggaagc tgtgtgatcg ccacaaacct tcaggaaata cgaaatggat 180
tttctgagat acggggcagt gtgcaagcca aagatggaaa cattgacatc agaatcttaa 240
ggaggactga gtctttgcaa gacacaaagc ctgcgaatcg atgctgcctc ctgcgccatt 300
tgctaagact ctatctggac agggtattta aaaactacca gacccctgac cattatactc 360
tccggaagat cagcagcctc gccaattcct ttcttaccat caagaaggac ctccggctct 420
gtcatgccca catgacatgc cattgtgggg aggaagcaat gaagaaatac agccagattc 480
tgagtcactt tgaaaagctg gaacctcagg cagcagttgt gaaggctttg ggggaactag 540
acattcttct gcaatggatg gaggagacag aataggagga aagtgatgct gctgctaaga 600
atattcgagg tcaagagctc cagtcttcaa tacctgcaga ggaggcatga ccccaaacca 660
ccatctcttt actgtactag tcttgtgctg gtcacagtgt atcttattta tgcattactt 720
gcttccttgc atgattgtct ttatgcatcc ccaatcttaa ttgagaccat acttgtataa 780
gatttttgta atatctttct gctattggat atatttatta gttaatatat ttatttattt 840
tttgctattt aatgtattta ttttttttact tggacatgaa actttaaaaa aattcacaga 900
ttatatttat aacctgacta gagca 925

<210> SEQ ID NO 51
<211> LENGTH: 3127
<212> TYPE: DNA
<213> ORGANISM: human herpesvirus 8

<400> SEQUENCE: 51
agaccagatt tcccgaggat ggcgcccccg ggaatgcgcc tgaggtcggg acggagcacc 60
ggcgcgccct taacgagagg aagttgtagg aaacgaaaca ggtctccgga aagatgtgac 120
cttggcgatg acctacatct acaaccgcga aggaagcatg tcgccgactc cgtcgacggc 180
cgggaatgtg gaccccacac cttgcctata ccaggaagtc ccacagtgtt cacatccggg 240
ctgccagcat ttgtgtctag tcctacttta ccggtggctt ccattccttc acccgctccc 300
gcaacacctt tacctccacc ggcactctta ccccccgtaa ccacgtcttc ctccccaatc 360
cctccatccc atcctgtgtc tccggggacc acggatactc attctccatc tcctgcattg 420
ccacccacgc agtctccaga gtcttctcaa aggccaccgc tttcaagtcc tacaggaagg 480
ccagactctt caacacctat gcgtccgcca ccctcgcagc agactacacc tccacactca 540
cccacgactc ctccacccga gcctccctcc aagtcgtcac cagactcttt agctccgtct 600
accctgcgta gcctgagaaa aagaaggcta tcgtcccccc aaggtccctc tacactaaac 660
ccaatatgtc agtcgccccc agtctctccc cctagatgtg acttcgccaa ccgtagtgtg 720
tacccccat gggccacaga gtccccgatc tacgtgggat catccagcga tggcgatact 780
ccgccacgcc aaccgcctac atctcccatc tccataggat catcatcccc gtctgaggga 840
tcctcgggtg atgacacagc catgttggtg ctccttgcgg agattgcaga agaagcatcc 900
aagaatgaaa aagaatgttc cgaaaataat caggctggcg aggataatgg ggacaacgag 960
attagcaagg aaagtcaggt tgacaaggat gacaatgaca ataaggatga tgaggaggag 1020
caggagacag atgaggagga cgaggaggat gacgaggagg atgacgagga ggatgacgag 1080
gaggatgacg aggaggatga cgaggaggat gacgaggagg atgacgagga ggatgacgag 1140
gaggatgacg aggaggatga cgaggaggat gacgaggagg atgacgagga ggaggacgag 1200
gaggaggacg aggaggagga cgaggaggag gaggacgagg aggaggagga ggacgaggag 1260
gatgacgatg atgaggacaa tgaggacgag gaggatgacg aggaggagga caagaaggag 1320
gacgaggagg acgggggcga tggaaacaaa acgttgagca tccaaagttc acaacagcag 1380
caggagccac aacagcagga gccacagcag caggagccac aacagcagga gccacagcag 1440
caggagccac agcagcagga gcccctgcag gagccacaac agcaggagcc acagcagcag 1500
gagccacaac agcaggagcc acagcagcag gagcccctgc aggagccaca gcagcaggag 1560
ccacagcagc aggagccaca gcagcaggag ccacaacagc aggagccaca gcagcaggat 1620
gagcagcagc aggatgagca gcagcaggat gagcagcagc aggatgagca gcagcagcag 1680
gatgagcagc agcaggatga gcagcagcag gatgagcagc agcaggatga gcaggagcag 1740
caggatgagc agcagcagga tgagcagcag cagcaggatg aacaggagca gcaggaggag 1800
caggagcagc aggaggagca ggagcaggag ttagaggagc aggagcagga gttagaggag 1860
caggagcagg agttagagga gcaggagcag gagttagagg agcaggagca ggagttagag 1920
gagcaggagc aggagttaga ggagcaggag caggagttag aggagcagga gcaggagtta 1980
gaggagcagg agcaggagtt agatgagcag gagcaggagt tagaggagca ggagcaggag 2040
ttagaggagc aggagcagga gttagaggag caggagcagg agttagagga gcaggagcag 2100
gagttagagg agcaggagca ggagttagag gagcaggagc aggagttaga ggagcaggag 2160
caggagttag aggagcagga gcaggagtta gaggagcagg agcaggagca ggagttagag 2220
gaggtggaag agcaagagca ggagcaggaa gagcaggaat tagaggaggt ggaggagcaa 2280
gagcaggagc aggaggagca ggaggagcag gagttagagg aggtggaaga gcaggaagag 2340
caggagttag aggaggtgga agagcaggaa gagcaggagt tagaggaggt ggaagagcag 2400
gagcagcagg gggtggaaca gcaggagcag gagacggtgg aagagcccat aatcttgcac 2460
gggtcgtcat ccgaggacga aatggaagtg gattaccctg ttgttagcac acatgaacaa 2520
attgccagta gcccaccagg agataataca ccagacgatg acccacaacc tggcccatct 2580
cgcgaatacc gctatgtact cagaacatca ccaccccaca gacctggagt tcgtatgagg 2640
cgcgttccag ttacccaccc aaaaaagcca catccaagat accaacaacc accggtccct 2700
tacagacaga tagatgattg tcctgcgaaa gctaggccac aacacatctt ttatagacgc 2760
tttttgggaa aggatggaag acgagatcca aagtgtcaat ggaagtttgc agtgattttt 2820
tggggcaatg acccatacgg acttaaaaaa ttatctcagg ccttccagtt tggaggagta 2880
aaggcaggcc ccgtgtcctg cttgccccac cctggaccag accagtcgcc cataacttat 2940
tgtgtatatg tgtattgtca gaacaaagac acaagtaaga aagtacaaat ggcccgccta 3000
gcctgggaag ctagtcaccc cctggcagga aacctacaat cttccatagt taagtttaaa 3060
aagcccctgc cattaaccca gccaggggaa aaccaaggtc ctggggactc tccacaggaa 3120
atgacat 3127

<210> SEQ ID NO 52
<211> LENGTH: 3012
<212> TYPE: DNA
<213> ORGANISM: Human herpesvirus 8

<400> SEQUENCE: 52
atggcgcccc cgggaatgcg cctgaggtcg ggacggagca ccggcgcgcc cttaacgaga 60
ggaagttgta ggaaacgaaa caggtctccg gaaagatgtc accttggcga tgacctacat 120
ctacaaccgc gaaggaagca tgtcgccgac tccgtcgacg gccgggaatg tggaccccac 180
accttgccta taccaggaag tcccacagtg ttcacatccg ggctgccagc atttgtgtct 240
agtcctactt taccggtggc tcccattcct tcacccgctc ccgcaacacc tttacctcca 300
ccggcactct tacccccccgt aaccacgtct tcctccccaa tccctccatc ccatcctgtg 360
tctccgggga ccacggatac tcattctcca tctcctgcat tgccacccac gcagtctcca 420
gagtcttctc aaaggccacc gctttcaagt cctacaggaa ggccagactc ttcaacacct 480
atgcgtccgc caccctcgca gcagactaca cctccacact cacccacgac tcctccaccc 540
gagcctccct ccaagtcgtc accagactct ttagctccgt ctaccctgcg tagcctgaga 600
aaaagaaggc tatcgtcccc ccaaggtccc tctacactaa acccaatatg tcagtcgccc 660
ccagtctctc cccctagatg tgacttcgcc aaccgtagtg tgtacccccc atgggccaca 720
gagtccccga tctacgtggg atcatccagc gatggcgata ctccgccacg ccaaccgcct 780
acatctccca tctccatagg atcatcatcc ccgtctgagg gatcctgggg tgatgacaca 840
gccatgttgg tgctccttgc ggagattgca gaagaagcat ccaagaatga aaaagaatgt 900
tccgaaaata atcaggctgg cgaggataat ggggacaacg agattagcaa ggaaagtcag 960
gttgacaagg atgacaatga caataaggat gatgaggagg agcaggagac agatgaggag 1020
gacgaggagg atgacgagga ggatgacgag gaggatgacg aggaggatga cgaggaggat 1080
gacgaggagg atgacgagga ggatgacgag gaggatgacg aggaggagga cgaggaggag 1140
gacgaggagg aggaggacga ggaggaggag gaggaggacg aggaggatga cgatgatgag 1200
gacaatgagg acgaggagga ggacaagaag gaggacgagg aggacggggg cgatggaaac 1260
aaaacgttga gcatccaaag ttcacaacag cagcaggagc cacagcagca ggagccacaa 1320
cagcaggagc cacagcagca ggagccacag cagcaggagc cctgcagga gccacagcag 1380

```
caggagccac aacagcagga gccacaacag caggagccac aacagcagga gccacaacag   1440
caggagccac aacagcagga gccacagcag caggatgagc agcagcagga tgagcagcag   1500
caggatgagc agcagcagga tgagcagcag caggatgagc aggagcagca ggatgagcag   1560
cagcaggatg agcagcagca ggatgagcag cagcagcagg atgaacagga gcagcaggag   1620
gagcaggagc agcaggagga gcaggagcag caggaggagc aggagcagga gttagaggag   1680
caggagcagg agttagagga gcaggagcag gagttagagg agcaggagca ggagttagag   1740
gagcaggagc aggagttaga ggagcaggag caggagttag aggagcagga gcaggagtta   1800
gaggagcagg agcaggagtt agaggagcag gagcaggagt tagaggagca ggagcaggag   1860
ttagaggagc aggagcagga gttagaggag caggagcagg agttagagga gcaggagcag   1920
gagttagagg agcaggagca ggagttagag gagcaggagc aggagttaga ggagcaggag   1980
caggagttag aggagcagga gcaggagtta gaggagcagg agcaggagtt agaggagcag   2040
gagcaggagt tagaggagca ggagcaggag ttagaggagc aggagcagga gcaggagtta   2100
gaggaggtgg aagagcaaga gcaggagcag gaagagcagg aattagagga ggtggaggag   2160
caagagcagg agcaggagga gcaggaggag caggagttag aggaggtgga agagcaggaa   2220
gagcaggagt tagaggaggt ggaagagcag gaagagcagg agttagagga ggtggaagag   2280
caggagcagc agggggtgga acagcaggag caggagacgg tggaagagcc cataatcttg   2340
cacgggtcgt catccgagga cgaaatggaa gtggattacc ctgttgttag cacacatgaa   2400
caaattgcca gtagcccacc aggagataat acaccagacg atgacccaca acctggccca   2460
tctcgcgaat accgctatgt actcagaaca tcaccacccc acagacctgg agttcgtatg   2520
aggcgcgttc cagttaccca cccaaaaaag ccacatccaa gataccaaca accaccggtc   2580
ccttacagac agatagatga ttgtcctgcg aaagctaggc cacaacacat cttttataga   2640
cgctttttgg gaaaggatgg aagacgagat ccaaagtgtc aatggaagtt tgcagtgatt   2700
ttttggggca atgacccata cggacttaaa aaattatctc aggccttcca gtttggagga   2760
gtaaaggcag gccccgtgtc ctgcttgccc caccctggac cagaccagtc gcccataact   2820
tattgtgtat atgtgtattg tcagaacaaa gacacaagta agaaagtaca aatggcccgc   2880
ctagcctggg aagctagtca ccccctggca ggaaacctac aatcttccat agttaagttt   2940
aaaaagcccc tgccattaac ccagccaggg gaaaaccaag gtcctgggga ctctccacag   3000
gaaatgacat aa                                                       3012
```

<210> SEQ ID NO 53
<211> LENGTH: 774
<212> TYPE: DNA
<213> ORGANISM: Human herpesvirus 8

<400> SEQUENCE: 53

```
atggcaactg ccaataaccc gccctcggga cttctggatc ccacgctatg tgaggatcgg     60
atcttttaca atattcttga aattgagccg cgctttttaa cttctgactc tgtatttggg    120
tcctttcaac aatctcttac ttcgcatatg cgtaagttac tgggcacatg gatgttttca    180
gtttgccagg aatacaacct agaacctaac gtggtcgcgt tggcccttaa tcttttggac    240
agactcctac ttataaagca ggtgtccaaa gaacactttc aaaagacagg gagcgcctgc    300
ctgttagtgg ccagtaagct cagaagcctc acgcctattt ctaccagttc actttgctat    360
gccgcggcag actccttttc ccgccaagaa cttatagacc aggagaaaga actccttgag    420
aagttggcgt ggcgaacaga ggcagtctta gcgacggacg taacttcctt cttgttactt    480
```

aaattgctgg ggggctccca acacctggac ttttggcacc acgaggtcga caccctgatt 540
acaaaagcct tagttgaccc aaagactggc tcattgcccg cctctattat cagcgctgca 600
ggctgtgcgc tgttggttcc tgccaacgtc attccgcagg atacccactc gggtggggta 660
gttcctcagc tggcaagcat attgggatgc gatgtttccg ttctacaggc ggcagtggaa 720
cagatcctaa catctgtttc ggactttgat ctgcgcattc tggacagcta ttaa 774

<210> SEQ ID NO 54
<211> LENGTH: 557
<212> TYPE: DNA
<213> ORGANISM: Human herpesvirus 4

<400> SEQUENCE: 54
ttagagagtg gctgctacgc attagagacc actttgagcc acccacagta accacccagc 60
gccaatctgt ctacatagaa gaagaagagg atgaagacta agtcacaggc ttagccagta 120
acccagcact ggcgtgtgac gtggtgtaaa gttttgcctg aacctgtggt tgggcaggta 180
acttaggaag cgtttcttga gcttccctgg gatgagcgtt tgggagagct gattctgcag 240
cccagagagt agtctcaggg catcctctgg agcctgacct gtgatcgtcg catcatagac 300
cgccagtaga cctgggagca gattcaccgc cgcggccgtc tcctttaagt gtgaatcatg 360
tctgacgagg ggccaggtac aggacctgga aatggcctag gagagaaggg agacacatct 420
ggaccagaag gctccggcgg cagtggacct caaagaagag gggtgataa ccatggacga 480 ggacggggaa gaggacgagg acgaggaggc ggaagaccag gagccccggg cggctcagga 540
tcagggccaa gacatag 557

<210> SEQ ID NO 55
<211> LENGTH: 2031
<212> TYPE: DNA
<213> ORGANISM: Human herpesvirus 4

<400> SEQUENCE: 55
aatccgccac ctcattctga aattcccata tccccgtct gctgcttcgt cacccgccga 60
cccttagccc tctatccgcc tcacccgcct ccccctacggt taccccacag ccttgcctca 120
cctgaacccc cctaaagcac agcctcccgc ctgccgacaa cgacctccca acgttgcgcg 180
ccctacgcct ctttgtgtgg attacactgc cgcttcccac aacactgctc actccccctt 240
gtgattgccg cactgccttt ccatttccct gtacgcttta ccaccgcatt cccacagctt 300
gcccctcggg gactcgcttt tctaacacaa acacacgctt tctacttcct cttttaacgc 360
ttacatgcac acacactacg cgctttcggg aaagcggcgc ccgtaccctg tccggcagac 420
cccgcaaatc cccccgggcc tccatcccca gaaacacgcg ttactctctc gtaggcggcc 480
tacataagcc tctgtcactg ctctgtcagc ttctttcctc agttgccttg ctcctgccac 540
actaccctga ccatggaacg cgaccttgag aggggcccac cgggcccgcc acggccccct 600
ctaggacccc ccctctcctc ttccataggc cttgctctcc ttctcctgct cttggcgcta 660
ctgttctggc tgtatatcgt tatgagtaac tggactggag gagcgctcct tgtcctctat 720
tcctttgctc tcatgcttat tattatcatt ctcatcatct ttatcaacag aagagacctt 780
ctctgtccac ttggaggcct tggtctactc ctactgatga gtaagtatta caccctttgc 840
cccccacccc ctttccctta cgcttccttc tctaacgcac tttctcctct ttccccagtc 900
accctcctac tcatcgctct ctggaatttg cacggacagg cattgtacct tggaattgtg 960
ctgttcatct ttggctgctt acttggtaag atctaacatt ccctaggact tatttaccac 1020
accctcacct ttccagccct aacactcttt tttcaacgca gtcttaggtc tctggatcta 1080
cttggagatt ctctggcggc ttggtgccac catctggcag cttttggcct tcatcctagc 1140
cttcttccta gccatcatcc tgcttattat tgctctctat ctacaacaaa actggtggac 1200
tctattggtt gatctccttt ggctcctcct gtttatggcc attttaatct ggatgtatta 1260
tcatggacca cgacacactg atgaacacca ccacgatgac tccctcccgc accctcaaca 1320
agctaccgtc gattctagcc atgaatctga ctctaactcc aacgagggca gacaccacct 1380
gctcgtgagt ggggccggcg acggaccccc actctgctct caaaacctag gcgcacctgg 1440
aggtggtcct gacaatggcc cacaggaccc tgacaacact gatgacaatg gcccacagga 1500
ccctgacaac actgatgaca atggcccaca ggaccctgac aacactgatg acaatggccc 1560
acaggaccct gacaacactg atgacaatgg cccacaggac cctgacaaca ctgatgacaa 1620
tggcccacat gacccgctgc ctcataaccc tagcgactct gctggaaatg atggaggccc 1680
tccaaaattg acggaagagg ttgaaaacaa aggaggtgac cggggcccgc cttcgatgac 1740
agacggtggc ggcggtcatc cacaccttcc tacactgctt ttgggtactt ctggttccgg 1800
tggagatgat gacgaccccc acggcccagt tcagctaagc tactatgact aacctttctt 1860
tacttctagg cattaccatg tcataggctt gcctgactga ctctccctcc atttactggg 1920
aatgccttag ctaatcacct taactggcac acactccctt agccacactg tctgtctagg 1980
ctgaaaagcc acattcatat tctatttcaa aacaagggga aggaggacat a 2031

<210> SEQ ID NO 56
<211> LENGTH: 351
<212> TYPE: DNA
<213> ORGANISM: Human herpesvirus 4

<400> SEQUENCE: 56
ccaatgggcg cgggtccccc tagccccggc ggggatccgg atggggacga tggcggaaac 60
aactcccaat atccatctgc ttctggctct tctgggaaca cccccacccc accgaacgat 120
gaggaacgtg aatctaatga agagccccca ccgccttatg aggacctaga ttggggcaat 180
ggcgaccgtc actcggacta tcaaccacta ggaaaccaag atccaagttt gtacttggga 240
ttgcaacacg acgggaatga cggctccct cccccctccct actctccacg ggatgactca 300
tctcaacaca tatacgaaga agcgggcaga ggaagtatga atccagtatg c 351

<210> SEQ ID NO 57
<211> LENGTH: 553
<212> TYPE: DNA
<213> ORGANISM: Human herpesvirus 4

<400> SEQUENCE: 57
actatggggt ccctagaagt gatgccaatg ggcgcgggtc cccctagccc cggcggggat 60
ccggatgggg acgatggcgg aaacaactcc caatatccat ctgcttctgg ctcttctggg 120
aacaccccca ccccaccgaa cgatgaggaa cgtgaatcta atgaagagcc cccaccgcct 180
tatgaggact cagattgggg caatggcgac cgtcactcgg actatcaacc actaggaaac 240
caagatccaa gtttgtactt gggattgcaa cacgacggga atgacgggct ccctccccct 300
ccctactctc cacgggatga ctcatctcaa cacatatacg aagaagcggg cagaggaagt 360
atgaatccag tatgcctgct tgtaattgtt gcgccctacc tgttttggct ggcggctatt 420
gccgcctcgt gtttcacggc ctcagttagt accgttgtga ccgccaccgg cttggccctc 480
tcacttttac tcttggcagc agtggccagc tcatatgccg ctgcacaaag gaaactgctg 540
acaccggtga cag 553

<210> SEQ ID NO 58
<211> LENGTH: 172281
<212> TYPE: DNA
<213> ORGANISM: Human herpesvirus 4

<400> SEQUENCE: 58
agaattcgtc ttgctctatt caccccttact tttcttcttg cccgttctct ttcttagtat 60
gaatccagta tgcctgcctg taattgttgc gccctacctc ttttggctgg cggctattgc 120
cgcctcgtgt ttcacggcct cagttagtac cgttgtgacc gccaccggct tggccctctc 180
acttctactc ttggcagcag tggccagctc atatgccgct gcacaaagga aactgctgac 240
accggtgaca gtgcttactg cggttgtcac ttgtgagtac acacgcacca tttacaatgc 300
atgatgttcg tgagattgat ctgtctctaa cagttcactt cctctgcttt tctcctcagt 360
ctttgcaatt tgcctaacat ggaggattga ggacccacct tttaattctc ttctgtttgc 420
attgctggcc gcagctggcg gactacaagg catttacggt tagtgtgcct ctgttatgaa 480
atgcaggttt gacttcatat gtatgccttg gcatgacgtc aactttactt ttatttcagt 540
tctggtgatg cttgtgctcc tgatactagc gtacagaagg agatggcgcc gtttgactgt 600
ttgtggcggc atcatgtttt tggcatgtgt acttgtcctc atcgtcgacg ctgttttgca 660
gctgagtccc ctccttggag ctgtaactgt ggtttccatg acgctgctgc tactggcttt 720
cgtcctctgg ctctcttcgc caggggggcct aggtactctt ggtgcagccc ttttaacatt 780
ggcagcaggt aagccacacg tgtgacattg cttgcctttt tgccacatgt tttctggaca 840
caggactaac catgccatct ctgattatag ctctggcact gctagcgtca ctgattttgg 900
gcacacttaa cttgactaca atgttccttc tcatgctcct atggacactt ggtaagtttt 960
cccttccttt aactcattac ttgttctttt gtaatcgcag ctctaacttg gcatctcttt 1020
tacagtggtt ctcctgattt gctcttcgtg ctcttcatgt ccactgagca agatccttct 1080
ggcacgactg ttcctatatg ctctcgcact cttgttgcta gcctccgcgc taatcgctgg 1140
tggcagtatt ttgcaaacaa acttcaagag tttaagcagc actgaattta tacccagtga 1200
gtatctattt gttactcctg tttagttgaa gaaaacaagc tattggattg taacacacat 1260
tttacgcttt gttccttaga tttgttctgc atgttattac tgattgtcgc tggcatactc 1320
ttcattcttg ctatcctgac cgaatggggc agtggaaata gaacatacgg tccagttttt 1380
atgtgcctcg gtggcctgct caccatggta gccggcgctg tgtggctgac ggtgatgtct 1440
aacacgcttt tgtctgcctg gattcttaca gcaggattcc tgattttcct cattggtaag 1500
tgtgacacca acaggtgttg ccttgttatg tcaccgttct gacacatgac ttacatgggt 1560
ttggcttttg taggctttgc cctctttggg gtcattagat gctgccgcta ctgctgctac 1620
tactgcctta cactggaaag tgaggagcgc ccaccgaccc catatcgcaa cactgtataa 1680
aggtaagtat tattaaattt tagagacact atcacgtgta acttgacgtg caaggatgga 1740
agagaggggc agggaaacgc aaatgccggt tgcccggtat gggggcccgt ttattatggt 1800
aaggctcttc gggcaagatg gagaggcaaa catacaggag gaaaggctat atgagctact 1860
ctctgaccca cgctccgcgc tcggcctaga cccggggccc ctgattgctg agaacctgct 1920
gctagtggcg ctgcgtggca ccaacaacga tcccaggcct cagcgtcagg agagggccag 1980
agaactggcc ctcgttggca ttctactagg aaacggcgag cagggtgaac acttgggcac 2040
ggagagtgcc ctggaggcct caggcaacaa ctatgtgtat gcctacggac cagactggat 2100

-continued

```
ggcaaggcct tccacatggt ccgcggaaat ccagcaattc ctgcgactcc tgggcgccac   2160
gtacgtgctt cgcgtggaga tgggcaggca gtttggcttc gaggtgcata gaagccggcc   2220
ctccttccgt cagttccagg ccatcaatca ccttgtcctg tttgacaacg cccttcgcaa   2280
gtacgattcc ggccaggtgg cggcgggctt ccagagggcc cttctggtgg ccgggccaga   2340
gaccgctgac acgaggccgg acctccgcaa gctgaatgag tgggtgtttg gtggcagggc   2400
tgctggtggc agacagctgg ccgacgagct aaagatcgtg tccgcgctgc gagacactta   2460
ctcgggccac ttggtccttc agcccacgga gacccttgac acatggaagg tgttgagcag   2520
ggacacacga accgctcata gtttggagca cggattcatt catgccgcgg ggaccatcca   2580
ggccaactgc ccacagctgt ttatgagacg ccagcacccc ggcctctttc ccttcgttaa   2640
tgcaatagca tcatcgctgg gctggtacta ccagaccgcc accggccccg gagcagatgc   2700
cagggcggcg gcccggcgcc aacaggcctt tcagaccagg gcggcggctg aatgccatgc   2760
caaaagcggg gtgccggtcg tggccggctt ctacaggacc atcaacgcca cgctcaaggg   2820
aggagagggc ctacagccca ctatgtttaa cggggagctg ggggccatca agcaccaggc   2880
acttgacact gtgaggtatg actacggcca ctatctcata atgttggggc cattccagcc   2940
atggagcgga ctgacggccc ctccgtgccc ctacgccgaa agttcatggg cacaggcggc   3000
cgtgcagacg gccctcgagc tgttctcggc cctgtacccg gccccgtgca tctcgggcta   3060
cgcgcgcccc ccgggcccca gtgctgtgat cgagcatctg ggtccctag ttccaaaggg   3120
gggtctgctg ttgtttctgt ctcacctacc ggatgatgtt aaggacgggc tcggagaaat   3180
ggggccggcc agggccacgg gacctggaat gcagcagttt gtcagcagct acttcctcaa   3240
ccccgcctgt tccaacgtct tcattacagt gaggcagcga ggggagaaga tcaacggccg   3300
taccgtcctc caagcgctcg gacgcgcatg cgatatggca ggctgccagc actatgtgct   3360
gggctccacg gttcccctcg gtggactcaa ctttgtcaac gacctggcgt ccccggtttc   3420
caccgccgag atgatggatg atttctctcc cttcttcacc gtggagtttc ccccgattca   3480
agaggagggc gcaagttctc cggtaccctt agatgtggac gagagcatgg acatctctcc   3540
gtcttacgag ttgccctggc tctcgctgga gtcatgcctc acaagcatcc tgtcacaccc   3600
caccgtggga agcaaggagc acttggtcag gcacacggac agggtcagcg gaggacgcgt   3660
ggcacagcag cccggggtag gtcccctgga cctgccgctg gcggactacg ccttcgttgc   3720
ccacagtcag gtctggacca ggcccggtgg ggctcctccc ttgccctatc gtacctggga   3780
tcgaatgaca gagaagctgc ttgtctccgc aaaacccggc ggagagaacg ttaaggtttc   3840
aggtaccgtg attacattgg gagaacaggg gtacaaagtg tcgttggatc tgagggaggg   3900
aaccaggctg gcaatggctg aggcgctgct gaacgcagca tgtgccccaa tcttggatcc   3960
ggaagacgtc ttgctcaccc tgcatctaca cctggatccg cgccgggcag acaactcggc   4020
cgtgatggag gctatgacgg cggcgagtga ctacgcgcgt ggcctgggcg tgaagctgac   4080
ctttggctcg gcctcctgcc ccgagaccgg ctcgtccgcc tccaacttca tgaccgtggt   4140
ggcctctgtc tccgccccag gggaattctc gggtcctctg atcacgccag tgcttcagaa   4200
gacgggcagt ctcctgattg cggtgcgttg cggggatggc aagatccagg gagggtcgct   4260
gtttgagcag ctctttagcg acgtggccac gaccccacgg gcacccgagg cgttgtctct   4320
gaagaatctc ttccgggcag tccagcagct ggtcaagagc ggcatcgtgc tgtcagggca   4380
tgacatcagc gacgggggcc tggtgacctg cctggtggag atggccctgg ccgggcagcg   4440
gggagtgacc atcactatgc cggtggcctc cgactacctc ccggagatgt ttgcagagca   4500
```

ccccggcctg gtgtttgagg tggaggagcg cagcgtgggt gaggtgctgc agaccctgcg 4560
ctccatgaac atgtacccgg cagtcctcgg tcgagtgggc gagcaaggtc cagatcaaat 4620
gtttgaggtg cagcacggcc cagagacggt gttgcgccag tcgctgcgcc tgctgctggg 4680
aacctggtca tcctttgcca gcgagcagta cgagtgcctg cgaccagatc ggattaaccg 4740
gtccatgcac gtgtccgact acggctataa cgaagcactg gcagtctccc cgttgacagg 4800
aaagaatctc agcccacgcc ggttggtgac agagcctgac ccacgatgtc aggtggccgt 4860
gctatgcgcc ccgggcacca ggggccatga aagcctcctg gcggccttca cgaatgccgg 4920
atgcctgtgc cgacgggtgt tctttcgcga ggttagggac aacacgttcc tcgacaagta 4980
cgtgggtctg gccatcggag gagttcatgg ggccagggac tctgccctgg caggccgtgc 5040
caccgtggcg ctgattaatc gtttccccgc cctgcgtgac gctattctaa agttcctcaa 5100
caggccagat acgttctcgg tggccttggg ggagctgggg gtgcaagttt tggctggcct 5160
gggggccgtg gggtcaacag ataatccacc cgcccctggc gtggaagtta atgtccagag 5220
atcacctctg attctggccc ccaacgcctc tggcatgttt gagtcccgct ggctgaacat 5280
tagcatcccg gcgaccacca gctctgtcat gctgcgtggc ctccggggct gcgtcctgcc 5340
ttgttgggtg caaggctcgt gcctgggcct gcaatttact aacctcggga tgccatatgt 5400
tttgcagaat gcccaccaga tcgcctgcca cttccacagc aatggcacgg atgcctggcg 5460
ctttgctatg aattatccaa gaaaccccac ggagcagggc aacattgcag ggctctgttc 5520
acgcgatggt cgtcatctgg ctctcctgtg tgacccctca ctttgtacag acttttggca 5580
atgggagcac attccccccg cctttgggca ccccacgggg tgctccccct ggacacttat 5640
gtttcaagca gctcacctat ggtcactcag gcacggtcgc ccctccgagt gaccagtcac 5700
cttccagact atgcatacac tgaatttagc ctgatattgt cccccctagcc ccgggcccag 5760
ccctcctcag aaaactctgc atggagaagc tggacgtgaa cctccccccc agacctgtgt 5820
gctgtattta caaacactac aataaaccca atgtgcaaat gtggtttgta tggctacttt 5880
gtgttcctaa aaaatgcaac aatagaagtg gaaaccctca gtcacgggac attaacctca 5940
accacaaaat gggggttgga gaaagtaacc acatatactg gagatgattc atgggctggg 6000
ggttcccgga caatacaccc atctggagtt caacctaatt acatggtaga taaattaaga 6060
gtccctcctc accactcgaa actatggcag acattctata agataacgag gagagatgag 6120
gtgagggcag aggacattgg gcaggtgtgg gccacggggc agctggccat atcccccgca 6180
ctacagaagt gtaagcaaag tgaagggctc ggaaggcagg cggggcctag caatgtcaca 6240
gctaaatgcc caccagggca cacactcaag cggggtctcg gagctcctag gtcagaccac 6300
gaaaggtcag cctgcaaggt ggatggcgtg ttttctgagg ttatccccgc tacgtgcagt 6360
gctgggtgat agagacccta gaatgtgtcg aaatgaccaa gcgtccccgc agcggggctc 6420
ccaacacggg ttcccagaga gggtaaaaga gggggccata aagcccaggg tgtaaaacac 6480
cgaccgcgcc accagatggc acacgtgggg gaaatgaggg ttagcatagg caaccccgc 6540
ctacacacca actatagcaa accccgcccc gtcacggtga cgtagtctgt cttgaggaga 6600
tgtagacttg tagacactgc aaaacctcag gacctacgct gccctagagg ttttgctagg 6660
gaggagacgt gtgtggctgt agccacccgt cccgggtaca agtcccgggt ggtgaggacg 6720
gtgtctgtgg ttgtcttccc agactctgct ttctgccgtc ttcggtcaag taccagctgg 6780
tggtccgcat gttttgatcc aaacttttgt tttaggattt atgcatccat tatcccgcag 6840
ttccacctaa acggggctta acgttgcatc ccagaagatg cacgcttaac cccgcctaca 6900

```
accgtgacgt agctgtttac cagcatgtat agagttacgg ttcgctacat caaacaggac   6960
agccgttgcc ctagtggttt cggacacacc gccaacgctc agtgcggtgc taccgacccg   7020
aggtcaagtc ccgggggagg agaagagagg cttcccgcct agagcatttg caagtcagga   7080
ttctctaatc cctctgggag aagggtattc ggcttgtccg ctattttttt gtggctagtt   7140
ttgcacccac aacatgtaag ggcccgctac ccctacaaca caaaacaaac tatctcccct   7200
aaccatcctt ttgccaatca attctgtgac agggtttcct ggacacccag tcttagttca   7260
ggtagacacc cagttatgca gtgccaccaa ttccaaccat ttttaaacct cctggaattc   7320
tatcattaaa cggcatgcag gaaaaggaca agcagcgaaa attcacgccc ccttgggagg   7380
tggcggcata tgcaaaggat agcactccca ctctactact gggtatcata tgctgactgt   7440
atatgcatga ggatagcata tgctacccgg atacagatta ggatagcata tactacccag   7500
atatagatta ggatagcata tgctacccag atatagatta ggatagccta tgctacccag   7560
atataaatta ggatagcata tactacccag atatagatta ggatagcata tgctacccag   7620
atatagatta ggatagccta tgctacccag atatagatta ggatagcata tgctacccag   7680
atatagatta ggatagcata tgctatccag atatttgggt agtatatgct acccagatat   7740
aaattaggat agcatatact accctaatct ctattaggat agcatatgct acccggatac   7800
agattaggat agcatatact acccagatat agattaggat agcatatgct acccagatat   7860
agattaggat agcctatgct acccagatat aaattaggat agcatatact acccagatat   7920
agattaggat agcatatgct acccagatat agattaggat agcctatgct acccagatat   7980
agattaggat agcatatgct atccagatat ttgggtagta tatgctaccc atggcaacat   8040
tagcccaccg tgctctcagc gacctcgtga atatgaggac caacaaccct gtgcttggcg   8100
ctcaggcgca agtgtgtgta atttgtcctc cagatcgcag caatcgcgcc cctatcttgg   8160
cccgcccacc tacttatgca ggtattcccc ggggtgccat tagtggtttt gtgggcaagt   8220
ggtttgaccg cagtggttag cggggttaca atcagccaag ttattacacc cttattttac   8280
agtccaaaac cgcagggcgg cgtgtggggg ctgacgcgtg cccccactcc acaatttcaa   8340
aaaaaagagt ggccacttgt ctttgtttat gggccccatt ggcgtggagc cccgtttaat   8400
tttcgggggt gttagagaca accagtggag tccgctgctg tcggcgtcca ctctctttcc   8460
ccttgttaca aatagagtgt aacaacatgg ttcacctgtc ttggtccctg cctgggacac   8520
atcttaataa ccccagtatc atattgcact aggattatgt gttgcccata gccataaatt   8580
cgtgtgagat ggacatccag tctttacggc ttgtccccac cccatggatt tctattgtta   8640
aagatattca gaatgtttca ttcctacact agtatttatt gcccaagggg tttgtgaggg   8700
ttatattggt gtcatagcac aatgccacca ctgaaccccc cgtccaaatt ttattctggg   8760
ggcgtcacct gaaaccttgt tttcgagcac ctcacataca ccttactgtt cacaactcag   8820
cagttattct attagctaaa cgaaggagaa tgaagaagca ggcgaagatt caggagagtt   8880
cactgcccgc tccttgatct tcagccactg ccccttgtgac taaaatggtt cactaccctc   8940
gtggaatcct gaccccatgt aaataaaacc gtgacagctc atggggtggg agatatcgct   9000
gttccttagg acccttttac taaccctaat tcgatagcat atgcttcccg ttgggtaaca   9060
tatgctattg aattagggtt agtctggata gtatatacta ctacccggga agcatatgct   9120
acccgtttag ggttaacaag ggggccttat aaacactatt gctaatgccc tcttgagggt   9180
ccgcttatcg gtagctacac aggcccctct gattgacgtt ggtgtagcct cccgtagtct   9240
tcctgggccc ctgggaggta catgtccccc agcattggtg taagagcttc agccaagagt   9300
```

tacacataaa ggcaatgttg tgttgcagtc cacagactgc aaagtctgct ccaggatgaa 9360
agccactcag tgttggcaaa tgtgcacatc catttataag gatgtcaact acagtcagag 9420
aacccctttg tgtttggtcc ccccccgtgt cacatgtgga acagggccca gttggcaagt 9480
tgtaccaacc aactgaaggg attacatgca ctgccccgcg ggaaatacgt cctacccagg 9540
aacccgaaac agtgtttccc agaagctgta aaaatagaac gccctggaac tgccccactg 9600
tgcaatgcag cttttagcca tgccatgctc tataaatcac ttccctatct caggtaggcc 9660
tgcacacctt aggtatggag cgaaggttag tggtcactct gcagtgcctg gtgctgcttt 9720
acctggcacc tgagtgtgga ggtacagacc aatgtgacaa ttttccccaa atgttgaggg 9780
acctaagaga tgccttcagt cgtgttaaaa ccttttttcca gacaaaggac gaggtagata 9840
accttttgct caaggagtct ctgctagagg actttaaggg ctaccttgga tgccaggccc 9900
tgtcagaaat gatccaattc tacctggagg aagtcatgcc acaggctgaa aaccaggacc 9960
ctgaagccaa agaccatgtc aattctttgg gtgaaaatct aaagacccta cggctccgcc 10020
tgcgcaggtg ccacaggttc ctgccgtgtg agaacaagag taaagctgtg gaacagataa 10080
aaaatgcctt taacaagctg caggaaaaag gaatttacaa agccatgagt gaatttgaca 10140
tttttattaa ctacatagaa gcatacatga caattaaagc caggtgataa ttccataccc 10200
tggaagcagg agatgggtgc atttcacccc aacccccccct ttcgactgtc atttacaata 10260
aaatgaaacc ttttattctt gattgcctct tgtgttcttg ccgcccaggt accttcctgt 10320
gttctcccca cgggaaaaag aatagcttct gcagaaggcc attgacgcaa gttttgcccg 10380
tggggattac ccgacccagc cacttacagc acattttgtt ctaggtccat cttaggagcc 10440
cgggccagca ttctatcagc ttaacgggaa gagaagtggg gagggcactc gcccactaac 10500
cttaacacct gcagcctaca aaagtacact agctgtttgc tctattcgcc actagagacc 10560
gccaagatgc gaaactacag gcccgggccc aggccttgca gggcagacgg ttaggctgac 10620
aaggggacaa gtgtggcagg tgggcgggaa ggggcacaag aatgccggcg aaactggacc 10680
acggtccacc ccgccctcaa gcgtccggga gccgggcggc tcggctaagg agggcggcct 10740
tgcgaacaat tattagtagc taccaacaag ggcccccaga tgccccccac cagtcacccg 10800
gccgtgtcca ctcacatatt ccactcttat ttttaaatta atgtgtccca attagaaacc 10860
caagcgcaga aattagttga gaggctagtg ttttaaacat gcaccctagg ccagccagag 10920
ataatgtcac aagattatca agttggtgta aacacgccgt gggaaaaaat ttatggttca 10980
gtgcgtcgag tgctatcttt ggaacagtag aaaattgaac cttgttggcg ggagaaggaa 11040
taacgcctta tctgggagga gcgacggatt atagccaata agagagctca agacgcaggg 11100
ctcgcaaagt atagtggccc cgtgggacct tagaggtgga gcaacgtcta aagtggtaat 11160
aacaccaggc ggggctgggc aaaggggtcc tacgggcggg attaattacg ccttgcttac 11220
gcaagctcag ttaattcgcc cacgacttga aaaatgtagc ccttaaccaa ttggcggccc 11280
ctaagggggg gactaaggtc ccactacaaa aactctgtgt tctgctgcaa attttagatc 11340
agatggcata gagacaagga caccgaagac ccccagagcc ctcatcgcag ggttcttacc 11400
atgcggccat gtaggcccac ttaacactac aagacctacg cctctccatt catcatgtaa 11460
cccacaaatc atctaaaccg taagtctaag ggcctcctga ggttttctca ggaggcccta 11520
atgtataatt aatcatgcat ttgattttaa aaaagtaggt tacactcatt ttaggccaga 11580
ctttatttgc agattaataa tttatgtgat tctccttccc tctaggactg aagaaacagc 11640
ctcctgcacg tgagcatgta tctgaaataa ttattatgtc ataagtgtaa tgattagaaa 11700

```
gtcataaacc cacttccctt tacatgaatc tgggcactga attttggggt acttctaaag  11760
actaacgtgt tcgatttcgg ggtcacttcc ccttttataa gtgtgtgaac agtgatttca  11820
gtaaaaccta agagatattt ggtgtcactt ccgcatttta agtttcagaa aattttaaaa  11880
ttaaaattga aatttctctc aaaataattc caatgaaaac ttcaaagaat cttatgtatg  11940
taattctttt gccccaaact gggcttcaga tgccttctat tgcactctca caaaaacatt  12000
ctggacacat gtgccagacg cctgggcctc taaggccctc gggtccccct ggaccccggc  12060
ctcagcaacc ctgctgctcc cctcctgcca ccccagcctc cccccctccc cgtcccccctt  12120
cgctcctgtt cctcccccgg tccccagtag ggccgcctgc ccccctgcac ccagtacctg  12180
cccctcttgg ccacgcaccc cgggccaggc caccttagac ccggccaagc cccatccctg  12240
aagacccagc ggccattctc tctggtaacg agcagagaag aagtagaggc ccgcggccat  12300
tgggcccaga ttgagagacc agtccagggg cccgaggttg gagccagcgg gcacccgagg  12360
tcccagcacc cggtccctcc ggggggcaga gacaggcagg gcccccccggc agctggcccc  12420
gaggaggcgc ccggagtggg gccggtcggc tgggctggcc gagcccgggt ctgggaggtc  12480
tggggtggcg agcctgctgt ctcaggaggg gcctggctcc gccgggtggc cctggggtaa  12540
gtctgggagg cagagggtcg gcctaggccc ggggaagtgg agggggatcg cccgggtctc  12600
tgttggcaga gtccgggcga tcctctgaga ccctccgggc ccggacggtc gccctcagcc  12660
ccccagacag accccagggt ctccaggcag ggtccggcat cttcaggggc agcaggctca  12720
ccaccacagg ccccccagac ccgggtctcg gccagccgag ccgaccggcc ccgcgcctgg  12780
cgcctcctcg gggccagccg ccggggttgg ttctgcccct ctctctgtcc ttcagaggaa  12840
ccagggacct cgggcacccc agagcccctc gggcccgcct ccaggcgccc tcctggtctc  12900
cgctcccctc tgagccccgt taaacccaaa gaatgtctga ggggagccac cctcggggcc  12960
caggccccag agtccagagg tcaggggcac ctcagggtgc ctccccgggt cccaggccag  13020
ccggagggac cccggcagcc cgggcggccc cagaggccgg ttcctcgccc cttccccggg  13080
cttcagagcc caggatgtcc cccagaaggg accctaggcg tcccctctcc tcccctccag  13140
gcccgagcct ctccctcgcg gagaggggcc tctttgggcc ctcaagtcca gccccaccga  13200
gacccgagtg gcccggatcc ccccaccggc ccttctctct gtccccctgc tcctctccaa  13260
ccttcgctcc accctagacc ccagcttctg gcctccccgg gtccaccagg ccagccggag  13320
ggaccccggc agcccgggcg agtcgccttc cctctcccct ggcctctcct tcccgcctcc  13380
cacccgagcc ccctcagctt gcctccccac cgggtccatc aggccggccg gagggacccc  13440
ggcggcccgg tgtcagtccc ccctgcagcc gcccagtctc tgcctccagg caagggcgcc  13500
agcttttctc cccccagcct gaggcccagt ctcctgtgca ctgtctgtaa agtccagcct  13560
cccacgcccg tccacggctc ccgggcccag cctcgtccac ccctccccac ggtggacagg  13620
ccctctgtcc acccgggcca tccccgcccc cctgtgtcca ccccagtccc gtccaggggg  13680
gactttatgt gacccttggg cctggctccc catagactcc catgtaagcc tgcctcgagt  13740
aggtgcctcc agagcccctt ttgccccccct ggcggcccag cccgaccccc gggcgccccc  13800
aaactttgtc cagatgtcca ggggtccccg agggtgaggc ccagcccccct cccgcccctg  13860
tccactgccc cggtcccccc agaagccccc aaaagtagag gctcaggcca tgcgcgccct  13920
gtcaccaggc ctgccaaaga gccagatcta aggccgggag aggcagcccc aaagcgggtg  13980
cagtaacagg taatctctgg tagtgatttg gacccgaaat ctgacacttt agagctctgg  14040
aggactttaa aactctaaaa atcaaaactt tagaggcgaa tgggcgccat tttgtcccca  14100
```

cgcgcgcata atggcggacc taggcctaaa acccccagga agcgggtcta tggttggctg 14160
cgctgctgct atctttagag gggaaaagag gaataagccc ccagacaggg gagtgggctt 14220
gtttgtgact tcaccaaagg tcagggccca agggggttcg cgttgctagg ccaccttctc 14280
agtccagcgc gtttacgtaa gccagacagc agccaattgt cagttctagg gaggggggacc 14340
actgcccctg gtataaagtg gtcctgcagc tatttctggt cgcatcagag cgccaggagt 14400
ccacacaaat gtaagagggg gtcttctacc tctccctagc cctccgcccc ctccaaggac 14460
tcgggcccag tttctaactt ttccccttcc ctccctcgtc ttgccctgcg cccggggcca 14520
ccttcatcac cgtcgctgac tccgccatcc aagcctaggg gagaccgaag tgaaggccct 14580
ggaccaaccc ggcccgggcc ccccggtatc gggccagagg taagtggact ttaatttttt 14640
ctgctaagcc caacactcca ccacacccag gcacacacta cacacaccca cccgtctcag 14700
ggtcccctcg gacagctcct aagaaggcac cggtcgccca gtcctaccag agggggccaa 14760
gaacccagac gagtccgtag aagggtcctc gtccagcaag aagaggaggt ggtaagcggt 14820
tcaccttcag gggtaagtaa cctgacctct ccagggctca cataaaggga ggcttagtat 14880
acatgcttct tgcttttcac aggaacctgg gggctagtct gggtgggatt aggctgcctc 14940
aagttgcatc agccagggct tcatgccctc ctcagttccc tagtccccgg gcttcaggcc 15000
ccctccgtcc ccgtcctcca gagacccggg cttcaggccc tgcctctcct gttacccttt 15060
tagaaccaca gcctggacac atgtgccaga cgccttggcc tctaaggccc tcgggtcccc 15120
ctggaccccg gcctcagcaa ccctgctgct cccctcctgc caccccagcc tccccccctc 15180
cccgtccccc ttcgctcctg atcctccccc ggtccccagt agggccgcct gccccccctgc 15240
acccagtacc tgcccctctt ggccacgcac cccgggccag gccaccttag acccggccaa 15300
gccccatccc tgaagaccca gcggccattc tctctggtaa cgagcagaga agaagtagag 15360
gcccgcggcc attgggccca gattgagaga ccagtccagg ggcccgaggt tggagccagc 15420
gggcacccga ggtcccagca cccggtccct ccgggggggca gagacaggca gggccccccg 15480
gcagctggcc ccgaggaggc gcccggagtg gggccggtcg gctgggctgg ccgagcccgg 15540
gtctgggagg tctggggtgg cgagcctgct gtctcaggag gggcctggct ccgccgggtg 15600
gccctggggt aagtctggga ggcagagggt cggcctaggc ccggggaagt ggagggggat 15660
cgcccgggtc tctgttggca gagtccgggc gatcctctga gaccctccgg gcccggacgg 15720
tcgccctcag ccccccagac agaccccagg gtctccaggc agggtccggc atcttcaggg 15780
gcagcaggct caccaccaca ggccccccag acccgggtct cggccagccg agccgaccgg 15840
ccccgcgcct ggcgcctcct cggggccagc cgccggggtt ggttctgccc ctctctctgt 15900
ccttcagagg aaccagggac ctcgggcacc ccagagcccc tcgggcccgc ctccaggcgc 15960
cctcctggtc tccgctcccc tctgagcccc gttaaaccca aagaatgtct gaggggagcc 16020
accctcgggg cccaggcccc agagtccaga ggtcaggggc acctcagggt gcctccccgg 16080
gtcccaggcc agccggaggg accccggcag cccgggcggc cccagaggcc ggttcctcgc 16140
cccttccccg ggcttcagag cccaggatgt cccccagaag ggaccctagg cgtcccctct 16200
cctcccctcc aggcccgagc ctctccctcg cggagagggg cctctttggg ccctcaagtc 16260
cagccccacc gagacccgag tggcccggat ccccccaccg gcccttctct ctgtcccccct 16320
gctcctctcc aaccttcgct ccaccctaga ccccagcttc tggcctcccc gggtccacca 16380
ggccagccgg agggaccccg gcagcccggg cgagtcgcct tccctctccc ctggcctctc 16440
cttcccgcct cccacccgag ccccctcagc ttgcctcccc accgggtcca tcaggccggc 16500
cggagggacc ccggcggccc ggtgtcagtc ccccctgcag ccgcccagtc tctgcctcca 16560
ggcaagggcg ccagcttttc tccccccagc ctgaggccca gtctcctgtg cactgtctgt 16620
aaagtccagc ctcccacgcc cgtccacggc tcccgggccc agcctcgtcc acccctcccc 16680
acggtggaca ggccctctgt ccacccgggc catccccgcc cccctgtgtc caccccagtc 16740
ccgtccaggg gggactttat gtgacccttg ggcctggctc cccatagact cccatgtaag 16800
cctgcctcga gtaggtgcct ccagagcccc ttttgccccc ctggcggccc agcccgaccc 16860
ccgggcgccc ccaaactttg tccagatgtc caggggtccc cgagggtgag gcccagcccc 16920
ctcccgcccc tgtccactgc cccggtcccc ccagaagccc ccaaaagtag aggctcaggc 16980
catgcgcgcc ctgtcaccag gcctgccaaa gagccagatc taaggccggg agaggcagcc 17040
ccaaagcggg tgcagtaaca ggtaatctct ggtagtgatt tggacccgaa atctgacact 17100
ttagagctct ggaggacttt aaaactctaa aaatcaaaac tttagaggcg aatgggcgcc 17160
attttgtccc cacgcgcgca taatggcgga cctaggccta aaacccccag gaagcgggtc 17220
tatggttggc tgcgctgctg ctatctttag aggggaaaag aggaataagc ccccagacag 17280
gggagtgggc ttgtttgtga cttcaccaaa ggtcagggcc caaggggggtt cgcgttgcta 17340
ggccaccttc tcagtccagc gcgtttacgt aagccagaca gcagccaatt gtcagttcta 17400
gggaggggga ccactgcccc tggtataaag tggtcctgca gctatttctg gtcgcatcag 17460
agcgccagga gtccacacaa atgtaagagg gggtcttcta cctctcccta gccctccgcc 17520
ccctccaagg actcgggccc agtttctaac ttttcccctt ccctccctcg tcttgccctg 17580
cgcccggggc caccttcatc accgtcgctg actccgccat ccaagcctag gggagaccga 17640
agtgaaggcc ctggaccaac ccggcccggg ccccccggta tcgggccaga ggtaagtgga 17700
ctttaatttt ttctgctaag cccaacactc caccacaccc aggcacacac tacacacacc 17760
cacccgtctc agggtcccct cggacagctc ctaagaaggc accggtcgcc cagtcctacc 17820
agagggggcc aagaacccag acgagtccgt agaagggtcc tcgtccagca agaagaggag 17880
gtggtaagcg gttcaccttc aggggtaagt aacctgacct ctccagggct cacataaagg 17940
gaggcttagt atacatgctt cttgcttttc acaggaacct gggggctagt ctgggtggga 18000
ttaggctgcc tcaagttgca tcagccaggg cttcatgccc tcctcagttc cctagtcccc 18060
gggcttcagg ccccctccgt ccccgtcctc cagagacccg ggcttcaggc cctgcctctc 18120
ctgttaccct tttagaacca cagcctggac acatgtgcca gacgccttgg cctctaaggc 18180
cctcgggtcc ccctggaccc cggcctcagc aaccctgctg ctcccctcct gccaccccag 18240
cctccccccc tccccgtccc ccttcgctcc tgatcctccc ccggtcccca gtagggccgc 18300
ctgcccccct gcacccagta cctgcccctc ttggccacgc accccgggcc aggccacctt 18360
agacccggcc aagccccatc cctgaagacc cagcggccat tctctctggt aacgagcaga 18420
gaagaagtag aggcccgcgg ccattgggcc cagattgaga gaccagtcca ggggcccgag 18480
gttggagcca gcgggcaccc gaggtcccag cacccggtcc ctccgggggg cagagacagg 18540
cagggccccc cggcagctgg ccccgaggag gcgcccggag tggggccggt cggctgggct 18600
ggccgagccc gggtctggga ggtctggggt ggcgagcctg ctgtctcagg aggggcctgg 18660
ctccgccggg tggccctggg gtaagtctgg gaggcagagg gtcggcctag gcccggggaa 18720
gtggaggggg atcgcccggg tctctgttgg cagagtccgg gcgatcctct gagaccctcc 18780
gggcccggac ggtcgccctc agccccccag acagacccca gggtctccag gcagggtccg 18840
gcatcttcag gggcagcagg ctcaccacca caggcccccc agacccgggt ctcggccagc 18900

-continued cgagccgacc ggccccgcgc ctggcgcctc ctcggggcca gccgccgggg ttggttctgc 18960
ccctctctct gtccttcaga ggaaccaggg acctcgggca ccccagagcc cctcgggccc 19020
gcctccaggc gccctcctgg tctccgctcc cctctgagcc ccgttaaacc caaagaatgt 19080
ctgaggggag ccaccctcgg ggcccaggcc ccagagtcca gaggtcaggg gcacctcagg 19140
gtgcctcccc gggtcccagg ccagccggag ggaccccggc agcccgggcg gccccagagg 19200
ccggttcctc gccccttccc cgggcttcag agcccaggat gtcccccaga agggacccta 19260
ggcgtcccct ctcctcccct ccaggcccga gcctctccct cgcggagagg ggcctctttg 19320
ggccctcaag tccagcccca ccgagacccg agtggcccgg atccccccac cggcccttct 19380
ctctgtcccc ctgctcctct ccaaccttcg ctccacccta gaccccagct tctggcctcc 19440
ccgggtccac caggccagcc ggagggaccc cggcagcccg ggcgagtcgc cttccctctc 19500
ccctggcctc tccttcccgc ctcccacccg agcccctca gcttgcctcc ccaccgggtc 19560
catcaggccg gccggaggga ccccggcggc ccggtgtcag tccccctgc agccgcccag 19620 tctctgcctc caggcaaggg cgccagcttt tctcccccca gcctgaggcc cagtctcctg 19680
tgcactgtct gtaaagtcca gcctcccacg cccgtccacg gctcccgggc ccagcctcgt 19740
ccacccctcc ccacggtgga caggccctct gtccacccgg gccatccccg cccccctgtg 19800
tccaccccag tcccgtccag gggggacttt atgtgaccct tgggcctggc tccccataga 19860
ctcccatgta agcctgcctc gagtaggtgc ctccagagcc ccttttgccc ccctggcggc 19920
ccagcccgac ccccgggcgc ccccaaactt tgtccagatg tccaggggtc cccgagggtg 19980
aggcccagcc ccctcccgcc cctgtccact gccccggtcc ccccagaagc ccccaaaagt 20040
agaggctcag gccatgcgcg ccctgtcacc aggcctgcca aagagccaga tctaaggccg 20100
ggagaggcag ccccaaagcg ggtgcagtaa caggtaatct ctggtagtga tttggacccg 20160
aaatctgaca ctttagagct ctggaggact ttaaaactct aaaaatcaaa actttagagg 20220
cgaatgggcg ccattttgtc cccacgcgcg cataatggcg gacctaggcc taaaaccccc 20280
aggaagcggg tctatggttg gctgcgctgc tgctatcttt agaggggaaa agaggaataa 20340
gcccccagac aggggagtgg gcttgtttgt gacttcacca aaggtcaggg cccaaggggg 20400
ttcgcgttgc taggccacct tctcagtcca gcgcgtttac gtaagccaga cagcagccaa 20460
ttgtcagttc tagggagggg gaccactgcc cctggtataa agtggtcctg cagctatttc 20520
tggtcgcatc agagcgccag gagtccacac aaatgtaaga gggggtcttc tacctctccc 20580
tagccctccg ccccctccaa ggactcgggc ccagtttcta acttttcccc ttccctccct 20640
cgtcttgccc tgcgcccggg gccaccttca tcaccgtcgc tgactccgcc atccaagcct 20700
aggggagacc gaagtgaagg ccctggacca acccggcccg ggccccccgg tatcgggcca 20760
gaggtaagtg gactttaatt ttttctgcta agcccaacac tccaccacac ccaggcacac 20820
actacacaca cccacccgtc tcagggtccc ctcggacagc tcctaagaag gcaccggtcg 20880
cccagtccta ccagaggggg ccaagaaccc agacgagtcc gtagaagggt cctcgtccag 20940
caagaagagg aggtggtaag cggttcacct tcaggggtaa gtaacctgac ctctccaggg 21000
ctcacataaa gggaggctta gtatacatgc ttcttgcttt tcacaggaac ctgggggcta 21060
gtctgggtgg gattaggctg cctcaagttg catcagccag ggcttcatgc cctcctcagt 21120
tccctagtcc ccgggcttca ggccccctcc gtccccgtcc tccagagacc cgggcttcag 21180
gccctgcctc tcctgttacc cttttagaac cacagcctgg acacatgtgc cagacgcctt 21240
ggcctctaag gccctcgggt ccccctggac cccggcctca gcaaccctgc tgctcccctc 21300

```
ctgccacccc agcctccccc cctccccgtc cccccttcgct cctgatcctc ccccggtccc  21360
cagtagggcc gcctgccccc ctgcacccag tacctgcccc tcttggccac gcaccccggg  21420
ccaggccacc ttagacccgg ccaagcccca tccctgaaga cccagcggcc attctctctg  21480
gtaacgagca gagaagaagt agaggcccgc ggccattggg cccagattga gagaccagtc  21540
caggggcccg aggttggagc cagcgggcac ccgaggtccc agcacccggt ccctccgggg  21600
ggcagagaca ggcagggccc cccggcagct ggccccgagg aggcgcccgg agtggggccg  21660
gtcggctggg ctggccgagc ccgggtctgg gaggtctggg gtggcgagcc tgctgtctca  21720
ggaggggcct ggctccgccg ggtggccctg gggtaagtct gggaggcaga gggtcggcct  21780
aggcccgggg aagtggaggg ggatcgcccg ggtctctgtt ggcagagtcc gggcgatcct  21840
ctgagaccct ccgggcccgg acggtcgccc tcagcccccc agacagaccc cagggtctcc  21900
aggcagggtc cggcatcttc aggggcagca ggctcaccac cacaggcccc ccagacccgg  21960
gtctcggcca gccgagccga ccggccccgc gcctggcgcc tcctcggggc cagccgccgg  22020
ggttggttct gcccctctct ctgtccttca gaggaaccag ggacctcggg caccccagag  22080
cccctcgggc ccgcctccag gcgccctcct ggtctccgct cccctctgag ccccgttaaa  22140
cccaaagaat gtctgagggg agccaccctc ggggcccagg ccccagagtc cagaggtcag  22200
gggcacctca gggtgcctcc ccgggtccca ggccagccgg agggaccccg gcagcccggg  22260
cggccccaga ggccggttcc tcgccccttc cccgggcttc agagcccagg atgtccccca  22320
gaagggaccc taggcgtccc ctctcctccc ctccaggccc gagcctctcc ctcgcggaga  22380
ggggcctctt tgggccctca agtccagccc caccgagacc cgagtggccc ggatcccccc  22440
accggccctt ctctctgtcc ccctgctcct ctccaacctt cgctccaccc tagaccccag  22500
cttctggcct ccccgggtcc accaggccag ccggagggac cccggcagcc cgggcgagtc  22560
gccttccctc tcccctggcc tctccttccc gcctcccacc cgagccccct cagcttgcct  22620
ccccaccggg tccatcaggc cggccggagg gaccccggcg gcccggtgtc agtcccccct  22680
gcagccgccc agtctctgcc tccaggcaag ggcgccagct tttctccccc cagcctgagg  22740
cccagtctcc tgtgcactgt ctgtaaagtc cagcctccca cgcccgtcca cggctcccgg  22800
gcccagcctc gtccacccct ccccacggtg gacaggccct ctgtccaccc gggccatccc  22860
cgccccccctg tgtccacccc agtcccgtcc agggggggact ttatgtgacc cttgggcctg  22920
gctccccata gactcccatg taagcctgcc tcgagtaggt gcctccagag cccctttttgc  22980
ccccctggcg gcccagcccg acccccgggc gcccccaaac tttgtccaga tgtccagggg  23040
tccccgaggg tgaggcccag ccccctcccg cccctgtcca ctgccccggt cccccccagaa  23100
gcccccaaaa gtagaggctc aggccatgcg cgccctgtca ccaggcctgc caaagagcca  23160
gatctaaggc cgggagaggc agccccaaag cgggtgcagt aacaggtaat ctctggtagt  23220
gatttggacc cgaaatctga cactttagag ctctggagga ctttaaaact ctaaaaatca  23280
aaactttaga ggcgaatggg cgccattttg tccccacgcg cgcataatgg cggacctagg  23340
cctaaaaccc ccaggaagcg ggtctatggt tggctgcgct gctgctatct ttagagggga  23400
aaagaggaat aagcccccag acaggggagt gggcttgttt gtgacttcac caaaggtcag  23460
ggcccaaggg ggttcgcgtt gctaggccac cttctcagtc cagcgcgttt acgtaagcca  23520
gacagcagcc aattgtcagt tctagggagg gggaccactg cccctggtat aaagtggtcc  23580
tgcagctatt tctggtcgca tcagagcgcc aggagtccac acaaatgtaa gagggggtct  23640
tctacctctc cctagccctc cgccccctcc aaggactcgg gcccagtttc taacttttcc  23700
```

ccttccctcc ctcgtcttgc cctgcgcccg gggccacctt catcaccgtc gctgactccg 23760
ccatccaagc ctaggggaga ccgaagtgaa ggccctggac caacccggcc cgggcccccc 23820
ggtatcgggc cagaggtaag tggactttaa ttttttctgc taagcccaac actccaccac 23880
acccaggcac acactacaca cacccacccg tctcagggtc ccctcggaca gctcctaaga 23940
aggcaccggt cgcccagtcc taccagaggg ggccaagaac ccagacgagt ccgtagaagg 24000
gtcctcgtcc agcaagaaga ggaggtggta agcggttcac cttcaggggt aagtaacctg 24060
acctctccag ggctcacata aagggaggct tagtatacat gcttcttgct tttcacagga 24120
acctgggggc tagtctgggt gggattaggc tgcctcaagt tgcatcagcc agggcttcat 24180
gccctcctca gttccctagt ccccgggctt caggcccccct ccgtccccgt cctccagaga 24240
cccgggcttc aggccctgcc tctcctgtta cccttttaga accacagcct ggacacatgt 24300
gccagacgcc ttggcctcta aggccctcgg gtccccctgg accccggcct cagcaaccct 24360
gctgctcccc tcctgccacc ccagcctccc cccctccccg tccccccttcg ctcctgatcc 24420
tcccccggtc cccagtaggg ccgcctgccc ccctgcaccc agtacctgcc cctcttggcc 24480
acgcaccccg ggccaggcca ccttagaccc ggccaagccc catccctgaa gacccagcgg 24540
ccattctctc tggtaacgag cagagaagaa gtagaggccc gcggccattg ggcccagatt 24600
gagagaccag tccaggggcc cgaggttgga gccagcgggc acccgaggtc ccagcacccg 24660
gtccctccgg ggggcagaga caggcagggc cccccggcag ctggccccga ggaggcgccc 24720
ggagtggggc cggtcggctg ggctggccga gcccgggtct gggaggtctg gggtggcgag 24780
cctgctgtct caggaggggc ctggctccgc cgggtggccc tggggtaagt ctgggaggca 24840
gagggtcggc ctaggcccgg ggaagtggag ggggatcgcc cgggtctctg ttggcagagt 24900
ccgggcgatc ctctgagacc ctccgggccc ggacggtcgc cctcagcccc ccagacagac 24960
cccagggtct ccaggcaggg tccggcatct tcaggggcag caggctcacc accacaggcc 25020
ccccagaccc gggtctcggc cagccgagcc gaccggcccc gcgcctggcg cctcctcggg 25080
gccagccgcc ggggttggtt ctgcccctct ctctgtcctt cagaggaacc agggacctcg 25140
ggcaccccag agcccctcgg gcccgcctcc aggcgccctc ctggtctccg ctcccctctg 25200
agccccgtta aacccaaaga atgtctgagg ggagccaccc tcggggccca ggccccagag 25260
tccagaggtc aggggcacct cagggtgcct ccccgggtcc caggccagcc ggagggaccc 25320
cggcagcccg ggcggcccca gaggccggtt cctcgcccct tccccgggct tcagagccca 25380
ggatgtcccc cagaagggac cctaggcgtc ccctctcctc ccctccaggc ccgagcctct 25440
ccctcgcgga gaggggcctc tttgggccct caagtccagc cccaccgaga cccgagtggc 25500
ccggatcccc ccaccggccc ttctctctgt ccccctgctc ctctccaacc ttcgctccac 25560
cctagacccc agcttctggc ctccccgggt ccaccaggcc agccggaggg accccggcag 25620
cccgggcgag tcgccttccc tctcccctgg cctctccttc ccgcctccca cccgagcccc 25680
ctcagcttgc ctccccaccg ggtccatcag gccggccgga gggaccccgg cggcccggtg 25740
tcagtccccc ctgcagccgc ccagtctctg cctccaggca agggcgccag cttttctccc 25800
cccagcctga ggcccagtct cctgtgcact gtctgtaaag tccagcctcc cacgcccgtc 25860
cacggctccc gggcccagcc tcgtccaccc ctccccacgg tggacaggcc ctctgtccac 25920
ccgggccatc cccgcccccc tgtgtccacc ccagtcccgt ccaggggggga ctttatgtga 25980
cccttgggcc tggctcccca tagactccca tgtaagcctg cctcgagtag gtgcctccag 26040
agccccttt gccccccctgg cggcccagcc cgacccccgg gcgcccccaa actttgtcca 26100
gatgtccagg ggtccccgag ggtgaggccc agccccctcc cgcccctgtc cactgccccg 26160
gtccccccag aagcccccaa aagtagaggc tcaggccatg cgcgccctgt caccaggcct 26220
gccaaagagc cagatctaag gccgggagag gcagccccaa agcgggtgca gtaacaggta 26280
atctctggta gtgatttgga cccgaaatct gacactttag agctctggag gactttaaaa 26340
ctctaaaaat caaaacttta gaggcgaatg ggcgccattt tgtccccacg cgcgcataat 26400
ggcggaccta ggcctaaaac ccccaggaag cgggtctatg gttggctgcg ctgctgctat 26460
ctttagaggg gaaaagagga ataagccccc agacagggga gtgggcttgt ttgtgacttc 26520
accaaaggtc agggcccaag gggttcgcg ttgctaggcc accttctcag tccagcgcgt 26580
ttacgtaagc cagacagcag ccaattgtca gttctaggga gggggaccac tgcccctggt 26640
ataaagtggt cctgcagcta tttctggtcg catcagagcg ccaggagtcc acacaaatgt 26700
aagagggggt cttctacctc tccctagccc tccgccccct ccaaggactc gggcccagtt 26760
tctaactttt ccccttccct ccctcgtctt gccctgcgcc cggggccacc ttcatcaccg 26820
tcgctgactc cgccatccaa gcctagggga gaccgaagtg aaggccctgg accaacccgg 26880
cccgggcccc ccggtatcgg gccagaggta agtggacttt aatttttctt gctaagccca 26940
acactccacc acacccaggc acacactaca cacacccacc cgtctcaggg tcccctcgga 27000
cagctcctaa gaaggcaccg gtcgcccagt cctaccagag gggccaaga acccagacga 27060
gtccgtagaa gggtcctcgt ccagcaagaa gaggaggtgg taagcggttc accttcaggg 27120
gtaagtaacc tgacctctcc agggctcaca taaagggagg cttagtatac atgcttcttg 27180
cttttcacag gaacctgggg gctagtctgg gtgggattag gctgcctcaa gttgcatcag 27240
ccagggcttc atgccctcct cagttcccta gtccccgggc ttcaggcccc ctccgtcccc 27300
gtcctccaga gacccgggct tcaggccctg cctctcctgt taccctttta gaaccacagc 27360
ctggacacat gtgccagacg ccttggcctc taaggccctc gggtcccccct ggaccccggc 27420
ctcagcaacc ctgctgctcc cctcctgcca ccccagcctc ccccctccc cgtcccccttt 27480
cgctcctgat cctcccccgg tccccagtag ggccgcctgc cccctgcac ccagtacctg 27540
cccctcttgg ccacgcaccc cgggccaggc caccttagac ccggccaagc cccatccctg 27600
aagacccagc ggccattctc tctggtaacg agcagagaag aagtagaggc ccgcggccat 27660
tgggcccaga ttgagagacc agtccagggg cccgaggttg gagccagcgg gcacccgagg 27720
tcccagcacc cggtccctcc ggggggcaga gacaggcagg gcccccggc agctggcccc 27780
gaggaggcgc ccggagtggg gccggtcggc tgggctggcc gagcccgggt ctgggaggtc 27840
tggggtggcg agcctgctgt ctcaggaggg gcctggctcc gccgggtggc cctggggtaa 27900
gtctgggagg cagagggtcg gcctaggccc ggggaagtgg agggggatcg cccgggtctc 27960
tgttggcaga gtccgggcga tcctctgaga ccctccgggc ccggacggtc gccctcagcc 28020
ccccagacag accccagggt ctccaggcag ggtccggcat cttcaggggc agcaggctca 28080
ccaccacagg ccccccagac ccgggtctcg gccagccgag ccgaccggcc ccgcgcctgg 28140
cgcctcctcg gggccagccg ccggggttgg ttctgcccct ctctctgtcc ttcagaggaa 28200
ccagggacct cgggcacccc agagcccctc gggcccgcct ccaggcgccc tcctggtctc 28260
cgctcccctc tgagccccgt taaacccaaa gaatgtctga ggggagccac cctcggggcc 28320
caggccccag agtccagagg tcaggggcac ctcagggtgc ctccccgggt cccaggccag 28380
ccggagggac cccggcagcc cgggcggccc cagaggccgg ttcctcgccc cttccccggg 28440
cttcagagcc caggatgtcc cccagaaggg accctaggcg tcccctctcc tcccctccag 28500

```
gcccgagcct ctccctcgcg gagaggggcc tctttgggcc ctcaagtcca gccccaccga  28560
gacccgagtg gcccggatcc ccccaccggc ccttctctct gtccccctgc tcctctccaa  28620
ccttcgctcc accctagacc ccagcttctg gcctccccgg gtccaccagg ccagccggag  28680
ggaccccggc agcccgggcg agtcgccttc cctctcccct ggcctctcct tcccgcctcc  28740
cacccgagcc ccctcagctt gcctccccac cgggtccatc aggccggccg gagggacccc  28800
ggcggcccgg tgtcagtccc ccctgcagcc gcccagtctc tgcctccagg caagggcgcc  28860
agcttttctc cccccagcct gaggcccagt ctcctgtgca ctgtctgtaa agtccagcct  28920
cccacgcccg tccacggctc ccgggcccag cctcgtccac ccctccccac ggtggacagg  28980
ccctctgtcc acccgggcca tccccgcccc cctgtgtcca ccccagtccc gtccaggggg  29040
gactttatgt gacccttggg cctggctccc catagactcc catgtaagcc tgcctcgagt  29100
aggtgcctcc agagcccctt ttgccccccct ggcggcccag cccgaccccc gggcgccccc  29160
aaactttgtc cagatgtcca ggggtccccg agggtgaggc ccagccccct cccgcccctg  29220
tccactgccc cggtccccccc agaagccccc aaaagtagag gctcaggcca tgcgcgccct  29280
gtcaccaggc ctgccaaaga gccagatcta aggccgggag aggcagcccc aaagcgggtg  29340
cagtaacagg taatctctgg tagtgatttg gacccgaaat ctgacacttt agagctctgg  29400
aggactttaa aactctaaaa atcaaaactt tagaggcgaa tgggcgccat tttgtcccca  29460
cgcgcgcata atggcggacc taggcctaaa acccccagga agcgggtcta tggttggctg  29520
cgctgctgct atctttagag gggaaaagag gaataagccc ccagacaggg gagtgggctt  29580
gtttgtgact tcaccaaagg tcagggccca agggggttcg cgttgctagg ccaccttctc  29640
agtccagcgc gtttacgtaa gccagacagc agccaattgt cagttctagg gagggggacc  29700
actgcccctg gtataaagtg gtcctgcagc tatttctggt cgcatcagag cgccaggagt  29760
ccacacaaat gtaagagggg gtcttctacc tctccctagc cctccgcccc ctccaaggac  29820
tcgggcccag tttctaactt ttccccttcc ctccctcgtc ttgccctgcg cccggggcca  29880
ccttcatcac cgtcgctgac tccgccatcc aagcctaggg gagaccgaag tgaaggccct  29940
ggaccaaccc ggcccgggcc ccccggtatc gggccagagg taagtggact ttaatttttt  30000
ctgctaagcc caacactcca ccacacccag gcacacacta cacacaccca cccgtctcag  30060
ggtcccctcg gacagctcct aagaaggcac cggtcgccca gtcctaccag agggggccaa  30120
gaacccagac gagtccgtag aagggtcctc gtccagcaag aagaggaggt ggtaagcggt  30180
tcaccttcag gggtaagtaa cctgacctct ccagggctca cataaaggga ggcttagtat  30240
acatgcttct tgcttttcac aggaacctgg gggctagtct gggtgggatt aggctgcctc  30300
aagttgcatc agccagggct tcatgccctc ctcagttccc tagtccccgg gcttcaggcc  30360
ccctccgtcc ccgtcctcca gagacccggg cttcaggccc tgcctctcct gttacccttt  30420
tagaaccaca gcctggacac atgtgccaga cgccttggcc tctaaggccc tcgggtcccc  30480
ctggaccccg gcctcagcaa ccctgctgct cccctcctgc caccccagcc tcccccccctc  30540
cccgtccccc ttcgctcctg atcctccccc ggtccccagt agggccgcct gcccccctgc  30600
acccagtacc tgcccctctt ggccacgcac cccgggccag gccaccttag acccggccaa  30660
gccccatccc tgaagaccca gcggccattc tctctggtaa cgagcagaga agaagtagag  30720
gcccgcggcc attgggccca gattgagaga ccagtccagg ggcccgaggt tggagccagc  30780
gggcacccga ggtcccagca cccggtccct ccggggggca gagacaggca gggccccccg  30840
gcagctggcc ccgaggaggc gcccggagtg gggccggtcg gctgggctgg ccgagcccgg  30900
```

gtctgggagg tctggggtgg cgagcctgct gtctcaggag gggcctggct ccgccgggtg 30960
gccctggggt aagtctggga ggcagagggt cggcctaggc ccggggaagt ggagggggat 31020
cgcccgggtc tctgttggca gagtccgggc gatcctctga gaccctccgg gcccggacgg 31080
tcgccctcag ccccccagac agaccccagg gtctccaggc agggtccggc atcttcaggg 31140
gcagcaggct caccaccaca ggccccccag acccgggtct cggccagccg agccgaccgg 31200
ccccgcgcct ggcgcctcct cggggccagc cgccggggtt ggttctgccc ctctctctgt 31260
ccttcagagg aaccagggac ctcgggcacc ccagagcccc tcgggcccgc ctccaggcgc 31320
cctcctggtc tccgctcccc tctgagcccc gttaaaccca aagaatgtct gaggggagcc 31380
accctcgggg cccaggcccc agagtccaga ggtcaggggc acctcagggt gcctccccgg 31440
gtcccaggcc agccggaggg accccggcag cccgggcggc cccagaggcc ggttcctcgc 31500
cccttccccg ggcttcagag cccaggatgt cccccagaag ggaccctagg cgtcccctct 31560
cctcccctcc aggcccgagc ctctccctcg cggagagggg cctctttggg ccctcaagtc 31620
cagccccacc gagacccgag tggcccggat ccccccaccg gcccttctct ctgtccccct 31680
gctcctctcc aaccttcgct ccaccctaga ccccagcttc tggcctcccc gggtccacca 31740
ggccagccgg agggaccccg gcagcccggg cgagtcgcct tccctctccc ctggcctctc 31800
cttcccgcct cccacccgag ccccctcagc ttgcctcccc accgggtcca tcaggccggc 31860
cggagggacc ccggcggccc ggtgtcagtc ccccctgcag ccgcccagtc tctgcctcca 31920
ggcaagggcg ccagcttttc tccccccagc ctgaggccca gtctcctgtg cactgtctgt 31980
aaagtccagc ctcccacgcc cgtccacggc tcccgggccc agcctcgtcc acccctcccc 32040
acggtggaca ggccctctgt ccacccgggc catccccgcc cccctgtgtc caccccagtc 32100
ccgtccaggg gggactttat gtgacccttg ggcctggctc cccatagact cccatgtaag 32160
cctgcctcga gtaggtgcct ccagagcccc ttttgccccc ctggcggccc agcccgaccc 32220
ccgggcgccc ccaaactttg tccagatgtc caggggtccc cgagggtgag gcccagcccc 32280
ctcccgcccc tgtccactgc cccggtcccc ccagaagccc ccaaaagtag aggctcaggc 32340
catgcgcgcc ctgtcaccag gcctgccaaa gagccagatc taaggccggg agaggcagcc 32400
ccaaagcggg tgcagtaaca ggtaatctct ggtagtgatt tggacccgaa atctgacact 32460
ttagagctct ggaggacttt aaaactctaa aaatcaaaac tttagaggcg aatgggcgcc 32520
attttgtccc cacgcgcgca taatggcgga cctaggccta aaacccccag gaagcgggtc 32580
tatggttggc tgcgctgctg ctatctttag aggggaaaag aggaataagc ccccagacag 32640
gggagtgggc ttgtttgtga cttcaccaaa ggtcagggcc caaggggggtt cgcgttgcta 32700
ggccaccttc tcagtccagc gcgtttacgt aagccagaca gcagccaatt gtcagttcta 32760
gggaggggga ccactgcccc tggtataaag tggtcctgca gctatttctg gtcgcatcag 32820
agcgccagga gtccacacaa atgtaagagg gggtcttcta cctctcccta gccctccgcc 32880
ccctccaagg actcgggccc agtttctaac ttttcccctt ccctccctcg tcttgccctg 32940
cgcccggggc caccttcatc accgtcgctg actccgccat ccaagcctag gggagaccga 33000
agtgaaggcc ctggaccaac ccggcccggg ccccccggta tcgggccaga ggtaagtgga 33060
ctttaatttt ttctgctaag cccaacactc caccacaccc aggcacacac tacacacacc 33120
cacccgtctc agggtcccct cggacagctc ctaagaaggc accggtcgcc cagtcctacc 33180
agagggggcc aagaacccag acgagtccgt agaagggtcc tcgtccagca agaagaggag 33240
gtggtaagcg gttcaccttc aggggtaagt aacctgacct ctccagggct cacataaagg 33300

-continued gaggcttagt atacatgctt cttgcttttc acaggaacct gggggctagt ctgggtggga 33360
ttaggctgcc tcaagttgca tcagccaggg cttcatgccc tcctcagttc cctagtcccc 33420
gggcttcagg ccccctccgt ccccgtcctc cagagacccg ggcttcaggc cctgcctctc 33480
ctgttaccct tttagaacca cagcctggac acatgtgcca gacgccttgg cctctaaggc 33540
cctcgggtcc ccctggaccc cggcctcagc aaccctgctg ctcccctcct gccaccccag 33600
cctccccccc tccccgtccc ccttcgctcc tgatcctccc ccggtcccca gtagggccgc 33660
ctgccccccct gcacccagta cctgcccctc ttggccacgc accccgggcc aggccacctt 33720
agacccggcc aagccccatc cctgaagacc cagcggccat tctctctggt aacgagcaga 33780
gaagaagtag aggcccgcgg ccattgggcc cagattgaga gaccagtcca ggggcccgag 33840
gttggagcca gcgggcaccc gaggtcccag cacccggtcc ctccgggggg cagagacagg 33900
cagggccccc cggcagctgg ccccgaggag gcgcccggag tggggccggt cggctgggct 33960
ggccgagccc gggtctggga ggtctggggt ggcgagcctg ctgtctcagg aggggcctgg 34020
ctccgccggg tggccctggg gtaagtctgg gaggcagagg gtcggcctag gcccggggaa 34080
gtggaggggg atcgcccggg tctctgttgg cagagtccgg gcgatcctct gagaccctcc 34140
gggcccggac ggtcgccctc agccccccag acagacccca gggtctccag gcagggtccg 34200
gcatcttcag gggcagcagg ctcaccacca caggcccccc agacccgggt ctcggccagc 34260
cgagccgacc ggccccgcgc ctggcgcctc ctcggggcca gccgccgggg ttggttctgc 34320
ccctctctct gtccttcaga ggaaccaggg acctcgggca ccccagagcc cctcgggccc 34380
gcctccaggc gccctcctgg tctccgctcc cctctgagcc ccgttaaacc caaagaatgt 34440
ctgaggggag ccaccctcgg ggcccaggcc ccagagtcca gaggtcaggg gcacctcagg 34500
gtgcctcccc gggtcccagg ccagccggag ggaccccggc agcccgggcg gccccagagg 34560
ccggttcctc gccccttccc cgggcttcag agcccaggat gtcccccaga agggacccta 34620
ggcgtcccct ctcctcccct ccaggcccga gcctctccct cgcggagagg ggcctctttg 34680
ggccctcaag tccagcccca ccgagacccg agtggcccgg atccccccac cggcccttct 34740
ctctgtcccc ctgctcctct ccaaccttcg ctccacccta gaccccagct tctggcctcc 34800
ccgggtccac caggccagcc ggagggaccc cggcagcccg ggcgagtcgc cttccctctc 34860
ccctggcctc tccttcccgc ctcccacccg agccccctca gcttgcctcc ccaccgggtc 34920
catcaggccg gccggaggga ccccggcggc ccggtgtcag tccccccctgc agccgcccag 34980
tctctgcctc caggcaaggg cgccagcttt tctcccccca gcctgaggcc cagtctcctg 35040
tgcactgtct gtaaagtcca gcctcccacg cccgtccacg gctcccgggc ccagcctcgt 35100
ccacccctcc ccacggtgga caggccctct gtccacccgg gccatccccg ccccccctgtg 35160
tccaccccag tcccgtccag gggggacttt atgtgaccct tgggcctggc tccccataga 35220
ctcccatgta agcctgcctc gagtaggtgc ctccagagcc ccttttgccc ccctggcggc 35280
ccagcccgac ccccgggcgc ccccaaactt tgtccagatg tccaggggtc cccgagggtg 35340
aggcccagcc ccctcccgcc cctgtccact gccccggtcc ccccagaagc ccccaaaagt 35400
agaggctcag gccatgcgcg ccctgtcacc aggcctgcca aagagccaga tctaaggccg 35460
ggagaggcag ccccaaagcg ggtgcagtaa caggtaatct ctggtagtga tttggacccg 35520
aaatctgaca ctttagagct ctggaggact ttaaaactct aaaaatcaaa actttagagg 35580
cgaatgggcg ccattttgtc cccacgcgcg cataatggcg gacctaggcc taaaaccccc 35640
aggaagcggg tctatggttg gctgcgctgc tgctatcttt agaggggaaa agaggaataa 35700
gcccccagac aggggagtgg gcttgtttgt gacttcacca aaggtcaggg cccaaggggg 35760
ttcgcgttgc taggccacct tctcagtcca gcgcgtttac gtaagccaga cagcagccaa 35820
ttgtcagttc tagggagggg gaccactgcc cctggtataa agtggtcctg cagctatttc 35880
tggtcgcatc agagcgccag gagtccacac aaatgtaaga gggggtcttc tacctctccc 35940
tagccctccg ccccctccaa ggactcgggc ccagtttcta acttttcccc ttccctccct 36000
cgtcttgccc tgcgcccggg gccaccttca tcaccgtcgc tgactccgcc atccaagcct 36060
aggggagacc gaagtgaagg ccctggacca acccggcccg ggccccccgg tatcgggcca 36120
gaggtaagtg gactttaatt ttttctgcta agcccaacac tccaccacac ccaggcacac 36180
actacacaca cccacccgtc tcagggtccc ctcggacagc tcctaagaag gcaccggtcg 36240
cccagtccta ccagaggggg ccaagaaccc agacgagtcc gtagaagggt cctcgtccag 36300
caagaagagg aggtggtaag cggttcacct tcaggggtaa gtaacctgac ctctccaggg 36360
ctcacataaa gggaggctta gtatacatgc ttcttgcttt tcacaggaac ctggggggcta 36420
gtctgggtgg gattaggctg cctcaagttg catcagccag ggcttcatgc cctcctcagt 36480
tccctagtcc ccgggcttca ggccccctcc gtccccgtcc tccagagacc cgggcttcag 36540
gccctgcctc tcctgttacc cttttagaac cacagcctgg acacatgtgc cagacgcctt 36600
ggcctctaag gccctcgggt cccccctggac cccggcctca gcaaccctgc tgctcccctc 36660
ctgccacccc agcctccccc cctccccgtc cccccttcgct cctgatcctc ccccggtccc 36720
cagtagggcc gcctgccccc ctgcacccag tacctgcccc tcttggccac gcaccccggg 36780
ccaggccacc ttagacccgg ccaagcccca tccctgaaga cccagcggcc attctctctg 36840
gtaacgagca gagaagaagt agaggcccgc ggccattggg cccagattga gagaccagtc 36900
caggggcccg aggttggagc cagcgggcac ccgaggtccc agcacccggt ccctccgggg 36960
ggcagagaca ggcagggccc cccggcagct ggccccgagg aggcgcccgg agtggggccg 37020
gtcggctggg ctggccgagc ccgggtctgg gaggtctggg gtggcgagcc tgctgtctca 37080
ggagggggcct ggctccgccg ggtggccctg gggtaagtct gggaggcaga gggtcggcct 37140
aggcccgggg aagtggaggg ggatcgcccg ggtctctgtt ggcagagtcc gggcgatcct 37200
ctgagaccct ccgggcccgg acggtcgccc tcagcccccc agacagaccc cagggtctcc 37260
aggcagggtc cggcatcttc aggggcagca ggctcaccac cacaggcccc ccagacccgg 37320
gtctcggcca gccgagccga ccggccccgc gcctggcgcc tcctcggggc cagccgccgg 37380
ggttggttct gcccctctct ctgtccttca gaggaaccag ggacctcggg caccccagag 37440
cccctcgggc ccgcctccag gcgccctcct ggtctccgct cccctctgag ccccgttaaa 37500
cccaaagaat gtctgagggg agccaccctc ggggcccagg ccccagagtc cagaggtcag 37560
gggcacctca gggtgcctcc ccgggtccca ggccagccgg agggaccccg gcagcccggg 37620
cggccccaga ggccggttcc tcgcccccttc cccgggcttc agagcccagg atgtccccca 37680
gaagggaccc taggcgtccc ctctcctccc ctccaggccc gagcctctcc ctcgcggaga 37740
ggggcctctt tgggccctca agtccagccc caccgagacc cgagtggccc ggatcccccc 37800
accggccctt ctctctgtcc ccctgctcct ctccaacctt cgctccaccc tagaccccag 37860
cttctggcct ccccgggtcc accaggccag ccggagggac cccggcagcc cgggcgagtc 37920
gccttccctc tcccctggcc tctccttccc gcctcccacc cgagccccct cagcttgcct 37980
ccccaccggg tccatcaggc cggccggagg gaccccggcg gcccggtgtc agtccccccct 38040
gcagccgccc agtctctgcc tccaggcaag ggcgccagct tttctccccc cagcctgagg 38100
cccagtctcc tgtgcactgt ctgtaaagtc cagcctccca cgcccgtcca cggctcccgg 38160
gcccagcctc gtccacccct ccccacggtg gacaggccct ctgtccaccc gggccatccc 38220 cgccccccctg tgtccacccc agtcccgtcc aggggggact ttatgtgacc cttgggcctg 38280
gctccccata gactcccatg taagcctgcc tcgagtaggt gcctccagag ccccttttgc 38340
ccccctggcg gcccagcccg acccccgggc gcccccaaac tttgtccaga tgtccagggg 38400
tccccgaggg tgaggcccag ccccctcccg cccctgtcca ctgccccggt ccccccagaa 38460
gcccccaaaa gtagaggctc aggccatgcg cgccctgtca ccaggcctgc caaagagcca 38520
gatctaaggc cgggagaggc agccccaaag cgggtgcagt aacaggtaat ctctggtagt 38580
gatttggacc cgaaatctga cactttagag ctctggagga ctttaaaact ctaaaaatca 38640
aaactttaga ggcgaatggg cgccattttg tccccacgcg cgcataatgg cggacctagg 38700
cctaaaaccc ccaggaagcg ggtctatggt tggctgcgct gctgctatct ttagagggga 38760
aaagaggaat aagcccccag acaggggagt gggcttgttt gtgacttcac caaaggtcag 38820
ggcccaaggg ggttcgcgtt gctaggccac cttctcagtc cagcgcgttt acgtaagcca 38880
gacagcagcc aattgtcagt tctagggagg gggaccactg cccctggtat aaagtggtcc 38940
tgcagctatt tctggtcgca tcagagcgcc aggagtccac acaaatgtaa gagggggtct 39000
tctacctctc cctagccctc cgccccctcc aaggactcgg gcccagtttc taacttttcc 39060
ccttccctcc ctcgtcttgc cctgcgcccg gggccacctt catcaccgtc gctgactccg 39120
ccatccaagc ctaggggaga ccgaagtgaa ggccctggac caacccggcc cgggcccccc 39180
ggtatcgggc cagaggtaag tggactttaa ttttttctgc taagcccaac actccaccac 39240
acccaggcac acactacaca cacccacccg tctcagggtc ccctcggaca gctcctaaga 39300
aggcaccggt cgcccagtcc taccagaggg ggccaagaac ccagacgagt ccgtagaagg 39360
gtcctcgtcc agcaagaaga ggaggtggta agcggttcac cttcaggggt aagtaacctg 39420
acctctccag ggctcacata aagggaggct tagtatacat gcttcttgct tttcacagga 39480
acctgggggc tagtctgggt gggattaggc tgcctcaagt tgcatcagcc agggcttcat 39540
gccctcctca gttccctagt ccccgggctt caggcccccct ccgtccccgt cctccagaga 39600
cccgggcttc aggccctgcc tctcctgtta ccctttttaga accacagcct ggacacatgt 39660
gccagacgcc ttggcctcta aggccctcgg gtccccctgg accccggcct cagcaaccct 39720
gctgctcccc tcctgccacc ccagcctccc cccctccccg tccccccttcg ctcctgatcc 39780 tcccccggtc cccagtaggg ccgcctgccc ccctgcaccc agtacctgcc cctcttggcc 39840
acgcaccccg ggccaggcca ccttagaccc ggccaagccc catccctgaa gacccagcgg 39900
ccattctctc tggtaacgag cagagaagaa gtagaggccc gcggccattg ggcccagatt 39960
gagagaccag tccaggggcc cgaggttgga gccagcgggc acccgaggtc ccagcacccg 40020
gtccctccgg ggggcagaga caggcagggc cccccggcag ctggccccga ggaggcgccc 40080
ggagtggggc cggtcggctg ggctggccga gcccgggtct gggaggtctg gggtggcgag 40140
cctgctgtct caggaggggc ctggctccgc cgggtggccc tggggtaagt ctgggaggca 40200
gagggtcggc ctaggcccgg ggaagtggag ggggatcgcc cgggtctctg ttggcagagt 40260
ccgggcgatc ctctgagacc ctccgggccc ggacggtcgc cctcagcccc ccagacagac 40320
cccagggtct ccaggcaggg tccggcatct tcaggggcag caggctcacc accacaggcc 40380
ccccagaccc gggtctcggc cagccgagcc gaccggcccc gcgcctggcg cctcctcggg 40440
gccagccgcc ggggttggtt ctgcccctct ctctgtcctt cagaggaacc agggacctcg 40500
ggcaccccag agcccctcgg gcccgcctcc aggcgccctc ctggtctccg ctcccctctg 40560
agccccgtta aacccaaaga atgtctgagg ggagccaccc tcggggccca ggccccagag 40620
tccagaggtc aggggcacct cagggtgcct ccccgggtcc caggccagcc ggagggaccc 40680
cggcagcccg ggcggcccca gaggccggtt cctcgcccct tccccgggct tcagagccca 40740
ggatgtcccc cagaagggac cctaggcgtc ccctctcctc ccctccaggc ccgagcctct 40800
ccctcgcgga gaggggcctc tttgggccct caagtccagc cccaccgaga cccgagtggc 40860
ccggatcccc ccaccggccc ttctctctgt ccccctgctc ctctccaacc ttcgctccac 40920
cctagacccc agcttctggc ctccccgggt ccaccaggcc agccggaggg accccggcag 40980
cccgggcgag tcgccttccc tctcccctgg cctctccttc ccgcctccca cccgagcccc 41040
ctcagcttgc ctccccaccg ggtccatcag gccggccgga gggaccccgg cggcccggtg 41100
tcagtccccc ctgcagccgc ccagtctctg cctccaggca agggcgccag cttttctccc 41160
cccagcctga ggcccagtct cctgtgcact gtctgtaaag tccagcctcc cacgcccgtc 41220
cacggctccc gggcccagcc tcgtccaccc ctccccacgg tggacaggcc ctctgtccac 41280
ccgggccatc cccgcccccc tgtgtccacc ccagtcccgt ccaggggggga ctttatgtga 41340 cccttgggcc tggctcccca tagactccca tgtaagcctg cctcgagtag gtgcctccag 41400 agccccttttt gccccccctgg cggcccagcc cgaccccccgg gcgcccccaa actttgtcca 41460
gatgtccagg ggtccccgag ggtgaggccc agccccctcc cgcccctgtc cactgccccg 41520
gtccccccag aagcccccaa aagtagaggc tcaggccatg cgcgccctgt caccaggcct 41580
gccaaagagc cagatctaag gccgggagag gcagccccaa agcgggtgca gtaacaggta 41640
atctctggta gtgatttgga cccgaaatct gacactttag agctctggag gactttaaaa 41700
ctctaaaaat caaaacttta gaggcgaatg ggcgccattt tgtccccacg cgcgcataat 41760
ggcggaccta ggcctaaaac ccccaggaag cgggtctatg gttggctgcg ctgctgctat 41820
ctttagaggg gaaaagagga ataagccccc agacagggga gtgggcttgt ttgtgacttc 41880
accaaaggtc agggcccaag ggggttcgcg ttgctaggcc accttctcag tccagcgcgt 41940
ttacgtaagc cagacagcag ccaattgtca gttctaggga gggggaccac tgcccctggt 42000
ataaagtggt cctgcagcta tttctggtcg catcagagcg ccaggagtcc acacaaatgt 42060
aagagggggt cttctacctc tccctagccc tccgcccccct ccaaggactc gggcccagtt 42120
tctaactttt cccctttccct ccctcgtctt gccctgcgcc cggggccacc ttcatcaccg 42180
tcgctgactc cgccatccaa gcctagggga gaccgaagtg aaggccctgg accaacccgg 42240
cccgggcccc ccggtatcgg gccagaggta agtggacttt aatttttttct gctaagccca 42300 acactccacc acacccaggc acacactaca cacacccacc cgtctcaggg tcccctcgga 42360
cagctcctaa gaaggcaccg gtcgcccagt cctaccagag gggggccaaga acccagacga 42420 gtccgtagaa gggtcctcgt ccagcaagaa gaggaggtgg taagcggttc accttcaggg 42480
gtaagtaacc tgacctctcc agggctcaca taaagggagg cttagtatac atgcttcttg 42540
cttttcacag gaacctgggg gctagtctgg gtgggattag gctgcctcaa gttgcatcag 42600
ccagggcttc atgccctcct cagttcccta gtccccgggc ttcaggcccc ctccgtcccc 42660
gtcctccaga gacccgggct tcaggccctg cctctcctgt taccctttta gaaccacagc 42720
ctggacacat gtgccagacg ccttggcctc taaggccctc gggtccccct ggaccccggc 42780
ctcagcaacc ctgctgctcc cctcctgcca ccccagcctc ccccccctccc cgtcccccctt 42840 cgctcctgat cctcccccgg tccccagtag ggccgcctgc ccccctgcac ccagtacctg 42900

-continued

```
cccctcttgg ccacgcaccc cgggccaggc caccttagac ccggccaagc cccatccctg  42960
aagacccagc ggccattctc tctggtaacg agcagagaag aagtagaggc ccgcggccat  43020
tgggcccaga ttgagagacc agtccagggg cccgaggttg gagccagcgg gcacccgagg  43080
tcccagcacc cggtccctcc ggggggcaga gacaggcagg gcccccggc agctggcccc   43140
gaggaggcgc ccggagtggg gccggtcggc tgggctggcc gagcccgggt ctgggaggtc  43200
tggggtggcg agcctgctgt ctcaggaggg gcctggctcc gccgggtggc cctggggtaa  43260
gtctgggagg cagagggtcg gcctaggccc ggggaagtgg agggggatcg cccgggtctc  43320
tgttggcaga gtccgggcga tcctctgaga ccctccgggc ccggacggtc gccctcagcc  43380
ccccagacag accccagggt ctccaggcag ggtccggcat cttcaggggc agcaggctca  43440
ccaccacagg ccccccagac ccgggtctcg gccagccgag ccgaccggcc ccgcgcctgg  43500
cgcctcctcg gggccagccg ccggggttgg ttctgcccct ctctctgtcc ttcagaggaa  43560
ccagggacct cgggcaccca agagcccctc gggcccgcct ccaggcgccc tcctggtctc  43620
cgctcccctc tgagccccgt taaacccaaa gaatgtctga ggggagccac cctcggggcc  43680
caggccccag agtccagagg tcaggggcac ctcagggtgc ctccccgggt cccaggccag  43740
ccggagggac cccggcagcc cgggcggccc cagaggccgg ttcctcgccc cttccccggg  43800
cttcagagcc caggatgtcc cccagaaggg accctaggcg tcccctctcc tcccctccag  43860
gcccgagcct ctccctcgcg gagaggggcc tctttgggcc ctcaagtcca gccccaccga  43920
gacccgagtg gcccggatcc ccccaccggc ccttctctct gtccccctgc tcctctccaa  43980
ccttcgctcc accctagacc ccagcttctg gcctccccgg gtccaccagg ccagccggag  44040
ggaccccggc agcccgggcg agtcgccttc cctctcccct ggcctctcct tcccgcctcc  44100
cacccgagcc ccctcagctt gcctccccac cgggtccatc aggccggccg gagggacccc  44160
ggcggcccgg tgtcagtccc ccctgcagcc gcccagtctc tgcctccagg caagggcgcc  44220
agcttttctc cccccagcct gaggcccagt ctcctgtgca ctgtctgtaa agtccagcct  44280
cccacgcccg tccacggctc ccgggcccag cctcgtccac ccctccccac ggtggacagg  44340
ccctctgtcc acccgggcca tccccgcccc cctgtgtcca ccccagtccc gtccaggggg  44400
gactttatgt gacccttggg cctggctccc catagactcc catgtaagcc tgcctcgagt  44460
aggtgcctcc agagcccctt ttgccccccct ggcggcccag cccgaccccc gggcgccccc  44520
aaactttgtc cagatgtcca ggggtccccg agggtgaggc ccagccccct cccgcccctg  44580
tccactgccc cggtcccccc agaagccccc aaaagtagag gctcaggcca tgcgcgccct  44640
gtcaccaggc ctgccaaaga gccagatcta aggccgggag aggcagcccc aaagcgggtg  44700
cagtaacagg taatctctgg tagtgatttg gacccgaaat ctgacacttt agagctctgg  44760
aggactttaa aactctaaaa atcaaaactt tagaggcgaa tgggcgccat tttgtcccca  44820
cgcgcgcata atggcggacc taggcctaaa acccccagga agcgggtcta tggttggctg  44880
cgctgctgct atctttagag gggaaaagag gaataagccc ccagacaggg gagtgggctt  44940
gtttgtgact tcaccaaagg tcagggccca agggggttcg cgttgctagg ccaccttctc  45000
agtccagcgc gtttacgtaa gccagacagc agccaattgt cagttctagg gagggggacc  45060
actgcccctg gtataaagtg gtcctgcagc tatttctggt cgcatcagag cgccaggagt  45120
ccacacaaat gtaagagggg gtcttctacc tctccctagc cctccgcccc ctccaaggac  45180
tcgggcccag tttctaactt ttccccttcc ctccctcgtc ttgccctgcg cccggggcca  45240
ccttcatcac cgtcgctgac tccgccatcc aagcctaggg gagaccgaag tgaaggccct  45300
```

ggaccaaccc ggcccgggcc ccccggtatc gggccagagg taagtggact ttaatttttt 45360
ctgctaagcc caacactcca ccacacccag gcacacacta cacacaccca cccgtctcag 45420
ggtcccctcg gacagctcct aagaaggcac cggtcgccca gtcctaccag agggggccaa 45480
gaacccagac gagtccgtag aagggtcctc gtccagcaag aagaggaggt ggtaagcggt 45540
tcaccttcag gggtaagtaa cctgacctct ccagggctca cataaaggga ggcttagtat 45600
acatgcttct tgcttttcac aggaacctgg gggctagtct gggtgggatt aggctgcctc 45660
aagttgcatc agccagggct tcatgccctc ctcagttccc tagtccccgg gcttcaggcc 45720
ccctccgtcc ccgtcctcca gagacccggg cttcaggccc tgcctctcct gttacccttt 45780
tagaaccaca gcctggacac atgtgccaga cgccttggcc tctaaggccc tcgggtcccc 45840
ctggaccccg gcctcagcaa ccctgctgct cccctcctgc caccccagcc tccccccctc 45900
cccgtccccc ttcgctcctg atcctccccc ggtccccagt agggccgcct gccccccctgc 45960 acccagtacc tgcccctctt ggccacgcac cccgggccag gccaccttag acccggccaa 46020
gccccatccc tgaagaccca gcggccattc tctctggtaa cgagcagaga agaagtagag 46080
gcccgcggcc attgggccca gattgagaga ccagtccagg ggcccgaggt tggagccagc 46140
gggcacccga ggtcccagca cccggtccct ccggggggca gagacaggca gggccccccg 46200
gcagctggcc ccgaggaggc gcccggagtg gggccggtcg gctgggctgg ccgagcccgg 46260
gtctgggagg tctggggtgg cgagcctgct gtctcaggag gggcctggct ccgccgggtg 46320
gccctggggt aagtctggga ggcagagggt cggcctaggc ccggggaagt ggagggggat 46380
cgcccgggtc tctgttggca gagtccgggc gatcctctga gaccctccgg gcccggacgg 46440
tcgccctcag ccccccagac agaccccagg gtctccaggc agggtccggc atcttcaggg 46500
gcagcaggct caccaccaca ggccccccag acccgggtct cggccagccg agccgaccgg 46560
ccccgcgcct ggcgcctcct cggggccagc cgccggggtt ggttctgccc ctctctctgt 46620
ccttcagagg aaccagggac ctcgggcacc ccagagcccc tcgggcccgc ctccaggcgc 46680
cctcctggtc tccgctcccc tctgagcccc gttaaaccca aagaatgtct gaggggagcc 46740
accctcgggg cccaggcccc agagtccaga ggtcaggggc acctcagggt gcctccccgg 46800
gtcccaggcc agccggaggg accccggcag cccgggcggc cccagaggcc ggttcctcgc 46860
cccttccccg ggcttcagag cccaggatgt cccccagaag ggaccctagg cgtcccctct 46920
cctcccctcc aggcccgagc ctctccctcg cggagagggg cctctttggg ccctcaagtc 46980
cagccccacc gagacccgag tggcccggat ccccccaccg gcccttctct ctgtccccct 47040
gctcctctcc aaccttcgct ccaccctaga ccccagcttc tggcctcccc gggtccacca 47100
ggccagccgg agggaccccg gcagcccggg cgagtcgcct tccctctccc ctggcctctc 47160
cttcccgcct cccacccgag ccccctcagc ttgcctcccc accgggtcca tcaggccggc 47220
cggagggacc ccggcggccc ggtgtcagtc ccccctgcag ccgcccagtc tctgcctcca 47280
ggcaagggcg ccagcttttc tccccccagc ctgaggccca gtctcctgtg cactgtctgt 47340
aaagtccagc ctcccacgcc cgtccacggc tcccgggccc agcctcgtcc acccctcccc 47400
acggtggaca ggccctctgt ccacccgggc catccccgcc cccctgtgtc caccccagtc 47460
ccgtccaggg gggactttat gtgacccttg ggcctggctc cccatagact cccatgtaag 47520
cctgcctcga gtaggtgcct ccagagcccc ttttgccccc ctggcggccc agcccgaccc 47580
ccgggcgccc ccaaactttg tccagatgtc caggggtccc cgagggtgag gcccagcccc 47640
ctctcgccca agctgctttg attcctggga tatttttggg aatggtgtta actttctccc 47700
cttgtatttg ctattcaatc aacctgattc cccctgctca tacctccact tacaaccaag 47760
ccactacggc cacgtccccg gcctcccgct cgggtaagtg ctttttcatt tttagcccca 47820
gcccctcctc tataagttct aggcaaacct ccaatcacca gccaccttcc aatgtagtct 47880
cttagagagt ggctgctacg cattagagac cactttgagc cacccacagt aaccacccag 47940
cgccaatctg tctacataga agaagaagag gatgaagact aagtcacagg cttagccagg 48000
tgatttgtga atttcagttt atttactttc ttccaatcaa gctttcccag cctccgcttg 48060
ttaggtccta gttatgggtt ttccatgggg gacttagtat ccgttctatt agattaacgt 48120
gcaagacgct aaacttaacc aaggtcagcc aagggacgcg tgttatccca ggctgcccac 48180
cctgaggatt tccccccaaa atcctcctac cctctcttta tgccatgtgt gttgttggct 48240
tgtgttagtg ctatgtaatg cgttgccgcc aggtggcagc ctgtttatag atgtgcagta 48300
ccccttaatg ttaggtctgc tttagggctg ccaggtggcg caatctagga ttaattcacc 48360
tgtatccctt tccctccacc cgcagtaacc cagcactggc gtgtgacgtg gtgtaaagtt 48420
ttgcctgaac ctgtggttgg gcaggtacat gccaacaacc ttctaagcac ccgcgcttgt 48480
gttttgcttt atctgccgcc atcatgccta cattctatct tgcgttacat gggggacaaa 48540
catatcatct aattgttgac acggatagtc ttggaaaccc gtcactctca gtaattccct 48600
cgaatcccta ccaggaacaa ctgtcagaca ctccattaat tccactaaca atctttgttg 48660
gggaaaacac gggggtgccc ccaccactcc caccaccccc cccaccacca cccccaccac 48720
ccccaccacc cccaccaccc ccaccacccc caccacctcc accaccttca ccaccacccc 48780
cgcccccacc acccccacca cctcagcgca gggatgcctg gacacaagag ccatcacctc 48840
ttgataggga tccgctagga tatgacgtcg ggcatggacc tctagcatct gctatgcgaa 48900
tgctttggat ggctaattat attgtaagac aatcacgggg tgaccggggc cttattttgc 48960
cacaaggccc acaaacagcc cctcaggcca ggttggtcca gccacatgtc ccccctctac 49020
gcccgacagc acccaccatt ttgtcacctc tgtcacaacc gaggcttacc cctccacaac 49080
cactcatgat gccaccaagg cctacccctc ctacccctct gccacctgca acactaacgg 49140
tgccaccaag gcctacccgt cctaccactc tgccacccac accactactc acggtactac 49200
aaaggcctac cgaacttcaa cccacaccat caccaccacg catgcatctc cctgtcttgc 49260
atgtgccaga ccaatcaatg caccctctta ctcatcaaag caccccaaat gatccagata 49320
gtccagaacc acggtccccg actgtatttt ataacattcc acctatgcca ttaccccccct 49380 cacaattgcc accaccagca gcaccagcac agccacctcc aggggtcatc aacgaccaac 49440
aattacatca tctaccctcg gggccaccat ggtggccacc catctgcgac cccccgcaac 49500
cctctaagac tcaaggccag agccggggac agagcagggg gaggggcagg ggcaggggca 49560
ggggcagggg caagggcaag tccagggaca agcaacgcaa gcccggtgga ccttggagac 49620
cagagccaaa cacctccagt cctagcatgc ctgaactaag tccagtcctc ggtcttcatc 49680
agggacaagg ggctggggac tcaccaactc ctggcccatc caatgccgcc cccgtttgta 49740
gaaattcaca cacggcaacc cctaacgttt caccaataca tgaaccggag tcccataata 49800
gcccagaggc tcccattctc ttccccgatg attggtatcc tccatctata gaccccgcag 49860
acttagacga aagttgggat tacatttttg agacaacaga atctcctagc tcagatgaag 49920
attatgtgga gggacccagt aaaagacctc gcccctccat ccagtaaaaa cccttgccct 49980
ctccagcaac caatgtatcc caaataaatg ttacttcttt tgctcttaac cattgacacg 50040
cctgtcattc tatcaattaa acaagggaaa aaggtttagc tattccacca acacgacccc 50100

-continued aaggaaggct tgccaaaatt ggtgccttgc tctcagcact ttgccagcaa cttatagcat 50160
ggtaggcagc tcaactcggc ccgtcttact gcccagccta ctctccactc ccagtccatg 50220
ttcgcactcc tatgcatttc ctgccctccc acttttaccc cagtcccaac ccaaaaccac 50280
acacaacaca tagaattgtt agtttaaaca gtttattgat aggtggctgc ttttagccta 50340
attgtgtatt gctctcgttg ccaaaacctg ttgtaagggc cggcacccgc aacatgggga 50400
aaacataacc gccgccatcc catggggagg gtagaggcgg ttgacatgta ggtgagtagt 50460
gtaagaagca tggcgaagta gacaggttac ttttagagtg tagtgtacag ggccgggcgc 50520
aacagtgcca ccaacccggg gtctgagcat tccatgggca gcagggacac tgcactaccg 50580
ccaggtcctg gggcagccgg ggttcctggc gctccggggg cagccgggcg gccgccggtg 50640
ggtccgctgg gccgctgccc cgctccgggt ggggggtggc cccgctgggc accgctgcgc 50700
cgccgccagg tcctggggca gccggggttc ctggcgctcc gggggcagcc gggcggccgc 50760
cggtgggtcc gctgggccgc tgccccgctc cgggtggggg gtggccccgc tgggcaccgc 50820
tgcgccgccg ccaggtcctg gggcagccgg ggttcctggc gctccggggg cagccgggcg 50880
gccgccggtg ggtccgctgg gccgctgccc cgctccgggt ggggggtggc cccgctgggc 50940
accgctgcgc cgccgccagg tcctggggca gccggggttc ctggcgctcc gggggcagcc 51000
gggcggccgc cggtgggtcc gctgggccgc tgccccgctc cgggtggggg gtggccccgc 51060
tgggcaccgc tgcgccgccg ccaggtcctg gggcagccgg ggttcctggc gctccggggg 51120
cagccgggcg gccgccggtg ggtccgctgg gccgctgccc cgctccgggt ggggggtggc 51180
cccgctgggc accgctgcgc cgccgccagg tcctggggca gccggggttc ctggcgctcc 51240
gggggcagcc gggcggccgc cggtgggtcc gctgggccgc tgccccgctc cgggtggggg 51300
gtggccccgc tgggcaccgc tgcgccgccg ccaggtcctg gggcagccgg ggttcctggc 51360
gctccggggg cagccgggcg gccgccggtg ggtccgctgg gccgctgccc cgctccgggt 51420
ggggggtggc cccgctgggc accgctgcgc cgccgccagg tcctggggca gccggggttc 51480
ctggcgctcc gggggcagcc gggcggccgc cggtgggtcc gctgggccgc tgccccgctc 51540
cgggtggggg gtggccccgc tgggcaccgc tgcgccgccg ccaggtcctg gggcagccgg 51600
ggttcctggc gctccggggg cagccgggcg gccgccggtg ggtccgctgg gccgctgccc 51660
cgctccgggt ggggggtggc cccgctgggc accgctgcgc cgccgccagg tcctggggca 51720
gccggggttc ctggcgctcc gggggcagcc gggcggccgc cggtgggtcc gctgggccgc 51780
tgccccgctc cgggtggggg gtggccccgc tgggcaccgc tgcgccgccg ccaggtcctg 51840
gggcagccgg ggttcctggc gctccggggg cagccgggcg gccgccggtg ggtccgctgg 51900
gccgctgccc cgctccgggt ggggggtggc cccgctgggc accgctgcgc cgccgccagg 51960
tcctggggca gccggggttc ctggcgctcc gggggcagcc gggcggccgc cggtgggtcc 52020
gctgggccgc tgccccgctc cgggtggggg gtggccccgc tgggcaccgc tgcgccgccg 52080
ccaggtcctg gggcagccgg ggttcctggc gctccactgc acctggaatg cagggtgggg 52140
gcgtggtccc ctggacccca gccccgccga tccctccccc agggcgtacc cggcttgcct 52200
ggttctgggg ctcctctggg ggtcgctgca tccgccggta gggttcgaat gggcgtggtc 52260
cgcttgctct gctggcccgg tacgcctgga ttgccggctg gggctgggg tcccgggacg 52320
ccccctccct gctcccaccc ggttccctcc cccagggcgt gccccgcttg cctggtcctg 52380
gagctcatcc ggggatgctg catccgctag tccgacctgg gtgggtgcgg tccgctggcc 52440
ccaccctggg ggtagccgcc gggtctgctg gtccggtgca cctggaaggc aggggggggg 52500
gcagtgaggg aggggcgtgg tcctgggacc ccgcgccgac tggcaggggg tccccatggc 52560
acaggcctag gggtccaggg ggcagccgcg gcccagcgcg ccccgttcac gggggaggac 52620
cgcggccgag ccaccagggg cccggcgggg gtggggggtg cgctcccagg ccggaccctg 52680
gtgccaggca gggaccccgc gccacccgct tcatgggggg ggaggccgcc gcaaggacgc 52740
cgggccggct gggaggtgtg cacccccgga gcgtctggac gacgctggcg agccgggccg 52800
gctcgccttc ttttatcctc tttttggggt ctctgtgtaa tactttaagg tttgctcagg 52860
agtgggggct tcttattggt taattcaggt gtgtcatttt agcccgttgg gtttcattaa 52920
ggtgtgtcac caggtgggtg gtacctggag gttattctat tgggataacg agaggaggag 52980
gggctagagg tccgcgagat ttggggtagg cggagcctca ggagggtccc ctccataggg 53040
ttgaaccagg agggggagga ttgggctccg ccccgatata cctagtgggt ggagcctaga 53100
ggtaggtatc catagggttc cattatcctg gaggtatcct aagctccgcc cctatatacc 53160
aggtgggtgg agctaggtag gattcagcta ggttcctact ggggtacccc cctaccctac 53220
cttaaggtgc gccacccttc ctccttccgt tttaatggta gaataaccta taggttatta 53280
acctagtggt ggaatagggt attgcagctg ggtatatacc tataggtata tagaacctag 53340
aggaagggaa ccctatagtg taatccctcc cccccctacc ccccctccc ttacggttgc 53400
ctgagcccat cccccacccc agcaccccgg ggtgacgtgg caccccgcgt gccttactga 53460
cttgtcacct ttgcacattt ggtcagctga ccgatgctcg ccacttcctg ggtcatgacc 53520
tggcctgtgc cttgtcccgt ggacaatgtc cctccagcgt ggtggctgcc tttgggatgc 53580
atcactttga gccactaagc ccccgttgct cgccttgcct gcctcaccat gacacactaa 53640
gcccctgcta atccatgagc cccgccttta ggaagcacca cgtcccgggg acggaagggg 53700
acttggggtg attttctatg tgggggtgga aatatgagca agaataagga cggctcctta 53760
ttaacctgat cagccccgga gttgcctgtt tcatcactaa ccccgggcct gaagaggttg 53820
acaagaaggg tcaaggtttc gtctgtgtgt tgaagggcag gggctgttgg gtgcatctgg 53880
aacggcttac ctcgggtaac tgtttgccat taaaaggttg gggattaggt ttagcccctt 53940
tagctgccat ttcgaaccgg ggtgtgcaga tgcaggtctc cgggtgggca ggcagtacga 54000
gatgtcacgt tgtgttgtct ttcctcccac ccctgtcctg gctgtggcaa atgcgaccct 54060
catagagttg tgtttcaggt ctgtgtcctg ttttgcggtg ggttatttct tccctcagtg 54120
tttgccagct tatttcccca gttttcacgt actggggcct gtggacacct gagggagcgg 54180
ccgttggtgg gtatgtgttg gaattgctcc caccctcaat tttcgcttgc cttcttccct 54240
tgttaacctg atagcatagc ctctaggttt ccttgtaggt ctgtttgggt ttgttggttc 54300
acgtggtgct aacttgaatt ttttggtttt ctagttccct cttaattaca tttgtgccag 54360
atcttgtaga gcaagatggc ctattcaaca agggagatac tgttagccct gtgtatacgg 54420
gacagtcgtg tgcatggaaa tggtaccctg catcctgtgt tggagctagc agcaagagaa 54480
acacctctcc gcctttcgcc agaggacact gtagttctgc gttatcatgt gttgcttgag 54540
gagataattg aacgaaattc agagacattt acagaaactt ggaacagatt tataacacac 54600
accgaacatg tggatctgga ttttaactca gtatttttag agatatttca ccgtggagac 54660
ccaagccttg ggcgcgcgtt ggcctggatg gcctggtgca tgcatgcctg caggacattg 54720
tgttgtaacc agtctactcc ttactatgtt gtggacctgt cagttcgtgg gatgttagaa 54780
gccagcgaag gcctggatgg ttggattcat caacagggcg gctggtctac attaattgaa 54840
gacaacattc ctggatccag aaggtttagc tggactttgt ttcttgctgg actgactttg 54900

```
agtctgttag ttatatgtag ttatttattt atctccagag gaagacacta atctatacat  54960
tttctcagca ctttatatga atcagggtca ttgggcctgc ggggaactga gccagtagga  55020
tattaggcaa gggtgacaca gtgcccatgc attataattt aaccaaacag tggtcgtgag  55080
ttttaggccg gccatggggg cttacaagaa taacatgcca atgacccggc cccccacttt  55140
aaattctgtt gcagcagata gctgataccc aatgttatct tttgcggcag aaattgaaag  55200
tgctggccat atctacaatt gggtgtccta ggtgggatat acgcctgtgg tgttctaacg  55260
ggaagtgtgt aagcacacac gtaatttgca agcggtgctt cacgctcttc gttaaaataa  55320
cacaaggaca agatactaaa gaaataactg aggtgagtgt gggaagatgg gaatactatg  55380
tgttatgtta acgggtgaga gcctatactg cagcccagac tcggggggag gaggaaatgg  55440
taagagttat actctactta tctttttga cactacattt aactgttatg taacaatgtt  55500
tgcttatttt catgttcaat aaacgctatg ttaatgatga agaacctgtg ttctttggaa  55560
gtgggcccaa tggggtagta ggttttggga gggtgccgtg ctagatattt caactgccac  55620
agaccccatt ttgtcccacc tgttaccaca ttctaggtcc tgcatccagt gggccaggtg  55680
tctcaccatg gctctttcta ggtggatacc acagtccagg cccccaaggc taccgtgcta  55740
attacctcct catgtccacc cccaccctgt gttactgtcg cctgattatc ctggcttagc  55800
agcctccaag ttttacaaga cgtcccattg ccctgccctt ggtccaagtc tcgccggttt  55860
tcagcagcct gttgtagcct gcccccaagt ttcgcaggtt tcccccatgc ttccacccgt  55920
taacccaata gcatgacagc caatccaaca cgaggcaagt tttaagagtt aaaagcaact  55980
actgtttatt ttccaaaatg agctgggtat agttgatgat ctgtaggcgc agctcatccc  56040
cacattccag gtccttgatg gcctcgtaga tggcatcttc gtcgacattg acagccttct  56100
catataccgt gtctctgggg ctgaccttta tacagaaggc gtcccctact aggtccacgg  56160
ccagctcgta ggtggggcct atgttttcac ataacagttt caagcaggtc tctgggatgt  56220
gaagggaggt gccctggagc aggagatgca tgattaggcg ccctttttcca tttgtgctga  56280
agatggggca gatggtgcca caaaagtgtc cggtgaccag gtaagcgtag agaaggctgg  56340
gttgggaaag tccagccttt actgcactgg gagagctgct gagcagagac acatagaagg  56400
tcttgttggg tattatcttg tggacattgt tgaagaagga gagctgggtg gagctaaact  56460
cctgaggcac atgaacctgg gacctattga tgcagatctc gcagtgagac cccagagtca  56520
ggctgtggcc gaagggagac aggcgaaggc agcgcccggg ggagagagtg cacagtgaca  56580
gtgggagaaa cacggcctct gagacatgta tgggggtgtt catctcacgc agaaaatctt  56640
tgcccagctc aaagttggca gagattcccc tgaagaagtc ccgtagtgaa aaatgggatc  56700
tgtctacacc atgtctggtg tgccgggaac atattgatcg ggccacactg ccaacccttt  56760
ccattcttcc cagctctgag cgagattttc cacacctgga caccgacttc acgctatgcg  56820
ccgaggcctt tgaggccgtg tagtttctgt ggtgcggatg cattaggcgg cgcaatgcgg  56880
gatctgccgg tcgctgttgg cgtgcattca cggcatctgg ggtgaccggg gccatcgggt  56940
ttacttttca cacgtagacc tgggaagttt gataggactg taccaggtca aggccgtgga  57000
tgcgcaggac cacgtccagt tccttagtga catccacgag gattgttttg cccactctgg  57060
ccacttgtgt ggatttaaat atgtacacaa gcgtaattaa cgagtcacag accccctgtt  57120
ccagattctg accggctgca agcgctgcct taaaggcctg gaagctgggt gggtaaatct  57180
gaccaaacag cacgctcgga ttcgtgatgc tgtggttgat ggcacacagg gggtcgcaga  57240
acaggtgctt gtggaagtct tgcggggtgc acatctgcag ccaggccctt agcctggggc  57300
```

atggcacatc cagcagcgtg ttttgggtct tgatgaggaa cacgatcctg tctaggattt 57360
tgatgttgtt gccgaacgag tcaagaatca ggctcttgaa gcggtcaagg gtgtccttgg 57420
cgtccgggtg ggccccgagg ctctcgcaga gtgggcagat ggtccgtgag gcattcttgt 57480
gccttagtcc aaacatgggg gccaggaggc aggggccctg cgaatggtcg ccagcctccg 57540
gtctggtgat ggccagggcc aactccgcca gctcatcgcc gctgtattcc gcgtttaaac 57600
cgatagcatg gtggcctggc cccccgagca ggtccgtccc ctgccacgta cctaatagta 57660
gtccacagta gtcggccttg gttgtaattt caggagagag tcctcccttt tcggccctga 57720
gaaatggatg ctgaactcgg tttctggtag gcaggtggca gcacagggcg gtgtacaggc 57780
ccctgccgac gtcccctggg acatcctggg aatctttgca ggttctgggt ccagggaggg 57840
taagaaaagt gggggtggtt ctgggccaca tggacttgaa gcagaagttg gccggggact 57900
ggccggtgag gatggatttc agaaactcca atttgtagta gccgaggttg gcatttctaa 57960
tcatgtcaga agaggacaca gggaggaagc accggcaaat gtaaaagtga agctggatgt 58020
caatggcaag aatcctggag ggcatgaaga gggaatccaa ccccccggcc atggggaagt 58080
attttatcag gatgtgtaaa aagtccatgc ctgtgatgag gctagagatc caggctcgtg 58140
gggcatttag acagtagtag cagagcaggg catagtcctc aaagaaggcc acgggggcat 58200
ctgagtgatt gaccagggtg tcgagcagat cacaaactcg gcaggtgctg gctggagaga 58260
gggactcgta ggtgtggacg agtggtgggt aggctatgcc ttcttccgcg ttggctggaa 58320
gataggagtg ggccatcaaa aggccgactg cctcgaactg gcttttcaga ttgtccacgg 58380
tccagggcac aaagtcctcc atctttggag ttctgcccgc gatctgtgcc acctctgtta 58440
cgccactcct cgtgaggggg cagctggaca gtctttttcc ggtcaggggg tttggctcgt 58500
ttgcgctcgt gactttgtga gccatgacac atctgggtgg caaggtgagg tcttctgggt 58560
ttttaatacc ggggtcggca ccagtttctg ggacaccgcc acaaggacaa ggtgggctag 58620
caagttctcg agtctacgaa gactccgggg gcagtctttt gagtttctcg cctatgatcc 58680
accccaatct cgccccccta attgcgccat ctgcctacgc gaggctgaac ctcctgaatc 58740
actgcatctt tcttgaggcg tttaaagaag agaatagtgg ccagggcctc ggtggggtcc 58800
agcgtgaggt cttattttg aaaagggata ttataaaaca ggtcattgct cggattgtgg 58860
cagccgatag caccctagat ctagtgaatc atggcgagcc cggaagagag gctcctagac 58920
gagctcaata acgtaattgt gtcatttctg tgtgactctg ggtctctgga agtggagaga 58980
tgctccgggg cgcatgtgtt ctccaggggc agctcccaac ccctctgcac cgtgaagctg 59040
cgccacggac agatttacca cctggagttt gtctacaagt tcctggcctt taagctgaag 59100
aactgcaact acccctcctc gcccgtgttt gtgatatcca acaacggcct ggccaccacc 59160
ctgaggtgct tttgcacgag gccgtcgggt ctcagatcgg gccagagcgg cccttgcctg 59220
ggtctctcaa cggatgttga cctaccaaag aactccatca ttatgctggg ccaggatgac 59280
ttcattaagt tcaaaagccc cctggtcttc cctgctgagc ttgatctcct gaaatctatg 59340
gtggtctgcc gggcctacat cacggaacac cggacgacga tgcagtttct ggtgtttcag 59400
gccgccaacg cccagaaggc ctcgcgggtc atggatatga ttagtgatat gtctcagcaa 59460
ctgtctcggt ctggtcaagt cgaggatacg ggcgccagag tcacaggtgg aggaggtccc 59520
aggcctggcg tcacgcactc ggggtgtctt ggggactcac acgttagggg gcgcggtggt 59580
tgggacttgg ataacttttc agaagctgag accgaagacg aggcgagtta cgctccttgg 59640
agggacaaag actcgtggtc ggaatccgag gcggcgccgt ggaagaagga actcgtgagg 59700

-continued

```
caccccatcc gcaggcaccg gacacgcgag actcgccgta tgcgcgggag ccattcacgg  59760
gtggaacacg tgccccccga gacccgggag acggtggtgg ggggagcatg gcgttattct  59820
tggcgcgcca caccttatct ggcacgggtg ctggctgtca cggccgtggc cctgctcctg  59880
atgtttctga ggtggacctg acgttgcagg cccttgggga gcgggggttc tccaggctcc  59940
tggatctggg gctggcctgc ctggatctga gctatgtgga aatgagggaa tttgtggttt  60000
ggggcaggcc cccagcttct gaggcggctg tggcctctac gccaggctcg cttttccgaa  60060
gccactcgtc cgcctactgg ttgtcggagg tggagaggcc cgggggcctt gtccgctggg  60120
ccaggtcaca gaccagcccc tcatccctga ccctcgcgcc ccatcttggc ccgtccctct  60180
tgtccctttc agtggtcacc ggtggtgggt gtggagccgt ggccttttgc aacgcctttt  60240
tcctagctta ttttttggtt gtgcggtctg ttttccccgc gttttccgat agaatagctg  60300
cctggatctg cgaccggtcc cctttctgcg aaaacacccg ggccgtggcc aggggttacc  60360
gaggcctcgt gaagaggttc ttggcattcg tgtttgagcg tagtagctat gacccccccct  60420
tgttgaggca aaactctagg cctgtggagc gctgctttgc catcaagaat tatgtcccgg  60480
gcctggactc acaaagctgt gtgacggtcc cgagcttctc ccgctgggcc cagtctcacg  60540
ccagcgagct cgatccccgg gagattcgcg acagagttac accagcgact gcaccttcgt  60600
tcgtggctga tcatgcctcg gctctattgg cctccctcca gaagaaggcc tccgacaccc  60660
cctgtgggaa tcccattcag tggatgtggt accgcctgtt ggtaaactcg tgcctgagga  60720
gtgcccactg tcttctgcct atacctgccg tctctgaggg ggggagaaag acgggcgggg  60780
gcgtagggga ggagctcgtg ggggccgggg ggccctgcct gagccgggat gttttcgtgg  60840
cgatcgtaag ccgcaatgtt ctctcgtgtc tgctgaacgt gcctgccgcg ggtccccggg  60900
cctacaagtg tttcagatcc cacgcctcca gaccggtgtc tggcccggat taccctccct  60960
tggccgtgtt ttgcatggac tgcggttact gcttgaactt tggaaagcag acaggtgtag  61020
gaggcaggct caattccttt agacccactc tccagtttta tccccgtgac cagaaggaga  61080
agcatgtgct gacctgccat gccagcggcc gtgtgtactg ctccaactgc ggctctgcgg  61140
cggtgggctg ccagaggctg gctgagccac cgagcgcccg ctcgggctgg cggccccgaa  61200
tccgggcagt gctgccgcac aacgcggcct acgagctcga ccgtggctcc cgcctcttgg  61260
atgccatcat cccctgcttg ggacccgacc gcacttgcat gcggccggtg gtcctgcggg  61320
gggtgacggt caggcagctc ctgtatttaa ctttgcggac agaggccaga gccgtttgct  61380
ccatctgtca gcaacgccaa gctccagagg acgcccgcga cgagcctcac ctgttctcct  61440
cctgtttaga ggtagaattg ccacctggtg agcggtgtgc gggctgccgt ctctatcaga  61500
cgcgttatgg cacgccggct gcccaagccc accctccagg ggaggctgga ggcggatttt  61560
ccagacagtc ccctgcttcc taaatttcaa gagctgaacc agaataatct ccccaatgat  61620
gtttttcggg aggctcaaag aagttacctg gtatttctga catcccagtt ctgctacgaa  61680
gagtacgtgc agaggacttt tggggtgcct cggcgccaac gcgccataga caagaggcag  61740
agagccagtg tggctggggc tggtgctcat gcacaccttg gcgggtcatc cgccaccccc  61800
gtccagcagg ctcaggccgc cgcatccgct gggaccgggg ccttggcatc atcagcgccg  61860
tccacggccg tagcccagtc cgcgaccccc tctgtttctt catctattag cagcctccgg  61920
gccgcgactt cgggggcgac tgccgccgcc tccgccgccg cagccgtcga taccgggtca  61980
ggtggcgggg gacaacccca cgacaccgcc ccacgcgggg cacgtaagaa acagtagagg  62040
gcacgaaaca tggtgtatgc actttattaa taaacaatta cagatacaaa aacttgagtc  62100
```

tctcgaggtc tgcgatgagg cggtgggtgg aacgctccag cttgcggcga agctggctca 62160
cgaagcgaga cagtactcgg ctagcctgac taagggtgag gctataacgc aggtcctgtt 62220
ccggggcggc ggtggataga gaggaggggg atccggaggg gaccactagg tcgccggagg 62280
tcgaccctcc tgtcaccacc tccctgataa tgtcttcaat agacagaaat tgggtgacca 62340
ctgagggagt gttccacagt aatgttgtct ggtcgctaga tggcgcgggt gaggccacgc 62400
tttgcgaaaa cgaaagtgct tgaaaaggcg cgggatagcg tgcgctaccg gatggcgggt 62460
aatacatgct atccttacat tttggcattt tgggcagctg ggaggcggcg gatgggggtg 62520
cttcttttcg cacggtgtat gtttggggac ccgcatgccg gtactgggat aggcgcacct 62580
cgggccgcgc gccaggctcc gagccggaat gcattggggg caatgggatt gcgggggatt 62640
gttgctgtct gctcctgaca gggagagaca cgcgcggcgg agatgcagcc gacggcgggg 62700
ccgcggtggg ctgcccccga ggacgggcgc cggccgccag cgcccccgtg gcctttggca 62760
cgggcctggc acccaccgct ttaattgtgg gggtgggcag ggcagctgca tcttggggcc 62820
tttgtgcttg cgtttttggg gggcgcggtg ccaatgcacc aactggggtg tgcgccgggg 62880
cggccaagcc ggaccccagg gcgggtgcct gggggatggg aaagccggac ggcgcttctc 62940
ccgggtcgaa cgctggagta gcggaggctg ctgcgccggc ggccaccacg ggcgcacggg 63000
gtcgcagccc gacggccgtg gggaggcggg tggcggaggg ccgaatctcc gcggcttctt 63060
cccggccccc ctgctgtttc ttctcccgtt gcatgataga atggccatag ggtgggtcct 63120
gagaggaggc ttgtgtgtcc tggggctgga gcccaaaagt cgttaaagat gccgctgatg 63180
gtgtgggagc tatgcctccc gtcgactggc cgggcttgta gggggctgag ggtggataac 63240
tgggcttctg tgaaggcacc aaccctggaa tctggatggt atgtttcttc tgtgaccccg 63300
aggcagtcga tggtgtagag tgtggagaca atgtgtagac gatgggccct tgttcagaag 63360
cccagggact tgagggggc tgttgtggtg ctggttgggg aaggagctcc agggaatctt 63420
tgggccatgg ccttggggag cttcccggag accggtctgg gctctcggaa gccctcgttt 63480
cggccccgaa atagggcctt gccatcaatc gggggcctgg gagagtgatg ggggcggcca 63540
atcccggggt aactgtcacg tcccgggggg aggaggtagg agacagccag tccctgggcc 63600 tgccagggc caccttctct aagaggggc tctgtgggct gggagggcca gaggcctcag 63660
attcagcagt agtgctcccc ttttccccct ggtccgtctc ccctcctccc aactgctgga 63720
gccggtcgga ggaggccggg gtgttatctg ctgactgaaa cccgtccccg ctgaccagtc 63780
cgtgccccac ccttgggggg aaaccggaga acagctcctg gacgttgcgt ggattcgggg 63840
gaagctggta tccaaccggc agtggaggat cttcgtgctc gtagaaggag gggttgagta 63900
catcggtcgg ccatcgtgag gccccggccg cgttaaagta gaactgcacg tccggcagat 63960
tgtgccgata ggtgaaacac ttccagatga tgtttttct gttggccagg atggccacgg 64020
tggggggcct ggcctcctta ggtttggcgg ccctggcctc ggtgagaagc tcgcgtagcc 64080
acacggcctg gcgtgcaaag atggacatct ctggctcgaa agactcggag tagccgtcca 64140
ggtcctgcag aaaattcagc gagatggtct ccaccaggga ccggaagggc tcagagtgcc 64200
cgtcgcagta gaggaggga gcaacgaccc tgacctgtcc cagggtcttc aggttaaaca 64260
gatattgaga ggagacaaag agagttaggg gccgaccgag gaaggccgcc gccacggccg 64320
cctcaaaaac ggagacgggg atggtgtcac cggagcccct cttaggaccg gtaatgggag 64380
tgccataagg cataagattt ctcagggccc ggccggtaac ggtgccgtag gaagacgggg 64440
tttcgcgggg gacctcgagt ccctccgccc tggggagctc ttctccgcgt gtataggcct 64500

-continued

```
gcttcacaaa gtcgcgcagg tagtcctgaa atgcgaccgg gccctccagc gggcgcaatg  64560
agtgccagag ctgctgaagg gcctcggggg cgaagcaccg gcgtgcgagg agcagcatgc  64620
aggctcgggc gcgggccgta ctttggttgt ggaccaggcc caagaactcg gggtgcggcc  64680
agagggcggc tcgggtatcc atctcctccc aggcgtcctg gaagaagatg aagccggtgg  64740
gtggaccggc gatgcggtgg cgggtgaggc ggcgcgcgtc ttccccgtcg ttgctgccgc  64800
gggtggttga gggcatgccc cccctcccgg aggctggact cctgaccagc ctgtaggtga  64860
ggaccgagtc cgacaggagg tctcccaaac ccccatctct cgctagagcc gagaccaggc  64920
cgagtcctgc gtagaacgat ggggcgccca ggaaggcggc agcgtaggcc ggatgtgtgc  64980
cgaccagcag cgccatcatc tcccgttgtt ccaatagaat aacttcccgg tctgtggccg  65040
gggctggata agggggggtga ttcctagagg cgatgagact ggcgtgcgct aaaagtgtca  65100
tggccacaat ggggttgtct gccaggtctt ccatcagggc tttgggcgca gagacgtatt  65160
cccgaagcag ctccccggcg ttggactcca cgtcgggcca ggtgtcccag taggagtcgg  65220
cggcggcggc gctgaggcgg gcggaagcta cactggccag ggttcttctc ctcctctctt  65280
ggtcatcctg cgggggacca atagcttggg ggcgtccggc tggggtcagg gaaaaggcct  65340
ctgggttctc cagcacggtg ggcatgacat attccagaaa gttgtggtag acggggatgt  65400
agttgagcgg ctcctgggtg tctgcggaga cgtaggccgg gttaaggggg tcgcagggag  65460
actctgtttc cagccagagg gtgccggcgt atttcgccgg ccctgccgcc gccagaaatt  65520
gtgcccgccg ggtcggggct ccattgcccc atccagttgg tggtgccgaa atcgtgatga  65580
ggaggggcag gttgttggtc aagggatgct taacgaaaac ggtaggctgg gcggtctcgt  65640
aaaaagccag gaaactctgc ttggccgagg catagcgcag cagcttgtcc ttgaggaggg  65700
catactggga gccagccgag gccccaagcg ccaggcccct ggcagcctcc accacgatct  65760
tgagctggcg cgggtcggtg tggcccctgg cctgggtgac cagatcctgc agcgttccct  65820
gcagctggga ctcttcctgg gcctcctgga tgatggcctc cagtcgggag aggcgccttt  65880
tccagtctgc gacggtctcc ttgccccccg cgacccgctt ggggtccaac gtggccagag  65940
ccaacctcag ctcctccatg ccatccatgg agttctgggc catgccctcg acttccagga  66000
gccgtgttag ctcatgaatt tcaccgtcag ccgcagcggc taggttcagc caggcacccg  66060
cgcccccagc taaggccagg gctccttcgg aaagaccccg cacggcctcg cagatgcccc  66120
ggatccactt ggcggctgcc aggatttcc ggtagggcca tgagccgttc ccggccgctg  66180
cccgggccag ggcggcctcg aggggagcct ggacaggggc tttgggcggg gagggaagca  66240
ggctccggag ttcatcgtcg gggcttcgt cgcgtgacct ggagaggacg gcctccagag  66300
ccgtgtgaaa gccccgccga gtgcttgccg ccatctcgtg ggccttcgcc atcagggtct  66360
ggctctcccg gacctgctct tccagcgccc ggacctcggc cgcctcggcc tcggtcagca  66420
gctccgagaa gaagtccccc gtggcctgga ggagatcgtc ccgctctcgc cttgtcagca  66480
gctggggctt cttaggccag agcgccgagt ccgaggccag cctgggcggg gcggttgcct  66540
gggggatagt tggaggagga ggcaggttag cctggcctgg gtcattagtg gcttcgggta  66600
gcgtccgatc cacgtactcg ctcacgatgg ccgtcagggc agcctcggct gctcgtcttt  66660
tttccagaag cccggccagc ccccgctcgt actccgcgta gggggcctcc agatccgtgt  66720
tgaccaccgc tgatttcatg tccggggact gcagggcctg gcgcgtctgc gcgagggccg  66780
aacggatggc atcggccgcc gtcctggcgc gaaagagggc cccggccgct tcctccgctc  66840
ctcgccctcc tcctccttct ttggcggtag ccgcgggggt ggcgggccaa gcgtccagtc  66900
```

tggccagagg gccggtctcg atatccgtga accagccggg ttccgcggcc tccattctct 66960
ccgccgcacc accatcgtcc acgagcaggg atcgcagtct ctccctcctc accctcgtta 67020
ttcccaatag catagcggca aggatctgtg tgagggagtc caagatgtcc gtgtttctgg 67080
ctactgccgc cgctgctgcc gcggctgagt ccgtattgtc tggcagcagg gaggccagca 67140
gggtgttcca gtcatcgggc gaagtgggag cgggctctgg gcgtgccccc agcgccttcc 67200
taattctggc ccaggcctca ttcgcctctc gcgctcgccg ctcctgcctc tccttgtctt 67260
cctgttctcg gagcttctcc ttttccttgc gcccggtctc cataagctgc cgcagcttct 67320
tctcatactg tcgcttgagc tctttgttgg gggcagtgtc cagaaaggcc tcgagctgtt 67380
cctcggtggc gggcttaaag ccttcggcct ccaggcgcca ggcctgcacc tccttctgtc 67440
tgagctgatc gttgttgtta ttcttcaatt tctgcaggta acttaggaag cgtttcttga 67500
gcttccctgg gatgagcgtt tgggagagct gattctgcag cccagagagt agtctcaggg 67560
catcctctgg agcctgacct gtgatcgtcg catcatagac cgccagtaga cctgggagca 67620
gattcaccgc cgcggccgtc tcctttaagg tgctgtgagt agcaaaattc tgcaaggcca 67680
ctaggcgcgc tggctccagc gtcagccggt tgcccatctc gaatgtgtgc agggcctctg 67740
agaccatggg gtccaggatg cggtcaatgc catcctgcac ctcagggtca aggaccggca 67800
agtcacgata gaggtggtct atgctctcct cgaaggaggc aatgtagtta tcgatggtgt 67860
agaaggtgat ggatttcagg atgttcatca ggtacttttt ggagcgaaca atctgctgta 67920
tagtgtcacg taggcggatg tacgtggggt tctttgcggc cccgactatc gaccctgcat 67980
ttgcgatgta cttttctatg acggggatgg tgagggccgc ggtgtcggcc agcggtggcg 68040
tggcttcggg gttgtcgtgg ttggcgggtg tcgcagaggg agaggcggga gagatggggg 68100
cgcctggggc cgaggccaca ccggccaggc ccaacattgc ctcgatgtcg tccaggatgg 68160
tgcggaggcg cttttcgttt tctctggtgg tctcgagctc cttctgtttt ttcgcgactg 68220
tctcaaactc tggaaggggg gcaatgctgg ggtcgtcctc ctcaactcgc tccaggggcc 68280
aggggatacc gctcatatca ctaagggcgg tgcccaggta gaggagctcg cgatagtccc 68340
attcaatgga cgtgtaccgg atgtttagga gaggcaggga ggcgatgatc tggcatgtgt 68400
gccgcaggtg tgtcaggagg tcgtcaaaat ccatcactgt tgggaggctt gggtcctcaa 68460
ggtaggagag ataatcggag gccgccgagg ccaccttgtc cctgatgtcc gccgtacacc 68520
tgcgcacgtg cagggccgca ttcttggacc ggacggccac gttgtggaca aagggggca 68580 ctgaggcggc gggagggcc ccatactcta tcgctgtcaa cagcgccaaa aagcggacgt 68640
cctcctcatc taccccagcc tgttgtctgg ccacggccgt tcgggcggcc tccgccaggg 68700
ataggaggcg cttccagctt tcgtcgtcca ggaccaaggg gacgtccacg tgcgggcccc 68760
tgtagatgga attatcctcg ggttctcctc ctccttcccc cgcctcctga tctccgcccg 68820
agagcaggtc ggtcaggcgt ctgcgggccg cctccaggtc aaatttcca tcgtcgctct 68880 cggccagctg gggaatttca gccagcatct tagcaccggc atctacacgg accgcgtcct 68940
tcgtggccag ggacggcagg caggcctcca gctttgcggc caggtgctta tggaactctc 69000
ccgctcttcc cttgttttct gatagcatgt ttgcgaggtt ttggatgtta agttcggaag 69060
tgagcagttg ctccaggtcc agcgtgggga cctgcagatg tcccgaccag tcctttaaga 69120
attccagcag atttagcaca gacgatcggt ccctactcct tattagcccc tgctcgagga 69180
ccactgtcac aagaagatag tctatcatgc tcaaggcatc tgcctctggc acttcccggt 69240
tagaggccgg gtcgtagacg atggcctgtt cctggtaggt atgtccggct attctcgcaa 69300

-continued

```
tgttgctctc gaggggcaca aagtccatct caggagtctc tatgtcaaag gtggtctgat  69360
agtattggct cctggcggtg tccagtgtga tgggggacgt gggggcactg gatcccgatt  69420
ccaggctgtt ggagaacact tcatcttcga acatgtcttc atcctctgtg gtggggatat  69480
cggaggctaa gtcgctctcc gcttcttcag agtcggacat ggataggaaa ggctcctcta  69540
ggtcagacag gtagcggacg aggccagaac ccccagatgc atcatcccca aaggagggct  69600
gctgcccgaa gggaggtgat ggggatatct ccgttccagc cctgtcagcg gccgggggat  69660
ggtttttttc tggttcgagt gtcgtggctg atggtgggag ctgctgagca ggaggaggag  69720
ccggggtagc tgatggcagg ggctgctgct gaggaggaag aggagaagga gcccgggcgg  69780
ctgatggcgg gggctgctgc tgaggaagaa gtggagaagg agccggggcg gctgatggcg  69840
tgggctgctg ctgaggaaga agtggagaag gagccggggc ggctgattgc gggggctgct  69900
gctgagttgg aggaggagaa agagtcgtgg tggtgggggc tgctgctgca gtcggggaag  69960
gggatggggt ggtcagaggg atttttgggt tcgagggagc tgcctgtggc agagggatgg  70020
gtatttgcaa agggaggcga ggagatggag tgactgaagg agcgatagtt gagactggcg  70080
cggggtgggg tgtcggggag gcgggtggtg attggtgagg gatggggatt actggagggg  70140
gaaggcgagc tgctgaaggg gggcgatggg gcggaacgtg ggtgcgtggc agctgatcat  70200
cctctgtgtc agtggtggag gacagaggga ggcggcggcc ggaggtgggc ttcttgtggg  70260
ggctatcttt gcccaatccc tttttcctct tgggagtctg aggcgctgcg ccgctcgacg  70320
cccttggtgg cgtggaggga gcggggaccc cgggggtgtg acctaggccg gggatgggga  70380
tgaagagggg agggctggag gccggggccg cggaggccgg ggccgcggag gccggggccg  70440
cggaggccgg ggccgcggag gccggggccg cggaggccgg ggccgcagag gccggggccg  70500
cagaggccgg ggccgcagag gccggagacg acggcgggga gttggtcttt gcaggactat  70560
acctggcggc agggaatgag tcggatgtga aagatcgaga gggcagtggc ctgaggttat  70620
acggtattat tcgccgttca aacggtagca tgacgggagg gctgctatca gcaccgggcg  70680
tccccgccgc ctccccatca ctggacacaa gctcgggccc caccaggtca aagccgctgc  70740
cgttggcctc ataaaagtca tacacgccat agtgttccag cataaagatg cgggggtcct  70800
ctgtctcaaa ggcctcgggt agaaaataga gatgcacgca agtgtactgg gcccctggtg  70860
cccccacgta ctgcaggatg tcgtgcgcat aggtgctgac tctgacatgg gcgggggtgc  70920
ccggggccgc atccttctgg cagtggggt caaacaagta gaaggagcca tctgtctcga  70980
tgatgatggc ccccgcgtag atgtcgcaga tgtagaggat gaactgggcc accccgttgt  71040
aactgccgtg caggacctcg gccagggact gaacaactgc cgagtttgcg atctgggcag  71100
ggaataggac gaggccaaag atctccgccg agcggtatat gtgcacgcgc ccaccgcccc  71160
tcaggaccac ggagctgggc acgtccgtca actgggccat ctcgtgcccc ttgaggatgc  71220
cgctctggcg catgagggca tccagccgcg ccccctcgtc caggacctcg tccagctcag  71280
ggcgggaggt cagggggcgg ccggccagga agctcttgac caggtagagg acgcagttgc  71340
tgacgcactg gatgccggca aagcggccaa acttgcagtg ggcctggttg cacgaggccg  71400
tgcctaggat gcggagggcc gagcctccac tcccgccccc gggggcattc acatccatgg  71460
tcctgattcc gcgcacgggg ccggttcccc gggtgcgctg gctttgcccc cagtcgccgt  71520
tactcatctt cggcggtggg gcggggagga cgccttgtcg cccccccttct ggtccggggt  71580
cttacgcggc tggcggcggc agccgccgag agataagggg ggtacgtgtg tgcctccgcc  71640
tctcctctgt ctgggccgcc gccgccgctt gcccgccttg aaggagaggg ggtagtccgc  71700
```

ggactgcgtc tgcgggggca ggaggtctca accttctggg ctcgggccgc ggtgtcgata 71760
tccgatggcc tttccctgtc ttcctcgtat gctccttctc ctcctcctcc cggcacgccc 71820
ctgagatctg cctcccctcc ctctccctcg tcctggtcgg aaaagtctga ggaggagaag 71880
gagaatgggg aggagtccaa aacggcacgc cacctgccgt ggggcggtgg tgacaggtcc 71940
cggctggccc ggcgcttgct cgcgttcctg ccgttaccca ggagaatggc cgcgagtttt 72000
ttggcgggga ggatgcggaa tggcgggggc gtttgtccca cgggtgaggg ggaatcgtcg 72060
gttagggccg gcacgaggtg gtgggtctgg acccgggccg tgcgagcaaa ggcggcgaga 72120
accgaggggc ttctgggggt gactgtgatc tgttccggat ttaggtccat ggcgggtgtg 72180
tatgttttaa taggggtggt ctctggcgcg gcaggatgat ggtcgaggac gtccaccagg 72240
gccttgcaga tgctcttgcc tagatacagg atgtcgtcca tgctgagggg aggtggggtg 72300
tctgctcccc cctgcggaag ccgcctgggt gcggggatga agacaggtgg tgggcgggcg 72360
tctcgccgga ctatggcctc ggcacgctcg gcgtcgatgg cgggtggctg gaacaggcgg 72420
gcgaatgtgt aatcccggaa ccggtaggcg acgctgcgcc tgagggcgcc cgtcaggctg 72480
tatcccagct ccagggcgtg ctccacccgc tcgttgagct cctcgagatc cggacgcagg 72540
ggctcgctgg tgtgggccca gagggggtga tccgcgatgc cccggctctc cctgagggcc 72600
ggcaccagga ggcgccttct gagggtggcc gtgtcggccg tggccagggc ccacctggcg 72660
gcggcgtccc ggcacacatc ctggatgccc tccacgacgc tctttagcgt ctggaggtcc 72720
gtggagtagt ggcgggggga ggatgaaacg ctcttttcct tcaccgctac caccgcctcc 72780
tcctcctctt ccgtcgccag agggatctgc accctcccgg tctctgcgtc gtacaggagc 72840
gggcgggagc acagcctcca agctgccccc gtcaagcgcg agatgtcctc cgagagggtc 72900
tcacccgaga ccagaaagcg gcgggtggcc aggcccaacg actccgccgt cgtgctgtat 72960
ctcagggtga agaggagtga aaagagggag gtgggccagg caagcggtgg tgcttccgcc 73020
gcccgctctg aagctgagat agtctcggag atgatgcctg agacctctcg gacggcgtcc 73080
atgatcctaa ggactgcgtc gtgggacgac agcccccagg ggcccccgcc ctcttcgtct 73140
tctgcaccct cggctcctgc gtccccggcc ttgccttccc cctctaagtt gagggggcgc 73200
agtccgaccg cctgggggga ctccccaggc atcggagggg ccccgtcata gatctcccag 73260
acggtggcgt atatgagctc gagaggacgg cgggcccggg tcagctcggg ggaagggagg 73320
gccaggtcgc tgccgaagga gaccagccag cgcagggcgg ccagagagcg ggttttgggc 73380
agctcgttgg agaggacccg gcgaagggcg ggccagattt ggaactcgat gaaggcggcc 73440
gggaagaagg ggctgtggac ataggccgga tccgcgcgcg ccgtttggcc ggccctcagg 73500
gaccggcagt atgcctcgac gtctgtccgc ggggccgccg ccaccgctgc cgtccactgc 73560
cttcttccct gctcgccggg gagtaggggg ggcttacagg ggagggccgg agccggggcc 73620
ggggcctgcc acaggcggct gtagcggacc catagcagag acctgaggag ttcggatgaa 73680
aggtcccccg ccacctgctc atactcggcc gcgggagggg ggacgatgaa gatgcgcaga 73740
ggggttacgg cgtcccaagg gtccgccgcc gcccccacac ccacagccgt cgcggcgggg 73800
gcggcggcgg gcgtagaggg gccgctggtg cgccgggctc gtctgtccac ggcctcggcc 73860
tccgcccgca ggtaggccgc ccgggccaca cgggcgaagc ggctcgtggg gctcgcggtg 73920
ggcagcagtc ggaaaaagtg cagggcaaag cccgatagac tctctaggag ggcggcggtg 73980
gcctcgagcc acctccaccg cgagcgggac acccggggca cagaggccag catcatggcg 74040
tagtcccccg ccacggtctc gttgagcccg gccgagagca gaaccgtggc cacctgctcg 74100
atggcggctg gagagaagga tgcccggctc cccgccgcct cctgcacacg agcggccagg 74160
gcctccatct ctgccgccat cccggccagg aaggcctcga tgaccgagtc tgggacgccg 74220
taagtctggt cccagagcag ggcctcgtac acatagtcgt aaaagagggc ccctgagggc 74280
tccaaaagcc ggagccgggc ggcgtcaaag gccaggacgg gcacagccgc gacggggggc 74340
gtttgtcccc cgctggcctc cgcgtacacg cccaggatct ctaccgcccg ccgccgggcc 74400
aggggcagcg aggccaccac gctggaaagt gactcggggc ggtgaaagag accaccaccg 74460
ctttcttcac cctctccccc gccggccccg cccccactgt gctccaccag ctccacggcc 74520
atggccttga tgtccgcggc cgtgggctga ccctgccctg cagccgccca ggggtagcgg 74580
ttggtctccg cgtatacggt gaccagccat ctccccagcg tcgttttcgc cgcgttaaaa 74640
gcgtagaatg acagcccctc ccgcgggaag gcgtcccacc gggccagata agtgtcggcc 74700
accagctctt ccacgaaggc aaaggtggcc gttgggccag agaccgcgag cacctccccg 74760
ctgccctctt cgatgatgcg ccggtacgcg gccgccaggg cccgggtctc tgcgatgagc 74820
cgagagccgt ccagcggatc gtcggtggcc ggagaggctg tcgtgggggg cagtgaggat 74880
gccagcacgt ccagggccgc ctccagatgg ccgaggccga agctgcgcct ggaaaaggag 74940
gccgcccgga gtaggtagta ggcgtggtgg cggaggaccg ccgccgggta agcgtggccg 75000
ctcatgaggg tgagagtatt taaaaaatcg cgcaccagca ccggctgggc caaatccccc 75060
agtccaaaga tccccagctc cagaggcatc agcgcgcgca ggcgggcagc ggggtcgtcc 75120
ccagacagca gcaactgacg cgtcacgcgg gcgagccccc cgtccacctc tgccaggggt 75180
ggctgggcgt ctgcccctcc gctaccgccg ctgctgtcac tctccatagc ggacgccatg 75240
aaggtccagg ggtccgtcga tcgccgccgt ctgcaacgcc gaatcgcggg gctgctgccc 75300
cctccggccc ggcgtctaaa tatttcccgg gggtccgaat tcacgcggga cgttcgtggg 75360
ctggttgagg aacacgcgca ggcctcctcg ctgagtgcgg cggccgtctg gcgcgcaggg 75420
ctgctggccc cgggggaggt ggcggtcgcc gggggtggca gtggaggggg gagcttcagc 75480
tggtctgggt ggcggccgcc agtctttggg gactttctga tacacgccag ctccttcaac 75540
aacgccgagg ccactggaac gccccttttc caattcaagc agagtgaccc gttctcgggc 75600
gtcgacgcgg tattcactcc tctctccctg tttatcctaa tgaatcacgg ccggggtgta 75660
gccgcccggg tcgaggcagg tgggggcctg acgcggatgg ccaacctgct gtacgacagc 75720
cccgcaaccc tggctgacct ggtcccggac tttgggcggc tggtggccga ccgccgcttc 75780
cacaacttca tcacccctgt gggcccccctg gtggagaata taaagagcac ctatctgaat 75840
aaaatcacca cggtggtcca cggcctgtg gtcagcaagg ccatccctcg cagcaccgtc 75900
aaggtgacgg tgccccagga ggcctttgtg gatctggacg cgtggctctc cggcggcgcc 75960
gggggtggcg gtggagtatg cttcgtcggg gggctgggcc tgcagccgtg ccccgccgat 76020
gcgcgcctct atgtcgctct gacctatgag gaagccgggc cgcggtttac gtttttccag 76080
tcgtcccgcg gccactgtca gatcatgaat atcttaagaa tttattactc accatccatc 76140
atgcaccgct atgctgtggt ccagccccta catatagagg agctaacctt cggggcggtt 76200
gcctgtctgg ggacatttag tgctactgac ggttggagga ggtctgcctt caattaccgt 76260
ggctctagcc tccccgtggt ggagattgac agcttttatt ccaacgtctc tgactgggag 76320
gtgattctct agacttaacg ggaggaaaca ggaggaggag ggggacaaga gcacaaaagt 76380
ggttcagtgg acacccacca cacagcatgg caacgaccag tcatgtcgag catgagctcc 76440
tctccaaatt gattgatgag ttaaaggtca aggccaactc agaccccgag gctgatgtcc 76500

-continued

```
tggccgggcg cctgctccac cgccttaagg ccgagtcagt tacacacaca gtagccgaat  76560
atctggaggt cttctctgac aaattctacg atgaggaatt cttccagatg caccgggatg  76620
agctggagac ccgagtctct gctttcgcgc agagcccggc ctacgagcgc atcgtctcca  76680
gcggctacct gtcggccctg cgctactatg acacctatct gtatgtgggg cgcagcggga  76740
agcaggagag tgtgcagcac ttttacatgc ggttagccgg cttctgtgcc tcaaccacct  76800
gcctctacgc gggtctcagg gcagccctgc agcgggccag gccggagatt gagagtgaca  76860
tggaggtgtt tgattactac tttgagcacc taacctccca gacggtgtgc tgctccacgc  76920
cctttatgcg ctttgccggg gtggaaaact ccactctggc cagctgcatc ctcaccaccc  76980
ccgacctcag ctccgagtgg gacgtgaccc aggccctcta taggcacctg gggcgctacc  77040
tctttcagcg agccggggtg ggtgtagggg tgacgggggc tggccaggat gggaaacaca  77100
tcagcctcct gatgaggatg atcaacagcc acgtggagta ccacaactat ggctgcaaga  77160
ggccggtcag tgtggcggcc tacatggagc cctggcacag ccagattttc aagtttttgg  77220
aaacgaagct gccggagaac cacgagaggt gcccgggcat ctttacgggg ctctttgtcc  77280
ccgagctctt cttcaagctt tttagggaca cgccctggtc ggactggtac ctgtttgacc  77340
ccaaggacgc cggggacctg gagaggctct acggggagga gtttgagcgc gagtactatc  77400
ggctggtgac agcgggcaag ttttgtgggc gggtctccat caagtccctg atgttctcta  77460
tcgtcaactg cgccgtcaag gccggcagcc ccttcatcct tttgaaggag gcctgcaacg  77520
cccacttttg gcgcgacctg cagggcgagg ccatgaacgc cgccaacctg tgcgccgagg  77580
tgctgcagcc ctcgaggaag tctgtggcca cctgcaatct ggccaacatc tgcctcccgc  77640
gctgcctggt gaatgcgcct ctggcggtgc gggcacagcg ggccgacacg caggggggatg  77700
aactcctgct ggccctccct cgactctcag tcaccctacc tggagagggg gcagtcggtg  77760
atggattctc gctagcccgc ctcagagatg ccacccagtg tgccaccttt gtggtggcct  77820
gctccattct tcagggatcc cccacttatg attccaggga tatggcctcc atgggcctcg  77880
gggtgcaggg cctggccgat gtctttgcgg acctgggctg gcagtacact gaccctccct  77940
ctcgctcgtt aaacaaggaa atattcgaac atatgtactt tacggccctc tgcaccagta  78000
gtctgattgg acttcacacc aggaagattt ttccgggttt caaacagagc aagtatgccg  78060
gggggtggtt tcactggcac gattgggcag gaacagacct ttctattccc agggaaattt  78120
ggtctcgcct ctctgaacgc attgtgaggg atgggctttt caattcacag tttatcgccc  78180
tgatgcccac ctcaggctgt gcccaggtga cgggctgttc ggacgccttc taccccttct  78240
atgccaatgc gtccaccaag gtcaccaaca aggaggaggc ccttaggcca aaccggtctt  78300
tttggcgtca tgtgcgtctg gatgacaggg aagctttgaa tcttgtcggg ggccgtgtct  78360
cctgcctccc ggaggctctg cggcagcgct acctgcgttt ccaaacggcc tttgattaca  78420
accaggagga cctgattcag atgtcccggg acagggcccc ctttgtggac cagagccaat  78480
ctcacagcct gtttttgcgt gaggaagatg ccgcgcgggc cagcacgcta gccaacctac  78540
tggtgcgcag ctacgagctg ggcctgaaga ctatcatgta ctattgtcgc attgagaagg  78600
ccgccgatct gggggtgatg gagtgtaagg ccagcgcggc tctgtcggtg ccgcgggagg  78660
aacagaatga gcggagtccc gctgagcaga tgccgcctcg tcccatggaa ccggcgcagg  78720
ttgcggggcc ggttgacatc atgagcaagg gcccagggga gggaccaggt gggtggtgtg  78780
tgcccggggg attggaagtg tgctataagt accgtcagct cttctcagag gatgatctgt  78840
tggagactga cggttttact gaacgagcct gtgaatcttg ccaataaacg tttattgcca  78900
```

-continued

```
tgtccaagtt gttgtacgtg cgtgatcatg agggctttgc ctgcctaacg gtcgaaaccc  78960
accgcaaccg ctggttcgcg gctcacattg tcctcaccaa ggactgcggg tgtctcaagc  79020
tactcaatga gagggacttg gagttttaca agttcctctt tacgttcctg gccatggccg  79080
agaagcttgt gaactttaac attgatgaac tggtcaccag cttcgagagc cacgacattg  79140
atcactacta caccgagcag aaggccatgg agaacgtcca cggggagact tatgctaaca  79200
ttttaaacat gctctttgat ggggacaggg cggcgatgaa cgcctacgca gaggccatca  79260
tggccgacga ggccctgcaa gccaagattt cctggctccg tgacaaggtg gcggccgccg  79320
tcaccctgcc ggagaagatt cttgtgttcc tgctgattga aggcatcttc ttcattagct  79380
ccttctacag catagccctg ctgcgggtcc ggggcctaat gcctggcatc tgcctggcca  79440
ataactacat aagtagggat gagctgctcc acacccgcgc tgcctccctg ttatacaata  79500
gcatgacagc caaggctgac cgaccaaggg ccacctggat ccaggagctg tttcgcactg  79560
cggtggaggt agagactgcc ttcatcgagg ctcgtggaga gggggttacc ttggtggatg  79620
tgcgagccat aaagcagttt ctggaggcca cggccgatcg catcctgggt gacattggtc  79680
aggctccctt gtatggcaca ccaccccccca aggactgccc gctcacctac atgactagca  79740
tcaagcaaac taatttcttt gagcaagaga gttccgatta caccatgctg gtggtagatg  79800
acctttgagt cagggtggct acttgctcag gtttctgggc ataaattctc ctgcctgcct  79860
ctgctctggt acgttggctt ctgctgctgc ttgtgatcat ggaaaccact cagactctcc  79920
gctttaagac caaggcccta gccgtcctgt ccaagtgcta tgaccatgcc cagactcatc  79980
tcaagggagg agtgctgcag gtaaaccttc tgtctgtaaa ctatggaggc ccccggctgg  80040
ccgccgtggc caacgcaggc acggccgggc taatcagctt cgaggtctcc cctgacgctg  80100
tggccgagtg gcagaatcac cagagcccag aggaggcccc ggccgccgtg tcatttagaa  80160
accttgccta cgggcgcacc tgtgtcctgg gcaaggagct gtttggctcg gctgtggagc  80220
aggcttccct gcaattttac aagcggccac aagggggttc ccggcctgaa tttgttaagc  80280
tcactatgga atatgatgat aaggtgtcca agagccacca cacctgcgcc ctgatgccct  80340
atatgccccc ggccagcgac aggctgagga acgagcagat gattgggcag gtgctgttga  80400
tgcccaagac ggcttcctcg ttgcagaagt gggcacgcca gcaaggctca ggcggcgtta  80460
aggtgacact caatccggat ctctacgtca ccacgtatac ttctggggag gcctgcctca  80520
ccctagacta caagcctctg agtgtggggc catacgaggc cttcactggc cctgtggcca  80580
aggctcagga cgtgggggcc gttgaggccc acgttgtctg ctcggtagca gcggactcgc  80640
tggcggcggc gcttagcctc tgccgcattc cggccgttag cgtgccaatc ttgaggtttt  80700
acaggtctgg catcatagct gtggtggccg gcctgctgac gtcagcgggg gacctgccgt  80760
tggatcttag tgttatttta tttaaccacg cctccgaaga ggcggccgcc agtacggcct  80820
ctgagccaga agataaaagt ccccgggtgc aaccactggg cacaggactc caacaacgcc  80880
ccagacatac ggtcagtcca tctccttcac ctccgccacc tcctaggacc cctacttggg  80940
agagtccggc aaggccagag acaccctcgc ctgccattcc cagccactcc agcaacaccg  81000
cactggagag gcctctggct gttcagctcg cgaggaaaag gacatcgtcg gaggccaggc  81060
agaagcagaa gcaccccaag aaagtgaagc aggcctttaa ccccctcatt taacaccatg  81120
ttctcgtgca agcagcacct gtccctgggg gcctgtgtct tctgtctcgg cctcctggcc  81180
agcaccccct tcatttggtg ctttgtcttt gccaacctgc tctctctgga gatcttctca  81240
ccgtggcaga cacacgtgta caggcttgga ttcccgacgg catgcctaat ggccgtcctc  81300
```

tggacgctgg tacccgccaa gcacgcggtg agggccgtca ctccagccat catgctgaat 81360
attgccagcg ccttgatctt cttctccctc agagtctact cgaccagcac gtgggtttct 81420
gccccctgtc tctttctggc caacctgcct ctcttatgcc tgtggccccg gctggccatc 81480
gagattgttt acatctgccc ggctatacac caaaggttct ttgaacttgg gttgctcttg 81540
gcctgcacca tctttgccct gtccgtggtc tccagggccc tggaggtgtc ggctgtcttc 81600
atgtctccat ttttcatctt tctggctttg ggctctggaa gcctggccgg tgctcggcgt 81660
aaccagattt acacctcggg tctcgagcgg agacgcagca ttttctgcgc ccggggagat 81720
cattcggtgg catccctgaa ggagaccctc cataaatgcc cgtgggatct gctggccatc 81780
tctgccttga ccgttcttgt cgtctgtgtg atgattgtgt tgcatgtgca cgcagaggtg 81840
ttctttggac tctctagata cctgcccctc tttctctgtg gggcgatggc ctccgggggg 81900
ctgtacctgg gccattccag catcattgca tgtgtcatgg ccaccctctg caccctgaca 81960
tctgttgtgg tatatttcct ccatgaaacc cttggacccc tgggcaagac cgtgctgttt 82020
atctcaatct ttgtctatta ctttagcggg gtagcggccc tgagcgcagc tatgcgctac 82080
aagcttaaga agtttgtgaa cggacccctg gtccatctcc gtgtggtata catgtgctgt 82140
tttgtcttta ctttttgtga atatctgttg gtgacattca ttaaatccta acgaccggag 82200
tcctgtctct ttgtgttctt gggggacttg agttagctgt ctttcctctt attacattgg 82260
gctaacggga ggaaatgaac ccaggggtgg cagtggatgg ggtcatttat gggcaaaact 82320
cacaggacat gtttggggag ttagcattgg cgtcgggaaa cacagctctg gcagttataa 82380
ccgcaccagc taacaggaca tgtttggggg agttggcatt ggcgtcagga gacacggctc 82440
tgtcagttat caccgtacca tgagtgccat gtgtgtccag tgcctaatca ccgttcctca 82500
ttttgtgtgc ctcctcaaat gttccagaag tcggccacag gggaggtggc tgaattaggg 82560
ccttttccct cattccccca tgagacccac gtggcaggcc taggggctac attcgcctcc 82620
cacgtttccc ttcgcgtgag gcatccgata tgactgaatt ttcgcagtct cttttccctc 82680
ttcccttgtt attcccatag aattacagtg aggttacaca ggtggagatt cagtttaacc 82740
atttattgat ttaatccagg aacaaaaaac agtcctagtg acccagtgcc cggagagaga 82800
atggccctga caagtcggct gcatgatgca cttcggcagt cacgtgtgtg agtctccacg 82860
gcctctgtca aaagggagct tagcgtgcca gggttgtaat tcttgatgta gtggcccagg 82920
aattcaactt catcgtgtct ccgtctgcag ttggcgttaa tgtaggctgg ggctactgcc 82980
gcatatgctg ccaagagaca gaggggctgc ttcacatatg agctgctcag ggtctccacc 83040
accttgtttt gacgggccgt ggcacaggtg atgtagaaga gttgcttcac aaagttgtag 83100
tctcgcgtgt taggaaggaa gcagggtgcc agctctttga gcttggtcag gatcaccttg 83160
ctaagactca tggcgcaggc caggaggatg tcttccgcgg gagctagggg caggtcgccg 83220
tggtaggtga tctcctggag ccaaaagatg gtctcttcta gcatggccac cagggtgcag 83280
agccccgcgt tctggatcgc ctgcatgcgt gcatccagcc atgtgtcctt gttggttgac 83340
ttggtgaaaa actcacgtag tgtcttgtag ctcctgcgca gctcgtgtct gggttgcact 83400
ttctgccagg ctccaatctc tggatgggcg gccaccgcca gcatcgactg taggaacggg 83460
tcttggatgg gctctagggt cagagaggcc agggggctgg gcaaggtgac aaatgtaatc 83520
ttggagacag gcttaaccag actcatgtca aaccacggtt tgttcggcag gggcctctgg 83580
ctgcgttctt gcctcgcctg cttccttgtg ctcctgccgg cccctcgaga ttctgaccgg 83640
ggacctctgg ttgctctgtt gcttcgggga gctcttggag acctcggtgc tctaggcacc 83700
ctgggggccc ttggggctct gggcgctctt gctcccgggg gcaggtgtcg gcgcttgcca 83760
taactttcat cggtgcagcc atggacctct ccgcgtcgcc ttttgtggcc tctggtgtaa 83820
gaggagttgc cagtctcctc cttctcgtcc tcgtccctgc acaggggtga gcgatgcaat 83880
gtgactgtct tgtcctgtag gtcccacttc tttctgggaa tcacaaacga tgccgaggta 83940
ggggttatga ccacgctgga gggccgtgca ggtatggcgt gggccggagt tggatcttca 84000
tcctcctcct ctgaggatga aatctctcca tctgtggagt gttcttcgct gccctccata 84060
gggtccagat cgcagtctgt gttggtgtct gagaccgctt cgagttccag aatgtggctc 84120
tctgcagagg ggagacaaaa ggtggagact gccttgagca cctctgtctc aggcaccgga 84180
tgcccccggc tccacggccc cggccactgg ccggtgtagc ttcttacctg cgggatcctc 84240
gttggaggaa atgctgctag ttcgggagag tctctgagaa ggaaccatct tgtctgtctc 84300
tacgacgggc tagctgggat gtagtgctgt cttgactggc ctcagcccta tttatgattc 84360
tggaggcggg cacgctgatg gagaaatggg cggtcggttg attggcccca cagcgaccgg 84420
cgaagcactg actcatgaag gtgaccgtga tggcctgtga tgtgtagtag agtaccagaa 84480
acaccctcac attcttggag ctggccctgt gggtatgcct caggcacgca aagttcctgc 84540
cccgggcatg gcacacctga actaagtttg gcccggtttg ctcaaacgtg acatggagaa 84600
actgggggaa tttgtcttct ggcacagctg ttgccagggt gctcatgagc gagggccaga 84660
tgcaggagct gacccaggcg acgagatcca ggcccagatg tccctctatc atggcgcaga 84720
cattctccac ggtggggggc agggtctcgc gggtcctctg gattagatag tcacgcccat 84780
catccgcgat gtggtagcag aaggttttgg gggccggcca gcccacgtgc agtgagtgat 84840
gtaagaggtt ttgaatgttg agggcattct taacatagct gtgcttgtct tcctcttccg 84900
gatgacagac aaagaggcgc agctgccggc taagaccacc gcccctgtcc accttgtagg 84960
tatgcggcag ccggatgcac cgcccggcgt gatacacgcc gctgtcaaaa agcggggccc 85020
caatctcttt gatcttgtga cgcatgcggc gcaggcaggc cgttaggccc atgagcttct 85080
gcagcacaga cacaaaccct tgtactgcgc ttgttcccac aatagcatgg cctctaggta 85140
ggggggtgat gacgcgaaag cccagttttc ccgtgcatat gcaaaagggg agcacatctt 85200
ccatattatc cgggtcggcg ggtggacaag ctgatttgaa aaaatagact gggtgggccc 85260
tggacactgg acccaggcgg cgcatgaggc gcagtacctc acgccgcacg gtccggcaca 85320
ggtcatagat ttcctccagc gaccaggggg ccccccttgat ctttagatcc aggtccaaga 85380
ccaggttgca gaccggaagc cggggattaa agtattcatg ccgggagaca aagagctgct 85440
cgctcaggct gttctgtgaa tagtacactg gggtgtagga gagggccctg gtgagacacg 85500
tgtctgggag gcggcagttg gtcggggtgg agacgacctc cgccaggtgg gatgagaagg 85560
ggtcagcggc tgtcattaca aagtagtgcc tgtctgcaaa atggcagagg aagaccggta 85620
gccgctgcac ccttcgaagg acggtgggtg ggaggaattg ttccttggga ttccactggc 85680
cccggcaggt ggcctggccg gccaagcata gaaacccttg aagcgtgggg gggtatgtgg 85740
gaccctcatc cgcgtgccag cgcgcgagct ccaccagctc ccgggccacg tccacactga 85800
gcccggccca ggcccgcatg agtccgtcat cggggtcggg gtcccacgtg tatggggccg 85860
ggggctccat gcggattttc agctgctgga cacgcacatg ctcagccagg taagtctccc 85920
gggtgaagta ggtgcgcatg tgctccgcaa agcccctgtc caggagcgag gggagcacga 85980
cgccccccga aggcagacac ccaatttctc ccatgctcgt taactgagag tatcgcttaa 86040
aggttccctc gttgaagcac tgtgcgtggg ccaaatagac gtagcgcacg agatcggccg 86100

```
aggccagggg aaggcgcccc ctgtaggcgt ctatcgtcct tgccacagcg cggatctctc  86160
gcgagtcccg ccgcagtttc tcgtgtgcaa agtgggcaaa agcctcggtc tgctccgccc  86220
atgccgagga gccaaagacc tcccccagct cggccaggga cgtgacggcg gccaggctct  86280
gaccagactc ggaagtaaat agctccgtga ggtgcgccag ggtctcaatc gtacaaggaa  86340
tgccccaaaa atagtaagca gccgtgacta gcacgaactg ggcctcgtgg gagccaaagg  86400
tgctaatgaa ccacctggcc gagatgttaa cgcggtagat gcggcgcaga cagcccacga  86460
tcttgggacg cagccacgcc acgcggcctc tggcatcccc ctgtggctgt ttcttagcgc  86520
tcagtgtgag cagttccacg aggggcgtga gcgagcgcag ggcccccgcg cgatctaggt  86580
aggtggatag acggtccgcg gtgagcggcg tgaggccgcg caggaagggg aaggcctcct  86640
ccgccggcag gtgcagcgtc agaaccaggc cgcagcggct ctgtgaggtc agccgcttct  86700
tgggcaggtg aagctgcagt tccacgagag aacccgccac gtggtggagg ggcgaggcgt  86760
tgtggcacaa acaaaacagg cggaagccct cgtcaggccg cgagaggatg gcatcgagga  86820
tggcctccgc aatgtcagtg tttgaggcca caagggcctt gatgacgacg gggggcggaca  86880
ttatttaaga ccgggaggcc ccaacggcgg gctaaacaga acgatggcct tctatctccc  86940
agactggtcg tgctgcgggc tctggctctt tggccggccc aggaatagat acagccagct  87000
ccctgaggag ccggagacct ttgagtgccc ggaccgctgg cgagccgaga tagatctggg  87060
cctgcccccct ggtgtgcagg tgggagattt gctaagaaat gagcagacga tgggctcact  87120
gagacaggtt tatttgctcg ctgttcaagc caatagcatc acggatcacc tgaagcgctt  87180
tgacgccgtc cgcgtccctg agagctgtcg tggggtggtg gaggcccagg tggccaagct  87240
tgaggccgtg cgctcagtca tctggaatac catgatctct ctggctgtaa gcggcatcga  87300
gatggacgag aatgggctca aggccctgct ggacaaacag gctggcgaca gcctggccct  87360
gatggagatg gagaaggtgg ccacggcgct caagatggac gagaccggtg cctgggcgca  87420
agagatctcg gccgttgtct catcggtgac cgccccctca gcctcggccc ctttcatcaa  87480
ctccgccttt gagcccgagg tgcccacccc cgtccttgca ccgcctcccg tggtgcggca  87540
gccggagcac tctgggccca cggagctcgc gttaacgtag caaccagact ccacaccaaa  87600
taaacatttt attggtaaaa caagggatat gaaggtgtca ttgacccgag gatccaaacc  87660
ccctcccctg tctcccctcg agcgcctcgc tcagcccact atcacccatg gccaggctcg  87720
gcacctcctc gaaggtgcag ctggcccacc taaagagaga tctggggcca aggacccccg  87780
cgtcactgtg gggctgtag aaggaggtga ggtggtgctt gtgaaggtaa acaagctgac  87840
agaagcgccg gtacttgtta aggaacacgg tctggtcact aaagttggtc aggctgacgt  87900
ccaccccacc ccggcgccac ctgcagggct tcactagaat accctgcatg gccaggcccg  87960
acctgccaaa gattgtcggc ctgtggtgag ggatagaagg ggggggcacg gtgagtgtca  88020
ctgagacggt ctgatggggg aagagggcca ggtcctttgg caaagagacg tccaggccca  88080
cgtccccggg gtactggggg tggttgatgg gacccttgtc ctcctccatc tggggggtgg  88140
catatctgaa ggcagccagg tggattttga gctccgatgg acgcagcgtg gagttgtagc  88200
gccgctgatt ctggaggatt agccggagtt cccccgtgta gccgggatcg atgatgccaa  88260
catgagacgt gaccggacgg gaggtgctgc cccacagcat gagcccatga ccctcgggtg  88320
ggcgggcata gaggcctagg tccacagttg tggtcttcat cgggcgcagc aggatggtgg  88380
tcttgttgac caaggtgagc cgccctacac tagcctgctg gagcaacagc ttgtcattct  88440
ggaaggcgta gcgtatgtgt ggacaggcct ccatggtgat gatctaacag acagggacgg  88500
```

cggcgctata tataagagcc caagacccgg ctctctttac tgcgaaatgg ggaaggtcct 88560
aagaaagccg tttgcaaagg ctgtgccact gctcttcctc gccgccacct ggcttctgac 88620
cggggtgctg ccggccggcg cttccagtcc cacaaacgcg gcggcggctt ccctgactga 88680
agcccaggac cagttctact cctacacatg taatgcggac acattctcgc cttctttgac 88740
cagctttgcc tccatctggg cacttctgac gcttgtctta gtcattatag cctcagccat 88800
ctacctgatg tacgtctgct ttaacaagtt tgtgaacacg ctgctgacgg attagatggg 88860
gatatttaaa aggggcagca atctcggctg tttgtacttc ttctctgctc gttaaaccaa 88920
tagcatgtca gctccacgca aagtcagatt gccttctgtt aaggctgttg acatgagcat 88980
ggaagacatg gccgcccgcc tggctcgcct ggagtctgag aataaggctc tgaagcaaca 89040
ggtcctcaga gggggtgcct gtgcctcgtc tacctctgtt ccttctgctc cagtgcctcc 89100
gcctgagccg cttacagctc gacagcgaga ggtaatgatt acgcaggcca cgggccgttt 89160
ggcgtctcag gctatgaaga agattgaaga caaggttcgg aaatctgttg acggtgtaac 89220
tacccgcaat gaaatggaaa atatattgca aaatctgacc ctccgcattc aagtatctat 89280
gttgggtgca aaaggccaac ccagccctgg tgagggaaca cgaccacgag aatcaaacga 89340
ccccaacgcc acccgacgtg cccgctcccg ctcccgggga cgtgaagcaa agaaagtgca 89400
aatttctgat taataaattt ttattgactt tatacatagg tctcggcgtc atcatatggt 89460
ggggtggtgt aggtatggga tgtagacaag ttacgcctaa aggcgcagtc cgccatgacc 89520
agcagcagca gaagggtcag cacagccaga gaggcccact gcagtactag catggagagg 89580
tttgagaatc tgggctggga cgttggcggg actggcacgg tggcttgggc tgtggtaacc 89640
ggtgggctcg taaaagtcca gcggggccgc agtttgctag aagtgctggg aggtagatag 89700
gtggtcgcat tgtatctcgg tcttggcgta gttgaatcac cgccgtaatc tgtggtgggc 89760
tctgtacttg tccgggctcc atgtcctgtg gtgtgctttc caccggtggt agaattggcc 89820
tttccacctg ttgaggtgac cgtgggaacc gccgtctttt ggccactggg ggcctggggc 89880
gacgttgcat tttggggggg cgtgcctttg gtgacattaa cctcccccgg ttttgtggat 89940
gtggaactgt ttccagggcc tgacgcttgg ctggtggtgc ctgggcgggg tgctggcgaa 90000
ctggtggaca catgatgtgt gctgatagag gctggtgtca cctgtgttat attttcacca 90060
cctgttgggt gagcggaggt tagtaaaggc atatgtgacg ttgaattgtc actggtggag 90120
gggctgagtg tctctgggtt tgaactgggt ctcagtgaca tggaagaggt tgaacttgaa 90180
gttatgttat gttggcctgt ggtaacagca ctggttgcat tttttggttg gctggtaact 90240
actggggtgg gacttgttcc tcctaaggtg tggttggtgg catttgcctg tggacttgtt 90300
tctcccacag tagggccggt ggcatttggg gttggggtag tcactgctga ggtggggctt 90360
gtttttccca aggtggggct ggtggcattt ggggttgggg tagtcactgc tgaggtgggg 90420
cttgtttttc ccaaggtggg gctggtggca tttggggttg gggtagtcac tgctgaggta 90480
ggacttgttt ttcccaaggt ggggctggtg gcatttgggg ttggggtagt cactgctggg 90540
gtggggctgg tggcatttgg ggttggggta gtcactgctg gggtggggct ggtggcattt 90600
ggggttgggg tagtcactgg tgaggtggag ctggtcatgt cgggggcctt actttctgtg 90660
ccgttgtccc atggagatgg acttggtgtc accggtgatg cgcctgacgt tgtgccggct 90720
ggtgttgggc tggtgacatc cgcggtggat acagtggggc ctgtgcttgc aggtgcggtg 90780
aggttggtag gcacgtgagt agagctgggt agacctgtcg ttgtattggg atcagcaaat 90840
ccagttgtat tcaaggtagg ggaggtggtg gtgctctcgg gtgccttgga gaatataacc 90900
ttgtgggttg ttgtggtggc attggtagcc gttcgtgtga taatgagtgt cttgggggcc 90960
gtgccaagac ccgagacagt aatgtcaaat gtccgattgc tcgcaaatgc accagaaata 91020
ttttcacaac ccgaaggtgt ccccgaggtg agagtccatt tgcacttaaa gtcagtttca 91080
gtgttgtttg gccaggccca aaaggcagtc actgtaacat ttggcgagtt tgcgtcctca 91140
gaagtgacca ttggcactga ataggtagca ttgtcaccca catatgtgat gtctgtggtg 91200
tttgtcggca tgtcctgtga agctggaatc tcatcagaga acacaatgtt ggactgaatg 91260
cagtaatctc ccccgctcgc cttcggtcca ttcccagagt aaaacacgta caggatactg 91320
ttattgccaa gaaatcgtga cactggacgt ggtgtcagac gcaggctgta tgcataccct 91380
gtaccaggta ttggggtggc cacgggactc gttgatgtga gaattccgcc gctgggaaca 91440
tggctctcgt atccactgca ggtgatgtta aatttgttgt ctccgggcag aacttgtgaa 91500
atttcgccat cctccataat acactcaata tctatctcat taccgagcat ttctgttttt 91560
acgctgaaat tcgagtcttg agctgacgtt ggcaaactta agggtagcgt gacatccagc 91620
ccctgtgccc tcactactgc cgttatattg gtagaattac agttatccca ctttatgtat 91680
ggcactgttt ctggtatcag gtacacgggg ttttgcattt ctgcatggtg gcaccacatg 91740
gttccaaaca catcttgaaa gtagacatct acagattcca ggcttacttg ttgctcctct 91800
ccggtggtga cgttaattgg aagcttctta gaccgcatag ttagagccaa ttctcctgca 91860
ccaaggagct ccagtagaaa gagattggtg gcattttctg agccaccaaa tgcacctcga 91920
ggttggtaga cagccttcgt atggggtgtc agctggccaa agtcaagatc aagttgatgc 91980
tttttgcccc cgacatcgaa attgatagtt acattgacat ctgccgtgca aacattgcat 92040
gtggggtaaa atgggaattc cggaatctca acattgaaaa aaccaggatc ttcacccgtg 92100
agatggatca ggctctggat ggtgtactga cacacaagca aggctgcctc cattgtctcg 92160
gcaccgattt ctaggcagca tcctctttaa taggtacaag gggggtgcgg tgttggtgag 92220
tcacactttt gttgcagaca aaatggacaa ggacaggccg ggtcccccgg ccctggatga 92280
caacatggaa gaagaagtcc catctacctc ggttgtgcag gaacaggtat cggcgggaga 92340
ttgggaaaat gtcctcatag agttatcaga tagcagctca gaaaaggaag cagaagatgc 92400
ccacctggag ccggcccaga agggtacgaa gagaaagcgg gtcgatcatg atgccggtgg 92460
gtcagctcca gcacgaccca tgctcccacc ccagccggat ctccctgggc gagaagccat 92520
tctccgcagg tttccactag atctaagaac acttcttcaa gcgattggag ccgcggctac 92580
ggtgagcatc cctatggcct aagtgtgtga tgtgtgtttt tacccatcac acaacaacaa 92640
ggtaagtaat ttgttgccgt tggtttcagc gcatcgacac acgagccata gaccagtttt 92700
tcggatccca gatttcaaat accgagatgt acataatgta tgccatggcc attcgacagg 92760
ccattagaga tcgtcggaga aatccagctt ctcgtagaga tcaggccaaa tggagactgc 92820
aaaccctggc cgccggatgg cctatgggtt accaggcata cagcagctgg atgtacagct 92880
acaccgatca ccagacgact cccacattcg tacatctcca ggcgacactt gggtgcacag 92940
gtggccgtag gtgtcacgtg accttttccg ccggcacctt taagctgccg cgatgtaccc 93000
ccggggatcg ccagtggttg tatgttcaga gctccgtggg taacattgta cagagctgta 93060
atccccgcta cagtattttc tttgactata tggctataca caggagcctc acgaaaatct 93120
gggaggaagt tttaacacct gaccagcgtg tttcatttat ggaattccta ggatttttgc 93180
agagaacgga tttgtcctat atcaagagct ttgtcagcga tgccctgggc accactagta 93240
tccaaacacc gtggatcgat gacaatccta gcacggagac ggcacaggct tggaatgccg 93300

```
gctttctccg gggtcgtgcg tatgggatag acttgcttag aactgaaggg gaacatgtcg  93360
aaggtgctac cggtgaaacg cgagaagaaa gtgaggacac ggagagcgat ggagatgatg  93420
aagatcttcc ttgtatagtg tccagaggtg gacctaaggt caaacgaccc cctatattta  93480
taagacgtct gcacaggttg ctgctgatga gagcgggcaa acgaacagaa cagggcaagg  93540
aggtactgga aaaggcccgt gggagcactt atggcacacc taggccgcct gttccgaaac  93600
caagaccaga ggtcccacaa agcgacgaga cagctaccag tcacgggtcg gcgcaagtcc  93660
cagaaccccc aaccattcac ctagcagctc agggaatggc atacccatta catgaacaac  93720
acggcatggc cccgtgtccg gtagcacagg ccccacctac gcccttgccc cctgtatctc  93780
caggggatca actcccaggt gtttttagcg acgggcgagt ggcgtgtgca ccagtacccg  93840
ccccggctgg gcctattgtc cggccctggg agccatccct gacacaggct gcggggcagg  93900
cctttgcacc cgttagacca caacacatgc cagtagaacc cgtccctgtc ccgacagtgg  93960
cacttgagcg accagtttac cccaagccag ttcgtccggc acctcctaag attgctatgc  94020
agggccccgg ggaaacttct ggcattagac gcgcgcggga gcgttggagg cccgcacctt  94080
ggacgccaaa tccaccccgt tctcccagtc agatgtccgt gcgtgaccgt ctggctcgtt  94140
tgcgtgctga ggcacaggtc aaacaggcta gtgttgaggt gcagcccccc cagttgaccc  94200
aagtatcccc tcagcaacca atggaggggc cgttggtacc agagcagcag atgttccctg  94260
gtgccccctt tagccaggtt gctgatgtgg tccgggcacc tggggtaccg gcgatgcagc  94320
cacagtactt tgacctcccc ttaattcaac ccattagcca gggggcaccc gtggccccgt  94380
tgagggctag tatgggcccg gtacctccgg taccggcaac acagccacag tatttttgaca  94440
tccccttaac tgaacccatt aaccaggggg catccgcggc ccattttctc cctcagcaac  94500
cgatggaggg gccgttggta cctgagcagt ggatgttccc aggtgccgcc ctgagccaga  94560
gtgttaggcc aggggtagcg cagtcacaat attttgacct ccccttaact caacccatta  94620
accatggggc acccgcagcc catttcctcc atcagccacc aatggagggg ccgtgggtac  94680
ccgagcagtg gatgttccaa ggtgcccccc ctagccaagg cactgacgtg gtccaacatc  94740
agctggatgc tttggggtat acactccatg gtcttaacca tcccggggtt cccgtgtctc  94800
ctgccgttaa ccaatatcat ctcagccagg ctgcctttgg gttacctatt gatgaggatg  94860
agagtggcga ggggtccgat acctccgagc cgtgtgaagc tcttgatttg tcaatccatg  94920
gcaggccctg ccctcaggcc cccgagtggc ctgttcaaga ggagggtggc caggatgcca  94980
ccgaggttct tgatttgtca atccatggca ggccccgccc tcggaccccc gagtggcctg  95040
ttcaagggga aggtggccaa aatgtcacag gccctgaaac tagaagggtg gtggtgtcag  95100
ctgttgttca catgtgtcag gatgacgagt ttccggatct acaagatcct ccagatgagg  95160
cctaagcaaa ggtgtagaag tgtgtccccc tccattccac ccactgataa tacgcccgac  95220
aataaagttg atgatattga attccacacc tgcttgtgtt tgtgatttta tttcatattc  95280
catgagagag acctcgcata tttgcagaag ggtcactgaa acatcttatc ttaaaacagt  95340
tacacctgaa taatgaagaa agcgtggctc agcagagcac agcaagccga tgccgggggg  95400
gcatctggct ccgaggaccc accagattat ggagatcaag gtaatgtgac acaggtggga  95460
tctgagccta tttcacctga gattggcccc tttgaactct ctgcggccag tgaggatgat  95520
cctcaatctg ggccagtgga agagaattta gatgccgctg caagagagga agaggaacct  95580
catgagcagg agcacaatgg tggtgacgat cccttggatg tccatactcg ccagcctaga  95640
tttgtggatg tgaacccaac gcaggctcca gtgatccaac tagtccacgc tgtctatgat  95700
```

-continued tccatgttgg taagaggcac ctagaacatt tccagatgtt tcgcttggat tttttggcca 95760
gtcttaattg attgtcattg gtttcagcaa tcggacctcc ggcccctagg cagtttattc 95820
cttgagcaaa acctgaacat cgaagaattt atatggatgt gcatgaccgt gcgtcacaga 95880
tgtcaggcca tcagaaaaaa accattacca attgttaagc agaggcgttg gaagctcctg 95940
tcatcttgca gatcctggcg tatgggttac cgcacgcata acctcaaagt aaacagtttt 96000
gagtcagggg gggacaatgt ccacccggtc cttgtgactg ctacgctagg atgtgatgag 96060
ggcacgcggc atgcaacaac gtacagtgct ggcattgtac agataccacg aatatcagac 96120
caaaaccaaa agatcgaaac agccttcctg atggcacgtc gtgctaggtc actttcggca 96180
gaaagatata ctttgttctt tgatttagta tcctccggaa acaccctgta tgctatatgg 96240
attgggctgg gcacgaaaaa ccgagtttca tttattgagt ttgtaggatg gttatgcaag 96300
aaggaccaca ctcatatacg cgaatggttc cgccagtgca ccgggagacc caaagcagcc 96360
aagccatggt taagagcgca tcctgtcgcc attccttatg atgatccgtt aacaaacgag 96420
gagattgatc tggcctatgc ccgcgggcag gccatgaata ttgaggctcc tagactgcca 96480
gatgatccta taattgttga ggatgacgac gaaagtgagg aaattgaagc tgaaagcgac 96540
gaggaggaag acaagagtgg aatggaatct cttaaaaata taccgcaaac actgccgtac 96600
aatccaacag tatacggcag gcccgcggtg tttgaccgaa agtcagatgc aaaatcaacc 96660
aaaaaatgca gggccatagt aactgacttt agtgtaatca aggccattga agaggaacac 96720
agaaagaaga aggcagccag aacagagcag ccaagagcca cgcctgaatc ccaggccccc 96780
acagtggtcc tccagcgacc acccacgcag caagagcctg gccccgtcgg cccactgagt 96840
gtccaggctc ggctggagcc atggcaacct ttgcctgggc cccaagtgac agcagttcta 96900
cttcacgaag aatccatgca gggtgtccaa gtacatggtt cgatgctaga ccttcttgaa 96960
aaagacgatg aagtcatgga gcagagggtt atggcaaccc tactgccacc agtaccacaa 97020
cagccccggg ctggcagaag aggcccttgt gtcttcaccg gtgacctagg catagagagt 97080
gatgagcccg cttcgacaga gccggttcat gatcagctac tgcctgcccc aggacctgac 97140
cctcttgaaa tccaaccact aacgtccccc accacgtctc aacttagcag ttcggcacca 97200
agctgcgcac aaactccatg gccggtggtt cagccaagtc agactccaga tgacccaacg 97260
aaacagtccc ggccaccgga aacagctgcc ccacgccagt ggccaatgcc cctgcgacct 97320
atccctatgc gccccttgcg gatgcagcca atcccattta atcatccagt gggacccact 97380
ccccatcaga cacctcaagt ggaaataaca ccatataagc ccacttgggc tcagataggg 97440
cacattccat atcagcctac accaacgggt cctgctacca tgctgttgcg ccagtgggca 97500
cccgccacca tgcagacacc accgagagcg cccactccca tgtcaccacc tgaggtgcca 97560
cccgttcccc ggcagaggcc tcgggggcg cccactccca cgccacctcc tcaggtgccg 97620
cccgttcccc ggcagaggcc tcgggggcg cccactccca cgccacctcc tcaggtgctg 97680
cccactccca tgcagctggc actaagggct cctgctggtc agcaggggcc gacaaagcaa 97740
attttgcgcc aattgttaac ggggggcgtc aagaaaggga gaccatcact taagttacag 97800
gccgcccttg agcgtcaagc cgctgcgggc tggcagcctt caccagggtc cggcaccagt 97860
gacaagattg tgcaggcgcc tattttctac ccacccgttt tgcagcccat acaggttatg 97920
gggcaagggg gttccccaac ggccatggcc gcctcagcgg tgacacaggc acccacggaa 97980
tataccaggg aaaggagggg agtggggcct atgcctccca ccgatattcc gccgtctaaa 98040
cgagcgaaga tcgaggccta tacagagccc gagatgccgc acggggggc ctcgcactct 98100 cccgtcgtta tcttggagaa tgtcggccag gggcaacagc agactctgga gtgcggagga 98160
actgctaaac aggaaaggga catgttgggg ctgggggaca ttgcagtttc ttccccttcc 98220
tcttctgaaa catcgaacga tgagtgattt cgcccatgta acaagaactg ggatgaaccc 98280
tggggcaaca gactgcgggg aggagggggg cagtgataag tcatgacaat tttagatgag 98340
gtagaaattt tgcatatttt cagacccacc atggaatcat ttgaaggaca gggggactct 98400
agacagtcac ccgacaatga gcggggagat aatgtacaga ctaccggcga gcatgatcag 98460
gaccctgggc cggggcctcc atccagtggg gcttctgaga gattggtacc agaagagtca 98520
tactcaagag atcagcaacc ttgggggcaa agcaggggtg atgaaaacag aggctggatg 98580
cagcgcatca ggcgaaggcg gagaagacgg gctgccttgt ccggccatct tttagacacg 98640
gaagacaatg tgccgccatg gttgcctcca cacgacatca caccatatac cgcaaggaat 98700
atcagggatg ctgcctgccg ggctgtcaag gtgagtatgc ctctaactgg gttcatgggg 98760
gccatctaag gcccacgtgt gacccatgtt tccattaatt ttagcaatcg cacctgcaag 98820
cgctatcaaa cctgatactc gatagtgggt tagacacaca acacatcttg tgcttcgtga 98880
tggcagccag gcagcgtctt caggacattc gacgtggacc cttggttgcg gagggcggtg 98940
tgggttggcg acattggctt ctaacatctc ccagccaatc ctggcccatg ggatatcgta 99000
cagcaacact acgcacatta actcccgtgc ctaacagggt tggggctgac agcatcatgt 99060
taactgccac atttggatgc caaaatgcgg cacgaactct aaacaccttc tctgccaccg 99120
tgtggacacc accccatgct ggaccaagag agcaagaaag atacgctcgg gaagccgagg 99180
tacgcttcct tcgtggtaaa tggcagaggc ggtaccgaag aatctatgat ttgatagaac 99240
tgtgtggctc tctgcaccac atctggcaaa acttgctcca gaccgaggag aacctttttag 99300
atttcgtgcg tttcatgggt gtcatgtcca gctgcaataa tccagctgtg aattactggt 99360
ttcacaagac aatcggaaac tttaagccat attacccgtg gaatgcacca cctaatgaaa 99420
atccatatca cgcgcggaga ggcataaaag aacacgtaat ccagaacgca tttcgaaagg 99480
cacaaataca gggtttatca atgttagcaa cgggaggtga acccagaggt gatgctacta 99540
gtgaaacgag cagtgatgag gacaccggta gacagggttc ggacgtggag ctagagtcct 99600
cggacgatga gctgccatat atcgatccca atatggagcc ggttcagcag aggcccgtca 99660
tgtttgtgag ccgtgtgcct gcaaagaaac cgaggaaact gccttggccc acgcccaaga 99720
cgcacccagt gaagcgcaca aatgttaaga cctctgatag atctgataag gcagaagcac 99780
aaagcacccc tgaaaggccg ggcccttccg aacaatcatc agtgaccgtg gagcccgccc 99840
acccgacccc ggtggagatg ccaatggtga ttctccatca accacctcca gtgcccaaac 99900
cggttccagt caagcctacg ccaccgcctt cccgtaggag aaggggagcg tgtgttgtgt 99960
acgacgatga tgtcatagag gtgattgatg ttgaaaccac cgaagattca tcgtcagtgt 100020
cacagccaaa taagccacat cggaaacatc aagacggctt tcaacgttca ggccgacgtc 100080
aaaaacgagc cgcgcctccc accgtgagtc cttcggatac tgggcctcct gccgtggggc 100140
ctcctgccgc ggggcctcct gccgcggggc ctcctgccgc ggggcctcct gccgcggggc 100200
ctcctgccgc ggggcctcct gccgcggggc ctcgcatact ggcgcctctt tccgctgggc 100260
ctcctgccgc ggggcctcac atagtgacgc ctccttccgc ccggcctcgt ataatggcgc 100320
ctcccgtcgt acgtatgttt atgagggagc gacagctccc ccagtccacc ggccgtaaac 100380
ctcagtgctt ctgggaaatg cgggctggtc gtgaaattac acaaatgcaa caagaaccaa 100440
gttcacacct gcagtccgcc actcagccta caacgcctcg cccatcatgg gccccatcag 100500
tctgcgccct ctcggtgatg gatgctggta aggcccagcc catagaaagt tcacacttga 100560
gttccatgtc gcccacacag ccgatatcgc acgaagaaca accccggtat gaggatcctg 100620
acgctcctct ggatttaagt ttacatccag acgttgctgc tcaaccagct ccccaggctc 100680
cataccaggg ataccaggag ccgccggccc cccaggctcc ataccaggga taccaggagc 100740
cgccgccccc ccaggctcca taccagggat accaggagcc gccggcccac gggctccaat 100800
catcttcata tccaggatat gcgggtccct ggaccccaag gtctcaacat ccatgttata 100860
ggcacccctg ggcaccatgg tctcaagatc ctgtgcatgg gcacacccag ggtccatggg 100920
atcccagggc accacatctc ccacctcagt gggatggatc tgcaggacat ggccaggatc 100980
aggtctccca gttcccacat ctgcaatcgg agacaggccc accacgtctt caactttcat 101040
tggtgccact ggtctcatcc tctgcaccat catggtcatc tccccagccc cgagccccca 101100
tacgccccat tccaacaaga ttcccccctc cccctatgcc gttacaagat agcatggccg 101160
tggggtgtga ctcatcaggt acagcatgcc caagcatgcc ctttgccagt gattacagtc 101220
aaggtgcatt taccccactg gacattaatg ccaccacgcc aaaaaggcct cgagtagaag 101280
aaagttctca cggacctgcc cggtgttccc aagctactgc tgaagcacag gagattctca 101340
gtgacaattc tgagatctcc gtgttcccaa aggacgcgaa gcagactgac tacgatgcat 101400
ccactgaaag tgagctagat taaggggatc caaggtgacc cctgttagct atttgatctt 101460
tgactgacac ataaacatgg tttaaggaat gaacactcat ggtgtgagac tggaactgta 101520
ctaaatttgc tgacatatgt acaatgagag ccaaaaattt gataaacctt aaaagtcccc 101580
ccatctaatg atgtccagtt cccttctccc accctgtaca ccccgaccca aagggactca 101640
atggcattca gatttctagt taccacaggt agaatatcgg gcgttggccc ataaaaataa 101700
gtgcatggat atagctctgc acaggcttgg aaacacccat tccaggtgtg cttctttttg 101760
gtgaaataaa aacagcatcc tttatatgaa aatgtgtatt ctctggtgtt gcagtatgta 101820
cagttagctt tggtatagtt ttggggtacc tgaaatgtgt gcagggtggg tgtccaatgt 101880
ggcagtttta cctctttgtc cccatactcc tgctcggccg tcttgttaaa gttaaccggc 101940
ggtggaggat ccaccggcca gacctctaca tttggtttgg gtacccaggt gatggccgcg 102000
gctgccaccc gccctcctcc tcttaccctg ggtggcaaaa agtatgccag gagtagaaca 102060
ataacaagtg cgatggcggt aaacaatggc accctcacct gcttaaatga aaccatggca 102120
accacttcaa agagagccga caggaagata tttattaata ttccattagt aaacgaggcg 102180
tgaagcaggc gtggtttcaa taacgggagt tagaaattta agagatcctc gtgtaaaaca 102240
tctggtgtcc gggggataat ggagtcaaca tccaggcttg ggcacatctg cttcaacagg 102300
aggcgcagcc tgtcattttc agatgatttg gcagcagcca cctgcggaca aaaatcaggc 102360
gtttagatgg ggcatttatg tttgggacgc tagccgcctg ggcattcgtg ttagtatata 102420
ctgacctcac ggtagtgctg cagcagttgc ttaaacttgg cccggcattt tctggaagcc 102480
acccgattct tgtatcgctt tatttctagt tcagaatcgc attcctccag ctgcgagcaa 102540
gggaatgcgt tactacaagt ggtgcctagt cagttgaaac aagccccacc atccgctgcc 102600
gcccctccat gagccccacc gtccgctgcc gcccctcctt gagcccctcc ttaccgattc 102660
tggctgttgt ggtttccgtg tgcgtcgtgc cggggcagcc actggtgcag gctgtggaac 102720
accaatgtct gctagctgtt gtccttggtt agccccgggg caagcaaaca ccactgctgc 102780
tgctgtttga acagtagaat tgtctccagg ttgaggtgct tctcccccgg cttggttagt 102840
ctgttgattc tgggttatgt cggagactgg gaacagctga ggtgctgcat aagcttgata 102900
agcattctca ggagcaggct gaggggcaga aaaccacgac ccagtcggag cggttgaaac 102960
atgataggca gttagctggc cttgtggcag aggctctggc agcaccggcc acagcacaca 103020
aggcaaagga gcttgcgatg gccctcccag gtcctgatag actctggtag cttggtcaaa 103080
agcttgtaca aaaggcacct ggtatgggtc aggtgtaaat tttacatctt cagaagtcga 103140
gtttgggtcc atcatcttca gcaaagatag caaaggtggc cggcaaggtg caatgtttag 103200
tgagttacct gtctaacatc tccccttttaa agccaaggca ccagcctcct ctgtgatgtc 103260
atggtttggg acgtgctaaa tttaggtgtg tctatgaggt acattagcaa tgcctgtggc 103320
tcatgcatag tttctaaaag aggaggaggc agttttcaga agtgtctaaa ataagctggt 103380
gtcaaaaata gacagcccag ttgaaatatg catggcatgc agcagacatt catcatttag 103440
aaatgtatcc aagatttcat taagttcggg ggtcaggggg gagtccagat tcaaatcctc 103500
tgtcatggac tctagtgttg tggtcagttc gtccaaatgg ccacgagggg gcgggtggct 103560
caggtccatc tgtccacata tggctgcttc ctccttctgg ggaataacag tgtcagccat 103620
ctcccttagg gccttcacgg cctgactggt ttcttcatca gggtcctcca acagatgact 103680
tgcctcgggg gttactgcgg gggccgggtc aagtggctgg ggcaccgggg ctggcgttag 103740
ggatccgacc ggttcatgga caggtcctgt gggggtggga gccaaagagg caggcagggg 103800
ccggttggcc cacggggatc cgggtggatg gaagggcctg atcctctttg gctgacacac 103860
ctctcgcccc tcgaacacgt cagatatggc actgcccgct tccggctttg gcaggaacat 103920
accttcccgg ctatccctga ggcccttctt ccttttaacg ggaggaagaa aggtgggctt 103980
tgaggggtgg gggaatatgg gtctctcatc gctctcttgg tggaccgctg ctatccaagg 104040
ctgttcaggt tccgccgcgt tggaaggaca tggagtttga ccacggttgg gcctggatgt 104100
ccggcgcgac tttggggccc gcaggcgcgg ggcctcggcc ctggcctctt cccgctcgct 104160
ctgctcggtg tcactgttgc ccgagtcact gctgctggaa ctgctgtcac cgcagtcggc 104220
gctttgggca ccgggcttca ggggcatggt cgggctcggg agactttcga gttcatctgt 104280
aaaagcatga aactgtccgg actccgagta gcgggcctcg gtgtgagagg cacccccatc 104340
attccccatg agctcctcgt ccatcctgtc ggctccggac acgaggatag gagtttccac 104400
tgccttggac ttggttgaca gcaggcacgc gggaagcacg ccgctcacgt agctcctctg 104460
tccggcgtgg ctggagtagg aggcccgggg cagtgtctta atcagagccc tgacatcctt 104520
aacatcgtcc gtcagatggc ctgtcttgga cgagaccata gtctggaaca tctcctcgag 104580
gacgggatag gtgaacaccc acttgcaaaa ggccttgaac ttggagctta ggaggccttc 104640
cttctccatc ctgttcaggt gttccactac ctgcttgccg gaggccatga tggccgcgcg 104700
gtccacgccc agcaccttgc tgtaggtgta ggcccgcacc cgactgtgtt ttaggagctt 104760
gtacatagcg gtgcctatgg tggcaggaat catcacccgg ttgctggggg cctggatgaa 104820
gaatctgtca gtgaccacta tcaggtggtc taacacgtag cgcatcacta tagggcacgc 104880
gatggaacat gcgtcgttgc cggcattctc agcccgtctt cttaccctgt tgtttcggag 104940
aatggcccaa aaattgcaga tgttgagcgt ggccattagc ccgccccatt ctcgcccgtg 105000
ggccttggcc tcatttataa atgccttgca tattttgtag gatctcagag taatctccac 105060
actcccggct gtaaattcct tgttgaggac gttgcagtag tcagagacca gagagcccag 105120
ctgctttttg atttcaggag ttagcctcag aaagtcttcc aagccatcct ttttaggcct 105180
catggctagt agtaacagag gaaatgcccg accattaaaa tctttcctcc atgagcttta 105240
cctgaaacac tatcccgaag tgggggatgt ggtgcatcta ctgaacacca tcggggtcga 105300
ctgcgacctc ccacctagcc acccactcct gacagcccag agggggctgt tcctggcaag 105360
agtcttgcag gctgtacagc agcacaagct gctggaagac accatcgtcc ccaagatctt 105420
aaagaagctg gcttatttct tagagctgct aagctactac tcccccaagg atgaacagcg 105480
tgacatcgcc gaggttcttg accacctcaa gacgaatcgg gacctggggc tggacgacag 105540
actctgggcc ctgattagga aactgcgcca agacagacac catgcctctg taaatgtcct 105600
catgccagga agcgactaca cagccgtgtc gctgcagtac tacgacggca tctccatagg 105660
tatgaggaag gtaatcgcgg atgtctgccg cagtggctat gcctccatgc cctccatgac 105720
ggccacgcac aacctctccc accagctctt gatggcgtcc gggcccagtg aggaaccgtg 105780
cgcctggcgc gggttcttta accaggtcct cctctggact gtggccctct gcaagtttcg 105840
cagatgcatt tactataact acattcaggg atctatagcc accatctccc agcttctgca 105900
cctcgagatc aaggccctct gcagctggat aatatcccag gatggcatgc gcctctttca 105960
acacagcagg cctctcctca ccctctggga gagcgtggcc gcaaatcagg aggtcacgga 106020
tgccattacc ctgcctgact gcgctgaata catagaccta ctaaagcaca caaaacatgt 106080
cttagaaaac tgttctgcca tgcaatacaa ataaatttct cttacctgcg tctgtttgtg 106140
tagtgaggtg ttgtgtcctg tatggtattc tactttaaaa aggccggctg acatggatta 106200
ctggtctttt atgagccatt ggcatgggcg ggacaatcgc aatataaaac cctgaccatc 106260
acatggggca ttaggcgact ctgcatcagc atcgcttaag tatgagtggg cagcagagag 106320
gctcggttat tttggttcct gaacatctgg ctggggcatt aactaagctt atgagcgatt 106380
ttatcacagg acaagatgtc actctttctg gaggaaatat tgcagtcaaa attcgcgatg 106440
ctataaacca gacccccggg ggtggtgatg tagctatact ttcttccctg tttgctttat 106500
ggaatgccct cccaacatct ggtagacaat cctccaggga cgatttaatc ccagccgccg 106560
tgcaggcctt aaccacggcc cacaacttat gtctgggtgt tattccaggt gagacctcac 106620
acaaggacac acccgagtca ttgctccggg ctatcgtgac gggtctccaa aaattgtggg 106680
tggattcgtg cggatgtcca gagtgcctac aatgtcttaa gggattgaag gcaattaagc 106740
ccggccttta tgaaatccct aggataatac cacacactaa gcagtgtagt cctgtcaatc 106800
tcctgaacat gttggtccac aagcttgtgg ctttacgtgg tcatgtgcag cttgcatacg 106860
acgcccgtgt cctgacgcct gactttcacg aaatccctga cctcgatgac tccgatgctg 106920
ttttcgcacg caccttattg gcagccttat ttcacctcaa tatgttcttt attctcaaag 106980
attacataac acaagactcc atgagcttga agcaggccct cagtggtcat tggatgtctg 107040
ccacgggcaa ccccctgcct gcagcaccgg aaaccctgcg agactacttg gaagctttcc 107100
gaaattcgga taatcacttt tatctcccga cgacagggcc tttaaacacc ttccaatttc 107160
ccgaagagct tctggggcgc gttgttgtta ttgattcctc tttgtgtgcc gccagtcacg 107220
ttcaggacgt tatcacccat ggtgttgggg cgggtgttcc tcgtcctcgg ttttcggccc 107280
tgcctccggc cccatcccgc gagccccagc agacatgctc tcagttaacg agcagaggga 107340
atgaaagctc acggcgaaac ttgggccagc ccggggggac ctcccctgct gttcccccag 107400
tttgccccat cgtttccctg acggcctcag gggccaagca aaaccgcggg ggcatgggat 107460
ccttgcactt agccaagcct gaggaaacct cccccgccgt ctccccagta tgccccatcg 107520
cttccccagc ggcctccagg tccaagcagc actgcggggt cactggatcc tcacaggccg 107580
cacccagctt ttcttccgtt gccccagtag catctctgtc tggtgacctt gaagaggaag 107640
aggaggggtc ccgagaatcc ccatccctac cgtccagcaa aaagggggac gaggaatttg 107700
aggcctggct tgaggctcag gacgcaaatc ttgaggatgt tcagcgggag ttttccgggc 107760
tgcgagtaat tggtgatgag gacgaggatg gttcggagga tggggaattt tcagacctgg 107820
atctgtctga cagcgaccat gaaggggatg agggtggggg ggctgttgga gggggcagga 107880
gtctgcactc cctgtattca ctgagcgtcg tctaataaag atgtctattg atctctttta 107940
gtgtgaatca tgtctgacga ggggccaggt acaggacctg gaaatggcct aggagagaag 108000
ggagacacat ctggaccaga aggctccggc ggcagtggac ctcaaagaag agggggtgat 108060
aaccatggac gaggacgggg aagaggacga ggacgaggag gcggaagacc aggagccccg 108120
ggcggctcag gatcagggcc aagacataga gatggtgtcc ggagacccca aaaacgtcca 108180
agttgcattg gctgcaaagg gacccacggt ggaacaggag caggagcagg agcgggaggg 108240
gcaggagcag gaggggcagg agcaggagga ggggcaggag caggaggagg ggcaggaggg 108300
gcaggagggg caggaggggc aggagcagga ggaggggcag gagcaggagg aggggcagga 108360
ggggcaggag gggcaggagc aggaggaggg gcaggagcag gaggaggggc aggaggggca 108420
ggagcaggag gaggggcagg aggggcagga ggggcaggag caggaggagg ggcaggagca 108480
ggaggagggg caggaggggc aggagcagga ggaggggcag gaggggcagg aggggcagga 108540
gcaggaggag gggcaggagc aggaggggca ggaggggcag gaggggcagg agcaggaggg 108600
gcaggagcag gaggaggggc aggaggggca ggaggggcag gagcaggagg ggcaggagca 108660
ggaggggcag gagcaggagg ggcaggagca ggaggggcag gaggggcagg agcaggaggg 108720
gcaggagggg caggagcagg aggggcagga ggggcaggag caggaggagg ggcaggaggg 108780
gcaggagcag gaggaggggc aggaggggca ggagcaggag gggcaggagg ggcaggagca 108840
ggaggggcag gaggggcagg agcaggaggg gcaggagggg caggagcagg aggaggggca 108900
ggagcaggag gggcaggagc aggaggtgga ggccggggtc gaggaggcag tggaggccgg 108960
ggtcgaggag gtagtggagg ccggggtcga ggaggtagtg gaggccgccg gggtagagga 109020
cgtgaaagag ccaggggggg aagtcgtgaa agagccaggg ggagaggtcg tggacgtgga 109080
gaaaagaggc ccaggagtcc cagtagtcag tcatcatcat ccgggtctcc accgcgcagg 109140
ccccctccag gtagaaggcc atttttccac cctgtagggg aagccgatta ttttgaatac 109200
caccaagaag gtggcccaga tggtgagcct gacgtgcccc cgggagcgat agagcagggc 109260
cccgcagatg acccaggaga aggcccaagc actggacccc ggggtcaggg tgatggaggc 109320
aggcgcaaaa aaggagggtg gtttggaaag catcgtggtc aaggaggttc caacccgaaa 109380
tttgagaaca ttgcagaagg tttaagagct ctcctggcta ggagtcacgt agaaaggact 109440
accgacgaag gaacttgggt cgccggtgtg ttcgtatatg gaggtagtaa gacctccctt 109500
tacaacctaa ggcgaggaac tgcccttgct attccacaat gtcgtcttac accattgagt 109560
cgtctcccct ttggaatggc ccctggaccc ggcccacaac ctggcccgct aagggagtcc 109620
attgtctgtt atttcatggt ctttttacaa actcatatat ttgctgaggt tttgaaggat 109680
gcgattaagg accttgttat gacaaagccc gctcctacct gcaatatcag ggtgactgtg 109740
tgcagctttg acgatggagt agatttgcct ccctggtttc cacctatggt ggaaggggct 109800
gccgcggagg gtgatgacgg agatgacgga gatgaaggag gtgatggaga tgagggtgag 109860
gaagggcagg agtgatgtaa cttgttagga gacgccctca atcgtattaa aagccgtgta 109920
ttcccccgca ctaaagaata aatccccagt agacatcatg cgtgctgttg gtgtatttct 109980
ggccatctgt cttgtcacca ttttcgtcct cccaacatgg ggcaattggg catacccatg 110040
ttgtcacgtc actcagctcc gcgctcaaca ccttctcgcg ttggaaaaca ttagcgacat 110100
ttacctggtg agcaatcaga catgcgacgg ctttagcctg gcctccttaa attcacctaa 110160
gaatgggagc aaccagctgg tcatcagccg ctgcgcaaac ggactcaacg tggtctcctt 110220
ctttatctcc atcctgaagc gaagcagctc cgccctcacg ggccatctcc gtgagttgtt 110280
aaccaccctg gagactcttt acggttcatt ctcagtggaa gacctgtttg gtgccaactt 110340
aaacagatac gcatggcatc gcgggggcta gacctctggc tggatgagca cgtgtggaag 110400
aggaaacagg agattggtgt gaaaggagaa aatctgcttc tccccgactt atggctagat 110460
ttcctacaac tcagccccat cttccagcgc aagcttgctg ccgttattgc ctgtgtccga 110520
cgcctgcgga ctcaggccac cgtctaccca gaggaggaca tgtgcatggc ctgggcccgc 110580
ttttgcgacc cctctgatat taaggtggtt attttgggcc aggaccccta tcacgggggt 110640
caagcaaacg gcctggcatt cagcgtcgca tacggctttc cagttccccc cagcctgagg 110700
aacatctacg cggagctgca ccggagcctg ccggagtttt ctcccccaga tcacggctgt 110760
ctagacgcgt gggcctccca gggggtgttg ctactcaaca ccatcctgac cgtgcaaaag 110820
ggcaagcccg gctcgcacgc agacattggc tgggcgtggt ttactgacca cgtaatttca 110880
ttgctctctg agcggttaaa agcgtgcgtg tttatgctgt ggggtgcgaa ggcgggagac 110940
aaagcttcac taatcaactc caagaagcat ctggttctga cctctcagca tccctctccc 111000
ctggcccaga acagcacccg aaagagtgcc cagcagaagt tcctgggcaa caaccacttt 111060
gtcctcgcta acaacttttt gcgtgagaag ggctcggtg agatagattg gaggctgtag 111120
aggggtcatc actatggcca tgtttctgaa gtcgcgtggg gtccggtctt gcagggaccg 111180
gcgcctcttg tcggacgagg aggaagagac ttcacagagc agcagctaca ctctggggtc 111240
tcaggcctcc cagtctatcc aggaggagga cgtgagtgac actgatgagt ctgactactc 111300
agatgaagac gaggagattg atttggagga agagtacccc agtgacgaag acccatctga 111360
gggcagtgat agcgacccct cgtggcatcc ttcagattca gacgagtctg actacagcga 111420
gagcgacgag gatgaagcaa cccccggctc tcaggcctca cgatcttcaa gagtctcgcc 111480
atctacccaa cagtcttcag gtctgacacc cacgccttcg ttctcccgac cacgcacccg 111540
ggcacctccg aggccgccgg ctcccgcgcc ggtcagggga cgggcctcag cacctcccag 111600
gccaccagcc ccagttcagc aatccaccaa agacaagggt ccccatagac ctacgcgacc 111660
tgtacttaga ggcccagctc cacgccgccc ccctccacct tcaagtccca atacatacaa 111720
taaacacatg atggaaacca cccccccat taagggcaat aacaactaca attggccatg 111780
gctgtaaata aaatgtcata acctggagtc tgcatgtctg ttgttttatt cagtaaacca 111840
gtagtgcgcg tgagttcttt agggcatcca cgatgtagcc gctcgcgggg ttcccctccc 111900
cagtgatcat ctcggatagg ggattcctgt ccatgaccac gcaattagag tgccgggccc 111960
gggacagcgc cacatacaca tggccgggtt tgatgtttct gtggctgccg aagcagatgg 112020
cgactttgtt tagggacaga ccctgggcct tggctatggt catggccagc tttgagctaa 112080
tgccatagtc acggatgctg cagaggttca gggacttgtc ctctatcgtc tcatacagtt 112140
tgttagtatt gtgttccagg cagcacacga agcctgcctc atccttgacc attagcctgg 112200
gcatgcgtga actgccagcg tcctgaggct gctgctttcc tcggatgcca aagaagacgt 112260
tgagatgcgt gtagcccaga agcgtgtagt tctcggtggt ggaggcgtag tccaggaggc 112320
cgtgaaggag aggctcgtct gaggtgaact ctatgttgtc gcgaatcagc atgttgttgg 112380
taaatgtgca gaaggggagg tccctgaact cccttccgcc atagcggacg gccacatcca 112440
ggcattgcct gaaataggcc ctgaggtcat tatatatgtt taacagggag cagaggggggg 112500

-continued cagaatttgc ggccggggga gccagtactc gggcatagaa gacagcggcg gggctccgct 112560
ccccatccca ggcaacctcc agcggcagtt cgcccagctc catcccagca gtcacctccg 112620
gatcccacgt acgcccgggc aggggcacag caccaagctc cgccacgtat tccccgtttt 112680
cacagagaga atgtcctccg tggctaaaag cgtagatgcc tccgtagatg agtcgggcca 112740
ggaagctgta gacatactcg ggctgctcat gcccgtgggc ctccacgaag ctgtccgcct 112800
cgagcgtgtc cataaagtcc ccgaaggtgc cggtatagcc acagatggac tttttggtct 112860
tgcagttgac cgacaccgag ctgtgcttga cgtaggtgac attgtaggtg accttgaccc 112920
gttcttcgtc ctgctcggtg cccaccggga ccatgtcttg gtcggcgaac tgcgagtagt 112980
taccgaggcg tgcataattc ttttggagcc aggtgtgggc cgtgaggccc ggaagcccga 113040
ccagggtctt gtactgggcc aggggatcga ggaagacctc gcactccacc gggcaggtaa 113100
acatggtcac cccgccccca tctcccccgg ttccccgcgc ggcacgcccc tgcccggcag 113160
tcttgagcgt ggcatggagg gtggtgagga aggtcttgac ctcggcgtgg gagaggaaga 113220
gccgggtcca gcccacgtac tgcgcggggt ccattatggc cgccctgggg acgacgaagc 113280
ggtcgacgta ggccaggatg tccggcgaga gctcgaggcc gtactcgagg gtcttcatga 113340
ggtgtccaaa ctggacgtcg gtgcagcgct tgttgttgat gaagagggcc cagttgcggg 113400
ccacgtccac gtaggtcgcg gccctggggt tgcccaccag gaaggtgagg atgttgtcgc 113460
actcgcgaat cttgtttacc tgggtctcgt ggctaaagga ggactgaaag gcgtctgtct 113520
gggtgggaga gcccacgcag acgatgcagg gaatgcggcc ccggcggtag agtggggtac 113580
gcagccaggc gttgaagaac cagtagcaaa agaccacggc tgttagaatg tgcacggaaa 113640
gcgttccagc ttcgtccacc acgatcacat tggtggtcca tagctgcccc tggtgcatgt 113700
ctctcaggac ctcaaaggcg gggccagaga ctcccgagta gagcccccctg ggcttggttc 113760
gcctgaactc ggcggcaatg tcggagagta ccggccagta tttggccagg tcccgccgct 113820
ggagttcctc tagggcggcg tccgtagagc gaccatgact gctgacccgc tgcgtcatat 113880
ttatgtggcg gctcttgaac ccaaaggcgc tatagacggt tgggcagtag gctcggagtg 113940
tctgggagag gttctgtgcg gccacggttg tggctcccgt gaccaggcag tccatcgtgt 114000
ggtggaggca gctaacgctg gtgctcttgc cagcccccgc cgttcccgta attacatagg 114060
ctgaaaaggg caggaagggg ggctccgaga gctccgggtc aaactcgggg gagaacgtct 114120
ccatatccgg gagttgttgg acgcggcgcc tagccagggt ccctatcctc ctgactatac 114180
gcctcacgga ggcgtctgag gtcatgttca acatgaacgt ggacgagagc gcctctggcg 114240
ccctcggctc ctcggccatt cctgttcacc ccacgccggc ctcggtccga ctttttgaga 114300
tcctgcaggg aaagtacgcc tacgtccagg gacagaccat ctacgccaac ctccgcaacc 114360
ccggagtctt ctcgaggcag gtgtttaccc atttgtttaa acgagccatc tctcattgca 114420
cgtacgatga cgtgctacat gactggaaca agttcgaggc ctgcatccag aagcgatggc 114480
cgagcgatga ctcgtgtgcg agccggtttc gtgagtccac cttcgagtcg tggtccacga 114540
ccatgaagct gaccgtgcgt gacctgctga ccaccaacat ctaccgagtg ctacacagcc 114600
gctccgtgct ctcctatgag cgttatgtgg actggatctg cgccaccggc atggtgcccg 114660
ccgttaagaa gcccataacc caagagctcc actccaagat aaagagcctg agggacaggt 114720
gcgtctgtcg ggaattgggg cacgagagga ccatcaggag tatcgggacg gaattatatg 114780
aggcaacgaa ggaaataata gagtcgctca actccacgtt catcccccag tttacggagg 114840
tgaccatcga gtaccttccg aggagcgacg agtatgtggc ctactactgt ggccgccgca 114900

-continued tcaggctgca tgtgctcttc cccccggcca tctttgccgg aacggtgacc ttcgacagcc 114960
cggtgcagcg cctctaccag aacattttca tgtgctaccg cacgctggag catgccaaga 115020
tctgccagct cctgaacacg gcccctctca aggccatcgt gggccacggg gggcgagaca 115080
tgtacaagga catcctggcc catctggagc agaactcaca gcgcaaggac cccaagaagg 115140
agctgctgaa cctgctggtc aagctctcgg agaacaagac catcagcggg gtcacggacg 115200
tggtggagga gttcataacg gatgcctcca acaacctggt ggaccgcaac cgtctatttg 115260
gccagcccgg ggagacagct gcacagggcc taaagaaaaa ggtctccaac acggtggtca 115320
agtgtctgac tgatcagata aacgagcaat ttgaccagat taatggccta gagaaggaga 115380
gggagctcta tctaaagaag atccgctcca tggagtctca gctgcaggcc tccctgggtc 115440
ccggcggcaa caacccagcg gcgtcagccc ccgccgcagt tgcggcagaa gccgcgtctg 115500
tagatatact gacgggcagc accgcctccg caatcgaaaa gctgttcaac tccccgtccg 115560
ccagcctggg tgccagggtg tctggtcaca atgaaagcat cctaaacagt ttcgtttctc 115620
aatacatccc cccttcgcgg gaaatgacta aggatctgac tgaactttgg gaaagcgagc 115680
tgtttaacac cttcaagtta acacccgtgg ttgataatca ggggcagcgt ctctacgtca 115740
gatactcgtc agacacgatc tctatattat tgggcccctt cacctatctg gtggcagagc 115800
tttcaccggt ggaactcgtg acagatgtct acgccaccct aggcatcgtg gagatcatcg 115860
acgagctcta ccggagcagt cgcctggcca tctacatcga ggacctcggt cgaaaatact 115920
gccccgcgag cgcgaccggg ggagatcatg gcatccggca agcaccatca gcccgggggg 115980
acacggagcc tgaccatgca aaaagtaagc ctgcgcgtga ccccccgcct ggtgctggaa 116040
gttaaccgcc ataacgccat ctgcgtggcc accaacgtcc ctgagttcta caatgccagg 116100
ggggacctta acatccgaga cctccgggcc cacgtcaagg cccggatgat ctcgtcccag 116160
ttttgcggct acgtcctcgt gagtctgctg gactccgagg accaggtcga ccacctcaac 116220
atattccccc acgtgttctc cgagaggatg atcctgtaca aacccaacaa tgtgaacctt 116280
atggagatgt gcgccctgct ctcgatgatt gagaatgcca agagcccctc cataggcctc 116340
tgccgggagg tgctgggtcg cctgaccctc ttgcactcca agtgcaacaa tctggactct 116400
ctgtttctgt acaatggggc caggacgctg ctgtccaccc tggtcaagta ccacgacctg 116460
gaggaggggg ctgccacccc cgggccgtgg aatgagggcc tgagtctctt taagctgcac 116520
aaggagctga agcgcgcccc atccgaagcc cgggacctca tgcagagcct ctttctgacc 116580
tcggggaaga tggggtgcct ggccaggtca cccaaggatt actgcgcgga tctaaacaag 116640
gaggaagatg ccaactcggg cttcacattt aacctgtttt atcaagattc tttattgacc 116700
aagcatttcc agtgccagac cgtcctccag accttgagac gcaagtgcct cgggagtgac 116760
acggtctcaa aaataattcc ctagaataaa ctgagaacag tcatcagtaa atctgtctct 116820
cgcgtgattt ccataggaat ggtgtagccg gggtggaggg ccgatatcac atcaagcaga 116880
aaggccataa tctctcgaaa gtaggcggtg gggctgagac catgctcagt ggccgtctgg 116940
cagggggccg ggcgcgctcc gtccttgtcc aggagacaca cgtggcttcc agagaggcgc 117000
agcccagccc tccgcagccg ctgaagccag gctcgcggaa gagcccaaaa cctgtttcgg 117060
cgccgcccgg gggccagtct ccgggtcagg tcgcggacca gggtcaacag gtggtcgtgg 117120
gatggcgggg ccttgtctgc ctcgggtctc gccgctagtt ggtccagggt ccaggagaag 117180
gcttcgtgcc aaaccaaaaa gggccccgag tgctccctac atccacccac gtaaagatcc 117240
ccctgaaaga tggccatcag taggcacccg ggcccgcgtc gagccttcac ccgaatgtgt 117300

-continued ctgcgggcca cggtggcctc tccacccatc acatcccggt cgagccggct ggcatcctcc 117360
gagtctttca cgccttgcag gaaagcctag gagatacagc aacagaaagc tattagccgg 117420
tggttccccc accatcattc ttcctgttaa cgggaagaat aagagttggg caaaccccgg 117480
gggccgcgct ctcccaccca gccccgcttc tcacctgtgc tagtggctcc tctgaaggat 117540
gggcggaggt tggtgccaca aagcccagga tgaactcgtc tgcataagcc caggtcagtc 117600
ctaggtcagc ggccgcgtgt aggagaaccc gggtgacggc ggtgtagagg cccccgagtg 117660
cccgtcgcgt gtctgaggtg ccatagcggt gaagggcccg cagccaggtt tgcgcgtccc 117720
gcgcctgccc tccgccatca ggcgttccca cgggggcgcc cctggcagag aggtggcagc 117780
gggccaattc gtagagccac caagtggcat cagcctcaag gatggctgtg gcctccgcgc 117840
gcccgaccac cgtcgtctcg tcctcccccc ctccctcgcc gccttcccgc gtgcaaacgt 117900
ggcgagggtt aatctccttt cgggtcgggg gccagatttg ttgtaggagc agcgagccgc 117960
gtcgttgccc tgaccgcgcg tcgaggccca ggagggcgtc tgccaggggc gtcccagaga 118020
ctcccaggtt caggtccagt agcaggagac cctcgctgtg tggcgcccgg tgccagaagg 118080
ccggcctcgc ccgtcccaca taatggatgg gcaggaaggg aaagcccggg acatagggct 118140
ggaaatctga gccccctggg cagagttcgg ggtccaggag gtagaagatg ggcttggtgc 118200
ctctgtggtt ggcgtagcag gaggcataga tactgcggag gaaggcgtag agcccgcccc 118260
cggccatact ccaagagttg acaagccagg actcgaatcc cccagccggc tcaagaattt 118320
tcaggctgac gcggtgccgt cgggcgtccc caccacggcc ggtggccccg tcggacgaca 118380
ccagatctac ttcataagtg accggtcgca ggatgtccct aaaggggacg ggagaggggt 118440
cgtcgggagt ctcggtggaa taggtgaaaa catccccacg cggtgtcctg atgtatacgt 118500
ccaactgtcc gggagactca gagtgcctct gagcatgggg gcatgtctgt tccccctcca 118560
tctcggaccc gaagccatca acaggtgggg gttgttggtc ccgcccatca tcccccgagc 118620
agctttggca gaccacctgt gctggaaaga gaggctggaa gatgaggccc tgctcatcct 118680
ccaccctggc ggcggacaag agtctgcggt ctcgggttct aaatgaaagg tcaaataggt 118740
ccttctcggc ggcatcggcg agcatagcaa tgagcccccc gctgcgcctg agctcccgct 118800
cccatcgcaa aaagttgagt tcggtagtcg agggcgcgtt gaccacgggg ggctccaggg 118860
agcctccaag cggcggctgg caggcctgca ccacgatcag agtctcaacg tcctcccttt 118920
tgatgggcac gatgcccacg acccaaatcg cccaccaccg ccctgcggtc tgggtaacat 118980
tataaaaggt aaccgagctg acgcgggccc tgacgctctc cgcgggtgtt tccatcattg 119040
tttgagatct gaggaggact ggaccccttta aaacatccgg tcacgccctt tgcaaattat 119100
ttaaaaggtg aatgctcaac tgagaccatc gcaatcatga agtcctccaa gaatgacacg 119160
ttcgtctata gaacgtgggt caaaacgctt gttgtgtact ttgtgatgtt tgtcatgtcg 119220
gcggtggtcc ccatcaccgc catgttcccc aacctggggt acccctgcta ctttaacgca 119280
ctggttgatt acggggcact taacctgacc aattacaacc tggcccacca cctgaccccc 119340
acgctctatc tggagccgcc ggagatgttt gtctacatca cactggtctt tatcgcggac 119400
tgcgtggctt tcatctacta cgcctgcggc gaggtggcgc taatcaaggc ccgaaaaaag 119460
gtctcgggtc ttacagacct ctcggcctgg gtctcggcag tgggctcccc aaccgtgctg 119520
tttttggcca tcctcaagct ctggtccata caggtcttca tccaggtcct ttcctacaag 119580
cacgtctttc tctcggcctt tgtgtacttt ttgcactttc tggcctcagt tctacacgcc 119640
tgcgcatgtg tgacccgctt ctccccggtc tgggtggtca aggcccagga caactctatt 119700
ccccaggaca ccttcttgtg gtgggtggtc ttctacctga agcccgtagt tacaaacctg 119760
tacctggggt gccttgccct ggagacgctg gtcttctcgc tcagcgtgtt cctggccctg 119820
ggcaacagct tttactttat ggtgggggac atggtgctgg gagccgtgaa cctcttcctc 119880
atcctgccca tcttctggta cattctgacg gaggtgtggc tggcctcctt cctgcggcac 119940
aactttggct tctactgcgg catgttcatc gcctccatca tcctgatcct gcccttggtc 120000
aggtacgagg ccgtctttgt ctccgccaag ctgcacacca ctgtggccat caatgtggcc 120060
atcataccta tcctgtgctc ggtggccatg ctcatcagga tatgccggat tttcaaaagc 120120
atgcgccagg gcactgacta tgtccctgtc tcggagacgg tggaactgga gctagagtca 120180
gagccgaggc ctaggccctc gcgcacgcca tcacccgggc gcaaccgccg ccgctcttct 120240
acgtcctcat cttcctccag gtcaaccagg agacagaggc ccgtctctac ccaagccctc 120300
gtctcctccg ttttaccgat gacgacggac agcgaggagg agatcttccc ctaatgcaat 120360
aaaaacttaa aacactgagg ttactttccc gtcattcttt cgggggaacg aggggaggcg 120420
ggaattgggt taagataggg gcgaagggtg ggggtgggtg caagaattgg ggctgggaat 120480
ggagagggga gtgggctagg tgccgacacc ggggtgccaa gataatggat tgagtaagca 120540
tggggctctg atcgggtccg ccgggttctc aggggtgtag tgggtgggca ttgcatattt 120600
ttgccgcggt gctgttgggc cttggactcg gggtgatcat ccgtaccatc acccgcaccc 120660
gcaccccagt ccacagccac cggccaaggt cctgggcctc ccaccaccgt tatgcctccc 120720
cctttaccca ttaattacaa gagatgttag tttggttttt tatttggcaa aaacagcaat 120780
tcatcatttt cagagtcctc atcatattcg agcccctcgt tggtttcccc gcaggccctc 120840
ccttcttcgg ccgctattag cttagtagtc tccaggttaa actcctcata gtcattatac 120900
aggttgatta ttcccccgtc cacgtcgcct atggagttga ctcgtcgtcg gcaaagagac 120960
cagagggcac ccatggcgcg gtgtcaaaag tattgtctgc gtacgctttc caggagccag 121020
ccgcggtgct caaggtctta cggatgacag agtccggcag gaccacgggt gtcaccagca 121080
ccgccacggg aatctccacc gaggcgtcca gaagcaggtc tgagccgagc gtgcaggtcg 121140
ccgggtctag aggcgaccgt tttcgaaaga aggccgtcac aatgttcacc cggggtgagc 121200
agtctctccc gggcttgcca ccccccactgt ggcggacgta gtctccaaca attttgtatt 121260
ggaggagcac ctggtagaag tagttgtgcc gtggattgat gaagatgttg actgggaccc 121320
ggtctttaat accaatgcgc cccgcatttt cgcttgggtc cgtcattacg tagagcatag 121380
actccacccc cctgttggca gctaggctgt ctgccaccag gtcatgaccg gggcccagtt 121440
tgcgcttacg gacatcttta agattccagg cctcatcctg cgtcaacaga tagtcaccct 121500
ccgagggcaa ccgcccatcc gggacgtact ccacggtagg acgagctata gaattgataa 121560
atctgataaa tgacctcttg catggcctct tgtaaagcgc agtgtaggat gggtagatgg 121620
ggtcaaattc tgacttggaa aagaggtact tgaagcggca cttaatctca taaatgcagc 121680
tccggtcggt gaacagtata aagtctccct gtgactccac attgacgcaa agatccagag 121740
acaccccaaa aatgccatcc gtgggactaa tcataaagcc aaattgacgg ttggcggatg 121800
cgtccccgca gatgagctta cagacaatgt ccttgaccgt gtcctcacac cgcaggccaa 121860
aggccacagg tcccccaaag tagtgatttg tggagatggg agctggctca aacaccttgg 121920
tgggtccatt cttaatggtg gagagcagct tggaagagga aattatgcca tttcgcaata 121980
tgtcccacat caggttctca gactgccccc tggtcatgga ctccacgtac gagcagagaa 122040
cagtcctctg ctcgtcggtg gcctcctgta gcccccagta aatggatttc agggagggac 122100
cgtccttgct gtcattctct tggactaacg aggagacaaa gtcacagaag ccagtttcac 122160
cagagaactc ttgtatttgt ttacagaggc aatagagata gacaaagcgc atggccggca 122220
tctgaggtgg acggtcaagg ttacggacaa aggcctcagt ctccggactg cggaggaagc 122280
gggcaaacgt gtaggaggtc atctcctcca tgggatcctc gagctcatcc acgtcggcca 122340
tctggaccaa agaagtcgtc tgccaagagt tcagctacca gacctggaag atgagggtgc 122400
tcaaaccgtg ggcgacagtt gaagaagtag ctctccttga acctcttttt aaggctccgg 122460
caccactgca agaattgact catatgctcc gccgtgacat ccacgcacgg actctcgcca 122520
cacgaggtca ggcccatgtc taagttcagg ttccacatct gcgacagcac ctccaacagc 122580
accacctttg gggctgcaaa ttgcaaaaag tagagcgggt cggatcggtc aaatcccatg 122640
tcagggttgg ggtaggggat tttgtgggtg gagtcagcga ggtgcatgat accatagagc 122700
agcgagtagc cgagcgactg cagatccagg cgaagggccg tctgcgcccc cacggggcca 122760
cacgccgagg ggtcagggat gtgcccagcc cccctcaaga tgtagcactt gctcaaaagg 122820
cagaggggct tataggtgtc cttggctata gaaaatggtt ccctctggca atagaggcga 122880
tagagctgcc ggcccttaga agactttagc cgcacatcca gcatcttgtt gcggtcgtgg 122940
agggaagcag tcccataatc agtcaggacc agcctaccca tgccccacat ggtgtctgtg 123000
aaatccacca ggatgttgct ggggctaatg tccgaatgga agaggccgca gtgccgattc 123060
agaaagtaaa cggcatcttt gaggccctga aagccccgca ccaggggctc aatactacca 123120
tcatgccagt ggccataatc ctggagactg catctgaact ggggcataaa cagggcgtgg 123180
caggacgtgc aggccgacag gtagtccacc agggccttgt cctgcccatc ctcggccgtg 123240
gccttcccaa tctgaatcat gtcacacacc atgagctcgt gatacagctc cgtcacagag 123300
tcatagagtt tgaccgtggc attatctgca tgtgcataca cggccccgta gctcccccgc 123360
cccagcagat actcgcaggt aatggggagg tgatcacagc gcgtcatgtt ctccggcagc 123420
tttacataga gggtctccgt catgtcatca atgttggtca ccttcaggtg tttgtgctga 123480
aaggtgaagt aatcaatgac agtcaccttc cccaaaaagg cctgggtctc tcgagggggt 123540
tctggggaga cactcaactc gccactgctg gaggagttcg tcgggctcaa ctccgcagcc 123600
atattcacat ccatgttcct caaatggctc gagggcctgt cgcagctcgt ctctggcctc 123660
aagctcctgc tcacggagct cctccacccg ctctagctgc ttgtagttga tttttggaaa 123720
ttgagtcttg gtcgcggtga ccaccctctg ataggtagaa attagctgtt tggactcaaa 123780
cgtctccctt gcgtggcgca gggactctaa ggcaccccga gcagatgtaa actgtgtttc 123840
aaacagagcg tggtccctcc caaatctgtc acgtgcgctc acagccgctc tcttttctac 123900
cgaggctctt agttgctggg ccaccagatc tcgcttagaa ctactcatct tcataagtca 123960
ccatgtccgc aactatggag cccagatcat acgtggggta gagtacggta gttccagtgg 124020
aggcttcccg gtaatttccc acagcgtcca ccatatatct ttctgcctct cccgttagaa 124080
ttaggcaagg atcatacgtg tccaccggcc ttttatactg agcgtttagg ttttgtttat 124140
gtagcaagca caaaaggcac acacgagtga tgcaaaaggg ttcctgaggc agcaggcaga 124200
gctgttttgc cattttattc aggcggctaa cgtcaaaggg aggagctata tcctcaccct 124260
tccagtcacg cacgtccaag tacagggcat acacacacct ggtgaggtgt gccaggaatg 124320
cctctatgtt ggcacatggt gtataaaccg cagtgggtag cagaataggg ccccttttgc 124380
cccgtgccgc agcgtaaacg cagtgacgct cttcgcagtg ggacctgggg ccgtagaaga 124440
gggcccacat ccaagggagt gggtcttcag gcaccaggga ggtccaggtt tgggagtggg 124500
ccaatatttg caaggcctga cctataacct catctttgtt ccaggccagc gcaattcgca 124560
taaggtcccc atcaaacacc tcaaaacaca gacccatgcc catttcaggc tgagagggct 124620
ccatccggct cgaccaacct tgtccaccaa actgccattc ttctggtaaa cgggggttga 124680
ggggcaagag ctccaaagcc aggctcgaga agtcatagtc atcctcggcc acacggccgg 124740
agctccgggc ctcgtgccag ggcctgttgt cctgggggag gatattggac acgagcagga 124800
agctcttgag tggcgtctcc accagcttaa attgctcggg cgtgtcctgg caggcctcca 124860
gtgccagttc cagacactgc ccatacctgc gggcgagcat cgggtcatcg ggcatatcgg 124920
ccttgaccgc gttgaacatg ctgtatgcct cgcagcgcgg ccgtctgacc gagaacctaa 124980
gaaacgccct tcagcaggac agcaccacgc aaggctgcct gggtgccgag accccgagta 125040
ttatgtacac aggggccaag tcagacaggt gggctcaccc tctggtgggc acaattcacg 125100
ccagtaattt atattgccca atgcttcgag catactgccg ccactatggc cccaggcccg 125160
tgtttgtagc ttctgatgaa tcattaccca tgttcggtgc gagccctgcc cttcacaccc 125220
cagtccaggt ccagatgtgc ctactaccag agctacgcga cacgttacag cgcctgctgc 125280
caccacccaa tcttgaagac tccgaggcct tgacggaatt caagaccagc gtgtcctctg 125340
cccgtgccat ccttgaggac cccaactttt tggagatgag agagtttgtc accagcctgg 125400
ccagcttcct gagtggtcag tacaagcaca agcccgcccg cctagaagca ttccagaaac 125460
aagtagtgtt acattctttt tattttctga tctcaatcaa atctttagag attacagaca 125520
ccatgtttga catctttcaa agtgctttcg gattggaaga aatgacgctg gagaagctgc 125580
acatttttaa gcaaaaagcc agcgtgtttc ttatccccag gcgccacggc aagacctgga 125640
tagtcgtggc catcatcagc ctcatcctct cgaatctctc caacgtgcaa ataggctacg 125700
tggctcacca gaaacatgtc gcgtccgccg ttttcactga aattattgac accttgacca 125760
agagcttcga ctccaagcgt gtagaggtca acaaggagac cagcaccatc acgtttaggc 125820
acagtgggaa aatctccagc accgtaatgt gtgccacctg cttcaataag aatgtaagac 125880
ctgacgtttc agtacttggc aattgtagag catagcccgg ctgtaaaggt cagaaaatcg 125940
cagcagggtc caaggttgtg ctgtacatgg gacctctttc ccattagcaa gaacccccctg 126000
caggacacgt gacatgtccg ggtgcatttt gggtgggtta aatctcagtc ccaccacaaa 126060
gggggcatcc tccggtttga acatcagacc caacaaagcc cgatgcccag ttatgggtac 126120
gtagtcgttg ttcagggccg tgcatggcag cagacaagga caggtgccag atgtgcctgg 126180
gctatcgtcc tccgtccagc cacgcaggat gttcacgtgg gccccggcac catagcatgt 126240
cacacattcc ccgttatcac atctggttag caggttgata aaatgggtca gtgatggaaa 126300
ggttggcata ttggggcagc acatcagcat gtccatgtta acgaaaaaca tgtacagggc 126360
cccttctgca taccaggcac caccccgtcc cagtgggatg atctccgagg gtgtgatatc 126420
ttgcagttct tctactgttt taacggcggt tgaggtggta aagacgtggg ccgtggtcag 126480
atctgtgcag gtgactacag ggttacccct aatctccaca ggcaccgcct cacccactgc 126540
atctgagaat accccaaagt acatgagagt caggctgtgt ggcccctgga ctgccttagt 126600
gaagagaacc tcgggcctgg ccacggtggc tagggttcca ttgatgtaga cggtcacata 126660
ggtgggcttc ttcttgggct tcagcacaat gagggtaaca ttcatgtagg ttttaggagg 126720
tccggctatc tgaggcacgt acacagctga cacggcggtt gtggccgtat agactttcat 126780
ctggggcgta gaggcatcgc tcagcaccca gaggcactcc ttgttgagga acttgcgaag 126840
ctgttcccgg ctactgttcg cggcggatgc catgacgtgc cagaatatat cccctctcct 126900
cgggggtgag tgccaattgg cctttaataa caaagccccc aggcagcacc aaaaatgcct 126960
gcccgtccga tgtggtggcc aggtggacgc agtgcccgtc agttccaagg gctactagct 127020
gggaagcagc cccaaccagc ccacccgggg gcctggagtc gatcacctta ccccaggccg 127080
aggccccttc ctcatacagc gggtggctat ctatccatag gcaggcatcc ggcgtctttg 127140
gtgcattgga gatagtagct ttcacccaac aactttccca actaacccgt gtctggacag 127200
tgaagaacgc ttccctgatc aggtctgaat ttttatagat acgggagtag gaggtgggaa 127260
taacaactgg gatttcttgt tgtgctgtcc aggcctgcat ggccagtttt tccctgaagc 127320
tagcagaaat tctgagggcc actgaaatga ggaagcgaaa ctccctctct ggagctccca 127380
aaattgaaac ctcagcaaga tctgttgctg gggaggcatg ggtgacagct gtcatcctgt 127440
gcagtctgcc ctgggcactc agctctggat atgtgacaac atagagagcg tgggggctaa 127500
aaatatgagc aattcccctg accagggccc tggactcacg aatggcccga cgggtcttag 127560
agaaagaaac aggcaccctc gagagtgccc ccgacccgac ccccacagtg ccgccagtcc 127620
ctgctcggcc tccgccgcct tccccaccgg cgctgccccg gatgttgctg gggttctcga 127680
gggctgggtg gtgcttggac acagaggtct cagcagccgc cttggtctcg gccccggccc 127740
taagtctgag ccccaggcaa agggccggac tcccagcgtg gcccaacctc tgctcccctc 127800
tattctcctc ttgcgttatc tccaatagaa tttgcttgag gtcatacgtt ttagggtgct 127860
cgacctgggc cgcggccacc ggcatatgct ctatacccgc ccctccgggg ggcccaggat 127920
ctataggtat gggctgcata gccgcagcag actcctggac cccagaggcc tctctgataa 127980
gatgcccgtc ggtcagagcc cttttggccc cctcaaagag agacaggtaa taaatctgta 128040
gctccccaac cagccctcct tcatcgtaaa atcgaagggc ggccacgtgg aaggggttgt 128100
agagctctgg aaggccctca tcgcagtaca ctggcacact ggtaaacgtg ccccgatggc 128160
taggccgtcc gggcagcatg ccccgagcag caaacacgcg gcagaccctc gtgagacccg 128220
tccggtcact gaagagagtc tggcaccagg ccccctcgca gtttggcacg cgattggggc 128280
aaagctctgc cataaccgtg tcgggaacaa ataggtgcac gaggaggggg gtcccgaggc 128340
cactcaacac ttggttgtca atgtggacat ccatagctct ctcatgcgtt tggctacagc 128400
atcatagcgc ttgtttctgg tggatttaaa taacagggcc ccgtagacag tcttttgtga 128460
gtaaatagag atgatgacat ggatgtagag actgaggacc acatccacca ccttctcgga 128520
ggaggccccc ctaaacagca tcaggcagca agggaacaca aaggaaacca gggccgggat 128580
gtgaggcctc agcgccccct cctgatcaaa gagggcctcg ctgaccccgg agatgacatt 128640
ctcattcaga aagtagtgat agaggtgatt gaccacagtc ttaaccaggc cctggacttg 128700
ttcaggctcc cacttgtccc gctggtcctg tgtgtcttgt cggatctcgg tccagggcct 128760
cagcgccggc tggaaatgcg gccccatgta gttgcctgta agggcgcaca ccactccctc 128820
atgggtctca atcagggtgc actcgctgga tccatcacat acgtggtact cgccacagcc 128880
ccagcaggca aacacggagg ccatgctctc aggtaacggg agatggaact ccagcttact 128940
atacgagcac aggtggcgag gattgggctc atccgtgccc ccctcccccc gcgggaggct 129000
caatcggcct tggtctgaca ttccaccccg gccaggtcca ggagggtgca aatattctcc 129060
aggcgctgca cctcagagac ctcctgctca aagagacctc ccaccgccac gtagacgcgg 129120
gccaccgtcc ggggaaggtc agtggggtcc cagctcagca attctccaaa ttctctctcc 129180
ccaatagtgc ctcgcttctt atcctgtctt tcagagcatc cgggggcaga catttcacct 129240
cttgtttgtg gacgaggcta actttatcaa gaaggaggcc ctgccggcga tcctgggctt 129300
tatgcttcag aaggatgcca agattatctt catctcgtct gtgaactcgg ctgaccaggc 129360
caccagcttt ctttataagc tgaaggatgc tcaggagcgg ctgctgaacg tggtaagtta 129420
tgtgtgtcag gagcatcggc aagattttga catgcaggac agcatggtct catgcccctg 129480
ctttcgcctg cacatcccgt cctacatcac catggacagc aacatccgag caaccaccaa 129540
cctctttctg gacggggcct ttagcaccga gctgatgggt gacacctcct cgctgagcca 129600
gggtagcctg agccgcactg tgcgtgacga tgccatcaac cagctggagc tctgccgggt 129660
tgacaccctc aacccccgag tagccggacg cctagcctcc tccctctacg tgtacgttga 129720
tccggcctat accaacaaca catccgcatc aggcaccgga atcgccgccg tgactcacga 129780
cagggcggac cctaacaggg tcatcgtcct gggcctggaa cacttcttcc tcaaggacct 129840
aacaggggac gctgccctcc agatcgccac ctgcgtcgtg gccctcgtct cctcgatcgt 129900
caccctgcac ccccacttgg aggaggtgaa ggtagccgtg gagggcaaca gcagtcagga 129960
ctctgcggtg gccattgcct caatcattgg ggaatcctgc cccctcccct gcgccttcgt 130020
gcacaccaag gacaagacgt ccagcctgca gtggcccatg tacctcctga ctaatgagaa 130080
gtccaaggcc tttgagaggc tcatctacgc agtgaacacg gccagccttt ctgccagtca 130140
ggtcaccgtc tccaacacca tccagctctc cttcgatccg gtcctctatc tcatctccca 130200
gatcagggcc atcaagccca tccctctccg cgacggtacc tacacctaca ccggcaagca 130260
gcgcaacctc tctgacgacg tgctggttgc gctagtcatg gctcattttc tcgcaacaac 130320
acagaagcac acgttcaaga aagttcatta aactttattg actacaccag tcccttgtaa 130380
agcgacgggt ctcgcgtgac ggcattcgtg agcagggctt cgtccagggg cttgttcttg 130440
gcggacatca ttagcccagc cgcaaatatc agaattagca tcagaaaagt gagccccaca 130500
aacaccagtg tccagagagg aagaccgtaa gataaagatg gctgcctctc atctggaacg 130560
gtgggaagct cagcagttgt ttttgtggca ttggacgtcc ctttggagga cagcgtgggg 130620
gccaaggtgg tagcgttggt aatacgggta gtagcactgg tggtggagga ggacctggtg 130680
gtgacattgc tagtcacacc cgtggaggtt cctgttccgg cctcggtggc agtgatgttc 130740
tgtgcagtaa ccttagtggt gacattgatg gtggatgcgt tggaagttgt tgggactggt 130800
gtgacagttg tcccagtgaa tgtcaccgtg gttgtgttgg tgctcagaat agcagttgtg 130860
gttatagggg cgctagtcgt ggtcaaggtc gtagactggt ttgtgctagg acccgatgcc 130920
gacggtgatg gtgtagtcac agccgttgtg cctgtcacgt tccccgccga ggccgtcgaa 130980
ctgccactag atgtccaaat aaggcttgtc tcacagatga gtatcatggc cataacagcg 131040
cctgccttgt ctctggcgtg tgccatcgcg tctggacgca gaaggcctcc cggcctcttt 131100
tatagctagt ctccacaccc aatactctac tgaaccatca catacatgac ctcctcgagg 131160
tatgcaggga atgagcggtc cgtgagccgg tcaacacgac attgcttccg tttcatgcct 131220
ccagctgccc ctgaccagtt aggaccccttg acggatgtct ttaacggcgc ggtgcagttg 131280
gtcaccaatg acggcctaaa ggccaacaca tccttgaagc agggcgtagg aatggtacca 131340
aactcggggc ccaccccatc aaagacataa tatgtctcat agtggcagtg atgatgcatc 131400
accaccacag cactcgccag gaccctctgc atatcttgta caaggcgcct ttcaactcgg 131460
ccactggctc tggtgacgtt aaatgtcctg ttcctattag tcacagcctg tagatttggg 131520
cacccagact caaaaagtgc agctacatga agggcagccg cctcaaatcc accatgaccc 131580
ccatggctgt ccgtgttgtt ggggtaataa gtcacattgt taatgaccac ggccgggata 131640
agggtgtaaa ccttgcagaa tggattggtc ggacacccat aagacagggg caccccaaaa 131700
tcacgcccct taccccgaag caccttggcc cccaccggca taaagctggg caaaaagagt 131760
gggttaaaac caaaggcgag tagggccagg aacgccaaat agcagcagta atagatgaaa 131820
acaaagctca gcatgaaaca gcgtggaggc tcagctaggg tctctgcctc tccatcatag 131880
acatcttcct tgaatctcat tctctcaccg catacctcgc tcttcatcca ggagggggcc 131940
atggctgcca ttctaccagt taacgaggag agagagagta ggtccgcgga aattggtgcc 132000
cctctctgcc ctcctgacga ggccatggtg tcatccatct ccgcagtccg ttcttcagct 132060
ttggcattgg tccgggtccg ggtggtctga ttttgattct gatcctgggt attggtcttg 132120
gtctctcctc ccccattggc atggattggc ataggtgggt gtggctcagg ctcaggttcc 132180
ggccctggga cggcagcagc cgccgggacg gtgaagtcgt ggaaggtaga ggcccgtccc 132240
tcccgaggtc gtggggccgg agccttataa aagacttcca ccctctcccc gctggccaag 132300
acacgccgct cgtggaccac gccatcttcc tcccggctga ttgtgtggct gacggtgccg 132360
tgttccaccg ccacttgttc atcgaccatg gtaccccctt tatcttaacc agcaagtggc 132420
cgtcagggtc tcttgagagt atgccgctgt ggccaagcga ggccccaaat taaatagtga 132480
tgccaaagac tgtaggtagg tcatcatcac acgcatgcgt gataaatcat ccgccactga 132540
caggtcatcc aggtctatcc gggctatctc atccggcacc atttcctgga agagattcaa 132600
gaggtcgtga tgctcatgcc ggataaggcc tcggaccagg cgcatactgg ccctgggcag 132660
cagggtcacc atgatgcaaa agtagagact cagattgtcc agcagggcca agccaagggg 132720
ccctggcacc tccgggaggg ccaactcgta gtggtgcccc aggtatgaaa cagagccaag 132780
atgcatgtgt acatcgagca tgtctgcgtt cccgggagcc tgcatgacaa cccgggagta 132840
cacgttaaac aggagaatct tctgcagcac ctcctctgct atgggcgtag gcagcaccat 132900
ggggaaaaca atgtccacat cattggactc taacttcacg gtggcatgct ctcgtccaaa 132960
taccgggggc ataacactga ggctcccggt cccatgccac tggaaaaagg gctggtactt 133020
gttcttaatg gcgtaggtct gacctggaac aatcttggtg agtatcaaac tgtccacgct 133080
aacctcatcc agcacggcca gggtgcaatc agacaggtag ttgtacatgg acacgtagtc 133140
cgggaccgtc tctagagagt acacctgacc caagcccaat ccctgcacat tctgcgtccc 133200
gtgagtggaa gccaggggta agatgcagcc aatcctctgt tgcatcttgg caatctcatc 133260
ggtatacaga cgagaggaga gagacactac cactttcaaa tccatcttta ttgacaatta 133320
tcaaaaaacc accttatttc caaactttaa tattcttcgt accggcgcca cctcttcaat 133380
tatatagtgt ccgtaatgga tgggggcgtg ggtctgtttg acagacataa actcatcgat 133440
gagtgcccgg gaggaggctg agagtgcggg gaatgcctcc tgcagaaagc tgcagggctg 133500
ctccagaaac acgtcagtgc cagcaatcac tacaaactgc acctctgtgt tgctggtggc 133560
tgggtgccct ccaagtcgct ggctgtactc gttgaccatg ttgtagagtc ccctgttgtt 133620
gcgcagaagc tcctccttgt tgaaaaatgc ccggcagggg ctgtagaggc ccgggacggc 133680
cgtctggcga taggaggagt tgtacatgat gtcacccaga gaacccagct gagatgccca 133740
gggattcaca gtgctccggt attcataggc ggcatccggg cgagaatggt catagatgag 133800
cccctcggca acctcctgat tgtagttttc acaggagacc acacaggcgg cccgtcccct 133860
tggagagttg gacttttgaa aataagccac gtctgccgtg accggtgtta cgataatctc 133920
acaggtggcc tgctggccgt ggcagagtcc tggagctcca ttaacattag tcatacctgc 133980
caggtatgtc ctggggtccc gaagcagcgt cccattgcgc tgagcgccca ccttggcctt 134040
gatgtagtca ttgacttgct ggttgccaaa ggcctcggcc ggaaagacgc taaagaagtc 134100
ttgggtgtgg atacccatgt cagtagtgat ggccgccacc ctggccggag tcatggtcga 134160
gctataacta agcccggtgt cgatggaggc catctcgtga tgcacctcaa aggttaccgc 134220
gtccaccctg gcctcccggc ggctaacatt tggggtccca atgaacatgg atgttgaggc 134280
cctggagcta aacaatatgt tttcagagag gatctcatcg gtcctgacca cggtcatggc 134340
cacccctggg tggatcttga gcttggcctg ggcaatatag gccatggggg acatcttgat 134400
gtgcatggcg gtcattccac tgattgaaac gagggaagga agacattcgg ccgcgtattt 134460
gcccatgggc gagcggtgcc actcccggta ctctgcaaag agctgctctg gccggttgaa 134520
ggcttccacg gcccgctgct gaggattgcg cataacaaag gtggcaacat cctggtgcat 134580
ggtggcagcc actcgcgggt ccccgtaaaa catatggaaa ggaatggcgt gaaagagaca 134640
ctgggtgacg gcccgggtcc tctcggagaa ggcaaaggcc accagcccgt tcaccaaaac 134700
agtctgctct gtccgcttgt cggcgggatt cggggccagc tgctgcgtaa cgtcattgtc 134760
caccgacaca cgcacggcac gggtgaaagt ggggcaggtc atgaatgagg cgctgaggtc 134820
cctgatcatg cccacggtgg ggcggaggtc ggagatctcc agcagatccc tgagcgtccc 134880
attctccaaa ttgtcgagga tgtcctcgtc cctggtaaaa tggtggctga aggctggccc 134940
gttgtaggcc agggtctggg ccacgtgctg aaagtccacc ccgaggccgc acatgtgggc 135000
attggtgcag gttgggagga aaacgtagta aaagatcttt tccagcacat ccgcatgccc 135060
ctcatctaca taagggccta ggtgcagacg gaaatcgtgg tcgtggtctc cgttaacccg 135120
gtagccgtac aaggccacaa attgggcagc catctcatcc atgtttccaa ccctctcaat 135180
aaactggggc gcggccaggg tgtcagcgta aacctcattt ccgataataa tctgggggc 135240
ccggtcacta acggtgagaa gatgggtgaa aatgtctgtg taggccaccg gggggagcag 135300
gttagggtcc aggagagcgc agacatactg acccacgctc tcatccccca caacatctga 135360
cccggccagg cgcatcaggg cctgctctag ggctataagt tccccataga tttttctata 135420
catggaatag gcctccttgg agatggcgtt atttcccagg tggcggcaga tgaacttgat 135480
catggaaaag ctgttcacaa aggcaagcct ccctgaccgt tcccagtagg tgttgatgca 135540
cagggacacc aaaggcacgt tcatgacaaa cttttcctca aacccgtgga tcatagcctc 135600
gactacgtag aagaaggctg gataggcagt gtcataggca gtatcctgca cagtctcaat 135660
aacggcctga tccaccacgt gggccagaga tgtggcggtc tcaaactgct gcccccgggc 135720
ctcttggaat gcagctgggg ccaggggagt cggcaggtta cccaccatta gccggtgcac 135780
agccctgtgc ctggccctct ccccggcatc cctgccaatg taaatatcat aaagggggtg 135840
cagctccagc cgcagcaggt cataattgga cgggtggagg aagtcttcgg tgggcagccc 135900
gcacttgaga gctatatctg tcacgggggc tgcatacttg ttatcataga actcgtccac 135960
aataacaagc acattcatgt gattgggcct cctgtgttgc agggagtagg tctcgcgcct 136020
gtctcgcggg gccggggccg cgttgaggct gtttagggta tgggcgggtg tgtggagtcg 136080
ggggtgacag agaaccttga gagcattctg taggttaaac gcgaggagaa ggttattctt 136140
gtttacgatc catgcctcca ccggtagctg ctgtgtgggg ttgtccagca ttttgatggc 136200
ggcggaggtc gtgtacttgg gattgggcat aaacaggccc actgggaaat agtagctgta 136260
ctgcattctt ctgttgaggg ggtatgggga ctgagtgtca ttgtacatct tttgcaggct 136320
ttccacggcc accgcgtggt tgcccagctt gatgacggcg gctgagatcg gcacccgggg 136380
ctgatcctcg acccctgcgg ccacagccgg caggtcagac ttggtgcttc cggctttttc 136440
cggtgagtcc acgatcctag ccatgaaatg ctcaaacgta cgcatcacgc gcccgtagct 136500

-continued cacggcagtg accaggttct ccccccgtac cacaaaagaa gcatagctcg agggccccat 136560
aatctggttg tcggcctcct cacccaggaa ggtcaagagc tggcgcagaa cgttgtcggt 136620
gacaataaac acccccccca ctggctctcc ccccttggcg gtcgtgtagg tactgacccc 136680
cttgagcacg ctctccccgg acacggccgc taccatctca gagagacggc ttcgcacgta 136740
ctgagaaaac ccggagccca tgttctcggc ccggtccagg aagaaggagt gctccagcag 136800
atgcctcttg aacatggcaa tgaggtcaga cttgacagtc ttggagaacc ccctctcagt 136860
gaaggtggga tccgccaggg tctgcaggat aaacatggga ggggcatggc gaagcttcac 136920
actcaggacg gtgttaatga ggcccctctc cagggcatcg accccaaact gtagggccga 136980
ggccacggtc ttgacagccc ccacgtactc tgcgtactcg accggggtct cggggatact 137040
atgcaggatc tccagatcca gcatggacag ttccatttcc gtactaatgt ggtgtttgtg 137100
gcaatttttg accacaatga atgtccgctg cttgctgggt ctccttccgt ccccgtgagc 137160
aatggtgggg acggagattc gaaattgaat cttgccatcc gtcatacgac tcaggtcttt 137220
gaattccgtg ttcacacagg acacggccag tgccgtctcc aggaagcgaa catattggat 137280
ggcgttcgtg tagaccccga gtagcacctc aaacttgatg cccgcctctc tggcatcctt 137340
gcccaccagc aggtcaaagc tatgaaacaa cccctcagcc gctgactgcc gcaggttcga 137400
gagcaggtcg gcatccaccg tcagataggg gaagggtctg ttttccacac cctcatttga 137460
ggccatgaca caaggtaaga gggagatggg gggaggtctc gagggcttct cttcacagct 137520
gggtctcttt tacgccctgg cctgcaaccg cagcccaccc acacttcccg aggatgctac 137580
ccttctaatc aaatggttgg acacggccct gggcagggag gccacctttt acgcgtgtcg 137640
ggctatgcgt cggcttctac tcggcgttat ccgaatgaat gactgccagg agctgccacc 137700
cggtttaata attctgagtc cgggcaccgt ccctggcccc cttggagtcc agagtctgga 137760
gcatacagac tgcgaaatat ggtcctctgc ccaccctgac cacgctgccc acctcccggt 137820
gcccagggtc atcacataca ccgactgccc gggttccata aacacgagct caatgtttcg 137880
ccttatcatc cgctacttgt ctcatcacca atttgagcgc tgcttcgagc agttctgccg 137940
cgtggtcccg cgtcggcttc ctagggacct gtaagcgaaa ctctgcaaag atgctggctc 138000
atctgaatca ggttaccagg atcccccccct gtccgccctt cagcgggcgg gaggccagac 138060
tcaagttcca cttcttctcc tggagcacat tcatgctgtc atggccaaac aatgccacac 138120
tccgggagat caggacgagg gccgccacca acctcaccca ccacccacat ctagtggata 138180
ctctgtacca cgcctctccg cagaccccat ttctgacacg cagcggtgct ctataccgct 138240
tcgtcacctg ttgcaactgc accctgccca atatctccat ccagcagtgc aaggccgggg 138300
acagaccggg ggacctggag atcattctac agagtaacgg cggagggagg cccgcgagct 138360
tccagttccc ctcctcccca actggctccc tattgcgatg catagttgct gcgtccctgc 138420
tgccggaggt gtccgtgggg caccaggagc tgtctccgct gcggtccaga agccagggag 138480
ggcagacgga tgtcaggtcg ggcccggacc cggcccggag actggtggcc ctcctgcgaa 138540
gggaagatgg ggcacctaaa gaccccccctc tgggaccgtt tggacacccc cgggggcccg 138600
gcccggccaa gagcgaagac gaggagtctg agcgtcgaga cgcccctcca cccccgctcg 138660
attccagctt ccaagcttcc cggttggtgc ccgtggggcc tgggtttcgc ctgctcgtgt 138720
tcaacaccaa tcgggtgatc aacactaaat tggtgtgctc agagcccctg gtgaagatgc 138780
gagtttgcaa tgtcccccgc ctcatcaaca actttgtagc ccgcaagtac gtggtgaaag 138840
agacggcgtt caccgtcagt ctattcttta cggacggggt gggggccaac ctagccatca 138900
atgtcaatat cagtggcacc tatctgagct tcctattggc catgacgtca ctgcggtgct 138960
tcctgcctgt ggaggctatt tatcccgcgg ccgtgtcaaa ctggaactcg actctagatc 139020
tccatgggct ggaaaatcag agcctagtca gagagaaccg aagcggggtc ttttggacta 139080
ccaactttcc ctcggtggtg tcctgccggg acggtctcaa cgtgtcctgg tttaaggccg 139140
caactgccac catatctcga gtgcacgggc agacattgga gcagcacctg atccgtgaaa 139200
tcacccccat cgtgacgcat cgagaggcaa aaatctcccg gattaaaaac cggctcttta 139260
ccctgctaga gctacgcaat cggagtcaga ttcaagtgct gcacaagcgt ttcctggaag 139320
gcctgctaga ctgcgcctcc ctcctgcgcc tggatcccag ctgtatcaac cgaatcgcct 139380
ccgagggcct gtttgatttc tccaagagaa gcatcgccca ctccaaaaac cgacacgagt 139440
gcgcgcttct gggtcacaga cattcggcga acgtgacaaa gctggtggta aacgagcgca 139500
agacccgcct ggacatactg ggccgtaacg ctaacttttt aacgaggtgt aagcatcagg 139560
ttaatctaag acagtcacct attttcctga ccctcctgag gcacatccgc cgacgtctgg 139620
gcctgggccg tgcttccgta aaacgagaga ttacccttct cctggcccac ctgcgcaaaa 139680
agacagcccc catccactgc cgtgatgctc aagtgtaagc agcccggggc ccgcttcatt 139740
cacggggccg tgcacctgcc atcgggacag attgtcttcc acaccatcca cagcccccact 139800
cttgcctcgg cgctgggact gcctggggaa aatgtaccca tcccggccct cttccgtgcc 139860
tcgggcctca acgtccgtga gagcctaccc atgaccaaca tgagggcacc gatcatctcg 139920
ctggctcgcc tcatcctggc ccccaacccc tatatcctag agggacagct gacggtgggc 139980
atgacacagg acaacggcat tcccgtgctt tttgccaggc ctgtcattga ggtaaaaagc 140040
gggcctgagt ccaacattaa agcctcctcg caacttatga tagcagaaga ctcctgcctg 140100
aatcagatcg ccccctttc cgcatcagag cacccccgcct tctccatggt tgagtccgta 140160
aaacgagtcc gggtcgatga gggagcaaac acccggcgca ccatccggga tattctggag 140220
atccccgtga ctgtgctctc atccctgcaa ctgtctccca ccaagtccat cctgaaaaag 140280
gcaccggagc cccacctcc ggagccccaa gccaccttcg atgccacccc ctatgcccgc 140340
atcttttacg acatcgggcg acaggtgccc aagctgggca atgcccccgc cgcgcaggtc 140400
agcaacgtgc tcatcgccaa ccgctcccac aactctctaa ggctggtgcc caatccggac 140460
ttgctgcctc tccagcattt gtacctcaag cacgtagtgc taaagagtct gaatctggag 140520
aatatagtgc aggactttga ggccatcttc acctccccgt ctgataccat cagtgaggct 140580
gaaaccaagg cctttgagaa gctggtggag caagccaaaa acaccgtaga gaacatagtc 140640
ttttgcctca acagcatctg ttccacctct acactcccag atgtcgtccc cgatgtcaat 140700
aacccaaaca ttagcctggc tctagagaag tattttctca tgttccctcc ctcaggcacc 140760
attatgagaa atgtcagatt cgccaccccc atcgtccggc tcttgtgcca aggggctgag 140820
cttggcacca tggcacagtt tctaggaaag tacatcaagg tcaagaagga aactggaatg 140880
tacacactgg tcaagcttta ttacctgctg cgcatctaaa ggaaaaacat aacaatcttg 140940
tgaaccagaa agatacccag agcaaaagca ataaagtaca ggattattgc caaaacaacg 141000
tgtgctcttt cttcatacag gcccgcaatt tccatgacag tcccgttggt ggtcagcagc 141060
agatagtgaa cgtggaggtt gtcaaaatca aagtagttgg agctcaagat ggagttttgg 141120
acttcctggg aggtgatgta ggttgtagtt tccaggcctt ccttttcatc ataactgagc 141180
agggcaaagc cacaaaaaat gcaggatttc tgcgtcctgg taaaattctg gatctttgga 141240
atctggcggg gctccccagc cacagcaccc tgcgaacatt tattcattat aacgggggag 141300

-continued agaaagagag agctgctgag ataggtggtg ctggcctcgt atagcgccga gcctcggacc 141360
tcacggtcac tagagattat gaatgtcaca ttgatgagcg ggataatcat cagaactttg 141420
tcgagcctgt ccacgcattt gtaggcgggg agatgccacg catccctgtc ttctcgctcc 141480
aaagagagcc gcccaagaaa cccatccaca gcatttgaaa cggccgcctg gtccagcgtt 141540
gcctcctggg gggccatgct cagcagcttg tctcgtgtga ggtcaaatcg taggctgagg 141600
tagcacggtg agaagagccc gctctctgtc cccagggcta gcccccgcaa aacctcccca 141660
atctctaggg ccgagcacag ggcggtggac agcagttggt atagggcaag gttgggcccc 141720
tgggtagtca cgttcagccg caactcgcgt agcaccacgt ggctgccgat aaacagggtc 141780
tctctcatca cggtatgcag ggctggaaa agggggtggc ggttgtaggc cgagagaagc 141840
acagatgtgg cgcctccaat gaggccactg taaaccccgg ccttggggta gccgacggtg 141900
gctaacctca gcgcgtactc ctgtttctca gtagtcaggt gacccagctc ctccatcttg 141960
accgtggcca tcagcatggc ggccaagcgc tccagcccgt aggattgcat gcccttgaca 142020
gtggccccat aacatatgcc gatgatgtct ttcaggacag tcagctcaaa gaagctcttg 142080
gccaaccagc ggaggtccac gcagccattg ccagtctcac ccacagcatg acccacctta 142140
aagaaggcca cagaaacctc aaacatggta gtcagcgttt ccgtgtccag ttccggctcc 142200
cggcagcctc ccttcatctc cagcaggacc agtttctgga gaacgtagcg agcgtagctg 142260
gcggctgtca tggtgacggc tcgggaaaac atatccttca ggttgggtac aaagtagttg 142320
tgaaagttgg cataatgcac aaaggttgta acaatcacca gggaatagtc cccgctttgg 142380
gcactggtta aggatgggta actaaaaggc cccctcagat ccggcaggtc cttcgtcttg 142440
ccaaagacca ggctcaacac atgctcatct cccttctcgg tcactcgctt gtaggtgccc 142500
atcagaaatt tagaagtcat ggcccccgtg tactgaaact tgtccccgtt gatggacagg 142560
gccacataag acaagtgaca gcgcagctga taaaagacat agctgtgtgg ccgcgtgttg 142620
ggcagcatgg tgccaatata gtagaagagc tgcttctcaa ggggggcact aagcatgcag 142680
gcaggggaat tcaggccgct aatgactccg ggatggacct tagatgcatc cacttgcatg 142740
gatccttcag agacagcagg gatatcgaca ggctcggcca gcgcaatacc aagggtacca 142800
gacgtcttgt aaattaactt gtagcggtta agcatagacg ccaaatcttc ggtgacattt 142860
gcctctctcc acagcgcctc tgggctaagg cctgggacct ttgccatcag ttcggtccat 142920
gggatggtgt aatgcgaagc atgcccctct atgtccaggt gcagcttaac ctcgctgagg 142980
ctggcagccc ccacctccca tagcaacacc aggcaaaaaa cacagagcaa ctgcatccta 143040
gtcccgattt cccctctcaa aatcagagat caccttgctc agaccagccc aatcgaaaaa 143100
ctgagatcgt attgccggat tcttcaatgc ctgcatgtaa atctccgtcc agcatccagg 143160
taaatcgtcc tgaaactctg agaggtccac aagcacaaac tgaaggtagg ctagcgttcg 143220
ggtgaacgca agacaaactt ccaacaacac cgcgtcggct cggaaaggct gtatgacttc 143280
cttaagtaca ctaaagatgc tgttcttata cagcttctcg gccacaccac ttcgaattat 143340
gggggtgtgg ctttgatgac atactgtcgt gattgttgtt agaccggcac ataccttcac 143400
aatgtcctcg ggggcaaaat actgtgttag gagccaggca cagtaaacgg cgtgatatgc 143460
atcgttgaca ctcttcaggt agccagcatc cagtcctgac tcatgtttcc tccctcgctt 143520
cttcaggcgg cgcatgttct cctccacgtt taacttcatc cagactatgg tgtcccccgg 143580
gtctgcggta aacgtggcca aaacttgaat aaagtcacta taggagagaa gctggctccg 143640
gagcagcatt agagggaaaa ccacggaggc cgacagcaaa tggcgatcat gcaaaatcca 143700
acaatccagg ggcgcgactg acctggcacc agactcggta accagcaagc tccgcttcct 143760
agaggccaag actctgaaag ggtggtaaa tttcatctgg catgctaaaa cctcagccga 143820
cgtgtcttcc cttccatgcc tcgcccgagt cacattcttg tgcatggcct taatggcatt 143880
ttcatacaca tgagtccagt accgcatcgg ttcagggact acaatggtca ggtccccaaa 143940
gacagccttc aaatgattca gcatagtagt ctttcccaca ccaggggcac cttccaaaaa 144000
tagggaacag gcaggtttga ttactggtac atgatttgtt aggtgggtca caattggaac 144060
ccgcatgctc tccttcctct gagccttggc ctggcgggtg tcttgggcat catccagatt 144120
cagaacattc atcacactcc cacttagccg cttcagctgg gcagcatgct tggataactt 144180
actaaactcg cgcccatggg cggccaggtg ttcgaagaga ccagaaggct taccettgcc 144240 accattcttt tgttttaacg cggaatgaga agagggcctg cggaaattag actcatcctc 144300
agactcacag tcagatttgt catcgagccc aaggccggcc aggccctcct caaagccttt 144360
ctggtacatg aagctccggc tcgtggagtc cgcacctcct tctgtgcacg aagttttgcg 144420
gaaccaggag aaggggtctg gcgtcttgct ggggccacac tcccggctac ggggcttcgg 144480
ggtaggggca gtaggctttt ggtgtgcggg tgctggtggc tgggctcccc tgggcagggt 144540
aaaggggcac gatgtgtgcc ggctacccgg agagtttcca gtattagatg tcacggcagc 144600
ctgggtccgg cacggcaccc tctccccaga cagtccggtc ggagccatca agggggggcca 144660 gtgggtgggc acctggtaga ggccgtcgtc atcttcctca cctgcccctg agtcactacc 144720
ggttggggta agaactgagg gggcaaagtc atcaatctca gcgtaaaagt tttcgtgtct 144780
ttcgttttca ggggactcat cctcctgaca ttttcgccag ccgccgggcg ggccggcctc 144840
ctttcctgga aatccagcca tggatcccac ccggggtctg tgtgccctct ccacacacga 144900
cctggcaaaa tttcacagtc ttcccccggc tagaaaggcg gcaggtaagc gagcgcacct 144960
tcggtgttac tccaagctgc tctctcttaa gagctgggag caactggcct ctttttttgtc 145020 tctgccccccg ggacccacgt ttacagactt tagactattt ttcgaagtca ccctgggtcg 145080
gagaatcgca gattgcgttg tggtagctct gcagccttat ccccggtgtt atattgtaga 145140
atttaagacg gccatgagca acacggccaa cccgcaaagc gttactcgca aggcacagag 145200
gctagagggc accgcccagt tgtgtgactg tgccaatttt cttcgcacgt cctgcccccc 145260
cgtgctgggc agtcagggcc tggaagtctt ggcggcgttg gtatttaaaa accagcgatc 145320
cctgagaacg ctccaggtag agtttccagc cctgggccaa aagaccctcc ccacctccac 145380
caccggcctg ctaaacctcc tctcccgctg gcaggatggc gctctccggg cacgtcttga 145440
tagaccccgc ccgactgccc agggacacag gccccgaact catgtgggcc ccaagccttc 145500
gcaactcact gcgcgtgtcc cccgaagcgc tcgagctggc agagcgggag gccgaaaggg 145560
ccaggtcgga gcggtgggac aggtgtgccc aggtgctcaa aaataggctg ctccgcgtgg 145620
agctggacgg catcatgcgt gaccacctgg ccagggcgga ggagatccgc caggacctgg 145680
atgctgtagt ggccttctct gatggcctgg agagcatgca ggtcaggtcc ccctccacgg 145740
gagggcgctc tgcgccagcc ccgccctccc catccccagc ccagccgttc actcggctca 145800
ccgggaacgc ccagtatgca gtctcaatct ctcccacgga cccccctctg atggtggccg 145860
gcagcctggc tcaaacgctg cttggtaatc tgtacgggaa catcaaccag tgggtaccgt 145920
ccttcggacc ctggtacagg accatgtcgg ctaatgccat gcagcggcgc gtgttcccta 145980
agcagctgag gggcaacctg aactttacca actccgtctc cctaaagctg atgacagaag 146040
tggtggcggt gcttgagggc accacccagg actttttctc agacgtcagg cacctgccag 146100
acctccaggc tgccctgatc ctctcggtgg cctacctgct actccagggg ggctcctcac 146160
accagcagcg ccccctccct gcctcacggg aagagctgct ggagctgggc ccggagagcc 146220
tagagaaaat catcgccgac ctcaaggcca agtcacccgg cggaaatttt atgattttaa 146280
caagcggaaa caaggaagcg cgccagtcaa tagcccctct caaccgacag gcggcatatc 146340
cacccggcac attcgcggac aataagattt acaacctgtt tgtgggagcg ggactactgc 146400
ccacgacggc cgcgctgaac gtgcccgggg cggcgggtcg ggaccgggac ctggtgtacc 146460
ggatcgccaa ccagatcttt ggggaggatg tgcccccctt ctcatctcac cagtggaacc 146520
tgcgcgtagg tttagccgca ctcgaggccc tgatgctcgt ctacacgctc tgcgagaccg 146580
ccaacctggc cgaggcggcc acccggcgtc tacacctatc gtccctgctc ccccaggcaa 146640
tgcagcggcg caagcctgcc atggcgtcag ctggtatgcc gggcgcctat ccagtccaga 146700
cgcttttccg ccacggggag ctcttccgct tcatctgggc ccactacgtg aggcccacgg 146760
tggcggcaga cccccaggcc tccatcagct ctcttttccc cgggctggtt ttgctggccc 146820
tggagctgaa gttgatggat gggcaggctc cctcccatta tgccataaac ctgaccggac 146880
aaaagtttga caccctcttt gagattatca accagaagct tttatttcac gacccggctg 146940
ccatgctggc ggcgcgcaca cagctgcgtc tagccttcga ggacggcgtc ggtgttgccc 147000
tggggcgccc ctcgcccatg cttgcggcgc gggagatcct ggagcgtcag ttctcagcct 147060
cggatgacta cgaccggctg tacttcctga cgctgggcta cctggcctcc ccggtggccc 147120
caagctgagc cagttcctcg cactggagtg ggtcattggc aaaaaggtaa ataaactcat 147180
cgcacggggg ttttgcctcc ttctcgtctc ttgtttcggg taggggagta aggccgctgc 147240
caggccgcca tgctcagggc cacggcgtgc cagaggccct cgtagtcgtg cgcatccgag 147300
aggatggcac ggtccagaag cagatagccg gccaggcaga ggaaggccac aaagaggggg 147360
cgaaggcgtg cccgaacccg ggtttcatgc tcgtctgcac cccagtggac aaggcagtag 147420
aggacaccca ccaccaggcg gttagggagg acactgccaa ggttgaagag cagatttccg 147480
tcagccaggg tgacctggct caggtccggc gccctgcgag tccaagctgc gcccacacac 147540
atgcacagac ggcccctgtg acatcaggcc ggtcatgcaa aaacagacaa agagaccgtg 147600
agcggttacc ggggcgcagg gcctctgccg ggaagcccac ccgggccagg gcccggtaaa 147660
gcaggtacca gtattcatcc ggcaccttgc gtgccaacac acgattcgtg cggtttccag 147720
tatttatcac ggcttcccgc cacaggtaaa agttaacact tagggtcagc agcttggtca 147780
gggataggtg caaaaacctg agctcgtcct cgcgcagagc gcaaagcggc cagttcttta 147840
gcatcttcag gaggagcccg tgaatcccag gtgtcattcg cgcgtcatcc ccgcgcaccc 147900
ccagtcccat taacatagcg ggcacaatgg tgcaggcacc gtctgtatac gtctgcggct 147960
tcgtggagcg cccggacgcc ccacccaagg acgcctgcct tcacctggat cccctcaccg 148020
tcaagagcca gctccctctg aagaagccct tgccactcac ggtggaacac ctgccggatg 148080
ctccggtcgg ctcagtcttt ggcctttacc agagccgagc gggtctcttt agcgcagcct 148140
cgattacctc tggggacttc ctgtccctgc tggactcaat ttaccacgat tgcgatattg 148200
cacagagtca gcgcctgccc ctccctcgag aacccaaggt ggaggctctg cacgcctggc 148260
tcccctcact gtcactggcc tccctccacc cagacatacc ccaaaccacc gcagatggag 148320
gcaagctgtc cttctttgac cacgtgtcta tctgtgccct gggtcgtcgg cgcggcacca 148380
cggcagtcta cggtacagac cttgcgtggg tcctgaagca ctttagtgac ctggaaccgt 148440
ctatcgccgc ccagattgag aatgacgcca atgccgcaaa gcgtgaatcc ggatgcccgg 148500
aagaccaccc tctgcccctc acgaagctca tagctaaggc aatcgatgct ggatttctga 148560
gaaaccgcgt ggagactctg aggcaggaca ggggtgtggc caatatccca gccgagtcgt 148620
atttaaaggc cagcgacgcc ccggacctac aaaagccgga caaggcactt cagagcccac 148680
caccggcctc cacagaccca gccaccatgc tatcaggtaa cgcaggagaa ggagcaacag 148740
cctgcggagg ttcggccgcc gcgggccagg acctcatcag cgtcccccgc aacaccttta 148800
tgacactgct tcagaccaac ctggacaaca aaccgccgag gcagaccccg ctaccctacg 148860
cggccccgct gcccccccttt tcccaccagg caatagccac cgcgccttcc tacggtcctg 148920
gggccggagc ggtcgccccg gccggcggct actttacctc cccaggaggt tactacgccg 148980
ggcccgcggg cggggacccg ggtgccttct tggcgatgga cgctcacacc taccaccccc 149040
acccacaccc ccctccggcc tactttggct tgccgggcct ctttggcccc cctccacccg 149100
tgcctcctta ctacggatcc cacttgcggg cagactacgt ccccgctccc tcgcgatcca 149160
acaagcggaa aagagacccc gaggaggatg aagaaggcgg ggggctattc ccgggggagg 149220
acgccaccct ctaccgcaag gacatagcgg gcctctccaa gagtgtgaat gagttacagc 149280
acacgctaca ggccctgcgc cgggagacgc tgtcctacgg ccacaccgga gtcggatact 149340
gcccccagca gggcccctgc tacacccact cggggcctta cggatttcag cctcatcaaa 149400
gctacgaagt gcccagatac gtccctcatc cgccccccacc accaacttct caccaggcag 149460
ctcaggcgca gcctccaccc ccgggcacac aggcccccga agcccactgt gtggccgagt 149520
ccacgatccc tgaggcggga gcagccggga actctggacc ccgggaggac accaaccctc 149580
agcagcccac caccgagggc caccaccgcg gaaagaaact ggtgcaggcc tctgcgtccg 149640
gagtggctca gtctaaggag cccaccaccc ccaaggccaa gtctgtgtca gcccacctca 149700
agtccatctt ttgcgaggaa ttgctgaata aacgcgtggc ttgaaagtaa actttattgc 149760
gtgttagtac ctgtccattc acaggggtat ccagcccttg cgccgcctcc cccagcccgc 149820
cagccacccc agacaggaga tgataatgat gaggagcacc ggagccacca cagcacaagt 149880
gattaggagc agggcccagt gcacccaggt ggtcttaggg cgccagggat cgattggaaa 149940
agggcccagg gtcactggct tatgcgtggg acgtttagaa acaggccgcc tatggggcct 150000
gtgactggtg cttgtggtgt gggagactaa tgtggtgggg gctatggtag tggctgggat 150060
aacagtaaga tgcatacgct gagtgagggt ccggttggca tggtattggt cgtcttcttc 150120
ccctgcagag taattgcagt ggaccccgga ggccacactg caatttctca gtgtcacatt 150180
gcacgtgtag taacctgcat gcgcaagggt cacattgggg attatcagag agacggaggt 150240
gttggagtca tttacccatt ctagggtaag gctataattg taaccccccgt tagttatatg 150300
agttccgttg ttggaagtag ctacggccaa gggcagttgt ccatccccgg gagtgtatcc 150360
ccggcccaac tcgatccgag agaccgactc attgctagga acgctgcagg tgagattcac 150420
tctagcacct gcatgggcgg tgacattttc aaatttaacc agatctgaga aaaatgcaca 150480
aacagacccc acacagcagc acaatagaag cactaaatga gtcattccta aactgtcagt 150540
tttaaaactc cctgcttctc aggcctaaat atgtggtggg gtgtgcttag gatcactttc 150600
atattctgca acaacagcca tacccggaag aggagctgcc ggttgccatt tttcaagctg 150660
ctaaaccacg agtggcagca ggcctaagaa gctcctcagc aacatggaga cctcgaaggg 150720
aaactggcag gagcagggag tcacgtaggc actagcctct tcatgtgagg taagagatcg 150780
ctaaaaatgg gatcagggta tgtaaaccga gttttgcggg ggatggtgag ccagacacgg 150840
cgggtggggg aaggagctga cacgattgag tagaaagggc caaaaataca ccagctataa 150900
ggaattgctc aggccaaagt tgttcctcag gtggctttag gcctaatgta ggcaattgcg 150960
tgcctagaac attgctaatg tgccctgggt ttcctgcctt catgcaaata ttctacctcc 151020
cccggcctgg tgcaaaatgt ctgcctcaga atactaacag ctaatccaag ctaacattct 151080
atcagtaaac gggcagaaaa ctgataagga ccgcggagtt tggccctccg cggtgtccgg 151140
tggtcctcac acgtgccctc cccccgggcc gatggctgag gcccggaata tgcaagtgca 151200
tctttctaac cagtaggggc ctccacctag gtgctttgtt aatctttagt gggaactagt 151260
gggagtgctg tgcctcgggt acccctatcc tataggtcct accggagctc cttgtcttga 151320
taatccctgt aaacacacac cacctaagaa caaggcattg ttaacctttg gtggaaccta 151380
gtgttagtgt tgtgctgtaa ataagtgtcc agcgcaccac tagtcaccag gtgtcaccgg 151440
aggctacttg cctcagtgcc acttttacct tctcaaatct atacgggggg gggggggggct 151500
ctgtaacatt tggtgggacc tgatgctgct ggtgtgctgt aaataagtgc ctagcacatc 151560
acgtaggcac caggtgtcac cagggctact tgcctcggca tctcctcacc ggagaagggg 151620
ttaacaaacc cgtggggggt cttagtggaa gtgacgtgct gtgaatacag gtccatagca 151680
ccgctatcca ctatgtctcg cccgggctat atgtcgcctt acctccccta tatagtcacg 151740
accccaccga accaggcatg atgtagaata aaattttatg catcatcttc taatctgtgc 151800
cgcttggagg gaaacatgac cacctgaagt ctgttaacca ggtcagtggt tttgtttcct 151860
tgatagagac acaaggactg ccagccccat tggggagggg gggtgggtac gggagagttt 151920
gggctcgttt aaacaaagtc tcatctgatg ctctgtggca cctcaaggtg aatatagctg 151980
cccatcgacg tatcgctgga aaccggtggg ccagggcctc gtaggccgag acgggcagcc 152040
ggagcttgtg gtactgtccc tccggcaggt ggagtgggac acagttagag aacattagtc 152100
ctctggtccc tatctccacc cgccaggcct gtgtgtcagt ttgcagggcc atcctcgcac 152160
tcaggtggac tggctaggca cccttctgaa gtatctggcg gtgactgtca cctggttctt 152220
gagagagtcc ataaaatggc tgaagctcca ggcgtatagt ataatgagca acagggccaa 152280
acaggcggcg gggcctgggt agtagcgggc aacgagagac tctgtgcaat caaaccccag 152340
gctcccggcc tcacccagga agagcagcgg cagggacagc ataaaccagg agaaggcgca 152400
aatgagtccg gtgaaggtga cgttgcatat caggcgcggc ttccttccga attttgtgcg 152460
caaaagtttc cagatgatga taactgtgag gaggacgatc aggactgccg ccagtaggta 152520
gcagccggct ttcagtcctt ggacggccgt gtgcatgcct ttggtggggc cttccctgca 152580
catgttgggg cctctgttga gattggcgtc ggggcccatg gtaatgagga ggatgataat 152640
cagcaggagt accagacaaa acacgcccat caggtacagg cacacatttc tgtgggaggt 152700
tctcttgggc gttcggctga acaatgctag ggtcttctcc aacgccatac ccaagtgagt 152760
ccatacggag cacatcaggc ccaagaacat catgttctgg gtcaaaaggc agagaccggt 152820
agacgagaac tcctgaatca tttttcccag cacccagagc agcagttcta tgagaagagc 152880
tatcagccag acatccattc ggtgaaccaa ttttcttaca aagatgataa acaagatgcc 152940
agccagtgtt agcagaatca gcaggacgag cagcaggctt gtcatgccgc tgaggaaggc 153000
gctgtaggat ttagtgcacg catcttccgt tgcattgacg gaagtcatgt tggccaccag 153060
ggtccccacg gtggacccgg gggccatggt ggagagcatc ttgctggtca gagccagact 153120
gggtggtgtc tgcagcaaaa gaggaacttg cccaggcagt cagttatttt gcatgccacc 153180
tccctgcctg gtggacttcc agactatttt ctgcattcgc ccttgcgtgt ccattgttgc 153240
aaggagcgat ttggagaaaa taaactgtga gtttcacaga tccacgggcc acgctcccct 153300
gggggcttca tgatcccacc gcctttcccg atgatgatga caaccgcggc tgtctgaagc 153360
ggctgacgaa atcggttgag attctgatga gaggcttggg ggggtctttg ccctcaaggc 153420
gaggctcctt ctcctaggaa tgccgagccc cctgcactag cttcgctcca ctggggatct 153480
ttgccagcct tcatactaga ttcagcgatc ccccggttgg gaatcttcgc cagccccccg 153540
tcctgctatc ccgctcgtcg ccgcgcctcc catgctaagg gccccccttcc tttcccttga 153600 ctttggggat attcggagtc tgctctcgcc gctctcttct ctcgtttaaa cgagagaata 153660
gtagtagggt ccagtctcag gccccctcac tttgggtctt agaatggtgg ccgggctgta 153720
aaattctgga ggacggagag ggcggccccg gagttgttat caaagaggca ctggaggatg 153780
ttggccgctc cttggagcag cttgtcgaaa taatgatcca cggccacggg aacgccgtgc 153840
cgctcggcgt aggccgggtc ctcggccatc tccgtctttc tcgccccctt cactcccccc 153900
ttgggctcca caaagacgta ctggatgcgg tcgtggatct ggggcagttc ctcgttgcgc 153960
tcgacgaact tctggtagac ggccaggtga ggcatctggg tgctcttgta ggctgagagc 154020
ttgcggctga gctccgttga aaagcagagc tcccccatgg ggaccctgcc ttcacggagg 154080
tctgtgtagg cctggtttag gatgtcaatg acgggcaaaa agcccacagg tagcccttgt 154140
gtaaatgact cttggaaggg ccggtgggag aggaggctgg ccgcctcctt tacccgggca 154200
tccgccagca ccaggtcgag cacgcgccgg cagcgtgtct gcacaaactt gcaggccgtc 154260
ttccggacga gctccacccc cttcatcagg gtcttgccgt ccgtcagcac ccccacatat 154320
ctcttctttg taatcagcat caggcaggag aaggtcttct cggcctccag ggagatgggg 154380
gccacaaaca ggctccgggt ggtgtgggcg gccagggcat cggcaaagcg cagggtctcg 154440
ctctctgaaa acccccggca ctcgataaac agcgagtccg tgtccccgta gatgactcga 154500
agctggccct cggggttgag gggcgcccag gcgtccgggg agggggccag ggcctgcagg 154560
ttggcggggc tcagggcctc cacgaaggcc ttggcccgct ccaacatcgt gcggccctgc 154620
agcgtcaccg tctcggcgat ggagaggcag ggaaagaggc cgttggccac cccggtgaag 154680
ccgtagacgg cgttgcacgt gcacttgatg gccagctgct gcttgtcgag gatggtcctt 154740
tggcgcggat cctcgcaggc cgccagcagc ttcttgatgg ccttgcgctt ggccagccag 154800
gaggtcaaca gactagccaa gaaggactcg tgcacgtgct tctttacaaa gtggtagacg 154860
ccccccgtga gcctgaagga ctcatagtct tctcccgggc gcaggccggc tagcctgtgc 154920
tcttctcccg gcgttatcat ggtagaataa cagagattat gagcctgaat gatgctcggg 154980
tagaggctgg caaagtccac caccagaacc ggggagttgt agaatccgga caggggctgg 155040
atgacggtgg ccccctggta gccgtcccgg tcagaggccg agggcatggg caggataaag 155100
ttttcctttt gggcggccgc caggaggcag gagaacacgc ggatctgctg cccatcgtcc 155160
agcacccgcc tgcaggggat gtgagcgatc ttggcaatct ctgccacctc cacgtggatc 155220
acgaaatggt ttagcagatc catgaccagg gccgagtcct gcacgcagta catgccgagc 155280
cgcctgcgcc cctcggggcc cgctgcaaag aggcgaggaa tctccttgta atgcacatcc 155340
tccttcttgg cccccagtag gtgcctggct actgtgtcca gcttgtagtc tgagaggctg 155400
agcttgtccc ggcacacggc gtacatgtcg atggggatga ggccggtgat gcggaccttg 155460
gtgttggccc gcaagaagcc cttgcccgca tcatggggtc gcctgacctc gcagacgccc 155520
ccagccctaa ttttgcccag agaggctggg ttgatgctgt agatgtgcct ggctctgtcc 155580
agaatgtagg gccagtcaaa gttggccacg ttgtagccgg tcacaatctc cacgctgagg 155640
tctctgatga gctggaagaa ggcgtagagc atgtccagct ccgatgggaa ctcgtagacc 155700 tcaacccccct ctatgtcttc gcaggtgccc agcgtcagca ggatgcgcct atagcgcccg 155760
gcctcctccc ctgtcgacca gaggacgcag gatatctgca ggatcaggtc agcctcgttg 155820
gtggccgtgg ggaagccctc ctcccccaga cactcgatat cgaaggccag ggcctggtag 155880
gagggccagg agctgtcttc acgccggacc gagaggtcgc ccacctcaca gtcgtactcg 155940
agctcggcgt acgagtcccg gtgctggagg cgggggatgg cgcggcggca gctgtaccag 156000
ccaaaggtga caaagtcatt gtccaggaca aagcggcgcg tggcatccac gttggcctca 156060
aagatccgac acccgtgctt gtcttgcagc cacgtggcca cgtgacacac actgttggga 156120
tgggagaggg tgatcttgtg gtagtcgccg gcatggttgc cgtagcccat aatggaacgg 156180
cgcgtgacct tctccaccga gacccggcag ggggtcctgc ggtcgaaggt gctggccttg 156240
agggcgctga ggactgcaaa ctccacgtcc agaccctgag gcgcgctggc gtagaagtag 156300
gcctgctgcc caaacacgtt cacacacacg ctggccccat cggccttgcg ccggcccagt 156360
agcttgatga cgatgccaca tggcaccaca taccoctgtt tatccgatgg aatgacggcg 156420
catttctcgt gcgtgtacac cgtctcgagt atgtcgtaga catggaagtc cagagggctt 156480
ccgtgggtgt ctgcctccgg ccttgccgtg ccctcttggg cacgctggcg ccaccacatg 156540
ccctttccat cctcgtcacc ccccaccacc gtcagggagt cttggtagaa gcacaggggg 156600
ggctgaggcc cccgcacatc caccacccct gcggcgcctg gtgtctggaa acacttggga 156660
atgagacgca ggtactcctt gtcaggcttt ttcagaaggc ctttattagg tcttaggaaa 156720
gggttataga agagtccccc agacatggtt aaaactcagt ctctgcctcc ccaagcagtg 156780
cggcggcggt ctctggatcg tgatagcgtc ttctgcgtag gcctggaaaa cggtccctgg 156840
ctgcctgcaa tgctctgctg gccactgagg gtccggccgc cctctgagct gctctctttt 156900
gctcctggtt ttgctcatgc agcgctaaca tgatggcttg taattctgtc ttactaatgg 156960
gattaatgcc tggaccctca ccagaggcat gttgctgagc gagctcgtcg atcccggggt 157020
agagcatctg caccggctgc tgcgacatct ggcgcgtgcg cctcgtgagg gaaataacca 157080
ggatcaccac ccccgccacc aggaccagaa tgagcatgcc gccgaagggg tttttgaaga 157140
aggagatgaa accagagacc aggctgctaa acaaaccccc caccgtgctg actaggttgg 157200
tgatggactg acccacgcta cccagactgt ccataagttc ccccaggccg tccacgaatt 157260
gatttcttcc gtttgacact gcattgtcca aatccttccg caggccggcg atgttttgcg 157320
cctggaagtt gtactcccgg aagatgccct ccaggtcaaa gacgttggag gcacgctgtt 157380
cgtcccgtga gtacagctcc agggaggcaa agtcaatgtt ctcgatgagg gaggtgttta 157440
gtgagatgaa ggtctgcagg gtggcaatgc cgtccagctc gatggtttta aagtggtggt 157500
agtcgttgta gacgtggatc tcgttgccgg actggaagta gtactggctg gtcgcctggc 157560
acacctccgt catctttttt gtgaggaaga tctcgttgtc ggtgcccagc tgtccctcgt 157620
aggtcttggt gtcgttgata aagctgaagg acaccagggg gcgcgagtag cacatggtct 157680
cggagccagg gaccctcatg ctcttgcgca gggtgacggt ggcctggtta acgggcacgc 157740
actgggagac tgagatgaca tcccccaggc gcttggccgc caccgcctta ccgtagatgc 157800
tggacatgac ggtggttgga ttaatcttgg ttagttctct cagcaccatg ttctgcctct 157860
tctgctccag gcaccaggcc cgcgcaaggt ctcccagcat gcggttgatc tggcggcgca 157920
gggagtcgta ggcaaattgg atctggacgg tggcgggatt gttgagggtg cccagggact 157980
tcccgggggc cgtgggggc accggtgtgg tggcgttccc cgcatcccgc ctccgacgcc 158040
tcagaacggc ggcgggggtg ctcccgcggg ccgcggatgg ggctgggggc gatggactgc 158100
tggggggtga ggaagtcgga gtggtaagct ccgtcaggtt cttgacggtg gccaacgagc 158160
gcggggtcag aggtagccaa gctaataaca atcctccgct cgttataaaa tatgtaatgg 158220
cttcctggcc cttcgtgtaa cgatcctgga cggcctcgta cttctcatgc atggtcttgt 158280
tcacctgctc ttcgatgcac ttgaaggcgt ccgggagctc tatgcccacg gttgtgttgg 158340
tcacgaagct agaggtgccc tcgtcagtca caaaatgtat tgacttccct gtttctgtgg 158400
cgatggtcga gtcaaaggtt tgccagtgtt gaagcgggca gtaggctgtc ctgttctcga 158460
gcttccaaga tagcgtgtaa gtgcccttgt ccaggaaggc tcggcgttcg ccttgcgggt 158520
tcgtccctcg gttgtcgtag tccactatct tgtagttagt tctcacgtgg aaggagtctg 158580
cccgctcatg gaaggtttcc ttatttttcc cgtcatagaa aggggacatt tccacagtct 158640
gcccggtggt ggtcacaaag aagtcgaagg ggctgttgga cttggccatc atgtcagtta 158700
tcaggcagtt gacggtagtt cttgttctgt aagtccatat caaccacccg gggggcgtcat 158760 agagctccgt ctggctggcg tagcggcgca ccccgttggc caggcccccg gtgggcttta 158820
ggttgacggt gatgttaact ccgtcgcggt ctacatacac gcgcgtcagc ccatcttttg 158880
tcatcttgac cgcgttgtag cactggtaga tggtatccat ctggtcagtt tcgtagctgt 158940
caacggagaa cttctcctcg tgccggttgg tcacggagtc cgcgtaccag ccattgtaga 159000
tgagaatgtt ggtcactatc ttggtgtagg agcggacctt aaacgagtag ggaataatgt 159060
tgtctttaaa caccatcaac aggccctccg tgtgattctc ccgcgtgcca aacgagggac 159120
actggatgtc cgaggagaag cggaacaggt cgccgtggct ggagagctcg cagactcgga 159180
aaggaaagct ggtttgctga cgcgtggcgg taggctgcac cgtggtggcg gggggtgcgg 159240
gctgctctgg ggtctgcgca ccgagacggc acgccagggc ggctagcagc acgaccacgc 159300
ttagcaccct acgccgagtc atctctcatt tggaggtgca ggtagagaag ggcatataga 159360
tccttaaata cccacccccct gcccttatac agaagaatta gggggcggtc agagtcgtac 159420
gtgaggtaaa gcccatccgg gggcagggcc tggccggggc tgaccgcgtc cgcccggcgc 159480
aggatcaagg accgccccca ggtcttgttg tagagggaca cggttaggac ggcctcgcgc 159540
agcgcccggc acagaatttg ctggctagat gccagtgagc cccgggtac gctgtagaag 159600 ctgttgaagg aggtctctat ccagtcgctc ggctcgatgc ctggccatat cagggaagtc 159660
aggaatgcct tctggtgggg cagcgtacct gcggcgtcac agcagcgagc cagggccacg 159720
ttgctgggtg ggggaaagag cccgctctcc tccgccaggg gccccgtgat gaaggtgtac 159780
aggctgtgcg tcagcgcgtg caggtgctcc gagctcaggg tctgggtaaa caggtgtgtt 159840
ttgatgtact tggaattctc aaaggcggca ccctcgccgg cgcgcctgtc ctcccaggga 159900
cccgagacga aggcccgtct gtagaggaag tggttgcgca tgcgggccag ctcccagtag 159960
accacgtccc cccagacgcg caggcacagg gtctcggtca gggtctcgct ctgttgcgcc 160020
aggcaggact gcagcttggc cagaccctcg gtggccacct ggcgcaggta ctgctccttg 160080
cgcttgagcg cgtccgagag ggcgccggac gggccgggct ctcgtgcccc agccggccgg 160140
ggcacctccg ggctctcccg ggacgcctcc tcctcgcctc ggcccaaccg ctgcatggct 160200
cggttgagcc gcgtgtacag ctcgttcctc ttttgcagga tggcccggta ctgggggtgc 160260
gccgtgaagg cggcggcgca gtccgccttc agcgcctcca ccgcgtcgcc cgaggagctg 160320
tagaccccgc cgcagaagag ccgctccgtg gccccgggag ccacggcgtc aaacaggtga 160380
gtcagccttg cccccgccag cgcctcctcg caggcccccc gcaccagggc caggcgacgc 160440
tcccgggcaa acagggcaga gaggcgggaa tggccgccac cctcccccctg ccccgttgca 160500 ccgatagcat ggccgccaga gttccaatag aggagctccg agagctccgc cacctccggg 160560
ggcactgtcg agaagacgtt gtaggtgtcc agcgctctgg tcgccccctc tgcctccggc 160620
cgccccgggc ccgggaccgc gccctcctct gggccgcccg gcctcgcctt ctcctcagcc 160680
tccaacaggt gcccgagccc cgcctggcgg acttcattct caaacagtcc cgagaccggc 160740
tccggattca ccggcaccgc caggtggtta caggagacgt gggtcccctc tgccgtggaa 160800
gggttgccgt ggttgggcag aaccatcagc tcgcccacac agcgccagca gggcacagag 160860
gtgatgtaga ggcgcgggtc tgggatggga cttacgcccc gaaagcggcc cagcagatcc 160920
agggcccgtt ccaggctctc cagccccatg gtgtgagaca tgcaataaaa cacgctattg 160980
attctcttca ttaaaatctc tatgtcattt attaggcaca aacttacatc gactttatgc 161040
cccccgtaaa actccacaga gtacgcgact gagggggtac ggagaggcgg gacccgggta 161100
ccctttctac caggggcgag cagcgcggca gaggcctctc tcgagttctc tagcaggtgc 161160
accagctcca gggacagggc gctgcatgca cggtcattct gccgtctcaa acggggaagg 161220
aggatggcct ccagctcggc cagcaggccg gcgttgcgca ccaccgcagc cacgtccaga 161280
ctccgggggt ccagccgggt gcacacgctc agctcaaccg ccagggcgta cacctggctg 161340
tacgccgccg ccagcagccc cgacatcgcc gccccagggg tctctagacc tcgagtccgg 161400
ggagaacggt ggccagacgg cgcttgcgtc tgcccccgga gccctgccct cctccaccca 161460
gcagcagccc ggccgaggcc tgcgacgcgg tgctgaccgg ctcggccacg ctgataaagt 161520
tgtcctgggc tgccccgggc ccaccccaca ctccctccag aaagtcccga gcggcctccg 161580
ccgtccactc tatcccgctg gaggcaatgg tcgccagggt ttctaggacg ctgtccgcca 161640
ggacggagaa gcggcccaat aagtactccg cgtcgtccct agtcagcgag gcgcatgcct 161700
cgcccatggc atccacaagg ttgcacacca catcaaacac acagtcttcc tcctgttttt 161760
gtgatataat ggcctccagg ccagccctga tgttctcaat ctcatatgtg gtcgcggctt 161820
gggtccggcg cttcacggtc aaccctaggg tgggggtggc aaagacaaac ttcttccgca 161880
tggaagagcc cccggcctgc ttgcgcagcc cagccccggg ggcctgcagc aggttcctgt 161940
ccacgccccg gcccataaag tatcccaggt tcccggcctg gaatatctgg ttgttgccgt 162000
tgacccccgt gtacttgttg atggtcactg gcagcgtgac aaccggacgg gccttgcaga 162060
cctggctaag acagtctgtg gccgcgcaga ccaccgtggt cgcagtaagg gaggaggtgg 162120
cctccgcgta ggccgctgcc gactccaccg cccgcgtgcc cagtacgtgg gggtagtcac 162180
gggcgggcac cgactgcgtc ctcggcacca gtccctgaat caggctgatg tagaactggg 162240
tctggccgca cgccttcagg atggcgttgt tgagcctctg cttggcgtaa gtgaccaggt 162300
tgccaggcac cacatctatg acgttgctct cttcgtgggc ccgggagccc ccgtccacaa 162360
agagggccag gtcagagtac tcctccgcgc tggccccgct ggggacaggg accgagcgcc 162420
gcctggaaaa gttgtgccac aggtacaggc ttgagagctt agtgtccggg aatagggtct 162480
tgtggtaggt gttgaggaat ttcatgtagg gcccgttgat gatgtagttc tccctcctgg 162540
tagtggactt gatgaagctg ttctggaggg cggcattctc ccccgtgaag accaccctgt 162600
tcttgatctt gatgttcctg gggcacagca tcagcacctt ggacatgcgc acaggcagcc 162660
gccggccgta cacccggccc tgcagggccg cgtccaggtc tggcaggtcg caggtgggct 162720
ccccatgcac caccttggcc tccttggccg tgaggacccc cttgtcgatg gccaggctcc 162780
taaagttggt gcacagcgtc tggtagtgac cctttagcca ctctgggggg ctctggccaa 162840
gcccggggtt gtcattctca tagcacatac agatgggcag ggagatgtcc tgcaggatgg 162900
tcagcagtga gcggtaaaac agctgggtga agatggggca ggcgggctgc gcaaaggggt 162960
tgcacgagta ctgcatcacg tggtagcagc tcttgaccag gtccttgtag gtgatgttgt 163020
tcttggccat gctgttcata aactggacca cttcggcgtc caccgccgca tccacgtcct 163080
tgaacatctt gacaaagtca cgcgggccat ggggctcctt ctctagcttt ccttcagcgt 163140
ctatgcccag ccgagacagc cgctccagca ggttctggtt cagctgccag taggtgtagc 163200
ggggctcgtc gtccggccgc tgcccgtcgt cctccttatc gatgaagttg agaaagttgc 163260
ccaaaaagtc cgtctcgttg taggagcccg aggcccccga gatcacatag ggtccctcc 163320 gctgcgtgga catgacgggg gggaagcggt ccctcagcct aaagaagagc gtgttcaggc 163380
acacggccgg ggcccggccc tcgcagagcg agcacatggg actggcggcc gcccccgcca 163440
cgtagctgcc cgtctccggc accggggtca gagagctctt ctgtccctgg caaaactgca 163500
ggtagtaggc atagcgggca agaaggttgg gcgagaagga ggccgcatag accaggtgct 163560
ccacagcgta gtttcccgga ccgttggttc cggtcacgtc tggcccaccc cagcccgaga 163620
agcagggtcg gcggcagggg tcccaggtcc cctcctgcag ggtccccagg ccgtgggtca 163680
tgtagaaact gttaaagaga ctctccttgc cctgaccggt tgacttcgag acccccgaga 163740
cgtagaggac ggaattggtg gcaaagatct gcgtggacac gtgggggcc aggctggcat 163800 tatatcggtg taacgcagcc acacgggcct ctggaccctc acagtcggca aacaggggcc 163860
acgagtcgta gttgaggctg gccggggtct cgtgcgaggc ctccagcatg gcgggtgcgt 163920
agctcaccgc cagctcgcat gccgcgctgt ccacaatcat taaggctccc gagtccgggt 163980
gactgatggt tgaggctggg aactccttga gggggccac cttggccacc ttggcctggt 164040
cctgcaggct ctgcttctcc agcagctcca ccagcttgcc cacccgtcgg acgcgcagcg 164100
cctgcgccag cccggtgtac agcgcctcgt gcatgcagcg gctgaggtcc gagttgtaaa 164160
actggcggag ctggggcacg ccctctggga acacctcctt gtcgtagagc gggaccctaa 164220
cgctcgcaga ctgccccacc gctacctcct gttttaacga tggaatggcc accaggtttc 164280
cgctgtagag tcgctccttg aaggcctcgg ttattgccac cgcccccagg taggcagagg 164340
gatctagccc ttcggggaag aagtcccccg gcttggagct ttccctcggt agggcgctgt 164400
aggcgtcgta cccaaacacc tccctggtct cgccacagag ggcctcgaga cccggcccct 164460
caaagatggg gggaaccata tgggcattgt ggaacacgta gatgtccctg tgataggagg 164520
tagcgcgtag gagcccgcag ttggggtcgg gcctcctgtg cagagccttg acattgatgc 164580
tgaagcccgg ctccacggtg atgccgcaaa ggagcggcac cgtcaggcac ctgtggcccg 164640
cgtagccggt ccccagtgtg gccacctccc taagagggta ggtggccagg gggtaaaagt 164700
agatgtagcc gcacggaccc ggctggctct ggctgcccag attatcctcg ctagtctgtg 164760
caccctgcat gatgcccaag gtatcgcccc ggcctcccag tcccacatta aatgttacac 164820
tttactcatc acgcaacacc cactgtttat tcatttacaa agatttcagg aagtcagtca 164880
ggctggccag ggcccacgtc acggggaact gacgtctcag cgatcttggc atgccgccca 164940
gcctcgcaaa ccagagtctg cgatagaggg ccaggtagtg ggcgattgcc cccagcacga 165000
aggcggcgct cttgtggtca tccaggtagt ttcgcaccgc aaacaccact gtgtagcaca 165060
gcaccaccct gagccgcgac cagtagtcgt agtggtcgtt gtacactgcg cgcaggacgc 165120
tgatgatgag ccgtacgtgc gtgtctttgc ccccgatgtc ggctgtcctg caggccagct 165180
ccgcgtacag cttcctatcc ttcctcaggg aggccttgat gagccggcag aggaccaggg 165240
ctggcaaagg caggtctttc tcatcccggg tgaacaccgc gtacatggcc ctgaacatga 165300

```
ggtagctgga ctcagccacc ttgtcgtccg gcggcgaggg cgcgacccac gcctcgaccg 165360
gggtcctcac aaacacagaa tctgtagact tggctggcct catggtctcg tcaggccagc 165420
tcacgggctt caggcttata tgataaaatg ggcgtggcag aatagtataa gacgcgaggc 165480
ctgggtgagg agagtccaga gcaatggcca ggttcatcgc tcagctcctc ctgttggcct 165540
cctgtgtggc cgccggccag gctgtcaccg ctttcttggg tgagcgagtc accctgacct 165600
cctactggag gagggtgagc ctcggtccag agattgaggt cagctggttt aaactgggcc 165660
caggagagga gcaggtgctt attgggcgca tgcaccacga tgtcatcttt atagagtggc 165720
ctttcagggg cttctttgat atccacagaa gtgccaacac cttcttttta gtagtcaccg 165780
ctgccaacat ctcccatgac ggcaactacc tgtgccgcat gaaactgggc gagaccgagg 165840
tcaccaagca ggaacacctg agcgtggtga agcctctaac gctgtctgtc cactccgaaa 165900
ggtctcagtt cccagacttc tctgtcctta ctgtgacatg caccgtgaat gcatttcccc 165960
atccccacgt ccagtggctc atgcccgagg gcgtggagcc cgcaccaact gcggcaaatg 166020
gcggtgttat gaaggaaaag gatgggagcc tctctgttgc tgttgacctg tcacttccca 166080
agccctggca cctgccagtg acctgcgttg ggaaaaatga caaggaggaa gcccacgggg 166140
tttatgtttc tggatacttg tcgcaataaa cgcacttgcc tatttcacct tgttttagtg 166200
tggcattggg ggggtggcat tgcgggtgga tagcctcgcg actcgtggga aaatgggcgg 166260
aagggcaccg tgggaaaata gttccaggtg acagcagcag tgtgtgaaga ttgtcacagc 166320
tgctggtttg gagaaaacgg gggtgggcgg tgatcaggga gaacaattcc ccggggacac 166380
ctgcacgaga cccctgggct ctcaggaact ccgcccaggt cttgccaatt ggggtgatcc 166440
tgtagcgccg cggtttcagc atcacaggtt attttgcctg aagcttgctg gggcgtaaat 166500
ccctctcgcc ttgtttctca gagagcattt caggccggtt ttgcagtcgc tgctgcagct 166560
atggggtccc tagaaatggt gccaatgggc gcgggtcccc ctagccccgg cggggatccg 166620
gatgggtacg atggcggaaa caactcccaa tatccatctg cttctggctc ttctgggaac 166680
acccccaccc caccgaacga tgaggaacgt gaatctaatg aagagccccc accgccttat 166740
gaggacccat attggggcaa tggcgaccgt cactcggact atcaaccact aggaacccaa 166800
gatcaaagtc tgtacttggg attgcaacac gacgggaatg acgggctccc tccccctccc 166860
tactctccac gggatgactc atctcaacac atatacgaag aagcgggcag aggaaggtaa 166920
gagtgccatc tatctgtact tttatttatt gcatcacaag tcacatcaat aataagggcg 166980
ccatctagcg ggagatgtta tccacaccat cccaattcac atctcaggga caacaggtca 167040
aagttctttg ttgacacccc cagcgctggc tccagggggt ggaagcgttg gatgcagtcc 167100
tccgcatcgg ggcggacgcc tcctcccaac gcgtttctgc ggatcagtcg ctggctggtg 167160
ggcatcggag tcggtgggcg gtcctccacg gggacacgct ccttcttggc cttgttcttt 167220
gaccttttgg acattcttct gaaggaacgg cggagagtag cgtagaatcc agccagtggt 167280
ctacccggtc gcatggtggc ttcttagatg aggagcaggc ataaaagtcc aaacaggaca 167340
cagagtacca ccaggagtag tcttagtctg ctgacgtctg ggtcctcggg gcaggggtgg 167400
ctaggcctgg tctccgtaga agagccgggc aggccgcagg cagaggactg ctgctctagc 167460
aaagcacgct ccaggacgtg taccatctcg agagtgaggc acagctgttt tcgtggactt 167520
ttatacagta aggacaagga aagaaggcca gaggaatgtg gaaagatgag cgaggacagg 167580
tgtggaggtt ttgggctagc tcttagtttc tgggtgtgag agagggatta aagtgcttat 167640
gcgcaaagaa tgtgtcaaca acaggtgttc ctgcctctgc tggcatgagt taggtgtggc 167700
```

ttgggctgaa tccaaatgtg tattggcaca agatggaaag caaagttgct ggagttactg 167760
ggtgggagac agggatgtat gtggtccccc gctggtatgc cagtaccctg tggaagtaag 167820
gggcctcatc tgcctggtag ttgtgttgtg cagaggtctg atgtgtgtag gaggggtggg 167880
ttcaacgcag gggcgttggt ggcggagtct ggcaacgccc gggtccttgc tacctgtgtg 167940
gtgtgttaag ggctgggtaa aggtgtctgc caattctcgc atgtcctcct ttccccttgt 168000
tttgaaatag aatatgaatg tggcttttca gcctagacag acagtgtggc taagggagtg 168060
tgtgccagtt aaggtgatta gctaaggcat tcccagtaaa tggagggaga gtcagtcagg 168120
caagcctatg acatggtaat gcctagaagt aaagaaaggt tagtcatagt agcttagctg 168180
aactgggccg tgggggtcgt catcatctcc accggaacca gaagaaccca aaagcagcgt 168240
aggaaggtgt ggatcaccgc cgccatggcc ggaatcatga ctatgaccgc cgcctccgtc 168300
tgtcatcaaa ggcgggccct ggtcacctcc tttgttttca acctcttccg tcaattgtgg 168360
agggcctcca tcatttccag cagagtcgct agggctatga ggcagcgggt catgtgggcc 168420
attgtcatca gtgttgtcag ggtcctgtgg gccattgtca tcagtgttgt cagggtcctg 168480
aggcagcggg tcatgtgggc cattgtcatc agtgttgtca gggtcctgtg ggccattgtc 168540
atcagtgttg tcagggtcct gtgggccatt gtcaggacca cctccaggtg cgcctaggtt 168600
ttgagagcag agtgggggtc cgtcgccggc tccactcacg agcaggtggt gtctgccctc 168660
gttggagtta gagtcagatt catggccaga atcatcggta gcttgttgag ggtgcgggag 168720
ggagtcatcg tggtggtgtt catcactgtg tcgttgtcca tggtaataca tccagattaa 168780
aatcgccaga aacaggagga gccaaaggag atcaaccaat agagtccacc agttttgttg 168840
tagatagaga gcaataatga gcaggatgag gtctaggaag aaggctagga agaaggccaa 168900
aagctgccag atggtggcac caagtcgcca gagcatctcc aataagtaga tccagatacc 168960
taagactgcg ttgaaaaaag agtgttaggg ttggaaaagt gggggtgtgg taaataattc 169020
ctagggaatg ttagatctta ccaagtaagc acccgaagat gaacagcaca attccaagga 169080
acaatgcctg tccgtgcaaa ttccagagag cgatgagcag gagggtgact ggggaaagag 169140
gagaaagtgc gttagagaag gaagagtaag ggaaaggggg tgtggggcaa agggtgtaat 169200
acttactcat cagtaggagt atacaaaggg ctccaagtgg acagagaagg tctcttctga 169260
agataaagat gatcaaaatt ataattataa gcatgagagc aaaggaatag aggacaagga 169320
gggctcctcc agtccagtca ctcataacga tgtacagcca aaacagtagc gccaagagga 169380
ggagaaggag agcaaggcct agggaagagg agaggggggg tcctcgaggg ggccgtcgcg 169440
ggcccggtgg gcccctctca aggtcgtgtt ccatcctcag ggcagtgtgt caggagcaag 169500
gcagttgagg aaagaagggg gcagagcagt gtgagaggct tatgtagggc ggctacgtca 169560
gagtaacgcg tgtttcttgg gatgtaggcc cggggggatt tgcggggtct gccggaggca 169620
gtacgggtac agatttcccg aaagcggcgg tgtgtgtgtg catgtaagcg tagaaagggg 169680
aagtagaaag cgtgtgtttg tgttagaaaa gcgggtcccc ggggggcaag ctgtgggaat 169740
gcggtggcca agtgcaacag gaaatggaaa ggcagtgcgg caatcagaag gggagtgcg 169800
tagtgttgtg ggaagcggca gtgtaatctg cacaaagagg cgcggggcgc gcaacgttgg 169860
gaggtcgttg gcggcaggcg ggaggccgtg ctttaggggg gttcaggtga ggcaaggctg 169920
tggggtaacc gtaggggagg cgggtgaggc ggctaagagg gctaagggtc ggcgggtgac 169980
gaagcagcag acggcggata tgggaatttc agaatgaggt ggcggattca ggcgaaaagg 170040
gtgtgggctg tgcgagtgtc atgaggcagg cgcggaaagt cgctgcggct tgctggggca 170100

```
tggggggccg cgcattcctg gaaaaagtgg agggggcgtg gccttccccc gcggcccccc 170160
agcccccccg cacagagcgg cgctacggcg ggcgggcggc ggggggtcgg ggtccgcggg 170220
ctccgggggc tgcgggcggt ggatggcggc ggacgttccg gggatcgggg gggtcggggg 170280
gcgccgcgcg ggcgcagcca tgcgtgaccg tgatgagggg gcagggtcgc agggggtgtg 170340
tctggtgggg gcgggagcgg ggggcggcgc gggagcctgc acgccgttgg agggtagaat 170400
gacagggggc ggggacagag aggcggtcgc gcccccggcc gcgccagcca agcccccaag 170460
gggggcgggg agcgggcaat ggagcgtgac gaagggcccc agggctgacc ccggcaaacg 170520
tgacccgggg ctccggggtg acccagccaa gcgtgaccaa ggggcccgtg ggtgacacag 170580
gcaaccctga caaaggcccc ccaggaaaga cccccggggg gcatcggggg gtggggcatg 170640
gggggccgcg cattcctgga aaaagtggag ggggcgtggc cttcccccgc ggcccccccag 170700
cccccccgca cagagcggcg ctacggcggg cgggcggcgg ggggtcgggg tccgcgggct 170760
ccgggggctg cgggcggtgg atggcggcgg acgttccggg gatcgggggg gtcgggggc 170820
gccgcgcggg cgcagccatg cgtgaccgtg atgaggggc agggtcgcag ggggtgtgtc 170880
tggtgggggc gggagcgggg ggcggcgcgg gagcctgcac gccgttggag ggtagaatga 170940
cagggggcgg ggacagagag gcggtcgcgc ccccggccgc gccagccaag cccccaaggg 171000
gggcggggag cgggcaatgg agcgtgacga agggccccag ggctgacccc ggcaaacgtg 171060
acccggggct ccggggtgac ccagccaagc gtgaccaagg ggcccgtggg tgacacaggc 171120
aaccctgaca aaggcccccc aggaaagacc cccgtggggc atggggggcc gcgcattcct 171180
ggaaaaagtg gagggggcgt ggccttcccc cgcggccccc cagccccccc gcacagagcg 171240
gcgctacggc gggcgggcgg cggggggtcg gggtccgcgg gctccggggg ctgcgggcgg 171300
tggatggcgg cggacgttcc ggggatcggg ggggtcgggg ggcgccgcgc gggcgcagcc 171360
atgcgtgacc gtgatgaggg ggcagggtcg cagggggtgt gtctggtggg ggcgggagcg 171420
gggggcggcg cgggagcctg cacgccgttg gagggtagaa tgacaggggg cggggacaga 171480
gaggcggtcg cgcccccggc cgcgccagcc aagcccccaa gggggggcggg gagcgggcaa 171540
tggagcgtga cgaagggccc cagggctgac cccggcaaac gtgacccggg gctccggggt 171600
gacccagcca agcgtgacca aggggcccgt gggtgacaca ggcaaccctg acaaaggccc 171660
cccaggaaag acccccgggg ggcatcgggg ggtggggcat ggggggccgc gcattcctgg 171720
aaaaagtgga gggggcgtgg ccttccccccg cggcccccca gccccccccgc acagagcggc 171780
gctacggcgg gcgggcggcg gggggtcggg gtccgcgggc tccgggggct gcgggcggtg 171840
gatggcggcg gacgttccgg ggatcggggg ggtcgggggg cgccgcgcgg gcgcagccat 171900
gcgtgaccgt gatgaggggg cagggtcgca gggggtgtgt ctggtggggg cgggagcggg 171960
gggcggcgcg ggagcctgca cgccgttgga gggtagaatg acagggggcg gggacagaga 172020
ggcggtcgcg cccccggccg cgccagccaa gcccccaagg ggggcgggga gcgggcaatg 172080
gagcgtgacg aagggcccca gggctgaccc cggcaaacgt gacccggggc tccggggtga 172140
cccagccaag cgtgaccaag gggcccgtgg gtgacacagg caaccctgac aaaggccccc 172200
caggaaagac cccgggggggg catcgggggg ggtgttggcg ggggcatggg ggggtcggat 172260
ttcgccctta ttgccctgtt t                                        172281
```

<210> SEQ ID NO 59
<211> LENGTH: 137508
<212> TYPE: DNA
<213> ORGANISM: Human herpesvirus 8

<400> SEQUENCE: 59
tactaatttt caaaggcggg gttctgccag gcatagtctt tttttctggc ggcccttgtg 60
taaacctgtc tttcagacct tgttggacat cctgtacaat caagatgttc ctgtatgttg 120
tctgcagtct ggcggtttgc tttcgaggac tattaagcct ttctctgcta tcgtctccaa 180
atttgtgccc tggagtgatt tcaacgcctt acacgttgac ctgtctgtct aatgcatcct 240
tgccaatatc ctggtattgc aacaatactc ggcttttgcg actgacggag agaagagtca 300
ttcttgacac cattgcctgc aattttactt gtgtggaaca atctgggcat cgacagagca 360
tttggattac atggcgtgca caacctgtct tacaaacctt gtgtgcacag ccatcaaaca 420
cagtcacttg tggtcagcat gttactttgt attgttctac ctctggaaat aatgttaccg 480
tttggcatct accaaacgga cgaaatgaaa ccgtgtcaca aactaaatac tataatttta 540
cgctgatgag ccaaactgag ggtgttatac cttgttctaa cgggctgtcg tctcgcctgt 600
caaatcgtat atgtttttgg gcgcgttgtg ccaatataac tccagaaact catactgtat 660
ctgtcagcag tactacaggc tttagaacat tgagtactaa tagcttagtg aagataatcc 720
atgcaaccac acgtgatgta gttgtagtga aagaagcaaa atctacacat tttcatattg 780
aagtgcattt tcttgtattt atgacactcg tagctctgat aggaaccatg tgtggtatct 840
taggaactat tatctttgcc cattgtcaaa aacaacgtga ctcaaacaaa acagtgccac 900
aacaattgca ggattattat tccctacacg atttgtgcac ggaagactat acgcaaccag 960
tggattggta ctgacattca ggtaagataa tctaaatatt ctctataaca taattgtaat 1020
gtgttttatg tttatagcta caaatgtttt atgcaaaata cattttatga ggtcggatac 1080
ttattaaaag cattgtctta agtacattaa aaggacattg tataaccgtg ctacttacag 1140
catggccttt ttaagacaaa cactgtggat tttatggaca tttaccatgg ttattggcca 1200
ggacaatgaa aagtgttccc aaaaaacctt aattggatat agacttaaaa tgtctcgtga 1260
cggtgacatt gcagttggag aaacagtgga attacgttgt agatctggat acactactta 1320
tgcccgcaat ataacagcaa catgtttaca aggtgggacg tggtctgaac caacggcaac 1380
atgtaacaaa aagtcctgtc caaacccagg tgaaatacaa aatggaaagg ttatatttca 1440
tggtggacaa gatgccttaa aatatggggc aaacatttca tatgtttgta atgaaggata 1500
ttttttggtt ggtcgagaat acgtgcgata ttgtatgatt ggagcatctg gccaaatggc 1560
gtggtcatct tctcctcctt tttgtgaaaa agaaaagtgt cacagaccga aaatcaaaaa 1620
tggagatttt aagcctgata aagattatta tgagtataat gatgcagttc attttgaatg 1680
taatgaagga tatactctag ttggaccaca ttccattgca tgtgcagtta ataacacgtg 1740
gacatctaac atgccaacct gtgaactcgc aggctgtaaa tttccatcgg tgactcatgg 1800
ttatccaatc caaggttttt ctcttactta taaacataag caaagtgtta cttttgcatg 1860
caatgatgga tttgttctca gaggatcccc cacaattacg tgtaacgtta ctgaatggga 1920
cccaccactt cctaagtgtg ttttggaaga tatagatgat ccaaacaatt caaatcctgg 1980
acgtttgcat ccaacaccca atgaaaaacc aaatggtaat gtctttcaac gctcaaacta 2040
tacagaacct ccaacaaagc ctgaagacac ccatacagca gctacttgtg ataccaactg 2100
tgaacagcca cctaaaatcc tgccaacatc cgaaggtttt aatgagacta ccacatctaa 2160
tacaattaca aaacaattag aggatgagaa aactatatcc cagccaaata cacatattac 2220
atctgcctta acatccatga aagcgaaagg taactttacc aacaagacca ataactctac 2280
tgatctacat atagcgtcta cacccacttc ccaagatgat gctacgcctt caatacctag 2340

```
tgtacagaca cccaattata atactaacgc accgacacgt acactaacgt ctctccatat   2400
tgaagaaggc ccatccaatt ctactacttc agaaaaggcc acttcctcta ctctctcaca   2460
caactcacac aaaaatgaca ccggaggcat atacacaaca ttaaacaaaa caacacagtt   2520
gccatccact aataaaccta caaacagtca agccaagagt tccactaagc cacgcgttga   2580
gacacacaat aaaacaacca gtaatcctgc catttcttta acagattctg cagatgtgcc   2640
tcagagaccg cgagaaccaa cactccctcc cattttcagg ccaccggcgt ctaaaaatcg   2700
ctatctggaa aagcaactag ttattggact actaaccgct gtcgccctaa cgtgtggact   2760
gattacctta tttcactatc tgttctttcg ttagcctaga acttgctcca gtgttagaca   2820
gggctatgat tgcttctcca cgctgtccac cttaacactt cccaataaca aatccggtat   2880
gcagcagcgt gacactacta atgtaaccta aaaaatgtgc atgtggtatg tattgtacta   2940
aagataccga ccaatacaag acaactaata ttaaccatag tgtgcgtttc tttgtataaa   3000
atacgcgtgt gggaaagcga cagaaggggg cggcgtttcc atatgaggcc aagtgcattg   3060
gctattttag gggcggtgac cacgcactat agtgcgcggt gtggcagaaa attcacaccg   3120
tatataaaca aggaaagggg actctgcgcg cttaagcgcc aagccattat acacacgggt   3180
tttttgttgt cttggccaat cgtgtctcca tggcgctaaa gggaccacaa accctcgagg   3240
aaaatattgg gtctgcggcc cccactggtc cctgcgggta cctctatgcc tatctgacac   3300
acaacttccc catagggggaa gcctccctgc tgggcaatgg ctacccggag gcaaaagtat   3360
tttcactacc tcttttgcac gggctcacag tggaatccga tttcccctta aacgtaaagg   3420
cggtgcacaa gaaaatcgat gcaaccacag cttctgtgaa attaacttca taccacaggg   3480
aggccatcgt ctttcataat actcacttat ttcagccaat ctttcaagga aagggactgg   3540
aaaagttatg tcgagagagc cgagagctgt ttggattttc aacgtttgtt gagcaacaac   3600
acaaagggac gctctggagc ccagaggcat gccctcagct accctgcgcg aatgagattt   3660
ttatggcggt catagttaca gagggattca aggagagact gtacggcggc aaactggtgc   3720
ccgtgccctc tcagacaacg cccgtacaca ttggggaaca ccaggcgttc aagataccct   3780
tgtatgacga ggatctgttt ggtccaagtc gcgcccaaga actatgtagg ttttacaacc   3840
ccgatatcag tagataccta catgactcca tattcactgg aatagcacag gctctaaggg   3900
taaaggacgt tagcacggtc atccaagcct cagaaaggca atttgtgcac gaccaataca   3960
agataccaaa gctggtccaa gccaaggact tcccccagtg tgcttccagg ggaaccgacg   4020
ggtctaccct aatggtgata gacagtctgg tggctgaact tggtatgagt tatggtctgt   4080
cctttattga gggaccccag gatagctgcg aggttctaaa ttatgacacg tggcccatct   4140
ttgaaaactg cgagacgcca gatgcccgcc ttcgtgcact agaagtttgg cacgcagagc   4200
aggccttgca tattggcgcc cagctgtttg cggccaactc tgtgctctac ctgaccagag   4260
tggcaaagct gcctcagaag aatcagagag gagacgccaa catgtacaac tcattctacc   4320
tacagcatgg cctgggatac ctctcagagg caacagtaaa ggaaaatgga gcctctgcct   4380
tcaagggcgt gccagtgtct gcactggatg ggtcatctta caccctccag cacctggcct   4440
acgcgtcctc tttctcccca catctcctgg caaggatgtg ttactatctg cagttcttgc   4500
cccaccataa aaacaccaac agtcagtcat acaatgtggt ggactacgtg ggcaccgcgg   4560
cacctagtca aatgtgtgac ctgtgtcagg ggcaatgtcc agctgtatgc atcaacacgc   4620
tgttttacag gatgaaggac aggttcccac ctgttctgtc aaacgttaag agagacccat   4680
atgtgatcac gggcacagcg ggaacgtaca atgacctaga gattctcgga aactttgcca   4740
```

```
ccttcaggga gagagaggag gaggggaatc ctgtggaaga tgctccaaag tatacatatt   4800
ggcaactatg ccagaatata accgagaagc tagcgtccat gggcatctcg gagggcggcg   4860
atgccctaag aaccctcatt gtggacatcc ccagcttcgt caaagtgttc aaggggatag   4920
acagcacggt agaggcagag ctcctaaagt ttattaactg catgatcaaa aacaattaca   4980
acttcagaga gaacatcaaa tccgtccatc acatccttca gtttgcatgc aacgtatact   5040
ggcaggcgcc gtgcccggtt tttctgaccc tttactacaa gtcactgctg acggtcatac   5100
aggacatatg tctgacgtca tgtatgatgt acgagcagga caacccggcc gtgggaattg   5160
taccatccga gtggcttaaa atgcactttc agacaatgtg gaccaacttc aagggtgcct   5220
gcttcgacaa aggagcaatc acgggcgggg aactaaaaat agtccaccag tccatgttct   5280
gtgacctctt tgacaccgac gctgccatag gagggatgtt tgcacccgct cggatgcagg   5340
tcaggatagc cagagcaatg ctcatggttc caaaaaccat aaaaataaaa aacaggatca   5400
tcttttccaa ctccaccgga gcagagtcga tccaggcagg ttttatgaag ccggccagcc   5460
aaagggattc atacatcgtc ggaggaccct acatgaaatt cctaaacgcc ctgcacaaaa   5520
cactttttcc ttccacaaaa acttctgccc tgtacttgtg gcataagatt ggccagacca   5580
caaaaaatcc catactacca ggtgtctcgg gggaacacct aacggagtta tgtaattatg   5640
taaaggcaag tagccaggct ttcgaagaga taaatgtttt ggaccttgtg ccagacaccc   5700
tgacatcata tgcgaaaata aaactaaaca gttccattct ccgggcttgc ggacagacac   5760
agttttatgc aactactctc tcttgccttt cgccagtgac tcagctggtt ccggccgagg   5820
agtaccccca cgtactgggg ccagtggggt tgtcatctcc agatgaatac agggcaaaag   5880
tcgccggcag gtctgtaacc attgtacagt caacactgaa gcaagctgtt tccaccaacg   5940
gacgactccg gcctatcatt accgtgccac tggtggtcaa caaatataca gggagcaacg   6000
ggaacacaaa cgtctttcac tgtgcaaacc tgggatactt ctcggggaga ggggtggaca   6060
gaaatctcag gccagaaagc gtcccccttta aaaagaataa tgtcagctct atgctaagaa   6120
aacgccacgt gattatgacc cccctggtag acaggctggt aaagagaata gttggcatca   6180
actctgggga attcgaggca gaagcggtta agagaagtgt gcagaatgtc ctggaagaca   6240
gagataaccc aaacctgccg aagacagttg tattagagtt ggttaagcca cctcggtgga   6300
gctcctgtgc aagtctcaca gaggaggacg tgatttacta cctgggccct tatgccgtac   6360
ttggggacga ggtcctgtca ttactgagca cagtgggcca ggcgggggtg ccatggacgg   6420
ccgagggtgt ggcctcggtc atccaggaca taatagatga ttgcgagtta cagtttgtgg   6480
gcccagaaga gccttgcctt atccaaggac agtcggtagt ggaggagctt tttccgtccc   6540
cgggcgtccc aagcctgaca gtgggtaaaa aacgaaaaat cgcatccctg ctctctgacc   6600
tggatttgta gttgtgtacc cgtaacgatg gcaaaggaac tggcggcggt ctatgccgat   6660
gtgtcagccc tagccatgga cctctgtctt cttagttacg cagacccggc aacactggac   6720
actaaaagtc tggccctcac tacagggaag tttcagagcc ttcacggcac actactcccc   6780
ctcctcagac gacaaaacgc acacgaatgc tcaggtctgt cactagaatt ggagcacttt   6840
tggaaaacgt ggctgatgct ctggccacgt tgggagtgtg cactagcaga aaactgtctc   6900
cagaagagca tttttccctc ctgcatttgg acacaacatg caacaagcaa ccggagcgtt   6960
aggtttaatt tttacggaaa ttgggccttg gagttaaagc tgtcactaat aaacgacgtt   7020
gaaattttct ttaaacgtct tagtagcgtt ttttattgta taggatcggg cagtgctctg   7080
gagggtttag gggaggtatt gcgtttcgtt gggaagctga ggggtatctc acccgtacct   7140
```

gggccggacc tatatgtctc aaatctgccc tgcctagaat gccttcagga agtgtgtctg 7200
actcccaacc agggcaccag tctgcaggcc atgctcccag acacggcctg cagtcacata 7260
tgtacccccg catgcggtga gcctgtccgg ggcctctttg agaacgagct aaaacagctc 7320
gggcttcaaa cccctgagtc catacctact accccctgtc agtcccgggt aaggcaagat 7380
gatgaaatca gacagagctc tctaatggcg gtaggagatc accacatttt cggagaggtg 7440
accagatctg tcctggaaat ctcaaacctg atctattgga gctctggcca ctcggatgcc 7500
acctgcgacg gagacagaga ctgctctcac ctggcctcgc tgtttactca cgaggctgac 7560
atgcataaaa ggcgcgtcga cctggccgga tgcttgggcg aacgcggcac gcccaaacac 7620
ttttttgact gctttcgccc agactcccta gaaacccttt tctgtggtgg tctttttagc 7680
tccgtggagg acaccataga aagtctccaa aaggactgct cttctgcctt ctaccaacag 7740
gtaaactaca ctactgcact gcaaaaacag aacgagtttt acgtccgact cagcaaactg 7800
ctggcagctg gtcagctaaa tttgggcaaa tgttccactg aaagttgcca atccgaggcc 7860
cgtaggcagc tggtaggtgg gggcaaacca gaggaagtgc tgagggatgc aaaacaccgg 7920
caagaactat accttcagaa agtggcacgc gacggtttta aaaaactctc tgattgtata 7980
agacaccagg gccacatcct gtctcagacc ctgggtctaa gactgtgggg gtctgtcatc 8040
tacaacgagg catctgccct acaaaaccac tttttacaca gagcacagtt catatccctc 8100
ccctggcagg acctgacggt cgactgtcca acgcggtttg aaaattctaa atatatcaaa 8160
aattctctgt actgccagcg tctggggcgg gaacacgtag agatcctgac actggagttc 8220
tacaaactta tcacgggccc gctgtcaaag cgacatactt tatttcccag tcctccaaat 8280
gtgacgctgg ctcagtgctt cgaggctgcg ggcatgcttc cccatcaaaa gatgatggta 8340
tcagagatga tctggcccag catagagccg aaggactgga tagagcccaa cttcaaccag 8400
ttctatagct ttgagaatca agacataaac catctgcaaa agagagcttg ggaatatatc 8460
agagagctgg tattatcggt ttctctgtac aacagaactt gggagaggga gctaaaaata 8520
cttctcacgc ctcagggctc accggggttt gaggaaccga aacccgcagg actcacaacg 8580
gggctgtacc taacatttga gacatctgcg ccccttggtgt tggtggataa aaaatatggc 8640
tggatattta aagacctgta cgcccttctg taccaccacc tgcaactgag caaccacaat 8700
gactcccagg tctagattgg ccaccctggg gactgtcatc ctgttggtct gcttttgcgc 8760
aggcgcggcg cactcgaggg gtgacacctt tcagacgtcc agttccccca cacccccagg 8820
atcttcctct aaggccccca ccaaacctgg tgaggaagca tctggtccta agagtgtgga 8880
cttttaccag ttcagagtgt gtagtgcatc gatcaccggg gagctttttc ggttcaacct 8940
ggagcagacg tgcccagaca ccaaagacaa gtaccaccaa gaaggaattt tactggtgta 9000
caaaaaaaac atagtgcctc atatctttaa ggtgcggcgc tataggaaaa ttgccacctc 9060
tgtcacggtc tacaggggct tgacagagtc cgccatcacc aacaagtatg aactcccgag 9120
acccgtgcca ctctatgaga taagccacat ggacagcacc tatcagtgct ttagttccat 9180
gaaggtaaat gtcaacgggg tagaaaacac atttactgac agagacgatg ttaacaccac 9240
agtattcctc caaccagtag aggggcttac ggataacatt caaaggtact ttagccagcc 9300
ggtcatctac gcggaacccg gctggtttcc cggcatatac agagttagga ccactgtcaa 9360
ttgcgagata gtggacatga tagccaggtc tgctgaacca tacaattact ttgtcacgtc 9420
actgggtgac acggtggaag tctccccttt ttgctataac gaatcctcat gcagcacaac 9480
ccccagcaac aaaaatggcc ttagcgtcca agtagttctc aaccacactg tggtcacgta 9540

```
ctctgacaga ggaaccagtc ccactcccca aaacaggatc tttgtggaaa cgggagcgta   9600
cacgctttcg tgggcctccg agagcaagac cacggccgtg tgtccgctgg cactgtggaa   9660
aaccttcccg cgctccatcc agactaccca cgaggacagc ttccactttg tggccaacga   9720
gatcacggcc accttcacgg ctcctctaac gccagtggcc aactttaccg acacgtactc   9780
ttgtctgacc tcggatatca acaccacgct aaacgccagc aaggccaaac tggcgagcac   9840
tcacgtccct aacgggacgg tccagtactt ccacacaaca ggcggactct atttggtctg   9900
gcagcccatg tccgcgatta acctgactca cgctcagggc gacagcggga accccacgtc   9960
atcgccgccc ccctccgcat cccccatgac cacctctgcc agccgcagaa agagacggtc  10020
agccagtacc gctgctgccg gcggcggggg gtccacggac aacctgtctt acacgcagct  10080
gcagtttgcc tacgacaaac tgcgggatgg cattaatcag gtgttagaag aactctccag  10140
ggcatggtgt cgcgagcagg tcagggacaa cctaatgtgg tacgagctca gtaaaatcaa  10200
ccccaccagc gttatgacag ccatctacgg tcgacctgta tccgccaagt tcgtaggaga  10260
cgccatttcc gtgaccgagt gcattaacgt ggaccagagc tccgtaaaca tccacaagag  10320
cctcagaacc aatagtaagg acgtgtgtta cgcgcgcccc ctggtgacgt ttaagttttt  10380
gaacagttcc aacctattca ccggccagct gggcgcgcgc aatgagataa tactgaccaa  10440
caaccaggtg gaaacctgca aagacacctg cgaacactac ttcatcaccc gcaacgagac  10500
tctggtgtat aaggactacg cgtacctgcg cactataaac accactgaca tatccaccct  10560
gaacactttt atcgccctga atctatcctt tattcaaaac atagacttca aggccatcga  10620
gctgtacagc agtgcagaga aacgactcgc gagtagcgtg tttgacctgg agacgatgtt  10680
cagggagtac aactactaca cacatcgtct cgcgggtttg cgcgaggatc tggacaacac  10740
catagatatg aacaaggagc gcttcgtaag ggacttgtcg gagatagtgg cggacctggg  10800
tggcatcgga aaaacggtgg tgaacgtggc cagcagcgtg gtcactctat gtggctcatt  10860
ggttaccgga ttcataaatt ttattaaaca cccccctaggt ggcatgctga tgatcattat  10920
cgttatagca atcatcctga tcatttttat gctcagtcgc cgcaccaata ccatagccca  10980
ggcgccggtg aagatgatct accccgacgt agatcgcagg gcacctccta gcggcggagc  11040
cccaacacgg gaggaaatca aaaacatcct gctgggaatg caccagctac aacaagagga  11100
gaggcagaag gcggatgatc tgaaaaaaag tacaccctcg gtgtttcagc gtaccgcaaa  11160
cggccttcgt cagcgtctga gaggatataa acctctgact caatcgctag acatcagtcc  11220
ggaaacgggg gagtgacagt ggattcgagg ttattgtttg atgtaaattt aggaaacacg  11280
gcccgcctct gaagcaccac atacagactg cagttatcaa ccctactcgt tgcacacaga  11340
cacaaattac cgtccgcaga tcatggattt tttcaatcca tttatcgacc caactcgcgg  11400
aggcccgaga aacactgtga ggcaacccac gccgtcacag tcgccaactg tcccctcgga  11460
gacaagagta tgcaggctta taccggcctg tttccaaacc ccggggcgac ccggcgtggt  11520
tgccgtggac accacatttc cacccaccta cttccagggc cccaagcggg gagaagtatt  11580
cgcgggagag actgggtcta tctggaaaac aaggcgcgga caggcacgca atgctcctat  11640
gtcgcacctc atattccacg tatacgacat cgtggagacc acctacacgg ccgaccgctg  11700
cgaggacgtg ccatttagct tccagactga tatcattccc agcggcaccg tcctcaagct  11760
gctcggcaga acactagatg gcgccagtgt ctgcgtgaac gttttcaggc agcgctgcta  11820
cttctacaca ctagcacccc agggggtaaa cctgacccac gtcctccagc aggccctcca  11880
ggctggcttc ggtcgcgcat cctgcggctt ctccaccgag ccggtcagaa aaaaaatctt  11940
```

gcgcgcgtac gacacacaac aatatgctgt gcaaaaaata accctgtcat ccagtccgat 12000
gatgcgaacg cttagcgacc gcctaacaac ctgtgggtgc gaggtgtttg agtccaatgt 12060
ggacgccatt aggcgcttcg tgctggacca cgggttctcg acattcgggt ggtacgagtg 12120
cagcaatccg gcccccgca cccaggccag agactcttgg acggaactgg agtttgactg 12180
cagctgggag gacctaaagt ttatcccgga gaggacggag tggcccccat actcaatcct 12240
atcctttgat atagaatgta tgggcgagaa gggttttccc aacgcgactc aagacgagga 12300
catgattata caaatctcgt gtgttttaca cacagtcggc aacgataaac cgtacacccg 12360
catgctactg ggcctgggga catgcgaccc ccttcctggg gtggaggtct ttgagtttcc 12420
ttcggagtac gacatgctgg ccgccttcct cagcatgctc cgcgattaca atgtggagtt 12480
tataacgggg tacaacatag caaactttga ccttccatac atcatagccc gggcaactca 12540
ggtgtacgac ttcaagctgc aggacttcac caaaataaaa actgggtccg tgtttgaggt 12600
ccaccaaccc agaggcggtt ccgatggggg caacttcatg aggtcccagt caaaggtcaa 12660
aatatcgggg atcgtcccca tagacatgta ccaggtttgc agggaaaagc tgagtctgtc 12720
agactacaag ctggacacag tggctaagca atgcctcggt cgacaaaaag atgacatctc 12780
atacaaggac atacccccgc tttttaaatc tgggcctgat ggtcgcgcaa aggtgggaaa 12840
ctactgtgtt attgactcgg tcctggttat ggatcttctg ctacggtttc agacccatgt 12900
tgagatctcg gaaatagcca agctggccaa gatccccacc cgtagggtac tgacggacgg 12960
ccaacagatc agggtatttt cctgcctctt ggaggctgct gccacggaag gttacattct 13020
ccccgtccca aaaggagacg cggttagcgg gtatcagggg gccactgtaa taagcccctc 13080
tccgggattc tatgacgacc ccgtactcgt ggtggatttt gccagcttgt accccagtat 13140
catccaagcg cacaacttgt gctactccac actgataccc ggcgattcgc tccacctgca 13200
cccacacctc tccccggacg actacgaaac ctttgtcctc agcggaggtc cggtccactt 13260
tgtaaaaaaa cacaaaaggg agtcccttct tgccaagctt ctgacggtat ggctcgcgaa 13320
gagaaaagaa ataagaaaga ccctggcatc atgcacggac cccgcactga aaactattct 13380
agacaaacaa caactggcca tcaaggttac ctgcaacgcc gtttacggct tcacgggcgt 13440
tgcctctggc atactgcctt gcctaaacat agcggagacc gtgacactac aagggcgaaa 13500
gatgctggag agatctcagg cctttgtaga ggccatctcg ccggaacgcc tagcgggtct 13560
cctgcggagg ccaatagacg tctcacccga cgcccgattc aaggtcatat acggcgacac 13620
tgactctctt ttcatatgct gcatgggttt caacatggac agcgtgtcag acttcgcgga 13680
ggagctagcg tcaatcacca ccaacacgct gtttcgtagc ccccatcaagc tggaggctga 13740
aaagatcttc aagtgccttc tgctcctgac taaaaagaga tacgtggggg tactcagtga 13800
cgacaaggtt ctgatgaagg gcgtagacct cattaggaaa acagcctgtc gttttgtcca 13860
ggaaaagagc agtcaggtcc tggacctcat actgcgggag ccgagcgtca aggccgcggc 13920
caagcttatt tcggggcagg cgacagactg ggtgtacagg gaagggctcc cagaggggtt 13980
cgtcaagata attcaagtgc tcaacgcgag ccaccgggaa ctgtgcgaac gcagcgtacc 14040
agtagacaaa ctgacgttta ccaccgagct aagccgcccg ctggcggact acaagacgca 14100
aaacctcccg cacctgaccg tgtaccaaaa gctacaagct agacaggagg agcttccaca 14160
gatacacgac agaatcccct acgtgttcgt cgacgcccca ggtagcctgc gctccgagct 14220
ggcagagcac cccgagtacg ttaagcagca cggactgcgc gtggcggtgg acctgtactt 14280
cgacaagctg gtacacgcgg tagccaacat catccaatgc ctcttccaga acaacacgtc 14340
ggcaaccgta gctatgttgt ataacttttt agacattccc gtgacttttc ccacgcccta 14400
gtgactcaga cgcggaaaca gcgcctagaa agtttcctct tgcgctatgt gggacaacta 14460
gagtccaacc tggcaagcag tggagcaaga cgccagacag ccgatctcga aaaaaataat 14520
gcagacagag gcaacgttca tcctaggtga ctgggagata acggtgtcta actgccggtt 14580
tacttgcagc agcctaacat gtggccccct ttacagatct agcggcgact acacgcggct 14640
aagaatcccc ttctctctgg atcgactaat acgtgaccat gccatctttg ggctagtgcc 14700
aaatattgag gatctgttaa cccatgggtc atgcgtcgcc gtagtggccg acgcaaacgc 14760
cacaggcggc aacgcgcgac gcatcgtcgc gcctggcgtg ataaacaatt tttcagaacc 14820
catcggcatt tgggtacgcg gccctccgcc gcaaacgcgc aaggaagcta ttaagttctg 14880
catatttttt gtcagtcccc tgcccccgcg ggagatgacc acatatgtgt tcaagggcgg 14940
cgatttgcct cccggagcag aggaacccga aacactacac tccgccgagg cacccctacc 15000
gtcgcgcgag acgctggtaa ctggacagct gcgatccacc tcgccgcgaa cgtatacggg 15060
atactttcac agtcctgtcc cgctctcttt tttggacctc ctgacattcg agtccattgg 15120
gtgtgacaac gtggaaggtg accccgagca attgacaccc aagtacttga cgttcacgca 15180
gacgggagaa agactttgca aagtaaccgt ttacaacacc cattcgacag catgcaagaa 15240
ggcccgtgtt cgtttcgtct acagaccgac gccgtccgcc cgtcagcttg tcatgggtca 15300
ggcttcaccc ctcataacaa cccctctggg agccagggta ttcgcagtct atccagactg 15360
tgagaaaact atcccacctc aggaaaccac caccctgagg attcaattgc tgttcgagca 15420
gcatggtgcc aacgccggag actgcgcctt tgtcatcatg gggctcgccc gtgaaacaaa 15480
gtttgtctca tttcccgcag tactccttcc gggcaagcac gaacacctta ttgtattcaa 15540
cccacagaca catcctctga ccattcaacg ggacacaata gtgggcgtgg caatggcttg 15600
ctatatccac ccccggtaagg cagccagcca ggcaccatac agcttctacg actgcaagga 15660
agagagctgg cacgtggggc tcttccagat caaacgcgga ccgggagggg tctgtacacc 15720
accttgccac gtagcgatta gggccgaccg ccacgaggaa cccatgcaat cgtgactgtc 15780
cgagcacata tggcgcagga gtcagagcag tgctcccgtg cgtttgcagt gtgcagtagt 15840
aaacgacagc tcgggcgcgg cgagcccgtg tgggattccg tcattcaccc gagccacatc 15900
gtcatctcta atcgagtacc cctcttacta agagaacagc acatatgtct cccttcgtgc 15960
cccagcgtcg gccagatcct ccacagagcc taccccaact ttacatttga caacacgcac 16020
cgcaagcagc aaacggagac ctacactgca ttctacgctt ttggggacca aaataacaag 16080
gttaggatct tgcccactgt tgtggaaagc tcctcgagcg tgctgatttt tagactgcgt 16140
gcatcggtct ctgcgaacat cgccgtggga gggctcaaaa taataatact tgctctcacc 16200
ctggtgcatg cccaaggagt gtacctgcgt tgcggtaagg acctttctac accacactgc 16260
gcaccggcta ttgttcagcg tgaggtgctg agcagcgggt ttgagccgca gtttaccgta 16320
actggcattc cagtgacatc ctcgaactta aaccaatgct actttctggt aagaaagcca 16380
aaaagccggc tggcaaagcc gtttgcacgc ctgtccgcgg agacgactga ggagtgtcgc 16440
gtcaggtcta tccgccttgg gaagacacac ctgcggatat cggtgactgc gcctgcgcag 16500
gaaacgcccg tctgggggct cgtgaccacg agcttcagcc ttacccccac cgcaccgctg 16560
gcctttgatc gtaacccgta caatcacgag acatttgcct gtaatgccaa gcactacatc 16620
ccagtcatct acagcggacc aaaaattacg ctggccccgc gcggccgcca ggtagtctgg 16680
cacaacaaca gctacacgtc ctccctgcca tgcaaagtca cagccatcgt gtcaaaccac 16740
tgctgtaact gtgacatatt tttagaggac tcggaatggc gcccaaacaa gccagcaccc 16800
ctgaaactgg tgaacacgag tgatcatccc gtcatattgg agccggacac acacattgga 16860
aacgccctct tcatcatcgc acccaaggcc cgaggtttac gcagactgac tcgcttaacc 16920
acaaaaacca ttgaacttcc tggcggggta aagatagaca gcaggaaatt acaaacattc 16980
agaaaaatgt atgttgccac cggacgcagt taggtgtccg gttcccaccc acacatttgt 17040
ctttattgct ttcaaataaa acggtgttct gtcaacctcc tccgggctca ctagtattgt 17100
gttcccatac gcgcctgtcg ccccaggatc aacacttcgt cccctatcca ccctaataca 17160
taacacacac aaagacatag tgactgtaga cagttaatct ttattgtcta gacacgcaaa 17220
gtatattagt gttataagaa attttatgtc acgtcgctct ttacttatcg tggacgtcag 17280
gagtcacgtc tgggatagag tccaaaacac gcaccgcttg acctgcaaac ttttccattg 17340
cactcagaac ataaaacgaa gcaaagtgtc tcacccaata cttaagtccc tgaagcctcc 17400
ctaatagacc gcggtcaaat ttgggtggac tgtagtgcgt cttagtcagc ttattgagct 17460
cttcctgtat gtcccatcct aaggtcttcg tcagaagctc catgacgtcc acgtttatca 17520
ctgattttcc aaactccgtc gttaaaaact taaacaacac ctcgaattca aaaaagccat 17580
cggcgagctt tttaaggcag ctagtctcat taaatcctat taacccgcag tgatcagtat 17640
cgttgatggc tggtagtttc agatgaaaaa tagcagcggg ctctagaata cccttgcaga 17700
tgccggtacg gtaacagagg tcgcggaagc attcatcgat cacccatagc atccaattga 17760
gtctctgaat gagaagatcc ttttcaaact cgggggcgtc cggcaacttg ccccgcgttc 17820
cagataccag cagtgaaccg accagcaaga gagaccacaa cttgaaccag cacatggctg 17880
ctaacgcggc atacactagc cggtggtgcc cgagcgggag ttacgaagtc tcactgaagg 17940
gcggggtcgc gggtcggggc cgctccaaat caggcaacgc cgtatccgaa ctctgagtca 18000
cttttatgta ggtctcaaac atgtaaaaga taccacgttc ttgaaaaacc ctctcttgct 18060
cgccaggctt ggggttcacg cgggcatacg cagccaagct atcatgcgag agaaacacgt 18120
cacacgcaaa gtcatgtaaa acccgggtta aaaatagcct aactggccag gggccagtga 18180
gcgcctcccg gtacaagtcc ccacccccga tgacccaaac cttgtcaatt tgctgtgcta 18240
gctctgggct tctcgccaac ccaagcgcgg catcgagcga actcgccaaa aagtgagcac 18300
cagggggcgg ggtttctaac gtgcgactta gaaccacatt gattctaccc gccaatggtc 18360
gacagcccgc gggaatcgaa agccatgtgc gccgccccat aacaaccatg ttttgttttc 18420
caggggcaca gtcggtagtc agctgtcgaa aacgcctcat gtctccccgc aatgcaggcc 18480
acgggagaca tctgtttttt ccgatcccga gtttggtatc aaccgcaact acacagtaaa 18540
gtgtaggatc catgccgcga gggtataggt aaacaccacc aaccacacag tgtgctctta 18600
tatactttta atgaaacata agggcagacg aaacagccga acgtttccta atcacgccca 18660
tggaaccata gccacccccca ggcaaaccct gtggaaggat atcaactaga gaggagggtc 18720
cagccttatt atggcaggag acactataag ccccatcgcc cgactgggca ccaacataac 18780
cgcccacagta agtggcccta taccgctcag cgcccaagtt gttacagtca cacccaaccg 18840
cggttggctc tacattgtca tcacgtccat cattatgtgt tggttctccc gcttccttgt 18900
accctgcagc ttcatccacg gattcttctg agtcgcgatg cacaggagcg ccatccgcgg 18960
ggccatcttg gtcgcctgga gctgcccccg cggggccatt ttggtcgcct ggagctgccc 19020
ccgcgggccc ctcctcgtcc tggttatccc cacggggaag aatttcctga agctcgatct 19080
cctctactgc acactctggt gatgtcggcc gaggtctata tggaaacact tcaacccgcg 19140

```
tgtttacagc agcgtatgcc cgccccacgt ggcgcatcat gtggaaaaac gcacccaacc  19200
caaaaacgac aaacaattgg taaaacacga aaaaaacgta gtacgcggct gcagcgacgt  19260
gatctatctc tgggtcatga ccgcccacta tatatagcca aacccacgtc gcagcggcaa  19320
ggccagcggc ccccaatgtc ataatgaaaa taaaaacaat cagttccaga ccctcctggt  19380
aagtcagccg aggcaatagc gtcatttcgc gcaagggtcg ccagaccacg cgcgtgttgt  19440
atacgacgcc acatatctga caggccgtgt ttctagagat agtgagccag gtgcttaaac  19500
aacttctatg gacgttctcg agctctcctg tgcatccaca ggctctaaat ctctcatttc  19560
cgagctcctc gttgcaaatc cagcagacag gaacatcctc atcttccata tcctgagaga  19620
gaacccacaa taaaacatgg cattaacccc tgcaacaagt gaccgtacca gggcacgcgt  19680
ccaggcaacc ggggtccccc tcgttggtct atacaattcc atgactacct actggtaatg  19740
ctacagccac tcactgtaca agccggttaa ctgggaggcg acgctggcgt ggtatcggcc  19800
aactgaaaca caccactcca ctccaaacac ttatgtactt tgtggctcgg ctttattgta  19860
acagccaaga ggggcgtttg tggctcagct ttattgtaac agccaagagg gacgtatgtg  19920
gctatctcac aaaaagtcac cgattcatgt agacaacccg ctcccacgaa ttcggttttt  19980
aaaaagccct cacgtataca gacgggccac taaatacgca catgagcggg catcctgttt  20040
ccgccttgac gcccaccact ctgaccgcac gctaaacatc gccctacctg ctatactgcc  20100
atttccatac gaatggtagg atgcgggcag tagtccacca gtctaaaatc atcaggtgta  20160
aactcttcca tggaagaaac agaccggagt atctccaggc gcggaaaggg acgtggagtg  20220
cgcgtcagct gcagccgtag tggctctata tgcgttttgt agatgtgggc atctcccaac  20280
gtgtgaataa actccccggg tctaagacca gtaacatgag caagcatata agttaagagg  20340
gaatagctgg caatgttaaa aggaactccc aaacccatgt ctcccgacct ctgatacagc  20400
tgacaggaaa gctcaccgtc agctacataa aattgacata acaagtgaca gggcggaagc  20460
gccatcaacg acaagtccgc cgggttccac gcacacataa tgattcttct atcgtgcgga  20520
ttatttttta ttaaatccac aatgtacgac aattggtcaa acccctggcc tgtatagtca  20580
gcatccgcgt ccacgtacgc cgccccaaag tgcctccact ggaaaccgta aacaggtccc  20640
aaatcccccct cccttctgtg cgccaggccg cgcccggcca ggaactccct ggagccattt  20700
ttgtcccata tcttgactcc tgttcttgaa agctccctgg agtcagtact cccccttcaga  20760
aaccaaagca gctcttgcac tacgcctcgc caaaacaccc gctttgtggt tagtaaggga  20820
aagtggtccc gcagactata cctggcctgc atgccaaata gagagagggt gcctatgccg  20880
gtgcggtcga gtcgatcgct gccacggcac aaaatttccc tcaactgcct gagatactga  20940
agttcctcgt ggggcgtctc agccccagtt acctcatgct gaatcgaaca agggtcaacc  21000
tcgggggcca aagccaagac gccaggcttt tgacagaagc gaaacccccct ggcacggaat  21060
aactttttgg cgacatacaa gcttaaaggt acaaacggaa acatgataga tcctggaagt  21120
ttgtgaagcc ctgtgcccgg agagacaccc ctcaactcgc agtgctcgga gacctacatg  21180
tatactcagg ctcttctata aaccctcccc aaaagtttat aaaacaccgt acgtaataca  21240
cattactcac agttcccacg gtgacgccca aacccatgca cacgggcgtg atcgatacca  21300
gaaaacatca caagaacaaa aagtgtgtgt ctgacattca catttatttt tacaagacaa  21360
ttttgtgcag tagagttgtg ccttccgaca ccccgcgccg ttcgctgttc tcctgtaatt  21420
gggagatccc actccttggc aggcacgttt cacgaaacgc tcttgtctcg ctggccttag  21480
acttgtggac ccaacatggg tatcgttaga gatccgtcgc gtaaatgcgc agctggcaaa  21540
```

gcattcttca gcgagcagtg actggtaatt gctgcatcag cttcttcacc cagtctttcg 21600
atttgtcggc acacacctgg cgaccacgct ttgtcaaaaa tatcacaccc ggcttgctgc 21660
acagttggga ggtggggtac cagctggaca gaagcacctg tggtaatggt cttttctggt 21720
aaccgagaca gcacttgtcc ggtctatgcc aggacgctcc cagcgtgtcc ccagattgca 21780
aacaaagcaa ggcagtcagc acagcgacga gcaggatgcc cttggtgtcc ataactcccc 21840
tcgtgtgtcc tcgtgtaaat gcgaaacggc gatgttaggt caggcgcggt aaacagctca 21900
actcggttca aaacacgtac gtgatgtagt gctggttcta cgacgcctac ctgtaaactc 21960
caggatcctg ggcttttatt acgaaggcca acaccccaaa aaatccacgc ccccgtgacc 22020
gcaggggcgg ttactaacga cggttacagg tccctcccga gccacgcacc tgccatgtaa 22080
cctgcaaggt aaccagacaa acatctagga agcgtaaata tccccaggta ggagaagtat 22140
tgcatatgtc acagactcaa cacacacggg ccgttacgca acggctaggg gcataaccct 22200
ttaccggcgc gaagcgctac gcgcttcgcg agaggtatct ccgtgtgctt ctccatcaga 22260
agacgcgtgc gccgcttcgc aggcgacccg catactttcc gccccgagtg cgttacaaaa 22320
atgactgcct tctggcgaca atacacggtg gacgtccagt accacccgca tatcagctta 22380
tccggtggca atctggcact ggacagggaa ttctcgcaac aatccgaggc catgatggtg 22440
gcaggaccgc tggccgcaca tagctcaatc acggccaccc agaagagcag ccccaaatgt 22500
gcgcgcaaca cccagcacat gctccacata cagttctggc gccacaacga tgatgcgcaa 22560
aggggtgcat taccctaaat cccagcctag ttataaatta ttgaagccca ggcgaccagg 22620
ggtcgccgcg cttttcctcc ccaaacgcga cgataaagac cagcgttgcc aaatgtaact 22680
tatgtataac ccaaaatatt gcgcatcgat aaggtttgcc aaaacacccg aaagtacaca 22740
cacaaaaaaa cagcaacaag acgctcacta gacattcacc ccttccccca cccccgaaaa 22800
caaaacaact tgacacaggg gaaacaccag gggcggcgga ggttgtcaat agtgtccagt 22860
atttcgttag acgcgggttc ttggacccga tgtcccaggt cattaaagtc tcaaatggga 22920
ttaaaggatc atagttccca ggtttaatac tccaagctat cccagaacag gaccccggca 22980
gaaccccgct taacagcacc aaatccactt gcggtcccag aaaaggtcgc cgaggtggca 23040
aggtgactga aaaggtcata gagaggacac cggtcccatt tcccacggtc caaaaatcca 23100
gcgcgcccca ccggctttcc gagaacttcg gcaaagctaa tttgcatgcg ctaatccttt 23160
tatgtgcata aattatgtag atgaggagtc gcgcatgcgc agaaaaattc agagcgcccg 23220
ggtgcacggg gtcacctcca ggtcacgccg ctaggtggga ccgtgagcga ctcgaaaaat 23280
tataattttt ggccatttca tgggcgccgc catcttgaat ttgctaatcc cccataatcc 23340
tctgccccgc tcccattggt ccgccggccc gtcaatcaaa gttttccgag ccgccattgg 23400
cccatccggc cgaccaatcc cgttcgagct aggcgaccgc gccattccat tggacgcccc 23460
agccgtcaat caaattcgga ggcctcccat tggcccctat ccctagaact cccaagctga 23520
ttggcccaga gcgggaacca atcagcgatt agagttttgt tttgattttt cctatatata 23580
tatatataat cctttaatcc tagcgcagct gagtcatcgc agcccctatt ccagtaggta 23640
tacccagctg ggtaatccag taggtatacc caggtgggtg aacccagctg ggtataccca 23700
gctgcaattc tataattaaa caaggtagaa accaacgggg tcctcaggtg gtatttccgg 23760
aagcattacc aaataaggca acctcagctg ggaataccag cggactaccc ccaactgtat 23820
tcaaccctcc tttgttttcc ggaagtatat ccatttatgg aaatcagctg ggtcactcta 23880
ctgggttatt ctttataata gggcccgatg agtcatgggg ttgggatttt tctactaggt 23940
cgtttcggtg gatgggtgcc aggattatag gggccctgtc cacggggttg ttcggtggcg 24000
gggggggggc tagtgagtca cgggcctgga atctcgcctc tgggtggttt cggtagatgg 24060
gggccgggag gatggggccc cgcccaccgc tggcgcgccc cagaacatgg gtggctaacg 24120
cctacatggg cagcttgtcc tacggttacg cccatttgag acgggttaac caactgttac 24180
accccttcgc cgggaacgct ataaaaacga gggacagcag cccccccctcg cgcactgcgc 24240 gcgcggcggc acgtgggacg gatctcttgg atttacccgt aacgaggagc cccggcagca 24300
ccccaggagc cccggcagca ccccaggagc cccggcagca ccccaggagc cccggcagca 24360
ccccaggagc cccggcagca ccccaggagc cccggcagca ccccaggagc cccggcagca 24420
ccccaggagc cccggcagca ccccaggagc cccggcagca ccccaggagc cccggcagca 24480
ccccaggagc cccggcagca ccccaggagc cccggcagca ccccaggagc cccggcagca 24540
ccccaggagc cccggcagca ccccaggagc cccggcagca ccccaggagc cccggcagca 24600
ccccaggagc cccggcgcgc caccctcccc ggagggggat cccggcgcgc caccctcccc 24660
ggagggggat cccggcgcgc caccctcccc ggagggggat cccggcgcgc caccctcccc 24720
ggagggggat cccggcgcgc caccctcccc ggagggggat cccggcgcgc caccctcccc 24780
ggagggggat cccggcgcgc caccctcccc ggagggggat cccggcgcgc caccctcccc 24840
ggagggggat cccggcgcgc caccctcccc ggagggggat cccggcgcgc caccctcccc 24900
ggcaacaacc tgttgccatg tatggcgatt tgtatcagtc acaagcacac aacccctgct 24960
agtattaatg gtgtttaaaa cgttctacac gtacggcgga ccgcatccgt cgcaagcacg 25020
cgcatataac ccccaaatgc accatgatga gaagcacagc cacgcgtcaa aaaactttaa 25080
aaacatcgtt atccaatatc attaaaaacc acaccgaaat ttacacaggt agcacgtcac 25140
cgtgttagtg tcacccactg tacacaaggc gtgtcgtata tgtagtatag gtatttgatg 25200
aggcggaagc atatcccgct tccagcgaac ggaaataaga atcatccgtt ccagcattta 25260
ttcaaagagg gcacagagga ttcacattgt ttagagagag tttttcttag tcaccattcc 25320
atacttgggc agtattggcc tacgatttgg gcgacgtttc aggctggtct attctccgtc 25380
cacttttccc cggctattct gtcccagcat aggctcttga aataaacaat gtttaccgag 25440
taaaaggttc cactcaccct catttgtcgt tgcacccatc cccccttttgc ttaatcaccc 25500 gaaaactaga ggacacggat ggaaaacata tcgcacgcgg gttgtttgaa agtcaacagc 25560
tacttgtttt taatgaggac agatttgggc acaggccaga gggtaaagcc ctacgtgtgc 25620
gcgggggggg gggtgtatac gctgcgaaaa cctgcacggt gcataacacc cagggcgtca 25680
cgtcacatat ctctgtgcac ccaagtggtt gttcaaccgt tgttttttgg atgatttttc 25740
cgcaccggct tttttgtggg cgcgcatagg tcggtacgcg ctgtcccccct aagtcccgca 25800 cggtcgttcg ggcccccgtc cggctcgtct ccggatgaac cgtcacgttc tttgtctcca 25860
gaggcgacgt ctccttcaga tgactcgtcc gtgggctcct cgtccgtccc gcccgcgggt 25920
ccgacaagga ccgtcaattc gatgttatct tcgttcgcgg ttggccggcg cggccgtcgg 25980
tatggcagta cggtcacccg ggtgttattt gccgcgtata atgccctcac agtgccactt 26040
acgcggcata tgccgccaaa tgcaaacaca ataaatattt ggtaaaaccc aaagaagcag 26100
agaaaaccga gcacggcccc gggggagaat gttcccgcag gagcagttag gatgaccagg 26160
agcgtccagg tgcacaacgc cacgccgaca agcccagcca ccaccacaga catcagcaga 26220
aacagttcaa aaatttcttg gcgctccatc tccggccaca ggttaaggcg actacgccac 26280
tgcgtgcgcg tgcggtatat aacgcgacac atttgacagg ccgtgtttcg agacactgtt 26340
agccaagtgc ttaaacactg cgggtggacg acatccagct ctccggtaca ggcgcagggg 26400
tgtatgccct cgttccccac ctcttcccta catatccagc agatgggtcc ctctacaccc 26460
tcttctacgt ccttagacgc catctctgca gctggggtgg aagtctgaaa aagggaaagg 26520
ggaggtgagc agagtgccca gttagtctcc gacccgccgt ccgccctact gtcgctatcc 26580
cgccttgaca gatgtctaac gtattcacgg acgccacatg tgtgtctatt ttcctacatc 26640
caggctttcc ctggaaaact gtcacaaccc accctgcttt agctctacat ctgtattttt 26700
gtttacgcac aggatcaacg cttcgtgccc gtccaccccc gcgctctccg cctgtgtttg 26760
gaggttttat gagtggttag ttctaggcag ctccggacaa gttgtccaaa acacggcgcg 26820
ccccgccctt ccttccctcc ggatccgccc acaccggacc tatgaaataa gggacacgcg 26880
tcatcactag ttatgagaga aaaaccacaa cagctttatt ggaaaacacc tgagtggatc 26940
ccccaccccc cgcgtacgac aggcgtttct gtggtgcgct tctgggaaaa acgtttttcc 27000
cccatttctt cctcgacagg tcttctaagg tagataaatc cccccccttt gcgcgtctcc 27060
tagaatggcc taggcgcacg atggcgttgt cgcctcgagc agttgggccg cagtgatatc 27120
ttcaactttc gaccgtctaa gctatggcag gcagccgctg catcagctgc ctaacccagt 27180
ttttggaagg gtctgcgcag atctgacgcc ctcgcttggt cagcaaaata actccgggtt 27240
ttgggcacgc tggggacgtg ggataccact cttttagaat ttggacgggc ggtgggtgct 27300
gctggaaccc gtagcagcag ctattaggcg tgtacgacac gagtgacccc gcgctttctg 27360
tgggcgtcag gtaaaacgtg gcaagcagta cgctaacgca gcataaaacg tggacggggg 27420
ccatctggag gtgccaagtt cgcaacagtc taaagaaaac cgtaaaggct atttggggtt 27480
tctgttctgt cagatgtaac gccgagttcc ttatatgctt acctgattct ggtctcacct 27540
gtttatttat agtggcgtat gctaaccgcc agcttacatg cgggataagt tggcctaact 27600
caccaaaaac gggttgcaga caaaagtgat tgttggggcg cttacttaga aggtgtgagg 27660
gtttctaaga aaccccgcca acgcccggaa accgcatgcg ttccagtcgg tgcggcctgc 27720
gccggcgtcg ctgtggcgcc tttgtgggct ttgagttctg tcattaagcc aggtttccat 27780
tgccacccgg gcgaaaacaa gccgggtagt ttcaggggtc atctggcgat cagtgtacca 27840
tattcccacg acccatcaac accgctgctt gaggcgtgtc tctgtatgtg tcaccggaga 27900
ctgcatgtat cgtgcatatc tgtattgtgc gcttgcgcgg agacaacata ccgacgacca 27960
agtcaggggt cacctccagt gcacgccgct aggtgggacc gtgggcgagc cgaaataatt 28020
atatattttt ttggcacggt tgtgagcaac gccatcgtga gttggttaat accctctaaa 28080
cgcatagtct ttttttattt gtcaaccaac cagtcaatca cctgtcatcg ccgctcagaa 28140
gcacacgtct tcggccaatg ccgtgttggc gggtttgacc acggttactg ataggtagac 28200
gagtccgaca atcacacacg tccgccagcg atttgcagcg cagctaaaat cgcgtggccg 28260
ggttggtaga agcaaattat ccaatggtcg tgtttgggtt tgttttgggg ttatctacat 28320
attatattcc ttatcccgac tggttgcgga agtattcgca gcttggctac tctgctcgat 28380
taccccgtga ataactgggc ggggggtgac ccaacatagt gattcggtag atttggggga 28440
ctggatgaac attaatgaaa gtttattaat gttcatccgt attgtgtata tgtaatttgg 28500
tttccatatt tggtaggagt atggagtttt cttatggatt attaagggtc agcttgaagg 28560
atgatgttaa tgacataaag gggcgtggct tccaaaaatg ggtggctaac ctgtccaaaa 28620
tatgggaaca ctggagataa aaggggccag cttgagtcag tttagcactg ggactgccca 28680
gtcaccttgg ctgccgcttc acctatggat tttgtgctcg ctgcttgcct tcttgccgct 28740
tctggttttc attggtgccg ccgattgtgg gttgattgcg tcgcttttgg caatataccc 28800
atcctggctt tcggctaggt tttccgtcct acttttccca cattggcctg agagctgtag 28860
tacaaaaaac accgcgcggt ctggagctct ccataagccc gcagaacaaa agctgcgatt 28920
tgcccaaaaa ccttgccatg gcaactatac agtcacccct tgcgggttat tgcattggat 28980
tcaatctcca ggccagttgt agcccccttt tatgatatgc gaggatactt aacgtgtctg 29040
aatgtggaat ataatgtgaa aggaaagcag cgcccactgg tgtatcagaa cagtggtgca 29100
ctacctatct gctcattcgt tgtttcggtt ctgtgtttgt ctgattctta gatagtgttg 29160
aggtaattct agaaagcgga ttgagtgtaa atcgggccac tttgccctaa atgtgacaat 29220
ctggatgtgt atcttattgg tgcgttgtga agcattttaa aatgcgtttt agattgtatc 29280
aggctagtgc tgtaatggtg tgtttatttt tccagtgtaa gcaagtcgat ttgaatgaca 29340
taggcgacaa agtgaggtgg catttgtcag aagtttcaaa gtcgtgtaag aacattggac 29400
taaagtggtg tgcggcagct gggagcgctc tttcaatgtt aatgttttaa tgtgtatgtt 29460
gtgttggaag ttccaggcta atatttgatg ttttgctagg ttgactaacg atgttttctt 29520
gtaggtgaaa gcgttgtgta acaatgataa cggtgttttg gctgggtttt tccttgttcg 29580
caccggacac ctccagtgac cagacggcaa ggtttttatc ccagtgtata ttggaaaaac 29640
atgttatact tttgacaatt taacgtgcct agagctcaaa ttaaactaat accataacgt 29700
aatgcaactt acaacataaa taaaggtcaa tgtttaatcc atatttcctg acttgtgtct 29760
tgacttgcgt cgattgggat gggggtgtgg gatgggggtg tgggatgggg gtgtgggatg 29820
gggggtgtggg atgggggtgt gggatggggg tgtgggatgg gggtgtggga tgggggtgtg 29880
ggatgggggt gtgggatggg ggtgtgggat gggggtgtgg gatgggggtg tgggatgggg 29940
gtaaatgaca atgggggtaa atgacaatgg ggcgcttggt gacacatttg ccccaccgtc 30000
gcctgcccgg aaccagcttg gtgatgtgct gtctggctct caggtgcact ttatgcaaag 30060
cagttgaggc gcattagata tataaaactt gggtacacac ccttggtgct gtgcgcgtgc 30120
tatgtgccct ggtgaccgtc cacaatggac gaggacgttt tgcctggaga ggtgttggcc 30180
attgaaggga tattcatggc ctgtggatta aacgaacctg agtacctgta ccatcctttg 30240
ctcagcccta ttaagctata catcacaggc ttaatgcgag acaaggagtc tttattcgag 30300
gccatgttgg ctaatgtgag atttcacagc accaccggta taaaccagct tgggttgagc 30360
atgctgcagg ttagcggcga tggaaacatg aactgggggc gagccctggc tatactgacc 30420
tttggcagtt ttgtggccca gaagttatcc aacgaacctc acctgcgaga ctttgctttg 30480
gccgttttac ctgtatatgc gtatgaagca atcggacccc agtggtttcg cgctcgcgga 30540
ggctggcgag gcctgaaggc gtattgtaca caggtgctta ccagaagaag gggacggaga 30600
atgacagcgc tattgggaag cattgcatta ttggccacta tattggcagc ggtcgcgatg 30660
agcaggagat aacgcgtaat tcgaggtccc cggaagagta gagggttgca tgttatacaa 30720
acaacataaa cattaaatga acattgttca aaacgtatgt ttattttttt tcaaacaggg 30780
gagtagggta ggaagggtac gtctaatacg taactgttcg ctactgcttg ttcaggagct 30840
cctcgcagaa catcttgcga attttagatt ttggactaga gcgactgctg gcttcaacgc 30900
ggttcgatgt agggttcggc gtaggagcgt ctttctccac cgccgcgcat ggtgtatgcg 30960
tggtctccgg tgcctgttgt tggatgctct gcgtgctgga ggcgggggtg ggttcagcgg 31020
gtggtgcgcc aactaccgcg agtcctgtag agactggcgg gtggctcaca tgtggctgag 31080
caaaaaggat gggcgccgct tgctggaact gaccgtgtgg cgcctgcacg taaatgggtg 31140
ggtgtacgta ggttcctccg tgctccttca ttgtcgggaa ttgacacggg accgctgaat 31200
tggcgtgggg cctgtagtgt ggatctactg cggctgctgc tgcagaggag gacggcggtg 31260
gccctgcgtg ccaaccgttc agtttcatct ctttgagttc agactgtatt tccgctatgt 31320
tctttgacat ggacaagata tccttgtgat acgccggctc ctctcctgga aagaggtgtc 31380
cttcgtcgtc ctctgcgccg cgcttgcgct tccccgtcct atatccaggc agctgtggcg 31440
agtaatacca tggatcgtat gggttcttgt aagcgtagcc gtatggtggc gctgggtttg 31500
aaacatacga aggtaggtga tggtcggtgg ggaacatctg gcccccacac cccattaggc 31560
ctggccctga aagtgtatgt gacatttttg ccgctgtggt cttcattcca tcgatgctgc 31620
tttgtagcat gctcaggaag gcggatttgg ggatggatat gatatcctct tgaccagagc 31680
tgttcatggc tggtctgggt ggtgtgacgg cttggatgcc gaccgggaat tggctggcct 31740
ttaaatacgc cgggctcaat atgctggcca cacctctgtc agttttcaat aggtcgaggc 31800
ggtcccgtat gaagctggca tctatagctt ttgccattaa ggtctccagg ggactgacga 31860
aatttggtgt ggaaaggtcc tccagcctgc agctacttac gtgctggagg atgtgggcgc 31920
gctccgactt agatactgat gagaatctgg aaaccaccca ctcggcgtcg tgtccgtaca 31980
cggccactgt gccgcgtcgg cgccccaggg cgcatagtga tacgtgttga aacacgggac 32040
cgctgggagt ctgggataac tcgcggggat gtatagacga taaagacagc cccgggagcc 32100
acgtgtggag tatctccaac agtggttcct tagggagatt tttcacgggg gctctggcca 32160
cgtgggaggt gtccgccagc ctggatgcca gctctaggaa ggctggcgac gtgatggctc 32220
cggtgcagaa aataccgtgg gacacttgaa atagacccag tgtccagccc acttctgtct 32280
ctggtaggtg ttcgattgtt attggaaggg gttctgtgac tgggagataa tccgtcacct 32340
gatccggatc gagatagagc tcttgctcca gcttggggca ggacacaaca tctacaaacc 32400
ctccgacgta caggccctgt gccatgctcg gaaaatacgt gtgtgagacc gagccgctga 32460
gcccggggct taggaggctc atgtggcgct ttttgcaaaa taagaattta aatacattcc 32520
acgcccaaga gctgcgtttt attcatttgg ttctctgcag gatgtacaat ttcggtctaa 32580
atgtgtacct gttaagggag gctactgcca atgccgggac ctacgacgag gtggtcctgg 32640
gacgcaaggt tcctgcggag gtgtggaagc tcgtgtacga tgggctcgag gagatgggcg 32700
tgtcaagtga gatgctgctg tgtgaggcat accgggacag cctctggatg cacttgaacg 32760
ataaggtggg gctcttgagg ggcctggcga attatctgtt tcaccggcta ggggtcaccc 32820
acgacgttcg catcgccccg gaaaacctgg tggacggaaa ctttttgttt aatctgggaa 32880
gtgtgctccc ctgcaggctg ctccttgcgg cgggctactg cctcgccttt tggggcagcg 32940
atgaacacga acgctgggtg cgcttcttcg cccagaagct tttcatttgc tacctgatag 33000
tctccgggcg tcttatgcca cagaggtctc tgctagtttg ggccagcgaa acgggctatc 33060
ccggtccggt ggaggcagtc tgtcgcgaca tccgctccat gtacggcata cgaacgtatg 33120
cggtctcggg ttatcttccg gctccgtccg aagcgcagct ggcctacctt ggtgcgttta 33180
acaacaacgc ggtttaaacg accgcgagga ccaccggcag gcagccaaga accataaagt 33240
acgctctatc gtagtcatcg ccgccgccaa actgggactt gataatctcc tggagaaggg 33300
tgggtgggga tgggtgtgaa agcaggacgt ccaggccctc ttctgttgcc aggcggaggg 33360
ctgttctcgc ctggagcagc gccagtggat ctcggaatgt aagctgctgg ttcaggattt 33420
cgaatatctc attaaaccta ctgcctgtca gatttacaaa tggtccgggt tgtttgtggg 33480
acacggtcga tcgcgcctcg agggcggcca gtattatgcc agggaagatg aaggacacgg 33540

```
gggcgtttgg attagcctgc agtgtgggga ttatgtagtg ctccgatatg aacgaaaata  33600
gctggcccct tttcagcatg gggcgtttg gatccggtag ggcaccgggc tgaaatttgg  33660
gtcccagcag ggataccagg ttcaagcggc ggtttgggtg ccctcgcgcg acttgcccaa  33720
actccagcaa tccatacgcg aggataaaca cctccagcgc aacaatcccc gctcgcaggt  33780
tccactggta tgcggaaaat ggtggtatat cggacccaaa catggcgctc gtaatggcga  33840
ataccaagtc catggcgggc gctgtccctg gcgcgcccgt acccttgttg tggggaaata  33900
atccagcctt agccatcatt gcgtgaagct tgtggcgctg gaagaaggct gtcggatagc  33960
ggctctcctt attgagaggc gccagcgagg cgcgctcctg gggtttgag tatgtgaagc  34020
tgaagtcccc aggaccgctt tcctgtttta gctgagtgat tagcaggtct agcttttgag  34080
gcaggtctgc taacaggtca tcgggagtag cgggcagttg cctggatgtc ttttgacaaa  34140
agtacgcgtt gacgaggcaa agcgcggcct gggtgtccgt gagatgcctg gcgtcggcga  34200
aaaagtcagc ggtggtcgag gcgaccgtcg tcagggtgtg agagatgagt ttgagcgatg  34260
tggaattctg aaagttaaca gtccccttta gttctttagg gaagacgcgc cgctgcatgg  34320
cgttgtccgt gaggctgatg aaccacggcc caaaggatgg caaccactga ttctggttca  34380
tgtacagggt gggcatgagc tcgccgcgca ggtccctgtc aacggagaag tgagggtccc  34440
cggggacgat cgccacggtg aagttacggt ggctggcctg cgggggggat gtcactaagg  34500
gaggctcatg ggaacggctt tggggcatgt ctatgttgtc agaccatgtc atgttgccta  34560
tcatctgttt caccgcgtcg atatctgcgt taatgacgcg gacgcgtgag tcatggacct  34620
gaacaagccg gtccagctct agggaaagca ggtgtgcctt tgtctttcgt tctcgatttc  34680
gcacgagttg gctgcgcagt ccaagggcga cccttcttgt ttcttccatg gtgggcttgt  34740
gaataaacag cacgttttcc gggtgtgggg cccagaatct tcccgcctct gtccatcttc  34800
ggttttttgg gtaccttaga taggaccttt ctgatgtcag cattttctct agcagtgaga  34860
aaggcgcaca attttccttc ggtggtgtgc accggcgtgg gaaacgcccc gggtgattca  34920
gagtatactg tctttagtgt tttctgattc ttaaatatca gcaggggcgt gatagtccac  34980
gcctcggtac ccggaggggc cgagtgagcg atgtaatgga tcgagtcgga gagttggcac  35040
aggccttgag ctcgctgtga cgttctcacg gtgttggttg ggatcagctg gtgactcaga  35100
caagtcttga gctctacaac gtaacatacg ggctgatgcc cacccgatac cagaattacg  35160
cagtcggcaa ttctgtgccc tagagtcacc tcaaagaata atctgtggtg tccaagggga  35220
gggttctggg gccggctact tagaaaccgc catagatcgg gcagggtgga gtacttgagg  35280
agccggcggt aggtggccag gtgggcccgg ttacctgctc ttttgcgtgc tgctggaagc  35340
ctgctcaggg atttcttaac ctcggcctcg gttggacgta ccatggcaga aggcggtttt  35400
ggagcggact cggtggggcg cggcggagaa aaggcctctg tgactagggg aggcaggtgg  35460
gacttgggga gctcggacga cgaatcaagc acctccacaa ccagcacgga tatggacgac  35520
ctccctgagg agaggaaacc actaacggga aagtctgtaa aaacctcgta catatacgac  35580
gtgcccaccg tcccgactag caagccgtgg catttaatgc acgacaactc cctctacgca  35640
acgcctaggt ttccgcccag acctctcata cggcaccctt ccgaaaaagg cagcattttt  35700
gccagtcggt tgtcagcgac tgacgacgac tcgggagact acgcgccaat ggatcgcttc  35760
gccttccaga gccccagggt gtgtggtcgc cctcccctc cgcctccaaa tcacccacct  35820
ccggcaacta ggccggcaga cgcgtcaatg gggacgtgg gctgggcgga tctgcaggga  35880
ctcaagagga ccccaaaggg atttttaaaa acatctacca agggggcag tctcaaagcc  35940
```

cgtggacgcg atgtaggtga ccgtctcagg gacggcggct ttgcctttag tcctaggggc 36000
gtgaaatctg ccatagggca aaacattaaa tcatggttgg ggatcggaga atcatcggcg 36060
actgctgtcc ccgtcaccac gcagcttatg gtaccggtgc acctcattag aacgcctgtg 36120
accgtggact acaggaatgt ttatttgctt tacttagagg gggtaatggg tgtgggcaaa 36180
tcaacgctgg tcaacgccgt gtgcgggatc ttgccccagg agagagtgac aagttttccc 36240
gagcccatgg tgtactggac gagggcattt acagattgtt acaaggaaat ttcccacctg 36300
atgaagtctg gtaaggcggg agacccgctg acgtctgcca aaatatactc atgccaaaac 36360
aagttttcgc tccccttccg gacgaacgcc accgctatcc tgcgaatgat gcagccctgg 36420
aacgttgggg gtgggtctgg gaggggcact cactggtgcg tctttgatag gcatctcctc 36480
tccccagcag tggtgttccc tctcatgcac ctgaagcacg gccgcctatc ttttgatcac 36540
ttctttcaat tactttccat ctttagagcc acagaaggcg acgtggtcgc cattctcacc 36600
ctctccagcg ccgagtcgtt gcggcgggtc agggcgaggg gaagaaagaa cgacgggacg 36660
gtggagcaaa actacatcag agaattggcg tgggcttatc acgccgtgta ctgttcatgg 36720
atcatgttgc agtacatcac tgtggagcag atggtacaac tatgcgtaca aaccacaaat 36780
attccggaaa tctgcttccg cagcgtgcgc ctggcacaca aggaggaaac tttgaaaaac 36840
cttcacgagc agagcatgct acctatgatc accggtgtac tggatcccgt gagacatcat 36900
cccgtcgtga tcgagctttg cttttgtttc ttcacagagc tgagaaaatt acaatttatc 36960
gtagccgacg cggataagtt ccacgacgac gtatgcggcc tgtggaccga aatctacagg 37020
cagatcctgt ccaatccggc tattaaaccc agggccatca actggccagc attagagagc 37080
cagtctaaag cagttaatca cctagaggag acatgcaggg tctagccttc ttggcggccc 37140
ttgcatgctg gcgatgcata tcgttgacat gtggagccac tggcgcgttg ccgacaacgg 37200
cgacgacaat aacccgctcc gccacgcagc tcatcaatgg gagaaccaac ctctccatag 37260
aactggaatt caacggcact agtttttttc taaattggca aaatctgttg aatgtgatca 37320
cggagccggc cctgacagag ttgtggacct ccgccgaagt cgccgaggac ctcagggtaa 37380
ctctgaaaaa gaggcaaagt ctttttttcc ccaacaagac agttgtgatc tctggagacg 37440
gccatcgcta tacgtgcgag gtgccgacgt cgtcgcaaac ttataacatc accaagggct 37500
ttaactatag cgctctgccc gggcaccttg gcggatttgg gatcaacgcg cgtctggtac 37560
tgggtgatat cttcgcatca aaatggtcgc tattcgcgag ggacacccca gagtatcggg 37620
tgttttaccc aatgattgtc atggccgtca agttttccat atccattggc aacaacgagt 37680
ccggcgtagc gctctatgga gtggtgtcgg aagatttcgt ggtcgtcacg ctccacaaca 37740
ggtccaaaga ggctaacgag acggcgtccc atcttctgtt cggtctcccg gattcactgc 37800
catctctgaa gggccatgcc acctatgatg aactcacgtt cgcccgaaac gcaaaatatg 37860
cgctagtggc gatcctgcct aaagattctt accagacact ccttacagag aattacactc 37920
gcatatttct gaacatgacg gagtcgacgc ccctcgagtt cacgcggacg atccagacta 37980
ggatcgtatc aatcgaggcc aggcgcgcct gcgcagctca agaggcggcg ccggacatat 38040
tcttggtgtt gtttcagatg ttggtggcac actttcttgt tgcgcggggc attaccgagc 38100
accgatttgt ggaggtggac tgcgtgtgtc ggcagtatgc ggaactgtat tttctccgcc 38160
gcatctcgcg tctgtgcatg cccacgttca ccactgtcgg gtataaccac accacccttg 38220
gcgctgtggc cgccacacaa atagctcgcg tgtccgccac gaagttggcc agtttgcccc 38280
gctcttccca ggaaacagtg ctggccatgg tccagcttgg cgcccgtgat ggcgccgtcc 38340
cttcctccat tctggagggc attgctatgg tcgtcgaaca tatgtatacc gcctacactt 38400
atgtgtacac actcggcgat actgaaagaa aattaatgtt ggacatacac acggtcctca 38460
ccgacagctg cccgcccaaa gactccggag tatcagaaaa gctactgaga acatatttga 38520
tgttcacatc aatgtgtacc aacatagagc tgggcgaaat gatcgcccgc ttttccaaac 38580
cggacagcct taacatctat agggcattct ccccctgctt tctaggacta aggtacgatt 38640
tgcatccagc caagttgcgc gccgaggcgc cgcagtcgtc cgctctgacg cggactgccg 38700
ttgccagagg aacatcggga ttcgcagaat tgctccacgc gctgcacctc gatagcttaa 38760
atttaattcc ggcgattaac tgttcaaaga ttacagccga caagataata gctacggtac 38820
ccttgcctca cgtcacgtat atcatcagtt ccgaagcact ctcgaacgct gttgtctacg 38880
aggtgtcgga gatcttcctc aagagtgcca tgtttatatc tgctatcaaa cccgattgct 38940
ccggctttaa cttttctcag attgataggc acattcccat agtctacaac atcagcacac 39000
caagaagagg ttgccccctt tgtgactctg taatcatgag ctacgatgag agcgatggcc 39060
tgcagtctct catgtatgtc actaatgaaa gggtgcagac caacctcttt ttagataagt 39120
cacctttctt tgataataac aacctacaca ttcattattt gtggctgagg gacaacggga 39180
ccgtagtgga gataaggggc atgtatagaa gacgcgcagc cagtgctttg tttctaattc 39240
tctcttttat tgggttctcg gggttatct actttcttta cagactgttt tccatccttt 39300
attagacggt caataaagcg tagattttta aaaggtttcc tgtgcattct ttttgtatgg 39360
gcatatactt ggcaagaaat ccgagcacct cagaaagtgg attgccgtca catatcagtt 39420
cgaccacccc tgcacctagc catgcggcgc tttgacggtc tttggggcta cacatcataa 39480
agtacttttc catggcttct ataagcacct tggaacaatc tgggggttgg cgaatgggtt 39540
ccctaaacgg gaaatcctct atggtattca ggcagaagac cgcgtcctcc acccgacgtt 39600
tgagtctttc tagcagagcg ccgaagaact cccgctcgtg tgttttcgca ggggcaagtt 39660
ctgcgccgta cagcgatgag aaacacgaca cgatgttttc cagccccatg ctgcgcagca 39720
acacgtgctt caggaacagg tgttgtagcc ggttcagttt tagcttgggt agaaaagtta 39780
tcgagttgtt agcacgctcc atgatggtaa cggtgttgaa gtcacagacc gggctttctc 39840
cgagtctcgg ccgcctgagt ccaatcatgt agaacataga cgcggcctcg ttgtctgtgt 39900
taagtgacac gatatcccgt tcgcaaacct gtgcgatgtt gtgtttcagt atagatctgg 39960
tctgaccggc acggggtgtt atggggtgac gcggtaaagg cgactctggg tcaaacacct 40020
ttatgcggtt ggcggcctcg tcgatgacga cacgcttgtt cgcggcgtgt atggggacgc 40080
gacggcatcc cgctggcaga tctataatct taaagttggt ataagactgg tcgctcgtta 40140
tggccagccg gcactccggt agtatctgcg tgtcctcgaa ttcgtggccg cgtacgactg 40200
gcttggagtg caggtaaacg ccaagagatg cggtctcttc gcctacgcac aagtggcttc 40260
ttaacgcgta ggggtgcggt gagagcatga tccgtagcaa cgatagttcc gggtgcctag 40320
ccgcgtagag tggcagggta gacgagtccg gagtcccaaa cttttcgaac aacagtggca 40380
tcgggacttc aggattagag actcccacca tggccgccac cgccggagag gtcaagacgt 40440
gaaacacgcg ctcgcctgtc gacaggcgcg ccgcgccctc tactagacta gccttcacgt 40500
ccggaactcg taacatagct tagaccagcg gacggacgca acgtacgtgg ggatcggctg 40560
gcggtgtctg ctcgttggac gcggccgttc ggtggcgcca gtgcaggcct agtttgcgaa 40620
tggcgtgacg gacaatttgt ggctttagag cggcgaaccg atgacccgtg gtggcgacga 40680
acgaaatgaa gtttgcattg cggcccaact cgtctagcct ggtcttcttg tttcgggcat 40740

-continued agattttcgg gattaggtta cactttttat atcccagtac tgcgcactcg tgtttgcttt 40800
tagtgtgact gattatcttc tttgagaagt caaacaggcc ccgggcggcg gctcgcctaa 40860
tgcaagccac gtcaagcctg agaaacgaac agcattccac cagacactcc aggaaccttt 40920
tgtgtagcgt ctgtatttgg gaacggtttc tgtgctcaag tagggagaat attctatttt 40980
tgtttccgtc gatgcgcgcg tgctggtccg tgagaatggg cgccagctcg tggcgaatct 41040
gttccacaag aggctgcccg tacactttag aaatcgtggc tgtcgcggcc ttaaaccagg 41100
acacgtttag cccatccttg ctggagacca cagatggaaa gtttgtggtc caaaatacgt 41160
tttttcgccc cattctcacc atgtactggt tttccagtcc gtgcaggtcc aacgtggagt 41220
tccaatttgc tatcgataca ggaaatatgt gcctgattgg cagaaagcat ttcagcgtac 41280
ccattgcgaa gagaaagtgc agcatgtccc cactgatgtt gatgtttatt gcggtgcctt 41340
gacacatgtt gtcggaaaaa aacacgctta tggtaaaaga aggttccttt acggagtact 41400
ttcgtataac aaaattgttg gtcaatctgg ggatgtttaa aatagtcttt tgcagggtgt 41460
taggaacgtg gcagcttatc ttagtgttaa tcaccatgtt ggtgttgaat atggtgatct 41520
tgaagttttc caaactgacg tgttttgtgg gttccagcat gtctgacact gtagagctgc 41580
ccagagtccg cgcgtccgtg gccgcgtatc gttggaagca cgcctgcaaa tttcctttca 41640
tggctgctcg ccggtctttc ggcgcgtacc ggattcttga aagcgtcgcc gccaggagac 41700
gcggtgtctc gtgggtgcct aaaaagtttg cgcaggggtg cagtccgctg cacgagtggc 41760
cgatgcagtc tgccactgcc atacacatga cgagtctgta gatggccggt gtgcccggat 41820
acactagata gtaggtacaa tctggggtac tgacgaccac cctgtatggc tttggtccgg 41880
ggtccttgcg ttggattttt acgtgcagac gggacacgag ctggtttaga gccagctgaa 41940
agcccaccag atcccgtccg ttaaccttga cgtcctggtg cttactctgt ttcgacaggt 42000
tcttcagcac ggtgggcagt cgctctacgt tgtgagcgat ggcacggcgc agcgagacca 42060
gctctccgtg ccaccccac gtggccatga agctgctgat gttaaacttt aaaaaatgta 42120
gctgtgcgtc tggggatgcg ggtggcatta ttgaaaacga gagatgcttc aggctctcca 42180
ggagtgcaaa ataattttga tagattgtgg gttgtagact atggggcaac accgccagaa 42240
acgcatgaaa acactgttcg aactcccaga actccaggta cctgcacact atcctgaaca 42300
tggctttgta acatatggtg cacgttagta gcgcgggaag atacagcgag cgtagctccc 42360
tgaattcgca gggtttatca caatcatcgg taagttccca tgatcccacc gcaggtaggt 42420
agttgtcggt gtctatctgt ccgcgcgtaa acactccacc accgtcaatt attaaacctt 42480
cgccgctgta ccgtcgaccc acttttccca aaagagtccc ttcttgatgt ataaaagggt 42540
ggaggcgttc ccccaggagt agtctgcgta tcgctctgca ggcgaaaaag gtgggctcgg 42600
gctgcatcat cttatcaaga ccttctaagg tcagctctgc ctgcaggtgc gagttggtgg 42660
ccagacagca gaatatttcc agctgtgatt cccaagtcgc ttgataacac gtggtctgcg 42720
gactcgtcgt cagggaggcg ctcggtggca gtagtagggg gccctcgagc gctgccatgg 42780
aggcgacctt ggagcaacga cctttcccgt acctcgccac ggaggccaac ctcctaacgc 42840
agattaagga gtcggctgcc gacggactct tcaagagctt tcagctattg ctcggcaagg 42900
acgccagaga aggcagtgtc cgtttcgaag cgctactggg cgtatatacc aatgtggtgg 42960
agtttgttaa gtttctggag accgccctcg ccgccgcttg cgtcaatacc gagttcaagg 43020
acctgcggag aatgatagat ggaaaaatac agtttaaaat ttcaatgccc actattgccc 43080
acggagacgg gaggaggccc aacaagcaga gacagtatat cgtcatgaag gcttgcaata 43140

-continued

```
agcaccacat cggtgcggag attgagcttg cggccgcaga catcgagctt ctcttcgccg  43200
agaaagagac gcccttggac ttcacagagt acgcgggtgc catcaagacg attacgtcgg  43260
ctttgcagtt tggtatggac gccctagaac gggggttagt ggacacggtt ctcgcagtta  43320
aacttcggca cgctccaccc gtctttattt taaagacgct gggcgatccc gtctactctg  43380
agaggggcct caaaaaggcc gtcaagtctg acatggtatc catgttcaag gcacacctca  43440
tagaacattc attttttcta gataaggccg agctcatgac aagggggaag cagtatgtcc  43500
taaccatgct ctccgacatg ctggccgcgg tgtgcgagga taccgtcttt aagggtgtca  43560
gcacgtacac cacggcctct gggcagcagg tggccggcgt cctggagacg acggacagcg  43620
tcatgagacg gctgatgaac ctgctggggc aagtggaaag tgccatgtcc gggcccgcgg  43680
cctacgccag ctacgttgtc aggggtgcca acctcgtcac cgccgttagc tacggaaggg  43740
cgatgagaaa ctttgaacag tttatggcac gcatagtgga ccatcccaac gctctgccgt  43800
ctgtggaagg tgacaaggcc gctctggcgg acggacacga cgagattcag agaacccgca  43860
tcgccgcctc tctcgtcaag atagggggata agtttgtggc cattgaaagt ttgcagcgca  43920
tgtacaacga gactcagttt ccctgcccac tgaaccggcg catccagtac acctatttct  43980
tccctgttgg ccttcacctt cccgtgcccc gctactcgac atccgtctca gtcaggggcg  44040
tagaatcccc ggccatccag tcgaccgaga cgtgggtggt taataaaaac aacgtgcctc  44100
tttgcttcgg ttaccaaaac gccctcaaaa gcatatgcca ccctcgaatg cacaacccca  44160
cccagtcagc ccaggcacta aaccaagctt ttcccgatcc cgacgggggga catgggtacg  44220
gtctcaggta tgagcagacg ccaaacatga acctattcag aacgttccac cagtattaca  44280
tggggaaaaa cgtggcattt gttcccgatg tggcccaaaa agcgctcgta accacggagg  44340
atctactgca cccaacctct caccgtctcc tcagattgga ggtccacccc ttctttgatt  44400
tttttgtgca cccctgtcct ggagcgagag gatcgtaccg cgccacccac agaacaatgg  44460
ttggaaatat accacaaccg ctcgctccaa gggagtttca ggaaagtaga ggggcgcagt  44520
tcgacgctgt gacgaatatg acacacgtca tagaccagct aactattgac gtcatacagg  44580
agacggcatt tgaccccgcg tatcccctgt tctgctatgt aatcgaagca atgattcacg  44640
gacaggaaga aaaattcgtg atgaacatgc ccctcattgc cctggtcatt caaacctact  44700
gggtcaactc gggaaaactg gcgtttgtga acagttatca catggttaga ttcatctgta  44760
cgcatatggg gaatggaagc atccctaagg aggcgcacgg ccactaccgg aaaatcttag  44820
gcgagctcat cgcccttgag caggcgcttc tcaagctcgc gggacacgag acggtgggtc  44880
ggacgccgat cacacatctg gtttcggctc tcctcgaccc gcatctgctg cctccctttg  44940
cctaccacga tgtctttacg gatcttatgc agaagtcatc cagacaaccc ataatcaaga  45000
tcggggatca aaactacgac aaccctcaaa atagggcgac attcatcaac ctcaggggtc  45060
gcatggagga cctagtcaat aaccttgtta acatttacca gacaagggtc aatgaggacc  45120
atgacgagag acacgtcctg gacgtggcgc ccctggacga gaatgactac aacccggtcc  45180
tcgagaagct attctactat gttttaatgc cggtgtgcag taacggccac atgtgcggta  45240
tgggggtcga ctatcaaaac gtggccctga cgctgactta caacggcccc gtctttgcgg  45300
acgtcgtgaa cgcacaggat gatattctac tgcacctgga gaacggaacc ttgaaggaca  45360
ttctgcaggc aggcgacata cgcccgacgg tggacatgat cagggtgctg tgcacctcgt  45420
ttctgacgtg ccctttcgtc acccaggccg ctcgcgtgat cacaaagcgg gacccggccc  45480
agagttttgc cacgcacgaa tacgggaagg atgtggcgca gaccgtgctt gttaatggct  45540
```

ttggtgcgtt cgcggtggcg gaccgctctc gcgaggcggc ggagactatg ttttatccgg 45600
taccctttaa caagctctac gctgacccgt tggtggctgc cacactgcat ccgctcctgg 45660
caaactatgt caccaggctc cccaaccaga gaaacgcggt ggtctttaac gtgccatcca 45720
atctcatggc agaatatgag gaatggcaca agtcgcccgt cgcggcgtat gccgcgtctt 45780
gtcaggccac cccgggcgcc attagcgcca tggtgagcat gcaccaaaaa ctatctgccc 45840
ccagtttcat ttgccaggca aaacaccgca tgcaccctgg ttttgccatg acagtcgtca 45900
ggacggacga ggttctagca gagcacatcc tatactgctc cagggcgtcg acatccatgt 45960
ttgtgggctt gccttcggtg gtacggcgcg aggtacgttc ggacgcggtg acttttgaaa 46020
ttacccacga gatcgcttcc ctgcacaccg cacttggcta ctcatcagtc atcgccccgg 46080
cccacgtggc cgccataact acagacatgg gagtacattg tcaggacctc tttatgattt 46140
tcccagggga cgcgtatcag gaccgccagc tgcatgacta tatcaaaatg aaagcgggcg 46200
tgcaaaccgg ctcaccggga aacagaatgg atcacgtggg atacactgct ggggttcctc 46260
gctgcgagaa cctgcccggt ttgagtcatg gtcagctggc aacctgcgag ataattccca 46320
cgccggtcac atctgacgtt gcctatttcc agacccccag caacccccgg gggcgtgcgg 46380
cgtgcgtggt gtcgtgtgat gcttacagta acgaaagcgc agagcgtttg ctctacgacc 46440
attcaatacc agaccccgcg tacgaatgcc ggtccaccaa caacccgtgg gcttcgcagc 46500
gtggctccct cggcgacgtg ctatacaata tcacctttcg ccagactgcg ctgccgggca 46560
tgtacagtcc ttgtcggcag ttcttccaca aggaagacat tatgcggtac aataggggggt 46620
tgtacacttt ggttaatgag tattctgcca ggcttgctgg ggcccccgcc accagcacta 46680
cagacctcca gtacgtcgtg gtcaacggta cagacgtgtt tttggaccag ccttgccata 46740
tgctgcagga ggcctatccc acgctcgccg ccagccacag agttatgctt gacgagtaca 46800
tgtcaaacaa gcagacacac gccccagtac acatgggcca gtatctcatt gaagaggtgg 46860
cgccgatgaa gagactatta aagctcggaa acaaggtggt gtattagcta acccttctag 46920
cgttggctag tcatggcact cgacaagagt atagtggtta acttcacctc cagactcttc 46980
gctgatgaac tggccgccct tcagtcaaaa atagggagcg tactgccgct cggagattgc 47040
caccgtttac aaaatataca ggcattgggc ctggggtgcg tatgctcacg tgagacatct 47100
ccggactaca tccaaattat gcagtatcta tccaagtgca cactcgctgt cctggaggag 47160
gttcgcccgg acagcctgcg cctaacgcgg atggatccct ctgacaacct tcagataaaa 47220
aacgtatatg cccccttttt tcagtgggac agcaacaccc agctagcagt gctaccccca 47280
ttttttagcc gaaaggattc caccattgtg ctcgaatcca acggatttga cctcgtgttc 47340
cccatggtcg tgccgcagca actggggcac gctattctgc agcagctgtt ggtgtaccac 47400
atctactcca aaatatcggc cggggccccg gatgatgtaa atatggcgga acttgatcta 47460
tataccacca atgtgtcatt tatggggcgc acatatcgtc tggacgtaga caacacggat 47520
ccacgtactg ccctgcgagt gcttgacgat ctgtccatgt acctttgtat cctatcagcc 47580
ttggttccca gggggtgtct ccgtctgctc acggcgctcg tgcggcacga caggcatcct 47640
ctgacagagg tgtttgaggg ggtggtgcca gatgaggtga ccaggataga tctcgaccag 47700
ttgagcgtcc cagatgacat caccaggatg cgcgtcatgt tctcctatct tcagagtctc 47760
agttctatat ttaatcttgg ccccagactg cacgtgtatg cctactcggc agagactttg 47820
gcggcctcct gttggtattc cccacgctaa cgatttgaag cggggggggg gtatggcgtc 47880
atctgatatt ctgtcggttg caaggacgga tgacggctcc gtctgtgaag tctccctgcg 47940
tggaggtagg aaaaaaacta ccgtctacct gccggacact gaaccctggg tggtagagac 48000
cgacgccatc aaagacgcct tcctcagcga cgggatcgtg gatatggctc gaaagcttca 48060
tcgtggtgcc ctgccctcaa attctcacaa cggcttgagg atggtgcttt tttgttattg 48120
ttacttgcaa aattgtgtgt acctagccct gtttctgtgc ccccttaatc cttacttggt 48180
aactccctca agcattgagt ttgccgagcc cgttgtggca cctgaggtgc tcttcccaca 48240
cccggctgag atgtctcgcg gttgcgatga cgcgattttc tgtaaactgc cctataccgt 48300
gcctataatc aacaccacgt ttggacgcat ttacccgaac tctacacgcg agccggacgg 48360
caggcctacg gattactcca tggcccttag aagggctttt gcagttatgg ttaacacgtc 48420
atgtgcagga gtgacattgt gccgcggaga aactcagacc gcatcccgta accacactga 48480
gtgggaaaat ctgctggcta tgttttctgt gattatctat gccttagatc acaactgtca 48540
cccggaagca ctgtctatcg cgagcggcat ctttgacgag cgtgactatg gattattcat 48600
ctctcagccc cggagcgtgc cctcgcctac cccttgcgac gtgtcgtggg aagatatcta 48660
caacgggact tacctagctc ggcctggaaa ctgtgacccc tggcccaatc tatccacccc 48720
tcccttgatt ctaaatttta aataaaggtg tgtcactggt tacaccacga ttaaaaacca 48780
ctcactgaga tgtcttttta accgctaagg gattataccg ggatttaaaa ccgcccactg 48840
atttttttac gctaagagtt gggtgcttgg ggggttttgc attgctctgt tgtaaactat 48900
atataagtta aaccaaaatt cgcagggaga caaggtgacg gtggtgagaa ctcagttgag 48960
agtcagagaa tacagtgcta atcagggtag atgagcatga cttccccgtc tccagtcacc 49020
ggaggaatgg tggacggctc cgtcctggtg cgaatggcca ccaagcctcc cgtgattggt 49080
cttataacag tgctcttcct cctagtcata ggcgcctgcg tctactgctg cattcgcgtg 49140
ttcctggcgg ctcgactgtg gcgcgccacc ccactaggca gggccaccgt ggcgtatcag 49200
gtccttcgca ccctgggacc gcaggccggg tcacatgcac cgccgacggt gggcatagct 49260
acccaggagc cctaccgtac aatatacatg ccagattaga acggggtgtg tgctataatg 49320
gatggctatg ggggggctgt agataattga gcgctgtgct tttattgtgg ggatatgggc 49380
ttgtacatgt gtctatcatc ggtagccata aaatgggcca tgacaactgc cacaagtaag 49440
tcgtccgaca tgtgcttttg cttggcgctg tatgactgcc ctccatccct aagcgggacg 49500
cacttgatcg cgcggacctg ttctaccagg taggtcaccg ggtcaaatga tattttgatg 49560
gtgttggaca ccaccgtctg gctggcgctc agggtgccgg agttcagagc gtagatgaat 49620
gtctcaaacg cggaggattt ctcgcctccc aacatgtaaa ttggccactg cagggcgctg 49680
ctcttgtcag tatagtgtag aaaatgtatg gggagcgggc atatttcgtt aaggacggtt 49740
gcaatggcca ccccagaatc ttggctgctg ttgccttcga ccgccgcgtt cacgcgctca 49800
attgtggggt ggagcacagc gatcgcctta atcatcgtgc atgcgcagga cgctatctcg 49860
taagcagctg cgccagtgag gtcgcgcagg aagaaatgct ccatgcccaa tatgaggctt 49920
ctggtgggag tctgagtact cgtgacaacg gcgcccacgc cagtaccgga cgcctccgtg 49980
ttgttcgtat acgcggggtc gatgtaaaca aacagctgtt ttccaaggca cttctgaacc 50040
tgctgggcgg tggtgtctac ccgacacatg tcaaactgtg tcagcgctgc gtcacccacc 50100
acgcggtaaa gcgtagcatt tgacgacgct gctccctcgc ccattagttc ggtgtcgaat 50160
gccccctcca taaagaggtt ggtggtggtt ttgatggatt cgtcgatggt gatgtacgtc 50220
ggaatgtgca gtctgtaaca aggacaggac actagtgcgt cttgcaggtg gaaatcttcg 50280
cggtggtccg cacacacgta actgaccaca ttcagcatct tttcctgggc gttcctgagg 50340
ttaagcagga aactcgtgga gcggtctgac gagttcacgg atgatataaa tataagcttg 50400
gcgtctttct gaagcatgaa acccagaata gccggcagtg catccttttt aataaaattc 50460
gcctcgtcta cgtagagcag gttaaaggtc tgtccccgaa tgctctgcag acacggaaag 50520
acacaaaaga ggggctcata agcggctaac agtaaaggag aggaggcgaa cagtgcgtgg 50580
ctcttgttct tgggaataaa agggggcgtg tgtgccgatc gtatgggtga gccagtggat 50640
cctggacatg tggtgaatga gaaagatttt gaggagtgtg aacaattttt cagtcaaccc 50700
cttagggagc aagtggtcgc gggggtcagg gcactcgacg gcctcggtct cgctgactct 50760
ctatgtcaca aaacagaaag actctgcctg ctgatggacc tggtgggcac ggagtgcttt 50820
gcgagggtgt gccgcctaga caccggtgcg aaatgaagag tgtggcgagt cccttatgtc 50880
agttccacgg cgtgttttgc ctgtaccagt gtcgccagtg cctggcatac cacgtgtgtg 50940
atgggggcgc cgaatgcgtt ctcctgcata cgccggagag cgtcatctgc gaactaacgg 51000
gtaactgcat gctcggcaac attcaagagg gccagttttt agggccggta ccgtatcgga 51060
ctttggataa ccaggttgac agggacgcat atcacgggat gctagcgtgt ctgaaacggg 51120
acattgtgcg gtatttgcag acatggccgg acaccaccgt aatcgtgcag gaaatagccc 51180
tgggggacgg cgtcaccgac accatctcgg ccattataga tgaaacattc ggtgagtgtc 51240
ttcccgtact gggggaggcc caaggcgggt acgccatggt ctgtagcatg tatctgcacg 51300
ttatcgtctc catctattcg acaaaaacgg tgtacaacag tatgctattt aaatgcacaa 51360
agaataaaaa gtacgactgc attgccaagc gggtgcggac aaaatggatg cgcatgctat 51420
caacgaaaga tacgtaggtc ctcgctgcca ccgtttggcc cacgtggtgc tgcctaggac 51480
ctttctgctg catcacgcca taccccctgga gcccgagatc atcttttcca cctacacccg 51540
gttcagccgg tcgccagggt catcccgccg gttggtggtg tgtgggaaac gtgtcctgcc 51600
aggggaggaa aaccaacttg cgtcttcacc ttctggcttg gcgcttagcc tgcctctgtt 51660
ttcccacgat gggaactttc atccatttga catctcggta ctgcgcattt cctgccctgg 51720
ttctaatctt agtcttactg tcagatttct ctatctatct ctggtggtgg ctatgggggc 51780
gggacggaat aatgcgcgga gtccgaccgt tgacggggta tcgccgccag agggcgccgt 51840
agcccaccct ttggaggaac tgcagaggct ggcgcgtgct acgccggacc cggcactcac 51900
ccgtggaccg ttgcaggtcc tgaccggcct tctccgcgca gggtcagacg gagaccgcgc 51960
cactcaccac atggcgctcg aggctccggg aaccgtgcgt ggagaaagcc tagacccgcc 52020
tgtttcacag aaggggccag cgcgcacacg ccacaggcca ccccccgtgc gactgagctt 52080
caaccccgtc aatgccgatg tacccgctac ctggcgagac gccactaacg tgtactcggg 52140
tgctccctac tatgtgtgtg tttacgaacg cggtggccgt caggaagacg actggctgcc 52200
gataccactg agcttcccag aagagcccgt gcccccgcca ccgggcttag tgttcatgga 52260
cgacttgttc attaacacga agcagtgcga ctttgtggac acgctagagg ccgcctgtcg 52320
cacgcaaggc tacacgttga gacagcgcgt gcctgtcgcc attcctcgcg acgcggaaat 52380
cgcagacgca gttaaatcgc actttttaga ggcgtgccta gtgttacggg ggctggcttc 52440
ggaggctagt gcctggataa gagctgccac gtccccgccc cttggccgcc acgcctgctg 52500
gatggacgtg ttaggattat gggaaagccg cccccacact ctaggtttgg agttacgcgg 52560
cgtaaactgt ggcggcacgg acggtgactg gttagagatt ttaaaacagc ccgatgtgca 52620
aaagacagtc agcgggagtc ttgtggcatg cgtgatcgtc acacccgcat tggaagcctg 52680
gcttgtgtta cctgggggtt ttgctattaa aggccgctat agggcgtcga aggaggatct 52740
ggtgttcatt cgaggccgct atggctagcc ggaggcgcaa acttcggaat ttcctaaaca 52800
aggaatgcat atggactgtt aacccaatgt caggggacca tatcaaggtc tttaacgcct 52860
gcacctctat ctcgccggtg tatgaccctg agctggtaac cagctacgca ctgagcgtgc 52920
ctgcttacaa tgtgtctgtg gctatcttgc tgcataaagt catgggaccg tgtgtggctg 52980
tgggaattaa cggagaaatg atcatgtacg tcgtaagcca gtgtgtttct gtgcggcccg 53040
tcccggggcg cgatggtatg gcgctcatct actttggaca gtttctggag gaagcatccg 53100
gactgagatt tccctacatt gctccgccgc cgtcgcgcga acacgtacct gacctgacca 53160
gacaagaatt agttcatacc tcccaggtgg tgcgccgcgg cgacctgacc aattgcacta 53220
tgggtctcga attcaggaat gtgaaccctt ttgtttggct cgggggcgga tcggtgtggc 53280
tgctgttctt gggcgtggac tacatggcgt tctgtccggg tgtcgacgga atgccgtcgt 53340
tggcaagagt ggccgccctg cttaccaggt gcgaccaccc agactgtgtc cactgccatg 53400
gactccgtgg acacgttaat gtatttcgtg ggtactgttc tgcgcagtcg ccgggtctat 53460
ctaacatctg tccctgtatc aaatcatgtg ggaccgggaa tggagtgact agggtcactg 53520
gaaacagaaa ttttctgggt cttctgttcg atcccattgt ccagagcagg gtaacagctc 53580
tgaagataac tagccaccca acccccacgc acgtcgagaa tgtgctaaca ggagtgctcg 53640
acgacggcac cttggtgccg tccgtccaag gcaccctggg tcctcttacg aatgtctgac 53700
tacttcagcc gcttgctgat atatgagtgt aaaaaactta aggccctggg cttacgttct 53760
tattgaagca tgttgcgcac atcagcgagc tggaccgtcc tccgggtcgc gtgtagatta 53820
tggttccgtt ctccttcttg atgtttaaat ttttgggggg gaaccaccga caaagcgtct 53880
ttatgatttc cgcgaacacg gagttggcta cgtgcttttg gtgggctacg tacccaatgt 53940
taatgttctc tacggatgcc agtagcatgc tgatgatcgc caccactatc catgtctttc 54000
cgtgtctcct tggtattagg aatacgcttg ccttttgctt aaacgtctgt aaaacactgt 54060
ttggagtttc aaataaaccg aagtactgct taaacaatcc aaacaactgg tgcgtctttt 54120
gtggggcctt gattgaaacc aaaaagaaaa aagtgtgcat tactagctgc tgttggaagg 54180
gctccagcca gtgcaccccg ggaacgtaac agccgttcag aaaggacgaa aggttaacca 54240
gaaaagcctg aagttcgcgg tagacagagc aggcgtgcag ggagtcgtgt gtttttctgg 54300
ccgcctggta ctcgaccagt tgatcggccg tggagacgtg cgcgtcctcg cgcacacacc 54360
gcatctgcaa gtatgttgat agggactcca ataggcgcgg ctttgcgggg acgttgtcct 54420
cggacggtct gggggttccc acgtcgggat ttgctgacgt gggcgtggcg ggatggtgcc 54480
gtgtgcagta tgtttccagg accgaactgt atgagtttat tctgtgcacc acgccaataa 54540
aagggtgcgc catccgtgcc gttttgggac agtgtcgcgt gaatgtcggg gcactcagtt 54600
cccacctctc tccggcgtct ttggcggtct cctgcaggtt ggcggcaagg cgctccctgt 54660
gacggctgag cagcatgttt gctttgagct cgctcgtgtc cgagggtgac ccggaggtga 54720
ccagtaggta cgtcaagggc gtacaacttg ccctggacct tagcgagaac acacctggac 54780
aatttaagtt gatagaaact cccctgaaca gcttcctctt ggtttccaac gtgatgcccg 54840
aggtccagcc aatctgcagt ggccggccgg ccttgcggcc agactttagt aatctccact 54900
tgcctagact ggagaagctc cagagagtcc tcgggcaggg tttcggggcg gcgggtgagg 54960
aaatcgcact ggacccgtct cacgtagaaa cacacgaaaa gggccaggtg ttctacaacc 55020
actatgctac cgaggagtgg acgtgggctt tgactctgaa taaggatgcg ctccttcggg 55080
aggctgtaga tggcctgtgt gaccccggaa cttggaaggg tcttcttcct gacgaccccc 55140

```
ttccgttgct atggctgctg ttcaacggac ccgcctcttt ttgtcgggcc gactgttgcc  55200
tgtacaagca gcactgcggt tacccgggcc cggtgctact tccaggtcac atgtacgctc  55260
ccaaacggga tcttttgtcg ttcgttaatc atgccctgaa gtacaccaag tttctatacg  55320
gagatttttc cgggacatgg gcggcggctt gccgcccgcc attcgctact tctcggatac  55380
aaagggtagt gagtcagatg aaaatcatag atgcttccga cacttacatt tcccacacct  55440
gcctcttgtg tcacatatat cagcaaaata gcataattgc gggtcagggg acccacgtgg  55500
gtggaatcct actgttgagt ggaaaaggga cccagtatat aacaggcaat gttcagaccc  55560
aaaggtgtcc aactacgggc gactatctaa tcatcccatc gtatgacata ccggcgatca  55620
tcaccatgat caaggagaat ggactcaacc aactctaaaa gagagtttat taagtcggct  55680
ctggaggcca acatcaacag gagggcagct gtatcgctat ttgatcgttt tgggggtagc  55740
agcgccgtgt ttgagaagca gtttcaggac gcacagcatg ccgtcagggc ccacggtgca  55800
ctgaagcgcg aagccgagct cgggactctg gtacgcaagg cgggccagag gtttgaggcg  55860
ctgaaaaggg aacggtcaat tttgcgccag ccgcgcgacc tcccacgggt cgccgacatt  55920
gacgccctgg tcgacgccgt cgcggacctc aaagaagagg tggccgtgcg cctagatgcg  55980
ctggaagaga atggagagga gacccccact cactcctctt cggagatcaa ggacacaatc  56040
gtcaggtgga ggcttgacga tttgcccccg gtgtgccctg aaactcccta aggctacccg  56100
gatttcagag agaccctggg cgtccacatg gcagctgaat cagcatatac aggtgtccaa  56160
gactaaaaag gccaccgcgt atcttaaagc gccccgtgaa tgggggcagt gcacgcacca  56220
ggatccagac tggtccaagc gtctgggtcg tggcgccttt ggcataatcg tccctatctc  56280
cgaggatctg tgtgtgaagc agtttgatag ccgccgggag tttttctacg aggcaattgc  56340
caacgacctg atgcaggcca cccgagagag gtaccccatg cattctggtg gatctagact  56400
gctaggattc gtgcagcctt gcataccctg tagatcgatt gtgtatccta gaatgaagtg  56460
caacctgctg cagctggact ggagtcaggt caacctgagt gtcatggcgg cggagttcac  56520
cggcctaatg gcggcggtgt cctttctaaa cagatactgt ggcatggtgc actgcgacgt  56580
tagtccagac aatattttgg ccacaggaga cctaacgccc atgaaccccg ggaggctggt  56640
ccttaccgat ttcggttccg ttgcgctaca ctctgggagc aagtggacta accttgtggt  56700
gacctctaac ctggggttta agcaacactg ctacgacttc agggtgccac ccaaactcat  56760
ttgtaagcat ctctataagc cgtcttgcgt cctcttccag tgttacctat ccagtctcgg  56820
taagatgcac gcgcaggtat tggaccaacc gtaccctatc agccctaaca tgggactgac  56880
catcgacatg tcctcgttgg gctacactct gctgacatgc ctggaactct atctcgatct  56940
gccgctaaac aaccctctga agttcttggg ttcagccacc agagacggac gccccgaacc  57000
catgtactac ttgggcttca tgattcccag ggtggtgatg actcagatcc tgtccgctgt  57060
gtggaccatg acgcttgacc tgggactaga ttgcaccggc aaagcccagg cgattcccat  57120
gcgacaggag caccagctgg cgtttcagaa gcagtgctat ttatataaag ccaaccaaaa  57180
ggcagagtcg ttagcgaact gctccgataa gctaaactgc cccatgttaa agtctctcgt  57240
tagaaagcta ctagagcgag actttttcaa ccatggaggc cacccccaca cccgcggact  57300
tgttttctga agactatctg gttgacaccc tggatgggtt aacagtggat gaccaacagg  57360
ctgtcctcgc aagcttgagc ttttcaaagt ttctaaagca cgccaaggtt cgagactggt  57420
gcgcacaggc caagatccaa cccagcatgc ctgcgctgcg catggcttac aactatttcc  57480
tttttcaaa agtgggcgag tttattggta gtgaggatgt gtgtaacttt ttcgtggacc  57540
```

```
gtgtgtttgg tggtgtcagg ttactggacg tggccagcgt gtacgccgcc tgttcgcaaa  57600
tgaacgcaca tcagcggcac cacatctgct gtctagtgga gagggccact agtagtcaga  57660
gtctgaaccc cgtgtgggac gccctgcgag acggaattat atcttcatcc aagtttcact  57720
gggcagttaa acaacagaac acttcaaaaa agatattcag cccatggcct ataacgaaca  57780
accactttgt cgcgggcccg cttgcctttg ggctgcggtg cgaggaggtg gtgaaaacgt  57840
tgctggccac ccttttgcac ccggacgaga caaattgtct cgattatggg tttatgcaga  57900
gtccgcaaaa tggaatattt ggcgtgtcgc tggatttcgc ggcgaacgtc aaaactgaca  57960
ccgagggtcg tctacagttt gaccctaact gtaaagtgta tgaaataaaa tgcaggttca  58020
agtacacctt tgcgaaaatg gagtgtgacc ccatatacgc cgcgtatcag cggctgtacg  58080
aggcacccgg aaagctggca ctgaaggact tcttctatag catttccaag cctgcggttg  58140
agtacgtggg acttggaaaa ctgcccagtg aatctgatta cttggtggct tatgatcagg  58200
aatgggaggc gtgtcctcgc aaaaagagga aattaacgcc ccttcacaat cttattaggg  58260
agtgtatttt gcacaactcg accacggagt ctgacgtcta cgtacttact gatcctcaag  58320
atactcgggg tcaaatcagt attaaagccc gcttcaaagc caacctcttc gtgaacgtcc  58380
gtcacagcta cttttatcag gtattgctgc agagttcgat cgtcgaggag tacattggcc  58440
tagatagcgg cattcctcgc ctcggatcac cgaaatacta catcgccacc ggcttcttca  58500
gaaagcgggg ctatcaggat cctgtcaact gtaccatcgg tggcgatgct ttagacccgc  58560
acgtggagat tcctacgctg ctaatcgtaa cccccgtcta ctttccccga ggcgcaaagc  58620
atcgtctgct tcaccaagct gccaactttt ggtcaagaag tgcgaaggac acctttccat  58680
atatcaaatg ggatttctcc tatctatctg caaacgtccc tcacagcccg tagacgtgga  58740
cggggaaccg ctcgacgtag tcgtggacta tgaccccatt cgcgtttcag aaaagggcat  58800
gttgcttgag caatcgcaat ccccatatcc cgcattaaaa aagaagaaaa aaaataaaga  58860
agcaatttat taagcaaaca gtatggtttt ctgtacgtat tttattccgt ggtgggtgaa  58920
aaataacggg ggatggagga agagggatgg gtttataatg ccaatatatc agctaaatga  58980
atatcatttg cgtttcgtcg atttcactgt cactttcatg gtcggactgg tattgggtcc  59040
tcggggcggg cgtcgatatg tccttcactt tggcgcgggc tctggtcttt gctgggaggg  59100
gcggcggttt ctggtgaaca gtcggagttc tatcgaccgt cggcgccgac gtcgccagag  59160
gcatgtatgc cgcactcggc gtacagagtc cccagtcgct ccttataacg cgtataacga  59220
tggctaggat gcacagtata gggatacagg agatattgat agccactatg tagtggagat  59280
tagcctgcac gaacgcgttt tcatacctga tgacaggcag cagtagaatc agataaccca  59340
ccaatactcc cacgtaaaag cctacctgcc gtctcataaa ctttaccagg aaaaattccg  59400
tgtttatgta ccacacgacc gtcaaggcta ggaacatgtt caccgcacca aaaatggcgt  59460
ctgacacgag cacgtaaaag ctgttgccaa cggccatcat ggtgctcaat gaaaacagca  59520
gcatttccaa ggcggttgtt gataggtaca ggttgacgca gaccggtttc caccgagtca  59580
gcagtgactc catcatggta ttatcaggta cgtgctgttc caggagaggt atttcccact  59640
gggcggagtt acatgttatc agtgactgga tgtgggcaaa ggatatgcaa aaatgaatgc  59700
agtagacaaa ggctgccata agtacgtgtt tatatgacag aacatggata aacagttgca  59760
tgctccacat ccttaagatg gcgacataaa gcacgctatg tgatccaagt agcgctatcc  59820
aggattgcat gctcatcatg gtagtggcgt gaacatgctt ggcccgatat acggccaccg  59880
ccgcgagaca gtagtatact atggcaatgc cgtccacgat aaaagtccaa aatatgtaca  59940
```

ccagcatctc tggtttctct aaaaacaggg tcggggtgag gtgcttcgct gagttgcgca 60000
ccgtgaggtt tagcgcgctg tagtttacca gattgttgaa gtagcagggg aaaccaaggc 60060
cctcgtacgt ggcggccatg ggcacgactg cagagcaaat gtacataatt acagccacaa 60120
acaacagctt gacccaggag gacatgagaa aacggtcgct ctttgaagcg cgcatgtttc 60180
tcggtctttt taactttcgc caggcggcgc tgcggcggga gagccaatct gatgccactg 60240
cctatcgcgg ttgactttta aatacgcgcc ccgggcagaa gccagaggta gtcgactcat 60300
tgactcaatg gcaacgagcg aagaaacggc ggccggttat gtcatcggtg tctactttca 60360
cagcgttcac gtccactgcc gcattattgt ctggcaggtt aattttctac ccctggaccc 60420
aaacgacggg gagactgaat gctactttgt ggtggacacg ctgacgaaag aggcgatgga 60480
gcgcatgccc gaaatccagg aatgcgtccc gtctattact gaacacgccc gtgacctggc 60540
gatctgggag ttggcgctgc gactgcagaa tcagacgatc gtcaaggccg tccggacagc 60600
gtcgcttccg gtggttctaa ttatgactgt gggtcgcata gtgaatgatg tgattccctg 60660
ccccaacgtc agaacaccca gaccactagc ctgtgcttac ctacactgtg aggcgacggt 60720
gacctttgag gtcccactaa ccgggcccgc ggcgtccacc ggaacgtggc acagctctat 60780
ctatagggaa tgtgcgatct cggctatcga gatatgcttg aagaccagtc gaggcatata 60840
ctcctgccag tcgaacgagg cccctgaggc caagagggaa aagcgaggtt tagacatatc 60900
agatgtgttt gtctgtctca cgtatgatat ccctatcgca gggcgggtcc tttctctgct 60960
ggtgccccac gcgcccgctt ttcacgtctt atggatcaat gaggacagca agtggaacgg 61020
ggcagccgtc gaatttttca gagccctaca ccataagctg ttcagtgaac gcaatggtat 61080
accccctctg tggttgtacg tgttcccggg agctgtggaa gagggcacag cctttgcgcc 61140
attacttccc gcattccctt gcataccttt gcggtatggg tcgcctacct ctctggacag 61200
ggcgtccgtg cagtgggacc tatttgaacc gcacatcctg acccactttg acgggataaa 61260
gcgaacttct ttggcagata cagtgtttgg gtacgactcc ctggccattt caagggaatg 61320
tgaagatcag tatgtgtggc ccacgcctgt cactgacatt aatattaatt tgtgcacgga 61380
tagtgacact atggccatcg ttagagaacc atccggtctg gtggccgtga atctagaagc 61440
cctgttgcgc accgactccg tattatcgcg ggtctcgtcc attgtctcac tcgatacgct 61500
cttggacctt tccaccccgg agtgccgtag gagcgtggag cttagataca actcactttt 61560
gtcgactgta ttatcatggt ccacctctag ggtcacaaa tgggccgcaa tcgtgaagtg 61620
gaagttattt ttcctcgtcc aagctttgga gcctgaggtg agacctactg tccctgcttg 61680
aagcggagag ggggtggtgc gagttggcag ttgacgggtt tgtgatagct ggagtgctga 61740
ccacggcaca ggacccatta actttcctat gtgtttattt ttagcaatgg tctccagaat 61800
tcaaggatct caaaagggcc tgccagatgg ccgggtttac tctgaagggg gggacttcgg 61860
gggatcttgt attctcatcg catgcgaact tgctcttttc aacctcgatg ggatatttcc 61920
tccatgcagg cagtccaagg tcgacagcgg ggacgggggg tgagcctaac ccacgtcaca 61980
tcaccggacc agacactgag ggaaatgggg aacacagaaa ctcccccaac ctctgcggct 62040
ttgttacctg gctgcaaagc ttaaccacat gcattgaacg agccctaaac atgcctcccg 62100
acacttcctg gctgcagctg atagaggaag tgataccccct gtattttcat aggcgaagac 62160
aaacatcatt ctggctcatc cccctatcgc actgtgaagg gatcccagta tgcccccctt 62220
taccatttga ctgcctagca ccaaggctgt ttatagtaac aaagtccgga cccatgtgtt 62280
accgggcagg cttttcgctt cctgtggatg ttaattacct gttctattta gagcagactc 62340

-continued

```
tgaaagctgt ccggcaagtt agcccacagg aacacaaccc ccaagacgca aaggaaatga  62400
ctctacagct agaggcctgg accaggcttt tatctttatt ttgaaaaaag ggaaacaatg  62460
gggggtttga aaagggtgca cattttcaga tattttaaaa cttcattgtt ctccaggtgc  62520
ttggtaaaga tggtatcaca ataaaaaatg tttactgggt ccgcgcaggt ttgtttgtca  62580
tcttcattct ctccactaga ctccagttta aaagactcta gataaatggg tttcattagt  62640
ccccccatgg gggttgaagc gtcgcctatc gccttatgaa gcttaaacat aacgagtggg  62700
gtggccctga aatgatcgtc cacggacagc tcgtaaacaa aggcggccgt ggcagtcaac  62760
gtctctatac cgtgcatgac gaaggccgcg tccatccccg gcgtcctctc atgtgtcttt  62820
ctggcgcgac aaataataga tctcaaaaac gttggtgaca tgtctcgaca gttctcgagc  62880
atcgataaca ggcagcagag ctcggttatg ccgggagatg taggtctaag gaggcacact  62940
cgctcttgga acacgtgagg gtgtaggtct atgtgggtca ccatgtcttc gtgctccacc  63000
aggcacacca ccgtaaatcc cacaaagttg ggcgaggaca ggcgagattt cacgtgctcc  63060
ctgagacacg ctatatctaa gtggcccatc acggacattt tgggggtatt gcttccaacc  63120
agtgcgttgt ttttcctatg cacttccagg acaaggcggg gcaccacagg gtgggggtat  63180
acgggacagg cctcttctga ctcgcgagtc ttcggggcat gagtactcat tggcactcca  63240
gtcagtctcg ccagggccct ttccagggac attctcgaag ggtggtgtaa ctagacagta  63300
tttctgtccc acgtcggtta tatacacaaa gagtctgcta gtctgatata aataggccgc  63360
gatgtcctgc aagctggagg atacgaagga gtgactaatg agctccatct gaagcaggtc  63420
cgcgatcaca tacgtgaatg gaccaagcag gatggatatg gtgtcctgag aataggtgac  63480
gctgagccgc tgcccttggt tgtcaacaac gggagccagc ttgtaggttt gaaacatctc  63540
gctttcccac aggttcgtga gatctttcat gctttctctc actgggggta tgtaagaaga  63600
gaaaaagcta tttagcacgg cactgcccga tgggatatgg gaagacgtta gctgcagaga  63660
ggggtcctgt aaacgtccca gagattgaaa tgtgttggcg gtcagcagat tcacactccc  63720
gggacccttt gcgtcaccgg gctgttggtg tgacagctgt gtctcaatac attttagcct  63780
cttcatgcag agctccctct ccttttcaag ttgagttatt gtgtcaaatt gttcgtttat  63840
ctggttggtg agacacttga aaacgctgtt ggacacctgg cgcctgagcc cctgagtggt  63900
cgtctcttgg cctgtgccga atagtttatt cttgtctact atgttttggg acacgtcggt  63960
gacaaagtcc tccacgacgt cggtgacacc gctcactgtc ttgttttctg ccagtttcat  64020
gagcaggttg aggagctctc gcttggggtc tgttctctga gaggcctgct ccaggtgggt  64080
catgatgtct ttgtacacat tgttacaggc gcttccaacg agggccttgg tgggggctgt  64140
gttcaggagc tggcaaagtt ttgcgtgctc tgccgtccgg tgacagctca taatgctggt  64200
atacatcctc tgaatggggc tgtcaaagat cacccgccca gccaagatgg cgggcatagt  64260
aatcacctcc acatgaaccc ttttctgctt atacaatccc acgaaagtgt ttttaacaca  64320
gtcatagtct atgctcacct ctgagtagcc cggaatatag agggcgctta aactagacac  64380
caggttgcta atctcctgag tcacgctggt gagtatccgg cctatggttt tttcaccaga  64440
ggccagacgc tggcaatctt tcatcagctg ttcctggata gagttaacca gcttgtggtc  64500
gggtgtgtgc ttgacgactg gtaccattcc taccgtgacc acccagtcta cgtatctctc  64560
atacgagagc tgtgtcttgg cgtagaggac ccggttgatg gcattgagaa gcaggtggtc  64620
taatgtcatg cgcatagtct gggcccagga gtcgaaggtt gaccttctgt aagaccccca  64680
ctgtgcttcc ttttctggcc acctggtttt tgctgaggac tcgtatgtcc tccagtcgga  64740
```

```
caagacgtgg tcgtagctac agttggccaa tgcattcttg tacaggtgga taaatagctg  64800
tctgaaaaaa acacccgggt ttcgcaggct gcagtgtaga gtctgacctc tgacataaga  64860
atacttgcct tgcaggatct caaagaggga gatggacagc tcggaagggt gcactgatat  64920
ggacgagccc agccccgggt tcatcctcaa catgacatcg gatgccaaag tcaggagcgt  64980
agtggaacag attgacaggt tgtcaaatat cactacctcg cccccggaga tgggctggta  65040
tgacctagag ttcgatccac tggaagacga aggccccttt ctgccgtttt cggcatacgt  65100
aataacgggg actgcaggag cggggaaaag caccagcgta tccgccctac atcagaatct  65160
caactgccta attacggggg ctacagtggt agcggcacag aatctttcca gggctttaaa  65220
gtcctactgt cccactatat accacgcctt cggattcaag agcagacaca ttaatatctg  65280
ccagaggaaa gtgcccaagg taactcagtc ctccatcgag caactccaga gatacgagct  65340
ggctaggtac tggccaactg tcaccgatat tattcgagaa tttatgcgca agaaacaaaa  65400
ggggcagtat agctccctct ctcaaagcgc tttcagactc ctttgccgta tgggtggagc  65460
caatttgtgg acgagtaaca ttatcgtgat agacgaagct ggaaccctct cgtcccatat  65520
tttgacggcc gtggtgttct tctattggtt ttacaacagt tggctggaca ccccgctata  65580
cagaaatggt gccgtgcctt gcatagtctg cgtggggtct cccacccaga cggacgcctt  65640
tcagtcggtc ttcaaccaca cgcagcagag aaacgagata tctgcctgtg ataatgtgct  65700
caccttccta ttgggaaaac gtgaggttgc agattatatt aggctggacg agaattgggc  65760
cctatttata aacaataagc gctgtacgga tccccagttt ggtcacttgc tgaagacctt  65820
agaatataat ctagacatat caccagagtt aatggactat atagataggt ttgtggttcc  65880
gaagagtaag attctggacc cgctcgagta tgcagggtgg acaagactct tcatctcaca  65940
ccaggaggtg aagtcttttc tggcaacgct gcacacctgc ctgtcgagta ataaggatgc  66000
tgtgtccaca aagcttttca cctgcccagt ggtctgtgag gtgtttacag agccatttga  66060
ggagtacaaa cgggcggtag gcctcacaca catgactccc atagaatggg taacaaaaaa  66120
tcttttcagg ctaagtaact actcgcagtt tgctgatcag gacatggctg tggttgggac  66180
ctatatcaca gacgcgtcca cacagatcac cttcgccact aaatttgtca aaaacagcta  66240
tgctaccctt actggaaaga ccaaaaaatg tatatgcggg tttcacgggt cataccaaag  66300
attcaagtcc atcctagacg gggagctatt tatcgaaagt cattcgcacg ataaccccgc  66360
ttatgtgtac agtttcctta gtaccctgct atataatgcc atgtactcat tttacgcgca  66420
cggggtgaag caggggcatg aagaattcct cagggacctc agggaactgc cggtgtctca  66480
agagctgatc tctgagatga gctccgagga cgttctgggg caggaggggg acacagatgc  66540
cttctacctc accgccagcc tcccaccatc ccccacccac gcggctcttc caacactggt  66600
ggcctattac tccggggcca aggaactatt ctgcaacagg ctggccctgg cacgccgaca  66660
ctttggtgac gagttcctcc actccgattt ttcaacgttt acggtgaaca tcgtggtgcg  66720
agatggcgtg gactttgtgt ccacttcccc cgggctccac ggtctagtgg catacgcatc  66780
cactatagac acctatataa tccagggata tacgttcctc ccagtgagat tcggccgtcc  66840
aggaggacag cgcctcagcg aggacctgcg cagaaagatg ccctccatag ttgtccagga  66900
ctcatcgggg ttcattgcct gcctggaaaa taacgtcacc aagatgacag agaccctcga  66960
aggtggcgac gtgtttaaca tatgttgtgc aggggactac ggtatcagtt ctaatctggc  67020
tatgaccata gtgaaggcac agggggtttc actaagtagg gtggccatat cgttcggcaa  67080
ccaccgcaat atcagagcca gtctagtgta tgtgggtgta tccagggcca tcgacgctcg  67140
```

ttacctggta atggacagta atccccttaa gctaatggac cgcggtgacg cccagtcccc 67200
atcctcaaag tacatcatca aagccctatg caaccccaag actactctga tctactgacc 67260
cgtacccctc tcttaggaca ctgatgtgtt tgggaataaa gcatgagact tgacacctat 67320
aatggtctgt attgacacca ttcttttatt tatcagtcca gccacggcca gttatatgca 67380
ccgtttccac acaggggtgg cgtggaggcc aggatgcggg ttgggtcgct gcacctggac 67440
cccgcggtag ttgtgcttcc tgatgaaatc gagtgggcgg aagtactggg agattgggtt 67500
gggaggtgac cctttgtgct cgacggagac acgatcacgc tcacggcgga cgagggctcc 67560
tcgtctgtgt cactccccga ggatataatt atcacggacg ccactgcttt gcggcttaag 67620
tttggttgtc tctggcagcg caccacatcc tcgctaccag aggaggcggt agactgcctt 67680
ttgcgcttct ggcccacgtc catgagcccg attctctgac tcaatacttc cccttggtct 67740
tctccgtcct cctcggacga gggtggctgg tgggaaaaat ggcgcgcgtc ggtaaacgcg 67800
gcctcattgt tcacgtccgg agagttggaa ctgtcatcgc tatcagagtc cgatgtcagg 67860
tcgacgatcg cggtgggtgc ggcgcgcagg gggcgccacg agggcccttc atcagggtcg 67920
ctgtatggtg aactttgtgt tccaggtaca ctatttctgg aagcaggtga aagtccgtat 67980
gccccggtcc cagtgtatgc cgccatcggt tccaggatag caaccccctc gtcgtctgaa 68040
ggtgagagcc cagcagggga aaatccgtca tcctgactaa cccatcccat ggacgcctcg 68100
gactccgccg tgtccgttga actgcgcacg cggcccgcta ccactgctac cggtttgggc 68160
gtatgggccc gtctggccag aggcctcggg cgcaagtgag ataaaggttg aaaaaagtct 68220
gcagggtacc cctctggctc gtcttcctcc tgaacatcgt cattttcttc ttcatcttca 68280
tcttcctcat cctcgtcata ttcagattcg ccgctcgact gatccgggga tatctgtaga 68340
tccagagggg ttgctggcgg cgatggcgtg tcctcggcga agacgtcgtc tggggcagac 68400
atatctatca ccgtgggtcc agcatagccg cgcggcctgc caaatcctgg aagtgatgaa 68460
agaggtggag gtgggaatat gaacttcacg gggggtcgtc tgcgaggcgc tccttcaatt 68520
ggaagcattc tctcttcatc gtgtgtgcta gacgaggtcc tcacaaacat cgccatggcc 68580
ttgtacgggg ttgaccgcta ggggcggaaa tttacaaagc acacgagtta ttgcctttac 68640
tgctccaaca ggccccagtc cacagtctca cgccggtggc gagtcaaata gtcgttggct 68700
aggttaaagt gattacagcc ctggaaccga ggccatcgcg agtgtcggcc accaagagag 68760
gccagcggag atggatgctg ggccgtaagc accaggtgtt tctgtgcgtt tatgagcgga 68820
gttctgtcaa tggccttgcg cccccacagg agaaaaacgc aatgttctaa ctttgaggat 68880
atgctactga tgatgaaact cgtgaaccaa tcccagccaa gtccctcgtg tgagccggcc 68940
ctccccttct ccaccgtcaa aactgtgttt agtagcaaca caccctggcg agcccagctg 69000
tcgaggcacc cgtgggaagg agtactgaaa ttggggacgg aagcctctag ctctctaaag 69060
atgcttctca aactgggtgg aacctgacat tgcggatcca cactaaacgc caggccagta 69120
gcttggccct tgtggtacgg gtcctggcct aagatcacca ctttaatatc ctctggatcg 69180
cagcagtggg accaccacat cagcttgtcc tgtgggggat acactgtggt ggttagccta 69240
agttcccgaa tctgtctgag cagcgagagc agtttctgtt tcagaaatga tgagaggctc 69300
agaaaggaaa tccacttagg tgccagtaac agatcccggt cgtccacccc ctgactgatg 69360
gatagggtgc ccctaaagac cgtctgttgc aaccatgcgt ccatgttgaa cttattttcc 69420
cttttgacct gcgtgcgctc tccggctgct gcttttagcc cgagtctgac ttccgctaac 69480
agaacctgtc cggttcatgg cctttcccac gcttattata attatgttta cgttgtgaat 69540
agagctatct gcagtggtcg cgttaaaacc tacagtatag gccgtcaaac ttcgttgtaa 69600
ataccacaac aacctcaggt tttcctgcga cgcccaggac cccaatcttc gaacgaccgc 69660
gactaaaaat gacctcagat taaacccatt cacgcatgtt tccacggtaa tgtcgcctgt 69720
tttgcttcgc agcttggcta tacagacccc gttgcagtga ttcggatcgg cgaagtggat 69780
agagtggacc gcaaagaaca acggcagggt agaggctgcc gatgcctgaa ttgcgcaaca 69840
tggtaaggcg acgtatgcgt gagatgtgac caatagggtg gtccacagga cggcaaatag 69900
cgcaaagatc cccatggggc aaatccgggt ttcacccttg tgttgcctgg ttcggtgctc 69960
cccagggagc cccctccgt aatatctgtt ttatatagtg agggttcacg catgcgcgag 70020
tcccgactaa tgaggacaat tactgaaatt gaccttttcg cgacacgggg gtgaggtcta 70080
tttcccacga catacttccg cggaaaaata cccacgctcc ttaatttccg tgggaagacg 70140
atgggggaaa tgtggcatta cctgacacgg tttcaatcat actcatcgtc ggagctgtca 70200
cacgtctggc tgagattttc taaaaagtca tccaatgaat catcggaatc atcagcacac 70260
tctagaacta ctccatatgc cggggtgcgc gggggtcccg agtagtgcac gtcgccatcg 70320
ggagacacag atgatgggtt tgaaatgtcc atacgggccg tgtgcacaag ggtcacgtcc 70380
ccatccccaa cacaaggacc tttagatacc ctctcccggc atgtgcgcgt atccgggcaa 70440
gcaagctggt gttctggatt ccaaacgtgc ccagcggtac ccaaaatcgc cagggcgtgt 70500
tttattattt ccacaggaac cggtttctct aattgcatca ccagggtatc caaaagccgg 70560
gcttccacgt tgatccggct taccgacagt tctttccagg gtttcctggt ggggcgcggc 70620
agctgactca aaaaggtcac tgcctctgcc catgggcggg tgggtgacag tccgccatac 70680
tcttccagga cactggccat gcatgactcc aaccgtctca cgtccgaggt aatgtgctct 70740
atgaagatgt ggtagagcca gcagacgttc aaacacgatg aaatcaagct aagctcccgc 70800
cggaactcca catccacaaa ggggtattgc tccggtgtct gtattaggtc tggaatagaa 70860
aactcagaaa aagacactga cccaccaagg agaacctggc gtcttgcaaa gttgatgagc 70920
cccgcagaaa gaatgtgtct cccgtgggac aaagagcttg ggggggcaga gatggcgcta 70980
cagtgggtga tttcttctac cacggtcata cattggtggc acccacaggc ctgttccagt 71040
atcagcataa atctatcttt gcagtcatcc cagatcaaag tcatgtcaga tgctgttgcc 71100
tggcattttg cccgcatgta catttcctgt cccacatatt ttaacatctg taatactgga 71160
agtagattca gtctggtgtt gagcccccc ggggaagcca gcgtatgctt caggaccacc 71220
agggacgcta agaaccccgg gtgtccgcgc tccggaaaca gacctctgag aatacgctcg 71280
gtcttgacga aacccgatgt ggtaccgaat gccacaatct gtgccctcca gctctcacaa 71340
ttttcatctc caatacccgg aattgggata cacacctcca tgttcagtca catgtacgct 71400
agggtctccc cacccaaccc ccataggacc cagctacagc ttatcctcca ctaaatacca 71460
ggcagctacc ggcgactcat taagccccgc ccagaaacca gtagctgggt ggcaatgaca 71520
cgtcccttt aaaaagtcaa ccttactccg caaggggtag tctgttgtga gaatactgtc 71580
caggcagcca caaaaatggc gcaagatgac aaggtaaaga tcgacctttt tattgtatac 71640
tgaacaatgc gtgtttacaa tggtgtaggt gggagcagag ttcgccaagc tctacgtccg 71700
aacagtcggg tgtcagggct cttattaagt gttcggtgta cttgaccaaa gccgcggaac 71760
ctaggttggg tctgtacagg tcgtaccagg caaaaaagga tcgggcggtg cttttcagga 71820
gagttaggga cgtgctgatt atgtggacaa gcttctgctc gtaaatgcac cgctggtaca 71880
tctgaacgac agctgtccaa aaaaaacaaa ggttcagctg cacgttaaaa tctgtatcct 71940

```
gaaagtcctc gtaaatgaca gtttctacca agaaaaactt ttttaccacg ctggccatcc  72000
actgaaagga gggagcacac gtcccgttgt gcgttgttag gatatcccta acttcggagc  72060
ggagacggcc ggacgctccc acaaaatggg agaggcacca ctctgtgcag tccgcggtct  72120
ggggttctga ttccaggggc gccgtgtggg ggtattggag agtcaaaact ctgggcagtc  72180
ccttaatgag ctctctctca aaacctatgc agccagcgtc cactagtggc agcatgccgt  72240
taataacacc ccttatcttg tcgttgccaa gtttgtacaa ctgctgcagg gaataagcca  72300
aattcgccct agccgcggga accaggtacg gctcgctttg tcggtgctgg accaatatct  72360
gaatggtctt tgcaaggtat agggtcttct caacgtttag agcgggtacg tggcagtctg  72420
gattgagggt ggcgacggac agggtatcta actcctgaag tatctgatcc caggacgggt  72480
aatgatacct aaacagatgg ttgaacaggt gatctttaag gggccttctc gatgtcattg  72540
taaaaactat gacacgccac tctctcctta gggtaagaag cttcggcggt cctgtgtgga  72600
aagcttcgtc ggcctctcgg acgaactgaa ggcccaactc taccagtgtg tgctccttat  72660
aaatgacgca tacgaaacaa tctacgatcc cagtgaccta aatagagtgg tggaagatgt  72720
gtgcattcgg attatgaaag aatgttccaa gcttggtgcg ctatgtggtc tgtttacaga  72780
cattaacatg tttaaccttt tctgcttttt tcgtgcctct cgaatgagga ccaaaggcgc  72840
ggccgggtac aacgtgccat gcgcagaggc atcccaaggc attattcgga tcctcacgga  72900
gaggatctta ttctgcacag aaaaggcatt tctgacagcc gcatgcagcg gggtgagcct  72960
gcctccagcc atatgtaagc tactacacga aatatacact gaaatgaagg ccaaatgcct  73020
gggggcctgg aggcgactcg tctgcaatcg gaggcccatt atgatattaa cctcttccct  73080
actgaagctc tacaacacgt acgataccgc cgggctgctc tctgagcagt ccagggccct  73140
ctgccttttg gttttccaac cggtctacct tccgaggatt atggcgccgc tggagatcat  73200
gaccaagggt cagctcgccc ctgaaaactt ttacagcatc accggttctg ctgagaaacg  73260
ccggccaatt accaccggca aggtcactgg actgtcctat ccaggaagcg gtctcatgcc  73320
agaatcttta attttgccaa tcctggagcc aggactgttg ccggcttcca tggtagacct  73380
cagcgatgtg ctggcaaaac ccgccgttat tctgagcgcc cctgccctga gccagtttgt  73440
cattagcaaa ccccatccca acatgccgca caccgtcagc atcatcccct ttaacccatc  73500
gggtacagac ccggcgttta ttagtacgtg gcaggccgcg tcacagaata tggtgtacaa  73560
cacatccacc gcgcccttaa aaccggccac cggtagttca cagacggtgt cagtcaaggc  73620
ggttgctcaa ggggccgtga ttactgcgac aacggtgccg caggcaatgc cagcgcgggg  73680
taccggaggg gagttgcctg taatgtcagc gtccactcct gcaagagatc aggtcgctgc  73740
atgttttgtc gcagagaaca ccggagattc tcccgacaac ccgagctctt tcctgacgtc  73800
atgtcaccct tgcgatccga acacggttat agtggcccag caatttcaac caccgcaatg  73860
cgttacgttg ttgcaggtta cctgtgcccc ctcttcgaca ccaccccccg attcaacagt  73920
ccgggccccg gtggtgcagt tgccaacagt agtccctctg ccggccagcg cgttcctccc  73980
ggcgctcgcc caaccagaag cctcgggcga agagcttccg ggcggtcatg acggagacca  74040
aggtgtgccg tgtagagatt caacggcggc ggctacggcg gcagaggcga caacacccaa  74100
acgaaagcag agaagcaaag agaggagctc aaagaagcgt aaggctttga ccgtgccaga  74160
agccgacacc acgccatcga ccacgacacc tggtacctct ttgggatcaa ttaccacccc  74220
ccaggatgtg cacgccacgg atgtcgccac gtctgaggga ccatcggagg cacaaccccc  74280
gctactgtcg ttacccccgc cactggacgt agatcagagt ctattcgccc tgttagacga  74340
```

agcgggccct gaaacatggg atgtcgggtc gcctctctcc cccactgacg acgcgctgtt 74400
gtccagtatt ctgcaaggac tgtaccagct ggacacgcca ccgcctctgc ggtcaccctc 74460
ccccgcttcc ttcggcccgg agtctccggc ggatataccg tcaccttctg gtggagagta 74520
tacgcaactg caaccggtca gggcgacctc ggcgacgccc gctaacgagg tacaggagtc 74580
cggcacactg taccagctgc accaatggcg taattacttc cgagactgaa gtgttcgcaa 74640
gggcgtctgt gcctgcgtta acttcccagg cagtttattt ttaacagttt ggtgcaaagt 74700
ggagttaacc tacagattct acttaaaata gctcattttc tcacgaatct ggttgattgt 74760
gactatttgt gaaacaataa tgattaaagg gggtggtatt tcctccgttg tcgactataa 74820
cctggcgtgt aaacgtgtaa ccctgccaaa tgcccagaat gaaggacata cctactaaga 74880
gttccccggg aacggacaat tctgagaaag atgaagctgt cattgaggaa gatctaagcc 74940
tcaacgggca accatttttt acggacaata ctgacggtgg ggaaaacgaa gtctcttgga 75000
caagctcgct gttgtcaacc tacgtaggtt gccagccccc ggccataccg gtctgtgaaa 75060
cggtcattga ccttacagcg ccttcccaaa gtggcgcgcc cggtgacgaa catctgccat 75120
gctcactgaa tgcagaaact aaattccaca tccccgatcc ttcctggacg ctctctcaca 75180
caccaccaag aggaccacac atttcgcaac agcttccaac tcgcagatcc aagaggcgac 75240
tacatagaaa gtttgaagag gaacgcttat gcactaaggc caaacagggc gcaggtcgcc 75300
ccgtgcctgc gtctgtagtt aaggtaggga acatcacccc ccattatggg gaagaactga 75360
caaggggtga cgccgtccca gccgccccta taacaccccc ctccccgcgc gttcaacgcc 75420
cagcacagcc cacacatgtc ctgttttctc ctgtttttgt ctctttaaag gccgaagtat 75480
gtgatcagtc acattctccc acgcgaaagc aaggcagata cggccgcgtg tcatcgaaag 75540
catacacaag acagctgcag caggtataga cgggaaacag gtgtctatct tggccggctg 75600
gttactcaaa tgggaacaat ggcgccacct tgctgtcttt gtaggcatta gaagaaaagg 75660
atgcacaact atgtttccta gcggcgagat tggaggcaca taaggaacag attattttcc 75720
ttcgcgacat gctgatgcga atgtgccagc agccagcgtc gccaacggac gcgccactcc 75780
caccatgttg aagcttggtt gtgccgtcgt ccgggagaac catgccagac tttgtgtggt 75840
aagaaggaat tgttatccgg cagcaatatt aaagggaccc aagttaatcc cttaatcctc 75900
tgggattaat aaccatgagt tccacacaga ttcgcacaga aatccctgtg gcgctcctaa 75960
tcctatgcct ttgtctggtg gcgtgccatg ccaattgtcc cacgtatcgt tcgcatttgg 76020
gattctggca agagggttgg agtggacagg tttatcagga ctggctaggc aggatgaact 76080
gttcctacga gaatatgacg gccctagagg ccgtctccct aaacgggacc agactagcag 76140
ctggatctcc gtcgagtgag tatccaaatg tctccgtatc tgttgaagat acgtctgcct 76200
ctgggtctgg agaagatgca atagatgaat cggggtcggg ggaggaagag cgtcccgtga 76260
cctcccacgt gacttttatg acacaaagcg tccaggccac cacagaactg accgatgcct 76320
taatatcagc cttttcaggt gtattacacg tttcaactgt aatccctcgc aattgggtaa 76380
accgtcggtg tgtagggata aagcgtaacc ttacgttctg tctcatctac aggatcatat 76440
tcatctgggg aaccatccag gaccacgcga attcgcgtat caccggtcgc agaaaacggc 76500
agaaatagtg gtgctagtaa ccgtgtgcca ttttctgcca ccactacaac gactagagga 76560
agagacgcgc actacaatgc agaaatacgg acccatcttt acatactatg ggctgtgggt 76620
ttattgctgg gacttgtcct tatactttac ctgtgcgttc cacgatgccg gcgtaagaaa 76680
ccctacatag tgtaacacaa aaccataaaa gtaaataaac gtgtttattg ttcacatgat 76740
aaagagtggt actctttact ggtttggggg ttgggttgtg gcgtggtggc tggtccgcgg 76800
ttcagtcatc aacccccgcc cgtgttgtcg aggctcctct tcgtcgcctg ttattggcac 76860
caggaggcgg tttagcggtg cccccgtctg acatgcagac gtcgattcta agcgaaagtc 76920
ccttcagggc atcgtccact tgcttttgtg ttacaacctt gctgaatatt gtcctgaccc 76980
tggcttcgat tttcttagcg gccgccgcac tcagtgcacc cacagtagcg gtaagctgcg 77040
cttccttctc ggtggccgtc agaggccgat ctctcggatc ggcagtggat cccagtgctt 77100
tccgaagctc ccgattctcc acagtcaatt ggcttatctt tgcggttagg tcttccatcg 77160
taaggtcctt tttgggtctg cccctgggcg cggccatgtc aggtacgcgt agatgtacgt 77220
gttggtgatg ctcacaacaa aagcccaaat ccctccttta tacccagctt taaatacttt 77280
attgaaaaac catagctttc gtcagcgctt gtgcgagtaa tcacatgcca gtctatgcat 77340
ggaccacctc gtccacaaac ttgaaaaaac aaagatatac cagatagaaa aatgtggcca 77400
cgacgactag taacgcgtta atcaaggccc agacgctaga aaagctagaa agggaggggc 77460
taaaactatc cgcggaacaa gcaacgtcat agaatcctgg ggtagtgact gatgtgggac 77520
cgggcgaagg cctggcgctg agcccagccg tactgggact agaacgctct gtagatgatg 77580
cgacacctgt cgagttggcc gtaacccagc agtgacctag tatcgaggcc acaaataaag 77640
ccagggccac cgtggacgct gtcattatga acaaccgccg aggctccaag ccgtctatcc 77700
aacgttccgc gttcgcctct tatatacact ctgcaatgca gtccgactct gcccctctac 77760
ccagggtgga atatgtgttc gaaacaagca aatttagaat gacgtcgaga gcaaatgaag 77820
ccagactcag actgacaaat gagtgtccga tactggtgag accccacgag ccgttcatca 77880
tgcccaccgg aatacacttc acgcgaaccc ctagctgcgc tttcatcctg accggagaga 77940
ccgacaagga tgtattttgc cacacgggcc taatcgacgg aggctaccgc ggggagatac 78000
aggttatttt actcaacaag aggaagtacc ctgtgacgct gtatcgcggg gagctcaaca 78060
tctgcctgtc tgctttcaat tacgtgctac ctccgttgag ggacgtatca ttcttaaccc 78120
cccctatgta tgcaaacgac gccggatttg acgtgatggt gatgcactct atggttatcc 78180
ctcctactac tgaccaaccg ttcatgatat atctaggagt ggagaccccca ggcccccctg 78240 aaccccacgt ggctctagca ttggggcgat ccggtctagc atctaggggt atagttatag 78300
acgttagtga gtggggaccg cgaggattgc agctgaagtt ttataactac tcggggcagc 78360
cgtggctggc gcagcccggt agccgcatat gccagattgt gtttgtggaa cgcagacaca 78420
tcctcaaggg cttcaaaaag tgcttgcgcc ataggaagct agctcctggc gtccgtttcc 78480
gggaggctcg agtgcatttt cgcgaggata caaatagcgt ccgaaaacat acccacgaag 78540
acaaccccgt ccacgaaccc aacgtagcca ccgcttccgc tgacattcgt ggaaccaagg 78600
ggctggggtc gtctgggttt tagagccgcc gccaaatgcg gccagtttat tagggcgatt 78660
cgatcccgca acccacagca tcccccaaat aaaaaaacga gtgtacacag ccaatgtttt 78720
tattattgtt cgattcatta ctggtaccag agaataaagc caacctatgt cgaacctatc 78780
gcgctttctg tcgtctcttc cagggttgac gaaggccggg gagggattga cgaatgcatc 78840
gcggaaacgg acgggtcttc ggtgggtggc ttgggtaaag ttgcctccgg ctggcgcgta 78900
acggcaggcg tgagaggcaa tacagaagtg ggttccgaca aggagtggct gatctcagag 78960
gcccatatta ccgagtcgtc tgacgccata gcagtcgcca gtttttccat ctccatgagc 79020
gaaacgcatt ccccggccct tttgtttaag agggactgga gcgcactgtc gtccacggta 79080
atctcgccga ccgccaaggc cagcattgtg ttccacacga cgttctgaat agactgcagt 79140

```
tttttcacct gggttttcac ggtctcctgg cagcccgccg gaattttagc cacgtcaaaa  79200
cgcttcaggt agtctgtgat cttgtttgac tgtacagcca gaaggtaggt ctggtgcagc  79260
gccgtcgtgc caaggttcga ctggacaacg tcacccagac acactccggg ggggaggccc  79320
aaatctatct cttgccgcca gcgctctgga cagccttcca gagggtcacc gaggcgcttg  79380
taagcgtggt tgccgcgtcc aaaaaggttt ataccgcaac acgtccaggt gtaccatgga  79440
gacgacatac cgccgcgagg cgctgacagt aagggttatt ttttgtacga gtggcgacag  79500
cgccgagacg atcgccgacg tccttacggg ggccccaacg tcagcgtcct tcttttctgt  79560
actccacgac ctttttttatt cccagatact cgcccccagg gtaaccctaa aattgtgcct  79620
ccccgcacgg cgtcctggca acggcacaag gtgttcgccc gtgttggtcc tacgtactga  79680
cgcatcagtg gcctcggggt tccttggcgg ccggccactg gaggcgtccg acattaaata  79740
tatgctgctc agcgaccaga ccgcggggtt gttcaagccg ctgttggaga taatcggtgg  79800
cgcgcgcgca ccaccaaatc aggacgcgtg cactttccag agccaggtgg cctggctcag  79860
aacgaaattt gttaccgcat tgagaaaact ttacaagatg actccctcac cctactggat  79920
gctgtctgca tttggcgctc aggaagccca gttcgtcctg accagctcat tctatttttt  79980
tgaacacact gtggtctgta ccacagagac agtttctcac ctgtctagac tgttttcgcc  80040
tcaacaggga cagacgctgg tttccgttac cagccacgag gagctggggc agctatacgg  80100
cacttcccct ttcaggcggc gcgtccccgc gttcgtcgct tatgtaaaag agaaattagc  80160
gagagacagt ctggagacgg aggccatcga ccgcaccata gaccagatca ggggcaaact  80220
catgctgtct aaccaggacc tggtccattt catatatatc tccttttatc agtgcctcaa  80280
caaacgggcg ttcctgcgct actctagaca gacgtcctct tcaagtgctc taagggagct  80340
gggggaagac cctcaattgt gtggcgccct acacggggag tttcgtgacc acgtccagtc  80400
ctactaccac aaaaaaacct acctatccac ttacatagac attcggtacg tgggtggcgt  80460
attaccagac ggctattttg gcgggagtct tgtaggcgag cggtgcgttt attggtgcgg  80520
gcagtcaaag gacacggcca gcctgttggc caccattagc caacaggtgc cgcacctgag  80580
gttgcaaaac gagttcgctg gcatgctaga cgtggccgca ctgcgaggtt ccgatgacgg  80640
tcagtttaaa gagggccttt tctcccacag tcaagcccta cccctgtaca ggtgcgagtt  80700
tctgggcaag cagtttttca caatgcttca ggaagacggc ctagagcgat actgggagca  80760
aagtgtgata tttccaggcg accaggactg ggatatgtta tctgacaaag acctcaccta  80820
ccgaattttt taccatgacc tcagcctatc gctgccaaca ctgaaggaac agctccttgt  80880
ttcaagacac gaatacttca accctcgctt gccagtgtat agatgggtat tagactttga  80940
cctgcccgtc tgccgcgaca ttgacaggac attcgaggag gtgcactctc tctgttgttc  81000
cctgcgtgag gccatactcg acatcattca actccttgga ccagtggatc ctcgaacaca  81060
cccagtatat tttttcaaat cagcctgtcc accggacgag tggcgcggcg aagacgtcgc  81120
cagcaccagc ttctgtcggt gtcatgacaa actgggtatg cgtattatcg tcccgttccc  81180
agaaggagta tgcgtcgttg ggtcggagcc catggtggca ctcactggca ttctaaacag  81240
gacgataaag cttgatccgg agctggtcca cagattcccg tcaatacaaa aaaagggggg  81300
ccctttcgac tgtggcatat acggccgagg acgaagcgtc cggcttcccc actgttacaa  81360
ggtgggctta gtgggggaac tctgccgcct actgaagata ctagtctgtc accccgcccc  81420
caacggcaag gcgcagtacg tgcggcgcgc ctttacgctt cgcgaactgc tccatcactc  81480
cccgggccac agcgccggtc atgtcggccg aatcatctat agcatcatgg atcgcaatga  81540
```

gaatttttta gaaaacaaga ccattagcta tctgccggcc aaaatacctc acatctttca 81600
gcggatagag accctatccg gtcgttcaat agaggactgg ctacactcgg ccgtttggga 81660
taaagcatac gacactatat gtaaattttt cccagatgaa aaagcacaac agttttctca 81720
cgttgcattt acgcaacaag gggaaaacat catccagtta agaccccgtc agggaagaca 81780
cttcctctgc atcaaccata atcataaaaa caagtcaaaa acagtccgtg tattccttac 81840
ccttcattcc attagggtga gcgaagtcac ggtaacactt atgagtcagt gttttgccag 81900
caagtgtaac aataatgttc ccacggccca tttttcgttt gtggtaccag tgggactggc 81960
cagttaatcc cactatataa cctggctgcc aggttcccaa aatagcccgc ggcatacggc 82020
tcacttcccc ccacattccc cccgtgcaca atataagaac caaaggacat ggtacaagca 82080
atgatagaca tggacattat gaagggcatc ctagagggta agtcctcgtc tacaacagac 82140
ttttcccatt tctaacgtat cgtgctatct tcgtcgcccg gcggaccatc cccccacccc 82200
tcatttatcg cgtttgatat tacagactct gtgtcctcct ctgagtttga cgaatcgagg 82260
gacgacgaga cggacgcacc gacactggaa gacgagcaat tgtccgaacc cgccgagcct 82320
ccggcagacg agcgcatccg tggtacccag tcggcccagg gaatcccacc ccccctgggc 82380
cgcatcccaa aaaaatctca aggtcgttct caactgcgca gtgagatcca gttttgctcc 82440
ccactgtctc gacccaggtc cccctcacca gtaaacaggt acggtaaaaa aatcaagttt 82500
ggaaccgccg gtcaaaacac acgtcctccc cctgaaaagc gtcctcggcg cagaccacgc 82560
gaccgcctac aatacggcag aacaacacgg ggcggacagt gtcgcgctgc accgaagcga 82620
gcgacccgcc gtccgcaggt caattgccag cggcaggatg acgacgtcag acagggtgtg 82680
tctgacgccg taaagaaact cagactccct gcgagcatga taattgacgg tgagagcccc 82740
cgcttcgacg actcgatcat cccccgccac catggcgcat gtttcaatgt cttcattccc 82800
gccccaccat cccacgtccc ggaggtgttt acggacaggg atatcaccgc tctcataaga 82860
gcagggggca aagacgacga actcataaac aaaaaaatca gcgcaaaaaa gattgaccac 82920
ctccacagac agatgctgtc ttttgtgacc agccgccata atcaagcgta ctgggtgagt 82980
tgccgtcgag aaaccgcagc cgccggaggc ctgcaaacgc ttggggcttt cgtggaggaa 83040
caaatgacgt gggcccagac ggttgtgcgc cacgggggt ggtttgatga gaaggacata 83100
gatataattt tggacaccgc aatatttgtc tgcaatgcgt ttgttaccag atttagatta 83160
cttcatcttt cctgcgtttt tgacaagcag agcgagctag cactgatcaa acaggtggca 83220
tatttggtag cgatgggaaa ccgcttagta gaggcatgta accttcttgg cgaggtcaag 83280
cttaacttca ggggagggct gctcttggcc tttgtcctaa ctatcccagg catgcagagt 83340
cgcagaagta tttctgcgcg cggacaggag ctgtttagaa cacttctgga atactacagg 83400
ccaggggatg tgatggggct actaaacgtg atagtaatgg aacatcacag cttgtgcaga 83460
aacagtgaat gtgcagcggc aacccgggcc gcaatggggt cggccaaatt taacaagggt 83520
ttattctttt atccactttc ttaaggattg ccaaacccca tggcagagtg tctcccgtat 83580
tccatgtaac tcacgtagcc tttctctaat aaacaagcta cctgcaaact atacacaaat 83640
gaaatgagtc aggcgtggtc tcttctctac cgtgaatcgc accttaaaca caacaccaga 83700
ccgccaccag gtggcaccca acatccatta tggaaaaacc ccgcgccacc ttccgccacg 83760
tggagccaac aaacaagaca cacccgccaa tgttttggtc tctttattga tatgatatac 83820
tccctcccat aacaatacgg tgtaggcatt ttgtattatt tattgcatgg catcccataa 83880
cggcttcggc attatttcga gtacgacgca ggcgtctgag aaattactgc acctcgccgc 83940
aaagtctcgc ggggacgggg cgtggggctc taacttgcca accgccaccg gtttccccag 84000
ccacagcttc accaaaggac acgtcacgtg agagggtgct ggtaacggtg aatttgccaa 84060
ccccaccaga aatgtattcg ggttaaatat cctcgtcggt tttccctggg gcagcaagag 84120
ggggccggag tcaggcggaa cggtatttcc aataaagtgc acgggcccgt tatgataaca 84180
tacgcaaaat atgccattac aagagctagt cagcagaatg ccttttgcac atgcgtccag 84240
cgtatcgcat agctcccgct tggctatctc gcaggccagg tttggcacat tgggtagcca 84300
tacctggccc ggagacccca ctgcacagta atgaactgcg gggtccctac gcaaggccga 84360
tgagattcga cagcccgact ggcttgtcgt cagtaactca tgaacctgtt cgccattata 84420
atacatcctg ataaacaacc gaccccagtc aatgacggcc tcctgaccct ctgccgtcgt 84480
acaagatggc acgggcgtta caatctcgcc tggcaagcac tgccccgggg aaaaaaatcc 84540
ctcttgcaag agacgtgcca tattgttaaa atcgtggacg gctccggcca cgactccaca 84600
ttccacgcat tgttcttcct ccggtttacg tactctaaag accagaaaat ggtgtccatc 84660
ctgagaaatg cctttgccaa tctcttgtaa accccgcgtc ctgcgtagcg cggcaagcat 84720
tcgcctgcgc cccctggtgc ctttaaacga ggcgtccacg ggcatgttac ccctttcgcg 84780
gatatacaca acacccaatt ccccgtctct gcgccattca aaacaggggt ccgcgagggg 84840
cgtaactggt atacggaagc gggtgcgctc ttcgtcttcc cactctactc cgggaaattt 84900
tccactgttg acttgacata ctatccaatc cttgattgac gctttcccct cactggcacc 84960
ggtagatatt cttagttgtc gtgtccggct ccactccgtt atcgcagcca ccacagcctg 85020
ccgtgtaata tcgcctgcgg ctgcagaacc cccggtcccg gagggtcctt ctcccggtga 85080
ctccgacctg gatggttcat cgcaaggagc cccggagcca gatgttcccg gtgacccttg 85140
tgacaaacaa ggttttttgg gtatcgcccc aggcgcccca aaagggttcg gtctttggcc 85200
tgggtccatt gtcccgcaac cagactagct cgcgccgcaa tgtccagtgg taagcacagc 85260
tatgccgggg agccaccggc catcagatat agagaggcga caggctctct atatatcacg 85320
gctaggtggc tgacatatta gtgggcctag ccgcagaatt gcctgggtag tcaaaaacca 85380
gcgtttctca aattaaccga aactacattt ttctatttta agtacgggat acaaagcagg 85440
gtctgaggca atctgccgcc ctccaccccc acccaccata cccaaaaaag atatgtcaga 85500
aagagcactc tacctattaa ctcgtggaga aacatcatac aaaatctgta cattattttt 85560
aatactttaa tttgtgcagg tttcttcacc ccacacctgc tttttgtctg gtacaaaaaa 85620
ccactgcagg gtcccgccta tagccaactc ctaagcgggt tttttgctaa agcacttttt 85680
tagactgtcc cagaaaccac atagcttcct tttcactcat ttgaaaaaca gccccgccca 85740
actgcctgga gaattttcca ccccctctac catttcgcgc ctttaccgct ggtgcgaaat 85800
ctagccatcc tatcaccgcg gatccgctgg accaatatac cacgcccact tttcgtaatc 85860
agcaaccctc tacgcctaca cccctatgac tgaatataac ccccaacaag gctatgaaat 85920
catgaatggt aactgtctgg acaccaatct tccgcggggt ggcggcagtg cgacgcaagt 85980
atccacaata aatggtgcaa taattggcga aatgtcgtgt ctggtttatt tggactacaa 86040
gattacatcc ggttttataa ttcacatata tgatcaatgt agactatccc aaatggagcc 86100
tataaaaatt ttaacagtca agggtacatt ttggaaattt tctgtagatg ccggggatgc 86160
gccgaaaaat accgtcccgc acgtcactgg gttgacgctc agcggtgtct gtgggattgc 86220
ggctgtggtt gccaggtatc gcgcggtgtt gaacagctgc tgcggaactc tggggctaaa 86280
gcttcggagg atgcgttcat agcgggaatt tggattacca aaccaccagc cttccacttg 86340
agtggcgttt ctggagtata ttccagacat cgagcaaaat attgggaatc cgtggccaag 86400
gccttcaaaa actcggttca aaatctccat ttgctcgggt gaggggactg taagacgcgg 86460
tatgcgaagc agttctggta cgaaactctg acataggtgc cccaacgtat ccccaacagg 86520
ccagctacat aacattgcct cgcccgcgtc accttcgcgt ctcagagttc cacgaaggtt 86580
cccatacaca aagatttcca caacaaaaga cacccgctga ctatcagggg gatcaaaaaa 86640
catctttgaa ggtggctttt cgggaccgga gtggctaacg ggcgtacgcc gcccgtgcgg 86700
ggacctggac ctcgggcgcc gcctatccgt ggcctgtctg gttgaggagc tcggttcctc 86760
ctgcagctca gacaaaatgt tacccaaccc ttcttcccac gtacatatat cctctccttg 86820
aaggttcgag agcgtaagag ggagacccaa aggcggcggc actaaagatt gttctggtcc 86880
ataacccccc actgcatatc tatctccagc atatgtacta acaagtggaa ctctgggcct 86940
ttcgccacta cccgggcaca cacactcccg ccgctccagc tctgtcggta aatgcgaaac 87000
ctcggggttc acagcgggct ccggtgcaga ataaagcacc gtaggttgga aaacgcgcgg 87060
cccactgaca ggtaggggcg tggatgctac agtggtagat ggggtatcgg aatccccagt 87120
gaggtcaata atctccactt cgagggcacc agaactagtt gtcacgcgtc tgtatccagt 87180
cgccatgttg tccccctggc agacgtacgg tattccagac gaggatggct cctgtcgctc 87240
tgccacctct ggggtgggtg gtgcgccggc ggagggcgtg gccgacgcgc caccctgcgt 87300
gtgggaaaga ccctggtttg gagcgcctcc actagaccac ggaatccaaa gcggtgtgcg 87360
aacttccggc accacggcgt gaccaactgg tgggtgccaa acaggcgcgc gtatgggtcg 87420
cgtagctggc ggttctgcca atggactcca attgtaacat gatggtttcg catacccggg 87480
cgcgggggcg ctgggcggtt gaggttcgaa gggatacacc cgctcactcg cagcaccctg 87540
aggagcccgg ccttctgtag atgccccgca agcgccttcg gcaccggttt cccggcgggg 87600
aagccacgcg cgagcacatt ggccgctttg ggggagcaat ccctgtggcg ccagaggtgc 87660
accctggctg aactcaccga caaatgttcc cgcttgggcg tgcggcggaa tccaactggg 87720
ggcagcagga ttcagctggc tgctaggaat ccccgtatat gtccaacggg gggaaagggg 87780
atcaaattgg cccgtggttg gcggatgcac tttctccggg agaccagacg cgccctgagg 87840
ccaccatccc gtgacaggaa gatctcccca tggaaaacac gcaggtatcc acggggacgt 87900
agatggcagc ctagacccat cgcgcatggg aggggctagt tgccccgtat cccccggcgt 87960
ctgtgcgacg ccggagaccc ctgacacagt accggcaagc cgtgtttcgt gctgcggctt 88020
gggcggcgcc gtgcccggta ggcctgcacc agatgagtga gggtctgaag ggccggtcag 88080
cgttgatgga gcaggcggat ctccgggaac ccgccacgta aaggacgagg cctgcgtaac 88140
ttgtcgcgtc ccagaggacc ccatacctga ggtagatgcg ccctcattca ctggtatcca 88200
cacggagcag gcagccttct gttcagtcgt tatatcgcca acattgtaat agcggttcga 88260
tttccgaggg cgacccctca gccccgatgg cgccttaggg ggagcaggtg ctgcagcccc 88320
tgcctcctcg tagctttgtt ctctaagtaa aaggcacgag agttaacgtg gttagggtac 88380
ctaaagtatt tcccgccgac accaacgcat caaacctcac accccccttcc ccgagttaca 88440
tacctagtgt cactgcgtcg cgtagccgtg gtttgcattg ggggggacaa cagacactga 88500
ataaatcgct gcagtttttc aggaccatac gcggccccat agcaatacgt acagttttta 88560
aacggcgttc gcaccaactg ccatactacg tagctaccac caaatgtgtc gctgtaccgt 88620
aaatcgttcc gcacgacggc cctcctggtt ccacgcaaca gtctcccaaa acgtccatac 88680
accgtctgtc ccacgacagg cgatggtccg tagactctat cacactcctc atcaaatgca 88740

-continued

```
tggtacaccg aataccagcc aggcgggata tcgctgccgg caggcagggg cgcgggggct  88800
gcaaaaagaa ggttgttcct atcaaaccag gaaaaatagg gaaacttatt gttttcaagg  88860
gcatcaataa tccataacgt ggcccattct gagccaccgg ctttaggcat ggtccgacac  88920
agaaaccgat cggcgttcgt ctttgaggca cagtcccgac tgagccttat agtgcccccc  88980
ttcttgctat gaaaaaaacc cacgaccgtt acgcaaattt gaggagctac tcacctaaaa  89040
gtagctcctt tgacaaatgt cctggtttta taccaattgt tcacaatgac atattgtgct  89100
ggcggaaaca ggtgtcccga tgtatcctcg gcaagtaagc accattacca tgtgccatca  89160
tattgtgtgg cacaaaaaaa gcaacttttc acgcacgcag cataagaccc gagccagtcg  89220
cgccctccat cgcgcctgcg aattttccca ccacccaata ttgtggcaga tctttcttat  89280
gtatatgtgg ttacaaacac cacgcccctt aagctgtcct ctctcccaag gggactagat  89340
tataacagtg acatacgaaa ccgagacgct ctcaaatgct ttctatttta tttatcgatt  89400
ccgggttaac ataatcacag gtagctataa aatccccatc ctcttgacct ggtaaccctg  89460
gcttgaggtt tcctctgtta tcaaacaaac ctgaccacaa ctgtacagag aaaagtgggt  89520
gaaatgtagt gtttatttta tcctcacact ttcacttaac cacagcccgt caaaccacag  89580
ggaccctgtt ggctgactat tagtcatcac atgtaactga acgcaatctg agcttgatga  89640
cgagggggac catatcgaac tgttctgccg acgttgggtc acctccgatg aacacagttg  89700
ttttttttaat gtgctcatgt ccctgtatgc gatattgtgc cacattaaaa acatccagaa  89760
cagccctaga tgacagtccg cagatcacac caaacttctt tggaggatta tttccatgat  89820
ataatacggt agacttgcac aaattcttaa cataaatgcc agatcggaga gaaactatca  89880
caagacccga agcaaacgag cgcagcacgg ccgccagcag gttaacgtct cctggccctg  89940
tgttattgtc gtcaggtttg ggcaacaaaa ctcttaaccc tttgcgcgaa tgcaagcaag  90000
agtggctaat gtctgccagt gggttctggg aacatagaat aaacaccttt cgttccactt  90060
ccaaagacat tgcagggcgg ccaaaataaa acacttccac accaagccta tcggttatca  90120
ttactggcgg ccgtgccact ctataatatg cggatctaag cttcctgtgg cgaatgcgcc  90180
tcgtggtagg cctctcgtgt ctccgtggcc catcatccca taaaaattcg ccaacaactg  90240
gccggcgtct ggacgccggc ggcagtccag caccatcatc gacttcttcg tcacttatct  90300
ccaacacata ttcccctgct acattctggg cctcgagtgc cccagctaag tacacatcct  90360
ctacacccgc cccgacagcc gaggcggcga ttgagccctc tgttaccacg ccgcttgcat  90420
ccgtgtcgcc tccgggctgt gatgttgcga taacatcctc tgggatgcca agcagatcaa  90480
agaggtcttc atcgcacatc gccctcatta gcatgtccat ctcctgtccc acgtggtaca  90540
tcaatgcaca tgcagattct ttatcaagca gtgtgaggtc atcttcaacg ttgtctgtgt  90600
gcaccgttgt ttcatcggcc ggggggggct gcgagtcgct atgacgcgtc gagggtcctt  90660
cgtctccaga gccaggagag tcggcattgg catcatcaac tggctgaacc ccagacgcac  90720
tatggcgcgt cgatggtccc tcgtctccag agtcctcaga ttccgcgccc gtctgcgtga  90780
ccggcacatc gcaaaaggct gggtgatcct cctcactgga atccgagttt tcacccacaa  90840
atggcctaca gaaaaaaaaa caaatatgtc aaccggacta gggtggccaa accatttgcc  90900
ccacccctcc ccactctttc cccaggggac acatcttacc ttggtcttct ccgatgcttc  90960
tcgagccgta cactgtgttg atacaaaatt tcccatagtg atgacccact gtgtaggtga  91020
gtcctggcat gaacgcacca ccagcattcc tttacctcgg cacacaggag gcgccacctt  91080
ctacaattaa ttccctgtac gacctcgtac tcttcacctg gcaagcgtct aaggcgccgc  91140
```

gacgtggtac atattttccc aaaagccgta atcggcgagc ccagtaaatc tctgggatgc 91200
aggcccttcg ataggcattc cctcttaaaa tcaatgaaaa actgtaggct atccagagga 91260
attacgtcat tacgggcagc cggagcaaga aatgttccag tagatctatc tagccacttg 91320
accaaaggat atttatcaga gtccaaagca cctacaataa actcagaaat ccaggtaagc 91380
ctgcgtcccg ccatgttgac ctgtcagaat ggtctgcctc cgagcattac cccacctcaa 91440
cagaagtaat ctactacgca aaccacaaca tgcttcctgc agctttaacc ttcagtcacg 91500
ggtcaaaaag cattgcctgt attagacaca tgtgtttctc actatgaatc gtgctctcca 91560
gcgctggcaa gaacatctgg ggtgatgctg ccccggacca gctttgaaac agggtattgc 91620
atgcataatg aagcccacat gtttgtctta ctttactaac ctcattacct tgcattgcag 91680
gggacacccc cttgccttgg cagctgagtg aatcccaacc gcctaggaaa aaaataacca 91740
ctcagacttt attttgcagc cacacggtgg cgctaacctt taatgatgtc ccactcagtg 91800
agtttggcca ctcccaagcc cacatgggcc tactataaca ggaaacatag aagttgcgga 91860
tagagcctgg tttctaacgg caatgatatt tatagtgcaa aacggagggc ggtaagacaa 91920
agggaggtac ccggacagag tgacaagaag acttgtcaaa attttagtct ctgtggtaaa 91980
atggggcaag gtaaatgtgc aaaatgactg gatagtgatc cgagtcatat tcaggcgacg 92040
gccggcggcc cagaaacagg gacgcgtacc gggacccttc aggttctcga ttatgtcgct 92100
ccacgtcaaa agcttgttgg atctcgtggc ggtgggacag gggcctacat ttgcctattc 92160
ttcttcgcga tgcatttcca acaaagtatg ctgggtattc caataatccc ttcagaaaaa 92220
tgcccatgtt tgtaccgatg gccacaactc ccatggaaaa cctgtccagc gtctgttcca 92280
aagttcggtt tgcgtccaca ctacagtggg ccgttctggg aagtaagcat ttatacgggg 92340
gtaccgtctg acatatgtgt tcaggggagg cctctgggac ttgggagcaa ataacgatgc 92400
cccccgttaa atcaaagtgg gtcttcacct tttctccgaa ataatacact tccaccacta 92460
ggggcacaag cttgtcaccc actttgtaaa tagcctgttt cttactcagg tatgctgcca 92520
cggattgggt ggcggttaag accttgggcc tcatgtcgct tccataccag taaaatgtct 92580
ggtcagcttt ctcttggtcc tcgacgtccc ggtcatcacg acacaacggt ggaatacaat 92640
caataaaatc atccacattg tcggaagctt ggaaagatga acccatgaca gaggccccag 92700
gtgccgaact ctcaagggga tgcgtggcgg gaagtactga gacactctcc gtggacccct 92760
cctcacctcc ctccgactgc atcgggccct gagggctcgc agtttcacac agaagttcac 92820
tcaggtcgcc taagtcagga agctcctggc ctgaacccat gacagaggcc ccaggtgccg 92880
aactctcaag gggatgcgtg gcgggaagta ctgagacact ctccgtggac ccctcctcac 92940
ctccctccga ctgcatcggg ccctgagggc tcgcagtttc acacagaagt tcacccaggt 93000
cgcctaagtc aggaagctcc tggccaacat ctgacaagag atctaacaaa cacccctcaa 93060
tgtgatccac catcggtagg caatcatcca gcccactgac atgactgggg acggggcctt 93120
ctggggaaaa tggggtttgc gactgtccag caggcggcgc taataagcct tgtgtctcat 93180
gtggaaaaat aacaggagaa ggtaaacccc ccgttggcaa acatagatcc gtcggggtgt 93240
gcacgtgtaa tgggccctgc acctggctcg tggagggacg cggggaatcc ggagctaata 93300
agctcgatga ctgaccagat gacccaaacc ccgacggttc tggctcttca aaaaacaaac 93360
tgtgcatatc cctccctaca aaaccctgag cccccaccca aagttcgttt tcgctgtcac 93420
tcgattccgt atcttcgctc tgtgaccgtg atgaaacttc agctgcggag gatgttgtgg 93480
gcgtggcgac tgccgccgcc tgtttcctgg cggcctccct aaacaaaagt taattacaca 93540
aaggtaagtc tgagtgacat ctccaatttc ccgtgatgcc cgctgcacgt acatcccgcc 93600
gcccacacaa cccaccgccc agtacatcaa ccatcctacc tctgggcttt ttttctaagg 93660
ctccttctaa gtgccttttc tctgtgtttg tcatcatggg gatagatccc aaacaatgct 93720
tttagcatgt ttttcatggc tggttcctgc gtcaagtaca caagacatcc ttcacatccc 93780
ttgtatggcc taggtgtcat aatccagcgg ttgagtttca tttttccctt atagatggta 93840
aagggcctct cctgtctggc tcgattggcg gtccttaata gccgtccaaa gcagcccagg 93900
ccagtctcag tctccgggat ttctggcagc ccgtgcctac gtcgctcctc caaaaatgcc 93960
tcatagaagt catcgaagcc ttctggcatt ctctcccgcc ggtttcgacc cggcacggtg 94020
aatattctct tttgttcatc caaccaccct accccccaga agcgtccact gtctaaagca 94080
tctataataa agtccgtgag ccattccgac tccgtgtagc gaggcatctt tttaggcaaa 94140
agccacgaca caaaacacct tttccgtggg cgactttctc gccacaacta gctggacccc 94200
aaccccactg gcacgtagac tctgtgccat ctaacaacaa aactcaatat atgcagctca 94260
acaccgcccc ccccagccgg ttgtcgggct gcggaaactt gtggttagaa ctcactacgg 94320
aaaagggaac caatgcagtt gaactactgg cacacaccca taacccggga cagcacccag 94380
gcactgtcca ccctctaata caagcggcct ttggacgcga gggaggggtg tcatggtcaa 94440
caaaccaaga aaaacacatg tattattcaa ttagccaaca actttattta ttaccgacag 94500
gagacatgag atacataaat ttccaaccgt gcatagggcc aataccatct gtggagcgtt 94560
aagtgccctg tggagttttc gcctaattag ctgaatctcg acccccattg cggccagcat 94620
gctcacgagg aataggcagc agaggcagga cctaactagg agcatatccg gacctgatcc 94680
aagtatgtgc accaaggtga gcaacactgc cgccaaaggc aggagaacaa atagcgctcg 94740
tcgggaggcg acggatacgc ccacgcatga cagtaaccca acataaaata gcgtcatata 94800
cttatccagg ccaatcagga ccggagtcag caggccgatc gaggccgtcg atatcagggt 94860
ggccagcagt aaggtcacaa acacgacaac ctcgcgccta cagtaggccc aggcctggaa 94920
cactgaatag gtgatgtact tcccgggcat gatgaatatg gccctcctcc tttgcattcc 94980
ggccctgatg tacacatgct gttccaggtg cctaaatgcc aaaagtcccc cgaccaagaa 95040
gacaatgaag ggcagccaga aaacgccgga cacaaagacc ttcttaaaca acagaaggta 95100
gtacaccata aatgctccgc agaagcccag ctcatagtac ctgtgtacta ttggcggcgc 95160
ctgatacacc gccgttgcgg tggctagcgg ataaggtaac agcagtaaac agttaagtac 95220
gcacagaccc ggtatgaagg gcacacgaga aaatgtaaac ccagaaaagg ccgcgcaaac 95280
tacagcagca aacactgctg acgcgcagat ccattccagc ctccggtcca gctgtttttg 95340
cgccgcaggg cacagacaca tgcatatcag ggccaagtgc gtgactggca gcgaccagaa 95400
aaacacggcc gtgatctctg tggtaaagag tgtgaacgag tacagggcct tgaagataaa 95460
acaccacaga aagggggtcg ccgccaacgt cccgctcaga taactgaaga gcgacagagc 95520
gcgctcactg tccaggcggc acatggtgtc aaatcagggg gttaaatgtg gttttgggca 95580
ccttcccacg atccctggac tggctcgagt ctgagcgcct cttgtgaggc ctctttgtgc 95640
tgtccttagt tggcgccgct ggggggcagc tggtgacaga ggcagcgtcc tcagaggcgt 95700
cctccagcgg cccaaaggga ccaactggtg tgagaggggg agaatccgga gactccaatt 95760
ccggctgcct cctggagtcc ggtatagaat cgggaacctt ttgcgaagac tcgcctccct 95820
cggcagacac agatcggttt acctctaaaa gtaggacact taactttacg tcacctgatt 95880
ggcagccagt gggcacacct tccacttcta atatttcgtt ggagtgccaa atcagcccgg 95940
gggtaaacca acccgggact ttacacagtc tcagggcggc gattaaggac tccaggctaa 96000
cccggctcag ggcgtcggtg tgcaccacgc ccacatccac cgacttcttc cccttcagac 96060
catcccagcc agaaacgggt ttggtttctg gcttgaaatc aatgatcttg ctcacgccac 96120
caagagaaaa tgtcacgatc gacagcgtct cgctgacaga cacagtcacc gtttggtcct 96180
cttttgtttt ttgctgcctt agccacttaa gtaggaatgc acccgttttg ccacagagga 96240
gaagcctggt ggtcctacca ccggcttcca tccgatcgtg gaaaggtagg ataccctttt 96300
ggtccaccac gcttttgtgc acggtggagg tgaggttgtc cccgtaggaa atggtggtcc 96360
tgacgaactg cggttgggcc cccgtatcgc atgcctcccc ctttcgataa aaggctatgc 96420
cagcgtcgag tacattcgca ccgaatagct cacgcgtgtg cgtgaagccg ctaccgacgg 96480
acgtattcct gaagctgaag ctaacgtctc cactgccttc cgtgtgtccc accaggggcg 96540
taagggcatt ctttattctt aaccccagaa cgccagctgt ccccacgctg gacagcacac 96600
tgagggttgg cgtgcaagcc gatccgtgca cttgcactac tccggtttta gtggcactct 96660
taatgtgttc attgaccctc ctgattttag acaggagggt cacgtccacc ctgaccccat 96720
agtgaaaatc cacaggcatg attgcggccg tagacgcaca gagaaatcac aggaaagctg 96780
cgcgcacact gggtgatctg gagacgatag actgccttaa atagaacttt taggggaggt 96840
ggaagtgtgc gacatggaca ggttaacctt cacaaatcgt cagtcacaca cgtggtgtaa 96900
tcagaattgt ctcgctcaaa aaaattcaca gccttgaaac tgccggtgta tgagaggggg 96960
cacgcttctg gcggaggcgt gccaaatatg ggaggaacga aaatatcacg cagaatcctg 97020
tcagcggtgg cttccaggaa cctccggatg tccaccacgt taacaagcgt caccccggcc 97080
gccttggcct ggataaaccg aatctcaata ttcactgcct ccctgaacag cgcctggacc 97140
tctgcgtgac tgggtttttc ctgtatctcc accatagtgt tgtacaacat actggcggcc 97200
ttggtgtgca gcagctcgtc cctggaaatg taatcgttgg caaggcacac cccgggcatg 97260
atgcctcgca ccctgcacaa actgatagag tagaaggagc taataaagta tatcccctcc 97320
acaatcaaaa acatcagaat cttctgagct ttggtggtcg ccttacgcac cctggagtga 97380
agccactcca gcttctcgca aagggcgggg tccaaaatga tcttggcagc atatgctaga 97440
agttcgcctc gactgttgtt gaaaaatatc ttcaagatat tggcatacac gacaccgtgg 97500
atattctcca tggcaacctg ttcggcataa tagtgggcca cgtcgtggct gttaaaattt 97560
gtgacaaggt cctcaatgtt aaagttaact aggcgttcgg ccattcccaa aaacgtaaac 97620
aaaaatctat aaaagtcctt gtcggcatcg ctgagctggt gcacgtggga aacatcaagg 97680
tgcaggggta tctggctagg aaaccatcgg ttctgccaag tctcgcgcgt tagcgccaaa 97740
aatccgtcgt gatcgcttgt atacagaaat cgatcaactg aatccattgg cctcacccgg 97800
cttgcagaga cctacctact gacagaccag gcactcgggg tctgccgcgc aggactcctc 97860
ctccgggttt ttaggtccgg gtaaccacgc cccatcttgt ttcatcccag agtgaggcgg 97920
tgaccctgga tctgccaggc actgaagagc cgtcagacta gattgcttct gaaccctaca 97980
gtagtacatg agggttttta gaccaagcct gtatccatgt agcagcaggt ccctaagata 98040
gctcgcattc ctgactctgt cctccttgag gaagaagctc atggactggc tctggtctac 98100
aaacggcgcc ctggcacgag ccctgtccag tagcttaaat ggacagtaat caaaggctgt 98160
taggaatacc ctatatcttt ccctgtgatg cttggggaac gtggaaacgt ccccaccata 98220
ctgtctaacc acccgaaggt cgtcggggag aaccttctta aaaaaagtca cattgggcct 98280
caacacctct tctttattgg tgaccttgga agatatatta gcaaaaaagg ggtacacaga 98340
ctcggcatag ccagttactt gcgaggtccc agccgtcggc atcaccgcca gaaactgaga 98400
attgaatatg ccatgctcgg caatgctctt tcccaacgcg tcccagcgat ggcgtggtac 98460
aaacgaagca tcctccccct cccatgtttg ccaatgaaac ctgcccttgg cgaagttact 98520
gacctcccag ccatgaaatg ggacaccctg tccctccaaa acaaggttgt gactagtctc 98580
caccgcggtg tagtacatag actggaatat attcttgtct aactcagcgc tctcagcatc 98640
gaggtacccg taccccaatt ccgcaaacac atccgccaac ccctgaacac caatccccat 98700
agacctctcc ttttgacctc gctcgacccc cggtgttgga tgggaaccac ccagaatgca 98760
ggcgttgatg acgaggactg ccacccttac tgcgtcgccc aaggcctcaa aacaaaaaaa 98820
cggcctgttg gcgtccgtgg tgccaaccct cgcgctttca acagttctca gacactttgg 98880
aaggcagata tttgccaggt tgcacaccga agtgtttctt cctggcagtt ggactatctc 98940
tgcacacaag tttgagcagt taatggccat gccctgagtg tcggtccagt ggtgttcatt 99000
gagcgcttct tttaaaagca cgtacggtga gcctgtcttt atgatggtgt ggataagagt 99060
gaacatcata gacttcaacg gcatgcaact aacgtacttt ccagcccgca ccaggcgctc 99120
gtattcgtta tcgaacgcag caccgtatag cttaatcaaa ttgggggcgg tggctggatc 99180
gaacaaatac cataacttgg atgggtcctt ttcatacatc ctgaaaaaca atgttgggat 99240
gcacacgccc tgaaagagac tgtgacatct gtcgggattc tccggtagtt tggcgttcaa 99300
aaaatcacag atttgactgt gccagagttc catgtatgcg ctcgcgccaa cgggcctgat 99360
gttattgtca ttgaaataat gaacctgggc atccaccagt ttgaggcaac tggctatgtt 99420
cttttggtgg gagaatgacg taacatccag acccacgcct gacttactgg ccagcaacgg 99480
actcatatcg tggtacaggg cgtccaaagt acccgactca ttcatcatgg agggctgcag 99540
aataaaacag ctggcgagtt gtccgccttc gactccagct gagcgcagta ttggcgtggc 99600
gcagcacacg tgctgcgcag cgaggtagcc aaaaacgtac tccactatag ccatctcaga 99660
tacagactta gcgtcctcaa taaggtcccg cgccaaccaa tacaggcatt catgctctaa 99720
gcactgacag gcaacaaaca cggaaaccct cataaacatt tgcgccacgc tttcatagac 99780
aggctctgtc cccatggtcc ttaggacgta agtatcatac aacctcacgg ccgataggta 99840
gccacagtta agtgtgtcct cgtaagcttt ggaccgtctg taggcgcaca acatatcttc 99900
caaggcatca atgttctttt gaataaacga ttccacccga tgtcccaaca cgcctcgaaa 99960
aatcccaaga tactgcttga gagtcgctgg gcacctagcc tccataattt ggtgccacag 100020
ccgccccgcc atggcattgg cccgcacgtc ccacccgacc ctaaccttta gaaagtctat 100080
gagagattgg gcacacatat caaaatccga caattgtccc gcagacacct gagacccgcg 100140
tcgctctggt gggacagctc ccaagtgaac ctgacaaaat gtccggacag acatgacctt 100200
acagaaacac agtccagggg ccacacgcgg cctcaaagtt cgcaaacacc agtacaggca 100260
aggacgtgcc cttcacgttc agactttggt gcaccggatg agaatcaaag ggaactgtgc 100320
ccagcgtaca aaccgcccca aaaacaagcc gatttatata cagctcgtgc ctcagctgaa 100380
tatacttggt ccggattaca tccgtaaagt gatcctttat catggccaca acctccgcaa 100440
agcccttccc agactggaaa aacgtcagcg ccatagatgg tctctggttc acacggagat 100500
aaaccaacga ggcataaata gtaacgttta ggcctgccgg ttcccggcgc tggaccatgg 100560
gacatgactc atccaaatca actagcatat cacaagggag ggtcaagcct acgtgtgcac 100620
ggggctcgtc ccgggccaac ccaactccct tcatggcgga ggtgaccttg gtcacgaagg 100680
tactgtggac actctggacc attggaccta ctggggtaag gagggtatga aactccccag 100740
tgtccatgag ttcactcaag ttagggatga aatccgccag gccggatcca cttccgtacc 100800
acacaccggc cactttgtga gtctgtggcg cttttgccgc ttccattcca gagagcataa 100860
acagggacgt gggtgttagc agcatatcca tagacgagcc gttgtcctcc tgcttgaatg 100920
aaaataaaaa ggttcccaga ggctcctggg gactaaaggt ctgtgaatac acgaggaaat 100980
ctccataggt cggctgccta aacggcgcct gccgcaaggc ctcatgcagc gagccaaccg 101040
tgggtcgtgt ggacgccgca tatttagaga gtaaatcccg caccccccctg gcaaactccg 101100
gtcctctagt gagggatacc cggtgagttg gtggaggtaa aagacccaac acttgcctac 101160
ccaggcgagc cgcattttca gcctgcacct tcatatccac gccggcaatg gacggcacag 101220
acgctcttga aaagcttacc aaaggcctga gtgggggagg cgggagcctt caccagacaa 101280
agctgttgat ggaatttcaa ctccgaggac tgccggtgcc tgccctctta aacagcagca 101340
caacagagca gtttttaaat actgttgccc aactgccgac ggacctatca aaatttatac 101400
gcgactatcg cgtgttcgca ctggttcgcg cggcgtattt tttagaaccc ccttctagca 101460
tcgacccccct tgaggcagcg cgcgctcttg gacgcctggt tgatatatta tcatcacaac 101520
caccgcagaa caccgcaccg gcgcagccac ccacctccga cgacaccctg aataactgta 101580
cattgctcaa actactagcc cactacgcgg atcagatagc aggtttcaaa acccccgctc 101640
tccctcccgt gccacctgga atcatcggcc tgttcacatg cgtggaacag atgtaccacg 101700
catgttttca gaaatactgg gcagctgcac tacccccaat gtggatactg acatacgacc 101760
ctcccacttc tccgttacag gactggctta tagtcgccta tggtaacaag gaaggactgc 101820
tactcccctc tggcataccc tcggaggagg tgttagccaa aacattagta acagaacacc 101880
acgagttgtt cgtatcgcgg tcgaattcga ccgagaccgc cgtcaccatg cccgtatcca 101940
aagaacgcgc cctcgccatc taccgggtgt tcgccaaggg tgaggtggtg gcggaaaata 102000
ctcccattct tgccttcacc gacgtggaac tatccacact caaaccccac tatctgttca 102060
tctatgattt tatcatagag gcattatgca agagctacac atactcatgc acccaggccc 102120
gcctggaatc ctttttgagc cgaggtatag acttcatgac tgacctaggt cagtacctag 102180
ataccgctac tagcggcaag cagcagctga cgcacagcca aataaaggaa atcaaataca 102240
ggctgctaag ctgcggtctc tcggcttccg cgtgtgatgt tttcagaact gtgatcatga 102300
ccctcccata tcgaccgacc cccaacctcg ctaacctgtc cacgtttatg ggatggttc 102360
accaactgac catgttcgga cactatttct accggtgcct gggcagctac agtcccaccg 102420
gcttggcctt cacagaattg caaaagatac tgacacgcgc cagcgcggag caaacggaac 102480
gtaacccgtg gagacatccg ggtatctcgg acattccact gcgttggaaa atatcgcgtg 102540
ctctagcatt cttcgtccct ccggccccca taaacacttt gcagcgcgtg tacgccgcgc 102600
tgccctcgca actcatgcgg gccatcttcg agatctcggt caagaccaca tggggaggcg 102660
ccgtaccggc aaacctggcg cgcgacattg acacaggacc gaacacacaa catatctcct 102720
ccacaccacc gcccaccctc aaggatgttg agacatactg tcaaggtctg cgggtgggag 102780
acacggagta cgatgaggac attgtgagaa gcccgctctt tgcagacgcg tttaccaaga 102840
gtcacttgtt gcctatactg cgcgaggttc tggaaaaccg cctgcagaaa aacagagctc 102900
tgtttcagat aagatggctg ataatatttg ctgccgaggc ggcaaccggg ctcatccctg 102960
ccaggcgccc gctagccaga gcctacttcc acatcatgga cattctggag gagagacatt 103020
cccaagacgc cctatacaac cttttggact gtatccagga gctcttcacc cacatcaggc 103080
aggctgttcc agacgcacag tgtccgcacg cctttctaca gtccctgttc gtctttcaat 103140
tccgcccttt cgtactcaaa caccagcagg gtgtaacctt gtttctagat ggcttgcaga 103200
catccctccc cccggtgata agtctggcca accttggaga caagctgtgt cgtctcgagt 103260
tcgagtacga cagcgagggc gacttcgtgc gcgtgccagt tgcaccgcca gaacaaccac 103320
cgcacgtaca tctgtcgcat ttcaagaaga caatacagac catcgaacag gccaccaggg 103380
aggccaccgt agccatgaca acaatcgcaa agccaatata ccccgcctac atccggttac 103440
tgcagcggct agaatatctt aacagactca accaccacat tctcaggatt cccttcccac 103500
aggacgccct ttctgaactc caggaaacct acctggcggc gtttgcacgg ttgacaaaat 103560
tggcagcgga cgcagcaaac acttgtagct actccctcac caagtacttt ggagttttat 103620
tccaacacca gctggtcccc acggccatcg ttaaaaaact gctacatttc gacgaggcta 103680
aagataccac agaagccttt ttacagagcc tggcacaacc cgtagtgcag ggacaacggc 103740
agggggcggc tggcgggtcg ggtgtcctga cgcagaaaga acttgagctc ttgaacaaaa 103800
taaacccaca gtttacagac gctcaggcta acattcctcc atctattaaa cgttcatatt 103860
caaataaata tgacgtccct gaggtctcag tcgactggga aacgtactcc cggtctgcct 103920
tcgaggcacc ggacgacgaa ctccgttttg tcccactgac gctggcaggc ctccggaaac 103980
tgtttgtcga atagaggcca tggcagccca gcctctgtac atggagggaa tggcctccac 104040
ccaccaagct aactgtatat tcggagaaca tgctggatcc cagtgcctca gcaactgcgt 104100
catgtacctg gcgtccagct attataacag cgaaaccccc ctcgtcgaca gagccagcct 104160
ggacgatgta cttgaacagg gcatgaggct ggacctcctc ctacgaaaat ctggcatgct 104220
gggatttaga caatatgccc aacttcatca catccccgga ttcctccgca cagacgactg 104280
ggccaccaag atcttccagt ctccagagtt ttatgggctc atcggacagg acgcggccat 104340
ccgcgagcca ttcatcgagt ccttgaggtc ggttttgagt cgaaactacg cgggcacggt 104400
acagtacctg atcattatct gccagtccaa agccggagca atcgtcgtca aggacaaaac 104460
gtattacatg tttgaccccc actgcatacc aaacatcccc aacagtcctg cacacgtcat 104520
aaagactaac gacgttggcg ttttattacc gtacatagcc acacatgaca ctgaatacac 104580
cgggtgcttc ctttacttta tcccacatga ctacatcagc ccagagcact acatcgcaaa 104640
ccactaccgc accattgtgt tcgaagaact ccacgggccc agaatggata tctcccgcgg 104700
ggtggaatca tgctccatca ccgaaatcac gtccccttct gtatccccccg cgcctagtga 104760
ggcaccattg cgcagggact ccacccaatc acaagacgaa acgcgcccgc gcagacctcg 104820
cgtcgtcatt cctccttacg atccgacaga ccgcccacga ccgcctcacc aagaccgccc 104880
gccagagcag gcagcgggat acggtggaaa caaaggacgc ggcggtaaca aaggacgcgg 104940
cggaaagacg ggacgtggcg gaaatgaagg acgcggtggc caccagccac cagacgagca 105000
ccagcccccca cacatcaccg cggaacacat ggaccagtcc gacggacaag gcgccgatgg 105060
agacatggat agtacacccg caaatggtga gacatccgtt acggaaaccc cgggccccga 105120
acccaatccc ccagcacggc ctgacagaga gccaccgccc actcccccgg cgaccccagg 105180
cgccacagcg ctgctctctg acctaactgc cacaagaggg cagaaacgca aatttttcctc 105240
gcttaaagaa tcttatccca tcgacagccc accctctgac gacgatgatg tgtcccagcc 105300
ctcccaacaa acggctccgg atactgaaga tatttggatt gacgacccac tcacaccctt 105360
gtacccacta acggatacac catctttcga cataacggcg gacgtcacac ccgacaacac 105420
ccaccccgag aaagcagcgg acggggactt taccaacaag accacaagca cggatgcgga 105480
caggtatgcc agcgccagtc aggaatcgct gggcaccctg gtctcgccat acgattttac 105540
aaacttggat acactgctgg cagagctggg ccggttggga acggcacagc ctatccctgt 105600
aatcgtggac agactaacat cgcgaccttt tcgagaagcc agcgctctac aggctatgga 105660
taggatacta acacacgtgg tcctagaata cggtctggtt tcgggttaca gcacagctgc 105720
cccatccaaa tgcacccacg tcctccagtt tttcattttg tggggcgaaa aactcggcat 105780
accaacggag gacgcaaaga cgctcctgga aagcgcactg gagatccccg caatgtgcga 105840
gatcgtccaa cagggccggt tgaaggagcc cacgttctcc cgccacatta taagcaagct 105900
aaacccctgc ttggaatccc tacacgccac tagtcgtcag gacttcaagt ccctgataca 105960
ggcattcaac gccgaaggga ttaggatcgc ctcgcgtgag agggagacgt ccatggccga 106020
actgatagaa acgataaccg cccgccttaa accaaatttt aacattgtct gtgcccgcca 106080
ggacgcacaa accattcaag acggcgtcgg tctcctcagg gccgaggtta acaagagaaa 106140
cgcacagata gcccaggagg ctgcgtattt tgagaatata atcacggccc tctccacatt 106200
ccaaccacct ccccaatcgc aacagacgtt cgaagtgctg ccggacctca aactgcgcac 106260
gctcgtggag cacctgaccc tggttgaggc gcaggtgaca acgcaaacgg tggaaagtct 106320
acaggcatac ctacagagcg ctgccactgc tgagcatcac cttaccaacg tgcccaacgt 106380
ccacagtata ctgtctaaca tatccaacac tctaaaagtt atagattatg taattccaaa 106440
atttataata aacaccgata cactggcccc atataaacag cagttttcat atctgggggg 106500
tgaactggca tctatgttct cccttgactg gcctcacgca cctgcagagg cggtagagcc 106560
actacccgtg ctgacttctc tgcgaggtaa aatcgcagag gcgctgacgc gtcaagaaaa 106620
caaaaacgct gtagatcaaa ttctaaccga cgccgaaggc ctccttaaga acattaccga 106680
tccaaacggc gcacacttcc acgcccaggc cgtatcaatt ccagtgttag aaaactacgt 106740
acataacgcg ggggtccttc tcaagggcga aaagagcgag aggttctccc ggctgaagac 106800
cgccatccaa aacctggtat cctccgaatc atttatcacc gtgaccctac acagtacaaa 106860
ccttggaaac ctagttacca acgtaccaaa acttggtgag gcgttcaccg gggcccgca 106920
cctcctgaca agcccgtccg tgagacagtc cctttccacc ctgtgcacaa ccctgctgcg 106980
agatgccctg gacgccctgg aaaaaaagga tccggccctt cttggtgagg ggaccacgtt 107040
ggcgctggag acactcctag gatacgggtc ggtgcaggac tacaaggaga cggtacagat 107100
aatatccagc cttgtgggca tccaaaaatt agtcagggac cagggcgcgg acaagtgggc 107160
cactgccgtg acaaggctaa ctgacctcaa atcaactctg gccacgaccg ccatcgagac 107220
ggctacgaaa cggaaactat acagattgat ccaaagggac ctcaaagagg ctcaaaaaca 107280
cgagaccaat cgggccatgg aggaatggaa gcagaaagta ctggctcttg acaatgcgtc 107340
tccggaacgt gtcgccaccc tcctgcaaca ggctcccacc gcgaaggcta gagagtttgc 107400
agagaagcac ttcaaaatac tactccccgt acccgcggac gcccccgtcc aagcgtctcc 107460
aacgccgatg gaatacagcg ccagcccccct cccggaccca aaggatatag acagagctac 107520
atccatccac ggggaacagg cgtggaagaa gatacagcag gcgttcaagg atttcaactt 107580
cgccgtcctg cggcccgctg actgggatgc cctggcagcg gagtaccaac gccgtggttc 107640
gcccccttccg gcggccgtgg gtccagcgct ctcagggttc ctggagacga tcctagggac 107700
gctgaacgac atctacatgg ataagctccg ctcctttctg cccgacgcgc agcctttca 107760
ggcgccgccc ttcgactggc taacgccgta tcaggaccaa gtcagctttt tcttgcgcac 107820
catagggctg ccgctggtgc gagcgctggc cgacaagatc agcgtgcagg cactgaggct 107880
tagccacgcg ctccagtccg gcgatttgca gcaggccacg gtgggcacgc ccctggagct 107940
ccctgccaca gagtacgcgc gcatcgcctc caacatgaag tccgtgttca acgaccacgg 108000
acttcaggtg cgatcagagg tcgcggatta tgtggaggcc caacgagccg acgcacacac 108060
gccacacgtc ccacgtccaa agatacaggc accaaagact ctgattccac atccggacgc 108120
aatcgtcgcg gacggactac ccgcctttct taagacgtcc ctactgcagc aagaggccaa 108180
acttctggcg ctacagcggg cggacttcga gtcgctcgag agcgacatgc gcgccgcaga 108240
ggcccagaga aaagcatcgc gcgaggaaac ccagcgcaaa atggcacacg ccatcactca 108300
gctcttacag caggcaccca gtgcgatctc ggggcgcccg ctatccttac aggacccggt 108360
gggcttcctc gagggcatca tatacgacaa ggtcctggag cgcgaatcct acgagacggg 108420
tctcgaggga ctgtcctggc tcgagcagac catcaagtcc atcaccgtat acgctcccgt 108480
agaggagaag caaagaatgc acgtgctgct ggacgaggtg aaaaagcagc gagcaaacac 108540
tgagaccgct ctcgagctag aggccgcggc tacgcacggc gacgacgcta gactcctgca 108600
gcgagcggtc gatgagctgt caccgttgcg cgttaagggg gggaaggccg cggtggaatc 108660
ctggcggcag aaaatccaaa ccctgaaatc cctggtacag gaagcggagc aggccggcct 108720
cctgttggcc accatagaca cggtggccgg ccaggcccag gagaccatat caccatccac 108780
actccaggga ctgtaccaac agggacagga ggccatggcg gccattaagc ggtttaggga 108840
ctcgccccag ctagctggcc tgcaggaaaa gctggccgag ctacagcagt acgtcaagta 108900
caagaagcag tatctggaac actttgaggc cacccaaagc gtagtgttta cagcctttcc 108960
gctcacacag gaggttacga tcccagccct gcattacgcg ggacctttcg acaacttgga 109020
gcggctctca cgatacctac acatcggcca gacgcagccg gctccgggac agtggctcct 109080
gacacttccc acattcgacc ccacgcgccc ggcctgcgtc ccagccggcg gccacgaacc 109140
cccgttgcac agacaggtgg tgttctccag ctttttggag gcccagatcc gattagcgtt 109200
gtccgtagcg ggccccgtgc ctggacgggg tctgcccgga acaccgcaga tccgaagggg 109260
cgtggaggct gccgcttgtt tcctccacca gtgggacgag atatctcgcc tccttccaga 109320
ggtactggac accttttttcc acaacgcgcc ccttcccgca gagtcttcct ccaatgcttt 109380
cctggccatg tgcgtattga cgcaccttgt ctacctagct gggcgcgccg tcttgggccc 109440
acgggagccg gagcacgccg ccccggacgc gtacccaagg gaggtggcgc tggccccgcg 109500
cgacctgacc taccttctac tggccatgtg gccatcttgg atctcggcaa ttttgaaaca 109560
gccttcgcac gcggaggcgg cgcacgcatg tcttgtcacg ctgccaacaa tgctcaaggc 109620
tgtgccgtac ctcacgctgg aagcctcagc tggaccactg ccggcggaca tgcgccactt 109680
cgccacgcca gaagcgcgtc tgtttttccc cgcgcgatgg caccacgtca acgtgcagga 109740
gaaactgtgg ctgcgtaatg attttatgtc gctgtgtcac cgttccccgg ggcgcgcgcg 109800
catagccgtc ttggtgtggg ccgtcacttg cctagatcct gaggtaataa ggcagctgtg 109860
gtccaccttg cggcccctta ctgcggatga atccgacacg gcttctggac tgctgcgggt 109920
gctagtagaa atggagtttg gtccgccgcc caagacgccg cggcgggagg cggtggcgcc 109980
cggcgcaaca ctgccaccgt acccctacgg ccttgccacc ggcgagcgcc tggtcggcca 110040
ggcgcaggaa cgctctggcg gcgctggcaa gatgccggtg tccgggtttg agatagtttt 110100
aggcgcactg ctgttccgcg ccccccctacg cattttcagc accgcatcaa cccacaggat 110160
ctcagatttc gagggcggtt tccagatact gactcctctc ctggactgtt gcccagatcg 110220
cgagccattc gcctccctgg ccgccgcacc acgaaggacg gtgccactgg gagacccgtg 110280
cgccaacatt cacacccccg aagagataca gatctttgcg cgtcaagccg cctggcttca 110340

```
atataccttc gcaaattacc agatccccag caccgacaac ccgataccga tcgttgtgct 110400
aaacgctaac aataaccttg aaaacagcta catccctcgc gatcgcaaag cggacccgct 110460
acgaccattc tatgtagtcc ctctgaagcc gcagggtaga tggcctgaaa taatgaccac 110520
agcaacaacc ccctgccgcc taccgacatc gccagaagag gcgggatcac agttcgccag 110580
actccttcag agccaggtga gcgccacatg gtctgacatc ttctccaggg ttcccgagcg 110640
cctcgctccc aatgcgcctc agaagagttc ccagacaatg tcagaaatcc acgaggtcgc 110700
cgccacgccg ccactcacaa tcaccccaaa taaaccgacc ggaacccctc acgtctcccc 110760
ggaggctgat ccaataacag aacgcaaacg cggacagcag ccgaagattg tcgcggacaa 110820
catgcctagt cgtattctcc cgtcgctacc gaccccgaaa cccagagagc ctagaatcac 110880
gctaccccac gcactgcccg ttatatcacc cccagcacat cgcccgtcgc ctataccgca 110940
tctgccagca ccgcaggtaa cggagcccaa aggggttctc caaagcaaac gtggaactct 111000
cgtgctgcgg cccgccgcgg tcattgaccc acggaagccc gtctcggcac cgatcacgcg 111060
atatgagagg acggcgctcc agcccccccg gactgagggc gaaggccggc gccctcccga 111120
cacgcaaccc gtcactttaa cctttcgtct cccacctacc gcacccactc ccgcaactgc 111180
agccctagaa accaaaacaa ctcccccatc cacgccccca cacgccatag acattagccc 111240
accacagaca cctcccatgt ccacctcacc tcacgcgaga gacacaagcc cccccgcaga 111300
aaagcgggcc gcacccgtca ttcgagtaat ggcgcccacg caaccgtcgg gagaggcaag 111360
agtcaagcga gtggagatcg aacagggcct ttccacacgc aatgaagccc ctccccttga 111420
acgctcgaat cacgccgtgc ccgccgttac cccaaggcgc accgtagccc gcgaaatcag 111480
gatcccgccg gagataaagg cgggttggga cactgcaccg gacattcctc tgccccacag 111540
ctccccggag tcatccccac cgacttcccc ccagcctatc cgcgtggatg ataaatcgcc 111600
tcttcccaac ctcgtagaga gatacgcgcg gggtttcctg gacacgccct ctgtagaggt 111660
gatgtccctg gaaaatcagg acatcgccgt ggaccccgga ctgctaaccc gccggattcc 111720
atccgtggtg cccatgcccc atccaattat gtggtcaccc atagtaccca tcagtttaca 111780
aaacacagac atagacactg caaagataac actgattagt tttattagac gcatcaaaca 111840
aaaagtggcc gccctatcgg cgtccctggc ggagacggtt gacagaataa agaagtggta 111900
cttgtgactc cacggttgtc caatcgttgc ctatttcttt ttgccagagg ggggtttcct 111960
cgcgtcggcc accgcggggg cggccgtttc cgtcgtggat gagagggttg tgagaatgtc 112020
tgacgccggc gacaatgaat ggggaccaga ggacagggtg gttatactgc ttcccgagac 112080
ccccagtgag tcctggcccc cgggcgtggt gccggatgca gggcctggcc tcgaaggcac 112140
ggtgaacgtc cccgcgtcgt aagccgacgc cgcggaaact cggtcagcgc gctcgcgcgg 112200
tttctgatcc ctaagggtct gcagatgatc ccgcctttga attccaccca tcctcctcag 112260
ataggcctca taataatgat gggcaattaa gaacacgaga tagtgtctct tttgcacgag 112320
gtattcggcc tgcgacatat ttccctgatc cagggtattc atgcgagcca ccaggggatg 112380
gtgagcgtag tcatgatcca gtcgctcctg gatcacgggg tctctcacct taaagttgga 112440
catcttccac acaggcgggc gaaatagcct caggaggaac acttcccgca acagaactcc 112500
agcagctgtg aggtgagctg aagcagtccg cgcacgtcac ggtgctttaa tagggcagcc 112560
tcgcagtcgg gcgtcccaag gcaaggcact acaaaactga cagtttgatc taggtctcga 112620
atggcaaggg ccgcgttgtt agctagaaca gccctgatta cgacgcgtgc tagggtcccg 112680
cgtccggtaa tatcgcacag gggatacacc ctcatatgtt cgctgccaca gtaagaacag 112740
```

tagatcctcc ccgtggtcgc acagatggtg aactgcttct ctttcctgtc cctgctgaaa 112800
aacacgttgg tgggaggaaa attgacagta tgaaacttgc ccctgccaaa gttaagacag 112860
tgtccacact ccatgcacac aaccgcccga gcgcaacgcg cccgcttggc aagggccgcg 112920
cgggccacgc gagaacagat gacgggtatg gacacgcagg gggagagaac attgtatgcc 112980
agaagcctcc tgccaaggtt ccgcacgaga ccaggtccct cctgctcgca ggcgggcagc 113040
actacgtggc gggacttaat aaggctcaaa aaacacagtg acccaagcat ggcgtcgaac 113100
gggttaccgc agggaaccgt aggggcgacg cgctccaagg cctcccggag gccggtatct 113160
gccgccccta tcccgagccc gttaccgtct tcggtcgcag ccacaccgcg acgggtgtgc 113220
gagggcacct ccaggagggg acgacgcggc aacggcccat gccacttctt ccttagccag 113280
ggtagcgacg gtgggggctt cgaacagcag gtcactaacg gaaagcgaga gcaaagcgcc 113340
aacagcttgc agagttgggc acaggccttg gaaaatggaa gcgacaggta ttttgcccat 113400
acgtggcgcg gtatcgccct agcatggtcg gcggcctggg cacgggacag cgtcaccaca 113460
acccatacgt gggcgccaag cagctgctgc gccgcacaaa tctgcgcctg tttggcgacg 113520
gtgtctgagc cagcgcgcaa cacggcgatc gcctgcgcca gcgacgggcg gtccaacagg 113580
tgcctggccc aggagggcat gtttccctgg aaaccccgct ccccgaatat gacaaaagcc 113640
acatattcct ccactggcac gccattctcg ccctcgaaca cgcggtgggc cgtcagctgg 113700
gcctcatcca aaccaaacca agacacaaga aagcgatccc agcgctgatc cagggccatg 113760
accttctcac cagcgcgacc gcacggccta agctccactg aaaggcgccc agaatccgca 113820
ccgtcctacc cccctggccc gcccaatata ccgctgtgac gtctgatgta caggcccgcg 113880
cgtcgcggcc gttggtggga aaaccggcac caccctgtgc ggccgaatcc gccacggggg 113940
ctgccagaca gtacactgtc tccagcagcg acttcagtct cttgtgactt ttgggcgtca 114000
ccaccaaaaa ttgcaaaacc tgcctgtagt ccgtgaagta ggtacggcat attaccatgg 114060
agttgtacac gcccaggttc tttgagaaca ccaggctcgc cttgaacttt gtaaagtcat 114120
cctgccccag cacgacagac gtatttttgg caaggtatac gtccgactcc acgggaagga 114180
cgtgcccaaa ctgggacacg gcgtcgcttg gtcggcacag aaagcacttc agggttgtgg 114240
aaaggccatt attcgatata acaaagcagg gagagaacgg gtagtgcatc tcctccagga 114300
ggtgcgccca aaacttatac acaaactcta agtggtacac gcaaccgtgc tgcattctaa 114360
ccgtacatat ggcggtagca ccgcccttag cataaactgg ggccccgtcg atgcaccgtt 114420
ccaaatccag ggactgacca gactgtccca agtatgagga taccacccga cacagttcgt 114480
ccactacacg cttaccaacg acactcatgg cgacagcggg gtggggctgg caaggccccc 114540
aaagcgcgac acccgcagtc aatcagggcc gtgcccgcgc ctcggagaat acggcgtccg 114600
tgctcacgat cttgcgcagg acctgcctta ccgtgtccac cttgctctcc aacaccagag 114660
tatgatcgca ggctgcaggc tgtgcccgct ggacgagaaa ggtttttaaa tactgacagt 114720
agttgatggc gttcaatcta caatagatcg tgggaaataa aatttgcatg tcacgaggca 114780
gaagctggtc agacgcgtac tccatgttgg gttccacggg gaggggaaca cacgccccaa 114840
gacacgacgg cgcacatagg gagcggagca aacaattgat tcaaatattt gactccgcag 114900
cgagccggtt tgcagagtgg tcacctgccc tgctccacac ccaccccccgc gtctcttcca 114960
actctcaact cacgatccag ggaaaccacc gtccagtggc catgtttgtt ccctggcaac 115020
tcggtacaat tacccgtcac cgagatgagc tccaaaaact actggcagcc tccctgctcc 115080
cggagcaccc ggaggagagc ctcggtaacc ccataatgac acagattcac cagtcgctcc 115140
aaccatcttc cccctgcagg gtctgtcagc tcctattttc tctggtccgc gattcgtcca 115200
cccccatggg tttcttcgag gactatgcct gcctctgctt cttctgtcta tacgccccac 115260
actgctggac ctcgaccatg gcggcagcgg cagacctgtg cgagatcatg catctgcact 115320
ttccagaaga ggaggcgaca tacgggctat tcggaccggg tcgccttatg ggtatcgact 115380
tgcagctgca cttctttgtt caaaagtgct ttaagaccac cgccgccgaa aaaatactgg 115440
gaatatccaa cctgcaattt ttaaaatcag aattcatccg gggcatgctc acaggcacca 115500
tcacctgcaa cttctgcttc aaaacgtcct ggcccaggac agacaaggag gaggccaccg 115560
gccccacccc atgctgccag attacagaca ccaccaccgc acccgcgagc ggcataccgg 115620
aactagcccg ggccacattc tgcggcgcaa gtcgccccac aaagcccagc ctacttcccg 115680
cgctaataga tatctggtcc acgagctcag agctccttga cgagccgcgc cctcgactga 115740
tcgcaagcga catgagtgaa ctcaaatccg tggtcgcatc ccacgatccg ttcttctctc 115800
ccccgcttca ggcagacacc tcacagggtc catgtctgat gcacccaacc ctggggctac 115860
gatacaaaaa cgggactgca tccgtctgcc tcctctgcga gtgccttgcg gcacacccag 115920
aggcacccaa ggcgctgcag acccttcagt gcgaggtaat gggccatata gaaaacaacg 115980
taaagctggt agacagaatt gcctttgtgt tggacaaccc attcgccatg ccatatgtat 116040
cagatccgct acttagagag ctgatccggg gctgtacccc acaggaaatt cacaagcacc 116100
tgttctgcga cccgctgtgc gccctcaatg ctaaggtggt gtcagaggac gtactattcc 116160
gcctgcccag ggagcaggag tataaaaagc tcagggcatc cgcggccgcc ggacagctcc 116220
tcgatgccaa caccctgttc gactgcgagg tcgtgcagac tttggtcttt ctctttaagg 116280
gtctccaaaa cgccagggtg gggaaaacca cctcactaga cattattcgg gagctaaccg 116340
cacaactaaa aagacaccgc ctagacctgg cccacccctc acagacgtca cacttgtacg 116400
cttgagctgg tcccgggcct tcgcacccca tccaccgatg ccgaaatcag tgtccagcca 116460
catcagcttg gcgacctcaa ccggtcgcag tggaccgcga gacatcagaa gatgcttgtc 116520
atcccgcctg cggtcggtcc cgcccggggc gcgaagcgcc agcgtcagca gcaagcacag 116580
aaacggcctt cgcaagttta tctcagacaa ggtatttttt agcatcctat cgcacagaca 116640
cgagctagga gtggactttc tccgtgagat ggagaccccg atatgcacct ccaaaacagt 116700
aatgctgccc ctagacctgt ctaccgtcgc acccggccgc tgcgtctccc tctctccgtt 116760
tggacactcc tcaaacatgg ggttccagtg cgctctgtgc ccatccacag aaaatcccac 116820
cgttgcccaa ggctcccggc ctcagacaat ggtgggcgat gcgctcaaaa aaaataacga 116880
gctatgctcg gtagcgctgg ccttttatca ccacgcagac aaagtgatcc aacacaagac 116940
gttttaccta tcactcctca gtcactccat ggatgtggtt cggcagagct tcctgcagcc 117000
tggtctactg tacgctaacc tggtcctaaa aacctttggg cacgatcccc tacccatctt 117060
cactaccaac aacggcatgc taacaatgtg catccttttt aaaacccggg cactacatct 117120
gggagaaact gcgcttaggc tgcttatgga taacctcccc aactacaaga tatcggcgga 117180
ctgctgcaga cagtcctacg tggtcaagtt tgtcccaacg cacccggaca ccgcaagcat 117240
tgcagtgcag gtacacacca tatgcgaagc ggttgcggcg ctagactgca ccgacgagat 117300
gcgggatgac attcaaaagg gaaccgcact tgtcaacgcc ctataacctc acatgtagcc 117360
tgtcacccca gctcctattg caactgacca tgttcaggtg gtaataaagt cattaaacga 117420
caaagtgatt cttttaatct gtttattgtt tttgaacatg tggcacacgc tgcaatgtac 117480
tgccatgaaa ggtggttcta tatccaccac ttggcgtctg ccgaagtcag tgccacaatt 117540
tcattaacaa acaaggtcaa tacattgtga gggagtgttt tttgccatgg taccattcgt 117600
gtggtttggg agagcggacg ccatttgcgt gcaaaatgtg ctttgctgga ggccaacttc 117660
cgtcgcgctg gttgatgcgc ggcacattgt gtcaaccagg gcaccctccc ccaccgagtg 117720
ctttaatgcg gagaggaatg gtggcctggt tgacaccgcg tgccggccat ctgaactgtg 117780
actgtgttat gagccacggg tatgccctcg atacgcctgc tcttcagcat tgtatgtgtt 117840
taatgttgtg cttggtgcaa ccgtgattgt gtttttgtat tttattttac tgacactctt 117900
tgggagggca cgctagcttc agtgcgcgcc cgttgcaact cgtgtcctga atgctacggg 117960
gccacgctgg ccactcgggg ggacaacact aatcgccaac agacaaacga gtggtggtat 118020
cgccccaagc ctccagcgcc acccatttag taacacatcc gggacatgaa ctgccacaaa 118080
caccgttaag cctctatcca tgcattggga ttggagtgag gagggaggag ggcaccaggt 118140
tcccggggag gagggcacca ggttcccggg gaggagggca ccaggttccc ggggaggagg 118200
gcaccaggtt cccggggagg agggcaccag gttcccgggg aggagggcac caggttcccg 118260
gggaggaggg caccaggttc ccggggagga gggcaccagg ttcccgggga ggagggcacc 118320
aggttcccgg ggaggagggc accaggttcc cggggaggag ggcaccaggt tcccggggag 118380
gagggcacca ggttcccggg gaggagggca ccaggttccc ggggaggagg ctggggtgcg 118440
ccgcgccggg ttcctggggt gcgccgcgcc gggttcctgg ggtgcgccgc gccgggttcc 118500
tggggtgcgc cgcgccgggt tcctggggtg cgccgcgccg ggttcctggg gtgcgccgcg 118560
ccgggttcct ggggtgcgcc gcgccgggtt cctggggtgc ggggtgcggg ggaccgcgcc 118620
ggggtactgc agggttcgca gggttcgggg gtactacctg gtttcctggg gtgtgccagg 118680
acgggttcct ggggtgccac cgctcctcga tacgtgtaaa tccaagagat ccgtcctccg 118740
tgccgccgcg cgcgtaatgc gcgagggggg tcggtctccc ctcttcttta tagcgtttcc 118800
tgcgaagggg gcgtaaccgt aggacaaact gcttatgtag gggttagcca cccatttccc 118860
ggggccgcgc cagaggtgag cgtggaccta gcatcccgct cccatttacc gaaaccaccc 118920
agaggcgaga ttccagggcc gtgactcact agctcccctc ccatcgaaca accacgcttg 118980
gctaacacgg ctggagtggc ggtgggcggg gcccctataa tcctggcccc catctactga 119040
aacgacccag tagaaaaatc ccaaccccat gactcatcag gccctattat atagaatatc 119100
ccagtagagt gacccagctg gtttccataa atggatatac ttccggaaaa cgaaggaggg 119160
ttgaatacag ttgggggtag tccgctggta ttcccagctg aggttgcctt atttggtaat 119220
gcttccggaa ataccacctg agtaccccat tggtttatac cttgtttaat tgtagaatta 119280
cagctggatt tacccagccg ggtttacgca gctgcgtata cccagctgtg tttacgcagc 119340
ggggtttacg cagctgggta gacccagctg ggtataccta ctggaatagg ggctgcgatg 119400
actcagctgc gctaggatta aaggattata tatatatata taggaaaaat caaaacaaaa 119460
ctctaatcgc tgattggttc ccgctctggg ccaatcagct tgggagttct agggataggg 119520
gccaatggga ggcctccgaa tttgattgac ggctggggcg tccaatggaa tggcgcggtc 119580
gcctagctcg aacgggattg gtcggccgga tgggccaatg gcggctcgga aaactttgat 119640
tgacgggccg gcggaccaat gggagcgggg cagaggatta tgggggatta gcaaattcaa 119700
gatggcggcg cccatgaaat ggccaaaaat tataattttt cgagtcgctc acggtcccac 119760
ctagcggcgt gacctggagg tgaccccgtg cacccgggcg ctctgaattt ttctgcgcat 119820
gcgcgactcc tcatctacat aatttatgca cataaaagga ttagcgcatg caaattagtc 119880
agatagcagg gccatccaca ctttatgttg gccgcgtgcc aggcgccggc gtgggcgccg 119940
cgcgcgtgct ctctcagtcg cgcctagctg cttccaacag acaaaagcgg ggcgttagtg 120000
agggagtgcg cgcgctgcgc tgacttggcc gatttccagt gcatgctttg tcaccccagc 120060
gcgagaatgg aattttcatt attgagcaat ttgggcaccc tgggcacgat aaccatacat 120120
ggatacacgg gttccaaata tgcaaagtag acactaaggt accatttggc atatttggac 120180
gtcctgggca ggttagctac ccaccagaat atatgggact ctgggcagga tagccaccca 120240
caattgtttt gcgcccctct ttggccaggg gaccaaggtc gtatggttcg cgctacacta 120300
agcccgaacg ttcagctttg cgtgctttcg acgtccaggc ggctggcaca cgggccgtga 120360
gcgccagcaa catgggatca tggtagtaag atacagcata aatccccgtc cggtggcgct 120420
caacgccaat atgcgcggct gcgtggtatc tcatcggtgg gcacgcgtac ggtggtctca 120480
tgggtattgg acttgtaggc gaggggaggc gcatacgaca aaaattgccg ccgtgaaggt 120540
cgggaacccg cccgcgcttc cgcaaggcac ggggccgcat cggacacagg ctaagcatta 120600
aggatcataa caccgcccta gaaatgttta agctgtgacc aaagcgaacc tcgcatgagg 120660
catacgcgag cgtggaggta ggattcccaa ggctattgag agacggtggg tgaaatgatg 120720
aagaacacac agaacaataa cgggcgacta gataaaaaga ctcgctcaac agcccgaaaa 120780
ccatcagccc gaccgccgat ggattaggtg ctgctggaca agtctttcta aacccgcgca 120840
gggtttgtgt cgatccagac gcttacgaac gcccgcttta aaaacactat tcataattaa 120900
cagaagttga caccagcccg cagttaccca accttctatt tttttggagt gttgacaagt 120960
ttccatcgcc cgtttggcgt ttcccgcatg gtgtcaaatt agtgacgcac cctccccccg 121020
tcactatggg tttaccctga tttagtaagt aaaactgccg cccccgccca ctcatttttt 121080
taccctgtta tttgctgtat ttacatctac ggaccccctt ttggtgagat tgccgtggtt 121140
ctaaataacg ttgtggtttt cggacccttt cagggaccaa atcttttacg tgttgccaag 121200
gtagcatttg ctggacccgc ataggttttt gtggcaccag gttatggtct tatgagcggg 121260
cttgaccggc aagttccagg catcctaagt gcttgatgta gacccttagg gcaccaggga 121320
ctacctaggt caaactcccc cttagtcatg acgccgtgcc cacgaggttt gagaggcgta 121380
gacatccgtg tcgactgctg gacggaggta gtataatcag ctaggcctca gtattctatg 121440
taacaaatga atgccctaga gtactgcggt ttagctagtt atactgcccg gttccaccag 121500
gcggcgttgt ggccacgggc ggttcgtcgc ttggacctgg aggggtgtca cattctgtga 121560
ccgcgacgtt gacgttagac acacgtcgct gccgtcctca gaatgtgata gcccatcaca 121620
ggcattgtag ctgttgcgtt ggttgggagt ttggggacca aatttctata attggtgtca 121680
ccgcggcagc tctagccctg gaagatctgg aagcttgctt caatggctca gatcgacccg 121740
gactacagtt agcgaagtag acccattata atcttaatct taaatctggt tgacggactt 121800
tcgcgccggg aacacgcagg tggcagcgga tgtgttttgc ccaaacacga gggttgcagg 121860
aaacaggtgc tgccggggat tatgtacagc ttacacccag tttcctgtaa tcgcccgcat 121920
ccggccgtcc tgggcagcac cgcaccctgc gtaaacaacc gcgtactttt tcctcctccc 121980
cccaccccca catccttcct cccaccctgc cagtccaacc cgcttcctgt tttattcgcc 122040
ttcaaacaga agcacgcatt ctaatgattc ttacaaaact tgttagtgtt tattaaatca 122100
gatacataca ttctacggac caaaaattag caacagcttg ttatctatgg tgtatggcga 122160
tagtgttggg agtgtgatgg gccggaaagg tgaaggccca ttagggtttg cacttggcgc 122220
tgtaggtcta ctcttgacaa agatctaagc attgacatta gggcatccac gtcagtggga 122280
cccagtaggt ctaagttttc catacagtac acccagtgta agaatgtctg tggtgtgctg 122340
cgagacccta tagtgtcctt gcttaaaaat atcaaagacc taatatccct cgcacacagc 122400
tccccgtcta cgtggagaac agtgagctga taagggctga aataactcat tgtgcccgct 122460
aggtggcgct ctaaaaaacg cgggtctaag tgaagcaggt cgcgcaagag gtctctgcga 122520
cctgcacgaa acagacattc cgctaacagg ggaaacgtta acctgccctc ctcctttaaa 122580
gctctaagag ctccaattaa ttgggccagt gtgggttgag gtatgaacac gtttaggagg 122640
aacaatacca cttccctgtc atccgtgccc agtttccgcg ccacctcaca gagaacctcg 122700
taagtggcca tggtgccggc ttgtatatgt gaaggcaccg atgtggaaaa acaaaggaaa 122760
atttattttt ccgccctaaa caaaatcaca agcttaatag ctgtccagaa tgcgcagatc 122820
aaagtccgaa acagatgtta ggatctgttc cactgccgcc tgtagaacgg aaacatcgca 122880
tcccaatatg cttgccagct gaggaactac cccacccgag tgggtatcct gcggaatgac 122940
gttggcagga accaacagcg cacagcctgc agcgctgata atagaggcgg gcaatgagcc 123000
agtctttggg tcaactaagg cttttgtaat cagggtgttg acctcgtggt gccaaaagtc 123060
caggtgttgg gagcccccca gcaatttaag taacaagaag gaagtgacgt ccgtcgctaa 123120
gactgcctct gttcgccacg ccaacttctc aaggagttct ttctcctggt ctataagttc 123180
ttggcgggaa aaggagtctg ccgcggcata gcaaagtgaa ctggtagaaa taggcgtgag 123240
gcttctgagc ttactggcca ctaacaggca ggcgctccct gtcttttgaa agtgttcttt 123300
ggacacctgc tttataagta ggagtctgtc caaaagatta agggccaacg cgaccacgtt 123360
aggttctagg ttgtattcct ggcaaactga aaacatccat gtgcccagta acttacgcat 123420
atgcgaagta agagattgtt gaaaggtccc aaatacagag tcagaagtta aaaagcgcgg 123480
ctcaatttca agaatattgt aaaagatccg atcctcacat agcgtgggat ccagaagtcc 123540
cgagggcggg ttattggcag ttgccatata gagtggcgag cgtatgtggc ctacctgtag 123600
agcctggagt ttcagggtgc tctgtcaggt tctcccatcg acgacgctgg gccgcgagag 123660
tacgctagcc gttgtccgtg tgttcagttg aggtagatgg gtcgtgagaa cactgccccc 123720
cacacacacc agcacccatg gcgccaaatg caagtgcgga gcggcgacgg tggcttctag 123780
ggaggaaaaa gggggagagg tgtggctttt atgtcatttc ctgtggagag tccccaggac 123840
cttggttttc ccctggctgg gttaatggca ggggcttttt aaacttaact atggaagatt 123900
gtaggtttcc tgccaggggg tgactagctt cccaggctag gcgggccatt tgtactttct 123960
tacttgtgtc tttgttctga caatacacat atacacaata agttatgggc gactggtctg 124020
gtccagggtg gggcaagcag gacacggggc ctgcctttac tcctccaaac tggaaggcct 124080
gagataattt tttaagtccg tatgggtcat tgccccaaaa aatcactgca aacttccatt 124140
gacactttgg atctcgtctt ccatcctttc ccaaaaagcg tctataaaag atgtgttgtg 124200
gcctagcttt cgcaggacaa tcatctatct gtctgtaagg gaccggtggt tgttggtatc 124260
ttggatgtgg ctttttgggg tgggtaactg gaacgcgcct catacgaact ccaggtctgt 124320
ggggtggtga tgttctgagt acatagcggt attcgcgaga tgggccaggt tgtgggtcat 124380
cgtctggtgt attatctcct ggtgggctac tggcaatttg ttcatgtgtg ctaacaacag 124440
ggtaatccac ttccatttcg tcctcggatg acgacccgtg caagattatg ggctcttcca 124500
ccgtctcctg ctcctgctgt tccaccccct gctgctcctg ctcttccacc tcctctaact 124560
cctgctgctc ctgctcttcc acctcctcta actcctgctc ttcctgctct tccacctcct 124620
ctaactcctg ctcttcctgc tcttccacct cctctaactc ctgctcctcc tgctcctcct 124680
gctcctgctc ttgctcctcc acctcctcta attcctgctc ttcctgctcc tgctcttgct 124740
cttccacctc ctgctcttgc tcttccacct cctgctcctc taactcctgc tcctgctcct 124800
ctaactcctg ctcctgctcc tctaactcct gctcctgctc ctctaactcc tgctcctgct 124860
cctctaactc ctgctcctgc tcctctaact cctgctcctg ctcctctaac tcctgctcct 124920
gctcctctaa ctcctgctcc tgctcctcta actcctgctc ctgatcctct aactcctgct 124980
cctgctcctc taactcctgc tcctgctcct cctgctgctc ctgctcctcc tgctgctcct 125040
gttcatcctg ctgctgctgc tcatcctgct gctgctgctc atcctgctgc tgctgctcat 125100
cctgctgctg ctgctcatcc tgctgctgct gctcatcctg ctgctgctca tcctgctgct 125160
cctgctcatc ctgctgctcc tgctcatcct gctgctcctg ctcatcctgc tgctgctcat 125220
cctgctgctg ctcatcctgc tgctgctcat cctgctgctg ctcatcctgc tgctgctcat 125280
cctgctgctg ctcatcctgc tgctgctcat cctgctgctg ctcatcctgc tgctgctcat 125340
cctgctgctg ctcatcctgc tgctgctcat cctgctgctg ctcatcctgc tgctgctcat 125400
cctgctgctg ctcatcctgc tgctgctcat cctgctgctg ctcatcctgc tgctgctcat 125460
cctgctgctg ctcatcctgc tgctgctcat cctgctgctg ctcatcctgc tgctgtggct 125520
cccgctgctg tggctcccgc tgctgtggct cccgctgctg tggctcccgc tgctgtggct 125580
cccgctgctg tggctcccgc tgctgtggct cccgctgctg gggctcccgc tgctgtggct 125640
cccgctgctg tggctcctgc tgctgtggct cctgctgctg tggctcctgc tgctgtggct 125700
cctgctgctg tggctcctgc tgctgtggct cctgctgctg tggctcctgc tgctgtggct 125760
cctgctgctg tggctcctgc tgttgtggct cctgctgttg tggctcctgc aggggctcct 125820
gctgctgtgg ctcctgctgt tgtggctcct gcaggggctc ctgctgctgt ggctcctgct 125880
gctgtggctc ctgctgttgt ggctcctgca ggggctcctg ctgctgtggc tcctgctgct 125940
gtggctcctg ctgttgtggc tcctgctgct gttgtgaact ttggatgctc aacgttttgt 126000
ttccatcgcc cccgtcctcc tcgtcctcct tcttgtcctc ctcctcgtca tcctcctcgt 126060
cctcattgtc ctcatcatcg tcatcctcct cgtcctcctc ctcctcgtcc tcctcctcgt 126120
cctcctcctc gtcctcctcc tcgtcatcct cctcgtcatc ctcctcgtca tcctcctcgt 126180
catcctcctc gtcatcctcc tcgtcatcct cctcgtcatc ctcctcgtca tcctcctcgt 126240
catcctcctc gtcatcctcc tcgtcatcct cctcgtcctc ctcatctgtc tcctgctcct 126300
cctcatcatc cttattgtca ttgtcatcct tgtcaacctg actttccttg ctaatctcgt 126360
tgtccccatt atcctcgcca gcctgattat tttcggaaca ttctttttca ttcttggatg 126420
cttcttctgc aatctccgca aggagcacca acatggctgt gtcatcaccc caggatccct 126480
cagacgggga tgatgatcct atggagatgg gagatgtagg cggttggcgt ggcggagtat 126540
cgccatcgct ggatgatccc acgtagatcg gggactctgt ggcccatggg gggtacacac 126600
tacggttggc gaagtcacat ctagggggag agactggggg cgactgacat attgggttta 126660
gtgtagaggg accttggggg gacgatagcc ttctttttct caggctacgc agggtagacg 126720
gagctaaaga gtctggtgac gacttggagg gaggctcggg tggaggagtc gtgggtgagt 126780
gtggaggtgt agtctgctgc gagggtggcg gacgcatagg tgttgaagag tctggccttc 126840
ctgtaggact tgaaagcggt ggcctttgag aagactctgg agactgcgtg ggtggcaatg 126900
caggagatgg agaatgagta tccgtggtcc ccggagacac aggatgggat ggagggattg 126960
gggaggaaga cgtggttacg gggggtaaga gtgccggtgg aggtaaaggt gttgcgggag 127020
cgggtgaagg aatgggagcc accggtaaag taggactaga cacaaatgct ggcagcccgg 127080
atgtgaacac tgtgggactt ccaggtatag gcaaggtgtg gggtccacat tcccggccgt 127140
cgatggagtc ggcgacatgc ttccttcgcg gttgtagatg taggtcatcg ccaaggtcac 127200
atctttccgg agacctgttt cgtttcctac aacttcctct cgttaagggc gcgccggtgc 127260
tccgtcccga cctcaggcgc attcccgggg gcgccatcct cgggaaatct ggtctgacaa 127320
ccaaagtaaa attatggagg cggtggcagt atattcacat tatgcaatac ccgtagtgac 127380
cacaaggggg agctctcaga caattaagcg gttacacaca gtagcaggct gcagtaccgc 127440
ccatggccac aggatgtaga tcgcagacac tgaaacgctg aaacacagca ttaagctgca 127500
ataccgccga tggccaccag atggcacgcg ccgccagcaa atttaagtcc tggtggctca 127560
cctgccaggt aaacaaggtt aaagtgggtt tgctggcctt gcgttgccat ggatgctacc 127620
taggcaagtc cagatatata atccgggcgt gagaaacaga aacggccaat aacccatgtt 127680
tttcgaaaac caccacacac cttaacacaa atcatgtaca cctggtatta ctatttccca 127740
cacatcttat agcatttcaa agataagggt gccttacggg ccgcccgaaa caagtgggcg 127800
ggcgctactc actgtttata agtcagccgg accaagctgc tgctcttggg gacgtgactg 127860
cttcgtggcg cagctgcctc caaatgatac acacattttt tgattgtccc gggcgccgcg 127920
tagtggaggg cggagttata tcaagctact ttctgattgg tgccccaggc aggactgcca 127980
taaaaactga agaaggcgtg tctgctttgc agaatttacc ccccactgtg ctcccggttg 128040
ctggcaccgg ttcagtggtc cgacctgtcg tctgtgctcc cccgtggacg acgccgagtg 128100
cctctcgggg gtccatgtct agcctcttca tttcattacc ttgggtggcg ttcatctggc 128160
tagccctcct tggcgcggtt gggggtgccc gcgttcaggg gcccatgcgg ggctctgctg 128220
ccctcacctg cgccatcacg ccccgtgctg acatagttag cgttacctgg caaaaaaggc 128280
agctccccgg tcccgtaaac gtcgccacgt acagccattc atatggggtg gtggttcaga 128340
cccagtaccg ccacaaggca aatataacct gtcctgggct ttggaactct acccttgtta 128400
tccataacct tgcagtggat gatgagggct gttacctgtg tatctttaac tcatttggtg 128460
gccggcaggt gtcatgcaca gcctgcctgg aagtgacatc tccccctact ggacacgtgc 128520
aggtaaatag cacagaagac gcagacaccg tcacctgttt ggcaactggt cgcccacccc 128580
ccaatgtcac ctgggccgca ccctggaaca acgcctcttc tacccaggag cagttcactg 128640
acagtgatgg tcttacagtt gcgtggagga ccgtgaggct gccgcgtggg gataatacca 128700
ccccaagtga gggaatatgt ctcatcacct ggggaaatga gagcatatca atcccggctt 128760
ctattcaagg ccccttggcc catgaccttc ccgcggccca gggaactctt gccggggttg 128820
ccattactct ggtgggccta tttgggatat tcgcattaca tcattgccgc cgcaagcagg 128880
gcggtgcatc acctacttca gatgacatgg accccctatc cacccagtga ctagatggac 128940
accccgtgaa ccgtcgtgct tacccacccc cttctgattc tgacagacaa cactactatg 129000
tcccaaagac tgtttttttac agcccgatgg ccccttcaggc ctccttgagt gtctagctgg 129060
tcccgtggtc attgtgtggt ttggcagtca cttccccatt ttggtgtcgc gttttgggtt 129120
ttgccctgcc cccagccaac gtggatcata ttctttcccg tcaggggagt gacaagctat 129180
aggacagaaa ggtcacctgg cccaaacgga ggatcctagg tgggtgtgca tttattagac 129240
gttggtgtgt tgaaggacgg atcaggcggg gaggaggggg tgggggagac ttactgcagc 129300
actaggttag gttgaaagcc ggggtaaaag gcgtggctaa acaacaccta tactacttgt 129360
tattgtaggc catggcggcc gaggatttcc taaccatctt cttagatgat gatgaatcct 129420
ggaatgaaac tctaaatatg agcggatatg actactctgg aaacttcagc ctagaagtga 129480
gcgtgtgtga gatgaccacc gtggtgcctt acacgtggaa cgttggaata ctctctctga 129540
ttttcctcat aaatgttctt ggaaatggat tggtcaccta catttttgc aagcaccgat 129600 cgcgggcagg agcgatagat atactgctcc tgggtatctg cctaaactcg ctgtgtctta 129660
gcatatctct attggcagaa gtgttgatgt ttttgtttcc caatatcatc tccacaggct 129720
tgtgcagact tgaaattttt ttttactatt tatatgtcta cttggatatc ttcagtgttg 129780
tgtgcgtcag tctagtgagg tacctcctgg tggcatattc tacgcgttcc tggcccaaga 129840
agcagtccct cggatgggta ctgacatccg ctgcactgtt aattgcattg gtgctgtcgg 129900
gggatgcctg tcgacacagg agcagggtgg tcgacccggt cagcaagcag gccatgtgtt 129960
atgagaacgc gggaaacatg actgcagact ggcgactgca tgtcagaacc gtgtcagtta 130020
ctgcaggttt cctgttaccc ctggccctcc ttattctgtt ttatgctctc acctggtgtg 130080
tggtgaggag gacaaagctg caagccaggc ggaaggtaag gggggtgatt gttgctgtgg 130140
tgctgctgtt ttttgtgttt tgcttccctt accacgtact aaatctactg gacactctgc 130200
taaggcgacg ctggatccgg gacagctgct atacgcgggg gttgataaac gtgggtctgg 130260
cagtaacctc gttactgcag gcactgtaca gcgccgtggt tcccctgata tactcctgcc 130320
tgggatccct ctttaggcag aggatgtacg gtctcttcca aagcctcagg cagtctttca 130380
tgtccggcgc caccacgtag cccgcggatg tctacgtgcc cttcccccctt aatttaatct 130440 agcctcccgt tcccatgatg cagagaggcg aatttggttt gtacacagat gtgactatgt 130500
atttgtttta ttatgcgatt aaatgagggg tctgatccca aaagcaatgt ttagtggtgg 130560
tcgttgatct tcttgacgct ccataggtag attgactgga acgccatggc ccacggggac 130620
atggacaggg gtgttaggtc tggtggaaca tgctgccact gccacggatg gaacatcaga 130680
gatgggtcta tgatcagggc agcgtgtcgc ccgtcactgg atgtaagtcc ggccaccgtg 130740
gagttgcctg tggggtttct gggatagtgt ctggctggca gggtctcatc cgcggcattt 130800
ccatggtagg tgagggttat ctcgcctcgc tgtctcagta tgtactcgag ggcgtcctgc 130860
tcgtaccgga cccccaggta ctctccctgg gcccagctgg gcagcaccgt cccccgcaac 130920
actcggagga aaacgctctt agtgttctga gggatctgta tgtttagcca gtggctgtca 130980
tacagcttgg acacgttggt ctccaggttt accgcccagc gctggggtgg tgtgggtccg 131040
tacgtgtatg gtgaggattc cgaccggccc actacaccca gggccaccag cagctggaag 131100
cccacctcgc cacagcagat ggagaatgtg tcgggtctgt ttagaaactc tgtcagggtg 131160
gaggcacagg tagggtcgtt acacagcgcc aggacccatc ccctggcgct ggcgtagctg 131220
gcctggcagc ctgttctgag acatgtaatc agaccagaga accccgacaa ggactgtcct 131280
cgtttaagct cttccacagt caccgtggcc acctcaaagc ccgtgttctg caacgcggcc 131340
atgagcgcgt acggggcact gctcccaggc agcaccaacg cggccacacg gcgcggggag 131400
gtggggcacg aaaacaggcg cagctgactc ccaaggcaca tggcccttag gctgcccagg 131460
tgatgctcca gacgacccag gtccttcctg tgcatgtcct ccagtgggtg caggggaggc 131520
gtcaccaggt tccacatttc gtcagaaaag gaggtccatg agacttgcaa ggaagtcagg 131580
gtctcttgaa acacaactgt ctcgttctgc aaaaccgtga cgttgttgcc ttgtccctcg 131640
gggccaacgg tgcccagtgg gtgtgccacg cagcggtagt ccctggccgc ccgcagcacc 131700
tctgacaagt gtacctgggg cacctcaacc agtgccccag gggtctctga aaccataagt 131760
tcgagcgggt tagggtgggc gggtagtgag agctgcagtc ccctgcagcc ggccagggcc 131820
atctcgattg cagatgggag aagccctccg tcccctatgt cgtgcccaga tacaatgagc 131880
ctcttggaca tcaggtactt aacaagcatg aacaggctgg cgaccgtgga cgggttcaga 131940
gggggtattg ggtgcctgga tgccaggaag ttgtgctcga aggtggaccc ggctatgaga 132000
cagctctgat tcacggccag gtataccagg gcgttgcctt cgacctttac gtccggggtg 132060
accctgtatc tggatccctt gacctcggcc cagctggtaa acaccaccga gttgaaggga 132120
aggacctcca ccgtttcttg ctgttgtgtg atgcgcacat ggcgctccga aagcgtcgga 132180
gagctggcag ccgaggagat ggacagtgcc actcccagct cccggcagaa ttccttgcag 132240
gcgaagaggc actcctgtag gaggccggct tggtggtcct ctggactcca cgccacggcg 132300
ccagttagca ctacgtcctg gagcttggac acgggactga acatgaggtt ggtgagagcc 132360
tcggtgatgg cataggtggc cccggtggat acattagtag ccatcttgta ggcctgctcc 132420
cccatggcca ttgcctgacc cctccacgct ggcactggaa gcagctcctg gggcagggcc 132480
ttcacccagg tctcgaagtc cttgtgtagg aggttggcca tggacggagt gatggcctcc 132540
accgtgtcgg gcactctggg cgccaccctc tcggccagca tggacgagtg cagcaccagg 132600
tggtagtctg aaaccggtat gtccaggggt cccacgccag cctgttgggc gatgaggccg 132660
ttggagcatc ggtccatgtg tcgcgtaaag aactccttgc tgccaaccgt cgagtggcga 132720
agtaactggt ggattgtgga gccggtggca aaaaggcccc agtcaacatc ctcggggtgc 132780
cccgagacgc ggacaccatc ggacagcgcc agccaggggg acgggggggt ggacgacggc 132840
tggtctacag agaagaccct cgtggtctcc ccggtcaggt cgtctactat tctgatgcct 132900
gggtgctccg aggtcctccc gaggaccgtt acctggcacg cgcacaggcg cgcggcgcgc 132960
tgcagtacct ccaacggggt ctcgcccaga tccccaggca ccgcgcccga ctctgccacc 133020
accgcaaaca ccagggagca atacacgttg agaaagtgct ctgccaccgc cgccttcacg 133080
gcatccggac cggccgcggg atccgcaggc aggtgggtgc gcacctcgtc gggtagcttg 133140
gagacaaaca gctccaggcc ggtccgcggc gccagcgcct gcaggtgcct caccaccggg 133200
gccgggtcat gcgatctgtt tagtccggag aagatagggc ccttggcaag ccgctggacc 133260
agcttcaggg tctccaagat gcgcaccgca ttgtcggagc tgtcgcgata gaggttaggg 133320
taggtgtccg gtccatccgt gggctcaaac ctgcccagac acaccactgt ctgctggggg 133380
atcatccttc tcagggagat gcattctttg gaagtagtgg tagagatgga gcagactgcc 133440
agggcgttgc caggagtggt ggcgatggtg cgcaccgttt ttaagaaacc ccccagggtg 133500
gggactcccg ctccctgcag catctcggcc tgctgtacgc ccttggcgaa tatgcgacgg 133560
aatcggctgt gcgcacgggg tcccagggcc ggttcggtgg catacaggcc ggtgagggcc 133620
ccctgtgtct gtccgcctgg aaacagggtg ctgtgaaaca gcaggttgcc aaggccgcga 133680
atacccctct gcacgctgct gtggacgtgg gtgtacgctc cgtggatccc gaacgcctgt 133740
ctggcacagt tccagggcca ccgttccatg gtgcatcttc ccggtatcac aaagtacctg 133800
gccacgttat aattgtcccc ggttgaagcc tgcaccgcca gcggtagcag gtctgccccc 133860
agggatatca taacagcctg cataatgaca tcatcttcaa tgtgtggcct agccacgggc 133920
tggggaccct cgggcacttc caacccctcg tacggtacca ggtcggtatt ttgtgtaaat 133980
gccctgataa actgaggtgg gtgtggttct agcagggtct gtgtgatttt ggacaccagg 134040
tgcctgccca cttccactct agcccactcc tgcaatccta gctcttgcag cagaactgca 134100
agctctgttg acaatgttgt gggccggtgg tgcatgtttg gcccgtagcc aaaggataca 134160
acacgctcgc tcccccgtgg cacagaccgc ctgatgacat ggggatatcc aaggagcggt 134220
gacagcacag cgagcaccgt ctgtatttcc acatcccgtc tctctcgctc ctccctcgaa 134280
gtgggaggtc ttcggaaagt tatccatagc agatagtagc ctccggtgcc accgggtacg 134340
agagtgagtg tgcccgtacg gcttgtataa aagttcacaa aagcttcctc atccgcggtg 134400
agatcactct ccaaccacag cccagtgacg tcgtaggcca tgcctagagg gcgcaccgcc 134460
cccggggaca ccctctgtag tcaggctgcc gagaaacccg cgagatctct ggggagtagg 134520
aagaaactta gaatccccaa atatgtcgca gtcacaggtt gtcgggcaga gtctgtttcc 134580
gctttcatgg gatccacagt tacttgtagc catgtcacta acctcaaata ctcaaaaaaa 134640
gctatcgatg gaaaaatgct gtggtcctag gttagtccgt gggaaacaaa acttcctcat 134700
acacttcatc tgcaggctga aatggtggcg gatccagact ccttacacca cagttgctca 134760
cattagagat acctgattgg ttaatacaag cggacgcacg cgttggtgga ggcgtgttgt 134820
cgcccaagat actagcatag gtgactgtgc gttcgctatg tagttgctgc atttcaagtt 134880
gggtcgttac ttctgtgttg caaaccctta ctggagataa tgccatgtct gttgtggaac 134940
ttaaaatacg cgagtgtata acatttctag atggtagagg tggtaaacgg cgagctaaat 135000
gattaacatc gggacatatc ctgcctgcat gagcatgtgg tgtgtcgtgt ggtgtatata 135060
ttggtaatct tgttgttaca ttgttgaacg acacaagtct gctctctcgg tagagataac 135120
ccaccagtac ggcttggcca gtacctaata agaaaaaata aaatcgttaa tctctgtttt 135180
tatgtggcgc tggtgttcca attataaata aaaacacaac tcacttaata tcacaattac 135240
acaaatcagt cctgaagtaa cacctgtagt ccaaccgtca gtgtagagca ggactaactt 135300
aacacagcat ccagcacatg tccatgctaa ggaaataaac caaagttatg tttcggtttg 135360
ctttatgacc agggagctgc tacccaggta caaaaaatcc ttacccaaaa atagaaacag 135420
gaagccacca gagagtgaag ctttgtgaaa gctttgccag cagaagaaac aatataataa 135480
aaagccacag cctgctagta atgttatact ccctgtaaat aaaaaatatg gacagtaata 135540
atttatgaca cccaataagt atgtggaaaa aatgtaatgt aaaccactat actggtaaaa 135600
acataccttc gttattggtg tcttgttcgc gctttataaa cagtatccct attgttgtgg 135660
ttagtgtaac caacactcct ccttgtaaaa gtaaaaatga cataagcccc ttagttgatc 135720
caatccaatg tcgtttcatt gttataaaca agccggtcat acctgtaata aagttattca 135780
ttacaaaatg ttataatagt attggtaatg tttagttaag ataatgtaaa cttcacagta 135840
gtcatatacc aatatgtatg cagcttatgc atcctgcgat gattacagaa aggcatgaat 135900
gggaaacgca aaaaaaggcc ggtgttgcct tgagtatacc tgtagtaaaa aataaataat 135960
attgttggtt gcaatgctta ggtgcaagca gacataattg catagcagta aaaaccagac 136020
ttaccaccac atattgcaaa cacacatgca gcgagcttga gacaaggccc attatctgtt 136080
gcaaagatat gtataaaaaa aacaagcaac aatgtccata atggcaaaaa aaactggcaa 136140
tgtgtccagt tgttgtaaat ctgcaatccc attgagaata taagtaccaa caccataaca 136200
atgcacagta atccgctatc aatagtgcat ttaacgactc ttaatgttcc accaagtgat 136260
agaatggctg aaaaacacat acaggggaat tacgtttttt taaaaaattg gaaatattag 136320
atacataatt tttatttaat aaaaaacctt tagtaaaact taccagtaat tatagacaat 136380
aaacttataa tacaaacaca aacagtactc aaagtacttt gagtagagaa actccaactg 136440
gcaaaggcaa tacatcctaa aacaaaagac aaatacacga gacatttaaa caatgtatac 136500
ttagaaagaa ataagttaaa catttaaaaa atgtaactta ccaacaatta tagatggtcc 136560
aatgggaggg gaagcttgaa aacgttgttt ttttgactgc acatatatgt tgttattgta 136620
caaaaaagtt ggtagtaaac acttatgtta ctgagcaaaa atatggtgtt ttgtaaattt 136680
atagttaaaa gacaaaacat aatagacaaa cacccacaac atgttataag tgctgcaaac 136740
caagtacccc acaggtattt tttgtaattc attgtagaca aaaagcccaa ggcccaaaaa 136800
tgaagtggac aaaagaaata tgtaattaag tgtagttgga caaggaatta tatagctgga 136860
tgagttagtt ttgcacagaa ccagacatcc tatttttgtt tggaaaccta aaatccggat 136920
gaagggctta taaaatggca cagctgcaaa aagctgataa tgtaacactg catcctggtg 136980
tttttgattg tagcggaaaa atgtaataaa ttttacagac agttttgcct actgagaaca 137040
tgttgaaaaa aaggcactaa gggctttttt gccaaaggaa aaatgccccc gtggggttag 137100
gggaaagggg ggatggggtg atgggggaat ggtgggaaag gggggatggg gtgatggggg 137160
aatggtggga aaggggtgat ggggtgatgg gggaatgggg ggaaaggggg aatgggggga 137220
aagggggaat ggggggaaag ggggaatggg gggaaagggg ggatgggggg aaagggggaa 137280 tgggggggaaa gggggaatgg ggggaaaggg gggatggggg gaaaggggga atgggggaa 137340 aggggggatg gggggaaacg ggggatgggg ggaaaggggg gatggggggg aaaggggga 137400 tgggggggaa aggggggatg gggggaaag gggggatggg ggggaaaggg gggatgggga 137460
aggggggggg gagggggaag ggggtgaagg gggaaggggg gaggcgaa 137508

<210> SEQ ID NO 60
<211> LENGTH: 3043
<212> TYPE: DNA
<213> ORGANISM: Homo sapiens

<400> SEQUENCE: 60
ttctcagagt ggctgcagtc tcgctgctgg atgtgcacat ggtggtcatt ccctctgctc 60
acaggggcag gggtcccccc ttactggact gaggttgccc cctgctccag gtcctgggtg 120
ggagcccatg tgaactgtca gtggggcagg tctgtgagag ctcccctcac actcaagtct 180
ctctcacagt ggccagagaa gaggaaggct ggagtcagaa tgaggcacca gggcgggcat 240
agcctgccca aaggcccctg ggattacagg caggatgggg agccctatct aagtgtctcc 300
cacgccccac cccagccatt ccaggccagg aagtccaaac tgtgcccctc agagggaggg 360
ggcagcctca ggcccattca gactgcccag ggagggctgg agagccctca ggaaggcggg 420
tgggtgggct gtcggttctt ggaaaggttc attaatgaaa acccccaagc ctgaccacct 480
agggaaaagg ctcaccgttc ccatgtgtgg ctgataaggg ccaggagatt ccacagttca 540
ggtagttccc ccgcctccct ggcattttgt ggtcaccatt aatcatttcc tctgtgtatt 600
taagagctct tttgccagtg agcccagcta cacagagaga aaggctaaag ttctctggag 660
gatgtggctg cagagcctgc tgctcttggg cactgtggcc tgcagcatct ctgcacccgc 720
ccgctcgccc agccccagca cgcagccctg ggagcatgtg aatgccatcc aggaggcccg 780
gcgtctcctg aacctgagta gagacactgc tgctgagatg gtaagtgaga gaatgtgggc 840
ctgtgctagg caccagtggc cctgactggc cacgcctgtc agcttgataa catgacattt 900
tccttttcta cagaatgaaa cagtagaagt catctcagaa atgtttgacc tccaggtaag 960
atgcttctct ctgacatagc tttccagaag cccctgccct ggggtggagg tggggactcc 1020
attttagatg gcaccacaca gggttgtcca ctttctctcc agtcagctgg ctgcaggagg 1080
agggggtagc aactgggtgc tcaagaggct gctggccgtg cccctatggc agtcacatga 1140
gctcctttat cagctgagcg gccatgggca gacctagcat tcaatggcca ggagtcacca 1200
ggggacaggt ggtaaagtgg gggtcacttc atgagacagg agctgtgggt ttggggcgct 1260
cactgtgccc cgagaccaag tcctgttgag acagtgctga ctacagagag gcacagaggg 1320
gtttcaggaa caacccttgc ccacccagca ggtccaggtg aggccccacc cccctctccc 1380

-continued

```
tgaatgatgg ggtgagagtc acctccttcc ctaaggctgg gctcctctcc aggtgccgct   1440
gagggtggcc tgggcggggc agtgagaagg gcaggttcgt gcctgccatg gacagggcag   1500
ggtctatgac tggacccagc ctgtgcccct cccaagccct actcctgggg gctgggggca   1560
gcagcaaaaa ggagtggtgg agagttcttg taccactgtg ggcacttggc cactgctcac   1620
cgacgaacga cattttccac aggagccgac ctgcctacag acccgcctgg agctgtacaa   1680
gcagggcctg cggggcagcc tcaccaagct caagggcccc ttgaccatga tggccagcca   1740
ctacaagcag cactgccctc caaccccggt gagtgcctac ggcagggcct ccagcaggaa   1800
tgtcttaatc tagggggtgg ggtcgacatg gggagagatc tatggctgtg gctgttcagg   1860
accccagggg gtttctgtgc caacagttat gtaatgatta gccctccaga gaggaggcag   1920
acagcccatt tcatcccaag gagtcagagc cacagagcgc tgaagcccac agtgctcccc   1980
agcaggagct gctcctatcc tggtcattat tgtcattacg gttaatgagg tcagaggtga   2040
gggcaaaccc aaggaaactt ggggcctgcc caaggcccag aggaagtgcc caggcccaag   2100
tgccaccttc tggcaggact ttcctctggc cccacatggg gtgcttgaat tgcagaggat   2160
caaggaaggg aggctacttg gaatggacaa ggacctcagg cactccttcc tgcgggaagg   2220
gagcaaagtt tgtggccttg actccactcc ttctgggtgc ccagagacga cctcagccca   2280
gctgccctgc tctgccctgg gaccaaaaag gcaggcgttt gactgcccag aaggccaacc   2340
tcaggctggc acttaagtca ggcccttgac tctggctgcc actggcagag ctatgcactc   2400
cttggggaac acgtgggtgg cagcagcgtc acctgaccca ggtcagtggg tgtgtcctgg   2460
agtgggcctc ctggcctctg agttctaaga ggcagtagag aaacatgctg gtgcttcctt   2520
cccccacgtt acccacttgc ctggactcaa gtgtttttta tttttctttt tttaaaggaa   2580
acttcctgtg caacccagat tatcaccttt gaaagtttca aagagaacct gaaggacttt   2640
ctgcttgtca tcccctttga ctgctgggag ccagtccagg agtgagaccg gccagatgag   2700
gctggccaag ccggggagct gctctctcat gaaacaagag ctagaaactc aggatggtca   2760
tcttggaggg accaaggggt gggccacagc catggtggga gtggcctgga cctgccctgg   2820
gcacactgac cctgatacag gcatggcaga agaatgggaa tattttatac tgacagaaat   2880
cagtaatatt tatatattta tatttttaaa atatttattt atttatttat ttaagttcat   2940
attccatatt tattcaagat gttttaccgt aataattatt attaaaaata tgcttctact   3000
tgtccagtgt tctagtttgt ttttaaccat gagcaaatgc cat                     3043
```

CANCER IMMUNOTHERAPY WITH A VIRAL ANTIGEN-DEFINED, IMMUNOMODULATOR-SECRETING CELL VACCINE

CROSS REFERENCE TO RELATED PATENT APPLICATIONS

This application is a Divisional of co-pending U.S. patent application Ser. No. 10/528,311, filed Mar. 24, 2006, which is a U.S. Nationalization under 35 U.S.C. §371 of international application no. PCT/US03/29684, filed Sep. 19, 2003, which claims priority under 35 U.S.C. §119(e) to U.S. Provisional Patent Application No. 60/411,990, filed Sep. 19, 2002, all of which applications are expressly incorporated herein by reference in their entireties.

STATEMENT REGARDING FEDERALLY SPONSORED RESEARCH AND DEVELOPMENT

This invention was made, in part, as a result of funding from the National Cancer Institute (NCI) Supplement through the University of Alabama for work sponsored by the AIDS Malignancy Consortium, grant no. 3U01CA70019-0751, from the NCI through Project 4, EBV Malignancies, Bone Marrow Transplantation in Human Disease, grant no. PO1 CA15396-28, and from the NCI through grant no. P50 CA 96888. Therefore, the U.S. government may have certain rights in the invention.

FIELD OF THE INVENTION

The present invention relates to cancer immunotherapy and cancer vaccine development.

BACKGROUND OF THE INVENTION

Despite ongoing efforts to define immunologically relevant tumor antigens, very little is known about most tumor rejection antigens for the majority of human cancers. Consequently, most cancer vaccine approaches currently use tumor cells as a source of antigen. Early generations of cell-based cancer vaccines have consisted of killed tumor cells or tumor cell lysates mixed with adjuvants, such as Bacillus Calmette Guerin (BCG) and *Corynebacterium parvum*, in an attempt to amplify tumor-specific immune responses (Berd et al., J. Clin. Oncol. 8: 1858-1867 (1990)). Subsequently, genetically modified tumor vaccines replaced the most complex and inconsistent mixtures of tumor cells and bacteria. Currently, the most popular genetically modified cell-based vaccines take advantage of the large set of cloned genes encoding cytokines and co-stimulatory molecules (Pardoll, Ann. Rev. Immunol. 13: 399-415 (1995)).

Among the different cytokines used to modify tumor immunogenicity, granulocyte-macrophage colony stimulating factor (GM-CSF) appears to be the most potent (Dranoff et al., PNAS USA 90: 3539-3543 (1993)). GM-CSF induces the differentiation of primitive hematopoietic precursors into dendritic cells (DC), a type of antigen-presenting cell (APC) that initiates the most potent T-cell responses (Banchereau et al., Nature 392 (6673): 245-252 (1998)) and promotes DC recruitment and differentiation at the site of vaccination. Thus, DC play a central role in priming immunological response.

GM-CSF-secreting cellular vaccines have been shown to eradicate small, pre-established tumors in mice (Dranoff et al., supra; and Levitsky et al., J. Immunol. 156: 3858-3865 (1996)). Furthermore, promising results have been obtained in human patients afflicted with melanoma (Soiffer et al., PNAS USA 95: 13141-13146 (1998)), prostate and renal cell carcinoma (Simons et al., Cancer Res. 59: 5160-5168 (1999); and Simons et al., Cancer Res. 57: 1537-1546 (1997)), and pancreatic cancer (Jaffee et al., J. Clin. Oncol. 19: 145-156 (2001)). These trials consistently demonstrated systemic anti-tumor immunity in patients and suggest an improvement in overall survival in those patients in whom evidence of vaccine efficacy was demonstrated by the development of tumor-specific delayed type hypersensitivity (DTH) responses (Jaffee et al., supra).

Unfortunately, modification of autologous tumor cells to express a cytokine, such as GM-CSF, is highly individualized, expensive, and labor-intensive. Therefore, simpler approaches that maintain the immunological activity of paracrine cytokine production have been developed. One such approach utilizes a universal bystander cell line altered to produce a large and stable amount of GM-CSF (see, e.g., Levitsky et al., U.S. Pat. No. 6,464,973 and Int'l Pat. App. No. PCT/US99/02253) in combination with an antigen of the cancer to be treated, such as, for example, tumor cells isolated from the patient (Borrello et al., Hum. Gene Ther. 10: 1983-1991 (1999); Borrello et al., Blood 95: 3011-3019 (2000)). This approach obviates the need for in vitro passaging or modification, such as by transduction, of each patient's tumor cells, thereby guaranteeing a constant amount of cytokine production without any intra- or inter-patient variability, while utilizing the patient-specific antigenic repertoire. An allogeneic, GM-CSF-secreting human erythroleukemia cell line, namely K562, is currently being used in two phase I trials at Johns Hopkins University for vaccination of multiple myeloma and acute myelogenous leukemia (AML), in combination with irradiated autologous tumor cells.

Vaccination of mice afflicted with lymphoma with a mixture of autologous tumor cells and GM-CSF-producing MHC class I- and MHC class II-negative cells, namely B78H1/GM-CSF cells, primed an anti-tumor immune response. The anti-tumor immune response was equivalent to or better than those achieved using autologous tumor cells directly transduced to secrete GM-CSF.

GM-CSF-secreting cellular vaccines, which are currently in use, are not specific for a defined tumor antigen. Hence, it is not possible to target such vaccines and evaluate fully their anti-tumor immune responses. It is an object of the present invention, therefore, to provide a GM-CSF-secreting cellular vaccine that is specific for a defined tumor antigen. Such a vaccine will enable one to evaluate more fully anti-tumor immune responses. This and other objects and advantages of the present invention, as well as additional inventive features, will become apparent from the detailed description provided herein.

BRIEF SUMMARY OF THE INVENTION

The present invention provides a human cell line, which lacks major histocompatibility class I (MHC-I) antigens and major histocompatibility class II (MHC-II) antigens and which has been modified to comprise and express (i) a nucleotide sequence encoding an immunomodulator and (ii) a nucleotide sequence encoding an antigen of Epstein-Barr virus (EBV). Further provided is a composition comprising a human cell line, which lacks MHC-I and MHC-II antigens and which has been modified to comprise and express a nucleotide sequence encoding an immunomodulator, and a human cell line, which lacks MHC-I and MHC-II antigens and which has been modified to comprise and express a nucleotide sequence encoding an antigen of EBV. Still further provided is a composition comprising an immunomodulator and a human cell line, which lacks MHC-I and MHC-II antigens and which has been modified to comprise and express a nucleotide sequence encoding an antigen of EBV.

Also provided by the present invention is a method of inducing or stimulating an immune response in a human to an EBV-associated cancer. The method comprises administering to the human the aforementioned human cell line or one of the aforementioned compositions in an amount sufficient to induce or stimulate an immune response to the antigen of EBV expressed by the human cell line, whereupon an immune response to the EBV-associated cancer is induced. Alternatively, a human cell line, which lacks MHC-I and MHC-II antigens and which has been modified to comprise and express a nucleotide sequence encoding an immunomodulator, and a human cell line, which lacks MHC-I and MHC-II antigens and which has been modified to comprise and express a nucleotide sequence encoding an antigen of EBV, can be administered, simultaneously or sequentially in either order, by the same or different routes, to the human in amounts sufficient to induce or stimulate an immune response to an EBV-associated cancer. Also, alternatively, an immunomodulator and a human cell line, which lacks MHC-I and MHC-II antigens and which has been modified to comprise and express a nucleotide sequence encoding an antigen of EBV, can be administered, simultaneously or sequentially in either order, by the same or different routes, to the human in amounts sufficient to induce or stimulate an immune response to an EBV-associated cancer.

BRIEF DESCRIPTION OF THE DRAWINGS

FIG. 3 is a compilation of various nucleotide (genomic, mRNA, cDNA; etc.) sequences that can be used in the context of the present invention.

DETAILED DESCRIPTION OF THE INVENTION

Figure 1:
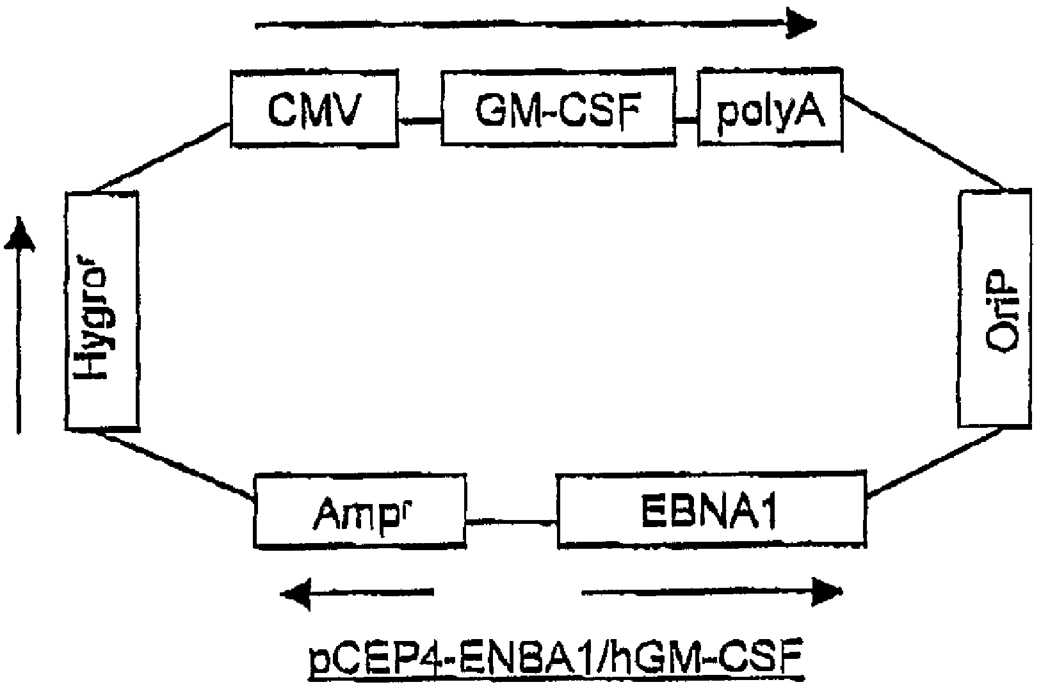
FIG. 1 is a diagram of a bi-cistronic plasmid (arrows indicate direction of transcription) containing the human GM-CSF gene (GM-CSF) operably linked to the CMV promoter (CMV) and a polyA tail (polyA), a hygromycin resistance gene (Hygro.sup.r), an EBV EBNA1 gene (EBNA1), an EBV origin of replication (OriP), and an ampicillin resistance gene (Amp.sup.r). The plasmid is designated pCEP4-EBNA1/hGM-CSF.

The present invention provides a human cell line, which lacks MHC-I antigens and MHC-II antigens and which has been modified to comprise and express (i) a nucleotide sequence encoding an immunomodulator and (ii) a nucleotide sequence encoding a viral antigen, in particular an antigen of a virus associated with a disease, such as cancer, e.g., EBV, human papilloma virus (HPV), or Kaposi sarcoma herpes virus (KSHV; also known as human herpes virus 8 (HHV8)). The human cell line can be any suitable cell line. Theoretically, any human cell line that is capable of paracrine production of an immunomodulator can be used. The capacity for paracrine production of an immunomodulator is not required when the cell line will not be used to express an immunomodulator in accordance with certain embodiments of the present invention as set forth herein.

The cell line can naturally lack MHC-I and MHC-II antigens or it can be manipulated or modified so that it does not express MHC-I and MHC-II antigens. In this regard, it will be understood by one of ordinary skill in the art that a cell line is deemed to lack MHC-I and MHC-II antigens if it does not constitutively express such antigens under normal biological conditions. However, a cell line that does not constitutively express MHC-I and MHC-II antigens can, under certain artificially created conditions, such as conditions that can be created in vitro, be induced to express MHC-I and/or MHC-II antigens. Such cell lines are considered to lack MHC-I and MHC-II antigens for purposes of the present invention. Likewise, cells having inactivated MHC antigens are also considered to lack such antigens for purposes of the present invention.

The cell line preferably grows in defined medium. One of ordinary skill in the art appreciates that defined medium is medium, the composition of which is known. In other words, the identity and amount of each and every component of the medium is known. Defined medium does not contain serum inasmuch as the composition of serum is undefined. Preferably, the cell line grows as a suspension.

A preferred human cell line for modification in accordance with the present invention is K562, which is deposited with the American Type Culture Collection (ATCC) as CCL-243. The K562 cell line is described by Lozzio et al., Blood 45(3): 321-334 (1975), and Klein et al., Int. J. Cancer 18: 421-431 (1976). Other suitable human cell lines include, but are not limited to, SK-MEL-33 (Wang et al., J. Clin. Invest. 91: 684-692 (1993)) and various melanoma cell lines (Ferrone et al., Immunol. Today 16(10): 487-494 (1995); K. ageshita et al., Cancer Res. 53(14): 3349-3354 (1993); and Wang et al., Tissue Antigens 47(5): 382-390 (1996)).

A human cell line that expresses MHC-I antigens can be modified so that it does not express such antigens in any of a number of different ways. For example, one can interfere with the expression and/or transport of the .alpha. chain. A human cell line that expresses MHC-II antigens also can be modified in various ways so that it does not express such antigens. For example, one can interfere with the expression and/or transport of the .alpha. chains and the .beta. chains. MHC-I and -II antigens also can be inactivated for purposes of the present invention. This can be accomplished in a variety of ways (see, for example, U.S. Pat. No. 5,574,205). For example, a "dominant negative" can be created. A single modified .beta.sub.2 microglobulin gene, whose protein product effectively complexes with MHC-I molecules and acts as a decoy, thereby preventing the insertion of MHC-I antigens into the membrane, can be overexpressed. A similar approach can be used with respect to MHC-II antigens by overexpressing modified genes encoding defective .alpha. or .beta. subunits that complex with the host cells' subunits, thereby rendering them nonfunctional. Transfection, retroviral infection or homologous recombination can be used to achieve expression of modified MHC or .beta.sub.2 microglobulin genes or inactivation of genes.

Levels of MHC-I antigen on the cell surface can be reduced by introducing into cells a sequence encoding adenoviral E19 protein by transfection or retroviral infection. The protein forms complexes specifically with MHC-I antigens in the rough endoplasmic reticulum preventing normal transport of MHC-I molecules to the plasma membrane (Andersson et al., Cell 43: 215-222 (1985); and Pabo et al., Advances in Cancer Research 42: 151-163 (1989)).

In addition to lacking MHC-I and MHC-II antigens, the human cell line is modified to comprise and express a nucleotide sequence encoding an immunomodulator and a nucleotide sequence encoding a viral antigen. By "modified" is meant the introduction into the cell line of a nucleic acid molecule, e.g., a vector, comprising a nucleotide sequence encoding a gene product, which, in the context of the present inventive cell line, is an immunomodulator or an antigen, such as an antigen of EBV, HPV, or KSHV, in operable linkage with a promoter and, as required for expression, various other regulatory sequences. Either the immunomodulator is not expressed in the cell line or, as a result of the introduction of the nucleic acid molecule is now expressed at a greater level.

A "vector" encompasses a nucleic acid molecule, such as a plasmid, virus or other vehicle, which contains one or more heterologous or recombinant nucleotide sequences, e.g., a nucleotide sequence encoding an immunomodulator and/or a nucleotide sequence encoding an antigen of EBV, HPV or KSHV, wherein the nucleotide sequences can be under the control of the same or different functional promoters, alone or in further combination with enhancer(s), and that is capable of functioning as a vector as that term is understood by those of ordinary skill in the art.

Any suitable vector can be employed that is appropriate for introduction of nucleic acids into eukaryotic cells, or more particularly animal cells, such as mammalian, e.g., human, cells. Preferably, the vector is compatible with the cell, e.g., can impart expression of the immunomodulator and/or viral antigen, and is stably maintained or relatively stably maintained in the cell. Desirably, the vector comprises an origin of replication. When an immunomodulator coding sequence or viral antigen coding sequence is transferred (i.e., as opposed to an immunomodulator gene having its own promoter or a viral antigen gene having its own promoter), optimally the vector also contains a promoter that can drive expression of the coding sequence and that is operably linked to the coding sequence. A coding sequence is "operably linked" to a promoter (e.g., when both the coding sequence and the promoter together constitute a native or recombinant immunomodulator gene or viral antigen gene) when the promoter can direct transcription of the coding sequence.

Appropriate viral vectors include, but are not limited to simian virus 40, bovine papilloma virus, Epstein-Barr virus, adenovirus, herpes virus, vaccinia virus, Moloney murine leukemia virus, Harvey murine sarcoma virus, murine mammary tumor virus, and Rous sarcoma virus. Any plasmid suitable for use in a eukaryote, in particular a mammal, e.g., a human, can be used in the context of the present invention. Desirably, the plasmid comprises a promoter, such as the cytomegalovirus promoter, an origin of replication, such as the SV40 origin of replication, a selectable marker, such as antibiotic resistance, and provides for mRNA with poly A tails. A preferred example of a plasmid is pCEP4 (See Examples 1 and 3).

Reference to a vector or other DNA sequences as "recombinant" merely acknowledges the linkage of DNA sequences, which are not typically conjoined as isolated from nature. A "gene" is any nucleic acid sequence coding for a protein or a nascent mRNA molecule. Whereas a gene comprises coding sequences and non-coding (e.g., regulatory) sequences, a "coding sequence" does not include any non-coding DNA. As used herein, "gene" or "coding sequence" includes genomic or cDNA sequences, greater and lesser sequences and mutations thereof, whether isolated from nature or synthesized in whole or in part, as long as the gene or coding sequence can express a protein having the characteristic function of the immunomodulator, i.e., the ability to stimulate the host immune response, or the characteristic antigenicity of an antigen of a virus. The means of modifying genes or coding sequences are well-known in the art, and also can be accomplished by means of commercially available kits (e.g., New England Biolabs, Inc., Beverly, Mass.; Clontech, Palo Alto, Calif.).

A "promoter" is a DNA sequence that directs the binding of RNA polymerase and thereby promotes RNA synthesis. "Enhancers" are cis-acting elements of DNA that stimulate or inhibit transcription of adjacent genes. An enhancer that inhibits transcription also is termed a "silencer." Enhancers differ from DNA-binding sites for sequence-specific DNA binding proteins found only in the promoter (which also are termed "promoter elements") in that enhancers can function in either orientation, and over distances of up to several kilobase pairs (kb), even from a position downstream of a transcribed region.

The "immunomodulator" can be any suitable immunomodulator, such as a cytokine, a chemokine or an adjuvant, for example, obtained from any suitable source, such as a mammal, e.g., a human. Desirably, the immunomodulator induces or stimulates an immune response to the viral antigen expressed by the cell line. Cell-targeting means also can be considered immunomodulators Likewise, antibodies (or antigenically reactive fragments thereof), antisense molecules, dsRNAi, and the like also can be considered immunomodulators to the extent that they inhibit or block the ability of a viral gene product to block the action of an interferon, if so desired. For example, the EBNA-2 protein of EBV blocks signal transduction of interferons, the EBER RNA of EBV blocks activation of Ph, and BCRF1 of EBV is an IL-10 homolog that inhibits IFN-.gamma., IL-1, IL-2, and TNF synthesis.

Examples of suitable immunomodulatory cytokines include interferons (e.g., IFN.alpha., IFN.beta. and IFN-.gamma.), interleukins (e.g., IL-1, IL-2, IL-3, IL-4, IL-5, IL-6, IL-7, IL-8, IL-9, IL-10, IL-12 and IL-20), tumor necrosis factors (e.g., TNF.alpha. and TNF.beta.), erythropoietin (EPO), FLT-3 ligand, gIp10, TCA-3, MCP-1, MIF, MIP-1.alpha., MIP-1.beta., Rantes, macrophage colony stimulating factor (M-CSF), granulocyte colony stimulating factor (G-CSF), and granulocyte-macrophage colony stimulating factor (GM-CSF), as well as functional fragments of any of the foregoing. The most preferred immunomodulatory cytokine is GM-CSF, such as human GM-CSF, including a functional fragment thereof. An alternatively preferred immunomodulatory cytokine is IL-2 or a functional fragment thereof. Any immunomodulatory chemokine that binds to a chemokine receptor, i.e., a CXC, CC, C, or CX3C chemokine receptor, can be used in the context of the present invention. Examples of chemokines include, but are not limited to, Mip1.alpha., Mip-1.beta., Mip-3.alpha. (Lax), Mip-3.beta., Rantes, Hcc-1, Mpif-1, Mpif-2, Mcp-1, Mcp-2, Mcp-3, Mcp-4, Mcp-5, Eotaxin, Tarc, Elc, I309, IL-8, Gcp-2 Gro-.alpha., Gro-.beta., Gro-.gamma., Nap-2, Ena-78, Gcp-2, Ip-10, Mig, I-Tac, Sdf-1, and Bca-1 (Blc), as well as functional fragments of any of the foregoing. Examples of adjuvants include, but are not limited to, heat shock protein, CpG, Listeria monocytogenes, aluminum hydroxide (for use with soluble antigen), aluminum phosphate (alum; for use with soluble antigen), muramyl dipeptide, muramyl tripeptide, *Mycobacterium tuberculosis*, QuilA (a purified saponin from the plant *Quillaja saponaria*), alone or in further combination with glycosides, cholesterol, and/or phospholids, empty adenoviral capsids; etc. One of ordinary skill in the art will appreciate that some of these adjuvants cannot be expressed from a vector, in which case the adjuvant, when used, in combination with one or more cell lines as described herein, is administered simultaneously or sequentially, in any order, with the one or more cell lines. Preferably, the adjuvant is administered with the viral-antigen-expressing cell line or the defined viral antigen, itself. Preferably, however, the immunomodulator nucleotide sequence encodes a GM-CSF sequence, particularly a human GM-CSF gene or coding sequence, including a human GM-CSF cDNA (e.g., as described by Cantrell et al., PNAS USA 82: 6250-6254 (1985)) or genomic sequence (e.g., as described by Miyatake et al., EMBO J. 4(10): 2561-2568 (1985)).

The viral antigen can be any defined antigen of a virus that is associated with a disease, such as cancer, in a human. For example, the viral antigen can be any defined antigen of an oncogenic virus. Oncogenic viruses include, but are not limited to, RNA viruses, such as Flaviviridae and Retroviridae, and DNA viruses, such as Hepadnaviridae, Papovaviridae, specifically papillomaviruses, Adenoviridae, Herpesviridae, and Poxviridae. Desirably, the viral antigen is one to which an immune response can be induced or stimulated in a human and is universally recognized. Preferably, the antigen is from EBV, HPV, or KSHV. Examples of suitable EBV antigens for expression in a human cell line in accordance with the present invention are described, for example, in Herbst et al., PNAS USA 88: 4766-4770 (1991). Preferred antigens of EBV include, but are not limited to, Epstein-Barr nuclear antigen-1 (EBNA1), latent membrane protein 1 (LMP1), or latent membrane protein 2 (LMP2). LMP2 is an especially preferred antigen of EBV. A cell line that expresses an antigen of EBV, in particular EBNA1, LMP1 or LMP2, can be used to induce or stimulate an immune response in a human to an EBV-associated disease or cancer. In the event that immune responses are to be measured in accordance with methods set forth herein, preferably the EBV antigen is one that results in a CD8+ T-cell response that can be readily/easily measured. Examples of suitable HPV antigens for expression in a human cell line in accordance with the present invention are described, for example, in Van Ranst et al.; Virology 190(2): 587-596 (1992); and Rho et al.; Virology 203(1): 158-161 (1994). Preferred antigens of HPV include, but are not limited, E5, E6, and E7. Examples of suitable KSHV antigens for expression in a human cell line in accordance with the present invention are described, for example, in Russo et al., PNAS USA 93(25): 14862-14867 (1996). Preferred antigens of KSHV include, but are not limited to, latency nuclear antigen (LANA) and v-cyclin.

Preferably, all proper transcription, translation and processing signals (e.g., splicing and polyadenylation signals) are correctly arranged on the vector, such that the immunomodulator (viral antigen) nucleotide sequence will be appropriately transcribed and translated in the cell into which it is introduced. The manipulation of such signals to ensure appropriate expression in host cells is well within the knowledge and expertise of the ordinary skilled artisan. Whereas an immunomodulator gene is controlled by (i.e., operably linked to) its own promoter, another promoter, including a constitutive promoter, such as, for instance the adenoviral type 2 (Ad2) or type 5 (Ad5) major late promoter (MLP) and tripartite leader, the cytomegalovirus (CMV) immediate early promoter/enhancer, the Rous sarcoma virus long terminal repeat (RSV-LTR), and others, can be employed to command expression of the immunomodulator coding sequence. The CMV promoter is a preferred promoter. The same can also be said for the viral antigen gene.

Alternately, a tissue-specific promoter (i.e., a promoter that is preferentially activated in a given tissue and results in expression of a gene product in the tissue where activated) can be used in the vector. Such promoters include, but are not limited to, the elastase I gene control region, which is active in pancreatic acinar cells as described by Swift et al., Cell 38: 639-646 (1984) and MacDonald, Hepatology 7: 425-515 (1987); the insulin gene control region, which is active in pancreatic beta cells as described by Hanahan, Nature 315: 115-122 (1985); the hepatocyte-specific promoter for albumin or .alpha.sub.1-antitrypsin described by Frain et al., Mol. Cell. Biol. 10: 991-999 (1990), and Ciliberto et al., Cell 41: 531-540 (1985); and the albumin and alpha.sub.1-antitrypsin gene control regions, which are both active in liver as described by Pinkert et al., Genes and Devel. 1: 268-276 (1987), and Kelsey et al., Genes and Devel. 1: 161-171 (1987).

Similarly, a tumor-specific promoter, such as the carcinoembryonic antigen for colon carcinoma described by Schrewe et al., Mol. Cell Biol. 10: 2738-2748 (1990), can be used in the vector. Along the same lines, promoters that are selectively activated at different developmental stages (e.g., globin genes are differentially transcribed in embryos and adults) can be employed for gene therapy of certain types of cancer.

Another option is to use an inducible promoter, such as the IL-8 promoter, which is responsive to TNF, or the 6-16 promoter, which is responsive to interferons, or to use other similar promoters responsive to other cytokines or other factors present in a host or that can be administered exogenously. Use of a cytokine-inducible promoter has the added advantage of allowing for auto-inducible expression of a cytokine gene. According to the invention, any promoter can be altered by mutagenesis, so long as it has the desired binding capability and promoter strength.

Various methods can be employed for delivering a nucleic acid molecule, e.g., a vector, to a cell in vitro. For instance, such methods include electroporation, membrane fusion with liposomes, high velocity bombardment with DNA-coated microprojectiles, incubation with calcium phosphate-DNA precipitate, DEAE-dextran mediated transfection, infection with modified viral nucleic acids, direct microinjection into single cells, and the like. Other methods are available and are known to those skilled in the art. The immunomodulator and the EBV antigen can be encoded on the same or different nucleic acid molecules.

If the cell line is to be used in the context of cancer immunotherapy, the immunomodulator desirably is one that induces or stimulates an immune response against a cancer cell or a cancer antigen, i.e., any protein, carbohydrate or other component that can elicit an immune response, in particular, a defined viral antigen as expressed by a cell line in accordance with the present invention. An inhibitory cytokine or a cytokine that prevents priming cannot be used in the context of cancer immunotherapy. While the nucleic acid molecule preferably encodes a single immunomodulator, the nucleic acid molecule can encode two or more immunomodulators, which can be of the same type, e.g., both cytokines, such as cytokines that act synergistically, or of different types, e.g., a cytokine and an adjuvant.

For purposes of identification and selection, preferably the nucleic acid molecule comprising a nucleotide sequence encoding an immunomodulator operably linked to a promoter and/or a nucleotide sequence encoding a viral antigen operably linked to a promoter further comprises a nucleotide sequence encoding a selectable marker operably linked to a promoter. In other words, the nucleotide sequence encoding the immunomodulator, the nucleotide sequence encoding the viral antigen, and the nucleotide sequence encoding the selectable marker can be on the same nucleic acid molecule or on different nucleic acid molecules in various combinations. Likewise, the nucleotide sequences can be under the control of the same or different promoters.

Preferably, the selectable marker is an antibiotic resistance gene, such as hygromycin resistance. When the selectable marker is hygromycin resistance, preferably the cell line is selected by growth in a culture medium comprising at least about 400 .mu.g/ml hygromycin, more preferably at least about 1,000 .mu.g/ml hygromycin.

A composition or implant, either one of which comprises an above-described cell line and which is appropriate for administration in vivo, can comprise appropriate carriers or diluents, which further can be pharmaceutically acceptable. The means of making such a composition or an implant have been described in the art, see, for instance, Remington's Pharmaceutical Sciences, 16th Ed., Mack, ed. (1980). Use of a balanced salt solution, such as Hanks' balanced salt solution, is preferred in the composition.

Alternatively, the composition can comprise a human cell line, which lacks MHC-I and MHC-II antigens and which has been modified to comprise and express a nucleotide sequence encoding an immunomodulator, and a human cell line, which lacks MHC-I and MHC-II antigens and which has been modified to comprise and express a nucleotide sequence encoding an antigen of a virus that causes disease or cancer, such as an antigen of EBV, HPV or KSHV. Also, alternatively, the composition can comprise an immunomodulator and a human cell line, which lacks MHC-I and MHC-II antigens and which has been modified to comprise and express a nucleotide sequence encoding an antigen of a virus that causes disease or cancer, such as an antigen of EBV, HPV or KSHV.

In pharmaceutical dosage form, a composition can be used alone or in appropriate association, as well as in combination, with other pharmaceutically active compounds as are known in the art.

A composition of the present invention can be provided in unit dosage form, wherein each dosage unit contains a predetermined amount of the composition, alone or in appropriate combination with other active agents. The term "unit dosage form" as used herein refers to physically discrete units suitable as unitary dosages for human and other mammalian subjects, each unit containing a predetermined quantity of the composition of the present invention, alone or in combination with another active agent, calculated in an amount sufficient to produce the desired effect, in association with a pharmaceutically acceptable diluent, carrier, or vehicle, where appropriate. The specifications for the novel unit dosage forms of the present invention depend on the particular pharmacodynamics associated with the pharmaceutical composition in the particular host.

In view of the foregoing, the present invention also provides a method of inducing or stimulating an immune response in a human to a virus associated with a disease, such as cancer. The induction or stimulation of an immune response can be prophylactic or therapeutic and use of the phrase "inducing or stimulating" is intended to cover prophylactic and therapeutic embodiments. For example, evidence is emerging that humans who have had infectious mononucleosis are at risk for developing Hodgkin's disease. Thus, the method of the present invention can be used to inhibit the onset of a virus-associated disease or virus-associated cancer/malignancy. In this regard, one of ordinary skill in the art will appreciate that, while prevention is desirable, "prophylactic" means any degree in the inhibition of the onset of virus-associated disease or virus-associated cancer inasmuch as any inhibition is beneficial. Likewise, one of ordinary skill in the art will appreciate that, while cure is desirable, "therapeutic" means any degree of inhibition/treatment of virus-associated disease or virus-associated cancer, ranging from no change in the disease or cancer, which can be beneficial inasmuch as the disease or cancer does not get worse, to a lessening or an improvement of the disease or a reduction in cancer (size of a tumor and/or number of tumor) or an inhibition of metastasis of the cancer.

In particular, the present invention provides a method of inducing or stimulating an immune response to an EBV-associated disease or cancer, in particular an EBV-associated cancer. Likewise, the present invention provides a method of inducing or stimulating an immune response to a KSHV-associated disease or cancer, such as a KSHV-associated cancer, and a method of inducing or stimulating an immune response to an HPV-associated disease or cancer, in particular an HPV-associated cancer. The method comprises administering to the human an above-described human cell line in an amount sufficient to induce or stimulate an immune response to the virus-associated disease or cancer, e.g., malignancy. Upon administration of the cell line, an immune response to the virus-associated disease or cancer, e.g., malignancy, is induced or stimulated.

Alternatively, a human cell line, which lacks MHC-I and MHC-II antigens and which has been modified to comprise and express a nucleotide sequence encoding an immunomodulator, and a human cell line, which lacks MHC-I and MHC-II antigens and which has been modified to comprise and express a nucleotide sequence encoding an antigen of EBV, can be administered, simultaneously or sequentially in either order, by the same or different routes, to the human in amounts sufficient to induce or stimulate an immune response to an EBV-associated cancer. Also, alternatively, an immunomodulator and a human cell line, which lacks MHC-I and MHC-II antigens and which has been modified to comprise and express a nucleotide sequence encoding an antigen of EBV, can be administered, simultaneously or sequentially in either order, by the same or different routes, to the human in amounts sufficient to induce or stimulate an immune response to an EBV-associated cancer.

Examples of EBV-associated cancers/malignancies include Burkitt's lymphoma, T-cell lymphoma, nasopharyngeal carcinoma, Hodgkin's lymphoma, B-cell lymphoma, gastric carcinoma, parotid carcinoma, breast carcinoma, and leiomyosarcoma. An example of an HPV-associated cancer/malignancy is cervical cancer. KSHV is associated with Kaposi's sarcoma, for example.

"Administering" means the actual physical introduction of the composition into or onto (as appropriate) the host. Any and all methods of introducing the composition into the host are contemplated according to the invention; the method is not dependent on any particular means of introduction and is not to be so construed. Means of introduction are well-known to those skilled in the art, and also are exemplified herein.

Any suitable route of administration can be used. Preferably, the composition is administered subcutaneously or intratumorally. One skilled in the art will recognize that, although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, intraportal, intrahepatic, peritoneal, subcutaneous, or intradermal administration. In the event that the tumor is in the central nervous system, the composition must be administered intratumorally because there is no priming of the immune system in the central nervous system.

The amount of cells to be administered to induce or stimulate an immune response to the defined viral antigen can be determined empirically (see, also, Examples 2 and 4 herein). For example, an initial low dosage of cells can be administered and the immune response to the defined viral antigen can be measured. If no immune response is induced or stimulated or it is deemed to be too low, the dosage of cells can be increased. This process can be repeated every week or two weeks or so until an effective dosage is administered.

One skilled in the art also is aware of means to monitor a therapeutic (i.e., systemic immune) response upon administering a composition of the present invention. In particular, the therapeutic response can be assessed by monitoring attenuation of tumor growth and/or tumor regression. The attenuation of tumor growth or tumor regression in response to treatment can be monitored using several end-points known to those skilled in the art including, for instance, number of tumors, tumor mass or size, or reduction/prevention of metastasis. Methods of assessing cervical cancer are described, for example, in U.S. Pat. No. 6,388,064. These described methods are by no means all-inclusive, and further methods to suit the specific application will be apparent to the ordinary skilled arts.

Any type of viral-associated cancer can be treated in accordance with the present inventive method as long as an antigen of the virus associated with the cancer has been defined and, desirably, is present on the surfaces of the cancerous cells. "Cancer" as used herein includes cancers, in particular those of epithelial origin, characterized by abnormal cellular proliferation and the absence of contact inhibition, which can be evidenced by tumor formation. The term encompasses cancer localized in tumors, as well as cancer not localized in tumors, such as, for instance, cancer cells that expand from a tumor locally by invasion. Thus, the method has applicability as a local adjuvant therapy for resected cancers as well as a local control of tumor growth.

The method of the present invention can be combined with other methods of cancer treatment. Examples of such methods include radiation, surgery and chemotherapy. In addition, the method of the present invention can be adapted for non-human mammals, for example, by employing a nonhuman mammalian cell line and a non-human mammalian source of an immunomodulator and viral antigen, as appropriate.

The present inventive cell line has other uses, other than as described above. For example, the present inventive cell line can be used to characterize a human's immune response to the antigen, e.g., viral antigen, such as an EBV, HPV or KSHV antigen, expressed by the cell line. For example, if the antigen expressed by the cell line is an EBV antigen, the human's immune response to the EBV antigen can be measured before and after administration of the cell line. By comparing the immune responses before and after administration, it is possible to determine whether or not a given human responds immunologically to the antigen of EBV and, if desired, characterize the nature and extent of the response. Tetramer assay and cytokine secretion assay can be used. If the human is to be treated for an EBV-expressing cancer, this information can be used to determine if the human can be treated using the EBV antigen-expressing cell line. This information also can be used to determine how best to administer the EBV antigen-expressing cell line, e.g., what dosage at what frequency. In much the same way, an immunocompromised human can be evaluated to determine suitability for cancer immunotherapy and, if found suitable, the manner of treatment, i.e., dosage and frequency of administration.

The present inventive cell line also can be used to assess an immune response to a cancer cell vaccine for which the antigen is undefined. For example, the present inventive cell line can be administered to a human in combination with the cancer cell vaccine, and the present inventive cell line can be used as a marker. The immune response to the defined antigen expressed by the present inventive cell line can be used to determine the human's immune responsiveness, thereby enabling grading of immune responses to the cancer cell vaccine under similar vaccine conditions, for example.

In view of the teachings set forth herein, Applicants reserve the right to pursue claims to the following embodiments. This reservation is not to be construed as a waiver of the right to pursue claims directed to other embodiments and modifications thereof as described herein.

A. A human cell line, which lacks MHC-I antigens and MHC-II antigens and which has been modified to comprise and express (i) a nucleotide sequence encoding an immunomodulator and (ii) a nucleotide sequence encoding an antigen of HPV or KSHV.

B. The human cell line of A, wherein the antigen of HPV is E5, E6 or E7 and the antigen of KSHV is LANA or v-cyclin.

C. The human cell line of A or B, wherein the immunomodulator is a cytokine, a chemokine or an adjuvant.

D. The human cell line of C, wherein the cytokine is an inteferon, an interleukin, a tumor necrosis factor, erythropoietin, FLT-3 ligand, macrophage colony stimulating factor (M-CSF), granulocyte colony stimulating factor (G-CSF), or granulocyte-macrophage colony stimulating factor (GM-CSF).

E. The human cell line of D, wherein the interferon (IFN) is IFN.alpha., IFN.beta. or IFN.gamma.

F. The human cell line of D, wherein the interleukin (IL) is IL-1, IL-2, IL-3, IL-4, IL-5, IL-6, IL-7, IL-8, IL-8, IL-10 or IL-12.

G. The human cell line of D, wherein the tumor necrosis factor (TNF) is TNF.alpha. or TNF.beta.

H. The human cell line of C, wherein the chemokine is Mip1.alpha., Mip-1.beta., Mip-3.alpha. (Lax), Mip-3.beta., Rantes, Hcc-1, Mpif-1, Mpif-2, Mcp-1, Mcp-2, Mcp-3, Mcp-4, Mcp-5, Eotaxin, Tarc, Elc, I309, IL-8, Gcp-2 Gro-.alpha., Gro-.beta., Gro-.gamma., Nap-2, Ena-78, Gcp-2, Ip-10, Mig, I-Tac, Sdf-1, or Bca-1 (Blc).

I. The human cell line of C, wherein the adjuvant is a heat shock protein or CpG.

J. The human cell line of A, wherein the immunomodulator is GM-CSF, and the antigen of HPV is E6 or E7.

K. The human cell line of A or B, wherein the human cell line that is modified is K562.

L. The human cell line of C, wherein the human cell line that is modified is K562.

M. The human cell line of J, wherein the human cell line that is modified is K562.

N. A method of inducing or stimulating an immune response in a human for an HPV-associated cancer, which method comprises administering to the human the human cell line of A or B in an amount sufficient to induce or stimulate an immune response to the HPV-associated cancer, whereupon an immune response to the HPV-associated cancer is induced or stimulated.

O. The method of N, wherein the human is female and has cervical cancer.

P. A method of inducing or stimulating an immune response in a human for an HPV-associated cancer, which method comprises administering to the human the human cell line of C in an amount sufficient to induce or stimulate an immune response to the HPV-associated cancer, whereupon an immune response to the HPV-associated cancer is induced or stimulated.

Q. The method of P, wherein the human is female and has cervical cancer.

R. A method of inducing or stimulating an immune response in a human for an HPV-associated cancer, which method comprises administering to the human the human cell line of J in an amount sufficient to induce or stimulate an immune response to the HPV-associated cancer, whereupon an immune response to the HPV-associated cancer is induced or stimulated.

S. The method of R, wherein the human is female and has cervical cancer.

T. A method of inducing or stimulating an immune response in a human for an HPV-associated cancer, which method comprises administering to the human the human cell line of K in an amount sufficient to induce or stimulate an immune response to the HPV-associated cancer, whereupon an immune response to the HPV-associated cancer is induced or stimulated.

U. The method of T, wherein the human is female and has cervical cancer.

V. A method of inducing or stimulating an immune response in a human for an HPV-associated cancer, which method comprises administering to the human the human cell line of L in an amount sufficient to induce or stimulate an immune response to the HPV-associated cancer, whereupon an immune response to the HPV-associated cancer is induced or stimulated.

W. The method of V, wherein the human is female and has cervical cancer.

X. A method of inducing or stimulating an immune response in a human for an HPV-associated cancer, which method comprises administering to the human the human cell line of M in an amount sufficient to induce or stimulate an immune response to the HPV-associated cancer, whereupon an immune response to the HPV-associated cancer is induced or stimulated.

Y. The method of X, wherein the human is female and has cervical cancer.

Z. A composition comprising a human cell line, which lacks MHC-I and MHC-II antigens and which has been modified to comprise and express a nucleotide sequence encoding an immunomodulator, and a human cell line, which lacks MHC-I and MHC-II antigens and which has been modified to comprise and express a nucleotide sequence encoding an antigen of HPV or KSHV.

AA. A composition comprising an immunomodulator and a human cell line, which lacks MHC-I and MHC-II antigens and which has been modified to comprise and express a nucleotide sequence encoding an antigen of HPV or KSHV.

AB. A method of inducing or stimulating an immune response in a human to an HPV-associated or KSHV-associated cancer, which method comprises administering to the human the composition of Z (expressing an antigen of HPV or KSHV, respectively) in an amount sufficient to induce or stimulate an immune response to the HPV-associated or KSHV-associated cancer, whereupon an immune response to the HPV-associated or KSHV-associated cancer is induced or stimulated.

AC. The method of AB, wherein the human is female and has cervical cancer associated with HPV or the human has Kaposi's sarcoma.

AD. A method of inducing or stimulating an immune response in a human to an HPV-associated or KSHV-associated cancer, which method comprises administering to the human the composition of AA (expressing an antigen of HPV or KSHV, respectively) in an amount sufficient to induce or stimulate an immune response to the HPV-associated or KSHV-associated cancer, whereupon an immune response to the HPV-associated or KSHV-associated cancer is induced or stimulated.

AE. The method of AD, wherein the human is female and has cervical cancer associated with HPV or the human has Kaposi's sarcoma.

AF. A method of inducing or stimulating an immune response in a human to an HPV-associated or KSHV-associated cancer, which method comprises administering to the human a composition comprising a human cell line, which lacks MHC-I and MHC-II antigens and which has been modified to comprise and express a nucleotide sequence encoding an immunomodulator, in an amount sufficient to induce or stimulate an immune response, and simultaneously or sequentially, in either order, by the same route or a different route, a human cell line, which lacks MHC-I and MHC-II antigens and which has been modified to comprise and express a nucleotide sequence encoding an antigen of HPV or KSHV, respectively, in an amount sufficient to induce to stimulate an immune response, whereupon an immune response to the HPV-associated or KSHV-associated cancer is induced or stimulated.

AG. The method of AF, wherein the human is female and has cervical cancer associated with HPV or the human has Kaposi's sarcoma.

AH. A method of inducing or stimulating an immune response in a human to an HPV-associated or KSHV-associated cancer, which method comprises administering to the human an immunomodulator in an amount sufficient to induce to stimulate an immune response, and simultaneously or sequentially, in either order, by the same route or a different route, a human cell line, which lacks MHC-I and MHC-II antigens and which has been modified to comprise and express a nucleotide sequence encoding an antigen of HPV or KSHV, respectively, in an amount sufficient to induce to stimulate an immune response, whereupon an immune response to the HPV-associated or KSHV-associated cancer is induced or stimulated.

AI. The method of AH, wherein the human is female and has cervical cancer associated with HPV or the human has Kaposi's sarcoma

EXAMPLES

Antibody generation and purification, diagnostic platforms, cloning procedures; etc., to the extent that they are not described herein, can be found in references such as the following:

Sambrook et al., Molecular Cloning, A Laboratory Manual, Vols. I-III, 1989, Cold Spring Harbor Laboratory Press, USA;

Harlowe and Lane, Antibodies: A Laboratory Manual, 1988 and 1998, Cold Spring Harbor Laboratory Press, USA; and Ausubel et al., Current Protocols, 2001, John Wiley and Sons, Inc.

The following examples serve to illustrate the present invention and are not intended to limit its scope in any way.

Example 1

This example describes the generation of an EBV antigen-specific, GM-CSF-secreting cellular vaccine.

The allogeneic human erythroleukemia cell line K562 was transfected with a plasmid containing human GM-CSF operably linked to the cytomegaloviral (CMV) promoter, a hygromycin resistance gene, and the Epstein-Barr virus (EBV) nuclear antigen-1 (EBNA1) gene, which is required for the function of the plasmid origin of replication. The plasmid, designated pCEP4-EBNA1/hGM-CSF, is shown in FIG. 1. Hygromycin-resistant clones were screened for the secretion of GM-CSF. A K562-EBNA1/GM-CSF clone producing over 2,000 ng of GM-CSF/10.sup.6 cells/24 hrs was selected. The high degree of expression of this clone minimizes the number of cells needed for vaccination, while leaving the margin for efficacy well above the threshold of 36 ng/10.sup.6 cells/24 hrs. The K562-EBNA1/GM-CSF clone also was determined to express EBNA1 by Western blot using a monoclonal antibody to EBNA1.

Figure 2:
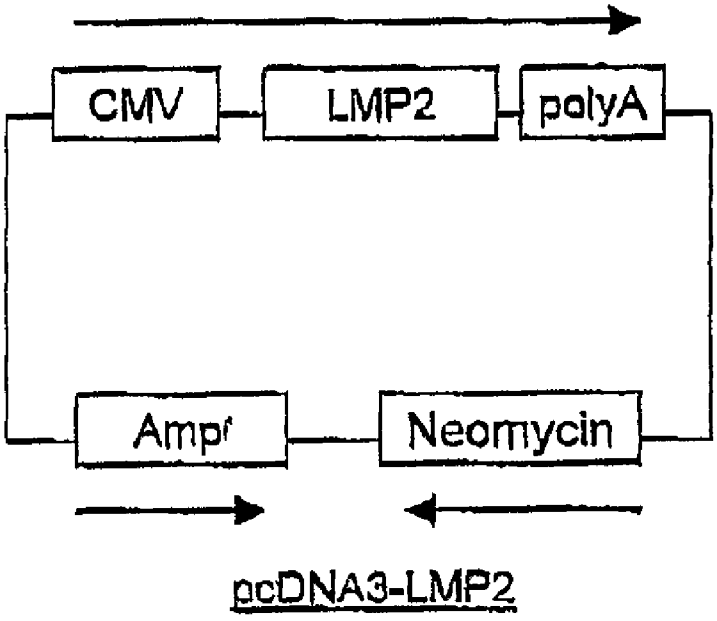
FIG. 2 is a diagram of a bi-cistronic plasmid (arrows indicate direction of transcription) containing the LMP2 coding sequence (LMP2) operably linked to the CMV promoter (CMV) and a polyA tail (polyA), a neomycin resistance gene (Neomycin), and an ampicillin resistance gene (Amp.sup.r). The plasmid is designated pcDNA3-LMP2.

The K562-EBNA1/GM-CSF clone was transfected with a plasmid expressing latent membrane protein 2 (LMP2) under the control of a CMV promoter. The plasmid, which is designated pcDNA3-LMP2, also contains a neomycin resistance gene and is shown in FIG. 2. G418-resistant clones were analyzed for the expression of LMP2 by immunofluorescent staining with a monoclonal antibody to LMP2. A clone expressing high levels of LMP2 was selected and designated K562-EBNA1/LMP2/GM-CSF. The clone has been determined to express high levels of LMP2 (of expected size) and GM-CSF, as well as EBNA1 RNA and LMP2 RNA. A master cell bank can be generated and a clinical grade vaccine can be generated from the master cell bank. The cells can be irradiated, frozen under controlled conditions, and stored in liquid nitrogen in vials containing 3.3.times.10.sup.7 cells.

Example 2

This example describes an EBV antigen-specific, GM-CSF-secreting cellular vaccine for treating EBV+ tumors.

Patients with EBV+ Hodgkin's lymphoma (HL) or nasophaaryngeal carcinoma (NPC) at high risk for relapse after primary therapy or those with relapsed or metastatic disease are treated. The patients are given a first vaccination six weeks after the completion of primary therapies, such as chemotherapy, radiation, or a combination thereof. Follow-up vaccinations are given monthly thereafter for a total of four vaccinations, spanning weeks 6 to 18 during immune reconstitution. On the day of vaccination, the cellular vaccine (K562-EBNA1/LMP2/GM-CSF) is removed from the liquid nitrogen storage and rapidly thawed in a 37.degree. C. water bath. Viability of the cellular vaccine is assessed by trypan blue exclusion, and the number of viable cells is used for calculation of dosages. The patients are intradermally injected with a total dose of 3.3.times.10.sup.7 cells per vaccination divided into 9 injections of 3.6.times.10.sup.8 cells in a volume of 0.5 ml. Three injections spaced 5 cm apart will be placed on each anterior thigh and the non-dominant arm. Patients are monitored for possible toxicities at the site of vaccination. Systemic toxicities are assessed from paracrine secretion of GM-CSF.

If desired, the generation and enhancement of LMP2/EBNA1-specific CD4 and CD8 T cell responses to LMP2 and EBNA1 are assessed using a modified IFN-.gamma. ELISPOT assay, which utilizes dendritic cells infected with recombinant vaccinia virus expressing LMP2 or EBNA1 as a stimulator. This abolishes the need to HLA-type each patient. Briefly, peripheral blood mononuclear cells (PBMCs) from patients are fractioned into CD4 and CD8 cells by a magnetic cell separation (MACS) system. Purified CD4 or CD8 cells are stimulated with dendritic cells transduced with recombinant vaccinia vector encoding LMP2 or EBNA1 in multi-screen hemagglutinin (HA) plates coated with a monoclonal antibody to IFN-.gamma. (capture antibody) for 16-18 hrs. The plates are then washed and stained for IFN-.gamma. with an immunoperoxidase technique. The IFN-.gamma.-positive spots are counted using a stereomicroscope. A tetramer assay also is used for HLA-A2, A11 and A24 patients in order to correlate with results from the IFN-Y ELISPOT assay.

Patients are compared at baseline and at six months or earlier after completion of vaccination. The baseline cellular response to LMP2 is expected to be less than about 50/million PBMCs. A vaccination is considered to be successful if the cellular response exceeds about 200/million PBMCs.

Example 3

This example describes the generation of an HPV antigen-specific, GM-CSF-secreting cellular vaccine.

The allogeneic human erythroleukemia cell line K562 was transfected with a plasmid containing human GM-CSF operably linked to the cytomegaloviral (CMV) promoter, a hygromycin resistance gene, and the Epstein-Barr virus (EBV) nuclear antigen-1 (EBNA1) gene, which is required for the function of the plasmid origin of replication. The plasmid, designated pCEP4-EBNA1/hGM-CSF, is shown in FIG. 1. Hygromycin-resistant clones were screened for the secretion of GM-CSF. A K562-EBNA1/GM-CSF clone producing over 2,000 ng of GM-CSF/10.sup.6 cells/24 hrs was selected. The high degree of expression of this clone minimizes the number of cells needed for vaccination, while leaving the margin for efficacy well above the threshold of 36 ng/10.sup.6 cells/24 hrs. The K562-EBNA1/GM-CSF clone also was determined to express EBNA1 by Western blot using a monoclonal antibody to EBNA1.

The K562-EBNA1/GM-CSF clone is transfected with a plasmid expressing E6 under the control of a CMV promoter. The plasmid, which is designated pcDNA3-E6, also contains a neomycin resistance gene. G418-resistant clones were analyzed for the expression of E6 by immunofluorescent staining with a monoclonal antibody to E6. A clone expressing high levels of E6 was selected and designated K562-EBNA1/E6/GM-CSF. A master cell bank can be generated and a clinical grade vaccine can be generated from the master cell bank. The cells can be irradiated, frozen under controlled conditions, and stored in liquid nitrogen in vials containing 3.3.times.10.sup.7 cells.

Example 4

This example describes an HPV antigen-specific, GM-CSF-secreting cellular vaccine for treating HPV+ tumors.

Patients with HPV+ cervical cancer at high risk for relapse after primary therapy or those with relapsed or metastatic disease are treated. The patients are given a first vaccination six weeks after the completion of primary therapies, such as chemotherapy, radiation, or a combination thereof. Follow-up vaccinations are given monthly thereafter for a total of four vaccinations, spanning weeks 6 to 18 during immune reconstitution. On the day of vaccination, the cellular vaccine (K562-EBNA1/E6/GM-CSF) is removed from the liquid nitrogen storage and rapidly thawed in a 37.degree. C. water bath. Viability of the cellular vaccine is assessed by trypan blue exclusion, and the number of viable cells is used for calculation of dosages. The patients are intradermally injected with a total dose of 3.3.times.10.sup.7 cells per vaccination divided into 9 injections of 3.6.times.10.sup.8 cells in a volume of 0.5 ml. Three injections spaced 5 cm apart will be placed on each anterior thigh and the non-dominant arm. Patients are monitored for possible toxicities at the site of vaccination. Systemic toxicities are assessed from paracrine secretion of GM-CSF.

If desired, the generation and enhancement of E6-specific CD4 and CD8 T cell responses to E6 is assessed using a modified IFN-Y ELISPOT assay, which utilizes dendritic cells infected with recombinant vaccinia virus expressing E6 as a stimulator. This abolishes the need to HLA-type each patient. Briefly, PBMCs from patients are fractioned into CD4 and CD8 cells by MACS separation system. Purified CD4 or CD8 cells are stimulated with dendritic cells transduced with recombinant vaccinia vector encoding E6 or EBNA1 in multiscreen HA plates coated with a monoclonal antibody to IFN-.gamma. (capture antibody) for 16-18 hrs. The plates are then washed and stained for IFN-.gamma. with an immunoperoxidase technique. The IFN-.gamma.-positive spots are counted using a stereomicroscope. A tetramer assay also is used for HLA-A2, A11 and A24 patients in order to correlate with results from the IFN-.gamma. ELISPOT assay.

Patients are compared at baseline and at six months or earlier after completion of vaccination. The baseline cellular response to E6 is expected to be less than about 50/million PBMCs. A vaccination is considered to be successful if the cellular response exceeds about 200/million PBMCs.

Example 5

This example describes the generation of a KSHV antigen-specific, GM-CSF-secreting cellular vaccine.

The allogeneic human erythroleukemia cell line K562 was transfected with a plasmid containing human GM-CSF operably linked to the cytomegaloviral (CMV) promoter, a hygromycin resistance gene, and the Epstein-Barr virus (EBV) nuclear antigen-1 (EBNA1) gene, which is required for the function of the plasmid origin of replication. The plasmid, designated pCEP4-EBNA1/hGM-CSF, is shown in FIG. 1. Hygromycin-resistant clones were screened for the secretion of GM-CSF. A K562-EBNA1/GM-CSF clone producing over 2,000 ng of GM-CSF/10.sup.6 cells/24 hrs was selected. The high degree of expression of this clone minimizes the number of cells needed for vaccination, while leaving the margin for efficacy well above the threshold of 36 ng/10.sup.6 cells/24 hrs. The K562-EBNA1/GM-CSF clone also was determined to express EBNA1 by Western blot using a monoclonal antibody to EBNA1.

The K562-EBNA1/GM-CSF clone is transfected with a plasmid expressing LANA under the control of a CMV promoter. The plasmid, which is designated pcDNA3-LANA, also contains a neomycin resistance gene. G418-resistant clones were analyzed for the expression of LANA by immunofluorescent staining with a monoclonal antibody to LANA. A clone expressing high levels of LANA was selected and designated K562-EBNA1/LANA/GM-CSF. A master cell bank can be generated and a clinical grade vaccine can be generated from the master cell bank. The cells can be irradiated, frozen under controlled conditions, and stored in liquid nitrogen in vials containing 3.3.times.10.sup.7 cells.

Example 6

This example describes an KSHV antigen-specific, GM-CSF-secreting cellular vaccine for treating KSHV+ tumors.

Patients with Kaposi sarcoma at high risk for relapse after primary therapy or those with relapsed or metastatic disease are treated. The patients are given a first vaccination six weeks after the completion of primary therapies, such as chemotherapy, radiation, or a combination thereof. Follow-up vaccinations are given monthly thereafter for a total of four vaccinations, spanning weeks 6 to 18 during immune reconstitution. On the day of vaccination, the cellular vaccine (K562-EBNA1/LANA/GM-CSF) is removed from the liquid nitrogen storage and rapidly thawed in a 37.degree. C. water bath. Viability of the cellular vaccine is assessed by trypan blue exclusion, and the number of viable cells is used for calculation of dosages. The patients are intradermally injected with a total dose of 3.3.times.10.sup.7 cells per vaccination divided into 9 injections of 3.6.times.10.sup.8 cells in a volume of 0.5 ml. Three injections spaced 5 cm apart will be placed on each anterior thigh and the non-dominant arm. Patients are monitored for possible toxicities at the site of vaccination. Systemic toxicities are assessed from paracrine secretion of GM-CSF.

If desired, the generation and enhancement of LANA-specific CD4 and CD8 T cell responses to LANA is assessed using a modified IFN-.gamma. ELISPOT assay, which utilizes dendritic cells infected with recombinant vaccinia virus expressing LANA as a stimulator. This abolishes the need to HLA-type each patient. Briefly, PBMCs from patients are fractioned into CD4 and CD8 cells by MACS separation system. Purified CD4 or CD8 cells are stimulated with dendritic cells transduced with recombinant vaccinia vector encoding LANA or EBNA1 in multiscreen HA plates coated with a monoclonal antibody to IFN-.gamma. (capture antibody) for 16-18 hrs. The plates are then washed and stained for IFN-IFN-.gamma. with an immunoperoxidase technique. The IFN-.gamma.-positive spots are counted using a stereomicroscope. A tetramer assay also is used for HLA-A2, A1 1 and A24 patients in order to correlate with results from the IFN-.gamma. ELISPOT assay.

Patients are compared at baseline and at six months or earlier after completion of vaccination. The baseline cellular response to LANA is expected to be less than about 50/million PBMCs. A vaccination is considered to be successful if the cellular response exceeds about 200/million PBMCs.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of inducing or stimulating an immune response in a human to an EBV-associated cancer, which method comprises administering to the human an immunomodulator in an amount sufficient to induce to stimulate an immune response, and simultaneously or sequentially, in either order, by the same route or a different route, a human cell line, which lacks MHC-I and MHC-II antigens and which has been modified to comprise and express a nucleotide sequence encoding an antigen of EBV, in an amount sufficient to induce to stimulate an immune response, whereupon an immune response to the EBV-associated cancer is induced or stimulated, wherein the human cell line is K562.

2. The method of claim 1, wherein the human has or is at risk for Hodgkin's lymphoma.

3. The method of claim 1, wherein the human has or is at risk for nasopharyngeal carcinoma.

4. The method of claim 1, wherein the human has or is at risk for gastric carcinoma, Burkitt's lymphoma, T-cell lymphoma, B-cell lymphoma, parotid carcinoma, breast carcinoma, and leiomyosarcoma.

5. The method of claim 1, wherein the immunomodulator is a cytokine, a chemokine or an adjuvant.

6. The method of claim 5, wherein the cytokine is an interferon, and interleukin, a tumor necrosis factor, erythropoietin, and FLT-3 ligand.

7. The method of claim 6, wherein interferon (IFN) is IFN.alpha., IFN.beta, or IFN.gamma.

8. The method of claim 6, wherein the interleukin (IL) is IL-1, IL-2, IL-3, IL-4, IL-5, IL-6, IL-7, IL-8, IL-8, IL-10, IL-12 or IL-20.

9. The method of claim 6, wherein the tumor necrosis factor (TNF) is TNF.alpha, or TNF.beta.

10. The method of claim 5, wherein the chemokine is Mip1.alpha., Mip-1.beta., Mip-3.alpha. (Larc), Mip-3.beta., Rantes, Hcc-1, Mpif-1, Mpif-2, Mcp-1, Mcp-2, Mcp-3, Mcp-4, Mcp-5, Eotaxin, Tare, Elc, I309, IL-8, Gcp-2 Gro-a, Gro-.alpha., Gro-.beta., Nap-2, Ena-78, Gcp-2, Ip-10, Mig, I-Tac, Sdf-1, or Bca-1 (Blc).

11. The method of claim 5, wherein the adjuvant is a heat shock protein or CpG.

* * * * *

UNITED STATES PATENT AND TRADEMARK OFFICE

CERTIFICATE OF CORRECTION

PATENT NO. : 8,383,096 B2
APPLICATION NO. : 12/756364
DATED : February 26, 2013
INVENTOR(S) : Ambinder et al.

It is certified that error appears in the above-identified patent and that said Letters Patent is hereby corrected as shown below:

In the Claims:

In Claim 8, Column 368, Line 62, immediately before “IL-10,” please delete “IL-8” and insert -- IL-9 -- therefor.

Signed and Sealed this
Twenty-third Day of April, 2013

Teresa Stanek Rea
*Acting Director of the United States Patent and Trademark Office*